US007196110B2

(12) United States Patent
Ho et al.

(10) Patent No.: US 7,196,110 B2
(45) Date of Patent: Mar. 27, 2007

(54) N-SUBSTITUTED TRICYCLIC 3-AMINOPYRAZOLES AS INHIBITORS FOR THE TREATMENT OF CELL PROLIFERATIVE DISORDERS

(75) Inventors: Chih Yung Ho, Lansdale, PA (US); Bengt Anders Brunmark, LaJolla, CA (US); Stuart Emanuel, Doylestown, PA (US); Robert A. Galemmo, Jr., Collegeville, PA (US); Dana L. Johnson, Upper Black Eddy, PA (US); Donald W. Ludovici, Quakertown, PA (US); Umar Maharoof, North Wales, PA (US); Jay M. Mei, North Wales, PA (US); Jan L. Sechler, Doylestown, PA (US); Eric D. Strobel, Hatboro, PA (US); Robert W. Tuman, Chalfont, PA (US); Hwa Kwo Yen, Malvern, PA (US)

(73) Assignee: Janssen Phamaceutica N.V. (BE)

( * ) Notice: Subject to any disclaimer, the term of this patent is extended or adjusted under 35 U.S.C. 154(b) by 19 days.

(21) Appl. No.: 10/438,152

(22) Filed: May 14, 2003

(65) Prior Publication Data

US 2004/0082639 A1 Apr. 29, 2004

Related U.S. Application Data

(60) Provisional application No. 60/380,735, filed on May 15, 2002.

(51) Int. Cl.
*A61K 31/416* (2006.01)
*C07D 231/54* (2006.01)

(52) U.S. Cl. .................................... 514/405; 548/359.1

(58) Field of Classification Search ............. 548/359.1; 514/405

See application file for complete search history.

(56) References Cited

U.S. PATENT DOCUMENTS

| | | | |
|---|---|---|---|
| 3,928,378 | A | 12/1975 | Bauer et al. |
| 4,140,785 | A | 2/1979 | Hoffman et al. |
| 4,220,776 | A | 9/1980 | Whitney et al. |
| 4,420,476 | A | 12/1983 | Philip et al. |
| 5,409,930 | A | 4/1995 | Spada et al. |
| 5,474,765 | A | 12/1995 | Thorpe |
| 5,476,851 | A | 12/1995 | Myers et al. |
| 5,476,871 | A | 12/1995 | Griffith et al. |
| 5,563,173 | A | 10/1996 | Yatsu et al. |
| 5,762,918 | A | 6/1998 | Thorpe |
| 5,855,866 | A | 1/1999 | Thorpe et al. |
| 5,932,580 | A | 8/1999 | Levitzki et al. |
| 6,342,219 | B1 | 1/2002 | Thorpe et al. |
| 6,451,834 | B1 | 9/2002 | Arnold et al. |
| 2002/0016625 | A1 | 2/2002 | Falotico et al. |

FOREIGN PATENT DOCUMENTS

| | | | |
|---|---|---|---|
| EP | 0620489 | A1 | 10/1994 |
| EP | 06/98611 | B1 | 10/1999 |
| JP | 6092963 | A | 4/1994 |
| JP | 6100561 | A | 4/1994 |
| JP | 6022109 | A | 1/1996 |
| JP | 11158149 | A | 6/1999 |
| WO | WO 95/07893 | A1 | 3/1995 |
| WO | WO 96/32907 | A1 | 10/1996 |
| WO | WO 99/17769 | A1 | 4/1999 |
| WO | WO 99/54308 | A1 | 10/1999 |
| WO | WO 00/07996 | A2 | 2/2000 |
| WO | WO 99/17770 | A1 | 3/2000 |
| WO | WO 00/59901 | A1 | 10/2000 |
| WO | WO 01/79198 | A1 | 10/2001 |
| WO | WO 02/12242 | A3 | 2/2002 |

OTHER PUBLICATIONS

Schenone et al., Farmaco (2000), 55(5), pp. 383-388.*

Reeve, W. et al., “The Synthesis of Hydrastic Acid.” *J. Amer. Chem. Soc.* (1951), pp. 1371-1372, vol. 73.

Baddeley, G., et al., “Friedel-Crafts Acylation and Alkylation. A Comparision of Inter-and Intra-molecular processes.” *J. Chem. Soc.* 1956, pp. 4647-4653.

Cantrell, T. S., et al., “The 2-Thiapentalenyl Anion.” *Tetrahedron Lett.* (1967), pp. 4477-4480, No. 45, Pergamon Press Ltd.

MacDowelli, D. W. H., et al., The Use of 2,5-Dichlorothiophene in the Synthesis of 3,4-Disubstituted Thiophene, *J. Org. Chem.*, (1967), vol. 32, pp. 1226-1229.

Hampel, W., et al., “Reactions with Diazoketones. XII. 3-Oxothionaphthene.” *Zeitschrift fuer Chemie*, (1970), p. 343, vol. 10, No. 9. (English Abstract included).

Schoen, J., et al., “Arylamides of 3-Hydroxy-Indene-2-Thionocarboxylic Acid.” *Roczniki Chemii*, (1971), pp. 73-77, vol. 45, No. 1. (English Abstract included.).

Muraro, G., et al., “Thieno (c) Cyclenones.” *Sciences Chimiques*, (1971), pp. 1362-1365, vol. 273, No. 20. English Abstract included.).

Akhrem, V.A. et al., “Reaction Of Some Aromatic Nitrile Oxides With Dimedone,” translation from *Khim. Geterotsiki. Seodin.*, (1974), pp. 784-787, No. 7.

Torii, S., et al., “Electrochemical Acetoxylation of N-Acetylindolines and N-Acetylindoles. A New Synthesis of Indigos.” *J. Org. Chem.*, (1978), pp. 2882-2885, vol. 43, No. 14.

(Continued)

*Primary Examiner*—Laura L. Stockton

(57) ABSTRACT

The invention is directed to N-substituted tricyclic 3-AMINOPYRAZOLE derivatives, which are useful as inhibitors of platelet-derived growth factor receptor (PDGF-R) kinase, and methods for the preparation of said derivatives. The present invention is further directed to pharmaceutical compositions comprising the compounds of the present invention and to methods for treating conditions such as tumors and other cell proliferative disorders.

37 Claims, No Drawings

OTHER PUBLICATIONS

Suebe, S. et al., "Synthesis Of Heterocyclic Chemistry." *J. Heterocyclic Chem.*, (1978), pp. 343-346, vol. 15, No. 2. (English Abstract included.).

Augustin, M., et al., "Synthesis and Reactions of Carbocyclic Acylketene-S, S-Acetals." *J. Fuer Praktische Chemie* (*Leipzig*), (1979), pp. 215-225, vol. 321, No. 2. (English Abstract included.).

Augustin, M., et al., "Synthesis and Reactions of 2-[bis (alkylthio) Methylidene] Indan-1-Diones." *J. Fuer Praktische Chemie* (*Leipzig*), (1979), pp. 205-214, vol. 321, No. 2. (English Abstract included.).

Caldwell, J; "The Significance of Phase II (Conjugation) Reactions in Drug Disposition and Toxicity." *Life Science*, (1979), vol. 24, pp. 571-578.

Sugasawa, T. et al., "Aminohaloborane in Organic Synthesis.2.[1] Simple Synthesis of Indoles and 1-Acyl-3-indolinones Using Specific Ortho -Chloroacetylation of Anilines [2]."*J. Org. Chem.*, (1979), pp. 578-586, vol. 44, No. 4.

Gehrig, K., et al. "ortho-Cyano-1-arylazonaphthalenes and 3-Amino-2-arylbenzo[g]Indazoles from Cyclopalladated 1-Arylazonaphthalenes." *Helvetica Chimica Acta*. (1983), pp. 2603-2606, vol. 66, Fasc. 8, No. 260.

Ranise, A., et al., "Derivatives of 4,5,6,7-Tetrahydro-7,8,8-Trimethyl-3-Phenylamino-4,7-Methano-2H-Indazole with Hypoglycemic and Hypotensive Activities." *Farmaco-Ed. Sc.*, (1983), pp. 101-111, vol. 38, Fasc. 2.

Maillard, J., et al., "Synthesis of Amino Derivatives of 4,5,6,7-Tetrahydrobenzothiazole. I. The 4-, 5-, 6- and 7-amino and N-Methylamino Derivatives With Central Dopaminergic Activity." *European J. Medicinal Chem*. (1984), pp. 451-456, vol. 19, No. 5. (English Abstract Included.).

Ranise, A., et al., "Reactions of Camphor Pyrrolldinoenamine and its N-Phenyl 3-Carbothioamide with Sulphur and Nitrogen Reagents." *J. Chem. Research*, (1984), pp. 42-43.

Ranise, A. et al., "Derivatives of 4,5,6,7-Tetrahydro-7,8,8-Trimethyl-3-Phenylamino-4-7-Methano-2H-Indazole With Hypotensive And Hypoglycemic Activities." II Farmaco—Ed. Sc., (1984), pp. 200-207, vol. 39, Fasc. 3.

Thorpe, P.E., "Antibody Carriers Of Cytotoxic Agents In Cancer Thereapy:A Review." *Monoclonal Antibodies '84: Biological and Clinical Applications*, (1984), pp. 475-506.

Arnon, R., "Monoclonal Antibodies For Immunotargeting of Drugs in Cancer Therapy," *Monoclonal Antibodies and Cancer Therapy*, (1985), pp. 243-256.

Suesse, M., et al., "Synthesis of Qulnazoline-4-Thione- and 1H-Indazole Derivatives." *J. Fuer Praktische Chemie* (*Leipzig*), (1986), pp. 635-639, vol. 328, No. 4. (English Abstract Included.).

Capon, B., et al., "Reversible Carbon Protonation In The Hydrolysis Of Heterocyclic Enol Methyl Ethers." *Tetrahedron*, (1987), pp. 69-76, vol. 43, No. 1.

Rhee, G.S., et al., "Studies of Inositol Phospholipid-Specific Phospholipase C." *Science*, (1989), pp. 546-550, vol. 244.

Hoye, T. R., et al., "Alkyne Insertion Reactions of Metal-Carbenes Derived from Enynyl α-Diazo Ketones [R'CN$^2$COCR$^2$CH$^2$≡C(CH$^2$)$^{n-2}$CH=CH$^2$]," *American Chemical Society*, (1990), pp. 4518-4520, 55.

Desphpande, A. R., et al., "Synthesis of 3-(3-Benzofuranyl)Coumarins," *Synthetic Communications*, (1990), pp. 809-816, vol. 20, No. 6.

Villemin, D., et al., "A Convenient One-Pot Synthesis of Ketene Dithioacetals," *Synthesis*, (1991), pp. 301-303, (4).

Majerus, P.W., et al., "Inositol Phosphate Biochemistry." *Annu. Rev. Biochem*. (1992), pp. 225-250, vol. 61.

Saa, J. M., et al., "A Novel Entry to 4,7-Indoloquinones via the Fremy's Salt Oxidative Degradation of 4-Formyl-7-Hydroxyindoles," *J. Org. Chem*., (1992), pp. 589-594, vol. 57.

Heldin, Carl-Henrik., "Structural And Functional Studies On Platelet-Derived Growth Factor," *Embo Journal*, (1992), pp. 4251-4259, vol. 11, No. 12.

Passaniti, A., et al., "A Simply, Quantitative Method For Assessing Angiogenesis And Antiangiogenio Agents Using Reconstituted Basement Membrane, Heparin, and Fibroblast Growth Factor," *Laboratory Investigation*, (1992), 519-528, vol. 67, No. 4.

Reimann, E., et al., "Intramolecular Alkylation of Aromatic Compounds, Part 32. Regioselective Synthesis of 4-Methyl-1-Pyrindan-5-One." *Pharmazie*, (1995), pp. 589-592, vol. 50, No. 9. (English Abstract included).

Kasama, T., et al., "Interleukin-10 Expression and Chemokine Regulation During the Evolution of Murine Type II Collagen-included Arthritis." *Chemokines and Interleukin-10*, (1995), pp. 2868-2876, vol. 95.

Mohamed, E.A., "Synthesis and biological activity of some 3-heterocyclyl-4-hydroxy-6-methyl-2 (1H)-quinolones." *Indian J. Chem*., (1995), pp. 21-26, vol. 34B.

Wu, S-Q., et al., "Extensive amplification of bcr/abl fusion genes clustered on three marker chromosomes in human leukemic cell line K-562," *Leukemia*, (1995), 858-862, vol. 9.

Buchdunger, E., et al., "Selective inhibition of the platelet-derived growth factor signal transduction pathway by a protein-tyrosine kinase inhibitor of the 2-phenylaminopyrlmidine class," *Proc. Natl. Acad. Sci, USA*, (1995), 2558-2562, vol. 92.

Schenone, S., et al., "2-Aryl-3-Phenylamino-4,5-Dihydro-2H-Benz[g]Indazoles With Antiarrhythmic and Local Anaesthetic Activities," *Farmaco*, (1995), pp. 179-182, vol. 50, No. 3.

Muller, N., "Dipyrazolebenzocycloheptenes with Lipophilic And Glycosidic Moiety." *Mecanique. Physique. Chemie. Astronomie*, (1996), pp. 781-784, vol. 323, No. 11 (English Abstract included).

Mandal, A. K., et al., "Cobalt(II) Porphyrin: A Versatile Catalyst for the Oxidation of Organic Substrates with Dioxygen and 2-Methyl Propanal," *Tetrahedron Lett*. (1996), pp. 3769-3772, vol. 37, No. 21.

Cho, H., et al., "Ring Construction Of Several Heterocycles With Phosphorus Pentoxide-Methanesulfonic Acid (PPMA)," *Heterocycles*, (1996), pp. 127-131, vol. 43, No. 1.

Hansen, P. E., "Intramolecular hydrogen bonding of the enol forms of β-ketoamides and β-ketathioamides. Deuterium isotope effects on $13^{C}$ chemical shifts." *J. Molecular Structure 378*, (1996), pp. 45-59.

Hanahan, D., "Patterns and Emerging Mechanisms of the Angiogenic Switch during Tumorigenesis." *Cell*, (1996), pp. 353-364, vol. 86.

Ishihara, K., et al., "Bis(pentafluorophenyl)borinic Acid as a Hightly Effective Oppenauer Oxidation Catalyst for Allylic and Benzylic Alcohols." *J. Org. Chem*., (1997), pp. 5664-5665, vol. 62.

Nayyar, N. K., "New Approach for the General Synthesis of Oxotetrahydroindoles via Intramolecular Cycloadditions of Azomethine Ylides with Tethered Alkynes." *J. Org. Chem*., (1997), pp. 982-991, vol. 62.

Buchdunger, E., "Inhibition of the Abl Protein-Tyrosine Kinase in Vitro and in Vivo by a 2-Phenylaminopyrimidine Derivatives." *Cancer Research*, (1996), pp. 100-104, vol. 56.

Kraus, G. A., et al., "Furan Synthesis via a 4+ 1 Ring-Building Strategy—An Approach to 1,3-Diacytfurans." *Synlett*, (1997), pp. 1259-1260, vol. 11.

Hanahan, D., et al., "Signaling Vascular Morphogenesis and Maintenance." *Science*, (1997), pp. 48-50, vol. 277.

Stojanovic, M. N., et al., "New flexible synthesis of 1,4,5,6-tetrahydrocyclopental [*b*] pyrrol-4-ones." *J. Serb. Chem. Soc*., (1997), pp. 749-753, vol. 9, No. 62.

Yagi, M. et al., "Selective Inhibition of Platelet-Derived Growth Factor (PDGF) Receptor Autophosphorylation and PDGF-Mediated Cellular Events by a Quinoline Derivative." *Exp. Cell. Res*., (1997), pp. 285-292, vol. 234.

Chiu, S. H. L., et al., "1996 Aspet N-Glucuronidation of Xenobiotics Symposium Species Differences in N-Glucuronidation." *Drug Metabolism & Disposition*, (1998), pp. 838-847, vol. 26, No. 9.

Reddy, R. R., et al., "New Hypoglycemic Agents-Part XV : Reaction Of Ethyl 4-(Chromone-3-Formimidyl) Benzoates With Hydrazine & Evaluation Of Blood-Sugar Lowering & AR Inhibiting Properties of Products." *Indian J. Heterocyclic Chem*., (1998), pp. 189-192, vol. 7.

Yagi, M., et al., "Beneficial Effects of a Novel Inhibitor of Platelet-Derived Growth Factor Receptor Autophosphorylation in the Rat with Mesangial Proliferative Glomerulonephritis." *Gen. Pharm*., (1998), pp. 765-773. vol. 31.

Binder, D., et al., "A Facile Route to Functionalized Cyclopenta [*b*] thiophenones Based on the Structure of the Selective COX-2 Inhibitor Flosulide." *Monatshefte fur Chemie*, (1998), pp. 887-896, vol. 129.

Heldin, C. H., "Signal transduction via platelet-derived growth factor receptors." *Biochimica et Biophysica. Acta*, (1998), pp. F79-F113. vol. 1378.

Huang, Y., et al., "The Improved Preparation Of 7,8-Dihydro-Quinoline-5(6H)-One And 6,7-Dihydro-5*H*-1-Pyrindin-5-One." *Synthetic Comm.*, (1998), pp. 1197-1200, vol. 28 (7).

Lee, R. Y., "Rhodium(II)-Catalyzed Cycloaddition Of Cyclic Diazodicarbonyl Compounds With Nitriles, Synthesis Of Tetrahydrobenzoxazoles, Tetrahydrobenzofurans, And Tetrahydrobenzodioxoles." *Heterocycles*, (1998), pp. 875-883, vol. 48, No. 5.

Springer, M.L., "VEGF Gene Delivery to Muscle: Potential Role for Vasculogenesis in Adults." *Molecular Cell*, (1998), pp. 549-558, vol. 2.

Luukkanen, L., et al., "Enzyme-Assisted Synthesis and Structural Characterization of Nitrocatecho Glucuronides." *Bioconjugate Chem.*, (1999), pp. 150-154, 10(1).

Bilder, G., "Restenosis Following Angioplasty in the Swine Coronary Artery Is Inhibited By an Orally Active PDGF-Receptor Tyrosine Kinase Inhibitor, RPR101511A." *Circulation*, (1999), pp. 3292-3299.

Keane, M. P., "Chemokine signaling in inflammation." *Crit. Care Med.* (2000), pp. N13-N26.

Hjelmstrom, P., et al., "Lymphoid Tissue Homing Chemokines Are Expressed in Chronic Inflammation." *A. J Pathology*, (2000), pp. 1133-1138.

Feng, L., et al., "Role of chemokines in inflammation and Immunoregulation." *Immunologic Research*, (2000), pp. 203-210, vol. 21/2-3.

Schenone, S., et al., N-Substituted 3-(arylamino)-4, 5-dihydro-2*H*-benz[*g*]indazol-2-yl acetamides with anti-inflammatory and analgesic activites. *Farmco*, (2000), pp. 383-388, 55(5).

Laird, D., et al., "SU6668 Is a Potent Antiangiogenic and Antitumor Agent That Induces Regression of Established Tumors[1]." *Cancer Research*, (2000), pp. 4152-4160, vol. 60.

Gogonas, E. P., et al., "[3+2]-Cycloaddition reactions of 2-phenyliodonio-5, 5-dimethyl-1,3,-dioxacyclohexanemethylide." *Tetrahedron Lett.* (2000), pp. 9299-9303, 41(48).

Druker, B. J., "Lessons Learned from the Development of an Abl tyrosine Kinase Inhibitor for Chronic Myelogenous Leukemia." *J. Clinical Investigation*, (2000), pp. 3-7, vol. 105, No. 1.

Ellingsen, T., et al., "Plasma Monocyte Chemoattractant Protein 1 Is a Marker for Joint Inflammation in Rheumatoid Arthritis." *J. Rheumatology*, (2001), pp. 41-46.

Ostman, Arne, et al., "Involvement of Platelet-Derived Growth Factor in Disease: Development of Specific Antagonists." *Cancer Research*, (2001), pp. 1-38, vol. 80.

Upadhyaya, P. et al., "Preparation of Pyridine-N-glucuronides of Tobacco-Specific Nitrosamines." *Chem. Res. Toxicol.* (2001), pp. 555-561. vol. 14, No. 5.

Wesolowska, A. et al., "Synthesis of the N-Allylthiomide Derivatives of Cyclic Oxo-and Dioxo-Acids and Their Cyclization to the Derivatives of 4,5-Dihydrothiazole." *Polish J. Chem.*, (2001), pp. 387-400, vol. 75.

Li, Wen-Sen et al., "Synthesis of substituted 2,3-dihydrobenzofuran in a process involving a facile acyl migration." *Tett. Lett.* (2002), pp. 1923-1925, vol. 43.

Advani, A. S. et al., "Bcr-Abl variants: biological and clinical aspects." *Leukemia Research*, (2002), pp. 713-720, vol. 26.

Kindler, T., et al., "BCR-ABL as a target for novel therapeutic interventions." *Expert Opinion Ther. Targets*, (2002), pp. 85-101, vol. 6.

Mukherjee, C. et al., "Application of Directed Metallation in Synthesis, Part 2[1]: An Expedient Synthesis of Methoxybenzo[*b*] thiophenes." *Synlett*, (2002), pp. 325-327, vol. 2.

Hellstrom et al., "Antibodies for Drug Delivery". Controlled Drug Delivery, (1987), pp. 623-653.

Vogel. A., Practical Organic Chemistry, (1956), pp. 723-749, Third Edition.

Capogrossi et al, "An invivo aniogenisis assay to study positive and negative regulators of neovascularization", Vascular Disease Molecular Biology and Gene Therapy Protocols, (1999), pp. 367-384.

Sperker et al., "The Role of B-Glucuronidase in Drug Disposition and Drug Targeting in Humans", Clin Pharmacokinet, (1997), pp. 18-31.

Bioreversible Carriers in Drug Design Theory and Application , Edited by Edward B. Roch, (1987) American Pharmaceutical Association, Table of Contents only, pp. v to vi. (ISBN 0-08-034681-2).

Protective Groups In Organic Chemistry, Edited by J.F.W. McOmie, School of Chemistry, University of Bristol, (1973), Plenum Publishing Company LTD., Table of Contents only, p. xi, (ISBN 0-306-30717-0).

International Search Report, International Application No. PCT/US 03/15193, Date of mailing of International Aug. 22, 2003.

* cited by examiner

N-SUBSTITUTED TRICYCLIC 3-AMINOPYRAZOLES AS INHIBITORS FOR THE TREATMENT OF CELL PROLIFERATIVE DISORDERS

CROSS REFERENCE

The present application claims priority under 35 U.S.C. § 119(e) from co-pending U.S. patent application Ser. No. 60/380,735, filed May 15, 2002, which is incorporated herein by reference in its entirety and for all purposes.

FIELD OF THE INVENTION

This invention relates to a novel series of N-substituted tricyclic 3-aminopyrazole compounds and the use of such compounds to treat cell proliferative disorders, such as tumors, restenosis, rheumatoid arthritis, diabetic retinopathy, and the like. More particularly, the compounds are inhibitors of the PDGF receptor tyrosine kinase.

BACKGROUND OF THE INVENTION

Accumulating evidence supports the concept that loss of growth control of cancer cells involves perturbation of signaling pathways that in the normal cell are controlled by growth regulatory factors. Platelet-derived growth factor (PDGF) is a connective tissue cell mitogen that has been implicated in tumorigenesis (Ostman and Heldin, *Adv. Can. Res.,* 80:1–38, 2001, and references therein) as well as a principal player in the complex process of angiogenesis that is critical for tumor growth.

PDGF exerts its cellular effects through binding to its specific receptor, PDGF-R. PDGF-R is a transmembrane receptor tyrosine kinase (RTK). It consists of two isozymes α and β. Each of these receptors has an extracellular part featuring five immunoglobulin-like domains and an intracellular part with a tyrosine kinase domain. Both α and β-containing receptors have been associated with mitogenic activity, stimulating edge ruffling and loss of stress fibers. Only the β-containing receptors has been associated with chemotaxis and actin reorganization (Heldin, C -H, *EMBO Journal* 11:4251–4259,1992).

Binding of PDGF to PDGF-R results in dimerization of the two subunits of the PDGF-R receptors, thereby allowing autophosphorylation of each subunit on specific tyrosine residues in the cytoplasmic domain. The autophosphorylation leads to increased kinase activity and produces docking sites for a large number of signaling molecules with SH2 domains, such as Grb2/Sos1, PLC-gamma, GAP, PI-3 kinase and Src. (Heldin et al., Biochem. *Biophys. Acta* 1378: F79–113, 1998, and references therein). Upon binding to PDGF-R, these SH2 domain-containing signaling molecules initiate signal transduction pathways that are involved in different cellular responses such as cell proliferation, cell mobility, cell permeability or apoptosis.

PDGF has several important cellular effects in vivo. It regulates cell growth, differentiation, and migration during embryonal development, and plays a possible role in neuroprotection and regeneration. It also stimulates wound healing in adults. In addition, PDGF also has specialized functions in the vascular system as well as in the homeostasis of connective tissue (Ostman and Heldin, *Adv. Can. Res.,* 80:1–38, 2001, and references therein).

Overactivity of PDGF has been implicated in the pathogenesis of a number of serious diseases, including cancers (glioma, lung, breast, colorectal, prostate, gastric and esophageal, leukemias and lymphomas), and other cell proliferative disorders, such as atherosclerosis, transplantation-induced vasculopathies, neointima formation, lung fibrosis, restenosis, pulmonary fibrosis, glomerulonephritis, glomerulosclerosis, congenital multicystic renal dysplasia, kidney fibrosis, and rheumatoid arthritis (Ostman A, Heldin C H., *Adv. Cancer Res,* 80:1–38,2001, and references therein).

A considerable body of direct and indirect experimental evidence showed that sustained tumor growth and metastasis are angiogenesis-dependent (see e.g., Hanahan, *Science,* 277:48–50, 1997). Angiogenesis is the development of new vasculature from preexisting blood vessels and/or circulating endothelial stem cells (see i.e., Springer et al., 1998). Angiogenesis plays a vital role in many physiological processes, such as embryogenesis, wound healing and menstruation. Angiogenesis also appears to be important in certain pathological events, such as solid tumor growth and metastasis, arthritis, psoriasis and diabetic retinopathy (Hanahan and Folkman, *Cell,* 86(3):353–364, 1996; ).

Anti-angiogenic therapy is currently being studied as a way to interfere with tumor growth. Indeed, numerous studies in animal models have demonstrated striking effects in tumor growth inhibition by targeting angiogenic growth factors such as vascular endothelial growth factor (VEGF), acidic and basic fibroblast growth factor (aFGF, bFGF) and PDGF. The receptors for VEGF and PDGF belong to one super family of receptor tyrosine kinases. Therefore, in addition to their role in treating other cell proliferative disorders, clinically useful PDGF-R tyrosine kinase inhibitors are useful for antiangiogenic therapy and to control tumor cell proliferation.

Small molecule inhibitors of the receptor tyrosine kinase constitute a novel class of drugs with large potential (Druker and Lydon, *J. Clin. Invest.,* 105:3–7, 2000, and references therein). Since 1995, a number of small molecule inhibitors for PDGF receptor autophosphorylation have been characterized. Some examples are listed below.

JP 06087834 (Zimmermann) discloses N-phenyl-2-pyrimidine-amine derivatives which have tumor inhibitory activity and are useful for treating tumors in warm-blooded animals including human beings. Derivatives of this group of compounds, compound CGP53716 (Buchdunger et al., PNAS, 92:2558–2562, 1995) and compound STI-571 (Buchdunger et al., Cancer Res, 56:100–4, 1996), have been shown to inhibit PDGF-R autophosphorylation.

JP 11158149 (Kubo et al.) discloses quinoline derivatives for the treatment of diseases such as tumors and diabetic retinopathy. Derivatives of this group of compounds, compound Ki6783 (Yagi et al., Exp. Cell Res. 243:285–292, 1997) and compound Ki6896 (Yagi et al., Gen. Pharmacol. 31:765–773, 1998), have been shown to inhibit PDGF-R autophosphorylation.

U.S. Pat. No. 5,932,580 (Levitzki et al.) discloses PDGF receptor kinase inhibitory compounds of the quinoxaline family including Tyrphostin, ATP-competitive inhibitors of the receptor kinase.

U.S. Pat. No. 5,409,930 (Spada, et al.) discloses bis mono- and/or bicyclic aryl and/or heteroaryl compounds exhibiting protein tyrosine kinase inhibition activity. Compound RPR101511A, a derivative of this group of compound, has been shown to inhibit PDGF-R autophosphorylation (Bilder et al., *Circulation.* 99(25):3292–9. 1999).

U.S. Pat. No. 5,563,173 (Yatsu, et al.) discloses a method of inhibiting the proliferation of smooth muscle cells by sodium butyrate, which inhibits PDGF-R kinase activity.

U.S. Pat. No. 5,476,851 (Myers, et al.) discloses Pyrazolo [3,4-g]quinoxaline compounds, as PDGF receptor protein tyrosine kinase inhibitors.

Compound SU-6668, an ATP competitive inhibitor, has been shown to inhibit PDGF-R autophosphorylation (Laird, et al., *Cancer Res.* 60:4152–4160, 2000].

WO01/79198 (Reich et al.) discloses amino-pyrazole compounds of the following formula that modulate and/or inhibit the activity of protein kinases.

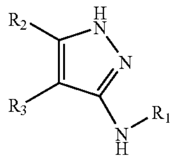

WO0212242 (Fancelli et al.) discloses bicyclo-pyrazole compounds that are useful for treating diseases linked to disregulated protein kinases.

Up to now, STI-571 (GLEEVEC) is the only compound to reach market with significant PDGFR activity, although it is not a selective antagonist of this enzyme. Therefore, PDGF-R remains an extremely attractive target for the design of potent and selective small molecule inhibitors that will represent an important new class of therapeutic agents for the treatment of tumors and other cell proliferative disorders.

References to a number of substituted tricyclic pyrazole derivatives include those disclosing use as: inhibitors of tyrosine kinase activity (WO 99/17769, WO 99/17770); cyclin dependent kinases inhibitors (WO 99/54308); selective estrogen receptor modulators (WO 00/07996); analgesics (U.S. Pat. No. 4,420,476); prophylaxis and therapy of diseases caused by rhinoviruses (U.S. Pat. No. 4,220,776; U.S. Pat. No. 4,140,785); analgesics/anti-inflammatory activity (U.S. Pat. No. 3,928,378; Schenone, Silvia et al. Farmaco (2000), 55(5), 383–388); cyan couplers for photographic dye (EP 0620489, JP 8022109); quinolines and naphthyridines as drugs (JP 6092963); and immunomodulators (JP 6100561); and hypoglycemic agents (Reddy, R. Raja et al., Indian Journal of Heterocyclic Chemistry (1998), 7(3), 189–192).

SUMMARY OF THE INVENTION

The present invention provides N-substituted tricyclic 3-aminopyrazole derivatives as inhibitors of the PDGF receptor (PDGF-R) tyrosine kinase and the use of such compounds to treat cell proliferative disorders or disorders related to (i.e., associated with or implicating with) platelet-derived growth factor receptor (PDGF-R) such as such as tumors, restenosis, rheumatoid arthritis, diabetic retinopathy, and the like.

Illustrative of the invention is a pharmaceutical composition comprising a pharmaceutically acceptable carrier and any of the compounds of Formulae (I) and (II). Another illustration of the invention is a process for making a pharmaceutical composition comprising mixing any of the compounds of Formulae (I) and (II) and a pharmaceutically acceptable carrier. Another illustration of the present invention is a pharmaceutical composition prepared by mixing any of the compounds of Formulae (I) and (II) and a pharmaceutically acceptable carrier.

The present invention is further related to the use of a compound of Formulae (I) and (II) for the treatment of a PDGF-R related disorder or a cell proliferative disorder in a subject comprising administering to the subject a therapeutically effective amount of a compound of Formulae (I) and (II). The disorder related to PDGF-R or a cell proliferative disorder is selected from neoplastic and other cell proliferative disorders. Preferably, said neoplastic disorder is a cancer selected from a glioma cancer, a lung cancer, a breast cancer, a colorectal cancer, a prostate cancer, a gastric cancer, an esophageal cancer, a colon cancer, a pancreatic cancer, an ovarian cancer, a melanoma, a myelodiys plasia, a multiple myeloma, a leukemia and a lymphoma, and said other cell proliferative disorder is selected from atherosclerosis, transplantation-induced vasculopathies, neointima formation, lung fibrosis, macular degeneration, restenosis, pulmonary fibrosis, glomerulonephritis, glomerulosclerosis, congenital multicystic renal dysplasia, kidney fibrosis, rheumatoid arthritis and diabetic retinopathy.

The invention is directed to a method of inhibiting the onset of a disorder related to PDGF-R or a cell proliferative disorder in a subject comprising administering to the subject a prophylactically effective amount of a compound of Formulae (I) and (II).

The invention further includes a combination therapy in treating or inhibiting the onset of a disorder related to PDGF-R or a cell proliferative disorder in a subject. The combination therapy comprises administering to the subject a therapeutically or prophylactically effective amount, respectively, of a compound of the invention and one or more other anti-cell proliferation therapies including, but not limited to, chemotherapy, radiation therapy, gene therapy and immunotherapy.

The present invention also provides a method for the treatment of a cell proliferative disorder, preferably restenosis, intimal hyperplasia, inflammation, or atherosclerosis in vessel walls, comprising the controlled delivery, by release from an intraluminal medical device, of a compound of the invention in therapeutic effective amounts.

The present invention further provides a method of treating a cell proliferative disorder in a subject, preferably, a neoplastic disorder selected from a glioma cancer, a lung cancer, a breast cancer, a colorectal cancer, a prostate cancer, a gastric cancer, an esophageal cancer, a colon cancer, a pancreatic cancer, an ovarian cancer, a melanoma, a myelodysplasia, a multiple myeloma, a leukemia and a lymphoma, comprising administering to the subject a therapeutic effective amount of a compound of the invention conjugated to a targeting agent.

The present invention further provides a method for reducing or inhibiting the kinase activity of PDGF-R or c-Abl in a cell comprising the step of contacting the cell with a compound of Formulae (I) or (II). The present invention also provides a method of inhibiting the kinase activity of PDGF-R or c-Abl in a subject comprising the step of administering a compound of Formula (I) or (II) to the subject. The present invention further provides a method of inhibiting cell proliferation in a cell comprising the step of contacting the cell with a compound of Formulae (I) or (II).

The present invention further provides a method of identifying novel PDGF-R kinase inhibitors. The method comprises the steps of:

(a) determining a three-dimensional structure of the compound of Fomulae (I) or (II) in the absence or presence of a polypeptide comprising the PDGF-R kinase catalytic domain;

(b) analyzing the three-dimensional structure for the compound alone or for the intermolecular interaction between said compound and PDGF-R;

(c) selecting a compound that mimics the structure for the compound alone or incorporates the predictive interaction;

(d) synthesizing said designed compound; and (e) determining the ability of the molecule to bind and inhibit PDGF-R kinase activity.

The present invention further provides a method of identifying novel c-Abl kinase inhibitors. The method comprises the steps of:

(a) determining a three-dimensional structure of the compound of Formulae (I) or (II) in the absence or presence of a polypeptide comprising the c-Abl kinase catalytic domain;

(b) analyzing the three-dimensional structure for the compound alone or for the intermolecular interaction between said compound and c-Abl;

(c) selecting a compound that mimics the structure for the compound alone or incorporates the predictive interaction;

(d) synthesizing said designed compound; and (e) determining the ability of the molecule to bind and inhibit c-Abl kinase activity.

The present invention is further directed to processes for the preparation of compounds of Formula (I) and compounds of Formula (II)

Other features and advantages of the invention will be apparent from the following detailed description of the invention thereof, and from the claims.

DETAILED DESCRIPTION OF THE INVENTION

The present invention relates to novel N-substituted tricyclic 3-aminopyrazole derivatives, their synthesis and the use of said compounds for the treatment and/or prevention of PDGF-R related disorders, such as tumors, restenosis, rheumatoid arthritis, diabetic retinopathy, and the like.

1. Formula (I)

The present invention is directed to compounds of Formula (I):

Formula (I)

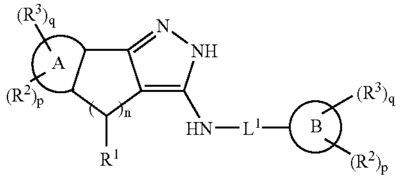

wherein, n is an integer from 1 to 4;

$R^1$ is selected from the group consisting of hydrogen, lower alkyl, —OH, alkoxy, -oxo, —$NH_2$, —NH(alkyl) and —$N(alkyl)_2$;

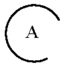

is selected from the group consisting of an aryl, a five to six membered monocyclic heteroaryl, a nine to ten membered benzo-fused heteroaryl, a nine to ten membered benzo-fused heterocycloalkyl group, and a nine to ten membered benzo-fused cycloalkyl group; wherein the benzo-fused heteroaryl, benzo-fused heterocycloalkyl or benzo-fused cycloalkyl group is attached to the molecule such that the phenyl ring is bound directly to the

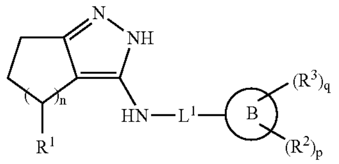

portion of the molecule;

p is an integer from 0 to 2;

$R^2$ is selected from the group consisting of

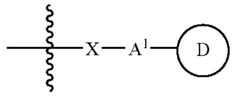

and —X-$A^1$-Y-$A^2$; wherein,

X and Y are each independently absent or selected from the group consisting of —O—, —NH—, —N(alkyl)-, —S—, —SO—, —$SO_2$—, —OC(═O), —C(═O)O—, —NHC(═O)—, —N(alkyl)C(═O)—, —C(═O)NH—, —C(═O)N(alkyl)-, —OC(═O)O—, —NHC(═O)O—, —OC(═O)NH—, —N(alkyl)C(═O)O—, —OC(═O)N(alkyl)-, —NHC(═O)NH—, —NHC(═O)N(alkyl)-, —N(alkyl)C(═O)NH—, —N(alkyl)C(═O)N(alkyl)-, —$NHSO_2$—, —$SO_2NH$—, —N(alkyl)$SO_2$— and —$SO_2N$(alkyl)-;

$A^1$ is absent or selected from alkyl or alkenyl; $A^2$ is selected from alkyl, alkenyl, or H; wherein, when $A^1$ or $A^2$ is alkyl or alkenyl, the alkyl or alkenyl group may be optionally substituted with one or more groups independently selected from halogen, cyano, hydroxy, alkoxy, thio, halogenated alkoxy, —OC(═O)alkyl, —OC(═O)Oalkyl, amino, alkylamino, —NHC(═O)alkyl, —N(alkyl)C(═O)alkyl, dialkylamino, —NHC(═O)$NH_2$, —NHC(═O)NHalkyl, —N(alkyl)C(═O)NHalkyl, —N(alkyl)C(═O)$NH_2$, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)$N(alkyl)_2$, —N(alkyl)C(═O)$N(alkyl)_2$ or —OC(═O)$N(alkyl)_2$;

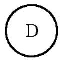

is selected from the group consisting of an aryl, a cycloalkyl, a partially unsaturated carbocycle, a heteroaryl, a heterocycloalkyl, a nine to ten membered benzo-fused cycloalkyl, and a nine to ten membered benzo-fused heterocycloalkyl; wherein, the aryl, cycloalkyl, partially unsaturated carbocycle, heteroaryl, heterocycloalkyl, benzo-fused cycloalkyl, or benzo-fused heterocycloalkyl, is optionally substituted with one or more substituents independently selected from halogen, hydroxy, amino, thio, nitro, cyano, alkyl, halogenated alkyl, alkoxy, halogenated alkoxy, alkylamino, —NHC(═O)alkyl, —N(alkyl)C(═O)alkyl, or dialkylamino, —NHC(═O)$NH_2$, —NHC(═O)NHalkyl, —N(alkyl)C(═O)NHalkyl, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)N$(alkyl)_2$, —N(alkyl)C(═O)N$(alkyl)_2$ or —OC(═O)N$(alkyl)_2$;

q is an integer from 0 to 4;

$R^3$ is selected from the group consisting of halogen, hydroxy, amino, thio, nitro, cyano, alkyl, halogenated alkyl, alkoxy, halogenated alkyloxy, alkylamino, —NHC(═O)alkyl, —N(alkyl)C(═O)alkyl, or dialkylamino, —NHC(═O)$NH_2$, —NHC(═O)NHalkyl, —N(alkyl)C(═O)NHalkyl, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)N$(alkyl)_2$, —N(alkyl)C(═O)N$(alkyl)_2$ and —OC(═O)N$(alkyl)_2$;

provided that the sum of p and q is an integer from 0 to 4;

$L^1$ is absent or selected from the group consisting of alkyl;

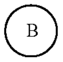

is selected from the group consisting of an aryl, a cycloalkyl, a partially unsaturated carbocycle, a heteroaryl, a heterocycloalkyl, a nine to ten membered benzo-fused cycloalkyl, and a nine to ten membered benzo-fused heterocycloalkyl;

or an optical isomer, enantiomer, diastereomer, racemate, or pharmaceutically acceptable salt thereof, useful for the treatment of a PDGF-R related disorders.

In formula (I), when

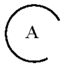

is a nine to ten membered benzo-fused heteroaryl, a nine to ten membered benzo-fused heterocycloalkyl, or a nine to ten membered benzo-fused cycloalkyl group, the benzo-fused heteroaryl, benzo-fused heterocycloalkyl, or benzo-fused cycloalkyl group is attached to the molecule such that the phenyl ring is bound directly to the

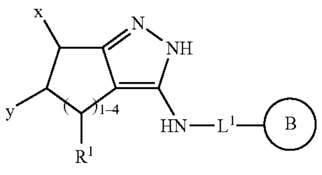

portion of the molecule at the carbons indicated as "x" and "y". For example, wherein

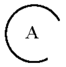

is unsubstituted 3,4-methylenedioxyphenyl, the 1,3-methylenedioxyphenyl group may be bound to the rest of the compound of formula (I) to form a compound of the formula (Im), (In) or (Ip):

(Im)

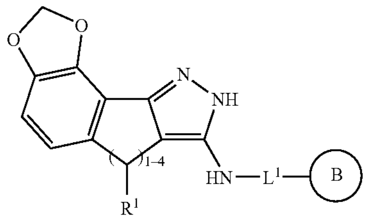

(In)

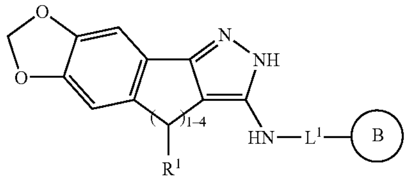

(Ip)

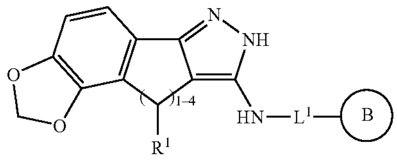

wherein the exact orientation would be evident from the structure or name of the compound prepared.

1.a Embodiments of Formula (I)

In an embodiment of the present invention

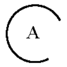

is selected from the group consisting of phenyl, thienyl, pyridyl, pyrimidinyl, furyl, isoxazolyl, imidazolyl, pyrazolyl and 3,4-methylenedioxyphenyl. Preferably

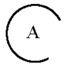

is selected form the group consisting of phenyl, thienyl and 3,4-methylenedioxyphenyl. In another embodiment of the present invention

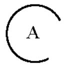

is selected form the group consisting of a five or six membered heteroaryl. In another embodiment of the present invention

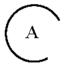

is selected from the group consisting of a nine or ten membered benzo-fused heteroaryl, a nine or ten membered benzo-fused cycloalkyl, and a nine or ten membered benzo-fused heterocycloalkyl.

In a preferred embodiment of the present invention $R^1$ is selected from the group consisting of hydrogen, hydroxy, methyl, and oxo, preferably $R^1$ is hydrogen or methyl.

In an embodiment of the present invention n is an integer from 1 to 2. In another embodiment of the present invention p is 0 and q is an integer from 0 to 2. In yet another embodiment of the present invention p is an integer from 1 to 2 and q is an integer from 0 to 1.

In an embodiment of the present invention, $R^2$ is

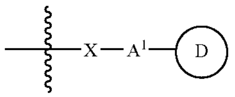

wherein X, $A^1$ and

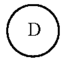

are as defined herein. Preferably, X is O. In another embodiment of the present invention, X is O and

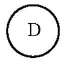

is a heterocycloalkyl or heteroaryl, wherein the heterocycloalkyl or heteroaryl is optionally substituted with one to three substituents independently selected from halogen, alkoxy, hydroxy, amino, alkylamino or dialkylamino.

In another embodiment of the present invention, $R^2$ is $—X-A^1-Y-A^2$ wherein X, $A^1$, Y, $A^2$ are as defined herein. Preferably, X and Y are each independently absent or O.

In an embodiment of the present invention, $R^3$ is selected from the group consisting of alkoxy, halogen, amino, dialkylamino, lower alkyl, and hydroxy. Preferably, $R^3$ is lower alkyl or lower alkoxy.

In an embodiment of the present invention $L^1$ is a lower alkyl, preferably methylene. In another embodiment of the present invention $L^1$ is absent.

A preferred embodiment of the present invention,

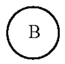

is aryl, heteroaryl, cycloalkyl, or herterocycloalkyl. Preferably

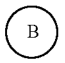

is aryl or heteroaryl.

In an embodiment of the present invention is a compound of Formula (Ia):

Formula (Ia)

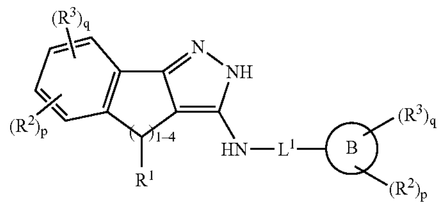

wherein n, $R^1$, p, $R^2$, q, $R^3$, $L^1$ and

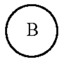

are as defined herein for Formula (I), or an optical isomer, enantiomer, diastereomer, racemate or pharmaceutically acceptable salt thereof.

Another preferred embodiment of the present invention is a compound of formula (I) wherein n is an integer from 1 to 2;

$R^1$ is hydrogen;

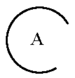

is selected from the group consisting of phenyl, a five to six membered heteroaryl and a nine to ten membered benzo-fused heterocycloalkyl group; wherein the nine to ten membered benzo-fused heterocycloalkyl group is attached to the molecule such that the phenyl ring is bound directly to the portion of the molecule; preferably,

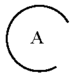

is selected from the group consisting of phenyl, thienyl and 1,3-benzodioxolyl;

p is an integer from 0 to 2;

$R^2$ is selected from the group consisting of di(lower alkyl) amino-alkoxy, lower alkyl-alkoxy, hydroxy substituted alkoxy and

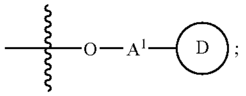

wherein $A^1$ is selected from the group consisting of lower alkyl; wherein the lower alkyl is optionally substituted with one to two substituents independently selected from hydroxy, amino, alkylamino or dialkylamino; and wherein

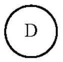

is selected from the group consisting of a five or six membered heteroaryl and a five or six membered heterocycloalkyl; wherein the heteroaryl or heterocycloalkyl is optionally substituted with one to two substituents independently selected from halogen, lower alkyl, lower alkoxy, amino, lower alkylamino or di(lower alkyl)amino; preferably, $R^2$ is selected from the group consisting of 3-dimethylamino-propoxy, 3-methoxy-propoxy, 2,3-dihydroxy-n-propoxy, 3-hydroxy-propoxy, 2-hydroxy-3-pyrrolid in-1-yl-propoxy and 3-(4-methyl-piperazin-1-yl-propoxy;

q is an integer from 0 to 2;

$R^3$ is selected from the group consisting of lower alkyl and lower alkoxy, and halogen; preferably, $R^3$ is selected from the group consisting of methyl, methoxy, ethoxy.

$L^1$ is absent or lower alkyl, preferably, $L^1$ is absent or $CH_2$;

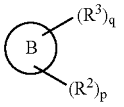

is selected from the group consisting of phenyl and a five or six membered heteroaryl group; wherein the phenyl or heteroaryl group is optionally substituted with one to two substituents independently selected from halogen, lower alkyl, lower alkoxy or benzyloxy; preferably,

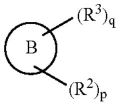

is selected from the group consisting of phenyl and pyridyl; wherein the phenyl is optionally substituted with one to two substituents independently selected from fluoro, chloro, methyl, methoxy or benzyloxy;

or an optical isomer, enantiomer, diastereomer, racemate or pharmaceutically acceptable salt thereof.

Another embodiment of the present invention is a compound of Formula (I) wherein $R^1$ is selected from the group consisting of hydrogen and lower alkyl; preferably $R^1$ is selected from hydrogen or methyl;

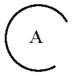

is selected from the group consisting of phenyl, a five to six membered heteroaryl and a nine to ten membered benzo-fused heteroaryl; wherein the phenyl, five to six membered heteroaryl or nine to ten membered benzo-fused heteroaryl is optionally substituted with one to two substituents independently selected from halogen, lower alkyl, lower alkoxy, trifluoromethyl, trifluoromethoxy, difluoromethoxy or lower alkoxy-lower alkoxy; preferably

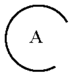

is selected from the group consisting of phenyl, 3,5-dimethoxyphenyl, 4,5-diethoxyphenyl, 4,5-di(trifluoromethoxy)-phenyl, 4,5-di(methoxyethoxy)-phenyl, 4,5-di (methoxypropoxy)-phenyl, 4,5-di(isopropoxy)-phenyl, 4,5-di(difluoromethoxy)-phenyl, 4-chloro-5-methoxy-phenyl, 4-methoxyethoxy-5-ethoxy-phenyl, pyridyl, pyrimidinyl, furyl, 5-chloro-thienyl, 3-ethoxy-thienyl, isoxazolyl, 3-methyl-isoxazolyl, 2-methyl-8-ethoxy-benzoxazolyl, benzothienyl, $L^1$ is absent or selected from lower alkyl, preferably $L^1$ is absent or selected from methyl or ethyl;

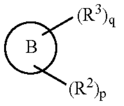

is selected from the group consisting of aryl, cycloalkyl and a five to six membered heteroaryl; wherein the aryl or heteroaryl group is optionally substituted with one to two substituents independently selected from halogen, lower alkyl, hydroxy substituted lower alkyl, lower alkoxy, aminosulfonyl, (lower alkyl)amino, di(lower alkyl)amino, di(lower alkyl)amino-alkoxycarbonyl, loweralkoxycarbonyl, heterocycloalkyl-loweralkylaminocarbonyl, di(lower alkyl)amino-lower alkylaminocarbonyl or heteroaryl-lower-alkylaminocarbonyl; wherein the heteroaryl or heterocycloalkyl portion of the heterocycloalkyl-loweralkylaminocarbonyl or heteroaryl-loweralkylaminocarbonyl substituent is optionally substituted with a substitutent selected from lower alkyl, hydroxy or hydroxy substituted lower alkyl;

preferably

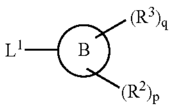

is selected from the group consisting of phenyl, benzyl, phenylethyl, cyclohexyl, cyclohexyl-methyl, 3-hydroxy-cyclohexyl, 4-hydroxy-cyclohexyl, 2-fluorobenzyl, 2-chlorobenzyl, 3-chlorobenzyl, 2,3-dichlorobenzyl, 2,6-dichlorobenzyl, 2-fluorophenylethyl, 3-fluorophenyl, 3-bromophenyl, 3-chlorophenyl, 2-methylbenzyl, 3-methylbenzyl, 3-methoxyphenyl, 4-methoxyphenyl, 3-hydroxymethylphenyl, 2-hydroxymethyl-benzyl, 3-chloro-4-fluorobenzyl, 2-aminosulfonyl-benzyl, 2-aminosulfonyl-phenyl, 3-aminosulfonyl-phenyl, 4-aminosulfonyl-phenyl, 3-dimethylamino-phenyl, 3-(dimethylamino-ethylaminocarbonyl)-phenyl, 3-ethoxycarbonyl-phenyl, 3-(2-pyrrolidin-1-yl-ethylaminocarbonyl)-phenyl, 3-(2-pyrrolidin-1-yl-n-propylaminocabronyl)-phenyl, 3-(dimethylamino-ethylaminocarbonyl)-phenyl, 3-(2-imidazol-1-yl-ethylaminocarbonyl-phenyl, 3-(2-(1-methyl-imidazol-2-yl)-ethylaminocarbonyl)-phenyl, 3-[3-(hydroxymethyl-pyrrolidin-1-yl-propyl)-aminocarbonyl]-phenyl, pyridyl-methyl, pyridyl-ethyl, pyrimidinyl-methyl and 3-methyl-imidazolyl-methyl;

or an optical isomer, enantiomer, diastereomer, racemate or pharmaceutically acceptable salt thereof.

1 . b. Preparation of Compounds of Formula (I)

The present invention is further directed to a process for the preparation of compounds of Formula (I)

Formula (I)

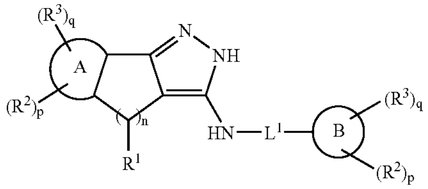

wherein, n is an integer from 1 to 4;

$R^1$ is selected from the group consisting of hydrogen, lower alkyl, —OH, alkoxy, -oxo, —$NH_2$, —NH(alkyl) and —$N(alkyl)_2$;

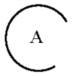

is selected from the group consisting of an aryl, a five to six membered monocyclic heteroaryl, a nine to ten membered benzo-fused heteroaryl, a nine to ten membered benzo-fused heterocycloalkyl group, and a nine to ten membered benzo-fused cycloalkyl group; wherein the benzo-fused heteroaryl, benzo-fused heterocycloalkyl or benzo-fused cycloalkyl group is attached to the molecule: such that the phenyl ring is bound directly to the

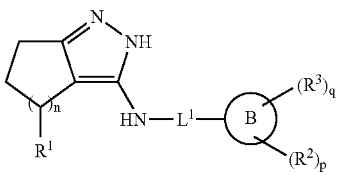

portion of the molecule;

p is an integer from 0 to 2;

$R^2$ is selected from the group consisting of

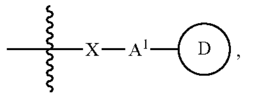

and —X-$A^1$-Y-$A^2$; wherein,

X and Y are each independently absent or selected from the group consisting of —O—, —NH—, —N(alkyl)-, —S—, —SO—, —$SO_2$—, —OC(═O), —C(═O)O—, —NHC(═O)—, —N(alkyl)C(═O)—, —C(═O)NH—, —C(═O)N(alkyl)-, —OC(═O)O—, —NHC(═O)O—, —OC(═O)NH—, —N(alkyl)C(═O)O—, —OC(═O)N(alkyl)-, —NHC(═O)NH—, —NHC(═O)N(alkyl)-, —N(alkyl)C(═O)NH—, —N(alkyl)C(═O)N(alkyl)-, —$NHSO_2$—, —$SO_2$NH—, —N(alkyl)$SO_2$— and —$SO_2$N(alkyl)-;

$A^1$ is absent or selected from alkyl or alkenyl; $A^2$ is selected from alkyl, alkenyl, or H; wherein, when $A^1$ or $A^2$ is alkyl or alkenyl, the alkyl or alkenyl group may be optionally substituted with one or more groups independently selected from halogen, cyano, hydroxy, alkoxy, thio, halogenated alkoxy, —OC(═O)alkyl, —OC(═O)Oalkyl, amino, alkylamino, —NHC(═O)alkyl, —N(alkyl)C(═O) alkyl, dialkylamino, —NHC(═O)$NH_2$, —NHC(═O) NHalkyl, —N(alkyl)C(═O)NHalkyl, —N(alkyl)C(═O) $NH_2$, —OC(═O)NHalkyl, —NHC(═O)Oalkyl, —N(alkyl)C(═O)Oalkyl, —$NHSO_2$alkyl, —N(alkyl) $SO_2$alkyl, thioalkyl, halogenated thioalkyl, —$SO_2$alkyl, halogenated —$SO_2$alkyl, —NHC(═O)$N(alkyl)_2$, —N(alkyl)C(═O)$N(alkyl)_2$ or —OC(═O)$N(alkyl)_2$;

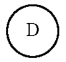

is selected from the group consisting of an aryl, a cycloalkyl, a partially unsaturated carbocycle, a heteroaryl, a heterocycloalkyl, a nine to ten membered benzo-fused cycloalkyl, and a nine to ten membered benzo-fused heterocycloalkyl; wherein, the aryl, cycloalkyl, partially unsaturated carbocycle, heteroaryl, heterocycloalkyl, benzo-fused cycloalkyl, or benzo-fused heterocycloalkyl, is optionally substituted with one or more substituents independently selected from halogen, hydroxy, amino, thio, nitro, cyano, alkyl, halogenated alkyl, alkoxy, halogenated alkoxy, alkylamino, —NHC(═O)alkyl, —N(alkyl)C(═O)alkyl, or dialkylamino, —NHC(═O)$NH_2$, —NHC(═O)NHalkyl, —N(alkyl)C(═O)NHalkyl, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)N$(alkyl)_2$, —N(alkyl)C(═O)$N(alkyl)_2$ or —OC(═O)N$(alkyl)_2$;

q is an integer from 0 to 4;

$R^3$ is selected from the group consisting of halogen, hydroxy, amino, thio, nitro, cyano, alkyl, halogenated alkyl, alkoxy, halogenated alkyloxy, alkylamino, —NHC(═O) alkyl, —N(alkyl)C(═O)alkyl, or dialkylamino, —NHC(═O)$NH_2$, —NHC(═O)NHalkyl, —N(alkyl)C(═O) NHalkyl, —OC(═O)NHalkyl, —NHC(═O)Oalkyl, —N(alkyl)C(═O)Oalkyl, —NHSO$_2$alkyl, —N(alkyl)SO$_2$alkyl, thioalkyl, halogenated thioalkyl, —SO$_2$alkyl, halogenated —SO$_2$alkyl, —NHC(═O)N(alkyl)$_2$, —N(alkyl)C(═O)N(alkyl)$_2$ and —OC(═O)N(alkyl)$_2$;

provided that the sum of p and q is an integer from 0 to 4;

$L^1$ is absent or selected from the group consisting of alkyl;

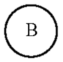

is selected from the group consisting of an aryl, a cycloalkyl, a partially unsaturated carbocycle, a heteroaryl, a heterocycloalkyl, a nine to ten membered benzo-fused cycloalkyl, and a nine to ten membered benzo-fused heterocycloalkyl;

or an optical isomer, enantiomer, diastereomer, racemate, or pharmaceutically acceptable salt thereof;

comprising

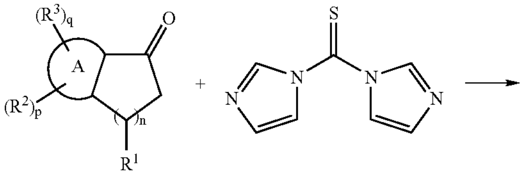

(S1)

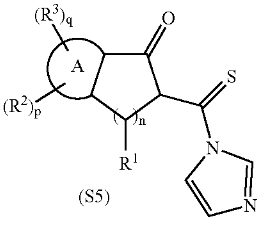

(S5)

reacting a compound of formula (S1) with 1,1'-thiocarbonylimidazole, in the presence of abase, in an aprotic solvent, to yield the corresponding compound of formula (S5);

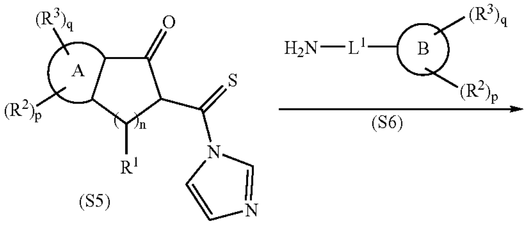

(S5)

(S6)

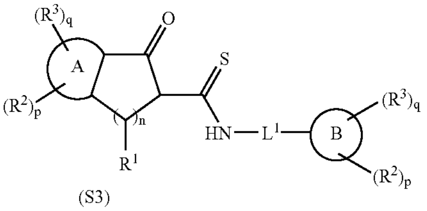

(S3)

reacting the compound of formula (S5) with a compound of formula (S6), in an aprotic solvent, to yield the corresponding compound of formula (S3);

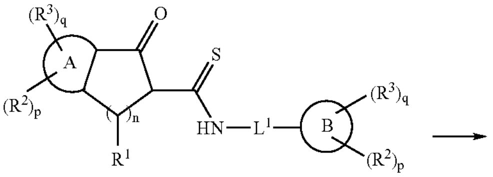

(S3)

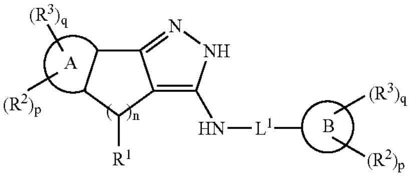

(I)

reacting the compound of formula (S3) with hydrazine, to yield the corresponding compound of formula (I).

2. Formula (II)

The present invention is further directed to compounds of Formula (II):

(II)

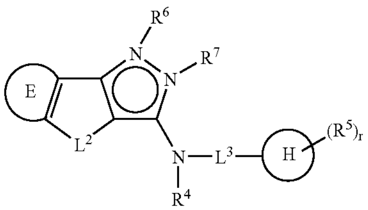

wherein:

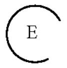

is selected from the group consisting of Formulae A-1, A-2 and A-3:

(Formula A-1)

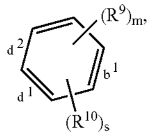

wherein Formula A-1 is attached on the $b^1$ side of Formula A-1 to the $L^2$ ring of formula (II) and optionally substituted with one substituent selected from the group consisting of Formulae A-1-a, A-1-b and A-1-c:

(Formula A-1-a)

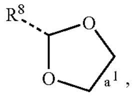

wherein Formula A-1-a is attached on the $a^1$ side to adjacent carbons on the $d^1$or $d^2$ side of Formula A-1;

(Formula A-1-b)

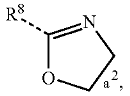

wherein Formula A-1-b is attached on the $a^2$side to adjacent carbons on the $d^1$or $d^2$ side of Formula A-1; and (Formula A-1-c)

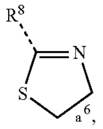

wherein Formula A-1-c is attached on the $a^6$ side to adjacent carbons on the $d^1$or $d^2$ side of Formula A-1; wherein $R^8$ is H or alkyl;

(Formula A-2)

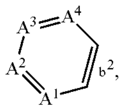

wherein Formula A-2 is attached on the $b^2$ side of Formula A-2 to the $L^2$ ring of formula (II), and $A^1$, $A^2$, $A^3$, $A^4$are (i) —N—; or (ii) —C— substituted with H or alkoxy, wherein the alkoxy may be optionally further substituted with alkoxy on a terminal carbon or up to 3 halogen atoms on a terminal carbon; provided that at least one and no more than two of $A^1$, $A^2$, $A^3$, $A^4$ are —N—; and (Formula A-3)

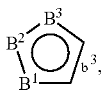

wherein Formula A-3 is attached on the $b^3$ side of Formula A-3 to the $L^2$ ring of formula (II), and $B^1$, $B^2$ and $B^3$are independently (i) —CH— optionally substituted with alkyl, aryl, alkoxy, or halogen, (ii) —S—; (iii) —O—; or (iv) —N—; provided that no more than one of $B^1$, $B^2$ or $B^3$ is —S— or —O—, and, provided that when one of $B^1$, $B^2$ or $B^3$ is —S— or —O—, then the adjacent ring members are not —S— or —O—;

$R^9$ is independently selected from the group consisting of: alkoxy, alkyl, alkylamino, amino, cyano, dialkylamino, halogen, halogenated alkyl, halogenated alkyloxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, nitro, —OC(═O)N(alkyl)$_2$, —OC(═O)NHalkyl, —$SO_2$alkyl, thio and thioalkyl;

$L^2$ is a linking group selected from the group consisting of: —$(CH_2)_{1-4}$—, —CH($R^{100}$)—, —C(═$R^{100}$)—, —C($R^{100}$)$_2$—, —O—, —O$(CH_2)_{1-4}$—, —OCH($R^{100}$)—, —OC($R^{100}$)$_2$—, —S—, —NH—, —N(lower alkyl)-, —N(COalkyl)-, —N(aryl)-, —N($CO_2$alkyl)-, —N(CONHalkyl)-, —N($SO_2$alkyl) and —N($SO_2$aryl)-; wherein $R^{100}$ is selected from: alkyl, hydroxy, aryl, alkoxy, oxo, —$NH_2$, —NH(alkyl) —N(alkyl)$_2$, ═N(OH) or —$NH_2OH$; provided that when $L^2$ is —$CH_2CH_2$—, neither $R^6$ nor $R^7$ is —$CH_2$—(C═O)NHalkyl, —$CH_2$—(C═O)N(alkyl)$_2$ or —$CH_2$C(═O)Oalkyl; provided that when $L^2$ is —OCH($R^{100}$)—, $R^{100}$ is alkoxy, and

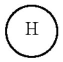

is phenyl, $R^5$ is not —C(═O)NH—$NH_2$; and provided that when $L^2$ is —O— or —S—, neither $R^6$ nor $R^7$ is —$CH_3$;

$R^{10}$ is independently selected from the group consisting of

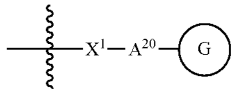

and —$X^1$-$A^{20}$-$Y^1$-$A^{21}$;

wherein $X^1$ and $Y^1$ are each independently absent or selected from the group consisting of: -(alkyl)C(═O)N(alkyl)-, —C(═O)N(alkyl)-, —C(═O)NH—, —C(═O)O—, —N(alkyl)-, —N(alkyl)C(═O)—, —N(alkyl)C(═O)NH—, —N(alkyl)C(═O)O—, —N(alkyl)$SO_2$—, —NH—, —NHC(═O)—, —NHC(═O)N(alkyl)-, —NHC(═O)NH, —NHC(═O)O—, —$NHSO_2$—, —O—, —OC(═O), —OC(═O)N(alkyl)-, —OC(═O)NH—, —OC(═O)O—, —S—, —SO—, —$SO_2$—, —$SO_2$N(alkyl)-, and —$SO_2$NH—;

$A^{20}$ is absent or selected from alkyl or alkenyl; and $A^{21}$ is selected from alkyl, alkenyl, or H;

wherein when $A^{20}$ or $A^{21}$ is alkyl or alkenyl, the alkyl or alkenyl may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC (=O)$NH_2$, —NHC(=O)NHalkyl, —NHC(=O)Oalkyl, —$NHSO_2$alkyl, —OC(=O)alkyl, —OC(=O)N$(alkyl)_2$, —OC(=O)NHalkyl, —OC(=O)Oalkyl, —$SO_2$alkyl, thio or thioalkyl;

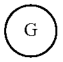

is selected from the group consisting of aryl, cycloalkyl, partially unsaturated carbocycle, heteroaryl, heterocycloalkyl, nine to ten membered benzo-fused cycloalkyl, and nine to ten membered benzo-fused heterocycloalkyl; wherein, the aryl, cycloalkyl, partially unsaturated carbocycle, heteroaryl, heterocycloalkyl, benzo-fused cycloalkyl, or benzo-fused heterocycloalkyl, are optionally substituted with one or more substituents independently selected from halogen, hydroxy, amino, thio, nitro, cyano, alkyl, halogenated alkyl, alkoxy, halogenated alkoxy, alkylamino, —NHC(=O)alkyl, —N(alkyl)C(=O)alkyl, or dialkylamino, —NHC(=O)$NH_2$, —NHC(=O)NHalkyl, —N(alkyl)C(=O)NHalkyl, —OC(=O)NHalkyl, —NHC(=O)Oalkyl, —N(alkyl)C(=O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(=O)N$(alkyl)_2$, —N(alkyl)C(=O)N$(alkyl)_2$ or —OC(=O)N$(alkyl)_2$;

s is an integer from 0 to 2;

m is an integer from 0 to 4; provided that when

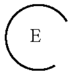

is not substituted with Formulae A-1-a, A-1-b or A-1-c, the sum of m and s is an integer from 0 to 4, and when

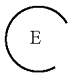

is substituted with one of Formulae A-1-a, A-1-b, or A-1-c, the sum of m and s is an integer from 0 to 2;

$R^6$ and $R^7$ are independently selected from the group consisting of:

(a) H;

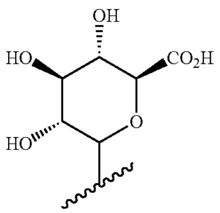

b) provided that $R^4$ is not

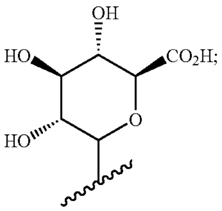

(c) —$CH_2$— substituted with one group selected from: —H, -methyl, —Oalkyl, —$CH_2OH$, —$CH(CH_3)OH$, —O(C=O)alkyl, —(C=O)OH, —C(=O)Oalkyl, —C(=O)Oaryl, —C(=O)Oheteroaryl, —(C=O)$NH_2$, —(C=O)NHalkyl, —(C=O)N$(alkyl)_2$, —C(=O)alkyl, -phenyl-$OCH_3$ or -phenyl-OC(=O)alkyl;

(d) —C(=O)$(CH_2CH_2O—)_{1-10}$ terminating with H, methyl, ethyl, or benzyl;

(e) —C(=O)$CH_2O(CH_2CH_2O—)_{1-10}$ terminating with H, methyl, ethyl, or benzyl;

(f) —C(=O)alkyl, or —C(=O)$(C_{3-6})$cycloalkyl, wherein said —C(=O)alkyl, and —C(=O)$(C_{3-6})$cycloalkyl may be optionally substituted with one or more groups independently selected from: —OH, —Oalkyl, —Oalkylaryl, —$NH_2$, —NHalkyl, —N$(alkyl)_2$, heterocycloalkyl, —NHC(=O)alkyl, —$NHSO_2$alkyl, or —OC(=O)alkyl;

(g) —C(=O)$(CH_2)_{1-3}$aryl, —C(=O)aryl, —C(=O)$(CH_2)_{1-3}$heteroaryl, or —C(=O)heteroaryl, wherein said —C(=O)$(CH_2)_{1-3}$aryl, —C(=O)aryl, —C(=O)$(CH_2)_{1-3}$heteroaryl, and —C(=O)heteroaryl may be optionally substituted with one or more groups independently selected from: —OH, —Oalkyl, —$NH_2$, —NHalkyl, —N$(alkyl)_2$, heterocycloalkyl, —NHC(=O)alkyl, —$NHSO_2$alkyl, halogen, nitrile, or —OC(=O)alkyl;

(h) —C(=O)$(CH_2)_{1-6}$C(=O)— terminating with methyl, ethyl, —OH, —Oalkyl, —$NH_2$, —NHalkyl, —N$(alkyl)_2$, or heterocycloalkyl;

(hh) —C(=O)alkylOC(=O)alkyl- terminating with —OH, —Oalkyl, —$NH_2$, —NHalkyl, —N$(alkyl)_2$, or heterocycloalkyl;

(i) —C(=O)O$(CH_2CH_2O—)_{1-10}$ terminating with H, methyl, ethyl, or benzyl;

(j) —C(=O)Oalkyl, or —C(=O)O$(C_{3-6})$cycloalkyl, wherein said —C(=O)Oalkyl, and —C(=O)O$(C_{3-6})$cycloalkyl may be optionally substituted with one or more groups independently selected from: —OH, —Oalkyl, —$NH_2$, —NHalkyl, —N$(alkyl)_2$, heterocycloalkyl, —NHC(=O)alkyl, —$NHSO_2$alkyl, —OC(=O)alkyl, —C(=O)OH, —C(=O)Oalkyl, —C(=O)$NH_2$, —C(=O)NHalkyl, or —C(=O)N$(alkyl)_2$;

(k) —C(=O)O$(CH_2)_{1-3}$aryl, —C(=O)Oaryl, —C(=O)O$(CH_2)_{1-3}$heteroaryl, or —C(=O)Oheteroaryl, wherein said —C(=O)O$(CH_2)_{1-3}$aryl, —C(=O)Oaryl, —C(=O)O$(CH_2)_{1-3}$heteroaryl, or —C(=O)Oheteroaryl may be optionally substituted with one or more groups independently selected from: —OH, —Oalkyl, —$NH_2$, —NHalkyl, —N$(alkyl)_2$, heterocycloalkyl, —NHC(=O)alkyl, —$NHSO_2$alkyl, halogen, nitrile, or —OC(=O)alkyl;

(l) —C(=O)NH$(CH_2CH_2O—)_{1-10}$ terminating with —H, methyl, ethyl, benzyl, —$CH_2CH_2NH_2$, —$CH_2CH_2$NHalkyl, —$CH_2CH_2$N$(alkyl)_2$, —$CH_2CH_2$-1- pyrrolidinyl, $-CH_2CH_2$-1-piperidinyl, $-CH_2CH_2$-4-morpholinyl, $-CH_2CH_2$-1-piperazinyl, $-CH_2CH_2$-1-(4-$CH_3$)-piperazinyl or —C(=O)alkyl;

(m) —C(=O)$NH_2$, —C(=O)NH($C_{1-20}$)alkyl, —C(=O)NH($C_{3-6}$)cycloalkyl, or —C(=O)N$(alkyl)_2$, wherein said —C(=O)NH($C_{1-20}$)alkyl, —C(=O)NH($C_{3-6}$)cycloalkyl, and —C(=O)N$(alkyl)_2$ may be optionally substituted with one or more groups independently selected from: —OH, —Oalkyl, $-NH_2$, —NHalkyl, —N$(alkyl)_2$, heterocycloalkyl, —NHC(=O)alkyl, $-NHSO_2$alkyl, —OC(=O)alkyl, —OC(=O)alkenyl, —NHC(=O)aryl, —C(=O)OH, —C(=O)Oalkyl, —C(=O)$NH_2$, —C(=O)NHalkyl, or —C(=O)N$(alkyl)_2$; and, wherein the aryl portion of said —NHC(=O)aryl may be optionally substituted with one or more groups independently selected from: alkyl, —OH, —Oalkyl, $-NH_2$, —NHalkyl, —N$(alkyl)_2$, halogen or nitrile;

(n) —C(=O)NH$(CH_2)_{1-3}$aryl, —C(=O)NHaryl, —C(=O)NH$(CH_2)_{1-3}$heteroaryl, or —C(=O)NHheteroaryl, wherein said —C(=O)NH$(CH_2)_{1-3}$aryl, —C(=O)NHaryl, —C(=O)NH$(CH_2)_{1-3}$heteroaryl, and —C(=O)NHheteroaryl may be optionally substituted with one or more groups independently selected from: —OH, —Oalkyl, $-NH_2$, —NHalkyl, —N$(alkyl)_2$, heterocycloalkyl, —NHC(=O)alkyl, $-NHSO_2$alkyl, halogen, nitrile, or —OC(=O)alkyl;

(o) —C(=O)$NHCH_2CH_2NH(CH_2CH_2NH-)_{0-3}$ terminating with H, methyl, ethyl, $-CH_2CH_2$NHalkyl, $-CH_2CH_2N(alkyl)_2$, $-CH_2CH_2$-1-pyrrolidinyl, $-CH_2CH_2$-1-piperidinyl, $-CH_2CH_2$-4-morpholinyl, $-CH_2CH_2$-1-piperazinyl, $-CH_2CH_2$-1-(4-$CH_3$)-piperazinyl, $-CH_2CH_2OH$, $-CH_2CH_2OCH_3$, $-CH_2CH_2OCH_2CH_3$, $-CH_2CH_2$)C(=O)alkyl, or —C(=O)aryl; wherein the aryl portion of said —C(=O)aryl may be optionally substituted with one or more groups independently selected from: alkyl, —OH, —Oalkyl, $-NH_2$, —NHalkyl, —N$(alkyl)_2$, halogen or nitrile;

(p) —C(=S)$NH_2$;

(q) —C(=S)NHalkyl;

(r) —C(=S)N$(alkyl)_2$;

(s) $-SO_2NH_2$;

(t) $-SO_2$NHalkyl;

(u) $-SO_2N(alkyl)_2$;

(v) —P(=O)$(OCH_3)_2$; and (w) —P(=O)$(OCH_2CH_3)_2$;

provided that when $R^6$ is present, $R^7$ is absent; and provided that when $R^7$ is present, $R^6$ is absent;

$R^4$ is selected from the group consisting of: H and

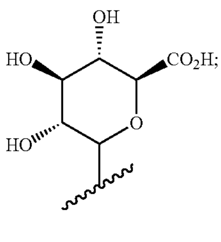

;

provided that if one of $R^6$and $R^7$ is

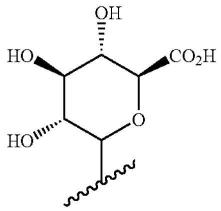

then $R^4$ is H;

$L^3$ is absent or is a linking group selected from the group consisting of alkyidiyl, carbonyl or $-SO_2-$;

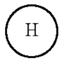

is selected from the group consisting of an aryl, a cycloalkyl, a partially unsaturated carbocycle, aralkyl, a heteroaryl, a heterocycloalkyl, a nine to ten membered benzo-fused cycloalkyl, a nine to ten membered benzo-fused heteroaryl, and a nine to ten membered benzo-fused heterocycloalkyl;

r is an integer from 0 to 4; and $R^5$ is independently selected from the group consisting of: alkyl, alkyl amino, alkyloxy, amino, —C(=O)$NH_2$, —C(=O)Oalkyl, —C(=O)OH, $-CH_2OH$, cyano, dialkylamino, halogen, halogenated alkyl, halogenated alkyloxy, halogenated $SO_2$-alkyl, halogenated thioalkyl, hydroxy, hydroxy alkyl, —N(alkyl)C(=O)alkyl, —N(alkyl)C(=O)N$(alkyl)_2$, —N(alkyl)C(=O)NHalkyl, —N(alkyl)C(=O)Oalkyl, —N(alkyl)$SO_2$alkyl, —NHC(=O)alkyl, —NHC(=O)N$(alkyl)_2$, —NHC(=O)$NH_2$, —NHC(=O)NHalkyl, —NHC(=O)Oalkyl, $-NHSO_2$alkyl, nitro, —OC(=O)N$(alkyl)_2$, —OC(=O)NHalkyl, $-SO_2$alkyl, $-SO_2NH_2$, thio, thioalkyl,

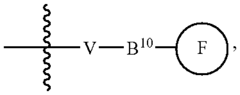

, and —V—$B^{10}$—W—$B^{20}$; wherein,

V and W are each independently absent or selected from the group consisting of: —C(=O), —C(=O)N(alkyl)-, —C(=O)NH—, —C(=O)O—, —N(alkyl)-, —N(alkyl)C(=O)—, —N(alkyl)C(=O)N(alkyl)-, —N(alkyl)C(=O)NH—, —N(alkyl)C(=O)O—, —N(alkyl)$SO_2$—, —NH—, —NHC(=O)—, —NHC(=O)N(alkyl)-, —NHC(=O)NH—, —NHC(=O)O—, $-NHSO_2-$, —O—, —OC(=O), —OC(=O)N(alkyl)-, —OC(=O)NH—, —OC(=O)O—, —S—, —SO—, $-SO_2$-, $-SO_2$N(alkyl)- and $-SO_2NH-$;

$B^{10}$ is absent or selected from alkyl or alkenyl;

$B^{20}$ is absent or selected from alkyl, alkenyl, or H;

wherein, when $B^{10}$ or $B^{20}$ is alkyl or alkenyl, the alkyl or alkenyl group may be optionally substituted with one or more groups independently selected from: alkoxy, alkylamino, amino, cyano, dialkylamino, halogen, halogenated alkoxy, halogenated $-SO_2$alkyl, halogenated thioalkyl, hydroxy —N(alkyl)C(=O)alkyl, —N(alkyl)C (=O)N(alkyl)$_2$, —N(alkyl)C(=O)NH$_2$, —N(alkyl)C(=O)NHalkyl, —N(alkyl)C(=O)Oalkyl, —N(alkyl)SO$_2$alkyl, —NHC(=O)alkyl, —NHC(=O)N(alkyl)$_2$, —NHC(=O)NH$_2$, —NHC(=O)NHalkyl, —NHC(=O)Oalkyl, —NHSO$_2$alkyl, —OC(=O)alkyl, —OC(=O)N(alkyl)$_2$, —OC(=O)NHalkyl, —OC(=O)Oalkyl, —SO$_2$alkyl, thio or thioalkyl; and

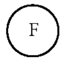

is selected from the group consisting of: an aryl, a cycloalkyl, a partially unsaturated carbocycle, a heteroaryl, a heterocycloalkyl, a nine to ten membered benzo-fused cycloalkyl, and a nine to ten membered benzo-fused heterocycloalkyl, wherein, the aryl, cycloalkyl, partially unsaturated carbocycle, heteroaryl, heterocycloalkyl, benzo-fused cycloalkyl, or benzo-fused heterocycloalkyl, is optionally substituted with one or more substituents independently selected from: alkoxy, alkylamino, amino, cyano, dialkylamino, halogen, halogenated alkoxy, halogenated alkyl, halogenated —SO$_2$alkyl, halogenated thioalkyl, heteroaryl, hydroxy, hydroxy alkyl, —N(alkyl)C(=O)alkyl, —N(alkyl)C(=O)N(alkyl)$_2$, —N(alkyl)C(=O)NHalkyl, —N(alkyl)C(=O)Oalkyl, —N(alkyl)SO$_2$alkyl, —NHC(=O)alkyl, —NHC(=O)N(alkyl)$_2$, —NHC(=O)NH$_2$, —NHC(=O)NHalkyl, —NHC(=O)Oalkyl, —NHSO$_2$alkyl, nitro, —OC(=O)N(alkyl)$_2$, —OC(=O)NHalkyl, —SO$_2$alkyl, thio or thioalkyl;

or an optical isomer, enantiomer, diastereomer, racemate, or pharmaceutically acceptable salt thereof.

In formula (II), "the L$^2$ ring of formula (II)" refers to the ring of Formula (II) containing the L$^2$ substituent.

The

ring of Formula (II) is attached to the L$^2$ ring of formula (II) such that the point of attachment for the

ring is the second and third carbon counterclockwise from the pyrazole nitrogen bearing the R$^6$ substituent. For example, where L$^2$ is —CH$_2$— and

is phenyl, the point of attachment is as shown below:

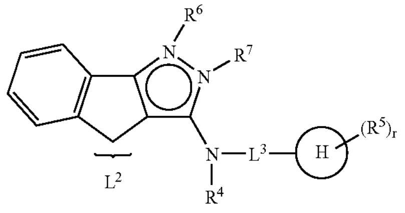

or, where

L$^2$ is —CH$_2$CH$_2$— and

is phenyl, the point of attachment is as shown below:

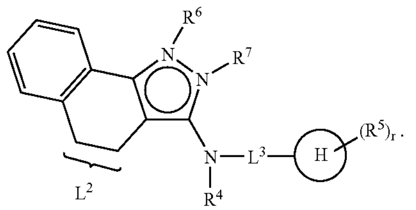

2.a Embodiments of Formula (II)

2.a.1

Further emobidments of the present invention include compounds of Formula II wherein E, L$^2$, R$^6$, R$^7$, R$^4$, L$^3$ H, and (R$^5$)$_r$, vary as set forth below individually and combinations of the variations thereof.

An embodiment of the present invention includes compounds of Formula (II) wherein:

is selected from the group consisting of Formulae A-1, A-2 and A-3:

(Formula A-1)

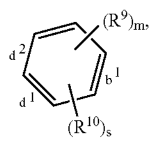

wherein Formula A-1 is attached on the b$^1$ side of Formula A-1 to the L$^2$ ring of formulae (II) and optionally substituted with one substituent selected from the group consisting of Formulae A-1-a, A-1-b and A-1-c:

(Formula A-1-a)

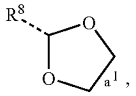

wherein Formula A-1-a is attached on the $a^1$ side to adjacent carbons on the $d^1$ or $d^2$ side of Formula A-1;

(Formula A-1-b)

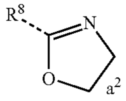

wherein Formula A-1-b is attached on the $a^2$ side to adjacent carbons on the $d^1$ or $d^2$ side of Formula A-1; and (Formula A-1-c)

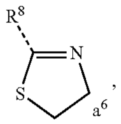

wherein Formula A-1-c is attached on the $a^6$ side to adjacent carbons on the $d^1$ or $d^2$ side of Formula A-1;

wherein $R^8$ is H or lower alkyl;

(Formula A-2)

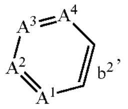

wherein Formula A-2 is attached on the $b^2$ side of Formula A-2 to the $L^2$ ring of formulae (II), and one or two of $A^1$, $A^2$, $A^3$, $A^4$ are —N—; the remainder being —C— substituted with H or alkoxy, wherein the alkoxy may be optionally further substituted with alkoxy on a terminal carbon or up to 3 halogen atoms on a terminal carbon; and (Formula A-3)

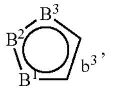

wherein Formula A-3 is attached on the $b^3$ side of Formula A-3 to the $L^2$ ring of formulae (II), and $B^1$, $B^2$ and $B^3$ are independently (i) —CH— optionally substituted with $C_{1-4}$alkyl, aryl, alkoxy, or halogen, (ii) —S—, (iii) —O— or (iv) —N—; provided that no more than one of $B^1$, $B^2$ or $B^3$ is —S— or —O—, and, provided that when one of $B^1$, $B^2$ or $B^3$ is —S— or —O—, then the adjacent ring members are not —S— or —O—;

An embodiment of the present invention includes compounds of Formula (II) wherein:

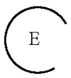

is selected from the group consisting of Formulae A-1, A-2 and A-3:

(Formula A-1)

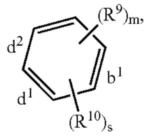

wherein Formula A-1 is attached on the $b^1$ side of Formula A-1 to the $L^2$ ring of formulae (II) and optionally substituted with one substituent selected from the group consisting of Formulae A-1-a, A-1-b and A-1-c:

(Formula A-1-a)

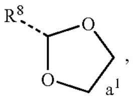

wherein Formula A-1-a is attached on the $a^1$ side to adjacent carbons on the $d^1$ or $d^2$ side of Formula A-1;

(Formula A-1-b)

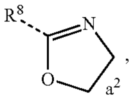

wherein Formula A-1-b is attached on the $a^2$ side to adjacent carbons on the $d^1$ or $d^2$ side of Formula A-1; and (Formula A-1-c)

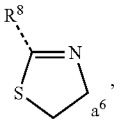

wherein Formula A-1-c is attached on the $a^6$ side to adjacent carbons on the $d^1$ or $d^2$ side of Formula A-1;

wherein $R^8$ is H or lower alkyl;

(Formula A-2)

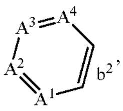

wherein Formula A-2 is selected from the group consisting of pyridyl and pyrimidinyl; is attached on the $b^2$ side of Formula A-2 to the $L^2$ ring of formulae (II); and is optionally substituted on a carbon ring member with H or alkoxy, wherein the alkoxy may be optionally further substituted with alkoxy on a terminal carbon or up to 3 halogen atoms on a terminal carbon; and (Formula A-3)

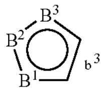

, wherein Formula A-3 is selected from the group consisting of thienyl, isoxazolyl and furyl; is attached on the $b^3$ side of Formula A-3 to the $L^2$ ring of formulae (II), and is optionally substituted on a carbon ring member with $C_{1-4}$alkyl, aryl, alkoxy, or halogen.

A embodiment of the present invention includes compounds of Formula (II) wherein

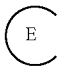

is selected from the group consisting of:

(Formula A-4)

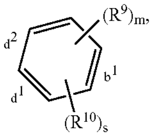

wherein Formula A-4 is attached on the $b^1$ side of Formula A-4 to the $L^2$ ring of formulae (II);

(Formula A-5)

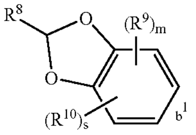

wherein Formula A-5 is attached on the $b^1$ side of Formula A-5 to the $L^2$ ring of Formula (II); wherein $R^8$ is H and lower alkyl;

(Formula A-6)

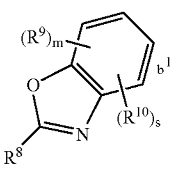

wherein Formula A-6 is attached on the be side of Formula A-6 to the $L^2$ ring of Formula (II); and Formula A-3-a

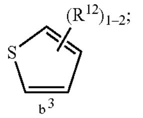

wherein Formulae A-3-a is attached on the $b^3$ side of Formulae A-3-a to the $L^2$ ring of formula (II), wherein $R^{12}$ is independently selected from H, methyl, phenyl, ethoxy, chloro or fluoro; and wherein m is an integer from 0 to 4; provided that when

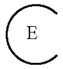

is Formula A-4, the sum of m and s is an integer from 0 to 4, and when

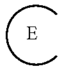

is Formulae A-5 or A-6, the sum of m and s is an integer from 0 to 2.

A embodiment of the present invention includes compounds of Formula (II) wherein

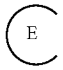

is selected from the group consisting of:

(Formula A-4)

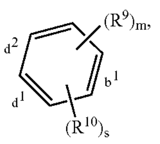

wherein Formula A-4 is attached on the $b^1$ side of Formula A-4 to the $L^2$ ring of formulae (II);

(Formula A-5)

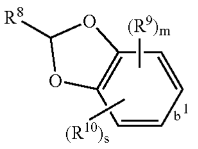

wherein Formula A-5 is attached on the $b^1$ side of Formula A-5 to the $L^2$ ring of Formula (II); wherein $R^8$ is H and lower alkyl; and Formula A-3-a

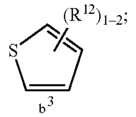

wherein Formulae A-3-a is attached on the $b^3$ side of Formulae A-3-a to the $L^2$ ring of formula (II), wherein $R^{12}$ is independently selected from H, methyl, phenyl, ethoxy, chloro or fluoro; and wherein m is an integer from 0 to 4; provided that when

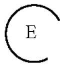

is Formula A-4, the sum of m and s is an integer from 0 to 4, and when

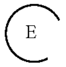

is Formula A-5, the sum of m and s is an integer from 0 to 2.

A embodiment of the present invention includes compounds of Formula (II) wherein

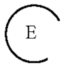

is:

(Formula A-4)

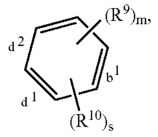

wherein Formula A-4 is attached on the $b^1$ side of Formula A-4 to the $L^2$ ring of formulae (II); and wherein m is an integer from 0 to 4; provided that when

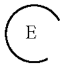

is Formula A-4, the sum of m and s is an integer from 0 to 4.

An embodiment of the present invention includes compounds of Formula (II) wherein:

$R^9$ is independently selected from the group consisting of: alkoxy, alkyl, alkylamino, amino, cyano, dialkylamino, halogen, halogenated alkyl, halogenated alkyloxy, halogenated thioalkyl, hydroxy, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)SO$_2$alkyl, —NHC(═O)alkyl, —NHC(═O)N(alkyl)$_2$, —NHC(═O)NH$_2$, —NHC(═O)NHalkyl, —NHC(═O)Oalkyl, —NHSO$_2$alkyl, —OC(═O)N(alkyl)$_2$, —OC(═O)NHalkyl and thioalkyl.

An embodiment of the present invention includes compounds of Formula (II) wherein:

$R^9$ is independently selected from the group consisting of: alkoxy, alkyl, alkylamino, amino, cyano, dialkylamino, halogen, halogenated alkyl, halogenated alkyloxy, hydroxy, —NHC(═O)alkyl, —NHC(═O)NHalkyl, —NHC(═O)Oalkyl, —NHSO$_2$alkyl, and thioalkyl.

A embodiment of the present invention includes compounds of Formula (II) wherein:

$R^9$ is independently selected from the group consisting of: alkoxy, alkyl, amino, cyano, dialkylamino, halogen, halogenated alkyl, halogenated alkyloxy, hydroxy and —NHC(═O)alkyl.

A embodiment of the present invention includes compounds of Formula (II) wherein:

$R^9$ is independently selected from the group consisting of: methoxy, ethoxy, isopropoxy, methyl, amino, cyano, N,N-dimethyl-amino, bromo, chloro, fluoro, trifluoromethyl, trifluoromethoxy, hydroxy and N-(1-oxo-ethyl)-amino.

An embodiment of the present invention includes compounds of Formulae (II) wherein:

$L^2$ is a linking group selected from the group consisting of: —(CH$_2$)—, —(CH$_2$)$_{3\text{-}4}$—, —CH(R$^{100}$)—, —C(+R$^{100}$)—, —C(R$^{100}$)$_2$—, —O—, —O(CH$_2$)$_{1\text{-}4}$—, —OCH(R$^{100}$)—, —OC(R$^{100}$)$_2$—, —S—, —NH—, —N(lower alkyl)-, —N(COalkyl)-, —N(aryl)-, —N(CO$_2$alkyl)-, —N(CONHalkyl)-, —N(SO$_2$alkyl) and —N(SO$_2$aryl)-.

An embodiment of the present invention includes compounds of Formula (II) wherein:

$L^2$ is a linking group selected from the group consisting of: —(CH$_2$)$_{1\text{-}4}$—, —CH(R$^{100}$)—, —C(═R$^{100}$)—, —C(R$^{100}$)$_2$—, —O—, —O(CH$_2$)$_{1\text{-}4}$—, —OCH(R$^{200}$)—, —OC(R$^{100}$)$_2$—, —S—, —NH—, —N(lower alkyl)-, —N(COalkyl)-, —N(aryl)-, —N(CO$_2$alkyl)-, —N(CONHalkyl)-, —N(SO$_2$alkyl) and —N(SO$_2$aryl)-; wherein $R^{200}$ is selected from: alkyl, hydroxy, aryl, oxo, —NH$_2$, —NH(alkyl) —N(alkyl)$_2$; ═N(OH) or —NH$_2$OH.

An embodiment of the present invention includes compounds of Formula (II) wherein:

$L^2$ is a linking group selected from the group consisting of: —(CH$_2$)$_{1\text{-}4}$—, —CH(R$^{100}$)—, —C(═R$^{100}$)—, —C(R$^{100}$)$_2$—, —O—, —O(CH$_2$)$_{1\text{-}4}$—, —OCH(R$^{100}$)—, —OC(R$^{100}$)$_2$—, —NH—, —N(lower alkyl)-, —N(COalkyl)-, —N(aryl)-, —N(CO$_2$alkyl)-, —N(CONHalkyl)-, —N(SO$_2$alkyl) and —N(SO$_2$aryl)-.

An embodiment of the present invention includes compounds of Formula (II) wherein:

$L^2$ is a linking group selected from the group consisting of: —(CH$_2$)$_{1\text{-}4}$—, —CH(R$^{100}$)—, —C(═R$^{100}$)—, —C(R$^{100}$)$_2$—, —O(CH$_2$)$_{1\text{-}4}$—, —OCH(R$^{100}$)—, —OC(R$^{100}$)$_2$—, —NH—, —N(lower alkyl)-, —N(COalkyl)-, —N(aryl)-, —N(CO$_2$alkyl)-, —N(CONHalkyl)-, —N(SO$_2$alkyl) and —N(SO$_2$aryl)-.

An embodiment of the present invention includes compounds of Formula (II) wherein:

$L^2$ is a linking group selected from the group consisting of: —(CH$_2$)—, —(CH$_2$)$_{3\text{-}4}$—, —CH(R$^{100}$)—, —C(═R$^{100}$)—, —C(R$^{100}$)$_2$—, —O(CH$_2$)$_{1\text{-}4}$—, —OCH(R$^{200}$)—, —OC(R$^{100}$)$_2$—, —NH—, —N(lower alkyl)-, —N(COalkyl)-, —N(aryl)-, —N(CO$_2$alkyl)-, —N(CONHalkyl)-, —N(SO$_2$alkyl) and —N(SO$_2$aryl)-; wherein $R^{200}$ is selected from: alkyl, hydroxy, aryl, oxo, —$NH_2$, —NH (alkyl) —N$(alkyl)_2$, =N(OH) or —$NH_2$OH.

An embodiment of the present invention includes compounds of Formula (II) wherein:

$L^2$ is a linking group selected from the group consisting of: —$(CH_2)_{1-4}$—, —CH($R^{100}$)—, —C(=$R^{100}$)—, —C$(R^{100})_2$—, —O—, O$(CH_2)_{1-4}$—, —OCH$(R^{100})_2$—, —OC$(R^{100})_2$—, —S—, —NH—, —N(lower alkyl)-, —N(COalkyl)-, —N(aryl)-, —N($CO_2$alkyl)-, —N(CONHalkyl)-, —N($SO_2$alkyl) and —N($SO_2$aryl)-; provided that when $L^2$ is —$CH_2CH_2$—, neither $R^6$ nor $R^7$ is —$CH_2$—(C=O)NHalkyl.

An embodiment of the present invention includes compounds of Formula (II) wherein:

$L^2$ is a linking group selected from the group consisting of: —$(CH_2)_{1-4}$—, —CH($R^{100}$)—, —C(=$R^{100}$)—, —C$(R^{100})_2$—, —O—, —O$(CH_2)_{1-4}$—, —OCH($R^{100}$)—, —OC$(R^{100})_2$—, —S—, —NH—, —N(lower alkyl)-, —N(COalkyl)-, —N(aryl)-, —N($CO_2$alkyl)-, —N(CONHalkyl)-, —N($SO_2$alkyl) and —N($SO_2$aryl)-; provided that when $L^2$ is —$CH_2CH_2$—, neither $R^6$ nor $R^7$ is —$CH_2$—(C=O)NHalkyl or —$CH_2$—(C=O)N$(alkyl)_2$.

An embodiment of the present invention includes compounds of Formula (II) wherein:

$L^2$ is a linking group selected from the group consisting of: —$(CH_2)_{1-4}$—, —CH($R^{100}$)—, —C(=$R^{100}$)—, —C$(R^{100})_2$-, —O—, —O$(CH_2)_{1-4}$—, —OCH($R^{100}$)—, —OC$(R^{100})_2$—, —S—, —NH—, —N(lower alkyl)-, —N(COalkyl)-, —N(aryl)-, —N($CO_2$alkyl)-, —N(CONHalkyl)-, —N($SO_2$alkyl) and —N($SO_2$aryl)-; provided that when $L^2$ is —$CH_2CH_2$—, neither $R^6$ nor $R^7$ is —$CH_2$C(=O)Oalkyl.

An embodiment of the present invention includes compounds of Formula (II) wherein:

$L^2$ is a linking group selected from the group consisting of: —$(CH_2)_{1-4}$—, —CH($R^{100}$)—, —C(=$R^{100}$)—, —C$(R^{100})_2$—, —O—, —O$(CH_2)_{1-4}$—, —OCH($R^{100}$)—, —OC$(R^{100})_2$—, —S—, —NH—, —N(lower alkyl)-, —N(COalkyl)-, —N(aryl)-, —N($CO_2$alkyl)-, —N(CONHalkyl)-, —N($SO_2$alkyl) and —N($SO_2$aryl)-; provided that when $L^2$ is —$CH_2CH_2$—, neither $R^6$ nor $R^7$ is —$CH_2$—(C=O)NHalkyl, —$CH_2$—(C=O)N$(alkyl)_2$ or —$CH_2$C(=O)Oalkyl.

An embodiment of the present invention includes compounds of Formula (II) wherein:

$L^2$ is a linking group selected from the group consisting of: —$(CH_2)_{1-4}$—, —CH($R^{100}$)—, —C(=$R^{100}$)—, —C$(R^{100})_2$—, —O—, —O$(CH_2)_{1-4}$—, —OCH($R^{100}$)—, —OC$(R^{100})_2$—, —S—, —NH—, —N(lower alkyl)-, —N(COalkyl)-, —N(aryl)-, —N($CO_2$alkyl)-, —N(CONHalkyl)-, —N($SO_2$alkyl) and —N($SO_2$aryl)-; provided that when $L^2$ is —OCH($R^{100}$)—, $R^{100}$ is alkoxy, and

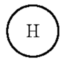

is phenyl, $R^5$ is not —C(=O)NH—$NH_2$.

An embodiment of the present invention includes compounds of Formula (II) wherein:

$L^2$ is a linking group selected from the group consisting of: —$(CH_2)_{1-4}$—, —CH($R^{100}$)—, —C(=$R^{100}$)—, —C$(R^{100})_2$—, —O—, —O$(CH_2)_{1-4}$—, —OCH($R^{100}$)—, —OC$(R^{00})_2$—, —S—, —NH—, —N(lower alkyl)-, —N(COalkyl)-, —N(aryl)-, —N($CO_2$alkyl)-, —N(CONHalkyl)-, —N($SO_2$alkyl) and —N($SO_2$aryl)-; provided that when $L^2$ is —O—, neither $R^6$ nor $R^7$ is —$CH_3$.

An embodiment of the present invention includes compounds of Formula (II) wherein:

$L^2$ is a linking group selected from the group consisting of: —$(CH_2)_{1-4}$—, —CH($R^{100}$)—, —C(=$R^{100}$)—, —C$(R^{100})_2$—, —O—, —O$(CH_2)_{1-4}$—, —OCH($R^{100}$)—, —OC$(R^{100})_2$—, —S—, —NH—, —N(lower alkyl)-, —N(COalkyl)-, —N(aryl)-, —N($CO_2$alkyl)-, —N(CONHalkyl)-, —N($SO_2$alkyl) and —N($SO_2$aryl)-; provided that when $L^2$ is —S—, neither $R^6$ nor $R^7$ is —$CH_3$.

An embodiment of the present invention includes compounds of Formula (II) wherein:

$L^2$ is a linking group selected from the group consisting of: —$(CH_2)_{1-4}$—, —CH($R^{100}$)—, —C(=$R^{100}$)—, —C$(R^{100})_2$—, —O—, —O$(CH_2)_{1-4}$—, —OC($R^{100}$)—, —OC$(R^{100})_2$—, —S—, —NH—, —N(lower alkyl)-, —N(COalkyl)-, —N(aryl)-, —N($CO_2$alkyl)-, —N(CONHalkyl)-, —N($SO_2$alkyl) and —N($SO_2$aryl)-; provided that when $L^2$ is —O— or —S—, neither $R^6$ nor $R^7$ is —$CH_3$.

A embodiment of the present invention includes compounds of Formula (II) wherein:

$L^2$ is a linking group selected from the group consisting of: —$(CH_2)_{1-4}$—, —CH($R^{100}$)—, —C(=$R^{1))}$)—, —C$(R^{100})_2$—, —O—, —O$(CH_2)_{1-4}$—, —N(COalkyl)-, —N(aryl)-, —N($CO_2$alkyl)-, —N(CONHalkyl)-, —N($SO_2$alkyl) and —N($SO_2$aryl)-.

A embodiment of the present invention includes compounds of Formula (II) wherein:

$L^2$ is a linking group selected from the group consisting of: —$(CH_2)_{1-4}$—, —CH($R^{100}$)—, —C(=$R^{100}$)—, —C$(R^{100})_2$—, —O—, and —O$(CH_2)_{1-4}$—.

A embodiment of the present invention includes compounds of Formula (II), wherein:

$R^{100}$ is selected from: alkyl, hydroxy, aryl, oxo or =N(OH).

A embodiment of the present invention includes compounds of Formula (II) wherein:

$R^{100}$ is selected from: alkyl, hydroxy, aryl, or oxo.

An embodiment of the present invention includes compounds of Formulae (II) wherein:

$R^{100}$ is selected from: methyl, hydroxy, phenyl, oxo or =N(OH).

A embodiment of the present invention includes compounds of Formulae (II) wherein:

$R^{100}$ is selected from: methyl, hydroxy, phenyl, or oxo.

An embodiment of the present invention includes compounds of Formula (II) wherein:

$R^{10}$ is independently selected from the group consisting of

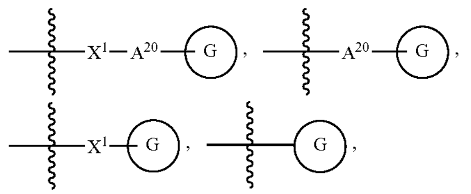

—$X^1$-$A^{20}$-$Y^1$-$A^{21}$, —$X^1$-$A^{20}$-$A^{21}$, —$X^1$-$A^{21}$, -$A^{20}$-$A^{21}$ and -$A^{21}$.

An embodiment of the present invention includes compounds of Formula (II) wherein:

$R^{10}$ is independently selected from the group consisting of

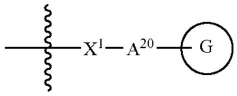, 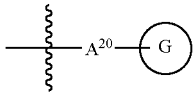,

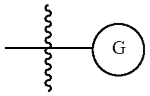,

—$X^1$-$A^{20}$-$Y^1A^{21}$, —$X^1$-$A^{20}$-$A^{21}$ and —$X^1$-$A^{21}$.

An embodiment of the present invention includes compounds of Formula (II):

wherein $X^1$ and $Y^1$ are each independently absent or selected from the group consisting of: —C(=O)NH—, —C(=O)O—, —NH—, —NHC(=O)—, —NHC(=O)NH, —NHC(=O)O—, —$NHSO_2$—, —O—, —OC(=O), —OC(=O)NH—, —OC(=O)O—, —S—, —SO—, —$SO_2$— and —$SO_2NH$—.

An embodiment of the present invention includes compounds of Formula (II):

wherein $X^1$ and $Y^1$ are each independently absent or selected from the group consisting of: —NH—, —O—, —$SO_2$— and —$SO_2NH$—.

An embodiment of the present invention includes compounds of Formula (II), wherein $X^1$ and $Y^1$ are each independently absent or —O—.

An embodiment of the present invention includes compounds of Formula (II), wherein $X^1$ is absent or —O—.

An embodiment of the present invention includes compounds of Formula (II), wherein $Y^1$ is absent.

An embodiment of the present invention includes compounds of Formula (II), wherein:

$A^{20}$ is absent or alkyl; and wherein when $A^{20}$ is alkyl, the alkyl may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy, —N(alkyl)C(=O)alkyl, —N(alkyl)C(=O)N(alkyl)$_2$, —N(alkyl)C(=O)$NH_2$, —N(alkyl)C(=O)NHalkyl, —N(alkyl)C(=O)Oalkyl, —N(alkyl)$SO_2$alkyl, —NHC(=O)alkyl, —NHC(=O)N(alkyl)$_2$, —NHC(=O)$NH_2$, —NHC(=O)NHalkyl, —NHC(=O)Oalkyl, —$NHSO_2$alkyl, —OC(=O)alkyl, —OC(=O)N(alkyl)$_2$, —OC(=O)NHalkyl, —OC(=O)Oalkyl, —$SO_2$alkyl, thio or thioalkyl.

An embodiment of the present invention includes compounds of Formula (II) wherein:

$A^{20}$ is absent or alkyl; and wherein when $A^{20}$ is alkyl, the alkyl may be optionally substituted with one or more groups independently selected from: alkoxy, alkylamino, amino, dialkylamino, halogen, halogenated alkoxy, hydroxy, —NHC(=O)$NH_2$, —$NHSO_2$alkyl, —$SO_2$alkyl orthioalkyl.

An embodiment of the present invention includes compounds of Formula (II) wherein:

$A^{20}$ is absent or selected from methyl, ethyl, propyl or isopropyl; wherein methyl, ethyl, propyl or isopropyl are optionally substituted with one or more groups independently selected from: alkoxy, dialkylamino or hydroxy.

An embodiment of the present invention includes compounds of Formula (II) wherein:

$A^{20}$ is absent or selected from methyl, ethyl, propyl or isopropyl; wherein methyl, ethyl, propyl or isopropyl are optionally substituted with one or more groups independently selected from methoxy, dimethyl-amino or hydroxy.

An embodiment of the present invention includes compounds of Formula (II) wherein:

$A^{21}$ is selected from alkyl, alkenyl, or H; and wherein when $A^{21}$ is alkyl or alkenyl, the alkyl or alkenyl may be optionally substituted with one or more groups independently selected from: alkoxy, alkylamino, amino, cyanob,dialkylamino, halogen, halogenated alkoxy, halogenated —$SO_2$alkyl, halogenated thioalkyl, hydroxy, —N(alkyl)C(=O)alkyl, —N(alkyl)C(=O)N(alkyl)$_2$, —N(alkyl)C(=O)$NH_2$, —N(alkyl)C(=O)NHalkyl, —N(alkyl)C(=O)Oalkyl, —N(alkyl)$SO_2$alkyl, —NHC(=O)alkyl, —NHC(=O)N(alkyl)$_2$, —NHC(=O)$NH_2$, —NHC(=O)NHalkyl, —NHC(=O)Oalkyl, —$NHSO_2$alkyl, —OC(=O)alkyl, —OC(=O)N(alkyl)$_2$, —OC(=O)NHalkyl, —OC(=O)Oalkyl, —$SO_2$alkyl, thio or thioalkyl.

An embodiment of the present invention includes compounds of Formula (II) wherein:

$A^{21}$ is selected from alkyl, alkenyl, or H; and wherein when $A^{21}$ is alkyl or alkenyl, the alkyl or alkenyl may be optionally substituted with one or more groups independently selected from: alkoxy, alkylamino, amino, dialkylamino, halogen, halogenated alkoxy, hydroxy, —NHC(=O)$NH_2$, —$NHSO_2$alkyl or thioalkyl.

An embodiment of the present invention includes compounds of Formula (II) wherein $A^{21}$ is H.

An embodiment of the present invention includes compounds of Formula (II) wherein

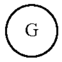

is selected from the group consisting of aryl, cycloalkyl, partially unsaturated carbocycle, heteroaryl and heterocycloalkyl optionally substituted with one or more substituents independently selected from halogen, hydroxy, amino, thio, nitro, cyano, alkyl, halogenated alkyl, alkoxy, halogenated alkoxy, alkylamino, —NHC(=O)alkyl, —N(alkyl)C(=O)alkyl, or dialkylamino, —NHC(=O)$NH_2$, —NHC(=O)NHalkyl, —N(alkyl)C(=O)NHalkyl, —OC(=O)NHalkyl, —NHC(=O)Oalkyl, —N(alkyl)C(=O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(=O)N(alkyl)$_2$, —N(alkyl)C(=O)N(alkyl)$_2$ or —OC(=O)N(alkyl)$_2$.

An embodiment of the present invention includes compounds of Formula (II) wherein

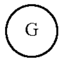

is selected from the group consisting of aryl, heteroaryl and heterocycloalkyl optionally substituted with one or more substituents independently selected from halogen, hydroxy, amino, thio, nitro, cyano, alkyl, halogenated alkyl, alkoxy, halogenated alkoxy, alkylamino, —NHC(=O)alkyl, —N(alkyl)C(=O)alkyl, or dialkylamino, —NHC(=O)$NH_2$, —NHC(=O)NHalkyl, —N(alkyl)C(=O)NHalkyl, —OC(=O)NHalkyl, —NHC(=O)Oalkyl, —N(alkyl)C(=O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)N(alkyl)$_2$, —N(alkyl)C(═O)N(alkyl)$_2$ or —OC(═O)N(alkyl)$_2$.

An embodiment of the present invention includes compounds of Formula (II) wherein

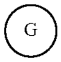

is selected from the group consisting of phenyl, imidazolyl, pyrrolidinyl, piperidinyl and morpholinyl optionally substituted with one or more substituents independently selected from halogen, hydroxy, amino, thio, nitro, cyano, alkyl, halogenated alkyl, alkoxy, halogenated alkoxy, alkylamino, —NHC(═O)alkyl, —N(alkyl)C(═O)alkyl, or dialkylamino, —NHC(═O)$NH_2$, —NHC(═O)NHalkyl, —N(alkyl)C(═O)NHalkyl, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)N(alkyl)$_2$, —N(alkyl)C(═O)N(alkyl)$_2$ or —OC(═O)N(alkyl)$_2$.

An embodiment of the present invention includes compounds of Formula (II) wherein

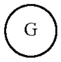

is selected from the group consisting of phenyl, imidazolyl, pyrrolidinyl, piperidinyl and morpholinyl optionally substituted with one or more substituents independently selected from halogen, hydroxy, amino, nitro, alkyl, halogenated alkyl, alkoxy, halogenated alkoxy, alkylamino, dialkylamino, —$NHSO_2$alkyl or —$SO_2$alkyl.

An embodiment of the present invention includes compounds of Formula (II) wherein

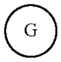

is selected from the group consisting of phenyl, imidazolyl, pyrrolidinyl, piperidinyl and morpholinyl optionally substituted with one or more substituents independently selected from chloro, fluoro, hydroxy or alkyl.

An embodiment of the present invention includes compounds of Formula (II) wherein $R^9$ and $R^{10}$ are independently selected from the group consisting of: 1-piperidinyl, 2-(pyrrolidin-1-yl)-ethoxy, 2,3-dihydroxy-propoxy, 2-hydroxy-3-pyrrolidin-1-yl-propoxy, 3-(4-methyl-piperazin-1-yl)-propoxy, 3-(N,N-dimethyl-amino)-propoxy, 3-hydroxy-propoxy, 3-imidazol-1-yl-propoxy, 3-methoxy-propoxy, 3-morpholin-4-yl-propoxy, 3-pyrrolidin-1-yl-2-hydroxy-propoxy, 3-pyrrolidin-1-yl-propoxy, 4-methyl-piperazin-1-yl, amino, benzyl, benzyloxy, bromo, chloro, cyano, ethoxy, fluoro, H, hydroxy, isopropoxy, methoxy, methyl, N-(1-oxo-ethyl)-amino, and N,N-dimethyl-amino.

An embodiment of the present invention includes compounds of Formula (II) wherein $R^6$ and $R^7$ are independently selected from the group consisting of:

(a) H;

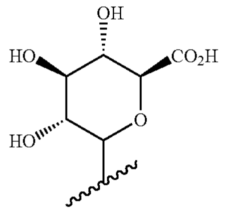

(b) provided that $R^4$ is not

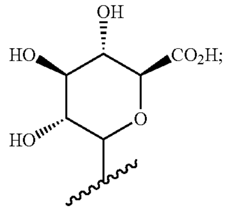

(c) —$CH_2$— substituted with one group selected from: —H, -methyl, —Oalkyl, —$CH_2OH$, —$CH(CH_3)OH$, —O(C═O)alkyl, —(C═O)OH, —C(═O)Oalkyl, —C(═O)Oaryl, —C(═O)Oheteroaryl, —(C═O)$NH_2$, —(C═O)NHalkyl, —(C═O)N(alkyl)$_2$, —C(═O)alkyl, -phenyl-$OCH_3$ or -phenyl-OC(═O)alkyl;

(d) —C(═O)$(CH_2CH_2)_{1-10}$ terminating with H;

(e) —C(═O)$CH_2O(CH_2CH_2O—)_{1-10}$ terminating with H;

(f) —C(═O)alkyl optionally substituted with one or more groups independently selected from: —OH, —Oalkyl, —Oalkylaryl, —$NH_2$, —NHalkyl, —N(alkyl)$_2$, heterocycloalkyl, —NHC(═O)alkyl, —$NHSO_2$alkyl, or —OC(═O)alkyl;

(g) —C(═O)$(CH_2)_{1-3}$aryl or —C(═O)aryl, wherein said —C(═O)aryl may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or —OC(═O)alkyl;

(h) —C(═O)$(CH_2)_{1-6}$C(═O)— terminating with methyl, ethyl, —OH, —Oalkyl, —$NH_2$, —NHalkyl, —N(alkyl)$_2$, or heterocycloalkyl;

(hh) —C(═O)alkylOC(═O)alkyl- terminating with —OH, —Oalkyl, —$NH_2$, —NHalkyl or —N(alkyl)$_2$;

(i) —C(═O)$O(CH_2CH_2O—)_{1-10}$ terminating with H, methyl, ethyl, or benzyl;

(j) —C(═O)Oalkyloptionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, —OC(═O)alkyl, —C(═O)OH, —C(═O)Oalkyl, —C(═O)$NH_2$, —C(═O)NHalkyl, or —C(═O)N(alkyl)$_2$;

(k) —C(═O)$O(CH_2)_{1-3}$aryl or —C(═O)Oaryl, wherein said —C(═O)Oaryl may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or —OC(═O)alkyl;

(l) —C(═O)$NH(CH_2CH_2O—)_{1-10}$ terminating with —H, methyl, ethyl, benzyl, —$CH_2CH_2NH_2$, $—CH_2CH_2NHalkyl$, $—CH_2CH_2N(alkyl)_2$, $—CH_2CH_2$-1-pyrrolidinyl, $—CH_2CH_2$-1-piperidinyl, $—CH_2CH_2$-4-morpholinyl, $—CH_2CH_2$-1-piperazinyl, $—CH_2CH_2$-1-(4-$CH_3$)-piperazinyl or —C(═O)alkyl;

(m) $—C(═O)NH_2$, $—C(═O)NH(C_{1-20})$alkyl, or —C(═O)$N(C_{1-20}alkyl)_2$, wherein said $—C(═O)NH(C_{1-20})$alkyl, may be optionally substituted with one or more groups independently selected from: —OH, —Oalkyl, $—NH_2$, —NHalkyl, $—N(alkyl)_2$, heterocycloalkyl, —NHC(═O)alkyl, $—NHSO_2$alkyl, —OC(═O)alkyl, —OC(═O)alkenyl, —NHC(═O)aryl, —C(═O)OH, —C(═O)Oalkyl, $—C(═O)NH_2$, —C(═O)NHalkyl, or —C(═O)$N(alkyl)_2$; and, wherein the aryl portion of said —NHC(═O)aryl may be optionally substituted with one or more groups independently selected from: alkyl, —OH, —Oalkyl, $—NH_2$, —NHalkyl, $—N(alkyl)_2$, halogen or nitrile;

(n) $—C(═O)NH(CH_2)_{1-3}$aryl or —C(═O)NHaryl, wherein said —C(═O)NHaryl may be optionally substituted with one or more groups independently selected from: —OH, —Oalkyl, $—NH_2$, —NHalkyl, $—N(alkyl)_2$, heterocycloalkyl, —NHC(═O)alkyl, $—NHSO_2$alkyl, halogen, nitrile, or —OC(═O)alkyl;

(o) $—C(═O)NHCH_2CH_2NH(CH_2CH_2NH—)_{0-3}$ terminating with H, methyl, ethyl, $—CH_2CH_2NHalkyl$, $—CH_2CH_2N(alkyl)_2$, $—CH_2CH_2$-1-pyrrolidinyl, $—CH_2CH_2$-1-piperidinyl, $—CH_2CH_2$-4-morpholinyl, $—CH_2CH_2$-1-piperazinyl, $—CH_2CH_2$-1-(4-$CH_3$)-piperazinyl, $—CH_2CH_2OH$, $—CH_2CH_2OCH_3$, $—CH_2CH_2OCH_2CH_3$, $—CH_2CH_2OC(═O)$alkyl or —C(═O)aryl; wherein the aryl portion of said —C(═O)aryl may be optionally substituted with one or more groups independently selected from: alkyl, —OH , —Oalkyl, $—NH_2$, —NHalkyl, $—N(alkyl)_2$, halogen or nitrile;

(p) $—C(═S)NH_2$;

(q) —C(═S)NHalkyl;

(r) $—C(═S)N(alkyl)_2$;

(s) $—SO_2NH_2$;

(t) $—SO_2NHalkyl$;

(u) $—SO_2N(alkyl)_2$;

(v) $—P(═O)(OCH_3)_2$; and (w) $—P(═O)(OCH_2CH_3)_2$;

provided that when $R^6$ is present, $R^7$ is absent; and provided that when $R^7$ is present, $R^6$ is absent.

An embodiment of the present invention includes compounds of Formula (II) wherein $R^6$ and $R^7$ are independently selected from the group consisting of:

(a) H;

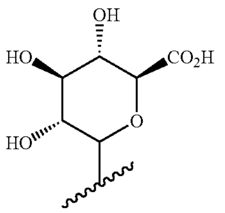

(b) provided that $R^4$ is not

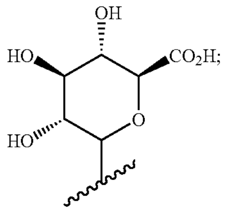

(c) $—CH_2—$ substituted with one group selected from: —H, -methyl, —Oalkyl, $—CH_2OH$, $—CH(CH_3)OH$, —O(C═O)alkyl, —(C═O)OH, —C(═O)Oalkyl, —C(═O)Oaryl, —C(═O)Oheteroaryl, $—(C═O)NH_2$, —(C═O)NHalkyl, $—(C═O)N(alkyl)_2$, —C(═O)alkyl, -phenyl—$OCH_3$ or -phenyl-OC(═O)alkyl;

(f) —C(═O)alkyl optionally substituted with one or more groups independently selected from: —OH, —Oalkyl, —Oalkylaryl, $—NH_2$, —NHalkyl, $—N(alkyl)_2$, heterocycloalkyl, —NHC(═O)alkyl, $—NHSO_2$alkyl, or —OC(═O)alkyl;

(g) $—C(═O)(CH_2)_{1-3}$aryl or —C(═O)aryl, wherein said —C(═O)aryl may be optionally substituted with one or more groups independently selected from: —OH, —Oalkyl, $—NH_2$, —NHalkyl, $—N(alkyl)_2$, heterocycloalkyl, —NHC(═O)alkyl, $—NHSO_2$alkyl, halogen, nitrile, or —OC(═O)alkyl;

(h) $—C(═O)(CH_2)_1—CC(═O)—$ terminating with methyl, ethyl, —OH, —Oalkyl, $—NH_2$, —NHalkyl, $—N(alkyl)_2$, or heterocycloalkyl;

(hh) —C(═O)alkylOC(═O)alkyl— terminating with —OH, —Oalkyl, $—NH_2$, —NHalkyl or $—N(alkyl)_2$;

(i) $—C(═O)O(CH_2CH_2O—)_{1-10}$ terminating with H, methyl, ethyl, or benzyl;

(j) —C(═O)Oalkyloptionally substituted with one or more groups independently selected from: —OH, —Oalkyl, $—NH_2$, —NHalkyl, $—N(alkyl)_2$, heterocycloalkyl, —NHC(═O)alkyl, $—NHSO_2$alkyl, —OC(═O)alkyl, —C(═O)OH, —C(═O)Oalkyl, $—C(═O)NH_2$, —C(═O)NHalkyl, or $—C(═O)N(alkyl)_2$;

(k) $—C(═O)O(CH_2)_{1-3}$aryl or —C(═O)Oaryl, wherein said —C(═O)Oaryl may be optionally substituted with one or more groups independently selected from: —OH, —Oalkyl, $—NH_2$, —NHalkyl, $—N(alkyl)_2$, heterocycloalkyl, —NHC(═O)alkyl, $—NHSO_2$alkyl, halogen, nitrile, or —OC(═O)alkyl;

(l) $—C(═O)NH(CH_2CH_2O—)_{1-10}$ terminating with —H, methyl, ethyl, benzyl, $—CH_2CH_2NH_2$, $—CH_2CH_2NHalkyl$, $—CH_2CH_2N(alkyl)_2$, $—CH_2CH_2$-1-pyrrolidinyl, $—CH_2CH_2$-1-piperidinyl, $—CH_2CH_2$-4-morpholinyl, $—CH_2CH_2$-1-piperazinyl, $—CH_2CH_2$-1-(4-$CH_3$)-piperazinyl or —C(═O)alkyl;

(m) $—C(═O)NH_2$, $—C(═O)NH(C_{1-20})$alkyl, or —C(═O)$N(C_{1-20}alkyl)_2$, wherein said $—C(═O)NH(C_{1-20})$alkyl, may be optionally substituted with one or more groups independently selected from: —OH, —Oalkyl, $—NH_2$, —NHalkyl, $—N(alkyl)_2$, heterocycloalkyl, —NHC(═O)alkyl, $—NHSO_2$alkyl, —OC(═O)alkyl, —OC(═O)alkenyl, —NHC(═O)aryl, —C(═O)OH, —C(═O)Oalkyl, $—C(═O)NH_2$, —C(═O)NHalkyl, or —C(═O)$N(alkyl)_2$; and, wherein the aryl portion of said —NHC(═O)aryl may be optionally substituted with one or more groups independently selected from: alkyl, —OH, —Oalkyl, —$NH_2$, —NHalkyl, —N(alkyl)$_2$, halogen or nitrile;

(n) —C(═O)NH$(CH_2)_{1-3}$aryl or —C(═O)NHaryl, wherein said —C(═O)NHaryl may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or —OC(═O)alkyl;

(o) —C(═O)$NHCH_2CH_2NH(CH_2CH_2NH—)_{0-3}$ terminating with H, methyl, ethyl, —$CH_2CH_2$NHalkyl, —$CH_2CH_2$N(alkyl)$_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl, —$CH_2CH_2OH$, —$CH_2CH_2OCH_3$, —$CH_2CH_2OCH_2CH_3$, —$CH_2CH_2$OC(═O)alkyl, or —C(═O)aryl; wherein the aryl portion of said —C(═O)aryl may be optionally substituted with one or more groups independently selected from: alkyl, —OH , —Oalkyl, —$NH_2$, —NHalkyl, —N(alkyl)$_2$, halogen or nitrile;

(p) —C(═S)$NH_2$;

(u) —$SO_2$N(alkyl)$_2$; and (w) —P(═O)$(OCH_2CH_3)_2$;

provided that when $R^6$ is present, $R^7$ is absent; and provided that when $R^7$ is present, $R^6$ is absent.

An embodiment of the present invention includes compounds of Formula (II) wherein $R^6$ and $R^7$ are independently selected from the group consisting of:

(a) H;

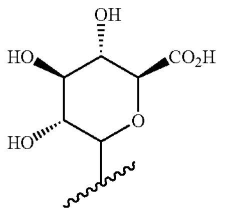

(b) provided that $R^4$ is not

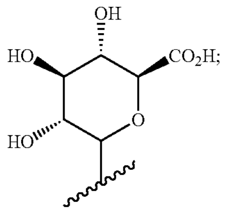

(c) —$CH_2$— substituted with one group selected from: —H, -methyl, —Oalkyl, —$CH_2OH$, —$CH(CH_3)OH$, —O(C═O)alkyl, —(C═O)OH, —C(═O)Oalkyl, —C(═O)Oaryl, —C(═O)Oheteroaryl, —(C═O)$NH_2$, —(C═O)NHalkyl, —(C═O)N(alkyl)$_2$, —C(═O)alkyl, -phenyl-$OCH_3$ or -phenyl-OC(═O)alkyl;

(f) —C(═O)alkyl optionally substituted with one or more groups independently selected from: —OH, —Oalkyl, —Oalkylaryl, —$NH_2$, —NHalkyl, —N(alkyl)$_2$, heterocycloalkyl, —NHC(═O)alkyl, —$NHSO_2$alkyl, or —OC(═O)alkyl;

(g) —C(═O)aryl optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or —OC(═O)alkyl;

(h) —C(═O)$(CH_2)_{1-6}$C(═O)— terminating with methyl, ethyl, —OH, —Oalkyl, —$NH_2$, —NHalkyl, —N(alkyl)$_2$, or heterocycloalkyl;

(hh) —C(═O)alkylOC(═O)alkyl-terminating with —OH, —Oalkyl, —$NH_2$, —NHalkyl or —N(alkyl)$_2$;

(i) —C(═O)$O(CH_2CH_2O—)_{1-10}$ terminating with H, methyl, ethyl, or benzyl;

(j) —C(═O)Oalkyloptionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, —OC(═O)alkyl, —C(═O)OH, —C(═O)Oalkyl, —C(═O)$NH_2$, —C(═O)NHalkyl, or —C(═O)N(alkyl)$_2$;

(k) —C(═O)Oaryl optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or —OC(═O)alkyl;

(l) —C(═O)$NH(CH_2CH_2O—)_{1-10}$ terminating with —H, methyl, ethyl, benzyl, —$CH_2CH_2NH_2$, —$CH_2CH_2$NHalkyl, —$CH_2CH_2$N(alkyl)$_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl or —C(═O)alkyl;

(m) —C(═O)NH$(C_{1-20})$alkyl optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, —OC(═O)alkyl, —OC(═O)alkenyl, —NHC(═O)aryl, —C(═O)OH, —C(═O)Oalkyl, —C(═O)$NH_2$, —C(═O)NHalkyl, or —C(═O)N(alkyl)$_2$; and, wherein the aryl portion of said —NHC(═O)aryl may be optionally substituted with one or more groups independently selected from: alkyl, —OH, —Oalkyl, —$NH_2$, —NHalkyl, —N(alkyl)$_2$, halogen or nitrile;

(n) —C(═O)NHaryl optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or —OC(═O)alkyl;

(o) —C(═O)$NHCH_2CH_2NH(CH_2CH_2NH—)_{0-3}$ terminating with H, methyl, ethyl, —$CH_2CH_2$NHalkyl, —$CH_2CH_2$N(alkyl)$_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl, —$CH_2CH_2OH$, —$CH_2CH_2OCH_3$, —$CH_2CH_2OCH_2CH_3$, —$CH_2CH_2$OC(═O)alkyl, or —C(═O)aryl; wherein the aryl portion of said —C(═O)aryl may be optionally substituted with one or more groups independently selected from: alkyl, —OH, —Oalkyl, —$NH_2$, —NHalkyl, —N(alkyl)$_2$, halogen or nitrile;

(p) —C(═S)$NH_2$;

(u) —$SO_2$N(alkyl)$_2$; and (w) —P(═O)$(OCH_2CH_3)_2$;

provided that when $R^6$ is present, $R^7$ is absent; and provided that when $R^7$ is present, $R^6$ is absent.

An embodiment of the present invention includes compounds of Formula (II) wherein $R^6$ and $R^7$ are independently selected from the group consisting of:

(a) H;

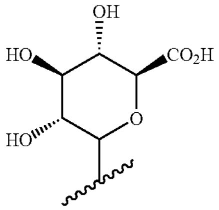

(b) provided that $R^4$ is not

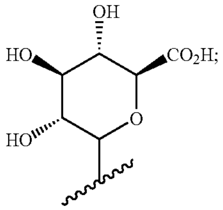

(c) —$CH_2$— substituted with one group selected from: —H, -methyl, —Oalkyl, —$CH_2OH$, —$CH(CH_3)OH$, —O(C═O)alkyl, —(C═O)OH, —C(═O)Oalkyl, —C(═O)Oaryl, —C(═O)Oheteroaryl, —(C═O)$NH_2$, —(C═O)NHalkyl, —(C═O)N$(alkyl)_2$, —C(═O)alkyl, -phenyl-$OCH_3$ or -phenyl-OC(═O)alkyl;

(f) —C(═O)alkyl optionally substituted with one or more groups independently selected from: —OH, —Oalkyl, —Oalkyl-phenyl, —$NH_2$, —NHalkyl, —N$(alkyl)_2$, heterocycloalkyl, —NHC(═O)alkyl, —$NHSO_2$alkyl, or —OC(═O)alkyl;

(g) —C(═O)aryl optionally substituted with one or more groups independently selected from: —OH, —Oalkyl, —$NH_2$, —NHalkyl, —N$(alkyl)_2$, heterocycloalkyl, —NHC(═O)alkyl, —$NHSO_2$alkyl, chloro, fluoro, nitrile, or —OC(═O)alkyl;

(h) —C(═O)$(CH_2)_{1-6}$C(═O)— terminating with methyl, ethyl, —OH, —Oalkyl, —$NH_2$, —NHalkyl, —N$(alkyl)_2$, or pyrrolidinyl;

(hh) —C(═O)alkylOC(═O)alkyl-terminating with —OH, —Oalkyl, —$NH_2$, —NHalkyl or —N$(alkyl)_2$;

(i) —C(═O)O$(CH_2CH_2O—)_{1-10}$ terminating with H, methyl, ethyl, or benzyl;

(j) —C(═O)Oalkyloptionally substituted with one or more groups independently selected from: —OH, —Oalkyl, —$NH_2$, —NHalkyl, —N$(alkyl)_2$, heterocycloalkyl, —NHC(═O)alkyl, —$NHSO_2$alkyl, —OC(═O)alkyl, —C(═O)OH, —C(═O)Oalkyl, —C(═O)$NH_2$, —C(═O)NHalkyl, or —C(═O)N$(alkyl)_2$;

(k) —C(═O)Oaryl optionally substituted with one or more groups independently selected from: —OH, —Oalkyl, —$NH_2$, —NHalkyl, —N$(alkyl)_2$, heterocycloalkyl, —NHC(═O)alkyl, —$NHSO_2$alkyl, chloro, fluoro, nitrile, or —OC(═O)alkyl;

(l) —C(═O)NH$(CH_2CH_2O—)_{1-10}$ terminating with —H, methyl, ethyl, benzyl, —$CH_2CH_2NH_2$, —$CH_2CH_2$NHalkyl, —$CH_2CH_2$N$(alkyl)_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl or —C(═O)alkyl;

(m) —C(═O)NH$(C_{1-20})$alkyl optionally substituted with one or more groups independently selected from: —OH, —Oalkyl, —$NH_2$, —NHalkyl, —N$(alkyl)_2$, pyrrolidinyl, morpholinyl, —NHC(═O)alkyl, —$NHSO_2$alkyl, —OC(═O)alkyl, —OC(═O)alkenyl, —NHC(═O)phenyl, —C(═O)OH, —C(═O)Oalkyl, —C(═O)$NH_2$, —C(═O)NHalkyl, or —C(=O)N$(alkyl)_2$; and, wherein the phenyl portion of said —NHC(═O)phenyl may be optionally substituted with one or more groups independently selected from: alkyl, —OH, —Oalkyl, —$NH_2$, —NHalkyl, —N$(alkyl)_2$, halogen or nitrile;

(n) —C(═O)NHaryl optionally substituted with one or more groups independently selected from: —OH, —Oalkyl, —$NH_2$, —NHalkyl, —N$(alkyl)_2$, heterocycloalkyl, —NHC(═O)alkyl, —$NHSO_2$alkyl, chloro, fluoro, nitrile, or —OC(═O)alkyl;

(o) —C(═O)$NHCH_2CH_2NH(CH_2CH_2NH—)_{0-3}$ terminating with H, methyl, ethyl, —$CH_2CH_2$NHalkyl, —$CH_2CH_2$N$(alkyl)_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl, —$CH_2CH_2OH$, —$CH_2CH_2OCH_3$, —$CH_2CH_2OCH_2CH_3$, —$CH_2CH_2$OC(═O)alkyl, or —C(═O)phenyl; wherein the phenyl portion of said —C(═O)phenyl may be optionally substituted with one or more groups independently selected from: alkyl, —OH, —Oalkyl, —$NH_2$, —NHalkyl, —N$(alkyl)_2$, halogen or nitrile;

(p) —C(═S)$NH_2$;

(u) —$SO_2$N$(alkyl)_2$; and (w) —P(═O)$(OCH_2CH_3)_2$;

provided that when $R^6$ is present, $R^7$ is absent; and provided that when $R^7$ is present, $R^6$ is absent.

An embodiment of the present invention includes compounds of Formula (II) wherein $R^6$ and $R^7$ are independently selected from the group consisting of:

(a) H;

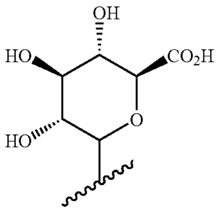

(b) provided that $R^4$ is not

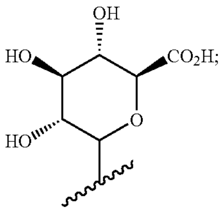

(c) —$CH_2$— substituted with one group selected from: —H, -methyl, —Oalkyl, —$CH_2OH$, —$CH(CH_3)OH$, —O(C═O)alkyl, —C(═O)Oalkyl, —(C═O)$NH_2$, —C(═O)alkyl or -phenyl-OC(═O)alkyl;

(f) —C(=O)alkyl optionally substituted with one or more groups independently selected from: —OH, —Oalkyl, —Oalkyl-phenyl or —OC(=O)alkyl;

(g) —C(=O)phenyl optionally substituted with one or more groups independently selected from: —OH, —Oalkyl, —$NH_2$, —NHalkyl, —$N(alkyl)_2$, heterocycloalkyl, —NHC(=O)alkyl, —$NHSO_2$alkyl, chloro, fluoro, nitrile, or —OC(=O)alkyl;

(h) —$C(=O)(CH_2)_{1-6}C(=O)$— terminating with —OH, —Oalkyl, —$NH_2$, —NHalkyl, —$N(alkyl)_2$, or pyrrolidinyl;

(hh) —C(=O)alkylOC(=O)alkyl-terminating with —Oalkyl;

(i) —$C(=O)O(CH_2CH_2O—)_{1-10}$ terminating with H or benzyl;

(j) —C(=O)Oalkyloptionally substituted with one or more —Oalkyl groups;

(k) —C(=O)Ophenyl optionally substituted with one or more groups independently selected from: —OH, —Oalkyl, —$NH_2$, —NHalkyl, —$N(alkyl)_2$, heterocycloalkyl, —NHC(=O)alkyl, —$NHSO_2$alkyl, chloro, fluoro, nitrile, or —OC(=O)alkyl;

(l) —$C(=O)NH(CH_2CH_2O—)_{1-10}$ terminating with —H;

(m) —$C(=O)NH(C_{1-20})$alkyl optionally substituted with one or more groups independently selected from: —$NH_2$, —NHalkyl, —$N(alkyl)_2$, pyrrolidinyl, morpholinyl, —NHC(=O)alkyl, —OC(=O)alkenyl, —NHC(=O)phenyl or —C(=O)Oalkyl; and, wherein the phenyl portion of said —NHC(=O)phenyl may be optionally substituted with one or more groups independently selected from: alkyl, —OH, —Oalkyl, —$NH_2$, —NHalkyl, —$N(alkyl)_2$, halogen or nitrile;

(n) —C(=O)NHphenyl optionally substituted with one or more groups independently selected from: —OH, —Oalkyl, —$NH_2$, —NHalkyl, —$N(alkyl)_2$, heterocycloalkyl, —NHC(=O)alkyl, —$NHSO_2$alkyl, chloro, fluoro, nitrile, or —OC(=O)alkyl;

(o) —$C(=O)NHCH_2CH_2NH(CH_2CH_2NH—)_{0-3}$ terminating with H, methyl, ethyl, —$CH_2CH_2$NHalkyl, —$CH_2CH_2N(alkyl)_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl, —$CH_2CH_2OH$, —$CH_2CH_2OCH_3$, —$CH_2CH_2OCH_2CH_3$, —$CH_2CH_2OC(=O)$alkyl, and —C(=O)phenyl; wherein the phenyl portion of said —C(=O)phenyl may be optionally substituted with one or more groups independently selected from: alkyl, —OH, —Oalkyl, —$NH_2$, —NHalkyl, —$N(alkyl)_2$, halogen and nitrile;

(p) —$C(=S)NH_2$;

(u) —$SO_2N(alkyl)_2$; and (w) —$P(=O)(OCH_2CH_3)_2$;

provided that when $R^6$ is present, $R^7$ is absent; and provided that when $R^7$ is present, $R^6$ is absent.

An embodiment of the present invention includes compounds of Formula (II) wherein $R^6$ and $R^7$ are independently selected from the group consisting of:

(a) H;

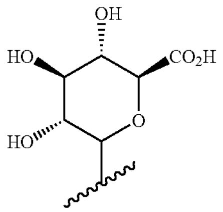

(b) provided that $R^4$ is not

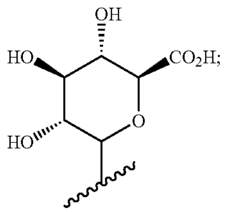

(c) —$CH_2$— substituted with one group selected from: —H, -methyl, —Oalkyl, —$CH_2OH$, —$CH(CH_3)OH$, —O(C=O)alkyl, —C(=O)Oalkyl, —$(C=O)NH_2$, —C(=O)alkyl or -phenyl-OC(=O)alkyl;

(f) —C(=O)alkyl optionally substituted with one or more groups independently selected from: —OH, —Oalkyl, —Oalkyl-phenyl or —OC(=O)alkyl;

(g) —C(=O)phenyl optionally substituted with one or more groups independently selected from: —OH, —Oalkyl, —$NH_2$, —NHalkyl, —$N(alkyl)_2$, heterocycloalkyl, —NHC(=O)alkyl, —$NHSO_2$alkyl, chloro, fluoro, nitrile, and —OC(=O)alkyl;

(h) —$C(=O)(CH_2)_{1-6}C(=O)$— terminating with —OH, —Oalkyl, —$NH_2$, —NHalkyl, —$N(alkyl)_2$, or pyrrolidinyl;

(hh) —C(=O)alkylOC(=O)alkyl-terminating with —Oalkyl;

(i) —$C(=O)O(CH_2CH_2O—)_{1-10}$ terminating with H or benzyl;

(j) —C(=O)Oalkyl optionally substituted with one or more —Oalkyl groups;

(k) —C(=O)Ophenyl optionally substituted with one or more groups independently selected from: —OH, —Oalkyl, —$NH_2$, —NHalkyl, —$N(alkyl)_2$, heterocycloalkyl, —NHC(=O)alkyl, —$NHSO_2$alkyl, chloro, fluoro, nitrile, and —OC(=O)alkyl;

(l) —$C(=O)NH(CH_2CH_2O—)_{1-10}$ terminating with —H;

(m) —$C(=O)NH(C_{1-20})$alkyl optionally substituted with one or more groups independently selected from: —$NH_2$, —NHalkyl, —$N(alkyl)_2$, pyrrolidinyl, morpholinyl, —NHC(=O)alkyl, —OC(=O)alkenyl, —NHC(=O)phenyl or —C(=O)Oalkyl; and, wherein the phenyl portion of said —NHC(=O)phenyl may be optionally substituted with one or more groups independently selected from: alkyl, —OH, —Oalkyl, —$NH_2$, —NHalkyl, —$N(alkyl)_2$, halogen and nitrile;

(n) —C(=O)NHphenyl optionally substituted with one or more groups independently selected from: —OH, —Oalkyl, —$NH_2$, —NHalkyl, —$N(alkyl)_2$, heterocycloalkyl, —NHC(=O)alkyl, —$NHSO_2$alkyl, chloro, fluoro, nitrile, and —OC(=O)alkyl;

(o) —C(═O)NHCH$_2$CH$_2$NH(CH$_2$CH$_2$NH—)$_{0\text{-}3}$ terminating with —CH$_2$CH$_2$OH and —C(═O)phenyl; wherein the phenyl portion of said —C(═O)phenyl may be optionally substituted with one or more groups independently selected from: alkyl, —OH, —Oalkyl, —NH$_2$, —NHalkyl, —N(alkyl)$_2$, halogen and nitrile;

(p) —C(═S)NH$_2$;

(u) —SO$_2$N(alkyl)$_2$; and (w) —P(═O)(OCH$_2$CH$_3$)$_2$;

provided that when $R^6$ is present, $R^7$ is absent; and provided that when $R^7$ is present, $R^6$ is absent.

An embodiment of the present invention includes compounds of Formula (II) wherein $R^6$ and $R^7$ are independently selected from the group consisting of:

(a) H;

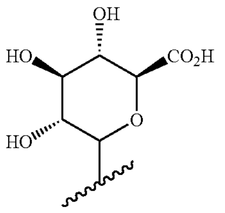

(b) provided that $R^4$ is not

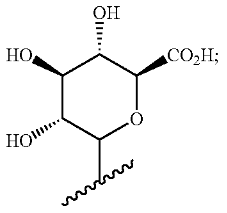

(c) —CH$_2$— substituted with one group selected from: —H, -methyl, —Oalkyl, —CH$_2$OH, —CH(CH$_3$)OH, —O(C═O)alkyl, —C(═O)Oalkyl, —(C═O)NH$_2$, —C(═O)alkyl or -phenyl-OC(═O)alkyl;

(f) —C(═O)alkyl optionally substituted with one or more groups independently selected from: —OH, —Oalkyl, —Oalkyl-phenyl or —OC(═O)alkyl;

(g) —C(═O)phenyl optionally substituted with one or more groups independently selected from: —Oalkyl, chloro or fluoro,;

(h) —C(═O)(CH$_2$)$_{1\text{-}6}$C(═O)— terminating with —OH, —Oalkyl, —NH$_2$, —NHalkyl, —N(alkyl)$_2$, or pyrrolidinyl;

(hh) —C(═O)alkylOC(═O)alkyl-terminating with —Oalkyl;

(i) —C(═O)O(CH$_2$CH$_2$O—)$_{1\text{-}10}$ terminating with H or benzyl;

(j) —C(═O)Oalkyloptionally substituted with one or more —Oalkyl groups;

(k) —C(═O)Ophenyl optionally substituted with one or more chloro, fluoro groups;

(l) —C(═O)NH(CH$_2$CH$_2$O—)$_{1\text{-}10}$ terminating with —H;

(m) —C(═O)NH(C$_{1\text{-}20}$)alkyl optionally substituted with one or more groups independently selected from: —NH$_2$, —NHalkyl, —N(alkyl)$_2$, pyrrolidinyl, morpholinyl, —NHC(═O)alkyl, —OC(═O)alkenyl, —NHC(═O)phenyl or —C(═O)Oalkyl; and, wherein the phenyl portion of said —NHC(═O)phenyl may be optionally substituted with one or more groups independently selected from: alkyl, —OH, —Oalkyl, —NH$_2$, —NHalkyl, —N(alkyl)$_2$, halogen and nitrile;

(n) —C(═O)NHphenyl optionally substituted with one or more fluoro groups;

(o) —C(═O)NHCH$_2$CH$_2$NH(CH$_2$CH$_2$NH—)$_{0\text{-}3}$ terminating with —CH$_2$CH$_2$OH and —C(═O)phenyl; wherein the phenyl portion of said —C(═O)phenyl may be optionally substituted with one or more —OHgroups;

(p) —C(═S)NH$_2$;

(u) —SO$_2$N(alkyl)$_2$; and (w) —P(═O)(OCH$_2$CH$_3$)$_2$;

provided that when $R^6$ is present, $R^7$ is absent; and provided that when $R^7$ is present, $R^6$ is absent.

An embodiment of the present invention includes compounds of Formulae (II) wherein $R^6$ and $R^7$ are independently selected from the group consisting of: H,

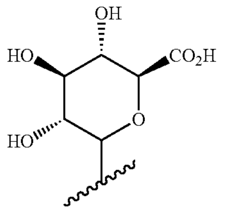

provided that $R^4$ is not

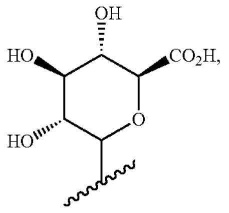

1-methoxy-1-oxo-ethyl, 1-methyl-ethoxy-carbonyl, 1-oxo-butoxy-methyl, 1-oxo-ethoxy-methyl, 1-oxo-ethyl, 1-oxo-propyl, 2-(1-oxo-ethoxy)-1-oxo-ethyl, 2-(2-methoxy-1-oxo-ethoxy)-1-oxo-ethyl, 2-(2-methyl-1-oxo-propoxy)-1-oxo-ethyl, 2-amino-2-oxo-ethyl, 2,2-dimethyl-1-oxo-propoxy-methyl, 2-ethoxy2-oxo-ethyl, 2-methoxy-2-oxo-ethyl, 2,6-difluoro-benzoyl, 2-[2-(2-hydroxy-ethoxy)-ethoxy]-ethoxy-carbonyl, 2-benzyloxy-1-oxo-ethyl, 2-benzyloxy-ethoxy-carbonyl, 2-chloro-phenoxy-carbonyl, 2-fluoro-benzoyl, 2-hydroxy-1-oxo-ethyl, 2-hydroxy-ethyl, 2-hydroxy-propyl, 2-methoxy-1-oxo-ethyl, 2-methoxy-ethoxy-carbonyl, 2-methyl-1-oxo-propyl, 2-oxo-propyl, 3-(N,N-diethyl amino)-1,3-dioxo-propyl, 3-1H-pyrrolidin-1-yl-1,3-dioxo-propyl, 3-ethoxy-1,3-dioxo-propyl, 3-1H-pyrrolidin-1-yl-1,3-dioxo-propyl, 4-(1-oxo-ethoxy)-benzyl, 4-amino-1,4-dioxo-n-butyl, 4-ethoxy-1,4-dioxo-n-butyl, 4-hydroxy-1,4-dioxo-n-butyl, 4-methoxy-1,4-dioxo-n-butyl, 4-chloro-benzoyl, 4-chloro-phenoxy-carbonyl, 4-fluoro-benzoyl, 4-fluoro-phenoxy-carbonyl, 4-methoxy-benzoyl, 5-(N-methyl-amino)-1,5-dioxo-pentyl, 5-methoxy-1,5-dioxo-pentyl, benzoyl, diethoxy-phosphinyl, ethoxy-carbonyl, methoxy-carbonyl, methoxy-methyl, methyl, N-(2-ethoxy-2-oxo-ethyl)-amino-carbonyl, N-(2-1H-pyrrolidin-1-ylethyl)-amino-carbonyl, N-(2-amino-ethyl)-amino-carbonyl, N-(2-morpholin-4-yl-ethyl)-amino-carbonyl, N-(3-ethoxy-3-oxo-propyl)-amino-carbonyl, N-(3-fluoro-phenyl)-amino-carbonyl, N-(pentadecyl)-amino-carbonyl, N,N-dimethyl-amino-sulfonyl, N-[2-(2-methenyl-1-oxo-propoxy)-ethyl]-amino-carbonyl, N-[2-(3-methyl-1-methoxy-1-oxo)-n-butyl]-amino-carbonyl, N-[2-(4-methyl-1-methoxy-1-oxo)-pentyl]-amino-carbonyl, N-[2-(N,N-dimethyl-amino)-ethyl]-amino-carbonyl, N-[2-(N-benzoyl-amino)-ethyl]-amino-carbonyl, N-[2-(N-methyl-amino)-ethyl]-amino-carbonyl, N-[2-[2-(2-hydroxy-ethoxy)-ethoxy]-ethyl]-amino-carbonyl, N-[2-[N-(1-oxo-ethyl)-amino]-ethyl]-amino-carbonyl, N-[2-[N-(2-hydroxy-benzoyl)-amino]-ethyl]-amino-carbonyl, N-[2-[N-(2-hydroxy-ethyl)-amino]-ethyl]-amino-carbonyl, N-[2-[N-(2-methyl-1-oxo-propyl)-amino]-ethyl]-amino-carbonyl, N-methyl-amino-carbonyl, N-methyl-amino-thiocarbonyl, and phenoxy-carbonyl, provided that when $R^6$ is present, $R^7$ is absent; and provided that when $R^7$ is present, $R^6$ is absent.

An embodiment of the present invention includes compounds of Formula (II) wherein $L^3$ is absent or is a linking group selected from the group consisting of methylene, ethylene, carbonyl or —$SO_2$—.

A embodiment of the present invention includes compounds of Formula (II) wherein $L^3$ is absent or is a linking group selected from the group consisting of methylene, ethylene or carbonyl.

An embodiment of the present invention includes compounds of Formula (II) wherein

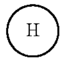

is selected from the group consisting of an aryl, a cycloalkyl, a heteroaryl, a heterocycloalkyl, a nine to ten membered benzo-fused cycloalkyl, a nine to ten membered benzo-fused heteroaryl, and a nine to ten membered benzo-fused heterocycloalkyl.

A embodiment of the present invention includes compounds of Formula (II) wherein

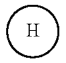

is selected from the group consisting of an aryl, a cycloalkyl, a heteroaryl, a heterocycloalkyl, a nine to ten membered benzo-fused cycloalkyl and a nine to ten membered benzo-fused heterocycloalkyl.

An embodiment of the present invention includes compounds of Formula (II) wherein

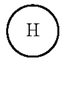

is selected from the group consisting of phenyl, cyclohexyl, furyl, imidazolyl, isoxazolyl, pyridyl, pyrimidinyl, indolyl, indazolyl, piperidinyl, morpholinyl, indanyl, 2,3-dihydro-1H-indolyl and benzodioxolyl.

A embodiment of the present invention includes compounds of Formula (II) wherein $R^5$ is independently selected from the group consisting of: alkyl, alkyloxy, amino, —C(=O)$NH_2$, —C(=O)Oalkyl, —C(=O)OH, cyano, dialkylamino, halogen, halogenated alkyl, halogenated alkyloxy, halogenated thioalkyl, hydroxy, hydroxy alkyl, —NHC(=O)$NH_2$, —$NHSQ_2$alkyl, nitro, —$SO_2$alkyl, —$SO_2NH_2$, thio, thioalkyl,

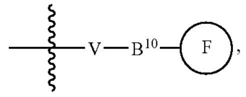

and —V—$B^{10}$—W—$B^{20}$.

A embodiment of the present invention includes compounds of Formula (II) wherein $R^5$ is independently selected from the group consisting of: alkyl, alkyloxy, —C(=O)$NH_2$, —C(=O)Oalkyl, —C(=O)OH, cyano, dialkylamino, halogen, halogenated alkyl, halogenated alkyloxy, halogenated thioalkyl, hydroxy, hydroxy alkyl, nitro, —$SO_2NH_2$, thioalkyl,

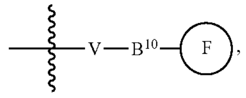

and —V—$B^{10}$—W—$B^{20}$.

An embodiment of the present invention includes compounds of Formula (II) wherein $R^5$ is independently selected from the group consisting of: methyl, ethyl, isopropyl, t-butyl, methoxy, ethoxy, —C(=O)$NH_2$, —C(=O)Omethyl, —C(=O)Oethyl, —C(=O)OH, cyano, dimethyl-amino, bromo, chloro, fluoro, trifluoromethyl, trifluoromethoxy, thio-trifluoromethyl, hydroxy, hydroxymethyl, hydroxyethyl, nitro, —$SO_2NH_2$, thiomethyl

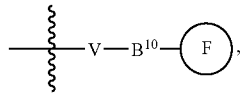

and —V—$B^{10}$—W—$B^{20}$.

An embodiment of the present invention includes compounds of Formula (II):

wherein V and W are each independently absent or selected from the group consisting of: —C(=O), —C(=O)N(alkyl)-, —C(=O)NH—, —C(=O)O—, —NH—, —NHC(=O)—, —NHC(=O)NH—, —NHC(=O)O—, —$NHSO_2$—, —O—, —OC(=O), —OC(=O)NH—, —OC(=O)O—, —S—, —SO—, —$SO_2$—, and —$SO_2$NH—.

An embodiment of the present invention includes compounds of Formula (II):

wherein V and W are each independently absent or selected from the group consisting of: —C(=O), —C(=O)N(alkyl)-, —C(=O)NH—, —C(=O)O—, —NH—, —O— and —$SO_2$—.

An embodiment of the present invention includes compounds of Formula (II) wherein V is absent or selected from the group consisting of: —C(=O), —C(=O)N(alkyl)-, —C(=O)NH—, —C(=O)O—, —NH—, —O— and —$SO_2$—.

An embodiment of the present invention includes compounds of Formula (II) wherein V is absent or selected from the group consisting of: —C(═O)NH—, —C(═O)O—, —NH—, —O— and —$SO_2$—.

An embodiment of the present invention includes compounds of Formula (II) wherein W is absent.

An embodiment of the present invention includes compounds of Formula (II) wherein:

$B^{10}$ is absent or alkyl; and wherein when $B^{10}$ is alkyl, the alkyl may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy —N(alkyl)C(═O)alkyl, —N(alkyl)C(═O)N(alkyl)$_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, —OC(═O)alkyl, —OC(═O)N(alkyl)$_2$, —OC(═O)NHalkyl, —OC(═O)Oalkyl, —$SO_2$alkyl, thio or thioalkyl.

An embodiment of the present invention includes compounds of Formula (II) wherein:

$B^{10}$ is absent or alkyl; and wherein when $B^{10}$ is alkyl, the alkyl may be optionally substituted with one or more groups independently selected from: alkoxy, alkylamino, amino, dialkylamino, halogen, halogenated alkoxy, hydroxy —NHC(═O)$NH_2$, —$NHSO_2$alkyl, —$SO_2$alkyl or thioalkyl.

An embodiment of the present invention includes compounds of Formula (II) wherein:

$B^{10}$ is absent or selected from methyl or ethyl,; wherein methyl or ethyl are optionally substituted with one or more groups independently selected from dialkylamino or hydroxy.

An embodiment of the present invention includes compounds of Formula (II) wherein:

$B^{10}$ is absent or selected from methyl or ethyl,; wherein methyl or ethyl are optionally substituted with one or more groups independently selected from dimethyl-amino or hydroxy.

An embodiment of the present invention includes compounds of Formula (II) wherein:

$B^{20}$ is absent or selected from alkyl, alkenyl, or H;

wherein, when $B^{20}$ is alkyl or alkenyl, the alkyl or alkenyl group may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy —N(alkyl)C(═O)alkyl, —N(alkyl)C(═O)N(alkyl)$_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, —OC(═O)alkyl, —OC(═O)N(alkyl)$_2$, —OC(═O)NHalkyl, —OC(═O)Oalkyl, —$SO_2$alkyl, thio or thioalkyl.

An embodiment of the present invention includes compounds of Formula (II) wherein:

$B^{20}$ is absent or selected from alkyl, alkenyl, or H;

wherein, when $B^{20}$ is alkyl or alkenyl, the alkyl or alkenyl group may be optionally substituted with one or more groups independently selected from: alkoxy, alkylamino, amino, dialkylamino, halogen, halogenated alkoxy, hydroxy, —NHC(═O)$NH_2$, —$NHSO_2$alkyl or thioalkyl.

An embodiment of the present invention includes compounds of Formula (II) wherein:

$B^{20}$ is absent or H.

An embodiment of the present invention includes compounds of Formula (II) wherein:

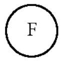

is selected from the group consisting of aryl, cycloalkyl, partially unsaturated carbocycle, heteroaryl and heterocycloalkyl optionally substituted with one or more substituents independently selected from alkoxy, alkyl, alkylamino, amino, cyano, dialkylamino, halogen, halogenated alkoxy, halogenated alkyl, halogenated —$SO_2$alkyl, halogenated thioalkyl, heteroaryl, hydroxy, hydroxy alkyl, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, nitro, —OC(═O)N(alkyl)$_2$, —OC(═O)NHalkyl, —$SO_2$alkyl, thio or thioalkyl.

An embodiment of the present invention includes compounds of Formula (II) wherein:

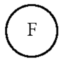

is selected from the group consisting of phenyl, imidazolyl, pyridinyl, pyrimidinyl, pyrrolidinyl, morpholinyl, piperazinyl and piperidinyl optionally substituted with one or more substituents independently selected from alkoxy, alkyl, alkylamino, amino, cyano, dialkylamino, halogen, halogenated alkoxy, halogenated alkyl, halogenated —$SO_2$alkyl, halogenated thioalkyl, heteroaryl, hydroxy, hydroxy alkyl, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, nitro, —OC(═O)N(alkyl)$_2$, —OC(═O)NHalkyl, —$SO_2$alkyl, thio or thioalkyl.

An embodiment of the present invention includes compounds of Formula (II) wherein:

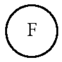

is selected from the group consisting of phenyl, imidazolyl, pyridinyl, pyrimidinyl, pyrrolidinyl, morpholinyl, piperazinyl and piperidinyl optionally substituted with one or more substituents independently selected from alkoxy, alkyl, alkylamino, amino, dialkylamino, halogen, halogenated alkoxy, halogenated alkyl, heteroaryl, hydroxy, hydroxy alkyl, —NHC(═O)$NH_2$, —$NHSO_2$alkyl, nitro or —$SO_2$alkyl.

An embodiment of the present invention includes compounds of Formula (II) wherein:

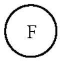

is selected from the group consisting of phenyl, imidazolyl, pyridinyl, pyrimidinyl, pyrrolidinyl, morpholinyl, piperazinyl and piperidinyl optionally substituted with one or more substituents independently selected from methoxy, ethoxy, methyl, ethyl, bromo, chloro, fluoro, trifluoromethyl, pyridinyl, hydroxy or hydroxymethyl.

A embodiment of the present invention includes compounds of Formula (II) wherein:

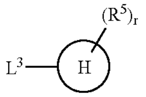

is selected from the group consisting of: 1-(3-methoxy-phenyl)-(S*)ethyl; 2-(3-bromo)-pyridyl; 2-(3-methyl)-pyridyl; 2-(3-methyl-5-bromo)-pyridyl; 2-(4,6-dimethyl)-pyridyl; 2-(4-bromo)-pyridyl; 2-(piperidin-1-yl)-ethyl; 2,2-difluoro-1,3-benzodioxol-4-yl; 2,3-dichloro-benzyl; 2,3-dichloro-phenyl; 2,3-dihydro-1H-indol-1-yl; 2,3-dimethoxy-benzyl; 2,4,6-trifluoro-phenyl; 2,4-dichloro-phenyl; 2,4-difluoro-benzyl; 2,4-dimethoxy-phenyl; 2,4-dimethoxy-phenyl; 2,5-dichloro-benzyl; 2,5-dichloro-phenyl; 2,5-difluoro-benzyl; 2,5-difluoro-phenyl; 2,5-dimethoxy-benzyl; 2,5-dimethoxy-phenyl; 2,6-dichloro-benzyl; 2,6-difluoro-benzyl; 2,6-difluoro-phenyl; 2-bromo-3-fluoro-phenyl; 2-bromo-benzyl; 2-bromo-phenyl; 2-chloro-benzyl; 2-chloro-phenyl; 2-ethyl-phenyl; 2-fluoro-benzyl; 2-fluoro-phenyl; 2-furyl; 2-isopropyl-phenyl; 2-methoxy-benzyl; 2-methoxy-phenyl; 2-methyl-benzyl; 2-methyl-phenyl; 2-morpholin-4-yl-ethyl; 2-pyridyl; 2-pyridyl-methyl; 2-trifluoromethoxy-benzyl; 2-trifluoromethoxy-phenyl; 2-trifluoromethyl-4-bromo-phenyl; 2-trifluoromethyl-benzyl; 2-trifluoromethyl-phenyl; 3-(1-hydroxy-ethyl)-phenyl; 3-(2,4-dimethoxy)-pyridyl; 3-(2-chloro)-pyridyl; 3-(2-hydroxy-ethyl-amino-carbonyl)-phenyl; 3-(4-methoxy)-pyridyl; 3-(4-methyl-piperazinyl-carbonyl)-phenyl; 3-(4-trifluoromethyl)-pyridyl; 3-(amino-carbonyl)-phenyl; 3-(amino-sulfonyl)-phenyl; 3-(ethoxy-carbonyl)-phenyl; 3-(methoxy-carbonyl)-phenyl; 3-(trifluoromethyl-thio)-phenyl; 3,4,5-trimethoxy-phenyl; 3,4-dichloro-benzyl; 3,4-dichloro-phenyl; 3,4-difluoro-benzyl; 3,4-dimethoxy-phenyl; 3,4-dimethyl-benzyl; 3,4-methylenedioxy-phenyl; 3,5-di(tert-butyl)-phenyl; 3,5-di(trifluoromethyl)-phenyl; 3,5-dichloro-benzyl; 3,5-dichloro-phenyl; 3,5-difluoro-phenyl; 3,5-dimethoxy-phenyl; 3,5-dimethyl-phenyl; 3-[N-(3-pyrrolidin-1-yl-propyl)-amino-carbonyl]-phenyl; 3-benzyloxy-phenyl; 3-bromo-phenyl; 3-carboxy-phenyl; 3-chloro-4-fluoro-phenyl; 3-chloro-4-methoxy-phenyl; 3-chloro-4-methyl-benzyl; 3-chloro-benzyl; 3-chloro-phenyl; 3-cyano-phenyl; 3-ethoxy-phenyl; 3-ethyl-phenyl; 3-fluoro-benzyl; 3-fluoro-phenyl; 3-hydroxymethyl-phenyl; 3-hydroxy-phenyl; 3-isopropoxy-phenyl; 3-methoxy-5-trifluoromethyl-phenyl; 3-methoxy-benzyl; 3-methyl-benzyl; 3-methyl-phenyl; 3-methylthio-phenyl; 3-pyridyl; 3-pyridyl-methyl; 3-trifluoromethoxy-phenyl; 3-trifluoromethyl-phenyl; 4-(4-methyl-piperazin-1-yl)-phenyl; 4-(ethoxy-carbonyl)-phenyl; 4-(N,N-dimethyl-amino)-phenyl; 4-(piperidin-4-yl-sulfonyl)-phenyl; 4-benzyloxy-phenyl; 4-bromo-phenyl; 4-chloro-3-methyl-benzyl; 4-chloro-phenyl; 4-cyano-phenyl; 4-dimethylamino-phenyl; 4-fluoro-3-chloro-phenyl; 4-fluoro-3-nitro-phenyl; 4-fluoro-3-trifluoromethyl-phenyl; 4-fluoro-benzyl; 4-fluoro-phenyl; 4-methoxy-benzyl; 4-methyl-3-[N-[4-(3-pyridyl)-pyrimidin-2-yl]amino]-phenyl; 4-methyl-benzyl; 4-methyl-phenyl; 4-trifluoromethoxy-phenyl; 4-trifluoromethyl-phenyl; 5-(phenyl)-isoxazol-3-yl-methyl; 5-bromo-2,3-dihydro-1H-indol-1-yl; 5-chloro-2-methoxy-phenyl; 5-chloro-2-methyl-phenyl; 5-indanyl; 5-indolyl; 5-indolyl; 5-trifluoromethyl-2-fluoro-phenyl; 6-indazolyl; benzyl; cyclohexyl; cyclohexyl-methyl; and phenyl.

2.a.2

An embodiment of the present invention includes compounds of Formula (II) wherein:

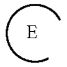

is selected from the group consisting of Formulae A-1, A-2 and A-3:

(Formula A-1)

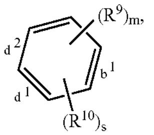

wherein Formula A-1 is attached on the $b^1$ side of Formula A-1 to the $L^2$ ring of Formula (II) and optionally substituted with one substituent selected from the group consisting of Formulae A-1-a, A-1-b and A-1-c:

(Formula A-1-a)

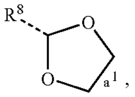

wherein Formula A-1-a is attached on the $a^1$ side to adjacent carbons on the $d^1$or $d^2$ side of Formula A-1;

(Formula A-1-b)

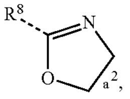

wherein Formula A-1-b is attached on the $a^2$ side to adjacent carbons on the $d^1$or $d^2$ side of Formula A-1;

(Formula A-1-c)

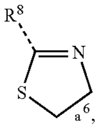

wherein Formula A-1-c is attached on the $a^6$ side to adjacent carbons on the $d^1$or $d^2$ side of Formula A-1;

wherein $R^8$ is H or lower alkyl;

(Formula A-2)

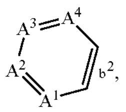

wherein Formula A-2 is selected from the group consisting of pyridyl and pyrimidinyl; is attached on the $b^2$ side of Formula A-2 to the $L^2$ ring of Formula (II); and is optionally substituted on a carbon ring member with H or alkoxy, wherein the alkoxy may be optionally further substituted with alkoxy on a terminal carbon or up to 3 halogen atoms on a terminal carbon; and (Formula A-3)

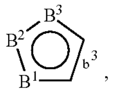

wherein Formula A-3 is selected from the group consisting of thienyl, isoxazolyl and furyl; is attached on the $b^3$ side of Formula A-3 to the $L^2$ ring of Formula (II), and is optionally substituted on a carbon ring member with $C_{1-4}$alkyl, aryl, alkoxy, or halogen;

s is an integer from 0 to 2; and m is an integer from 0 to 4; provided that when

is not substituted with Formulae A-1-a, A-1-b or A-1-c, the sum of m and s is an integer from 0 to 4, and when

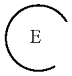

is substituted with one of Formulae A-1-a, A-1-b, or A-1-c, the sum of m and s is an integer from 0 to 2;

$R^9$ is independently selected from the group consisting of: alkoxy, alkyl, alkylamino, amino, cyano, dialkylamino, halogen, halogenated alkyl, halogenated alkyloxy, hydroxy, —NHC(═O)alkyl, —NHC(═O)NHalkyl, —NHC(═O)Oalkyl, —$NHSO_2$alkyl, and thioalkyl;

$L^2$ is a linking group selected from the group consisting of: —$(CH_2)$—, —$(CH_2)_{3-4}$—, —$CH(R^{100})$—, —$C(=R^{100})$—, —$C(R^{100})_2$—, —O—, —$O(CH_2)_{1-4}$—, —$OCH(R^{100})$—, —$OC(R^{100})_2$—, —S—, —NH—, —N(lower alkyl)-, —N(COalkyl)-, —N(aryl)-, —$N(CO_2$alkyl)-, —N(CONHalkyl)-, —$N(SO_2$alkyl) and —$N(SO_2$aryl)-; provided that when $L^2$ is —O—, neither $R^6$ nor $R^7$ is —$CH_3$;

$R^{100}$ is selected from: alkyl, hydroxy, aryl, oxo or ═N(OH);

$R^{10}$ is independently selected from the group consisting of

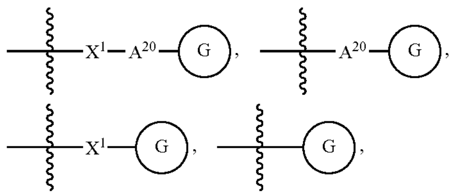

—$X^1$-$A^{20}$-$Y^1$-$A^{21}$, —$X^1$-$A^{20}$-$A^{21}$, —$X^1$-$A^{21}$, -$A^{20}$-$A^{21}$ and -$A^{21}$, wherein $X^1$ and $Y^1$ are each independently absent or selected from the group consisting of: —NH—, —O—, —$SO_2$— and —$SO_2$NH—;

$A^{20}$ is absent or alkyl;

wherein when $A^{20}$ is alkyl, the alkyl may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy, —N(alkyl)C(═O)alkyl, —N(alkyl)C(═O)N$(alkyl)_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N$(alkyl)_2$, —NHC(═O)$NH_2$, —NHC(═O)NHalkyl, —NHC(═O)Oalkyl, —$NHSO_2$alkyl, —OC(═O)alkyl, —OC(═O)N$(alkyl)_2$, —OC(═O)NHalkyl, —OC(═O)Oalkyl, —$SO_2$alkyl, thio or thioalkyl;

$A^{21}$ is selected from alkyl, alkenyl, or H;

wherein when $A^{21}$ is alkyl or alkenyl, the alkyl or alkenyl may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy, —N(alkyl)C(═O)alkyl, —N(alkyl)C(═O)N$(alkyl)_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N$(alkyl)_2$, —NHC(═O)$NH_2$, —NHC(═O)NHalkyl, —NHC(═O)Oalkyl, —$NHSO_2$alkyl, —OC(═O)alkyl, —OC(═O)N$(alkyl)_2$, —OC(═O)NHalkyl, —OC(═O)Oalkyl, —$SO_2$alkyl, thio or thioalkyl; and

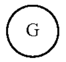

is selected from the group consisting of aryl, cycloalkyl, partially unsaturated carbocycle, heteroaryl and heterocycloalkyl optionally substituted with one or more substituents independently selected from halogen, hydroxy, amino, thio, nitro, cyano, alkyl, halogenated alkyl, alkoxy, halogenated alkoxy, alkylamino, —NHC(═O)alkyl, —N(alkyl)C(═O)alkyl, or dialkylamino, —NHC(═O)$NH_2$, —NHC(═O)NHalkyl, —N(alkyl)C(═O)NHalkyl, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)N$(alkyl)_2$, —N(alkyl)C(═O)N$(alkyl)_2$ or —OC(═O)N$(alkyl)_2$;

$R^6$ and $R^7$ are independently selected from the group consisting of:

(a) H;

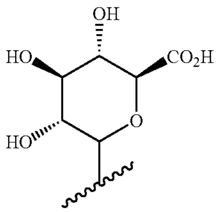

(b) provided that $R^4$ is not

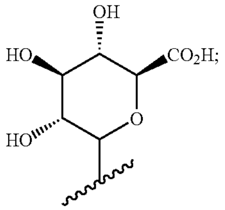

(c) —$CH_2$— substituted with one group selected from: —H, -methyl, —Oalkyl, —$CH_2OH$, —$CH(CH_3)OH$, —O(C═O)alkyl, —(C═O)OH, —C(═O)Oalkyl, —C(═O)Oaryl, —C(═O)Oheteroaryl, —(C═O)$NH_2$, —(C═O)NHalkyl, —(C═O)N(alkyl)$_2$, —C(═O)alkyl, -phenyl-$OCH_3$ or -phenyl-OC(═O)alkyl;

(d) —C(═O)($CH_2CH_2O$—)$_{1-10}$ terminating with H;

(e) —C(═O)$CH_2O$($CH_2CH_2O$—)$_{1-10}$ terminating with H;

(f) —C(═O)alkyl optionally substituted with one or more groups independently selected from: —OH, —Oalkyl, —Oalkylaryl, —$NH_2$, —NHalkyl, —N(alkyl)$_2$, heterocycloalkyl, —NHC(═O)alkyl, —$NHSO_2$alkyl, or —OC(═O)alkyl;

(g) —C(═O)($CH_2$)$_{1-3}$aryl or —C(═O)aryl, wherein said —C(═O)aryl may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or —OC(═O)alkyl;

(h) —C(═O)($CH_2$)$_{1-6}$C(═O)— terminating with methyl, ethyl, —OH, —Oalkyl, —$NH_2$, —NHalkyl, —N(alkyl)$_2$, or heterocycloalkyl;

(hh) —C(═O)alkylOC(═O)alkyl-terminating with —OH, —Oalkyl, —$NH_2$, —NHalkyl or —N(alkyl)$_2$;

(i) —C(═O)O($CH_2CH_2O$—)$_{1-10}$ terminating with H, methyl, ethyl, or benzyl;

(j) —C(═O)Oalkyloptionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, —OC(═O)alkyl, —C(═O)OH, —C(═O)Oalkyl, —C(═O)$NH_2$, —C(═O)NHalkyl, or —C(═O)N(alkyl)$_2$;

(k) —C(═O)O($CH_2$)$_{1-3}$aryl or —C(═O)Oaryl, wherein said —C(═O)Oaryl may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or-OC(═O)alkyl;

(l) —C(═O)NH($CH_2CH_2O$—)$_{1-10}$ terminating with —H, methyl, ethyl, benzyl, —$CH_2CH_2NH_2$, —$CH_2CH_2$NHalkyl, —$CH_2CH_2$N(alkyl)$_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl or —C(═O)alkyl;

(m) —C(═O)$NH_2$, —C(═O)NH($C_{1-20}$)alkyl, or —C(═O)N($C_{1-20}$alkyl)$_2$, wherein said —C(═O)NH($C_{1-20}$)alkyl, may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, —OC(═O)alkyl, —OC(═O)alkenyl, —NHC(═O)aryl, —C(═O)OH, —C(═O)Oalkyl, —C(═O)$NH_2$, —C(═O)NHalkyl, or —C(═O)N(alkyl)$_2$; and, wherein the aryl portion of said —NHC(═O)aryl may be optionally substituted with one or more groups independently selected from: alkyl, —OH, —Oalkyl, —$NH_2$, —NHalkyl, —N(alkyl)$_2$, halogen or nitrile;

(n) —C(═O)NH($CH_2$)$_{1-3}$aryl or —C(═O)NHaryl, wherein said —C(═O)NHaryl may be optionally substituted with one or more groups independently selected from: —OH, —Oalkyl, —$NH_2$, —NHalkyl, —N(alkyl )$_2$, heterocycloalkyl, —NHC(═O)alkyl, —$NHSO_2$alkyl, halogen, nitrile, or —OC(═O)alkyl;

(o) —C(═O)$NHCH_2CH_2NH$($CH_2CH_2NH$—)$_{0-3}$ terminating with H, methyl, ethyl, —$CH_2CH_2$NHalkyl, —$CH_2CH_2$N(alkyl)$_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl, —$CH_2CH_2OH$, —$CH_2CH_2OCH_3$, —$CH_2CH_2OCH_2CH_3$, —$CH_2CH_2$OC(═O)alkyl or —C(═O)aryl; wherein the aryl portion of said —C(═O)aryl may be optionally substituted with one or more groups independently selected from: alkyl, —OH, —Oalkyl, —$NH_2$, —NHalkyl, —N(alkyl)$_2$, halogen or nitrile;

(p) —C(═S)$NH_2$;

(q) —C(═S)NHalkyl;

(r) —C(═S)N(alkyl)$_2$;

(s) —$SO_2NH_2$;

(t) —$SO_2$NHalkyl;

(u) —$SO_2$N(alkyl)$_2$;

(v) —P(═O)($OCH_3$)$_2$; and (w) —P(═O)($OCH_2CH_3$)$_2$;

provided that when $R^6$ is present, $R^7$ is absent; and provided that when $R^7$ is present, $R^6$ is absent;

$R^4$ is selected from the group consisting of: H and

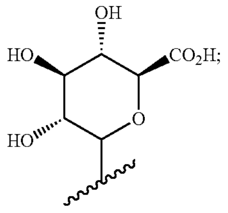

provided that if one of $R^6$ and $R^7$ is

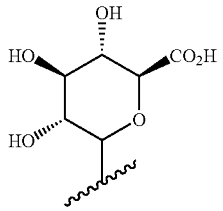

then $R^4$ is H;

$L^3$ is absent or is a linking group selected from the group consisting of methylene, ethylene, carbonyl or —$SO_2$—;

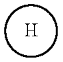

is selected from the group consisting of an aryl, a cycloalkyl, a heteroaryl, a heterocycloalkyl, a nine to ten membered benzo-fused cycloalkyl, a nine to ten membered benzo-fused heteroaryl, and a nine to ten membered benzo-fused heterocycloalkyl;

r is an integer from 0 to 4; and $R^5$ is independently selected from the group consisting of: alkyl, alkyloxy, amino, —C(═O)$NH_2$, —C(═O)Oalkyl, —C(═O)OH, cyano, dialkylamino, halogen, halogenated alkyl, halogenated alkyloxy, halogenated thioalkyl, hydroxy, hydroxy alkyl, —NHC(═O)$NH_2$, —$NHSO_2$alkyl, nitro, —$SO_2$alkyl, —$SO_2NH_2$, thio, thioalkyl,

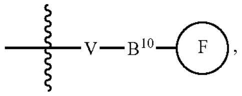

and —V—$B^{10}$—W—$B^{20}$;

wherein

V and W are each independently absent or selected from the group consisting of: —C(═O), —C(═O)N(alkyl)-, —C(═O)NH—, —C(═O)O—, —NH—, —NHC(═O)—, —NHC(═O)NH—, —NHC(═O)O—, —$NHSO_2$—, —O—, —OC(═O), —OC(═O)NH—, —OC(═O)O—, —S—, —SO—, —$SO_2$—, and —$SO_2$NH—;

$B^{10}$ is absent or alkyl;

wherein when $B^{10}$ is alkyl, the alkyl may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy —N(alkyl)C(═O)alkyl, —N(alkyl)C(═O)N(alkyl)$_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, —OC(═O)alkyl, —OC(═O)N(alkyl)$_2$, —OC(═O)NHalkyl, —OC(═O)Oalkyl, —$SO_2$alkyl, thio or thioalkyl;

$B^{20}$ is absent or selected from alkyl, alkenyl, or H;

wherein, when $B^{20}$ is alkyl or alkenyl, the alkyl or alkenyl group may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy —N(alkyl)C(═O)alkyl, —N(alkyl)C(═O)N(alkyl)$_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, —OC(═O)alkyl, —OC(═O)N(alkyl)$_2$, —OC(═O)NHalkyl, —OC(═O)Oalkyl, —$SO_2$alkyl, thio or thioalkyl; and

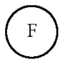

is selected from the group consisting of aryl, cycloalkyl, partially unsaturated carbocycle, heteroaryl and heterocycloalkyl optionally substituted with one or more substituents independently selected from alkoxy, alkyl, alkylamino, amino, cyano, dialkylamino, halogen, halogenated alkoxy, halogenated alkyl, halogenated —$SO_2$alkyl, halogenated thioalkyl, heteroaryl, hydroxy, hydroxy alkyl, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, nitro, —OC(═O)N(alkyl)$_2$, —OC(═O)NHalkyl, -$SO_2$alkyl, thio or thioalkyl;

or an optical isomer, enantiomer, diastereomer, racemate, or pharmaceutically acceptable salt thereof.

An embodiment of the present invention includes compounds of Formula (II) wherein

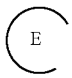

is selected from the group consisting of:

(Formula A-4)

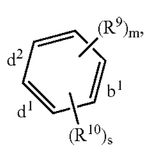

wherein Formula A-4 is attached on the $b^1$ side of Formula A-4 to the $L^2$ ring of Formula (II);

(Formula A-5)

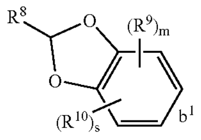

wherein Formula A-5 is attached on the $b^1$ side of Formula A-5 to the $L^2$ ring of Formula (II); wherein $R^8$ is H and lower alkyl;

(Formula A-6)

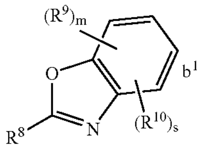

wherein Formula A-6 is attached on the $b^1$ side of Formula A-6 to the $L^2$ ring of Formula (II); and (Formula A-3-a)

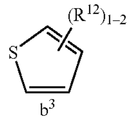

wherein Formula A-3-a is attached on the $b^3$ side of Formula A-3-a to the $L^2$ ring of formula (II), wherein $R^{12}$ is independently selected from H, methyl, phenyl, ethoxy, chloro or fluoro;

s is an integer from 0 to 2; and m is an integer from 0 to 4; provided that when

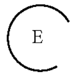

is Formula A-4, the sum of m and s is an integer from 0 to 4, and when

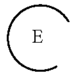

is Formulae A-5 or A-6, the sum of m and s is an integer from 0 to 2;

$R^9$ is independently selected from the group consisting of: alkoxy, alkyl, amino, cyano, dialkylamino, halogen, halogenated alkyl, halogenated alkyloxy, hydroxy and —NHC(=O)alkyl;

$L^2$ is a linking group selected from the group consisting of: $-(CH_2)-$, $-(CH_2)_{3-4}-$, $-CH(R^{100})-$, $-C(=R^{100})-$, $-C(R^{100})_2-$, $-O(CH_2)_{1-4}-$, $-OCH(R^{100})-$, $-OC(R^{100})_2-$, —S—, —NH—, —N(lower alkyl)-, —N(COalkyl)-, —N(aryl)-, $-N(CO_2alkyl)-$, —N(CONHalkyl)-, $-N(SO_2alkyl)$ and $-N(SO_2aryl)-$;

$R^{100}$ is selected from: alkyl, hydroxy, aryl, oxo or =N(OH);

$R^{10}$ is independently selected from the group consisting of

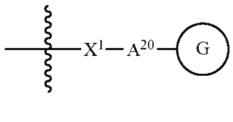,
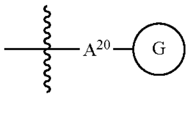,

-continued

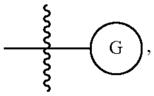, $-X^1-A^{20}-Y^1-A^{21}$, $-X^1-A^{20}-A^{21}$ and $-X^1A^{21}$, wherein $X^1$ and $Y^1$ are each independently absent or —O—;

$A^{20}$ is absent or alkyl;

wherein when $A^{20}$ is alkyl, the alkyl may be optionally substituted with one or more groups independently selected from: alkoxy, alkylamino, amino, dialkylamino, halogen, halogenated alkoxy, hydroxy, $-NHC(=O)NH_2$, $-NHSO_2alkyl$, $-SO_2alkyl$ or thioalkyl;

$A^{21}$ is selected from alkyl, alkenyl, or H;

wherein when $A^{21}$ is alkyl or alkenyl, the alkyl or alkenyl may be optionally substituted with one or more groups independently selected from: alkoxy, alkylamino, amino, dialkylamino, halogen, halogenated alkoxy, hydroxy, $-NHC(=O)NH_2$, $-NHSO_2alkyl$ or thioalkyl; and

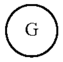

is selected from the group consisting of aryl, heteroaryl and heterocycloalkyl optionally substituted with one or more substituents independently selected from halogen, hydroxy, amino, thio, nitro, cyano, alkyl, halogenated alkyl, alkoxy, halogenated alkoxy, alkylamino, —NHC(=O)alkyl, —N(alkyl)C(=O)alkyl, or dialkylamino, $-NHC(=O)NH_2$, —NHC(=O)NHalkyl, —N(alkyl)C(=O)NHalkyl, —OC(=O)NHalkyl, —NHC(=O)Oalkyl, —N(alkyl)C(=O)Oalkyl, $-NHSO_2alkyl$, $-N(alkyl)SO_2alkyl$, thioalkyl, halogenated thioalkyl, $-SO_2alkyl$, halogenated $-SO_2alkyl$, $-NHC(=O)N(alkyl)_2$, $-N(alkyl)C(=O)N(alkyl)_2$ or $-OC(=O)N(alkyl)_2$;

$R^6$ and $R^7$ are independently selected from the group consisting of:

(a) H;

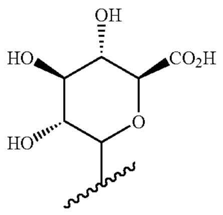

(b) provided that $R^4$ is not

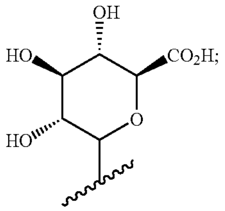

(c) —$CH_2$— substituted with one group selected from: —H, -methyl, —Oalkyl, —$CH_2OH$, —$CH(CH_3)OH$, —O(C═O)alkyl, —(C═O)OH, —C(═O)Oalkyl, —C(═O)Oaryl, —C(═O)Oheteroaryl, —(C═O)$NH_2$, —(C═O)NHalkyl, —(C═O)N(alkyl)$_2$, —C(═O)alkyl, -phenyl-$OCH_3$ or -phenyl-OC(═O)alkyl;

(f) —C(═O)alkyl optionally substituted with one or more groups independently selected from: —OH, —Oalkyl, —Oalkylaryl, —$NH_2$, —NHalkyl, —N(alkyl)$_2$, heterocycloalkyl, —NHC(═O)alkyl, —$NHSO_2$alkyl, or —OC(═O)alkyl;

(g) —C(═O)$(CH_2)_{1-3}$aryl or —C(═O)aryl, wherein said —C(═O)aryl may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or —OC(═O)alkyl;

(h) —C(═O)$(CH_2)_{1-6}$C(═O)— terminating with methyl, ethyl, —OH, —Oalkyl, —$NH_2$, —NHalkyl, —N(alkyl)$_2$, or heterocycloalkyl;

(hh) —C(═O)alkylOC(═O)alkyl-terminating with —OH, —Oalkyl, —$NH_2$, —NHalkyl or —N(alkyl)$_2$;

(i) —C(═O)O$(CH_2CH_2O—)_{1-10}$ terminating with H, methyl, ethyl, or benzyl;

(j) —C(═O)Oalkyloptionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, —OC(═O)alkyl, —C(═O)OH, —C(═O)Oalkyl, —C(═O)$NH_2$, —C(═O)NHalkyl, or —C(═O)N(alkyl)$_2$;

(k) —C(═O)O$(CH_2)_{1-3}$aryl or —C(═O)Oaryl, wherein said —C(═O)Oaryl may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or —OC(═O)alkyl;

(l) —C(═O)NH$(CH_2CH_2O—)_{1-10}$ terminating with —H, methyl, ethyl, benzyl, —$CH_2CH_2NH_2$, —$CH_2CH_2$NHalkyl, —$CH_2CH_2$N(alkyl)$_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl or —C(═O)alkyl;

(m) —C(═O)$NH_2$, —C(═O)NH($C_{1-20}$)alkyl, or —C(═O)N($C_{1-20}$alkyl)$_2$, wherein said —C(═O)NH($C_{1-20}$)alkyl, may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, —OC(O)alkyl, —OC(═O)alkenyl, —NHC(═O)aryl, —C(═O)OH, —C(═O)Oalkyl, —C(═O)$NH_2$, —C(═O)NHalkyl, or —C(═O)N(alkyl)$_2$; and, wherein the aryl portion of said —NHC(═O)aryl may be optionally substituted with one or more groups independently selected from: alkyl, —OH, —Oalkyl, —$NH_2$, —NHalkyl, —N(alkyl)$_2$, halogen or nitrile;

(n) —C(═O)NH$(CH_2)_{1-3}$aryl or —C(═O)NHaryl, wherein said —C(═O)NHaryl may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or —OC(═O)alkyl;

(o) —C(═O)NH$CH_2CH_2$NH$(CH_2CH_2NH—)_{0-3}$ terminating with H, methyl, ethyl, —$CH_2CH_2$NHalkyl, —$CH_2CH_2$N(alkyl)$_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl, —$CH_2CH_2OH$, —$CH_2CH_2OCH_3$, —$CH_2CH_2OCH_2CH_3$, —$CH_2CH_2$OC(═O)alkyl, or —C(═O)aryl; wherein the aryl portion of said —C(═O)aryl may be optionally substituted with one or more groups independently selected from: alkyl, —OH, —Oalkyl, —$NH_2$, —NHalkyl, —N(alkyl)$_2$, halogen or nitrile;

(p) —C(═S)$NH_2$;

(u) —$SO_2$N(alkyl)$_2$; and (w) —P(═O)$(OCH_2CH_3)_2$;

provided that when $R^6$ is present, $R^7$ is absent; and provided that when $R^7$ is present, $R^6$ is absent;

$R^4$ is selected from the group consisting of: H and

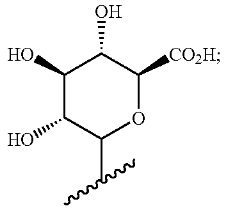

provided that if one of $R^6$ and $R^7$ is

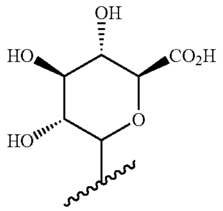

then $R^4$ is H;

$L^3$ is absent or is a linking group selected from the group consisting of methylene, ethylene or carbonyl;

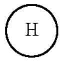

is selected from the group consisting of an aryl, a cycloalkyl, a heteroaryl, a heterocycloalkyl, a nine to ten membered benzo-fused cycloalkyl and a nine to ten membered benzo-fused heterocycloalkyl;

r is an integer from 0 to 4; and $R^5$ is independently selected from the group consisting of: alkyl, alkyloxy, —C(═O)$NH_2$, —C(═O)Oalkyl, —C(═O)OH, cyano, dialkylamino, halogen, halogenated alkyl, halogenated alkyloxy, halogenated thioalkyl, hydroxy, hydroxy alkyl, nitro, —$SO_2NH_2$, thioalkyl,

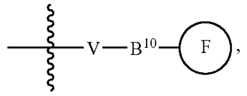

and —V—$B^{10}$—W—$B^{20}$; wherein

V and W are each independently absent or selected from the group consisting of: —C(═O), —C(═O)N(alkyl)-, —C(═O)NH—, —C(═O)O—, —NH—, —O— and —$SO_2$—;

$B^{10}$ is absent or alkyl;

wherein when $B^{10}$ is alkyl, the alkyl may be optionally substituted with one or more groups independently selected from: alkoxy, alkylamino, amino, dialkylamino, halogen, halogenated alkoxy, hydroxy —NHC(═O)$NH_2$, —$NHSO_2$alkyl, —$SO_2$alkyl or thioalkyl;

$B^{20}$ is absent or selected from alkyl, alkenyl, or H;

wherein, when $B^{20}$ is alkyl or alkenyl, the alkyl or alkenyl group may be optionally substituted with one or more groups independently selected from: alkoxy, alkylamino, amino, dialkylamino, halogen, halogenated alkoxy, hydroxy, —NHC(═O)$NH_2$, —$NHSO_2$alkyl or thioalkyl; and

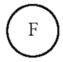

is selected from the group consisting of phenyl, imidazolyl, pyridinyl, pyrimidinyl, pyrrolidinyl, morpholinyl, piperazinyl and piperidinyl optionally substituted with one or more substituents independently selected from alkoxy, alkyl, alkylamino, amino, cyano, dialkylamino, halogen, halogenated alkoxy, halogenated alkyl, halogenated —$SO_2$alkyl, halogenated thioalkyl, heteroaryl, hydroxy, hydroxy alkyl, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, nitro, —OC(═O)N(alkyl)$_2$, —OC(═O)NHalkyl, —$SO_2$alkyl, thio or thioalkyl;

or an optical isomer, enantiomer, diastereomer, racemate, or pharmaceutically acceptable salt thereof.

2. b Formulae (II-AA) Through (II-JJ)

The present invention is further directed to compounds of Formula (II-AA)

(II-AA)

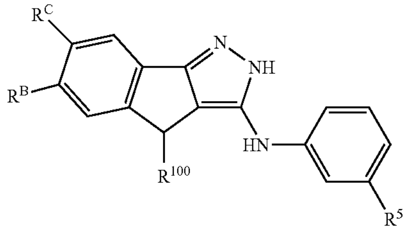

wherein:

$R^{100}$ is selected from the group consisting of: H and alkyl;

$R^B$ and $R^C$ are independently selected from the group consisting of: alkoxy; and $R^5$ is selected from the group consisting of: alkoxy and halogen;

or an optical isomer, enantiomer, diastereomer, racemate, or pharmaceutically acceptable salt thereof.

A preferred embodiment of the present invention includes compounds of Formula (II-AA) wherein $R^{100}$ is selected from the group consisting of: H, methyl, ethyl; $R^B$ and $R^C$ are independently selected from the group consisting of: methoxy and ethoxy; and $R^5$ is selected from the group consisting of: methoxy, ethoxy, isopropoxy, chloro, bromo, and fluoro.

The present invention is further directed to compounds of Formula (II-BB)

(II-BB)

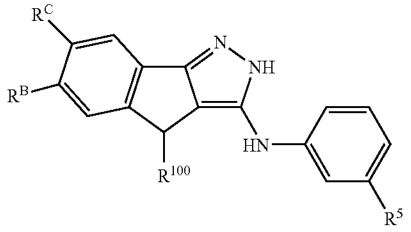

wherein $R^C$ is —O$(CH_2)_3$OH;

$R^{100}$ is selected from the group consisting of: H and alkyl;

$R^B$ is selected from the group consisting of: alkoxy; and $R^5$ is selected from the group consisting of: alkoxy and halogen;

or an optical isomer, enantiomer, diastereomer, racemate, or pharmaceutically acceptable salt thereof.

A preferred embodiment of the present invention includes compounds of Formula (II-BB) wherein $R^{100}$ is selected from the group consisting of: H, methyl, ethyl; $R^B$ is selected from the group consisting of: methoxy and ethoxy; and $R^5$ is selected from the group consisting of: methoxy, ethoxy, isopropoxy, chloro, bromo, and fluoro.

The present invention is further directed to compounds of Formula (II-CC)

(II-CC)

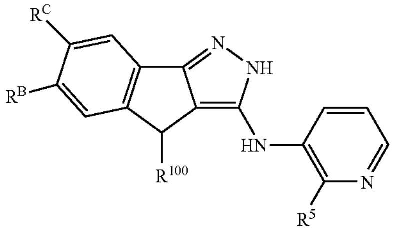

wherein $R^{100}$ is selected from the group consisting of: H and alkyl;

$R^B$ and $R^C$ are independently selected from the group consisting of: alkoxy; and $R^5$ is selected from the group consisting of: alkyl, cyano, hydroxy, alkoxy and halogen;

or an optical isomer, enantiomer, diastereomer, racemate, or pharmaceutically acceptable salt thereof.

A preferred embodiment of the present invention includes compounds of Formula (II-CC) wherein $R^{100}$ is selected from the group consisting of: H, methyl, ethyl; $R^B$ and $R^C$ are independently selected from the group consisting of: methoxy and ethoxy; and $R^5$ is selected from the group consisting of: methoxy, ethoxy, isopropoxy, chloro, methyl, cyano and hydroxy.

The present invention is further directed to compounds of Formula (II-DD)

(II-DD)

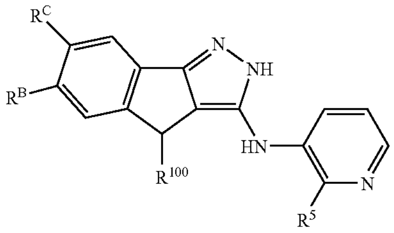

wherein $R^C$ is $—O(CH_2)_3OH$;

$R^{100}$ is selected from the group consisting of: H and alkyl;

$R^B$ is selected from the group consisting of: alkoxy; and $R^5$ is selected from the group consisting of: alkyl, cyano, hydroxy, alkoxy and halogen;

or an optical isomer, enantiomer, diastereomer, racemate, or pharmaceutically acceptable salt thereof.

A preferred embodiment of the present invention includes compounds of Formula (II-DD) wherein $R^{100}$ is selected from the group consisting of: H, methyl, and ethyl; $R^B$ is selected from the group consisting of: methoxy and ethoxy; and $R^5$ is selected from the group consisting of: methoxy, ethoxy, isopropoxy, chloro, methyl, cyano and hydroxy.

The present invention is further directed to compounds of Formula (II-EE)

(II-EE)

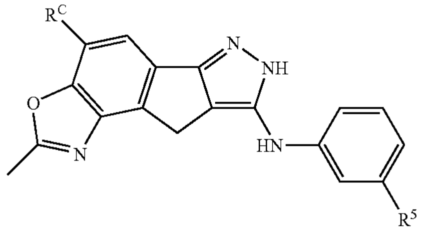

wherein $R^5$ is selected from the group consisting of: alkoxy and halogen; and $R^C$ is selected from the group consisting of: alkoxy,

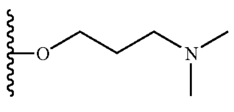 , 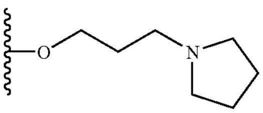 ,

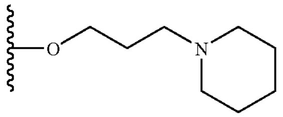 ,

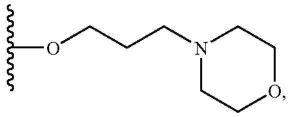 ,

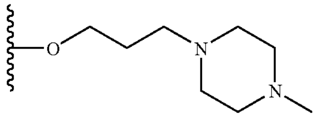 ,

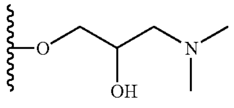 , 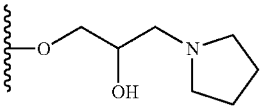 ,

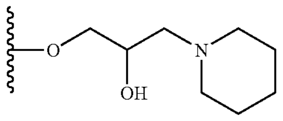 ,

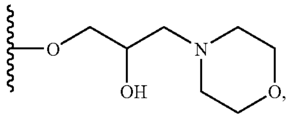 , and

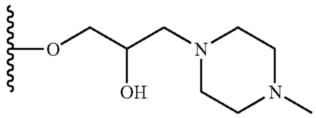 , or an optical isomer, enantiomer, diastereomer, racemate, or pharmaceutically acceptable salt thereof.

In a preferred embodiment, the present invention is further directed to compounds of Formula (II-FF)

(II-FF)

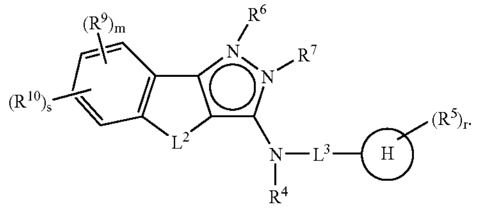

wherein $R^9$ is independently selected from the group consisting of: alkoxy, alkyl, alkylamino, amino, cyano, dialkylamino, halogen, halogenated alkyl, halogenated alkyloxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, nitro, —OC(═O)N(alkyl)$_2$, —OC(═O)NHalkyl, —$SO_2$alkyl, thio and thioalkyl;

$L^2$ is a linking group selected from the group consisting of: —$(CH_2)_{1-4}$—, —CH($R^{100}$)—, —C(═$R^{100}$)—, —C($R^{100}$)$_2$—, —O—, —O$(CH_2)_{1-4}$—, —OCH($R^{100}$)—, —OC($R^{100}$)$_2$—, —S—, —NH—, —N(lower alkyl)-, —N(COalkyl)-, —N(aryl)-, —N($CO_2$alkyl)-, —N(CONHalkyl)-, —N($SO_2$alkyl) and —N($SO_2$aryl)-; wherein $R^{100}$ is selected from: alkyl, hydroxy, aryl, alkoxy, oxo, —$NH_2$, —NH(alkyl) —N(alkyl)$_2$, ═N(OH) or —$NH_2$OH; provided that when $L^2$ is —$CH_2CH_2$—, neither $R^6$ nor $R^7$ is —$CH_2$—(C═O)NHalkyl, —$CH_2$—(C═O)N(alkyl)$_2$ or —$CH_2$C(═O)Oalkyl; provided that when $L^2$ is —OCH($R^{100}$)—, $R^{100}$ is alkoxy, and

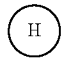

is phenyl, $R^5$ is not —C(═O)NH—$NH_2$; and provided that when $L^2$ is —O— or —S—, neither $R^6$ nor $R^7$ is —$CH_3$;

$R^{10}$ is independently selected from the group consisting of

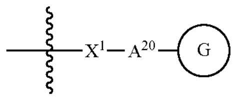

and —$X^1$-$A^{20}$-$Y^1$-$A^{21}$;

wherein $X^1$ and $Y^1$ are each independently absent or selected from the group consisting of: —(alkyl)C(═O)N(alkyl)-, —C(═O)N(alkyl)-, —C(═O)NH—, —C(═O)O—, —N(alkyl)-, —N(alkyl)C(═O)—, —N(alkyl)C(═O)NH—, —N(alkyl)C(═O)O—, —N(alkyl)$SO_2$—, —NH—, —NHC(═O)—, —NHC(═O)N(alkyl)-, —NHC(═O)NH, —NHC(═O)O—, —$NHSO_2$—, —O—, —OC(═O), —OC(═O)N(alkyl)-, —OC(═O)NH—, —OC(═O)O—, —S—, —SO—, —$SO_2$—, —$SO_2$N(alkyl)-, and —$SO_2$NH—;

$A^{20}$ is absent or selected from alkyl or alkenyl; and $A^{21}$ is selected from alkyl, alkenyl, or H;

wherein when $A^{20}$ or $A^{21}$ is alkyl or alkenyl, the alkyl or alkenyl may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, —OC(═O)alkyl, —OC(═O)N(alkyl)$_2$, —OC(═O)NHalkyl, —OC(═O)Oalkyl, —$SO_2$alkyl, thio or thioalkyl;

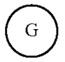

is selected from the group consisting of aryl, cycloalkyl, partially unsaturated carbocycle, heteroaryl, heterocycloalkyl, nine to ten membered benzo-fused cycloalkyl, and nine to ten membered benzo-fused heterocycloalkyl; wherein, the aryl, cycloalkyl, partially unsaturated carbocycle, heteroaryl, heterocycloalkyl, benzo-fused cycloalkyl, or benzo-fused heterocycloalkyl, are optionally substituted with one or more substituents independently selected from halogen, hydroxy, amino, thio, nitro, cyano, alkyl, halogenated alkyl, alkoxy, halogenated alkoxy, alkylamino, —NHC(═O)alkyl, —N(alkyl)C(═O)alkyl, or dialkylamino, —NHC(═O)$NH_2$, —NHC(═O)NHalkyl, —N(alkyl)C(═O)NHalkyl, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)N(alkyl)$_2$, —N(alkyl)C(═O)N(alkyl)$_2$ or —OC(═O)N(alkyl)$_2$;

s is an integer from 0 to 2;

m is an integer from 0 to 4; provided that the sum of m and s is an integer from 0 to 4;

$R^6$ and $R^7$ are independently selected from the group consisting of:

(a)

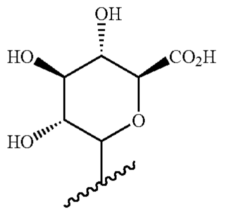

(b) provided that $R^4$ is not

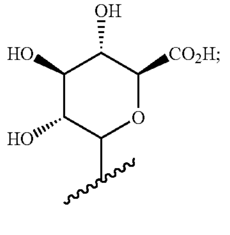

(c) —CH$_2$— substituted with one group selected from: —H, -methyl, —Oalkyl, —CH$_2$OH, —CH(CH$_3$)OH, —O(C═O)alkyl, —(C═O)OH, —C(═O)Oalkyl, —C(═O)Oaryl, —C(═O)Oheteroaryl, —(C═O)NH$_2$, —(C═O)NHalkyl, —(C═O)N(alkyl)$_2$, —C(═O)alkyl, -phenyl-OCH$_3$ or -phenyl-OC(═O)alkyl;

(d) —C(═O)(CH$_2$CH$_2$O—)$_{1-10}$ terminating with H, methyl, ethyl, or benzyl;

(e) —C(═O)CH$_2$O(CH$_2$CH$_2$O—)$_{1-10}$ terminating with H, methyl, ethyl, or benzyl;

(f) —C(═O)alkyl, or —C(═O)(C$_{3-6}$)cycloalkyl, wherein said —C(═O)alkyl, and —C(═O)(C$_{3-6}$)cycloalkyl may be optionally substituted with one or more groups independently selected from: —OH, —Oalkyl, —Oalkylaryl, —NH$_2$, —NHalkyl, —N(alkyl)$_2$, heterocycloalkyl, —NHC(═O)alkyl, —NHSO$_2$alkyl, or —OC(═O)alkyl;

(g) —C(═O)(CH$_2$)$_{1-3}$aryl, —C(═O)aryl, —C(═O)(CH$_2$)$_{1-3}$heteroaryl, or —C(═O)heteroaryl, wherein said —C(═O)(CH$_2$)$_{1-3}$aryl, —C(═O)aryl, —C(═O)(CH$_2$)$_{1-3}$heteroaryl, and —C(═O)heteroaryl may be optionally substituted with one or more groups independently selected from: —OH, —Oalkyl, —NH$_2$, —NHalkyl, —N(alkyl)$_2$, heterocycloalkyl, —NHC(═O)alkyl, —NHSO$_2$alkyl, halogen, nitrile, or —OC(═O)alkyl;

(h) —C(═O)(CH$_2$)$_{1-6}$C(═O)— terminating with methyl, ethyl, —OH, —Oalkyl, —NH$_2$, —NHalkyl, —N(alkyl)$_2$, or heterocycloalkyl;

(hh) —C(═O)alkylOC(═O)alkyl-terminating with —OH, —Oalkyl, —NH$_2$, —NHalkyl, —N(alkyl)$_2$, or heterocycloalkyl;

(i) —C(═O)O(CH$_2$CH$_2$O—)$_{1-10}$ terminating with H, methyl, ethyl, or benzyl;

(j) —C(═O)Oalkyl, or —C(═O)O(C$_{3-6}$)cycloalkyl, wherein said —C(═O)Oalkyl, and —C(═O)O(C$_{3-6}$)cycloalkyl may be optionally substituted with one or more groups independently selected from: —OH, —Oalkyl, —NH$_2$, —NHalkyl, —N(alkyl)$_2$, heterocycloalkyl, —NHC(═O)alkyl, —NHSO$_2$alkyl, —OC(═O)alkyl, —C(═O)OH, —C(═O)Oalkyl, —C(═O)NH$_2$, —C(═O)NHalkyl, or —C(═O)N(alkyl)$_2$;

(k) —C(═O)O(CH$_2$)$_{1-3}$aryl, —C(═O)Oaryl, —C(═O)O(CH$_2$)$_{1-3}$heteroaryl, or —C(═O)Oheteroaryl, wherein said —C(═O)O(CH$_2$)$_{1-3}$aryl, —C(═O)Oaryl, —C(═O)O(CH$_2$)$_{1-3}$heteroaryl, or —C(═O)Oheteroaryl may be optionally substituted with one or more groups independently selected from: —OH, —Oalkyl, —NH$_2$, —NHalkyl, —N(alkyl)$_2$, heterocycloalkyl, —NHC(═O)alkyl, —NHSO$_2$alkyl, halogen, nitrile, or —OC(═O)alkyl;

(l) —C(═O)NH(CH$_2$CH$_2$O—)$_{1-10}$ terminating with —H, methyl, ethyl, benzyl, —CH$_2$CH$_2$NH$_2$, —CH$_2$CH$_2$NHalkyl, —CH$_2$CH$_2$N(alkyl)$_2$, —CH$_2$CH$_2$-1-pyrrolidinyl, —CH$_2$CH$_2$-1-piperidinyl, —CH$_2$CH$_2$-4-morpholinyl, —CH$_2$CH$_2$-1-piperazinyl, —CH$_2$CH$_2$-1-(4-CH$_3$)-piperazinyl or —C(═O)alkyl;

(m) —C(═O)NH$_2$, —C(═O)NH(C$_{1-20}$)alkyl, —C(═O)NH(C$_{3-6}$)cycloalkyl, or —C(═O)N(alkyl)$_2$, wherein said —C(═O)NH(C$_{1-20}$)alkyl, —C(═O)NH(C$_{3-6}$)cycloalkyl, and —C(═O)N(alkyl)$_2$ may be optionally substituted with one or more groups independently selected from: —OH, —Oalkyl, —NH$_2$, —NHalkyl, —N(alkyl)$_2$, heterocycloalkyl, —NHC(═O)alkyl, —NHSO$_2$alkyl, —OC(═O)alkyl, —OC(═O)alkenyl, —NHC(═O)aryl, —C(═O)OH, —C(═O)Oalkyl, —C(═O)NH$_2$, —C(═O)NHalkyl, or —C(═O)N(alkyl)$_2$; and, wherein the aryl portion of said —NHC(═O)aryl may be optionally substituted with one or more groups independently selected from: alkyl, —OH, —Oalkyl, —NH$_2$, —NHalkyl, —N(alkyl)$_2$, halogen or nitrile;

(n) —C(═O)NH(CH$_2$)$_{1-3}$aryl, —C(═O)NHaryl, —C(═O)NH(CH$_2$)$_{1-3}$heteroaryl, or —C(═O)NHheteroaryl, wherein said —C(═O)NH(CH$_2$)$_1$-3aryl, —C(═O)NHaryl, —C(═O)NH(CH$_2$)$_{1-3}$heteroaryl, and —C(═O)NHheteroaryl may be optionally substituted with one or more groups independently selected from: —OH, —Oalkyl, —NH$_2$, —NHalkyl, —N(alkyl)$_2$, heterocycloalkyl, —NHC(═O)alkyl, —NHSO$_2$alkyl, halogen, nitrile, or —OC(═O)alkyl;

(o) —C(═O)NHCH$_2$CH$_2$NH(CH$_2$CH$_2$NH—)$_{0-3}$ terminating with H, methyl, ethyl, —CH$_2$CH$_2$NHalkyl, —CH$_2$CH$_2$N(alkyl)$_2$, —CH$_2$CH$_2$-1-pyrrolidinyl, —CH$_2$CH$_2$-1-piperidinyl, —CH$_2$CH$_2$-4-morpholinyl, —CH$_2$CH$_2$-1-piperazinyl, —CH$_2$CH$_2$-1-(4-CH$_3$)-piperazinyl, —CH$_2$CH$_2$OH, —CH$_2$CH$_2$OCH$_3$, —CH$_2$CH$_2$OCH$_2$CH$_3$, —CH$_2$CH$_2$OC(═O)alkyl, or —C(═O)aryl; wherein the aryl portion of said —C(═O)aryl may be optionally substituted with one or more groups independently selected from: alkyl, —OH, —Oalkyl, —NH$_2$, —NHalkyl, —N(alkyl)$_2$, halogen or nitrile;

(p) —C(═S)NH$_2$;

(q) —C(═S)NHalkyl;

(r) —C(═S)N(alkyl)$_2$;

(s) —SO$_2$NH$_2$;

(t) —SO$_2$NHalkyl;

(u) —SO$_2$N(alkyl)$_2$;

(v) —P(═O)(OCH$_3$)$_2$; and (w) —P(═O)(OCH$_2$CH$_3$)$_2$;

provided that when $R^6$ is present, $R^7$ is absent; and provided that when $R^7$ is present, $R^6$ is absent;

$R^4$ is selected from the group consisting of: H and

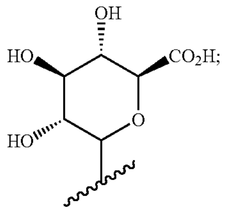

provided that if one of $R^6$ and $R^7$ is

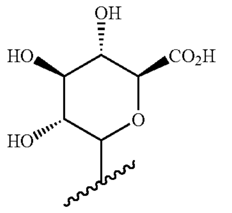

then $R^4$ is H;

$L^3$ is absent or is a linking group selected from the group consisting of alkyldiyl, carbonyl or —SO$_2$—;

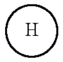

is selected from the group consisting of an aryl, a cycloalkyl, a partially unsaturated carbocycle, aralkyl, a heteroaryl, a heterocycloalkyl, a nine to ten membered benzo-fused cycloalkyl, a nine to ten membered benzo-fused heteroaryl, and a nine to ten membered benzo-fused heterocycloalkyl;

r is an integer from 0 to 4; and $R^5$ is independently selected from the group consisting of: alkyl, alkyl amino, alkyloxy, amino, —C(═O)$NH_2$, —C(═O)Oalkyl, —C(═O)OH, —$CH_2$OH, cyano, dialkylamino, halogen, halogenated alkyl, halogenated alkyloxy, halogenated $SO_2$-alkyl, halogenated thioalkyl, hydroxy, hydroxy alkyl, —N(alkyl)C(═O)alkyl, —N(alkyl)C(═O)N$(alkyl)_2$, —N(alkyl)C(═O)NHalkyl, —N(alkyl)C(═O)Oalkyl, —N(alkyl)$SO_2$alkyl, —NHC(═O)alkyl, —NHC(═O)N$(alkyl)_2$, —NHC(═O)$NH_2$, —NHC(═O)NHalkyl, —NHC(═O)Oalkyl, —NH$SO_2$alkyl, nitro, —OC(═O)N$(alkyl)_2$, —OC(═O)NHalkyl, —$SO_2$alkyl, —$SO_2NH_2$, thio, thioalkyl,

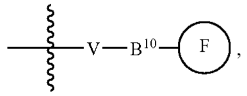

and —V—$B^{10}$—W—$B^{20}$; wherein,

V and W are each independently absent or selected from the group consisting of: —C(═O), —C(═O)N(alkyl)-, —C(═O)NH—, —C(═O)O—, —N(alkyl)-, —N(alkyl)C(═O)—, —N(alkyl)C(═O)N(alkyl)-, —N(alkyl)C(═O)NH—, —N(alkyl)C(═O)O—, —N(alkyl)$SO_2$—, —NH—, —NHC(═O)—, —NHC(═O)N(alkyl)-, —NHC(═O)NH—, —NHC(═O)O—, —NH$SO_2$—, —O—, —OC(═O), —OC(═O)N(alkyl)-, —OC(═O)NH—, —OC(═O)O—, —S—, —SO—, —$SO_2$—, —$SO_2$N(alkyl)- and —$SO_2$NH—;

$B^{10}$ is absent or selected from alkyl or alkenyl;

$B^{20}$ is absent or selected from alkyl, alkenyl, or H;

wherein, when $B^{10}$ or $B^{20}$ is alkyl or alkenyl, the alkyl or alkenyl group may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy —N(alkyl)C(═O)alkyl, —N(alkyl)C(═O)N$(alkyl)_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N$(alkyl)_2$, —NHC(═O)$NH_2$, —NHC(═O)NHalkyl, —NHC(═O)Oalkyl, —NH$SO_2$alkyl, —OC(═O)alkyl, —OC(═O)N$(alkyl)_2$, —OC(═O)NHalkyl, —OC(═O)Oalkyl, —$SO_2$alkyl, thio or thioalkyl; and

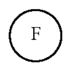

is selected from the group consisting of: an aryl, a cycloalkyl, a partially unsaturated carbocycle, a heteroaryl, a heterocycloalkyl, a nine to ten membered benzo-fused cycloalkyl, and a nine to ten membered benzo-fused heterocycloalkyl, wherein, the aryl, cycloalkyl, partially unsaturated carbocycle, heteroaryl, heterocycloalkyl, benzo-fused cycloalkyl, or benzo-fused heterocycloalkyl, is optionally substituted with one or more substituents independently selected from: alkoxy, alkylamino, amino, cyano, dialkylamino, halogen, halogenated alkoxy, halogenated alkyl, halogenated —$SO_2$alkyl, halogenated thioalkyl, heteroaryl, hydroxy, hydroxy alkyl, —N(alkyl)C(═O)alkyl, —N(alkyl)C(═O)N$(alkyl)_2$, —N(alkyl)C(═O)NHalkyl, —N(alkyl)C(═O)Oalkyl, —N(alkyl)$SO_2$alkyl, —NHC(═O)alkyl, —NHC(═O)N$(alkyl)_2$, —NHC(═O)$NH_2$, —NHC(═O)NHalkyl, —NHC(═O)Oalkyl, —NH$SO_2$alkyl, nitro, —OC(═O)N$(alkyl)_2$, —OC(═O)NHalkyl, —$SO_2$alkyl, thio or thioalkyl;

or an optical isomer, enantiomer, diastereomer, racemate, or pharmaceutically acceptable salt thereof.

Further embodiments of the invention include compounds of Formula II-FF wherein $L^2$, $R^4$, $R^6$, $R^7$, $L^3$ H, and $(R^5)_r$ vary as set forth in section 2.a.1 above for Formula II and combinations of the variations thereof.

In a preferred embodiment, the present invention is further directed to compounds of Formula (II-GG):

(II-GG)

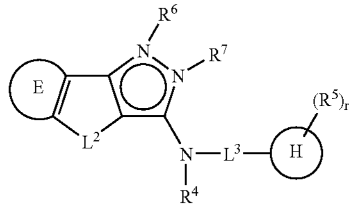

wherein:

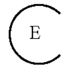

is selected from the group consisting of Formulae A-1, A-2 and A-3:

(Formula A-1)

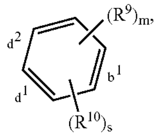

wherein Formula A-1 is attached on the by side of Formula A-1 to the $L^2$ ring of Formula (II-GG) and optionally substituted with one substituent selected from the group consisting of Formulae A-1-a, A-1-b and A-1-c:

(Formula A-1-a)

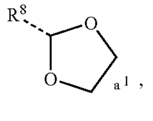

wherein Formula A-1-a is attached on the $a^1$ side to adjacent carbons on the $d^1$or $d^2$ side of Formula A-1;

(Formula A-1-b)

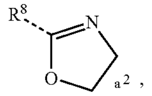

wherein Formula A-1-b is attached on the $a^2$side to adjacent carbons on the $d^1$or $d^2$ side of Formula A-1; and (Formula A-1-c)

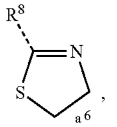

wherein Formula A-1-c is attached on the $a^6$ side to adjacent carbons on the $d^1$or $d^2$ side of Formula A-1; wherein $R^8$ is H or alkyl;

(Formula A-2)

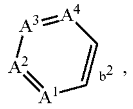

wherein Formula A-2 is attached on the $b^2$ side of Formula A-2 to the $L^2$ ring of Formula (II-GG), and $A^1$, $A^2$, $A^3$, $A^4$ are (i) —N—; or (ii) —C— substituted with H or alkoxy, wherein the alkoxy may be optionally further substituted with alkoxy on a terminal carbon or up to 3 halogen atoms on a terminal carbon; provided that at least one and no more than two of $A^1$, $A^2$, $A^3$, $A^4$ are —N—; and (Formula A-3)

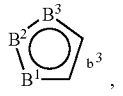

wherein Formula A-3 is attached on the $b^3$ side of Formula A-3 to the $L^2$ ring of Formula (II-GG), and $B^1$, $B^2$ and $B^3$ are independently (i) —CH— optionally substituted with alkyl, aryl, alkoxy, or halogen, (ii) —S—; (iii) —O—; or (iv) —N—; provided that no more than one of $B^1$, $B^2$ or $B^3$ is —S— or —O—, and, provided that when one of $B^1$, $B^2$ or $B^3$ is —S— or —O—, then the adjacent ring members are not —S— or —O—;

$R^9$ is independently selected from the group consisting of: alkoxy, alkyl, alkylamino, amino, cyano, dialkylamino, halogen, halogenated alkyl, halogenated alkyloxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, nitro, —OC(═O)N(alkyl)$_2$, —OC(═O)NHalkyl, —$SO_2$alkyl, thio and thioalkyl;

$L^2$ is a linking group selected from the group consisting of: —$(CH_2)_{1-4}$—, —CH($R^{100}$)—, —C(═$R^{100}$)—, —C($R^{100}$)$_2$—, —O—, —O$(CH_2)_{1-4}$—, —OCH($R^{100}$)—, —OC($R^{100}$)$_2$—, —S—, —NH—, —N(lower alkyl)-, —N(COalkyl)-, —N(aryl)-, —N($CO_2$alkyl)-, —N(CONHalkyl)-, —N($SO_2$alkyl) and —N($SO_2$aryl)-; wherein $R^{100}$ is selected from: alkyl, hydroxy, aryl, alkoxy, oxo, —$NH_2$, —NH(alkyl) —N(alkyl)$_2$, ═N(OH) or —$NH_2$OH; provided that when $L^2$ is —OCH($R^{100}$)—, $R^{100}$ is alkoxy, and

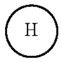

is phenyl, $R^5$ is not —C(═O)NH—$NH_2$;

$R^{10}$ is independently selected from the group consisting of

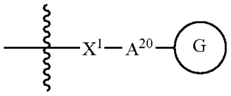

and —$X^1$-$A^{20}$-Y-$A^{21}$;

wherein $X^1$ and $Y^1$ are each independently absent or selected from the group consisting of: —(alkyl)C(═O)N(alkyl)-, —C(═O)N(alkyl)-, —C(═O)NH—, —C(═O)O—, —N(alkyl)-, —N(alkyl)C(═O)—, —N(alkyl)C(═O)NH—, —N(alkyl)C(═O)O—, —N(alkyl)$SO_2$—, —NH—, —NHC(═O)—, —NHC(═O)N(alkyl)-, —NHC(═O)NH, —NHC(═O)O—, —$NHSO_2$—, —O—, —OC(═O), —OC(═O)N(alkyl)-, —OC(═O)NH—, —OC(═O)O—, —S—, —SO—, —$SO_2$—, —$SO_2$N(alkyl)-, and —$SO_2$NH—;

$A^{20}$ is absent or selected from alkyl or alkenyl; and $A^{21}$ is selected from alkyl, alkenyl, or H;

wherein when $A^{20}$ or $A^{21}$ is alkyl or alkenyl, the alkyl or alkenyl may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, —OC(═O)alkyl, —OC(═O)N(alkyl)$_2$, —OC(═O)NHalkyl, —OC(═O)Oalkyl, —$SO_2$alkyl, thio or thioalkyl;

is selected from the group consisting of aryl, cycloalkyl, partially unsaturated carbocycle, heteroaryl, heterocycloalkyl, nine to ten membered benzo-fused cycloalkyl, and nine to ten membered benzo-fused heterocycloalkyl; wherein, the aryl, cycloalkyl, partially unsaturated carbocycle, heteroaryl, heterocycloalkyl, benzo-fused cycloalkyl, or benzo-fused heterocycloalkyl, are optionally substituted with one or more substituents indepen dently selected from halogen, hydroxy, amino, thio, nitro, cyano, alkyl, halogenated alkyl, alkoxy, halogenated alkoxy, alkylamino, —NHC(═O)alkyl, —N(alkyl)C(═O)alkyl, or dialkylamino, —NHC(═O)$NH_2$, —NHC(═O)NHalkyl, —N(alkyl)C(═O)NHalkyl, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)N$(alkyl)_2$, —N(alkyl)C(═O)N$(alkyl)_2$ or —OC(═O)N$(alkyl)_2$;

s is an integer from 0 to 2;

m is an integer from 0 to 4; provided that when

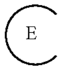

is not substituted with Formulae A-1-a, A-1-b or A-1-c, the sum of m and s is an integer from 0 to 4, and when

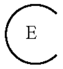

is substituted with one of Formulae A-1-a, A-1-b, or A-1-c, the sum of m and s is an integer from 0 to 2;

$R^6$ and $R^7$ are independently selected from the group consisting of:

(a) H;

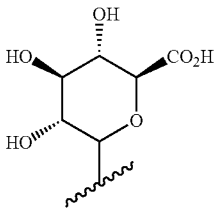

(b) provided that $R^4$ is not

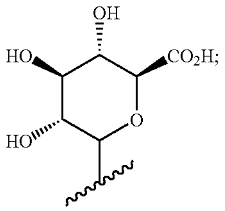

(c) alkyl (d) —C(═O)alkylOH; and (e) —C(═O)$CH_2$Oalkoxy;

provided that when $R^6$ is present, $R^7$ is absent; and provided that when $R^7$ is present, $R^6$ is absent;

$R^4$ is selected from the group consisting of: H and

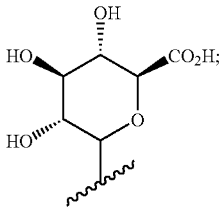

provided that if one of $R^6$ and $R^7$ is

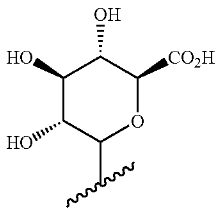

then $R^4$ is H;

$L^3$ is absent or is a linking group selected from the group consisting of alkyldiyl, carbonyl or —$SO_2$—;

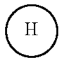

is selected from the group consisting of an aryl, a cycloalkyl, a partially unsaturated carbocycle, aralkyl, a heteroaryl, a heterocycloalkyl, a nine to ten membered benzo-fused cycloalkyl, a nine to ten membered benzo-fused heteroaryl, and a nine to ten membered benzo-fused heterocycloalkyl;

r is an integer from 0 to 4; and $R^5$ is independently selected from the group consisting of: alkyl, alkyl amino, alkyloxy, amino, —C(═O)$NH_2$, —C(═O)Oalkyl, —C(═O)OH, —$CH_2$OH, cyano, dialkylamino, halogen, halogenated alkyl, halogenated alkyloxy, halogenated $SO_2$-alkyl, halogenated thioalkyl, hydroxy, hydroxy alkyl, —N(alkyl)C(═O)alkyl, —N(alkyl)C(═O)N$(alkyl)_2$, —N(alkyl)C(═O)NHalkyl, —N(alkyl)C(═O)Oalkyl, —N(alkyl)$SO_2$alkyl, —NHC(═O)alkyl, —NHC(═O)N$(alkyl)_2$, —NHC(═O)$NH_2$, —NHC(═O)NHalkyl, —NHC(═O)Oalkyl, —$NHSO_2$alkyl, nitro, —OC(═O)N$(alkyl)_2$, —OC(═O)NHalkyl, —$SO_2$alkyl, —$SO_2NH_2$, thio, thioalkyl,

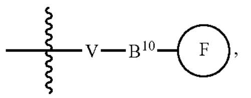

and —V—$B^{10}$—W—$B^{20}$; wherein,

V and W are each independently absent or selected from the group consisting of: —C(═O), —C(═O)N(alkyl)-, —C(═O)NH—, —C(═O)O—, —N(alkyl)-, —N(alkyl)

C(═O)—, —N(alkyl)C(═O)N(alkyl)-, —N(alkyl)C(═O)NH—, —N(alkyl)C(═O)O—, —N(alkyl)$SO_2$—, —NH—, —NHC(═O)—, —NHC(═O)N(alkyl)-, —NHC(═O)NH—, —NHC(═O)O—, —$NHSO_2$—, —O—, —OC(═O), —OC(═O)N(alkyl)-, —OC(═O)NH—, —OC(═O)O—, —S—, —SO—, —$SO_2$—, —$SO_2$N(alkyl)- and —$SO_2$NH—;

$B^{10}$ is absent or selected from alkyl or alkenyl;

$B^{20}$ is absent or selected from alkyl, alkenyl, or H;

wherein, when $B^{10}$ or $B^{20}$ is alkyl or alkenyl, the alkyl or alkenyl group may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy —N(alkyl)C(═O)alkyl, —N(alkyl)C(═O)N$(alkyl)_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N$(alkyl)_2$, —NHC(═O)$NH_2$, —NHC(═O)NHalkyl, —NHC(═O)Oalkyl, —$NHSO_2$alkyl, —OC(═O)alkyl, —OC(═O)N$(alkyl)_2$, —OC(═O)NHalkyl, —OC(═O)Oalkyl, —$SO_2$alkyl, thio or thioalkyl; and

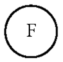

is selected from the group consisting of: an aryl, a cycloalkyl, a partially unsaturated carbocycle, a heteroaryl, a heterocycloalkyl, a nine to ten membered benzo-fused cycloalkyl, and a nine to ten membered benzo-fused heterocycloalkyl, wherein, the aryl, cycloalkyl, partially unsaturated carbocycle, heteroaryl, heterocycloalkyl, benzo-fused cycloalkyl, or benzo-fused heterocycloalkyl, is optionally substituted with one or more substituents independently selected from: alkoxy, alkylamino, amino, cyano, dialkylamino, halogen, halogenated alkoxy, halogenated alkyl, halogenated —$SO_2$alkyl, halogenated thioalkyl, heteroaryl, hydroxy, hydroxy alkyl, —N(alkyl)C(═O)alkyl, —N(alkyl)C(═O)N$(alkyl)_2$, —N(alkyl)C(═O)NHalkyl, —N(alkyl)C(═O)Oalkyl, —N(alkyl)$SO_2$alkyl, —NHC(═O)alkyl, —NHC(═O)N$(alkyl)_2$, —NHC(═O)$NH_2$, —NHC(═O)NHalkyl, —NHC(═O)Oalkyl, —$NHSO_2$alkyl, nitro, —OC(═O)N$(alkyl)_2$, —OC(═O)NHalkyl, —$SO_2$alkyl, thio or thioalkyl;

or an optical isomer, enantiomer, diastereomer, racemate, or pharmaceutically acceptable salt thereof.

Further embodiments of the invention include compounds of Formula II-GG wherein E, $L^2$, $R^4$, $L^3$ H, and $(R^5)_r$, vary as set forth in section 2. a.1 above for Formula II, and $R^6$ and $R^7$ vary as set forth below, and combinations of the aforementioned variations of E, $L^2$, $R^4$, $L^3$ H, $(R^5)_r$, $R^6$ and $R^7$.

In a preferred embodiment of the invention are compounds of Formula II-GG, wherein $R^7$ is absent, and $R^6$ is selected from the group consisting of:

(a) H;

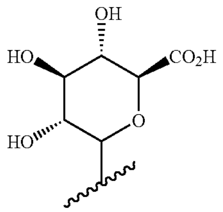

(b) provided that $R^4$ is not

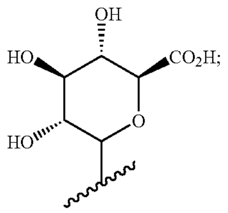

(c) methyl (d) —C(═O)$CH_2$OH; and (e) —C(═O)$CH_2$Omethoxy;

In a preferred embodiment, the present invention is further directed to compounds of Formula (II-HH):

(II-HH)

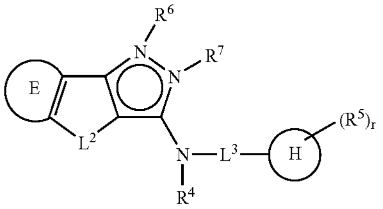

wherein:

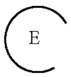

is selected from the group consisting of Formulae A-1, A-2 and A-3:

(Formula A-1)

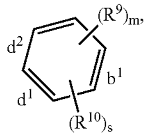

wherein Formula A-1 is attached on the $b^1$ side of Formula A-1 to the $^2$ ring of formula (II-HH) and optionally substituted with one substituent selected from the group consisting of Formulae A-1-a, A-1-b and A-1-c:

(Formula A-1-a)

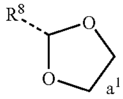

, wherein Formula A-1-a is attached on the $a^1$ side to adjacent carbons on the $d^1$or $d^2$ side of Formula A-1;

(Formula A-1-b)

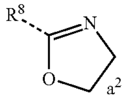

, wherein Formula A-1-b is attached on the $a^2$side to adjacent carbons on the $d^1$or $d^2$ side of Formula A-1; and (Formula A-1-c)

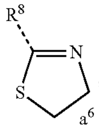

, wherein Formula A-1-c is attached on the $a^6$ side to adjacent carbons on the $d^1$or $d^2$ side of Formula A-1; wherein $R^8$ is H or alkyl;

(Formula A-2)

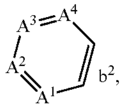

, wherein Formula A-2 is attached on the $b^2$ side of Formula A-2 to the $L^2$ ring of formula (II-HH), and $A^1$, $A^2$, $A^3$, $A^4$ are (i) —N—; or (ii) —C— substituted with H or alkoxy, wherein the alkoxy may be optionally further substituted with alkoxy on a terminal carbon or up to 3 halogen atoms on a terminal carbon; provided that at least one and no more than two of $A^1$, $A^2$, $A^3$, $A^4$ are —N—; and (Formula A-3)

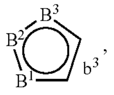

, wherein Formula A-3 is attached on the $b^3$ side of Formula A-3 to the $L^2$ ring of formula (II-HH), and $B^1$, $B^2$ and $B^3$ are independently (i) —CH— optionally substituted with alkyl, aryl, alkoxy, or halogen, (ii) —S—; (iii) —O—; or (iv) —N—; provided that no more than one of $B^1$, $B^2$ or $B^3$ is —S— or —O—, and, provided that when one of $B^1$, $B^2$ or $B^3$ is —S— or —O—, then the adjacent ring members are not —S— or —O—;

$R^9$ is independently selected from the group consisting of: alkoxy, alkyl, alkylamino, amino, cyano, dialkylamino, halogen, halogenated alkyl, halogenated alkyloxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, nitro, —OC(═O)N(alkyl)$_2$, —OC(═O)NHalkyl, —$SO_2$alkyl, thio and thioalkyl;

$L^2$ is a linking group selected from the group consisting of: —($CH_2$)—, —CH($CH_3$)—, —CH($CH_2CH_3$)—, and —O—, provided that when $L^2$ is —O—, neither $R^6$ nor $R^7$ is —$CH_3$;

$R^{10}$ is independently selected from the group consisting of

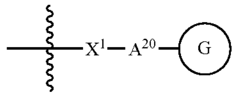

and —$X^1$-$A^{20}$-$Y^1$-$A^{21}$, wherein $X^1$ and $Y^1$ are each independently absent or selected from the group consisting of: -(alkyl)C(═O)N(alkyl)-, —C(═O)N(alkyl)-, —C(═O)NH—, —C(═O)O—, —N(alkyl)-, —N(alkyl)C(═O)—, —N(alkyl)C(═O)NH—, —N(alkyl)C(═O)O—, —N(alkyl)$SO_2$—, —NH—, —NHC(═O)—, —NHC(═O)N(alkyl)-, —NHC(═O)NH, —NHC(═O)O—, —$NHSO_2$—, —O—, —OC(═O), —OC(═O)N(alkyl)-, —OC(═O)NH—, —OC(═O)O—, —S—, —SO—, —$SO_2$—, —$SO_2$N(alkyl)-, and —$SO_2$NH—;

$A^{20}$ is absent or selected from alkyl or alkenyl; and $A^{21}$ is selected from alkyl, alkenyl, or H;

wherein when $A^{20}$ or $A^{21}$ is alkyl or alkenyl, the alkyl or alkenyl may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, —OC(═O)alkyl, —OC(═O)N(alkyl)$_2$, —OC(═O)NHalkyl, —OC(═O)Oalkyl, —$SO_2$alkyl, thio or thioalkyl;

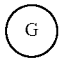

is selected from the group consisting of aryl, cycloalkyl, partially unsaturated carbocycle, heteroaryl, heterocycloalkyl, nine to ten membered benzo-fused cycloalkyl, and nine to ten membered benzo-fused heterocycloalkyl; wherein, the aryl, cycloalkyl, partially unsaturated carbocycle, heteroaryl, heterocycloalkyl, benzo-fused cycloalkyl, or benzo-fused heterocycloalkyl, are optionally substituted with one or more substituents independently selected from halogen, hydroxy, amino, thio, nitro, cyano, alkyl, halogenated alkyl, alkoxy, halogenated alkoxy, alkylamino, —NHC(═O)alkyl, —N(alkyl)C(═O)alkyl, or dialkylamino, —NHC(═O)$NH_2$—NHC(═O)NHalkyl, —N(alkyl)C(═O)NHalkyl, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(=O)N(alkyl)$_2$, —N(alkyl)C(=O)N(alkyl)$_2$ or —OC(=O)N(alkyl)$_2$;

s is an integer from 0 to 2;

m is an integer from 0 to 4; provided that when

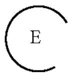

is not substituted with Formulae A-1-a, A-1-b or A-1-c, the sum of m and s is an integer from 0 to 4, and when

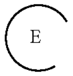

is substituted with one of Formulae A-1-a, A-1-b, or A-1-c, the sum of m and s is an integer from 0 to 2;

$R^6$ and $R^7$ are independently selected from the group consisting of:

(a) H;

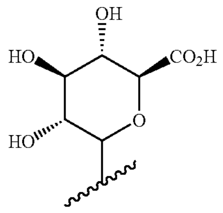

(b) provided that $R^4$ is not

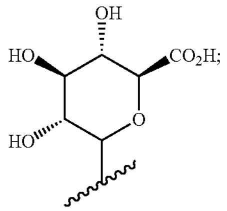

(c) —$CH_2$— substituted with one group selected from: —H, -methyl, —Oalkyl, —$CH_2$OH, —CH($CH_3$)OH, —O(C=O)alkyl, —(C=O)OH, —C(=O)Oalkyl, —C(=O)Oaryl, —C(=O)Oheteroaryl, —(C=O)$NH_2$, —(C=O)NHalkyl, —(C=O)N(alkyl)$_2$, —C(=O)alkyl, -phenyl-$OCH_3$ or -phenyl-OC(=O)alkyl;

(d) —C(=O)($CH_2CH_2O$—)$_{1-10}$ terminating with H, methyl, ethyl, or benzyl;

(e) —C(=O)$CH_2O$($CH_2CH_2O$—)$_{1-10}$ terminating with H, methyl, ethyl, or benzyl;

(f) —C(=O)alkyl, or —C(=O)($C_{3-6}$)cycloalkyl, wherein said —C(=O)alkyl, and —C(=O)($C_{3-6}$)cycloalkyl may be optionally substituted with one or more groups independently selected from: —OH, —Oalkyl, —Oalkylaryl, —$NH_2$, —NHalkyl, —N(alkyl)$_2$, heterocycloalkyl, —NHC(=O)alkyl, —$NHSO_2$alkyl, or —OC(=O)alkyl;

(g) —C(=O)($CH_2$)$_{1-3}$aryl, —C(=O)aryl, —C(=O)($CH_2$)$_{1-3}$heteroaryl, or —C(=O)heteroaryl, wherein said —C(=O)($CH_2$)$_{1-3}$aryl, —C(=O)aryl, —C(=O)($CH_2$)$_{1-3}$heteroaryl, and —C(=O)heteroaryl may be optionally substituted with one or more groups independently selected from: —OH, —Oalkyl, —$NH_2$, —NHalkyl, —N(alkyl)$_2$, heterocycloalkyl, —NHC(=O)alkyl, —$NHSO_2$alkyl, halogen, nitrile, or —OC(=O)alkyl;

(h) —C(=O)($CH_2$)$_{1-6}$C(=O)— terminating with methyl, ethyl, —OH, —Oalkyl, —$NH_2$, —NHalkyl, —N(alkyl)$_2$, or heterocycloalkyl;

(hh) —C(=O)alkylOC(=O)alkyl-terminating with —OH, —Oalkyl, —$NH_2$, —NHalkyl, —N(alkyl)$_2$, or heterocycloalkyl;

(i) —C(=O)O($CH_2CH_2O$—)$_{1-10}$ terminating with H, methyl, ethyl, or benzyl;

(j) —C(=O)Oalkyl, or —C(=O)O($C_{3-6}$)cycloalkyl, wherein said —C(=O)Oalkyl, and —C(=O)O($C_{3-6}$)cycloalkyl may be optionally substituted with one or more groups independently selected from: —OH, —Oalkyl, —$NH_2$, —NHalkyl, —N(alkyl)$_2$, heterocycloalkyl, —NHC(=O)alkyl, —$NHSO_2$alkyl, —OC(=O)alkyl, —C(=O)OH, —C(=O)Oalkyl, —C(=O)$NH_2$, —C(=O)NHalkyl, or —C(=O)N(alkyl)$_2$;

(k) —C(=O)O($CH_2$)$_{1-3}$aryl, —C(=O)Oaryl, —C(=O)O($CH_2$)$_{1-3}$heteroaryl, or —C(=O)Oheteroaryl, wherein said —C(=O)O($CH_2$)$_{1-3}$aryl, —C(=O)Oaryl, —C(=O)O($CH_2$)$_{1-3}$heteroaryl, or —C(=O)Oheteroaryl may be optionally substituted with one or more groups independently selected from: —OH, —Oalkyl, —$NH_2$, —NHalkyl, —N(alkyl)$_2$, heterocycloalkyl, —NHC(=O)alkyl, —$NHSO_2$alkyl, halogen, nitrile, or —OC(=O)alkyl;

(l) —C(=O)NH($CH_2CH_2O$—)$_{1-10}$ terminating with —H, methyl, ethyl, benzyl, —$CH_2CH_2NH_2$, —$CH_2CH_2$NHalkyl, —$CH_2CH_2$N(alkyl)$_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl or —C(=O)alkyl;

(m) —C(=O)$NH_2$, —C(=O)NH($C_{1-20}$)alkyl, —C(=O)NH($C_{3-6}$)cycloalkyl, or —C(=O)N(alkyl)$_2$, wherein said —C(=O)NH($C_{1-20}$)alkyl, —C(=O)NH($C_{3-6}$)cycloalkyl, and —C(=O)N(alkyl)$_2$ may be optionally substituted with one or more groups independently selected from: —OH, —Oalkyl, —$NH_2$, —NHalkyl, —N(alkyl)$_2$, heterocycloalkyl, —NHC(=O)alkyl, —$NHSO_2$alkyl, —OC(=O)alkyl, —OC(=O)alkenyl, —NHC(=O)aryl, —C(=O)OH, —C(=O)Oalkyl, —C(=O)$NH_2$, —C(=O)NHalkyl, or —C(=O)N(alkyl)$_2$; and, wherein the aryl portion of said —NHC(=O)aryl may be optionally substituted with one or more groups independently selected from: alkyl, —OH, —Oalkyl, —$NH_2$, —NHalkyl, —N(alkyl)$_2$, halogen or nitrile;

(n) —C(=O)NH($CH_2$)$_{1-3}$aryl, —C(=O)NHaryl, —C(=O)NH($CH_2$)$_{1-3}$heteroaryl, or —C(=O)NHheteroaryl, wherein said —C(=O)NH($CH_2$)$_{1-3}$aryl, —C(=O)NHaryl, —C(=O)NH($CH_2$)$_{1-3}$heteroaryl, and —C(=O)NHheteroaryl may be optionally substituted with one or more groups independently selected from: —OH, —Oalkyl, —$NH_2$, —NHalkyl, —N(alkyl)$_2$, heterocycloalkyl, —NHC(=O)alkyl, —$NHSO_2$alkyl, halogen, nitrile, or —OC(=O)alkyl;

(o) —C(=O)$NHCH_2CH_2NH$($CH_2CH_2NH$—)$_{0-3}$ terminating with H, methyl, ethyl, —$CH_2CH_2$NHalkyl, —$CH_2CH_2$N(alkyl)$_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl, —$CH_2CH_2OH$, —$CH_2CH_2OCH_3$, —$CH_2CH_2OCH_2CH_3$, —$CH_2CH_2$OC(=O)alkyl, or —C(=O)aryl; wherein the aryl portion of said —C(=O) aryl may be optionally substituted with one or more groups independently selected from: alkyl, —OH, —Oalkyl, —$NH_2$, —NHalkyl, —N(alkyl)$_2$, halogen or nitrile;

(p) —C(=S)$NH_2$;

(q) —C(=S)NHalkyl;

(r) —C(=S)N(alkyl)$_2$;

(s) —$SO_2NH_2$;

(t) —$SO_2$NHalkyl;

(u) —$SO_2$N(alkyl)$_2$;

(v) —P(=O)($OCH_3$)$_2$; and (w) —P(=O)($OCH_2CH_3$)$_2$;

provided that when $R^6$ is present, $R^7$ is absent; and provided that when $R^7$ is present, $R^6$ is absent;

$R^4$ is selected from the group consisting of: H and

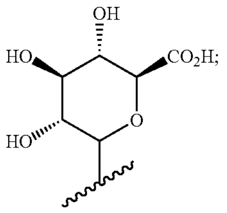

provided that if one of $R^6$and $R^7$ is

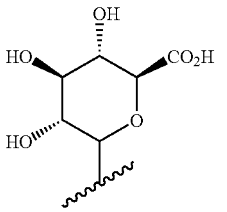

then $R^4$ is H;

$L^3$ is absent or is a linking group selected from the group consisting of alkyldiyl, carbonyl or —$SO_2$—;

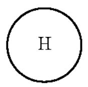

is selected from the group consisting of an aryl, a cycloalkyl, a partially unsaturated carbocycle, aralkyl, a heteroaryl, a heterocycloalkyl, a nine to ten membered benzo-fused cycloalkyl, a nine to ten membered benzo-fused heteroaryl, and a nine to ten membered benzo-fused heterocycloalkyl;

r is an integer from 0 to 4; and $R^5$ is independently selected from the group consisting of: alkyl, alkyl amino, alkyloxy, amino, —C(=O)$NH_2$, —C(=O)Oalkyl, —C(=O)OH, —$CH_2$OH, cyano, dialkylamino, halogen, halogenated alkyl, halogenated alkyloxy, halogenated $SO_2$-alkyl, halogenated thioalkyl, hydroxy, hydroxy alkyl, —N(alkyl)C(=O)alkyl, —N(alkyl)C(=O)N(alkyl)$_2$, —N(alkyl)C(=O)NHalkyl, —N(alkyl)C(=O)Oalkyl, —N(alkyl)$SO_2$alkyl, —NHC(=O)alkyl, —NHC(=O)N(alkyl)$_2$, —NHC(=O)$NH_2$, —NHC(=O)NHalkyl, —NHC(=O)Oalkyl, —$NHSO_2$alkyl, nitro, —OC(=O)N(alkyl)$_2$, —OC(=O)NHalkyl, —$SO_2$alkyl, —$SO_2NH_2$, thio, thioalkyl,

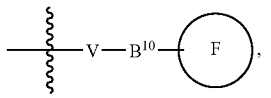

and —V—$B^{10}$—W—$B^{20}$; wherein,

V and W are each independently absent or selected from the group consisting of: —C(=O), —C(=O)N(alkyl)-, —C(=O)NH—, —C(=O)O—, —N(alkyl)-, —N(alkyl)C(=O)—, —N(alkyl)C(=O)N(alkyl)-, —N(alkyl)C(=O)NH—, —N(alkyl)C(=O)O—, —N(alkyl)$SO_2$—, —NH—, —NHC(=O)—, —NHC(=O)N(alkyl)-, —NHC(=O)NH—, —NHC(=O)O—, —$NHSO_2$—, —O—, —OC(=O), —OC(=O)N(alkyl)-, —OC(=O)NH—, —OC(=O)O—, —S—, —SO—, —$SO_2$—, —$SO_2$N(alkyl)- and —$SO_2$NH—;

$B^{10}$ is absent or selected from alkyl or alkenyl;

$B^{20}$ is absent or selected from alkyl, alkenyl, or H;

wherein, when $B^{10}$ or $B^{20}$ is alkyl or alkenyl, the alkyl or alkenyl group may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy —N(alkyl)C(=O)alkyl, —N(alkyl)C(=O)N(alkyl)$_2$, —N(alkyl)C(=O)$NH_2$, —N(alkyl)C(=O)NHalkyl, —N(alkyl)C(=O)Oalkyl, —N(alkyl)$SO_2$alkyl, —NHC(=O)alkyl, —NHC(=O)N(alkyl)$_2$, —NHC(=O)$NH_2$, —NHC(=O)NHalkyl, —NHC(=O)Oalkyl, —$NHSO_2$alkyl, —OC(=O)alkyl, —OC(=O)N(alkyl)$_2$, —OC(=O)NHalkyl, —OC(=O)Oalkyl, —$SO_2$alkyl, thio or thioalkyl; and

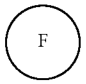

is selected from the group consisting of: an aryl, a cycloalkyl, a partially unsaturated carbocycle, a heteroaryl, a heterocycloalkyl, a nine to ten membered benzo-fused cycloalkyl, and a nine to ten membered benzo-fused heterocycloalkyl, wherein, the aryl, cycloalkyl, partially unsaturated carbocycle, heteroaryl, heterocycloalkyl, benzo-fused cycloalkyl, or benzo-fused heterocycloalkyl, is optionally substituted with one or more substituents independently selected from: alkoxy, alkylamino, amino, cyano, dialkylamino, halogen, halogenated alkoxy, halogenated alkyl, halogenated —$SO_2$alkyl, halogenated thioalkyl, heteroaryl, hydroxy, hydroxy alkyl, —N(alkyl)C(=O)alkyl, —N(alkyl)C(=O)N(alkyl)$_2$, —N(alkyl)C(=O)NHalkyl, —N(alkyl)C(=O)Oalkyl, —N(alkyl)$SO_2$alkyl, —NHC(=O)alkyl, —NHC(=O)N(alkyl)$_2$, —NHC(=O)$NH_2$, —NHC(=O)NHalkyl, —NHC(=O)Oalkyl, —$NHSO_2$alkyl, nitro, —OC(=O)N(alkyl)$_2$, —OC(=O)NHalkyl, —$SO_2$alkyl, thio or thioalkyl;

or an optical isomer, enantiomer, diastereomer, racemate, or pharmaceutically acceptable salt thereof.

Further embodiments of the invention include compounds of Formula II-HH wherein E, $R^4$, $R^6$, $R^7$, $L^3$ H, and $(R^5)_r$ vary as set forth in section 2. a.1 above for Formula II, and $L^2$ varies as set forth below, and combinations of the aforementioned variations of E, $L^2$, $R^4$, $R^6$, $R^7$, $L^3$ H, $(R^5)_r$.

In a preferred embodiment of the invention are compounds of Formula II-HH, wherein $L^2$ is a linking group selected from the group consisting of: $—(CH_2)—$, $—CH(CH_3)—$, $—CH(CH_2CH_3)—$.

In a preferred embodiment, the present invention is further directed to compounds of Formula (II-JJ):

(II-JJ)

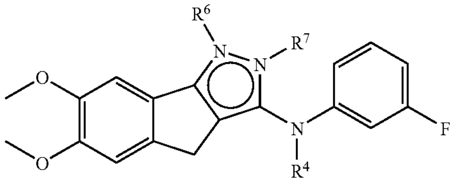

wherein $R^6$ and $R^7$ are independently selected from the group consisting of:

(a) H;

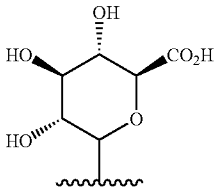

(b) provided that $R^4$ is not

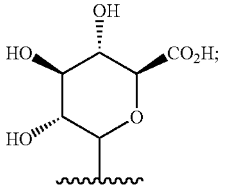

(c) $—CH_2—$ substituted with one group selected from: —H, -methyl, —Oalkyl, $—CH_2OH$, $—CH(CH_3)OH$, —O(C═O)alkyl, —(C═O)OH, —C(═O)Oalkyl, —C(═O)Oaryl, —C(═O)Oheteroaryl, $—(C═O)NH_2$, —(C═O)NHalkyl, $—(C═O)N(alkyl)_2$, —C(═O)alkyl, -phenyl-$OCH_3$ or -phenyl-OC(═O)alkyl;

(d) $—C(═O)(CH_2CH_2O—)_{1-10}$ terminating with H, methyl, ethyl, or benzyl;

(e) $—C(═O)CH_2O(CH_2CH_2O—)_{1-10}$ terminating with H, methyl, ethyl, or benzyl;

(f) —C(═O)alkyl, or $—C(═O)(C_{3-6})$cycloalkyl, wherein said —C(═O)alkyl, and $—C(═O)(C_{3-6})$cycloalkyl may be optionally substituted with one or more groups independently selected from: —OH, —Oalkyl, —Oalkylaryl, $—NH_2$, —NHalkyl, $—N(alkyl)_2$, heterocycloalkyl, —NHC(═O)alkyl, $—NHSO_2$alkyl, or —OC(═O)alkyl;

(g) $—C(═O)(CH_2)_{1-3}$aryl, —C(═O)aryl, —C(═O)$(CH_2)_{1-3}$heteroaryl, or —C(═O)heteroaryl, wherein said $—C(═O)(CH_2)_{1-3}$aryl, —C(═O)aryl, —C(═O)$(CH_2)_{1-3}$heteroaryl, and —C(═O)heteroaryl may be optionally substituted with one or more groups independently selected from: —OH, —Oalkyl, $—NH_2$, —NHalkyl, $—N(alkyl)_2$, heterocycloalkyl, —NHC(═O)alkyl, $—NHSO_2$alkyl, halogen, nitrile, or —OC(═O)alkyl;

(h) $—C(═O)(CH_2)_{1-6}C(═O)—$ terminating with methyl, ethyl, —OH, —Oalkyl, $—NH_2$, —NHalkyl, $—N(alkyl)_2$, or heterocycloalkyl;

(hh) —C(═O)alkylOC(═O)alkyl-terminating with —OH, —Oalkyl, $—NH_2$, —NHalkyl, $—N(alkyl)_2$, or heterocycloalkyl;

(i) $—C(═O)O(CH_2CH_2O—)_{1-10}$ terminating with H, methyl, ethyl, or benzyl;

(j) —C(═O)Oalkyl, or $—C(═O)O(C_{3-6})$cycloalkyl, wherein said —C(═O)Oalkyl, and $—C(═O)O(C_{3-6})$cycloalkyl may be optionally substituted with one or more groups independently selected from: —OH, —Oalkyl, $—NH_2$, —NHalkyl, $—N(alkyl)_2$, heterocycloalkyl, —NHC(═O)alkyl, $—NHSO_2$alkyl, —OC(═O)alkyl, —C(═O)OH, —C(═O)Oalkyl, $—C(═O)NH_2$, —C(═O)NHalkyl, or $—C(═O)N(alkyl)_2$;

(k) $—C(═O)O(CH_2)_{1-3}$aryl, —C(═O)Oaryl, —C(═O)O$(CH_2)_{1-3}$heteroaryl, or —C(═O)Oheteroaryl, wherein said $—C(═O)O(CH_2)_{1-3}$aryl, —C(═O)Oaryl, —C(═O)O$(CH_2)_{1-3}$heteroaryl, or —C(═O)Oheteroaryl may be optionally substituted with one or more groups independently selected from: —OH, —Oalkyl, $—NH_2$, —NHalkyl, $—N(alkyl)_2$, heterocycloalkyl, —NHC(═O)alkyl, $—NHSO_2$alkyl, halogen, nitrile, or —OC(═O)alkyl;

(l) $—C(═O)NH(CH_2CH_2O—)_{1-10}$ terminating with —H, methyl, ethyl, benzyl, $—CH_2CH_2NH_2$, $—CH_2CH_2$NHalkyl, $—CH_2CH_2N(alkyl)_2$, $—CH_2CH_2$-1-pyrrolidinyl, $—CH_2CH_2$-1-piperidinyl, $—CH_2CH_2$-4-morpholinyl, $—CH_2CH_2$-1-piperazinyl, $—CH_2CH_2$-1-(4-$CH_3$)-piperazinyl or —C(═O)alkyl;

(m) $—C(═O)NH_2$, $—C(═O)NH(C_{1-20})$alkyl, —C(═O)NH$(C_{3-6})$cycloalkyl, or $—C(═O)N(alkyl)_2$, wherein said $—C(═O)NH(C_{1-20})$alkyl, $—C(═O)NH(C_{3-6})$cycloalkyl, and $—C(═O)N(alkyl)_2$ may be optionally substituted with one or more groups independently selected from: —OH, —Oalkyl, $—NH_2$, —NHalkyl, $—N(alkyl)_2$, heterocycloalkyl, —NHC(═O)alkyl, $—NHSO_2$alkyl, —OC(═O)alkyl, —OC(═O)alkenyl, —NHC(═O)aryl, —C(═O)OH, —C(═O)Oalkyl, $—C(═O)NH_2$, —C(═O)NHalkyl, or $—C(═O)N(alkyl)_2$; and, wherein the aryl portion of said —NHC(═O)aryl may be optionally substituted with one or more groups independently selected from: alkyl, —OH, —Oalkyl, $—NH_2$, —NHalkyl, $—N(alkyl)_2$, halogen or nitrile;

(n) $—C(═O)NH(CH_2)_{1-3}$aryl, —C(═O)NHaryl, —C(═O)NH$(CH_2)_{1-3}$heteroaryl, or —C(═O)NHheteroaryl, wherein said $—C(═O)NH(CH_2)_{1-3}$aryl, —C(═O)NHaryl, $—C(═O)NH(CH_2)_{1-3}$heteroaryl, and —C(═O)NHheteroaryl may be optionally substituted with one or more groups independently selected from: —OH, —Oalkyl, $—NH_2$, —NHalkyl, $—N(alkyl)_2$, heterocycloalkyl, —NHC(═O)alkyl, $—NHSO_2$alkyl, halogen, nitrile, or —OC(═O)alkyl;

(o) $—C(═O)NHCH_2CH_2NH(CH_2CH_2NH—)_{0-3}$ terminating with H, methyl, ethyl, $—CH_2CH_2$NHalkyl, $—CH_2CH_2N(alkyl)_2$, $—CH_2CH_2$-1-pyrrolidinyl, $—CH_2CH_2$-1-piperidinyl, $—CH_2CH_2$-4-morpholinyl, $—CH_2CH_2$-1-piperazinyl, $—CH_2CH_2$-1-(4-$CH_3$)-piperazinyl, $—CH_2CH_2OH$, $—CH_2CH_2OCH_3$, $—CH_2CH_2OCH_2CH_3$, $—CH_2CH_2OC(═O)$alkyl, or —C(═O)aryl; wherein the aryl portion of said —C(═O)aryl may be optionally substituted with one or more groups independently selected from: alkyl, —OH, —Oalkyl, —$NH_2$, —NHalkyl, —N(alkyl)$_2$, halogen or nitrile;

(p) —C(=S)$NH_2$;

(q) —C(=S)NHalkyl;

(r) —C(=S)N(alkyl)$_2$;

(s) —$SO_2NH_2$;

(t) —$SO_2$NHalkyl;

(u) —$SO_2$N(alkyl)$_2$;

(v) —P(=O)($OCH_3$)$_2$; and (w) —P(=O)($OCH_2CH_3$)$_2$;

provided that when $R^6$ is present, $R^7$ is absent; and provided that when $R^7$ is present, $R^6$ is absent;

$R^4$ is selected from the group consisting of: H and

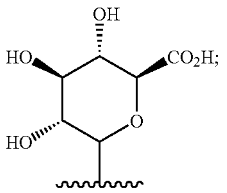

provided that if one of $R^6$ and $R^7$ is

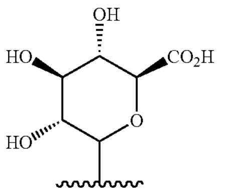

then $R^4$ is H;

or an optical isomer, enantiomer, diastereomer, racemate, or pharmaceutically acceptable salt thereof.

Further embodiments of the invention include compounds of Formula II-JJ wherein $R^6$ and $R^7$ vary as set forth in section 2. a.1 above for Formula II.

2.c Preferred Compounds

In a preferred embodiment, the present invention is further directed to a compound selected from the group consisting of:

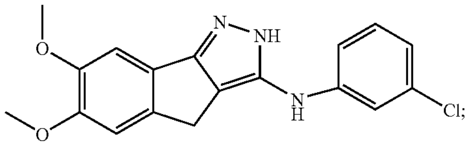

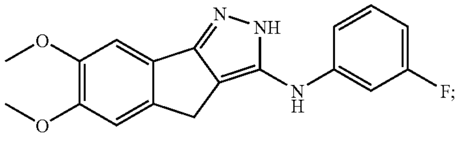

-continued

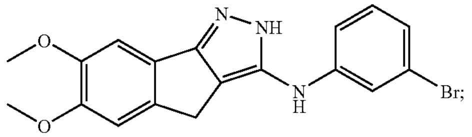

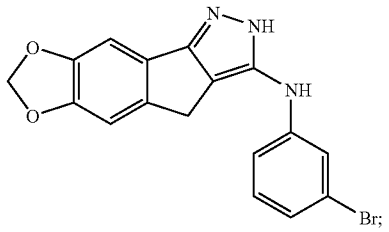

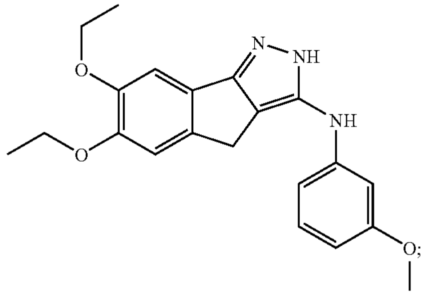

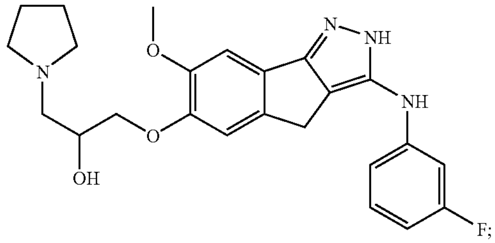

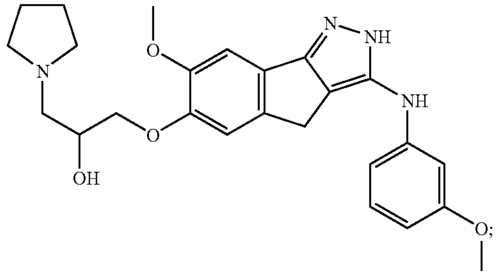

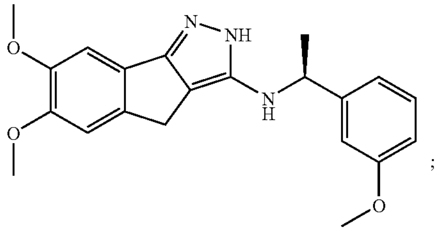

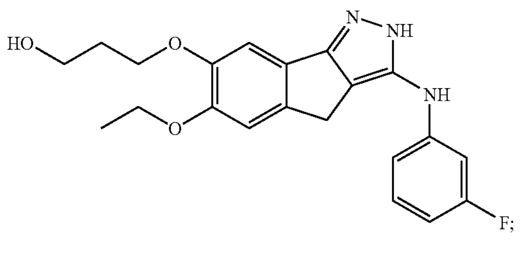

-continued
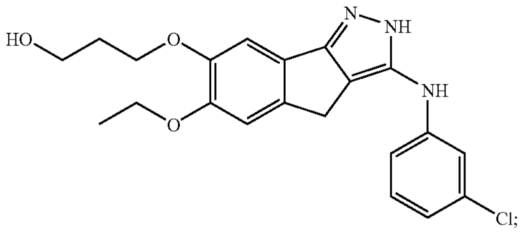
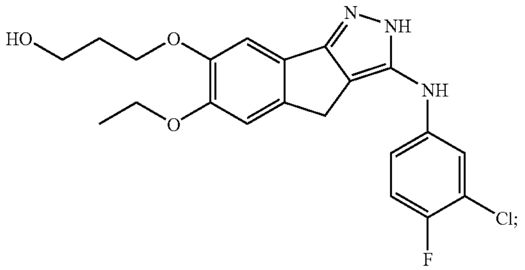
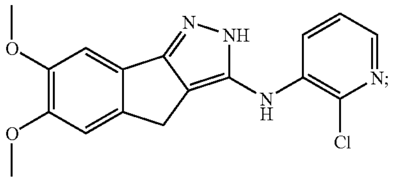
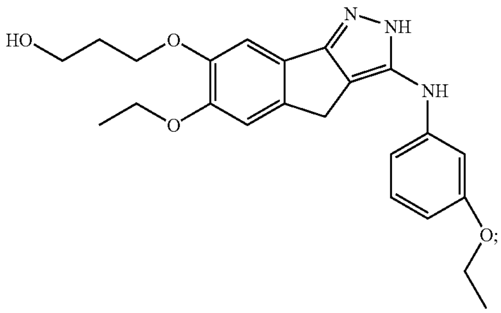
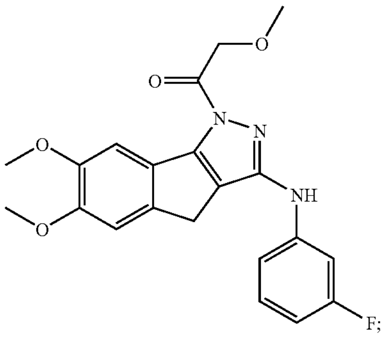
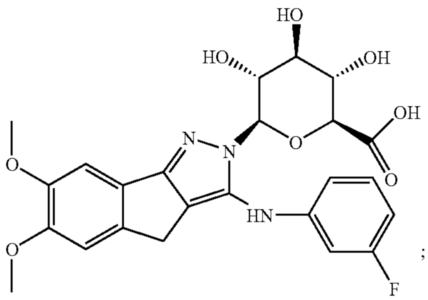
;
-continued
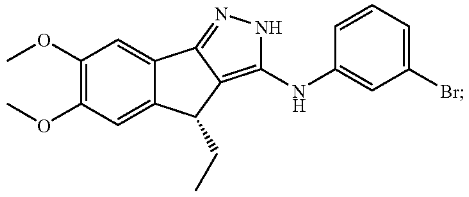
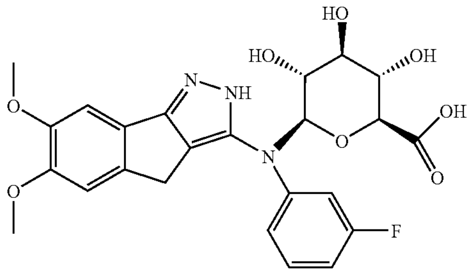
;
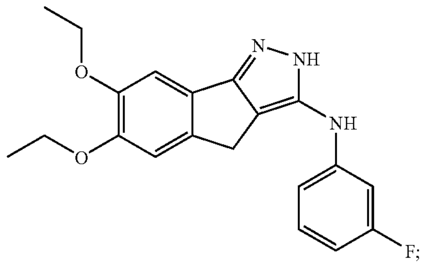
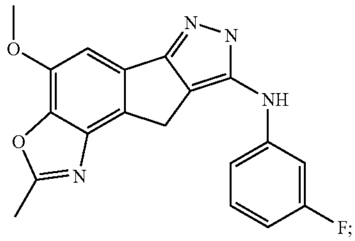
and,
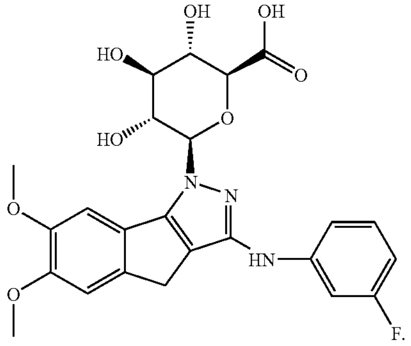
In a preferred embodiment, the present invention is further directed to a compound selected from the group consisting of:
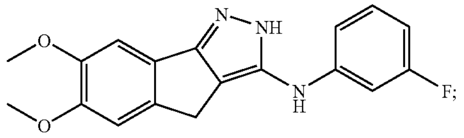

-continued

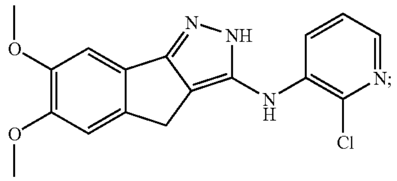

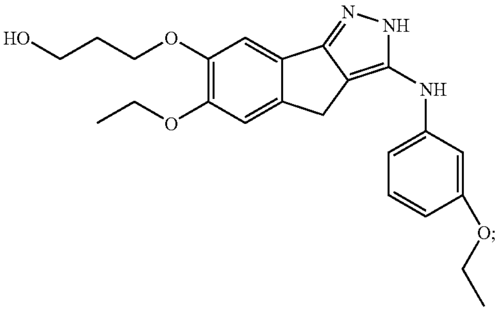

and,

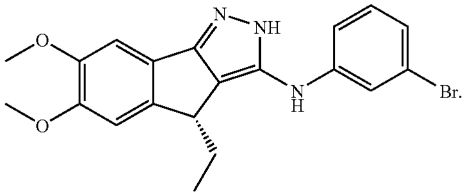

In a preferred embodiment, the present invention is further directed to a compound of the following formula:

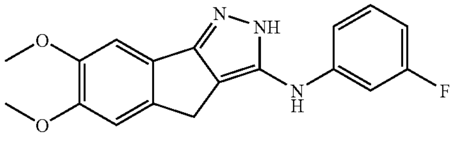

In a preferred embodiment, the present invention is further directed to a compound of the following formula:

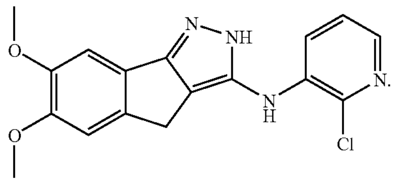

In a preferred embodiment, the present invention is further directed to a compound of the following formula:

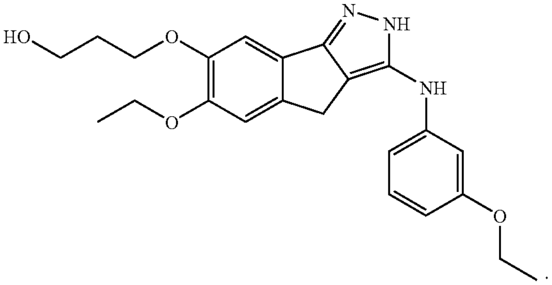

In a preferred embodiment, the present invention is further directed to a compound of the following formula:

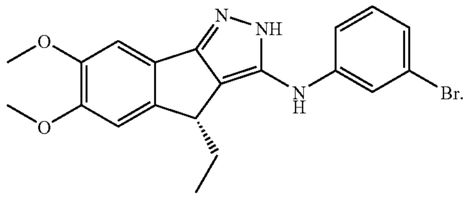

2.d. Preparation of Compounds of Formula (IIa)

The present invention is further directed to a process for the preparation of compounds of Formula (IIa):

(IIa)

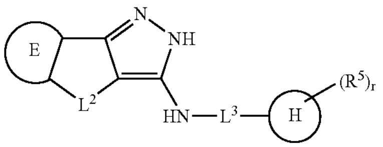

wherein:

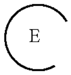

is selected from the group consisting of Formulae A-1, A-2 and A-3:

(Formula A-1)

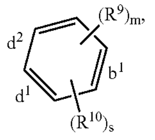

wherein Formula A-1 is attached on the $b^1$ side of Formula A-1 to the $L^2$ ring of formula (II) and optionally substituted with one substituent selected from the group consisting of Formulae A-1-a, A-1-b and A-1-c:

(Formula A-1-a)

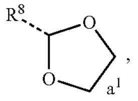

wherein Formula A-1-a is attached on the $a^1$ side to adjacent carbons on the $d^1$or $d^2$ side of Formula A-1;

(Formula A-1-b)

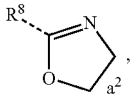

wherein Formula A-1-b is attached on the $a^2$side to adjacent carbons on the $d^1$or $d^2$ side of Formula A-1; and (Formula A-1-c)

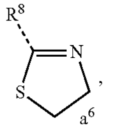

wherein Formula A-1-c is attached on the $a^6$ side to adjacent carbons on the $d^1$or $d^2$ side of Formula A-1; wherein $R^8$ is H or alkyl;

(Formula A-2)

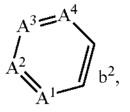

wherein Formula A-2 is attached on the $b^2$ side of Formula A-2 to the $L^2$ ring of formula (II), and $A^1$, $A^2$, $A^3$, $A^4$are (i) —N—; or (ii) —C— substituted with H or alkoxy, wherein the alkoxy may be optionally further substituted with alkoxy on a terminal carbon or up to 3 halogen atoms on a terminal carbon; provided that at least one and no more than two of $A^1$, $A^2$, $A^3$, $A^4$ are —N—; and (Formula A-3)

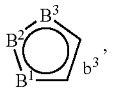

wherein Formula A-3 is attached on the $b^3$ side of Formula A-3 to the $L^2$ ring of formula (II), and $B^1$, $B^2$ and $B^3$ are independently (i) —CH— optionally substituted with $C_{1-4}$alkyl, aryl, alkoxy, or halogen, (ii) —S—; (iii) —O—; or (iv) —N—; provided that no more than one of $B^1$, $B^2$ or $B^3$ is —S— or —O—, and, provided that when one of $B^1$, $B^2$ or $B^3$ is —S— or —O—, then the adjacent ring members are not —S— or —O—;

$R^9$ is independently selected from the group consisting of: alkoxy, alkyl, alkylamino, amino, cyano, dialkylamino, halogen, halogenated alkyl, halogenated alkyloxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, nitro, —OC(═O)N(alkyl)$_2$, —OC(═O)NHalkyl, —$SO_2$alkyl, thio and thioalkyl;

$L^2$ is a linking group selected from the group consisting of: —$(CH_2)_{1-4}$—, —CH($R^{100}$)—, —C(═$R^{100}$)—, —C($R^{100}$)$_2$—, —O—, —O$(CH_2)_{1-4}$—, —OCH($R^{100}$)—, —OC($R^{100}$)$_2$—, —S—, —NH—, —N(lower alkyl)-, —N(COalkyl)-, —N(aryl)-, —N($CO_2$alkyl)-, —N(CONHalkyl)-, —N($SO_2$alkyl) and —N($SO_2$aryl)-; wherein $R^{100}$ is selected from: alkyl, hydroxy, aryl, alkoxy, oxo, —$NH_2$, —NH(alkyl) —N(alkyl)$_2$, ═N(OH) or —$NH_2$OH; provided that when $L^2$ is —OCH($R^{100}$)—, $R^{100}$ is alkoxy, and

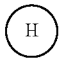

is phenyl, $R^5$ is not —C(═O)NH—$NH_2$;

$R^{10}$ is independently selected from the group consisting of

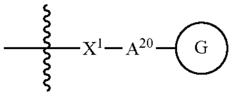

and —$X^1$-$A^{20}$-$Y^1$-$A^{21}$;

wherein $X^1$ and $Y^1$ are each independently absent or selected from the group consisting of: —(alkyl)C(═O)N(alkyl)-, —C(═O)N(alkyl)-, —C(═O)NH—, —C(═O)O—, —N(alkyl)-, —N(alkyl)C(═O)—, —N(alkyl)C(═O)NH—, —N(alkyl)C(═O)O—, —N(alkyl)$SO_2$—, —NH—, —NHC(═O)—, —NHC(═O)N(alkyl)-, —NHC(═O)NH, —NHC(═O)O—, —$NHSO_2$—, —O—, —OC(═O), —OC(═O)N(alkyl)-, —OC(═O)NH—, —OC(═O)O—, —S—, —SO—, —$SO_2$—, —$SO_2$N(alkyl)-, and —$SO_2$NH—;

$A^{20}$ is absent or selected from alkyl or alkenyl; and $A^{21}$ is selected from alkyl, alkenyl, or H;

wherein when $A^{20}$ or $A^{21}$ is alkyl or alkenyl, the alkyl or alkenyl may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, —OC(═O)alkyl, —OC(═O)N(alkyl)$_2$, —OC(═O)NHalkyl, —OC(═O)Oalkyl, —$SO_2$alkyl, thio or thioalkyl;

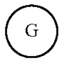

is selected from the group consisting of aryl, cycloalkyl, partially unsaturated carbocycle, heteroaryl, heterocycloalkyl, nine to ten membered benzo-fused cycloalkyl, and nine to ten membered benzo-fused heterocycloalkyl; wherein, the aryl, cycloalkyl, partially unsaturated carbocycle, heteroaryl, heterocycloalkyl, benzo-fused cycloalkyl, or benzo-fused heterocycloalkyl, are optionally substituted with one or more substituents independently selected from halogen, hydroxy, amino, thio, nitro, cyano, alkyl, halogenated alkyl, alkoxy, halogenated alkoxy, alkylamino, —NHC(═O)alkyl, —N(alkyl)C(═O)alkyl, or dialkylamino, —NHC(═O)$NH_2$, —NHC(═O)NHalkyl, —N(alkyl)C(═O)NHalkyl, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)$N(alkyl)_2$, —N(alkyl)C(═O)$N(alkyl)_2$ or —OC(═O)$N(alkyl)_2$;

s is an integer from 0 to 2;

m is an integer from 0 to 4; provided that when

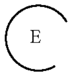

is not substituted with Formulae A-1-a, A-1-b or A-1-c, the sum of m and s is an integer from 0 to 4, and when

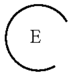

is substituted with one of Formulae A-1-a, A-1-b, or A-1-c, the sum of m and s is an integer from 0 to 2;

$L^3$ is absent or is a linking group selected from the group consisting of alkyldiyl, carbonyl or —$SO_2$—;

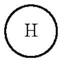

is selected from the group consisting of an aryl, a cycloalkyl, a partially unsaturated carbocycle, aralkyl, a heteroaryl, a heterocycloalkyl, a nine to ten membered benzo-fused cycloalkyl, a nine to ten membered benzo-fused heteroaryl, and a nine to ten membered benzo-fused heterocycloalkyl;

r is an integer from 0 to 4; and $R^5$ is independently selected from the group consisting of: alkyl, alkyl amino, alkyloxy, amino, —C(═O)$NH_2$, —C(═O)Oalkyl, —C(═O)OH, —$CH_2$OH, cyano, dialkylamino, halogen, halogenated alkyl, halogenated alkyloxy, halogenated $SO_2$-alkyl, halogenated thioalkyl, hydroxy, hydroxy alkyl, —N(alkyl)C(═O)alkyl, —N(alkyl)C(═O)$N(alkyl)_2$, —N(alkyl)C(═O)NHalkyl, —N(alkyl)C(═O)Oalkyl, —N(alkyl)$SO_2$alkyl, —NHC(═O)alkyl, —NHC(═O)$N(alkyl)_2$, —NHC(═O)$NH_2$, —NHC(═O)NHalkyl, —NHC(═O)Oalkyl, —$NHSO_2$alkyl, nitro, —OC(═O)$N(alkyl)_2$, —OC(═O)NHalkyl, —$SO_2$alkyl, —$SO_2NH_2$, thio, thioalkyl,

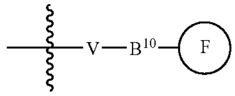, and —V—$B^{10}$—W—$B^{20}$; wherein,

V and W are each independently absent or selected from the group consisting of: —C(═O), —C(═O)N(alkyl)-, —C(═O)NH—, —C(═O)O—, —N(alkyl)-, —N(alkyl)C(═O)—, —N(alkyl)C(═O)N(alkyl)-, —N(alkyl)C(═O)NH—, —N(alkyl)C(═O)O—, —N(alkyl)$SO_2$—, —NH—, —NHC(═O)—, —NHC(═O)N(alkyl)-, —NHC(═O)NH—, —NHC(═O)O—, —$NHSO_2$—, —O—, —OC(═O), —OC(═O)N(alkyl)-, —OC(═O)NH—, —OC(═O)O—, —S—, —SO—, —$SO_2$—, —$SO_2$N(alkyl)- and —$SO_2$NH—;

$B^{10}$ is absent or selected from alkyl or alkenyl;

$B^{20}$ is absent or selected from alkyl, alkenyl, or H;

wherein, when $B^{10}$ or $B^{20}$ is alkyl or alkenyl, the alkyl or alkenyl group may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy —N(alkyl)C(═O)alkyl, —N(alkyl)C(═O)$N(alkyl)_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)$N(alkyl)_2$, —NHC(═O)$NH_2$, —NHC(═O)NHalkyl, —NHC(═O)Oalkyl, —$NHSO_2$alkyl, —OC(═O)alkyl, —OC(═O)$N(alkyl)_2$, —OC(═O)NHalkyl, —OC(═O)Oalkyl, —$SO_2$alkyl, thio or thioalkyl; and

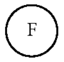

is selected from the group consisting of: an aryl, a cycloalkyl, a partially unsaturated carbocycle, a heteroaryl, a heterocycloalkyl, a nine to ten membered benzo-fused cycloalkyl, and a nine to ten membered benzo-fused heterocycloalkyl, wherein, the aryl, cycloalkyl, partially unsaturated carbocycle, heteroaryl, heterocycloalkyl, benzo-fused cycloalkyl, or benzo-fused heterocycloalkyl, is optionally substituted with one or more substituents independently selected from: alkoxy, alkylamino, amino, cyano, dialkylamino, halogen, halogenated alkoxy, halogenated alkyl, halogenated —$SO_2$alkyl, halogenated thioalkyl, heteroaryl, hydroxy, hydroxy alkyl, —N(alkyl)C(═O)alkyl, —N(alkyl)C(═O)$N(alkyl)_2$, —N(alkyl)C(═O)NHalkyl, —N(alkyl)C(═O)Oalkyl, —N(alkyl)$SO_2$alkyl, —NHC(═O)alkyl, —NHC(═O)$N(alkyl)_2$, —NHC(═O)$NH_2$, —NHC(═O)NHalkyl, —NHC(═O)Oalkyl, —$NHSO_2$alkyl, nitro, —OC(═O)$N(alkyl)_2$, —OC(═O)NHalkyl, —$SO_2$alkyl, thio or thioalkyl;

or an optical isomer, enantiomer, diastereomer, racemate, or pharmaceutically acceptable salt thereof;

comprising

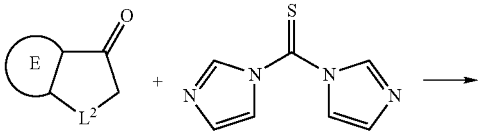

(T1)

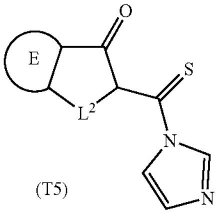

(T5)

reacting a compound of formula (T1) with 1,1'-thiocarbonyldiimidazole, in the presence of a base, in an aprotic solvent, to yield the corresponding compound of formula (T5);

(T5)

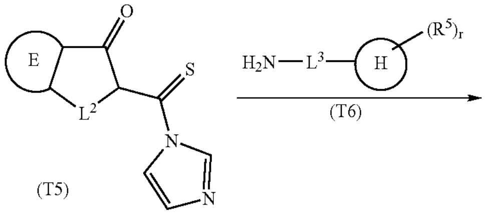

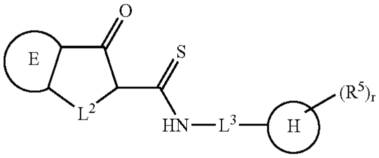

(T3)

reacting a compound of formula (T5) with a compound of formula (T6), in an aprotic solvent, to yield the corresponding compound of formula (T3);

reacting a compound of formula (T3) with hydrazine,

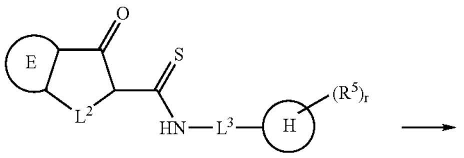

(T3)

-continued

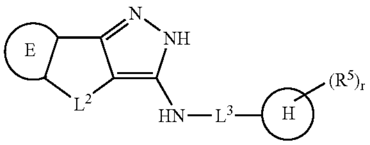

(IIa)

to yield the corresponding compound of formula (IIa).

The present invention is further directed to a process for the preparation of compounds of formula (T5)

(T5)

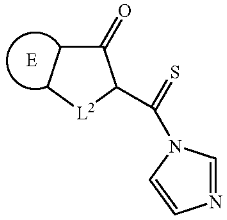

wherein:

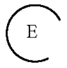

is selected from the group consisting of Formulae A-1, A-2 and A-3:

(Formula A-1)

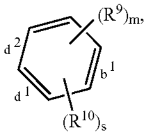

wherein Formula A-1 is attached on the $b^1$ side of Formula A-1 to the $L^2$ ring of formula (II) and optionally substituted with one substituent selected from the group consisting of Formulae A-1-a, A-1-b and A-1-c:

(Formula A-1-a)

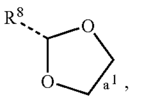

wherein Formula A-1-a is attached on the $a^1$ side to adjacent carbons on the $d^1$or $d^2$ side of Formula A-1;

(Formula A-1-b)

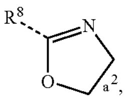

wherein Formula A-1-b is attached on the $a^2$side to adjacent carbons on the $d^1$or $d^2$ side of Formula A-1; and (Formula A-1-c)

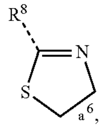

wherein Formula A-1-c is attached on the $a^6$ side to adjacent carbons on the $d^1$or $d^2$ side of Formula A-1;

wherein $R^8$ is H or alkyl;

(Formula A-2)

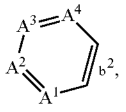

wherein Formula A-2 is attached on the $b^2$ side of Formula A-2 to the $L^2$ ring of formula (II), and $A^1$, $A^2$, $A^3$, $A^4$ are (i) —N—; or (ii) —C— substituted with H or alkoxy, wherein the alkoxy may be optionally further substituted with alkoxy on a terminal carbon or up to 3 halogen atoms on a terminal carbon; provided that at least one and no more than two of $A^1$, $A^2$, $A^3$, $A^4$ are —N—; and (Formula A-3)

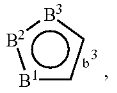

wherein Formula A-3 is attached on the $b^3$ side of Formula A-3 to the $L^2$ ring of formula (II), and $B^1$, $B^2$ and $B^3$ are independently (i) —CH— optionally substituted with alkyl, aryl, alkoxy, or halogen, (ii) —S—; (iii) —O—; or (iv) —N—; provided that no more than one of $B^1$, $B^2$ or $B^3$ is —S— or —O—, and, provided that when one of $B^1$, $B^2$ or $B^3$ is —S— or —O—, then the adjacent ring members are not —S— or —O—;

$R^9$ is independently selected from the group consisting of: alkoxy, alkyl, alkylamino, amino, cyano, dialkylamino, halogen, halogenated alkyl, halogenated alkyloxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, nitro, —OC(═O)N(alkyl)$_2$, —OC(═O)NHalkyl, —$SO_2$alkyl, thio and thioalkyl;

$L^2$ is a linking group selected from the group consisting of: —$(CH_2)_{1-4}$—, —CH($R^{100}$)—, —C(═$R^{100}$)—, —C($R^{100}$)$_2$—, —O—, —O$(CH_2)_{1-4}$—, —OCH($R^{100}$)—, —OC($R^{100}$)$_2$—, —S, —NH—, —N(lower alkyl)-, —N(COalkyl)-, —N(aryl)-, —N($CO_2$alkyl)-, —N(CONHalkyl)-, —N($SO_2$alkyl) and —N($SO_2$aryl)-; wherein $R^{100}$ is selected from: alkyl, hydroxy, aryl, alkoxy, oxo, —$NH_2$, —NH(alkyl) —N(alkyl)$_2$, ═N(OH) or —$NH_2$OH;

$R^{10}$ is independently selected from the group consisting of

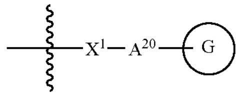

and —$X^1$-$A^{20}$-$Y^1$-$A^{21}$;

wherein $X^1$ and $Y^1$ are each independently absent or selected from the group consisting of: -(alkyl)C(═O)N(alkyl)-, —C(═O)N(alkyl)-, —C(═O)NH—, —C(═O)O—, —N(alkyl)-, —N(alkyl)C(═O)—, —N(alkyl)C(═O)NH—, —N(alkyl)C(═O)O—, —N(alkyl)$SO_2$—, —NH—, —NHC(═O)—, —NHC(═O)N(alkyl)-, —NHC(═O)NH, —NHC(═O)O—, —$NHSO_2$—, —O—, —OC(═O), —OC(═O)N(alkyl)-, —OC(═O)NH—, —OC(═O)O—, —S—, —SO—, —$SO_2$—, —$SO_2$N(alkyl)-, and —$SO_2$NH—;

$A^{20}$ is absent or selected from alkyl or alkenyl; and $A^{21}$ is selected from alkyl, alkenyl, or H;

wherein when $A^{20}$ or $A^{21}$ is alkyl or alkenyl, the alkyl or alkenyl may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, —OC(═O)alkyl, —OC(═O)N(alkyl)$_2$, —OC(═O)NHalkyl, —OC(═O)Oalkyl, —$SO_2$alkyl, thio or thioalkyl;

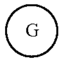

is selected from the group consisting of aryl, cycloalkyl, partially unsaturated carbocycle, heteroaryl, heterocycloalkyl, nine to ten membered benzo-fused cycloalkyl, and nine to ten membered benzo-fused heterocycloalkyl; wherein, the aryl, cycloalkyl, partially unsaturated carbocycle, heteroaryl, heterocycloalkyl, benzo-fused cycloalkyl, or benzo-fused heterocycloalkyl, are optionally substituted with one or more substituents independently selected from halogen, hydroxy, amino, thio, nitro, cyano, alkyl, halogenated alkyl, alkoxy, halogenated alkoxy, alkylamino, —NHC(═O)alkyl, —N(alkyl)C(═O)alkyl, or dialkylamino, —NHC(═O)$NH_2$, —NHC(═O)NHalkyl, —N(alkyl)C(═O)NHalkyl, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)N(alkyl)$_2$, —N(alkyl)C(═O)N(alkyl)$_2$ or —OC(═O)N(alkyl)$_2$;

s is an integer from 0 to 2;

m is an integer from 0 to 4; provided that when

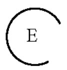

is not substituted with Formulae A-1-a, A-1-b or A-1-c, the sum of m and s is an integer from 0 to 4, and when

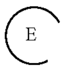

is substituted with one of Formulae A-1-a, A-1-b, or A-1-c, the sum of m and s is an integer from 0 to 2;

or an optical isomer, enantiomer, diastereomer, racemate, or pharmaceutically acceptable salt thereof;

comprising

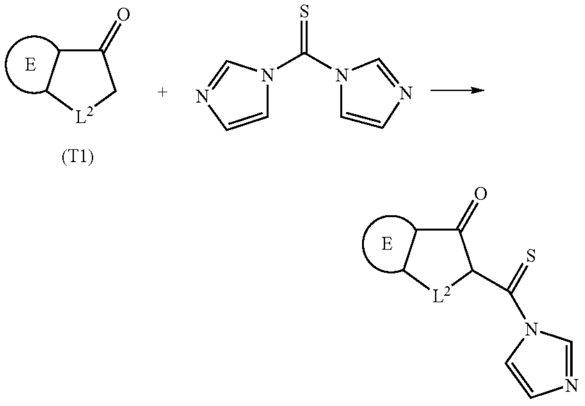

(T1)

(T5)

reacting a compound of formula (T1) with 1,1'-thiocarbonyldiimidazole, in the presence of a base, in an aprotic solvent, to yield the corresponding compound of formula (T5).

The present invention is further directed to a process for the preparation of compounds of formula (T3)

(T3)

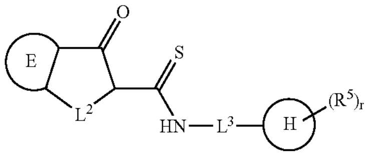

wherein:

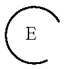

is selected from the group consisting of Formulae A-1, A-2 and A-3:

(Formula A-1)

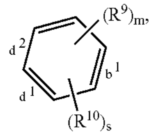

wherein Formula A-1 is attached on the $b^1$ side of Formula A-1 to the $L^2$ ring of formula (II) and optionally substituted with one substituent selected from the group consisting of Formulae A-1-a, A-1-b and A-1-c:

(Formula A-1-a)

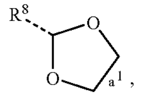

wherein Formula A-1-a is attached on the $a^1$ side to adjacent carbons on the $d^1$or $d^2$ side of Formula A-1;

(Formula A-1-b)

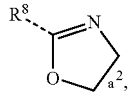

wherein Formula A-1-b is attached on the $a^2$side to adjacent carbons on the $d^1$or $d^2$ side of Formula A-1; and (Formula A-1-c)

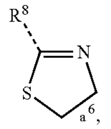

wherein Formula A-1-c is attached on the $a^6$ side to adjacent carbons on the $d^1$or $d^2$ side of Formula A-1;

wherein $R^8$ is H or alkyl;

(Formula A-2)

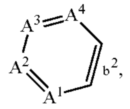

wherein Formula A-2 is attached on the $b^2$ side of Formula A-2 to the $L^2$ ring of formula (II), and $A^1$, $A^2$, $A^3$, $A^4$ are (i) —N—; or (ii) —C— substituted with H or alkoxy, wherein the alkoxy may be optionally further substituted with alkoxy on a terminal carbon or up to 3 halogen atoms on a terminal carbon; provided that at least one and no more than two of $A^1$, $A^2$, $A^3$, $A^4$ are —N—; and (Formula A-3)

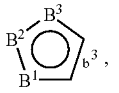

wherein Formula A-3 is attached on the $b^3$ side of Formula A-3 to the $L^2$ ring of formula (II), and $B^1$, $B^2$ and $B^3$ are independently (i) —CH— optionally substituted with alkyl, aryl, alkoxy, or halogen, (ii) —S—; (iii) —O—; or (iv) —N—; provided that no more than one of $B^1$, $B^2$ or $B^3$ is —S— or —O—, and, provided that when one of $B^1$, $B^2$ or $B^3$ is —S— or —O—, then the adjacent ring members are not —S— or —O—;

$R^9$ is independently selected from the group consisting of: alkoxy, alkyl, alkylamino, amino, cyano, dialkylamino, halogen, halogenated alkyl, halogenated alkyloxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, nitro, —OC(═O)N(alkyl)$_2$, —OC(═O)NHalkyl, —$SO_2$alkyl, thio and thioalkyl;

$L^2$ is a linking group selected from the group consisting of: —$(CH_2)_{1-4}$—, —CH($R^{100}$)—, —C(═$R^{100}$)—, —C($R^{100}$)$_2$—, —O—, —O$(CH_2)_{1-4}$—, —OCH($R^{100}$)—, —OC($R^{100}$)$_2$—, —S—, —NH—, —N(lower alkyl)-, —N(COalkyl)-, —N(aryl)-, —N($CO_2$alkyl)-, —N(CONHalkyl)-, —N($SO_2$alkyl) and —N($SO_2$aryl)-; wherein $R^{100}$ is selected from: alkyl, hydroxy, aryl, alkoxy, oxo, —$NH_2$, —NH(alkyl) —N(alkyl)$_2$, ═N(OH) or —NH2OH; provided that when $L^2$ is —OCH($R^{100}$)—, $R^{100}$ is alkoxy, and

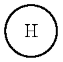

phenyl, $R^5$ is not —C(═O)NH—$NH_2$;

$R^{10}$ is independently selected from the group consisting of

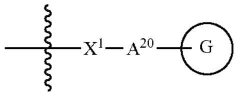

and —$X^1$-$A^{20}$-$Y^1$-$A^{21}$;

wherein $X^1$ and $Y^1$ are each independently absent or selected from the group consisting of: -(alkyl)C(═O)N(alkyl)-, —C(═O)N(alkyl)-, —C(═O)NH—, —C(═O)O—, —N(alkyl)-, —N(alkyl)C(═O)—, —N(alkyl)C(═O)NH—, —N(alkyl)C(═O)O—, —N(alkyl)$SO_2$—, —NH—, —NHC(═O)—, —NHC(═O)N(alkyl)-, —NHC(═O)NH, —NHC(═O)O—, —$NHSO_2$—, —O—, —OC(═O), —OC(═O)N(alkyl)-, —OC(═O)NH—, —OC(═O)O—, —S—, —SO—, —$SO_2$—, —$SO_2$N(alkyl)-, and —$SO_2$NH—;

$A^{20}$ is absent or selected from alkyl or alkenyl; and $A^{21}$ is selected from alkyl, alkenyl, or H;

wherein when $A^{20}$ or $A^{21}$ is alkyl or alkenyl, the alkyl or alkenyl may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)N $H_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, —OC(═O)alkyl, —OC(═O)N(alkyl)$_2$, —OC(═O)NHalkyl, —OC(═O)Oalkyl, —$SO_2$alkyl, thio or thioalkyl;

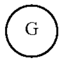

is selected from the group consisting of aryl, cycloalkyl, partially unsaturated carbocycle, heteroaryl, heterocycloalkyl, nine to ten membered benzo-fused cycloalkyl, and nine to ten membered benzo-fused heterocycloalkyl; wherein, the aryl, cycloalkyl, partially unsaturated carbocycle, heteroaryl, heterocycloalkyl, benzo-fused cycloalkyl, or benzo-fused heterocycloalkyl, are optionally substituted with one or more substituents independently selected from halogen, hydroxy, amino, thio, nitro, cyano, alkyl, halogenated alkyl, alkoxy, halogenated alkoxy, alkylamino, —NHC(═O)alkyl, —N(alkyl)C(═O)alkyl, or dialkylamino, —NHC(—O)$NH_2$, —NHC(═O)NHalkyl, —N(alkyl)C(═O)NHalkyl, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)N(alkyl)$_2$, —N(alkyl)C(═O)N(alkyl)$_2$ or —OC(═O)N(alkyl)$_2$;

s is an integer from 0 to 2;

m is an integer from 0 to 4; provided that when

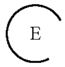

is not substituted with Formulae A-1-a, A-1-b or A-1-c, the sum of m and s is an integer from 0 to 4, and when

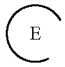

is substituted with one of Formulae A-1-a, A-1-b, or A-1-c, the sum of m and s is an integer from 0 to 2;

$L^3$ is absent or is a linking group selected from the group consisting of alkyldiyl, carbonyl or —$SO_2$—;

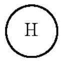

is selected from the group consisting of an aryl, a cycloalkyl, a partially unsaturated carbocycle, aralkyl, a heteroaryl, a heterocycloalkyl, a nine to ten membered benzo-fused cycloalkyl, a nine to ten membered benzo-fused heteroaryl, and a nine to ten membered benzo-fused heterocycloalkyl;

r is an integer from 0 to 4; and $R^5$ is independently selected from the group consisting of: alkyl, alkyl amino, alkyloxy, amino, —C(═O)$NH_2$, —C(═O)Oalkyl, —C(═O)OH, —$CH_2OH$, cyano, dialkylamino, halogen, halogenated alkyl, halogenated alkyloxy, halogenated $SO_2$-alkyl, halogenated thioalkyl, hydroxy, hydroxy alkyl, —N(alkyl)C(═O)alkyl, —N(alkyl)C(═O)N$(alkyl)_2$, —N(alkyl)C(═O)NHalkyl, —N(alkyl)C(═O)Oalkyl, —N(alkyl)$SO_2$alkyl, —NHC(═O)alkyl, —NHC(═O)N$(alkyl)_2$, —NHC(═O)$NH_2$, —NHC(═O)NHalkyl, —NHC(═O)Oalkyl, —$NHSO_2$alkyl, nitro, —OC(═O)N$(alkyl)_2$, —OC(═O)NHalkyl, —$SO_2$alkyl, —$SO_2NH_2$, thio, thioalkyl,

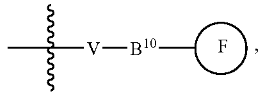

and —V—$B^{10}$—W—$B^{20}$; wherein,

V and W are each independently absent or selected from the group consisting of: —C(═O), —C(═O)N(alkyl)-, —C(═O)NH—, —C(═O)O—, —N(alkyl)-, —N(alkyl)C(═O)—, —N(alkyl)C(═O)N(alkyl)-, —N(alkyl)C(═O)NH—, —N(alkyl)C(═O)O—, —N(alkyl)$SO_2$—, —NH—, —NHC(═O)—, —NHC(═O)N(alkyl)-, —NHC(═O)NH—, —NHC(═O)O—, —$NHSO_2$—, —O—, —OC(═O), —OC(═O)N(alkyl)-, —OC(═O)NH—, —OC(═O)O—, —S—, —SO—, —$SO_2$—, —$SO_2$N(alkyl)- and —$SO_2$NH—;

$B^{10}$ is absent or selected from alkyl or alkenyl;

$B^{20}$ is absent or selected from alkyl, alkenyl, or H;

wherein, when $B^{10}$ or $B^{20}$ is alkyl or alkenyl, the alkyl or alkenyl group may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy —N(alkyl)C(═O)alkyl, —N(alkyl)C(═O)N$(alkyl)_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N$(alkyl)_2$, —NHC(═O)$NH_2$, —NHC(═O)NHalkyl, —NHC(═O)Oalkyl, —$NHSO_2$alkyl, —OC(═O)alkyl, —OC(═O)N$(alkyl)_2$, —OC(═O)NHalkyl, —OC(═O)Oalkyl, —$SO_2$alkyl, thio or thioalkyl; and

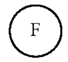

is selected from the group consisting of: an aryl, a cycloalkyl, a partially unsaturated carbocycle, a heteroaryl, a heterocycloalkyl, a nine to ten membered benzo-fused cycloalkyl, and a nine to ten membered benzo-fused heterocycloalkyl, wherein, the aryl, cycloalkyl, partially unsaturated carbocycle, heteroaryl, heterocycloalkyl, benzo-fused cycloalkyl, or benzo-fused heterocycloalkyl, is optionally substituted with one or more substituents independently selected from: alkoxy, alkylamino, amino, cyano, dialkylamino, halogen, halogenated alkoxy, halogenated alkyl, halogenated —$SO_2$alkyl, halogenated thioalkyl, heteroaryl, hydroxy, hydroxy alkyl, —N(alkyl)C(═O)alkyl, —N(alkyl)C(═O)N$(alkyl)_2$, —N(alkyl)C(═O)NHalkyl, —N(alkyl)C(═O)Oalkyl, —N(alkyl)$SO_2$alkyl, —NHC(═O)alkyl, —NHC(═O)N$(alkyl)_2$, —NHC(═O)$NH_2$, —NHC(═O)NHalkyl, —NHC(═O)Oalkyl, —$NHSO_2$alkyl, nitro, —OC(═O)N$(alkyl)_2$, —OC(═O)NHalkyl, —$SO_2$alkyl, thio or thioalkyl;

or an optical isomer, enantiomer, diastereomer, racemate, or pharmaceutically acceptable salt thereof;

comprising

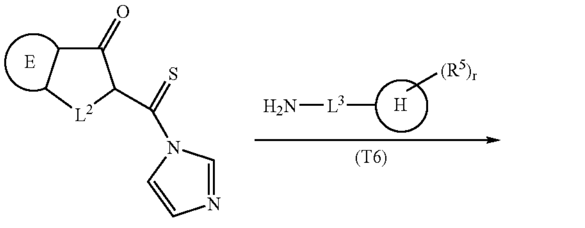

(T5)

(T3)

reacting a compound of formula (T5) with a compound of formula (T6), in an aprotic solvent, to yield the corresponding compound of formula (T3).

Representative Compounds

In an embodiment of the present invention are compounds as listed in Tables 1 through 13; below. Molecular weight indicated by "MS," expressed in m/z $(M+H)^+$ units. Compounds which have been synthesized are as listed in Tables 1 through 5 and 7 through 13.

(In reference to compounds of formulae (I) and (II), G represents

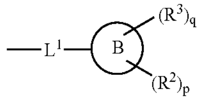

in Formula (I) and

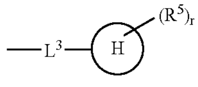

in Formula (II); $R^A$, $R^B$, $R^C$ and $R^D$ represent an $R^2$ or $R^3$ group in Formula (I), and/or an $R^9$ or $R^{10}$ group in Formula (II). Additional representative examples of compounds within the scope of the invention, are listed in Table 6.

In Tables 4 and 6 below, the

ring (the A/E ring,), representing the

(A ring) in Formula (I) and the

(E ring) in Formula (II) are numbered based on convention, counting clockwise, unless otherwise indicated by convention, with the leading numbers indicating the carbon atoms bound to the rest of the core molecule. Thus, for example, for in the structure below

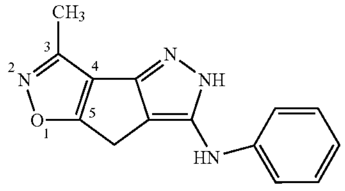

the A/E ring, substituent would be named 4,5-(3-methyl-isoxazolyl).

Named A/E ring, substituents followed by an * are numbered counterclockwise, following convention. For example, in the structure below

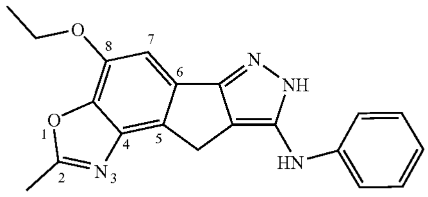

the A/E ring, substituent would be named 5,6-(2-methyl-8-ethoxy-benzoxazolyl)*.

Otherwise, when the A/E ring, is a phenyl, the phenyl group, by definition, is bound at the 1,2 positions, and the phenyl ring substituents are numbered counting clockwise, as in the first structure (4,5-isoxazolyl) shown above.

TABLE 1

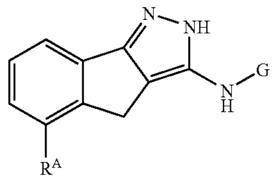

| Cpd | G | $R^A$ | MS |
|---|---|---|---|
| 8 | phenyl | methyl | 278 |
| 23 | phenyl | methyl | 262 |
| 71 | phenyl | 3-(N,N-dimethyl-amino)-propoxy | 349 |
| 72 | 3-chloro-phenyl | 3-(N,N-dimethyl-amino)-propoxy | 383 |
| 73 | 4-fluoro-phenyl | 3-(N,N-dimethyl-amino)-propoxy | 367 |
| 74 | 3-methoxy-phenyl | 3-(N,N-dimethyl-amino)-propoxy | 379 |
| 75 | 3-pyridyl | 3-(N,N-dimethyl-amino)-propoxy | 350 |
| 77 | 3-(methoxy-carbonyl)-phenyl | 3-(N,N-dimethyl-amino)-propoxy | 407 |
| 90 | 3-fluoro-phenyl | 3-(N,N-dimethyl-amino)-propoxy | 367 |
| 98 | 4-fluoro-phenyl | methyl | 280 |
| 99 | 3-fluoro-phenyl | methyl | 280 |
| 100 | 3-pyridyl | methyl | 263 |
| 101 | 2,5-dimethoxy-phenyl | methyl | 322 |
| 102 | 2,4-dimethoxy-phenyl | methyl | 322 |
| 103 | 2,5-difluoro-phenyl | methyl | 298 |
| 104 | 4-trifluoromethoxy-phenyl | methyl | 346 |
| 105 | 4-trifluoromethyl-phenyl | methyl | 330 |
| 144 | 4-fluoro-phenyl | methoxy | 296 |
| 145 | 4-methoxy-phenyl | methoxy | 308 |
| 146 | 3-pyridyl | methoxy | 279 |
| 147 | 2,5-dimethoxy-phenyl | methoxy | 338 |
| 148 | 2,4-dimethoxy-phenyl | methoxy | 338 |
| 149 | 3-trifluoromethoxy-phenyl | methoxy | 362 |
| 150 | 3-trifluoromethyl-phenyl | methoxy | 346 |
| 392 | 3-chloro-phenyl | 3-morpholin-4-yl-propoxy | 425 |
| 393 | 3-fluoro-phenyl | 3-morpholin-4-yl-propoxy | 409 |
| 394 | 3-ethoxy-phenyl | 3-morpholin-4-yl-propoxy | 435 |
| 414 | 2,6-difluoro-benzyl | 3-morpholin-4-yl-propoxy | 441 |
| 415 | 2,6-dichloro-benzyl | 3-morpholin-4-yl-propoxy | 474 |
| 416 | 2-fluoro-benzyl | 3-morpholin-4-yl-propoxy | 423 |
| 417 | 3-methoxy-5-trifluoromethyl-phenyl | methoxy | 376 |
| 418 | 3-(amino-sulfonyl)-phenyl | methoxy | 357 |
| 422 | 3-fluoro-phenyl | methoxy | 296 |
| 423 | 2,6-difluoro-benzyl | methoxy | 328 |
| 440 | 3-chloro-phenyl | 3-hydroxy-propoxy | 356 |
| 441 | 3-ethoxy-phenyl | 3-hydroxy-propoxy | 366 |
| 442 | 3-fluoro-phenyl | 3-hydroxy-propoxy | 340 |
| 443 | 2,6-difluoro-benzyl | 3-hydroxy-propoxy | 372 |
| 444 | 2-fluoro-benzyl | 3-hydroxy-propoxy | 354 |
| 445 | 2-methyl-benzyl | 3-hydroxy-propoxy | 350 |
| 468 | 3-bromo-phenyl | 2,3-dihydroxy-propoxy | 417 |
| 469 | 3-fluoro-phenyl | 2,3-dihydroxy-propoxy | 356 |
| 478 | 3-bromo-phenyl | 2-(pyrrolidin-1-yl)-ethoxy | 440 |
| 479 | 2,6-difluoro-benzyl | 2,3-dihydroxy-propoxy | 421 |

TABLE 2

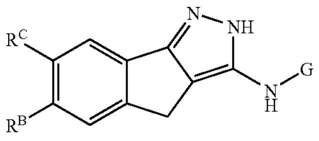

| Cpd | G | $R^B$ | $R^C$ | MS |
|---|---|---|---|---|
| 1 | phenyl | H | H | 248 |
| 2 | phenyl | methoxy | methoxy | 308 |
| 3 | 4-chloro-phenyl | H | H | 282 |
| 4 | 3-chloro-phenyl | methoxy | methoxy | 342 |
| 5 | 4-chloro-phenyl | methoxy | methoxy | 342 |
| 6 | 4-methoxy-phenyl | methoxy | methoxy | 338 |
| 7 | phenyl | methoxy | H | 278 |
| 9 | 2-chloro-phenyl | methoxy | methoxy | 342 |
| 10 | 4-(ethoxy-carbonyl)-phenyl | methoxy | methoxy | 380 |
| 11 | 3-(methoxy-carbonyl)-phenyl | methoxy | methoxy | 366 |
| 12 | 2-fluoro-phenyl | methoxy | methoxy | 326 |
| 13 | 4-fluoro-phenyl | methoxy | methoxy | 326 |
| 14 | 3-fluoro-phenyl | methoxy | methoxy | 326 |
| 15 | 2-trifluoromethoxy-phenyl | methoxy | methoxy | 392 |
| 16 | 4-trifluoromethoxy-phenyl | methoxy | methoxy | 392 |
| 17 | 2,4-dichloro-phenyl | methoxy | methoxy | 377 |
| 18 | 3,4-dichloro-phenyl | methoxy | methoxy | 377 |
| 19 | 3,5-dichloro-phenyl | methoxy | methoxy | 377 |
| 20 | 2,3-dichloro-phenyl | methoxy | methoxy | 377 |
| 21 | phenyl | chloro | H | 282 |
| 22 | phenyl | H | methyl | 262 |
| 24 | phenyl | fluoro | H | 266 |
| 25 | 4-trifluoromethyl-phenyl | methoxy | methoxy | 376 |
| 26 | 3-trifluoromethyl-phenyl | methoxy | methoxy | 376 |
| 27 | 2-methoxy-phenyl | methoxy | methoxy | 338 |
| 28 | 2-trifluoromethyl-phenyl | methoxy | methoxy | 376 |
| 29 | 3-methoxy-phenyl | methoxy | methoxy | 338 |
| 30 | 3-pyridyl | methoxy | methoxy | 309 |
| 31 | 2-methyl-phenyl | methoxy | methoxy | 322 |
| 32 | 3-methyl-phenyl | methoxy | methoxy | 322 |
| 33 | 4-methyl-phenyl | methoxy | methoxy | 322 |
| 34 | 2,5-dichloro-phenyl | methoxy | methoxy | 377 |
| 36 | 3-hydroxy-methyl-phenyl | methoxy | methoxy | 338 |
| 37 | 6-indazolyl | methoxy | methoxy | 348 |
| 38 | 3-hydroxy-phenyl | methoxy | methoxy | 324 |
| 39 | phenyl | H | methoxy | 278 |
| 40 | 4-(N,N-dimethyl-amino)-phenyl | methoxy | methoxy | 351 |
| 41 | 3,5-dimethoxy-phenyl | methoxy | methoxy | 368 |
| 42 | 3,4,5-trimethoxy-phenyl | methoxy | methoxy | 398 |
| 43 | 2-bromo-phenyl | methoxy | methoxy | 387 |
| 44 | 3-bromo-phenyl | methoxy | methoxy | 387 |
| 45 | 4-bromo-phenyl | methoxy | methoxy | 387 |
| 46 | 5-chloro-2-methyl-phenyl | methoxy | methoxy | 356 |
| 47 | 2,4-dimethoxy-phenyl | methoxy | methoxy | 386 |
| 48 | 2,5-dimethoxy-phenyl | methoxy | methoxy | 368 |
| 49 | 3,4-dimethoxy-phenyl | methoxy | methoxy | 368 |
| 51 | 4-(4-methyl-piperazin-1-yl)-phenyl | methoxy | methoxy | 406 |
| 53 | 3-chloro-4-fluoro-phenyl | methoxy | methoxy | 360 |
| 54 | 3-benzyloxy-phenyl | methoxy | methoxy | 414 |
| 55 | 2,5-difluoro-phenyl | methoxy | methoxy | 344 |

TABLE 2-continued

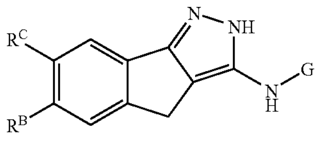

| Cpd | G | $R^B$ | $R^C$ | MS |
|---|---|---|---|---|
| 56 | 5-chloro-2-methoxy-phenyl | methoxy | methoxy | 372 |
| 57 | 2-isopropyl-phenyl | methoxy | methoxy | 350 |
| 58 | 2-ethyl-phenyl | methoxy | methoxy | 336 |
| 59 | 4-cyano-phenyl | methoxy | methoxy | 333 |
| 61 | 3-cyano-phenyl | methoxy | methoxy | 333 |
| 62 | 3,4-methylenedioxy-phenyl | methoxy | methoxy | 352 |
| 64 | phenyl | 4-methyl-piperazin-1-yl | H | 346 |
| 65 | phenyl | 1-piperidinyl | H | 331 |
| 66 | phenyl | amino | H | 263 |
| 67 | cyclohexyl | methoxy | methoxy | 314 |
| 70 | 3,5-di(trifluoromethyl)-phenyl | methoxy | methoxy | 444 |
| 76 | 2-trifluoromethyl-4-bromo-phenyl | methoxy | methoxy | 455 |
| 78 | 2-furyl | methoxy | methoxy | 298 |
| 79 | 5-indanyl | methoxy | methoxy | 348 |
| 81 | 2-(piperidin-1-yl)-ethyl | methoxy | methoxy | 343 |
| 82 | 4-fluoro-phenyl | methoxy | H | 296 |
| 83 | 3-bromo-phenyl | methoxy | H | 357 |
| 84 | 3-pyridyl | methoxy | H | 279 |
| 85 | 2,5-dimethoxy-phenyl | methoxy | H | 338 |
| 86 | 3,4-dimethoxy-phenyl | methoxy | H | 338 |
| 87 | 2,5-difluoro-phenyl | methoxy | H | 314 |
| 88 | 4-trifluoromethoxy-phenyl | methoxy | H | 362 |
| 89 | 4-trifluoromethyl-phenyl | methoxy | H | 346 |
| 92 | phenyl | N,N-dimethyl-amino | H | 291 |
| 115 | 3-carboxy-phenyl | methoxy | methoxy | 352 |
| 116 | 3-(amino-carbonyl)-phenyl | methoxy | methoxy | 351 |
| 117 | 3-bromo-phenyl | amino | H | 342 |
| 118 | 3-methoxy-phenyl | amino | H | 293 |
| 119 | 3-chloro-phenyl | amino | H | 297 |
| 120 | 3-(methoxy-carbonyl)-phenyl | amino | H | 321 |
| 121 | 3-fluoro-phenyl | amino | H | 281 |
| 122 | 3-bromo-phenyl | 4-methyl-piperazin-1-yl | H | 425 |
| 123 | 3-methoxy-phenyl | 4-methyl-piperazin-1-yl | H | 376 |
| 124 | 3-chloro-phenyl | 4-methyl-piperazin-1-yl | H | 380 |
| 125 | 3-bromo-phenyl | hydroxy | hydroxy | 359 |
| 129 | 3-pyridyl | 3-morpholin-4-yl-propoxy | methoxy | 422 |
| 130 | 3-bromo-phenyl | 3-morpholin-4-yl-propoxy | methoxy | 500 |
| 131 | 3-methoxy-phenyl | 3-morpholin-4-yl-propoxy | methoxy | 451 |
| 132 | 3-chloro-phenyl | 3-morpholin-4-yl-propoxy | methoxy | 455 |
| 133 | 3-(methoxy-carbonyl)-phenyl | 3-morpholin-4-yl-propoxy | methoxy | 479 |
| 134 | 3-fluoro-phenyl | 3-morpholin-4-yl-propoxy | methoxy | 439 |
| 135 | 3-chloro-phenyl | 3-methoxy-propoxy | H | 370 |
| 136 | 3-fluoro-phenyl | 3-methoxy-propoxy | H | 354 |

TABLE 2-continued

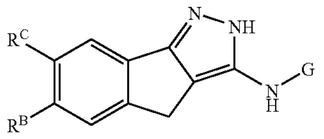

| Cpd | G | $R^B$ | $R^C$ | MS |
|---|---|---|---|---|
| 137 | 3-(methoxy-carbonyl)-phenyl | 3-methoxy-propoxy | H | 394 |
| 138 | 3-fluoro-phenyl | 3-methoxy-propoxy | H | 354 |
| 139 | 3-methoxy-phenyl | 3-methoxy-propoxy | H | 366 |
| 140 | phenyl | 3-methoxy-propoxy | H | 336 |
| 141 | 3-bromo-phenyl | 3-methoxy-propoxy | H | 415 |
| 142 | 3-pyridyl | 3-methoxy-propoxy | H | 337 |
| 143 | 4-methoxy-phenyl | 3-methoxy-propoxy | H | 366 |
| 151 | 3-fluoro-phenyl | bromo | H | 345 |
| 152 | 3-pyridyl | bromo | H | 328 |
| 153 | 2,5-difluoro-phenyl | bromo | H | 363 |
| 154 | 3-trifluoromethoxy-phenyl | bromo | H | 411 |
| 155 | 3-trifluoromethyl-phenyl | bromo | H | 395 |
| 156 | 3-methoxy-phenyl | 3-pyrrolidin-1-yl-propoxy | methoxy | 435 |
| 157 | 3-(methoxy-carbonyl)-phenyl | 3-pyrrolidin-1-yl-propoxy | methoxy | 463 |
| 158 | phenyl | bromo | H | 327 |
| 159 | 4-fluoro-phenyl | 3-(N,N-dimethyl-amino)-propoxy | H | 367 |
| 160 | 3-fluoro-phenyl | 3-(N,N-dimethyl-amino)-propoxy | H | 367 |
| 161 | 3-pyridyl | 3-(N,N-dimethyl-amino)-propoxy | H | 350 |
| 162 | 2,5-dimethoxy-phenyl | 3-(N,N-dimethyl-amino)-propoxy | H | 409 |
| 163 | 2,5-difluoro-phenyl | 3-(N,N-dimethyl-amino)-propoxy | H | 385 |
| 165 | 3-trifluoromethyl-phenyl | 3-(N,N-dimethyl-amino)-propoxy | H | 417 |
| 166 | 3-chloro-4-fluoro-phenyl | 3-methoxy-propoxy | methoxy | 418 |
| 167 | 3-chloro-4-fluoro-phenyl | isopropoxy | isopropoxy | 416 |
| 168 | 3-methoxy-phenyl | isopropoxy | isopropoxy | 394 |
| 169 | 3-fluoro-phenyl | isopropoxy | isopropoxy | 382 |
| 170 | 4-fluoro-phenyl | H | methoxy | 296 |
| 171 | 4-methoxy-phenyl | H | methoxy | 308 |
| 172 | 3-fluoro-phenyl | H | methoxy | 296 |
| 173 | 3-pyridyl | H | methoxy | 279 |
| 174 | 2,5-dimethoxy-phenyl | H | methoxy | 338 |
| 175 | 2,4-dimethoxy-phenyl | H | methoxy | 338 |
| 176 | 2,5-difluoro-phenyl | H | methoxy | 314 |
| 177 | 4-trifluoromethoxy-phenyl | H | methoxy | 362 |
| 178 | 4-trifluoromethyl-phenyl | H | methoxy | 346 |
| 179 | 3-chloro-4-fluoro-phenyl | 3-morpholin-4-yl-propoxy | methoxy | 473 |
| 180 | 3-fluoro-phenyl | 3-pyrrolidin-1-yl-propoxy | methoxy | 423 |
| 181 | 3-chloro-4-fluoro-phenyl | 3-pyrrolidin-1-yl-propoxy | methoxy | 457 |
| 182 | 3-fluoro-phenyl | H | methyl | 280 |
| 183 | 4-methoxy-phenyl | H | methyl | 292 |
| 184 | 2,5-dimethoxy-phenyl | H | methyl | 322 |
| 185 | 2,5-difluoro-phenyl | H | methyl | 298 |

TABLE 2-continued

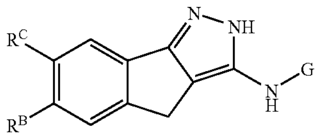

| Cpd | G | $R^B$ | $R^C$ | MS |
|---|---|---|---|---|
| 186 | 4-trifluoromethoxy-phenyl | H | methyl | 346 |
| 187 | 3-trifluoromethyl-phenyl | H | methyl | 330 |
| 188 | 3-pyridyl | chloro | H | 283 |
| 189 | 4-methoxy-phenyl | chloro | H | 312 |
| 190 | 3-methoxy-phenyl | chloro | H | 312 |
| 191 | 3-fluoro-phenyl | chloro | H | 300 |
| 192 | 2,5-difluoro-phenyl | chloro | H | 318 |
| 193 | 4-trifluoromethyl-phenyl | chloro | H | 350 |
| 194 | 4-trifluoromethoxy-phenyl | chloro | H | 366 |
| 195 | 3,5-di(trifluoromethyl)-phenyl | chloro | H | 418 |
| 196 | 4-dimethylamino-phenyl | chloro | H | 325 |
| 197 | 3-methyl-phenyl | chloro | H | 296 |
| 198 | 4-methyl-phenyl | chloro | H | 296 |
| 199 | 3-fluoro-phenyl | 3-(N,N-dimethyl-amino)-propoxy | methoxy | 397 |
| 200 | 3-chloro-4-fluoro-phenyl | 3-(N,N-dimethyl-amino)-propoxy | methoxy | 431 |
| 201 | 4-fluoro-phenyl | fluoro | H | 284 |
| 202 | 3-chloro-4-fluoro-phenyl | fluoro | H | 318 |
| 203 | 2,5-dimethoxy-phenyl | fluoro | H | 326 |
| 204 | 3,5-dimethoxy-phenyl | fluoro | H | 326 |
| 205 | 3,4-dimethoxy-phenyl | fluoro | H | 326 |
| 206 | 3,5-dimethyl-phenyl | methoxy | methoxy | 336 |
| 207 | 3,5-difluoro-phenyl | methoxy | methoxy | 344 |
| 208 | 3-methylthio-phenyl | methoxy | methoxy | 354 |
| 209 | 3-ethyl-phenyl | methoxy | methoxy | 336 |
| 210 | 3-(ethoxy-carbonyl)-phenyl | methoxy | methoxy | 380 |
| 211 | 3-(trifluoromethyl-thio)-phenyl | methoxy | methoxy | 408 |
| 212 | 4-fluoro-3-trifluoromethyl-phenyl | methoxy | methoxy | 394 |
| 213 | 3-chloro-phenyl | 3-(4-methyl-piperazin-1-yl)-propoxy | methoxy | 468 |
| 214 | 3-chloro-4-fluoro-phenyl | 3-(4-methyl-piperazin-1-yl)-propoxy | methoxy | 486 |
| 215 | 3-methoxy-phenyl | 3-(4-methyl-piperazin-1-yl)-propoxy | methoxy | 464 |
| 216 | 3-fluoro-phenyl | 3-(4-methyl-piperazin-1-yl)-propoxy | methoxy | 452 |
| 217 | 4-trifluoromethoxy-phenyl | 3-(N,N-dimethyl-amino)-propoxy | H | 433 |
| 218 | 4-benzyloxy-phenyl | methoxy | methoxy | 414 |
| 221 | 4-(piperidin-4-yl-sulfonyl)-phenyl | methoxy | methoxy | 455 |
| 226 | 3-fluoro-phenyl | 3-imidazol-1-yl-propoxy | methoxy | 420 |
| 227 | 3-chloro-4-fluoro-phenyl | 3-imidazol-1-yl-propoxy | methoxy | 454 |
| 233 | 4-methoxy-phenyl | fluoro | H | 296 |
| 234 | 3-methoxy-phenyl | fluoro | H | 296 |
| 235 | 3-fluoro-phenyl | fluoro | H | 284 |
| 236 | 2,5-difluoro-phenyl | fluoro | H | 302 |

TABLE 2-continued

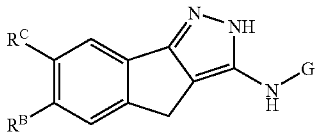

| Cpd | G | $R^B$ | $R^C$ | MS |
|---|---|---|---|---|
| 237 | 4-trifluoromethyl-phenyl | fluoro | H | 334 |
| 238 | 4-trifluoromethoxy-phenyl | fluoro | H | 350 |
| 239 | 3,5-di(trifluoromethyl)-phenyl | fluoro | H | 402 |
| 240 | 3-methyl-phenyl | fluoro | H | 280 |
| 242 | 3-fluoro-phenyl | 3-methoxy-propoxy | methoxy | 384 |
| 244 | 3-methoxy-phenyl | 3-methoxy-propoxy | methoxy | 396 |
| 245 | 3-methoxy-phenyl | ethoxy | ethoxy | 366 |
| 246 | 3-chloro-4-fluoro-phenyl | ethoxy | ethoxy | 388 |
| 259 | 3-chloro-phenyl | 2,3-dihydroxy-propoxy | methoxy | 402 |
| 260 | 3-methoxy-phenyl | 2,3-dihydroxy-propoxy | methoxy | 398 |
| 261 | 3-chloro-4-fluoro-phenyl | 2,3-dihydroxy-propoxy | methoxy | 420 |
| 262 | 3-fluoro-phenyl | 2,3-dihydroxy-propoxy | methoxy | 386 |
| 263 | 3-pyridyl | 2,3-dihydroxy-propoxy | methoxy | 369 |
| 265 | 3-fluoro-phenyl | 3-hydroxy-propoxy | methoxy | 370 |
| 266 | 3-methoxy-phenyl | 3-hydroxy-propoxy | methoxy | 382 |
| 267 | 3-chloro-4-fluoro-phenyl | 3-hydroxy-propoxy | methoxy | 404 |
| 268 | 3-chloro-phenyl | 3-hydroxy-propoxy | methoxy | 386 |
| 269 | 3-fluoro-phenyl | 2-hydroxy-3-pyrrolidin-1-yl-propoxy | methoxy | 439 |
| 270 | 3-methoxy-phenyl | 2-hydroxy-3-pyrrolidin-1-yl-propoxy | methoxy | 451 |
| 276 | 4-fluoro-3-nitro-phenyl | methoxy | methoxy | 371 |
| 277 | 3-chloro-4-methoxy-phenyl | methoxy | methoxy | 372 |
| 278 | 3-(1-hydroxy-ethyl)-phenyl | methoxy | methoxy | 352 |
| 279 | 3,5-di(tert-butyl)-phenyl | methoxy | methoxy | 420 |
| 280 | 3-chloro-4-fluoro-phenyl | 2-hydroxy-3-pyrrolidin-1-yl-propoxy | methoxy | 473 |
| 281 | 3-pyridyl | 2-hydroxy-3-pyrrolidin-1-yl-propoxy | methoxy | 422 |
| 282 | 3-chloro-phenyl | 2-hydroxy-3-pyrrolidin-1-yl-propoxy | methoxy | 455 |
| 283 | 3-fluoro-phenyl | 3-methoxy-propoxy | 3-methoxy-propoxy | 442 |
| 284 | 3-methoxy-phenyl | 3-methoxy-propoxy | 3-methoxy-propoxy | 454 |
| 285 | 3-chloro-phenyl | 3-methoxy-propoxy | 3-methoxy-propoxy | 458 |
| 286 | 3-pyridyl | 3-methoxy-propoxy | 3-methoxy-propoxy | 425 |
| 287 | 3-chloro-4-fluoro-phenyl | 3-methoxy-propoxy | 3-methoxy-propoxy | 476 |
| 288 | 3-chloro-4-methoxy-phenyl | fluoro | H | 330 |

TABLE 2-continued

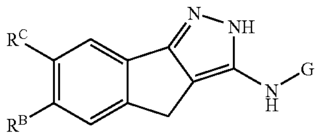

| Cpd | G | $R^B$ | $R^C$ | MS |
|---|---|---|---|---|
| 289 | 3-(1-hydroxy-ethyl)-phenyl | fluoro | H | 310 |
| 290 | 5-indolyl | fluoro | H | 305 |
| 291 | 3-fluoro-phenyl | benzyloxy | methoxy | 402 |
| 297 | 3-(2-hydroxy-ethyl-amino-carbonyl)-phenyl | methoxy | methoxy | 395 |
| 298 | 3-[N-(3-pyrrolidin-1-yl-propyl)-amino-carbonyl]-phenyl | methoxy | methoxy | 462 |
| 299 | phenyl | H | fluoro | 266 |
| 303 | 3,5-di(tert-butyl)-phenyl | fluoro | H | 378 |
| 309 | 3-chloro-4-methoxy-phenyl | H | methyl | 326 |
| 310 | 3-(1-hydroxy-ethyl)-phenyl | H | methyl | 306 |
| 311 | 5-indolyl | H | methyl | 301 |
| 312 | 3,5-di(tert-butyl)-phenyl | H | methyl | 374 |
| 319 | 3-(4-methyl-piperazinyl-carbonyl)-phenyl | methoxy | methoxy | 434 |
| 334 | 3-fluoro-phenyl | H | fluoro | 284 |
| 337 | 3-fluoro-phenyl | H | H | 266 |
| 338 | 5-chloro-2-methyl-phenyl | H | H | 296 |
| 339 | 2,5-difluoro-phenyl | H | H | 284 |
| 340 | 5-trifluoromethyl-2-fluoro-phenyl | H | H | 334 |
| 341 | 2,5-dimethoxy-phenyl | H | H | 308 |
| 342 | 5-chloro-2-methoxy-phenyl | H | H | 312 |
| 343 | 3-methoxy-phenyl | H | H | 278 |
| 357 | 3-fluoro-phenyl | fluoro | methoxy | 314 |
| 358 | 3-bromo-phenyl | fluoro | methoxy | 375 |
| 359 | 3-chloro-4-fluoro-phenyl | fluoro | methoxy | 348 |
| 360 | 3-methoxy-phenyl | fluoro | methoxy | 326 |
| 361 | 4-fluoro-phenyl | fluoro | methoxy | 314 |
| 362 | 3-fluoro-phenyl | hydroxy | hydroxy | 298 |
| 363 | 3-fluoro-phenyl | hydroxy | methoxy | 312 |
| 364 | 3-pyridyl | fluoro | methoxy | 297 |
| 365 | 3-fluoro-phenyl | ethoxy | 3-hydroxy-propoxy | 384 |
| 366 | 3-methoxy-phenyl | ethoxy | 3-hydroxy-propoxy | 396 |
| 367 | 3-chloro-phenyl | ethoxy | 3-hydroxy-propoxy | 400 |
| 368 | 3-chloro-4-fluoro-phenyl | ethoxy | 3-hydroxy-propoxy | 418 |
| 369 | 3-fluoro-phenyl | bromo | methoxy | 375 |
| 370 | 3-methoxy-phenyl | bromo | methoxy | 387 |
| 371 | 3-pyridyl | ethoxy | 3-hydroxy-propoxy | 367 |
| 372 | 3-pyridyl | 3-hydroxy-propoxy | 3-hydroxy-propoxy | 397 |
| 373 | 3-chloro-phenyl | 3-hydroxy-propoxy | 3-hydroxy-propoxy | 430 |
| 374 | 3-ethoxy-phenyl | methoxy | methoxy | 352 |
| 375 | 3-ethoxy-phenyl | ethoxy | ethoxy | 380 |
| 376 | 3-ethoxy-phenyl | 3-hydroxy-propoxy | methoxy | 396 |
| 377 | 3-(2-chloro)-pyridyl | methoxy | methoxy | 343 |
| 379 | 3-ethoxy-phenyl | 2,3-dihydroxy-propoxy | methoxy | 412 |
| 382 | 3-fluoro-phenyl | 3-hydroxy-propoxy | ethoxy | 384 |

TABLE 2-continued

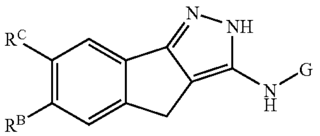

| Cpd | G | $R^B$ | $R^C$ | MS |
|---|---|---|---|---|
| 383 | 3-pyridyl | 3-hydroxy-propoxy | ethoxy | 367 |
| 384 | 3-methoxy-phenyl | 3-hydroxy-propoxy | ethoxy | 396 |
| 388 | 3-ethoxy-phenyl | ethoxy | 3-hydroxy-propoxy | 410 |
| 389 | 3-chloro-4-fluoro-phenyl | 3-hydroxy-propoxy | 3-hydroxy-propoxy | 448 |
| 398 | 3-fluoro-phenyl | 3-hydroxy-propoxy | 3-hydroxy-propoxy | 414 |
| 400 | 3-methoxy-phenyl | 3-hydroxy-propoxy | 3-hydroxy-propoxy | 426 |
| 401 | 3-ethoxy-phenyl | 3-hydroxy-propoxy | 3-hydroxy-propoxy | 440 |
| 410 | 2-bromo-3-fluoro-phenyl | methoxy | methoxy | 405 |
| 452 | 4-methyl-3-[N-[4-(3-pyridyl)-pyrimidin-2-yl]amino]-phenyl | methoxy | methoxy | 492 |
| 453 | 3-(4-methoxy)-pyridyl | methoxy | methoxy | 339 |
| 454 | 3-(2,4-dimethoxy)-pyridyl | methoxy | methoxy | 369 |
| 460 | 3-fluoro-phenyl | ethoxy | 3-pyrrolidin-1-yl-2-hydroxy-propoxy | 453 |
| 461 | 3-pyridyl | ethoxy | 3-pyrrolidin-1-yl-2-hydroxy-propoxy | 436 |
| 462 | 3-methoxy-phenyl | ethoxy | 3-pyrrolidin-1-yl-2-hydroxy-propoxy | 465 |
| 463 | 3-ethoxy-phenyl | ethoxy | 3-pyrrolidin-1-yl-2-hydroxy-propoxy | 479 |
| 476 | 2,6-difluoro-phenyl | methoxy | methoxy | 344 |
| 477 | 2,4,6-trifluoro-phenyl | methoxy | methoxy | 362 |
| 549 | 3-fluoro-phenyl | methoxy | benzyloxy | 402 |
| 562 | 2-pyridyl | methoxy | methoxy | 309 |
| 565 | 2,2-difluoro-1,3-benzodioxol-4-yl | methoxy | methoxy | 388 |
| 566 | 2,3-dihydro-1H-indol-1-yl | methoxy | methoxy | 334 |
| 567 | 5-bromo-2,3-dihydro-1H-indol-1-yl | methoxy | methoxy | 413 |
| 576 | 2-(3-methyl-5-bromo)-pyridyl | methoxy | methoxy | 402 |
| 577 | 3-(4-trifluoro-methyl)-pyridyl | methoxy | methoxy | 377 |
| 582 | 2-(3-bromo)-pyridyl | methoxy | methoxy | 388 |
| 583 | 2-(4-bromo)-pyridyl | methoxy | methoxy | 388 |
| 584 | 3-isopropoxy-phenyl | methoxy | methoxy | 367 |
| 587 | 2-(3-methyl)-pyridyl | methoxy | methoxy | 324 |
| 588 | 2-(4,6-dimethyl)-pyridyl | methoxy | methoxy | 338 |
| 594 | 3-fluoro-phenyl | ethoxy | ethoxy | 355 |
| 608 | 3-fluoro-phenyl | methoxy | hydroxy | 313 |

TABLE 3

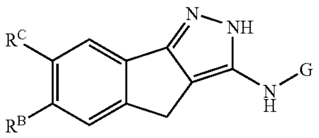

| Cpd | G | $R^B$ | $R^C$ | MS |
|---|---|---|---|---|
| 63 | benzyl | methoxy | methoxy | 322 |
| 69 | 2-morpholin-4-yl-ethyl | methoxy | methoxy | 345 |
| 219 | 3,4-dichloro-benzyl | methoxy | methoxy | 391 |
| 220 | cyclohexyl-methyl | methoxy | methoxy | 328 |
| 222 | 4-methyl-benzyl | methoxy | methoxy | 336 |
| 223 | 2-methyl-benzyl | methoxy | methoxy | 336 |
| 224 | 2-methoxy-benzyl | methoxy | methoxy | 352 |
| 225 | 3-methoxy-benzyl | methoxy | methoxy | 352 |
| 230 | 2-chloro-benzyl | methoxy | methoxy | 356 |
| 231 | 4-methoxy-benzyl | methoxy | methoxy | 352 |
| 264 | benzyl | ethoxy | ethoxy | 350 |
| 271 | 3,5-dichloro-benzyl | methoxy | methoxy | 390 |
| 272 | 3-methyl-benzyl | methoxy | methoxy | 336 |
| 273 | 4-chloro-3-methyl-benzyl | methoxy | methoxy | 370 |
| 274 | 2,5-dimethoxy-benzyl | methoxy | methoxy | 382 |
| 275 | 3,4-difluoro-benzyl | methoxy | methoxy | 358 |
| 293 | 2-fluoro-benzyl | ethoxy | ethoxy | 368 |
| 294 | 3-fluoro-benzyl | ethoxy | ethoxy | 368 |
| 295 | 2,6-dichloro-benzyl | ethoxy | ethoxy | 418 |
| 296 | 2-methoxy-benzyl | ethoxy | ethoxy | 380 |
| 301 | 2-trifluoromethoxy-benzyl | ethoxy | ethoxy | 434 |
| 292 | 2-chloro-benzyl | ethoxy | ethoxy | 384 |
| 304 | 3,5-dichloro-benzyl | fluoro | H | 349 |
| 305 | 3-methyl-benzyl | fluoro | H | 294 |
| 306 | 3-chloro-4-methyl-benzyl | fluoro | H | 328 |
| 307 | 2,5-dimethoxy-benzyl | fluoro | H | 340 |
| 308 | 3,4-difluoro-benzyl | fluoro | H | 316 |
| 313 | 3,5-dichloro-benzyl | H | methyl | 345 |
| 314 | 3-methyl-benzyl | H | methyl | 290 |
| 315 | 3-chloro-4-methyl-benzyl | H | methyl | 324 |
| 316 | 2,5-dimethoxy-benzyl | H | methyl | 336 |
| 317 | 3,4-difluoro-benzyl | H | methyl | 312 |
| 320 | 3,4-dimethyl-benzyl | methoxy | methoxy | 350 |
| 321 | 2,6-difluoro-benzyl | methoxy | methoxy | 358 |
| 322 | 2,3-dimethoxy-benzyl | methoxy | methoxy | 382 |
| 323 | 2,5-difluoro-benzyl | methoxy | methoxy | 358 |
| 324 | 1-(3-methoxy-phenyl)-(S*)ethyl | methoxy | methoxy | 366 |
| 325 | 2-fluoro-benzyl | methoxy | methoxy | 340 |
| 326 | 2,3-dichloro-benzyl | methoxy | methoxy | 391 |
| 327 | 3-fluoro-benzyl | methoxy | methoxy | 340 |
| 328 | 2,4-difluoro-benzyl | methoxy | methoxy | 358 |
| 329 | 2-trifluoromethyl-benzyl | methoxy | methoxy | 390 |
| 330 | 2,5-dichloro-benzyl | methoxy | methoxy | 391 |
| 331 | 4-fluoro-benzyl | methoxy | methoxy | 340 |
| 333 | 3-chloro-benzyl | methoxy | methoxy | 370 |
| 378 | 2-methyl-benzyl | fluoro | H | 296 |
| 385 | 2-chloro-benzyl | 3-hydroxy-propoxy | methoxy | 400 |
| 386 | 2-fluoro-benzyl | 3-hydroxy-propoxy | methoxy | 384 |
| 387 | 2-fluoro-benzyl | 2,3-dihydroxy-propoxy | methoxy | 400 |
| 390 | 2,6-dichloro-benzyl | methoxy | 3-pyrrolidin-1-yl-2-hydroxy-propoxy | 504 |
| 391 | 2,6-difluoro-benzyl | methoxy | 3-pyrrolidin-1-yl-2-hydroxy-propoxy | 471 |
| 396 | 2-chloro-benzyl | methoxy | 3-pyrrolidin-1-yl-2-hydroxy-propoxy | 469 |
| 397 | 2-fluoro-benzyl | methoxy | 3-pyrrolidin-1-yl-2-hydroxy-propoxy | 453 |

TABLE 3-continued

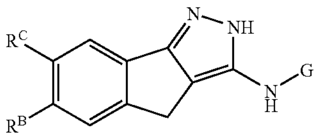

| Cpd | G | $R^B$ | $R^C$ | MS |
|---|---|---|---|---|
| 424 | 3-chloro-benzyl | methoxy | methoxy | 370 |
| 425 | 2-methyl-benzyl | fluoro | methoxy | 324 |
| 426 | 2-fluoro-benzyl | fluoro | methoxy | 328 |
| 448 | 2,6-dichloro-benzyl | 3-hydroxy-propoxy | methoxy | 435 |
| 449 | 2,6-difluoro-benzyl | 3-hydroxy-propoxy | methoxy | 402 |
| 450 | 2,6-dichloro-benzyl | 2,3-dihydroxy-propoxy | methoxy | 451 |
| 451 | 2-chloro-benzyl | 2,3-dihydroxy-propoxy | methoxy | 416 |
| 455 | 5-(phenyl)-isoxazol-3-yl-methyl | methoxy | methoxy | 389 |
| 457 | 2,6-difluoro-benzyl | 2,3-dihydroxy-propoxy | methoxy | 418 |
| 563 | 2-pyridyl-methyl | methoxy | methoxy | 323 |
| 564 | 3-pyridyl-methyl | methoxy | methoxy | 323 |
| 575 | 2-bromo-benzyl | methoxy | methoxy | 401 |

TABLE 4

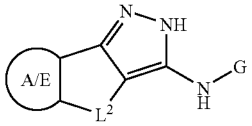

| Cpd | $L^2$ | G | A/E Ring | MS |
|---|---|---|---|---|
| 52 | $-(CH_2)_2-$ | phenyl | 4,5-thienyl | 268 |
| 93 | $-(CH_2)_2-$ | phenyl | phenyl | 262 |
| 94 | $-CH_2-$ | phenyl | 4,5-thienyl | 254 |
| 95 | $-CH_2-$ | 3-bromo-phenyl | 5,6-(1,3-benzodioxolyl) | 371 |
| 96 | $-CH_2-$ | 3-fluoro-phenyl | 5,6-(1,3-benzodioxolyl) | 310 |
| 97 | $-CH_2-$ | 3-methoxy-phenyl | 5,6-(1,3-benzodioxolyl) | 322 |
| 126 | $-CH_2-$ | 3-pyridyl | 5,6-(1,3-benzodioxolyl) | 293 |
| 127 | $-CH_2-$ | 3-(methoxy-carbonyl)-phenyl | 5,6-(1,3-benzodioxolyl) | 350 |
| 128 | $-CH_2-$ | 3-chloro-phenyl | 5,6-(1,3-benzodioxolyl) | 326 |
| 232 | $-CH_2-$ | 3-methoxy-phenyl | 4,5-thienyl | 284 |
| 335 | $-CH_2-$ | 3-fluoro-phenyl | 4,5-thienyl | 272 |
| 402 | $-CH_2-$ | 3-pyridyl | 4,5-thienyl | 255 |
| 403 | $-CH_2-$ | 3-chloro-phenyl | 4,5-thienyl | 288 |
| 404 | $-CH_2-$ | 4-fluoro-3-chloro-phenyl | 4,5-thienyl | 306 |
| 405 | $-CH_2-$ | 3-ethoxy-phenyl | 4,5-thienyl | 298 |

TABLE 5

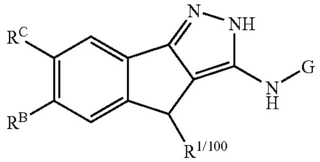

| Cpd | G | $R^B$ | $R^C$ | $R^{1/100}$ | MS |
|---|---|---|---|---|---|
| 35 | phenyl | H | H | oxo | 262 |
| 50 | phenyl | H | H | hydroxy | 264 |
| 106 | 4-fluoro-phenyl | H | H | methyl | 280 |
| 107 | 4-methoxy-phenyl | H | H | methyl | 292 |
| 108 | 3-fluoro-phenyl | H | H | methyl | 280 |
| 109 | 3-pyridyl | H | H | methyl | 263 |
| 110 | 2,5-dimethoxy-phenyl | H | H | methyl | 322 |
| 111 | 2,4-dimethoxy-phenyl | H | H | methyl | 322 |
| 112 | 2,5-difluoro-phenyl | H | H | methyl | 298 |
| 113 | 4-trifluoromethoxy-phenyl | H | H | methyl | 346 |
| 114 | 4-trifluoromethyl-phenyl | H | H | methyl | 330 |
| 247 | phenyl | methoxy | methoxy | methyl | 322 |
| 248 | 4-fluoro-phenyl | methoxy | methoxy | methyl | 340 |
| 249 | 3-fluoro-phenyl | methoxy | methoxy | methyl | 340 |
| 250 | 3-chloro-4-fluoro-phenyl | methoxy | methoxy | methyl | 374 |
| 251 | 3,5-difluoro-phenyl | methoxy | methoxy | methyl | 358 |
| 252 | 2,5-difluoro-phenyl | methoxy | methoxy | methyl | 358 |

TABLE 5-continued

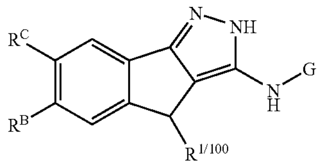

| Cpd | G | $R^B$ | $R^C$ | $R^{1/100}$ | MS |
|---|---|---|---|---|---|
| 253 | 3-methoxy-phenyl | methoxy | methoxy | methyl | 352 |
| 254 | 3-benzyloxy-phenyl | methoxy | methoxy | methyl | 428 |
| 255 | 3-methylthio-phenyl | methoxy | methoxy | methyl | 368 |
| 256 | 3-bromo-phenyl | methoxy | methoxy | methyl | 400 |
| 257 | 3-chloro-phenyl | methoxy | methoxy | methyl | 356 |
| 258 | 2,5-dimethoxy-phenyl | methoxy | methoxy | methyl | 382 |
| 344 | 3-fluoro-phenyl | ethoxy | ethoxy | methyl | 368 |
| 345 | 3-pyridyl | ethoxy | ethoxy | methyl | 351 |
| 346 | 3-bromo-phenyl | ethoxy | ethoxy | methyl | 429 |
| 347 | 4-fluoro-3-chloro-phenyl | ethoxy | ethoxy | methyl | 402 |
| 348 | 3-methoxy-phenyl | ethoxy | ethoxy | methyl | 380 |
| 349 | 4-fluoro-phenyl | ethoxy | ethoxy | methyl | 368 |
| 351 | 3-fluoro-phenyl | isopropoxy | isopropoxy | methyl | 396 |
| 352 | 3-pyridyl | isopropoxy | isopropoxy | methyl | 379 |
| 353 | 3-bromo-phenyl | isopropoxy | isopropoxy | methyl | 457 |
| 354 | 4-fluoro-3-chloro-phenyl | isopropoxy | isopropoxy | methyl | 430 |
| 355 | 3-methoxy-phenyl | isopropoxy | isopropoxy | methyl | 408 |
| 356 | 4-fluoro-phenyl | isopropoxy | isopropoxy | methyl | 396 |
| 419 | 3-chloro-phenyl | methoxy | methoxy | ethyl | 370 |
| 420 | 3-bromo-phenyl | methoxy | methoxy | ethyl | 415 |
| 421 | 4-fluoro-phenyl | methoxy | methoxy | ethyl | 354 |
| 482 | 3-bromo-phenyl | methoxy | methoxy | (R*)ethyl | 415 |
| 483 | 3-bromo-phenyl | methoxy | methoxy | (S*)ethyl | 415 |
| 485 | 3-bromo-phenyl | methoxy | methoxy | 4,4-dimethyl | 415 |
| 486 | 3-chloro-phenyl | methoxy | methoxy | 4,4-dimethyl | 370 |
| 487 | 3-fluoro-phenyl | methoxy | methoxy | 4,4-dimethyl | 354 |
| 488 | 3-methoxy-phenyl | methoxy | methoxy | 4,4-dimethyl | 366 |
| 489 | 3-ethoxy-phenyl | methoxy | methoxy | 4,4-dimethyl | 380 |
| 504 | 3-ethoxy-phenyl | ethoxy | ethoxy | methyl | 394 |
| 505 | 3-ethoxy-phenyl | methoxy | methoxy | ethyl | 380 |
| 512 | 3-methoxy-phenyl | methoxy | methoxy | ethyl | 366 |
| 538 | 3-bromo-phenyl | methoxy | methoxy | 2-isopropyl | 429 |
| 540 | 3-chloro-phenyl | methoxy | methoxy | 2-isopropyl | 384 |
| 541 | 3-methoxy-phenyl | methoxy | methoxy | 2-isopropyl | 380 |
| 553 | 3-bromo-phenyl | methoxy | methoxy | (R*)methyl | 401 |
| 554 | 3-methoxy-phenyl | methoxy | methoxy | (R*)methyl | 366 |
| 555 | 3-bromo-phenyl | methoxy | methoxy | (R*)ethyl | 415 |
| 556 | 3-methoxy-phenyl | methoxy | methoxy | (R*)ethyl | 380 |
| 559 | 3-(2-chloro)-pyridyl | methoxy | methoxy | (R*)methyl | 357 |
| 568 | 3-bromo-phenyl | methoxy | methoxy | (S*)methyl | 401 |
| 569 | 3-ethoxy-phenyl | methoxy | methoxy | (S*)methyl | 366 |
| 570 | 3-bromo-phenyl | methoxy | methoxy | (S*)ethyl | 415 |
| 571 | 3-ethoxy-phenyl | methoxy | methoxy | (S*)ethyl | 380 |
| 585 | 2,6-dichloro-benzyl | methoxy | methoxy | (S*)ethyl | 420 |
| 586 | 2,6-dichloro-benzyl | methoxy | methoxy | (S*)methyl | 405 |
| 607 | 3-(2-chloro)-pyridyl | methoxy | methoxy | (R*)ethyl | 371 |

TABLE 6

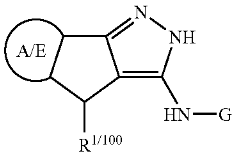

| ID No | A/E Ring | $R^{1/100}$ | G |
|---|---|---|---|
| ID-1 | 5,6-pyridyl | H | 3-fluoro-phenyl |
| ID-2 | 5,6-pyridyl | H | 3-bromo-phenyl |

TABLE 6-continued

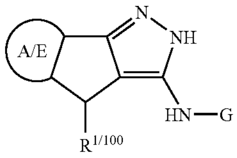

| ID No | A/E Ring | $R^{1/100}$ | G |
|---|---|---|---|
| ID-3 | 5,6-pyridyl | H | benzyl |
| ID-4 | 4,5-pyridyl | H | 3-fluoro-phenyl |

TABLE 6-continued

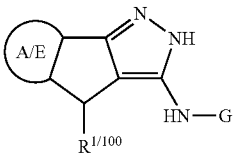

| ID No | A/E Ring | $R^{1/100}$ | G |
|---|---|---|---|
| ID-5 | 4,5-pyridyl | H | 3-methoxy-phenyl |
| ID-6 | 4,5-pyridyl | H | 3-chloro-benzyl |
| ID-7 | 3,4-pyridyl | H | 3-fluoro-phenyl |
| ID-8 | 3,4-pyridyl | H | 3-chloro-phenyl |
| ID-9 | 3,4-pyridyl | H | 3-fluoro-benzyl |
| ID-10 | 5,6-pyrimidinyl | H | 3-hydroxymethyl-phenyl |
| ID-11 | 5,6-pyrimidinyl | H | 3-bromo-phenyl |
| ID-12 | 5,6-pyrimidinyl | H | 2-fluoro-benzyl |
| ID-13 | 4,5-pyrimidinyl | H | 3-hydroxymethyl-phenyl |
| ID-14 | 4,5-pyrimidinyl | H | 3-bromo-phenyl |
| ID-15 | 4,5-pyrimidinyl | H | 2-fluoro-benzyl |
| ID-16 | 2,3-(5-chloro-thienyl) | H | 3-fluoro-phenyl |
| ID-17 | 2,3-(5-chloro-thienyl) | H | 3-pyridyl |
| ID-18 | 2,3-(5-chloro-thienyl) | H | 2-chloro-benzyl |
| ID-19 | 4,5-(2-phenyl-furyl) | H | phenyl |
| ID-20 | 4,5-(2-phenyl-furyl) | H | 3-chloro-4-fluoro-benzyl |
| ID-21 | 4,5-thienyl | H | 3-fluoro-phenyl |
| ID-22 | 4,5-thienyl | H | 3-chloro-phenyl |
| ID-23 | 4,5-thienyl | H | benzyl |
| ID-24 | 3,4-furyl | H | 3-hydroxymethyl-phenyl |
| ID-25 | 3,4-furyl | H | 3-chloro-phenyl |
| ID-26 | 3,4-furyl | H | 2-aminosulfonyl-benzyl |
| ID-27 | 3,4-isoxazolyl* | H | 3-dimethylamino-phenyl |
| ID-28 | 3,4-isoxazolyl* | H | 3-chloro-phenyl |
| ID-29 | 3,4-isoxazolyl* | H | 2,6-dichloro-benzyl |
| ID-30 | 4,5-(3-methyl-isoxazolyl) | H | 4-methoxy-phenyl |
| ID-31 | 4,5-(3-methyl-isoxazolyl) | H | 3-chloro-phenyl |
| ID-32 | 4,5-(3-methyl-isoxazolyl) | H | 2-fluoro-benzyl |
| ID-33 | 1,2-[4,5-di(trifluoro-methoxy)-phenyl] | | 3-fluoro-phenyl |
| ID-34 | 1,2-[4,5-di(trifluoro-methoxy)-phenyl] | H | 3-bromo-phenyl |
| ID-35 | 1,2-[4,5-di(trifluoro-methoxy)-phenyl] | H | 3-methyl-benzyl |
| ID-36 | 1,2-(3,5-dimethoxy-phenyl) | H | 3-methoxy-phenyl |
| ID-37 | 1,2-(3,5-dimethoxy-phenyl) | H | 3-bromo-phenyl |
| ID-38 | 1,2-(3,5-dimethoxy-phenyl) | H | 2-chloro-benzyl |
| ID-39 | 1,2-(4-chloro-5-methoxy-phenyl) | H | 3-chloro-phenyl |
| ID-40 | 1,2-(4-chloro-5-methoxy-phenyl) | H | 3-bromo-phenyl |
| ID-41 | 1,2-(4-chloro-5-methoxy-phenyl) | H | 3-chloro-benzyl |
| ID-42 | 1,2-(4-methoxy-ethoxy-5-ethoxy-phenyl) | H | 3-fluoro-phenyl |
| ID-43 | 1,2-(4-methoxy-ethoxy-5-ethoxy-phenyl) | H | 3-methoxy-phenyl |
| ID-44 | 1,2-(4-methoxy-ethoxy-5-ethoxy-phenyl) | H | 2-methyl-benzyl |
| ID-45 | 5,6-(2-methyl-8-ethoxy-benzoxazolyl)* | H | 3-fluoro-phenyl |
| ID-46 | 5,6-(2-methyl-8-ethoxy-benzoxazolyl)* | H | 3-bromo-phenyl |
| ID-47 | 5,6-(2-methyl-8-ethoxy-benzoxazolyl)* | H | 2-methyl-benzyl |
| ID-48 | 5,6-benzothiazolyl | H | 3-chloro-phenyl |
| ID-49 | 5,6-benzothiazolyl | H | 3-methoxy-phenyl |
| ID-50 | 5,6-benzothiazolyl | H | 3-chloro-benzyl |
| ID-51 | 1,2-(4,5-diethoxy-phenyl) | H | 2,3-dichloro-benzyl |
| ID-52 | 1,2-(4,5-diethoxy-phenyl) | H | 3-chloro-benzyl |
| ID-53 | 1,2-(4,5-diethoxy-phenyl) | H | benzyl |
| ID-54 | 1,2-(4,5-di(3-methoxy-propoxy)-phenyl) | H | 3-fluoro-phenyl |
| ID-55 | 1,2-(4,5-di(methoxy-ethoxy)-phenyl) | H | 3-methoxy-phenyl |
| ID-56 | 1,2-(4,5-di(methoxy-ethoxy)-phenyl) | H | 2-methyl-benzyl |

TABLE 6-continued

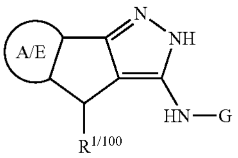

| ID No | A/E Ring | $R^{1/100}$ | G |
|---|---|---|---|
| ID-57 | 1,2-[4,5-di(isopropoxy)-phenyl] | H | 2,3-dichloro-benzyl |
| ID-58 | 1,2-[4,5-di(isopropoxy)-phenyl] | H | 3-chloro-benzyl |
| ID-59 | 1,2-[4,5-di(isopropoxy)-phenyl] | H | 2-methyl-benzyl |
| ID-60 | 1,2-[4,5-di(isopropoxy)-phenyl] | methyl | 2,3-dichloro-benzyl |
| ID-61 | 1,2-[4,5-di(isopropoxy)-phenyl] | methyl | 3-chloro-benzyl |
| ID-62 | 1,2-[4,5-di(isopropoxy)-phenyl] | methyl | 2-methyl-benzyl |
| ID-63 | 1,2-(4,5-diethoxy-phenyl) | methyl | 2,3-dichloro-benzyl |
| ID-64 | 1,2-(4,5-diethoxy-phenyl) | methyl | 3-chloro-benzyl |
| ID-65 | 1,2-(4,5-diethoxy-phenyl) | methyl | 2-methyl-benzyl |
| ID-66 | 1,2-(4,5-diethoxy-phenyl) | H | 3-(dimethylamino-ethylamino-carbonyl)-phenyl |
| ID-67 | 1,2-(4,5-diethoxy-phenyl) | H | 3-(2-pyrrolidin-1-yl-ethylamino-carbonyl)-phenyl |
| ID-68 | 1,2-(4,5-diethoxy-phenyl) | H | 3-(2-pyrrolidin-1-yl-n-propylamino-carbonyl)-phenyl |
| ID-69 | 1,2-(4-methoxyethoxy-5-ethoxy-phenyl) | H | 3-(2-dimethylamino-ethylamino-carbonyl)-phenyl |
| ID-70 | 1,2-(4-methoxyethoxy-5-ethoxy-phenyl) | H | 3-(2-pyrrolidin-1-yl-ethylamino-carbonyl)-phenyl |
| ID-71 | 1,2-(4-methoxyethoxy-5-ethoxy-phenyl) | H | 3-(3-pyrrolidin-1-yl-propylamino-carbonyl)-phenyl |
| ID-72 | 1,2-(4,5-diethoxy-phenyl) | H | 3-[2-(1-methyl-imidazol-5-yl-ethylamino-carbonyl)-phenyl] |
| ID-73 | 1,2-(4,5-diethoxy-phenyl) | H | 3-[2-(imidazol-1-yl ethylamino-carbonyl)-phenyl] |
| ID-74 | 1,2-(4,5-diethoxy-phenyl) | H | 3-[N-(3-hydroxymethyl-1-pyrrolidin-1-yl-propyl)-amino-carbonyl]-phenyl |
| ID-75 | 1,2-(4,5-diethoxy-phenyl) | H | 2-aminosulfonyl-phenyl |
| ID-76 | 1,2-(4,5-diethoxy-phenyl) | H | 3-aminosulfonyl-phenyl |
| ID-77 | 1,2-(4,5-diethoxy-phenyl) | H | 4-aminosulfonyl-phenyl |
| ID-78 | 1,2-(4,5-di(difluoro-methoxy)-phenyl) | H | 3-fluoro-phenyl |
| ID-79 | 1,2-(4,5-di(difluoro-methoxy)-phenyl) | H | 3-aminosulfonyl-phenyl |
| ID-80 | 1,2-(4,5-di(difluoro-methoxy)-phenyl) | H | 3-(ethoxy-carbonyl)-phenyl |
| ID-81 | 4,5-(3-ethoxy-thienyl) | H | 3-pyridyl-methyl |
| ID-82 | 4,5-(3-ethoxy-thienyl) | H | 3-chloro-benzyl |
| ID-83 | 4,5-(3-ethoxy-thienyl) | H | benzyl |
| ID-84 | 4,5-(3-ethoxy-thienyl) | H | cyclohexylmethyl |
| ID-85 | 4,5-(3-ethoxy-thienyl) | H | cyclohexylmethyl |
| ID-86 | 4,5-(3-ethoxy-thienyl) | H | phenethyl |
| ID-87 | 5,6-pyrimidinyl | H | cyclohexylmethyl |
| ID-88 | 5,6-pyrimidinyl | H | phenethyl |
| ID-89 | 4,5-(3-methyl-isoxazolyl) | H | cyclohexyl |
| ID-90 | 4,5-(3-methyl-isoxazolyl) | H | 2-fluoro-phenylethyl |
| ID-91 | 4,5-pyridyl | H | 3-hydroxy-cyclohexyl |
| ID-92 | 4,5-pyridyl | H | 2-methylbenzyl |
| ID-93 | 4,5-pyridyl | H | 3-methoxy-phenyl ethyl |
| ID-94 | 5,6-pyrimidinyl | H | 4-hydroxy-cyclohexyl |
| ID-95 | 5,6-pyrimidinyl | H | 2-hydroxymethyl-benzyl |
| ID-96 | 5,6-pyrimidinyl | H | 2-fluoro-phenyl ethyl |

TABLE 6-continued

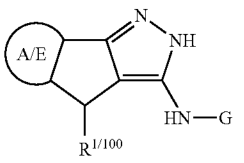

| ID No | A/E Ring | $R^{1/100}$ | G |
|---|---|---|---|
| ID-97 | 4,5-pyrimidinyl | H | 4-hydroxy-cyclohexyl |
| ID-98 | 4,5-pyrimidinyl | H | 2-hydroxymethyl-benzyl |
| ID-99 | 4,5-pyrimidinyl | H | 2-fluoro-phenyl ethyl |
| ID-100 | 1,2-(4,5-diethoxy-phenyl) | H | 3-pyridylmethyl |
| ID-101 | 1,2-(4,5-diethoxy-phenyl) | H | 1-methyl-5-imidazolylmethyl |
| ID-102 | 1,2-(4,5-diethoxy-phenyl) | H | 6-pyrimidinylmethyl |
| ID-103 | 1,2-(4,5-diethoxy-phenyl) | H | 3-pyridylethyl |
| ID-104 | 1,2-(4,5-diethoxy-phenyl) | H | 1-methyl-5-imidazolylmethyl |
| ID-105 | 1,2-(4,5-diethoxy-phenyl) | H | 6-pyrimidinylmethyl |

TABLE 7

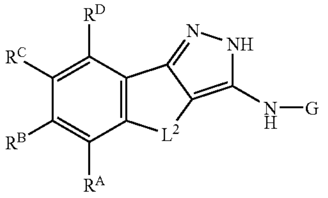

| Cpd | $R^A$ | $R^B$ | $R^C$ | $R^D$ | $L^2$ | G | MS |
|---|---|---|---|---|---|---|---|
| 318 | H | H | H | H | oxy-ethylene | phenyl | 278 |
| 350 | H | cyano | H | H | ethylene | phenyl | 287 |
| 380 | H | H | H | H | oxy | 3-fluoro-phenyl | 268 |
| 381 | H | H | H | H | oxy | 3-chloro-4-fluoro-phenyl | 302 |
| 595 | meth-oxy | H | H | H | oxy | phenyl | 281 |
| 606 | H | meth-oxy | hydroxy | benzyl | methylene | 3-fluoro-phenyl | 403 |

TABLE 8

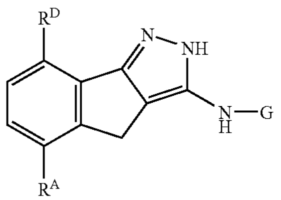

| Cpd | $R^A$ | $R^D$ | G | MS |
|---|---|---|---|---|
| 332 | methoxy | methoxy | phenyl | 308 |

TABLE 9

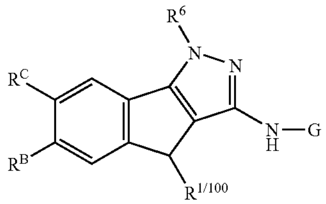

| Cpd | $R^B$ | $R^C$ | $R^{1/100}$ | $R^6$ | G | MS |
|---|---|---|---|---|---|---|
| 91 | meth-oxy | meth-oxy | H | methyl | 3-bromo-phenyl | 401 |
| 409 | meth-oxy | meth-oxy | H | 2,2-dimethyl-1-oxo-propoxy-methyl | 3-fluoro-phenyl | 440 |
| 427 | meth-oxy | meth-oxy | H | benzoyl | 3-fluoro-phenyl | 430 |
| 428 | meth-oxy | meth-oxy | H | 4-methoxy-1,4-dioxo-n-butyl | 3-fluoro-phenyl | 440 |
| 429 | meth-oxy | meth-oxy | H | 4-ethoxy-1,4-dioxo-n-butyl | 3-fluoro-phenyl | 454 |
| 430 | meth-oxy | meth-oxy | H | 1-oxo-propyl | 3-fluoro-phenyl | 382 |
| 431 | meth-oxy | meth-oxy | H | 2-methyl-1-oxo-propyl | 3-fluoro-phenyl | 396 |
| 432 | meth-oxy | meth-oxy | H | 2-hydroxy-1-oxo-ethyl | 3-fluoro-phenyl | 384 |
| 433 | meth-oxy | meth-oxy | H | phenoxy-carbonyl | 3-fluoro-phenyl | 446 |
| 438 | meth-oxy | meth-oxy | H | 2-methoxy-ethoxy-carbonyl | 3-fluoro-phenyl | 428 |
| 439 | meth-oxy | meth-oxy | H | methoxy-carbonyl | 3-fluoro-phenyl | 384 |
| 446 | meth-oxy | meth-oxy | H | diethoxy-phosphinyl | 3-fluoro-phenyl | 462 |
| 447 | meth-oxy | meth-oxy | H | N,N-dimethyl-amino-sulfonyl | 3-fluoro-phenyl | 433 |
| 458 | meth-oxy | meth-oxy | H | 4-methoxy-benzoyl | 3-fluoro-phenyl | 460 |
| 459 | meth-oxy | meth-oxy | H | 3-ethoxy-1,3-dioxo-propyl | 3-fluoro-phenyl | 440 |
| 464 | meth-oxy | meth-oxy | H | 5-methoxy-1,5-dioxo-pentyl | 3-fluoro-phenyl | 454 |
| 465 | meth-oxy | meth-oxy | H | 2-methoxy-1-oxo-ethyl | 3-fluoro-phenyl | 398 |
| 466 | meth-oxy | meth-oxy | H | 4-hydroxy-1,4-dioxo-n-butyl | 3-fluoro-phenyl | 426 |
| 467 | meth-oxy | meth-oxy | H | 2-(1-oxo-ethoxy)-1-oxo-ethyl | 3-fluoro-phenyl | 426 |
| 470 | meth-oxy | meth-oxy | H | 2-benzyloxy-ethoxy-carbonyl | 3-fluoro-phenyl | 504 |
| 471 | meth-oxy | meth-oxy | H | 2-[2-(2-hydroxy-ethoxy)-ethoxy]-ethoxy-carbonyl | 3-fluoro-phenyl | 502 |
| 472 | meth-oxy | meth-oxy | H | methoxy-methyl | 3-fluoro-phenyl | 370 |
| 473 | meth-oxy | meth-oxy | H | 2-(2-methoxy-1-oxo-ethoxy)-1-oxo-ethyl | 3-fluoro-phenyl | 456 |
| 474 | meth-oxy | meth-oxy | H | 2-(2-methyl-1-oxo-propoxy)-1-oxo-ethyl | 3-fluoro-phenyl | 454 |
| 480 | meth-oxy | meth-oxy | H | 2,6-difluoro-benzoyl | 3-fluoro-phenyl | 466 |
| 481 | meth-oxy | meth-oxy | H | 2-fluoro-benzoyl | 3-fluoro-phenyl | 448 |
| 484 | meth-oxy | meth-oxy | H | 2-oxo-propyl | 3-fluoro-phenyl | 382 |
| 490 | meth-oxy | meth-oxy | H | 1-oxo-butoxy-methyl | 3-fluoro-phenyl | 426 |
| 492 | meth-oxy | meth-oxy | H | 4-fluoro-benzoyl | 3-fluoro-phenyl | 448 |
| 494 | meth-oxy | meth-oxy | H | 4-chloro-benzoyl | 3-fluoro-phenyl | 464 |
| 496 | meth-oxy | meth-oxy | H | 1-oxo-ethoxy-methyl | 3-fluoro-phenyl | 398 |

TABLE 9-continued

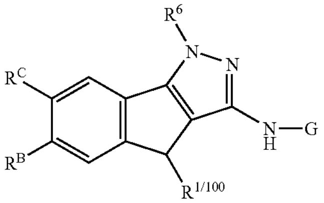

| Cpd | $R^B$ | $R^C$ | $R^{1/100}$ | $R^6$ | G | MS |
|---|---|---|---|---|---|---|
| 498 | meth-oxy | meth-oxy | H | 4-(1-oxo-ethoxy)-benzyl | 3-fluoro-phenyl | 474 |
| 500 | meth-oxy | meth-oxy | H | 4-fluoro-phenoxy-carbonyl | 3-fluoro-phenyl | 464 |
| 501 | meth-oxy | meth-oxy | H | 4-chloro-phenoxy-carbonyl | 3-fluoro-phenyl | 480 |
| 502 | meth-oxy | meth-oxy | H | 2-hydroxy-propyl | 3-fluoro-phenyl | 384 |
| 506 | meth-oxy | meth-oxy | H | 5-(N-methyl-amino)-1,5-dioxo-pentyl | 3-fluoro-phenyl | 453 |
| 509 | meth-oxy | meth-oxy | H | 2-methoxy-2-oxo-ethyl | 3-fluoro-phenyl | 398 |
| 511 | meth-oxy | meth-oxy | H | 2-ethoxy-2-oxo-ethyl | 3-fluoro-phenyl | 412 |
| 513 | meth-oxy | meth-oxy | H | 2-chloro-phenoxy-carbonyl | 3-fluoro-phenyl | 480 |
| 514 | meth-oxy | meth-oxy | ethyl | 2-methoxy-1-oxo-ethyl | 3-bromo-phenyl | 487 |
| 516 | meth-oxy | meth-oxy | H | N-(2-amino-ethyl)-amino-carbonyl | 3-fluoro-phenyl | 412 |
| 517 | meth-oxy | meth-oxy | H | N-[2-(N,N-dimethyl-amino)-ethyl]-amino-carbonyl | 3-fluoro-phenyl | 440 |
| 519 | meth-oxy | meth-oxy | ethyl | 2-benzyloxy-1-oxo-ethyl | 3-fluoro-phenyl | 563 |
| 520 | meth-oxy | meth-oxy | H | N-(2-1H-pyrrolidin-1-yl-ethyl)-amino-carbonyl | 3-fluoro-phenyl | 466 |
| 521 | meth-oxy | meth-oxy | H | N-(2-morpholin-4-yl-ethyl)-amino-carbonyl | 3-fluoro-phenyl | 482 |
| 523 | meth-oxy | meth-oxy | H | N-[2-[N-(2-hydroxy-ethyl)-amino]-ethyl]-amino-carbonyl | 3-fluoro-phenyl | 456 |
| 524 | meth-oxy | meth-oxy | H | N-[2-(N-methyl-amino)-ethyl]-amino-carbonyl | 3-fluoro-phenyl | 426 |
| 525 | meth-oxy | meth-oxy | H | N-[2-[N-(2-methyl-1-oxo-propyl)-amino]-ethyl]-amino-carbonyl | 3-fluoro-phenyl | 482 |
| 526 | meth-oxy | meth-oxy | H | N-[2-[N-(1-oxo-ethyl)-amino]-ethyl]-amino-carbonyl | 3-fluoro-phenyl | 454 |
| 527 | meth-oxy | meth-oxy | H | N-[2-(2-methenyl-1-oxo-propoxy)-ethyl]-amino-carbonyl | 3-fluoro-phenyl | 481 |
| 530 | meth-oxy | meth-oxy | H | N-[2-(3-methyl-1-methoxy-1-oxo)-n-butyl]-amino-carbonyl | 3-fluoro-phenyl | 483 |
| 531 | meth-oxy | meth-oxy | H | 4-amino-1,4-dioxo-n-butyl | 3-fluoro-phenyl | 424 |
| 532 | meth-oxy | meth-oxy | H | N-[2-(N-benzoyl-amino)-ethyl]-amino-carbonyl | 3-fluoro-phenyl | 516 |
| 534 | meth-oxy | meth-oxy | H | 2-amino-2-oxo-ethyl | 3-fluoro-phenyl | 383 |
| 536 | meth-oxy | meth-oxy | H | 3-1H-pyrrolidin-1-yl-1,3-dioxo-propyl | 3-fluoro-phenyl | 465 |
| 537 | meth-oxy | meth-oxy | H | 3-(N,N-diethyl-amino)-1,3-dioxo-propyl | 3-fluoro-phenyl | 467 |

TABLE 9-continued

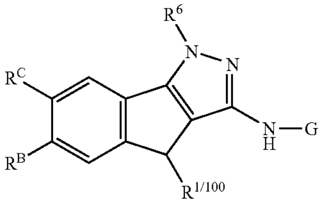

| Cpd | $R^B$ | $R^C$ | $R^{1/100}$ | $R^6$ | G | MS |
|---|---|---|---|---|---|---|
| 542 | meth-oxy | meth-oxy | H | N-[2-[N-(2-hydroxy-benzoyl)-amino]-ethyl]-amino-carbonyl | 3-fluoro-phenyl | 532 |
| 544 | meth-oxy | meth-oxy | H | N-[2-[2-(2-hydroxy-ethoxy)-ethoxy]-ethyl]-amino-carbonyl | 3-fluoro-phenyl | 501 |
| 546 | meth-oxy | meth-oxy | ethyl | benzoyl | 3-bromo-phenyl | 519 |
| 547 | meth-oxy | meth-oxy | ethyl | 2-[2-(2-hydroxy-ethoxy)-ethoxy]-ethoxy-carbonyl | 3-bromo-phenyl | 591 |
| 548 | meth-oxy | meth-oxy | methyl | 2-[2-(2-hydroxy-ethoxy)-ethoxy]-ethoxy-carbonyl | 3-bromo-phenyl | 577 |
| 572 | meth-oxy | meth-oxy | H | 2-hydroxy-ethyl | 3-fluoro-phenyl | 370 |
| 578 | meth-oxy | meth-oxy | H | N-methyl-amino-carbonyl | 3-fluoro-phenyl | 383 |
| 581 | meth-oxy | meth-oxy | H | N-methyl-amino-thiocarbonyl | 3-fluoro-phenyl | 399 |
| 609 | meth-oxy | meth-oxy | H | methyl | 3-fluoro-phenyl | 340 |
| 611 | meth-oxy | meth-oxy | H | (R)3,(S)4,(S)5-trihydroxy-(S)6-carboxy-tetrahydro-(R)2-pyran | 3-fluoro-phenyl | 503 |

TABLE 10

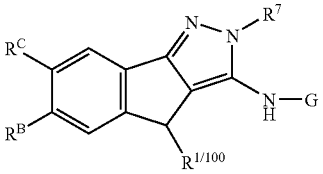

| Cpd | $R^B$ | $R^C$ | $R^{1/100}$ | $R^7$ | G | MS |
|---|---|---|---|---|---|---|
| 300 | meth-oxy | meth-oxy | phenyl | H | phenyl | 384 |
| 302 | meth-oxy | meth-oxy | phenyl | H | 3-fluoro-phenyl | 402 |
| 395 | meth-oxy | meth-oxy | H | N-(3-fluoro-phenyl)-amino-carbonyl | 3-fluoro-phenyl | 463 |
| 406 | meth-oxy | meth-oxy | H | 1-oxo-ethyl | 3-fluoro-phenyl | 368 |
| 407 | meth-oxy | meth-oxy | H | N-(2-ethoxy-2-oxo-ethyl)-amino-carbonyl | 3-fluoro-phenyl | 455 |
| 408 | meth-oxy | meth-oxy | H | 2,2-dimethyl-1-oxo-propoxy-methyl | 3-fluoro-phenyl | 440 |
| 411 | meth-oxy | meth-oxy | H | N-(3-ethoxy-3-oxo-propyl)-amino-carbonyl | phenyl | 451 |

TABLE 10-continued

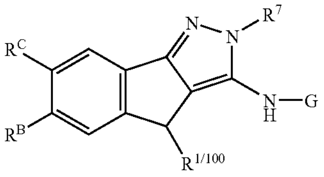

| Cpd | $R^B$ | $R^C$ | $R^{1/100}$ | $R^7$ | G | MS |
|---|---|---|---|---|---|---|
| 412 | meth-oxy | meth-oxy | H | N-[2-(4-methyl-1-methoxy-1-oxo)-pentyl]-amino-carbonyl | 3-fluoro-phenyl | 497 |
| 413 | meth-oxy | meth-oxy | H | N-[2-(3-methyl-1-methoxy-1-oxo)-n-butyl]-amino-carbonyl | 3-fluoro-phenyl | 483 |
| 434 | meth-oxy | meth-oxy | H | methoxy-carbonyl | 3-fluoro-phenyl | 384 |
| 435 | meth-oxy | meth-oxy | H | ethoxy-carbonyl | 3-fluoro-phenyl | 398 |
| 436 | meth-oxy | meth-oxy | H | 1-methyl-ethoxy-carbonyl | 3-fluoro-phenyl | 412 |
| 437 | meth-oxy | meth-oxy | H | 2-methoxy-ethoxy-carbonyl | 3-fluoro-phenyl | 428 |
| 475 | meth-oxy | meth-oxy | H | methoxy-methyl | 3-fluoro-phenyl | 370 |
| 491 | meth-oxy | meth-oxy | H | 1-oxo-butoxy-methyl | 3-fluoro-phenyl | 426 |
| 497 | meth-oxy | meth-oxy | H | 1-oxo-ethoxy-methyl | 3-fluoro-phenyl | 398 |
| 499 | meth-oxy | meth-oxy | H | 4-(1-oxo-ethoxy)-benzyl | 3-fluoro-phenyl | 474 |
| 503 | meth-oxy | meth-oxy | H | 4-fluoro-phenoxy-carbonyl | 3-fluoro-phenyl | 464 |
| 510 | meth-oxy | meth-oxy | H | 2-ethoxy-2-oxo-ethyl | 3-fluoro-phenyl | 412 |
| 515 | meth-oxy | meth-oxy | ethyl | 2-methoxy-1-oxo-ethyl | 3-bromo-phenyl | 487 |
| 518 | meth-oxy | meth-oxy | ethyl | 2-benzyloxy-1-oxo-ethyl | 3-fluoro-phenyl | 563 |
| 522 | meth-oxy | meth-oxy | H | N-(2-morpholin-4-yl-ethyl)-amino-carbonyl | 3-fluoro-phenyl | 482 |
| 528 | meth-oxy | meth-oxy | H | N-[2-(2-methenyl-1-oxo-propoxy)-ethyl]-amino-carbonyl | 3-fluoro-phenyl | 481 |
| 529 | meth-oxy | meth-oxy | H | (R)3,(S)4,(S)5-trihydroxy-(S)6-carboxy-tetrahydro-(R)2-pyran | 3-fluoro-phenyl | 503 |
| 535 | meth-oxy | meth-oxy | H | 3-1H-pyrrolidin-1-yl-1,3-dioxo-propyl | 3-fluoro-phenyl | 465 |
| 573 | meth-oxy | meth-oxy | H | 2-hydroxy-ethyl | 3-fluoro-phenyl | 370 |
| 579 | meth-oxy | meth-oxy | H | N-methyl-amino-carbonyl | 3-fluoro-phenyl | 383 |
| 580 | meth-oxy | meth-oxy | H | N-methyl-amino-thiocarbonyl | 3-fluoro-phenyl | 399 |
| 598 | meth-oxy | meth-oxy | H | N-(pentadecyl)-amino-carbonyl | 3-fluoro-phenyl | 580 |
| 602 | meth-oxy | meth-oxy | H | 1-methoxy-1-oxo-ethyl | 3-fluoro-phenyl | 399 |
| 604 | meth-oxy | meth-oxy | H | N-[2-[2-(2-hydroxy-ethoxy)-ethoxy]-ethyl]-amino-carbonyl | 3-fluoro-phenyl | 502 |
| 608 | meth-oxy | meth-oxy | H | methyl | 3-fluoro-phenyl | 340 |

TABLE 11

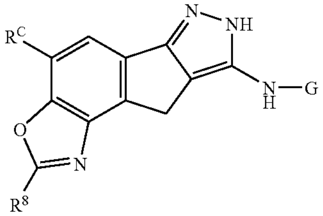

| Cpd | $R^C$ | $R^8$ | G | MS |
|---|---|---|---|---|
| 560 | methoxy | methyl | 3-methoxy-phenyl | 363 |
| 574 | methoxy | methyl | 2-fluoro-benzyl | 365 |
| 605 | methoxy | methyl | 3-fluoro-phenyl | 352 |

TABLE 12

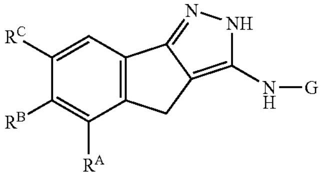

| Cpd | $R^A$ | $R^B$ | $R^C$ | G | MS |
|---|---|---|---|---|---|
| 557 | N-(1-oxo-ethyl)-amino | methoxy | methoxy | 3-fluoro-phenyl | 383 |
| 558 | amino | methoxy | methoxy | 3-fluoro-phenyl | 341 |

TABLE 13

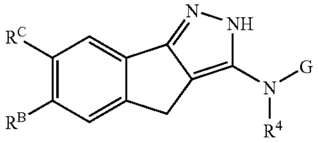

| Cpd | $R^B$ | $R^C$ | $R^4$ | G | MS |
|---|---|---|---|---|---|
| 591 | methoxy | methoxy | (R)3,(S)4,(S)5-trihydroxy-(S)6-carboxy-tetrahydro-(R)2-pyran | 3-fluoro-phenyl | 503 |

Unless otherwise noted, the term "alkyl" as used herein, whether used alone or as part of a substituent group, includes straight and branched chains having 1 to 10 carbon atoms, or any number within this range. For example, alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl, 2-methylpentyl, and the like. Unless otherwise noted, lower alkyl shall include straight and branched chains having 1 to 4 carbon atoms, or any number within this range.

Unless otherwise noted, the terms "alkoxy" or "alkyloxy" are used synonymously herein, and as used herein, whether used alone or as part of a substituent group, denotes an oxygen ether radical of the above described straight or branched chain alkyl groups. For example, alkoxy radicals include methoxy, ethoxy, n-propoxy, sec-butoxy, t-butoxy, n-hexyloxy and the like. Specific placement of the oxygen atom in relation to the alkyl portion is specified in the following manner, "—Oalkyl" or "-alkylO—", to describe —$OCH_3$ and —$CH_2O$— respectively (wherein alkyl is methyl for purposes of the example).

Unless otherwise stated, "aryl," employed alone or in combination with other terms (e.g., aryloxy, arylthioxy, arylalkyl), shall mean an aromatic ring structure comprising carbon atoms, for example, phenyl, naphthyl, fluorenyl, and the like.

As used herein, unless otherwise noted, "aralkyl" shall mean any lower alkyl group substituted with an aryl group such as phenyl, naphthyl and the like, for example, benzyl, phenylethyl, phenylpropyl, naphthylmethyl, and the like.

Unless otherwise noted, the term "cycloalkyl" as used herein, whether used alone or as part of a substituent group, shall mean any stable 3–10 membered, saturated ring system, for example cyclopropyl, cyclobutyl, cyclopentyl, cyclohexyl, cycloheptyl and cyclooctyl.

Unless otherwise noted, the term "partially unsaturated carbocycle" as used herein, whether used alone or as part of a substituent group, shall mean any stable 5–10 membered, partially unsaturated ring system, wherein the carbocycle contains, at least one unsaturated bond, for example cyclopentenyl, cyclohexenyl, cycloheptenyl, and the like.

Unless otherwise noted, the term "heteroaryl group" as used herein, whether used alone or as part of a substituent group, shall denote any five to ten membered monocyclic or bicyclic aromatic ring structure which containing carbon atoms and at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure. Examples of suitable heteroaryl groups include, but are not limited to, pyrrolyl, furyl, thienyl, oxazolyl, imidazolyl, pyrazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the term "heterocycloalkyl" shall denote any five to ten membered monocyclic or bicyclic, saturated or partially unsaturated ring structure containing C atoms and at least one heteroatom selected from the group consisting of O, N and S, optionally containing one to four additional heteroatoms independently selected from the group consisting of O, N and S. The monocyclic or bicyclic heteroalkyl group may be attached at any heteroatom or carbon atom of the ring such that the result is a stable structure. Examples of suitable monocyclic or bicyclic heteroalkyl groups include, but are not limited to, pyrrolinyl, pyrrolidinyl, dioxolanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 1,3-methylenedioxyphenyl (equivalent to benzofused dioxolyl), 1,4-ethylenedioxyphenyl (equivalent to benzofused dioxanyl), 2,3-dihydrobenzofuryl, and the like.

As used herein, unless otherwise noted, the term "benzo-fused heteroaryl" shall mean a bicyclic ring structure wherein one of the rings is phenyl and the other is a five to six membered heteroaryl. The benzo-fused heteroaryls are a subset of heteroaryls. Suitable example include, but are not limited to, indolyl, isoindolyl, benzofuryl, benzothienyl, indazolyl, benzthiazolyl, quinolinyl, isoquinolinyl, cinnolinyl, phthalazinyl, quinazolinyl, pteridinyl, and the like.

As used herein, unless otherwise noted, the term "benzo-fused heterocycloalkyl" shall mean a bicyclic ring structure wherein one of the rings is phenyl and the other is a five to six membered heterocycloalkyl. The benzo-fused heterocycloalkyls are a subset of the heterocycloalkyl groups. Suitable examples include, but are not limited to, 1,3-benzodioxolyl (also known as 1,3-methylenedioxyphenyl), indolinyl, 1,4-benzodioxolanyl (also known as 1,4-ethylenedioxyphenyl), benzodihydrofuranyl, benzotetrahydropyranyl, benzodihydrothiophene and the like.

As used herein, unless otherwise noted, the term "benzo-fused cycloalkyl" shall mean a bicyclic ring structure wherein one of the rings is phenyl and the other is a three to eight membered cycloalkyl. Suitable examples include, but are not limited to indanyl, 1,2,3,4-tetrahydronaphthyl, 6,7,8,9,-tetrahydro-5H-benzocycloheptenyl, 5,6,7,8,9,10-hexahydro-benzocyclooctenyl, and the like.

As used herein, the term "linking group" is intended to refer to a divalent radical derived by, for example, the removal of at least one hydrogen atom from each of two different atoms, or the removal of two hydrogen atoms from a single atom, such that the two monovalent radical centers, or the single divalent radical center, form bonds with different atoms.

As used herein, the term "alkyldiyl" shall include straight and branched chain of 1 to 10 carbon atoms, or any number within this range, divalent or monovalent hydrocarbon radicals derived by the removal of one hydrogen atom from each of two different carbon atoms, or by the removal of two hydrogen atoms from a single carbon atom. Examples include methyldiyl (also referred to herein as methylene), and ethyidiyls (also referred to herein as ethylene), such as ethan-1,1-diyl, and ethan-1,2-diyl.

In general, IUPAC nomenclature rules are used throughout this disclosure. Nomenclature for radical substituents is derived by first indicating the functionality having the point of attachment with a hyphen, followed by the adjacent functionality toward the terminal portion of the side chain, as in:

—$(C_{1-10})$alkyl-C(O)NH—$(C_{1-10})$alkyl-Phenyl or, when a lead hyphen is not used, by describing the terminal portion of the side chain first, followed by the adjacent functionality toward the point of attachment, as in:

phenyl-$(C_{1-10})$alkylamido$(C_{1-10})$alkyl, or phenylalkylamidoalkyl all three of which refer to a radical of the formula:

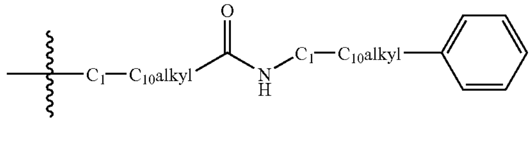

Where the are two point of attachment, for example in a linking group, or a ring member, the two points of attachment are indicated with a lead hyphen and a final hypen. For example, the points of attachment of a linking group having two monvalent radical centers would be indicated as —$(CH_2)_2$— or —$O(CH_2)_2$— and the like; and the points of attachment of a linking group having a single divalent radical center would be indicated as —NH— or —N(C═O alkyl)- and the like. Points of attachment for an aromatic ring member would be indicated as —N—., —S— or —CH— and the like, for example.

Where the phrase "terminating with" is used, the point of attachment for the terminal substituent is indicated by the second dash. For example, for the phrase "—C(=O)—($CH_2CH_2O$—)$_{1,10}$ terminating with —H, methyl, ethyl, or benzyl" the point of attachment for the selected terminal substituent is the terminal oxygen, for example, —C(=O)—($CH_2CH_2OH$) or —C(=O)—($CH_2CH_2OCH_2CH_2OCH_2CH_2OCH_3$).

When a particular group is "substituted" (e.g., phenyl, aryl, heteroalkyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Compounds exemplified in the present invention were named according to nomenclature well known in the art, either using Autonom Version 2.2 (brand of nomenclature software provided in the ChemDraw Ultra® 7.0.1 Office Suite marketed by CambridgeSoft.com)

Abbreviations used in the specification, particularly the Schemes and Examples, are as follows:

| | |
|---|---|
| Aq. = | Aqueous |
| ATP = | Adenosine triphosphate |
| DBU = | 2,2'-Diazabicycloundecane |
| DCM = | Dichloromethane |
| DME = | Dimethoxyethylene |
| DMF = | N,N-Dimethylformamide |
| DMSO = | Dimethylsulfoxide |
| DTT = | Dithiothreitol |
| EtOAc = | Ethyl acetate |
| HPLC = | High Pressure Liquid Chromatography |
| IprOH = | Isopropyl alcohol |
| MeOH = | Methanol |
| PBS = | Phosphate buffer saline |
| PLC = | Phospholipase C |
| RAR = | Rat aortic ring |
| Sat. = | Saturated |
| SMGS = | Smooth muscle growth supplement |
| TFA = | Trifluoroacetic Acid |
| THF = | Tetrahydrofuran |
| TLC = | Thin Layer Chromatography |
| Tris HCl or = Tris-Cl | Tris[hydroxymethyl]aminomethyl hydrochloride |

The compounds of the present invention may be prepared by any number of processes as described generally below and more specifically as described in the Examples which follow herein.

During any of the processes for preparation of the compounds of the present invention described herein, it may be necessary and/or desirable to protect sensitive or reactive groups on any of the molecules concerned (for example hydroxy, amino, thio, oxo or carboxy groups). This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Methods of Synthesis

Methods of synthesizing the compounds of the present invention include, but are not limited to, the methods described below. The starting materials used in Methods A through E are generally, starting ketones of the Formula (S1)

(S1)

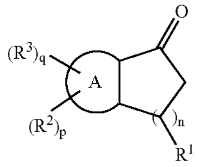

wherein $R^1$, $R^2$, $R^3$, p, q, and n are as described herein for Formula (I) Compounds of the formula (S1) are either known or commercially available compounds or compounds which may be prepared from known compounds by known chemistry.

Aromatic ketones may be prepared by the Friedel-Crafts reaction (See *Practical Organic Chemistry* by Vogel, Third Edition, pp724–749). For example, Friedel-Crafts acylation of substituted aryl propanoic acids of formula (S1a), or their derivatives will yield substituted indan-1-ones of formula (S1b), as described in the literature. Similarly, Friedel-Crafts acylation of substituted aryl butanoic acids or their derivatives will yield substituted alpha-tetralones (For example, see Cho, H. et al., *Heterocycles* (1996), 43(1), 127–131; Baddeley et al., *J. Chem. Soc*, (1956), 4647; Reeve et al., *J. Amer. Chem. Soc.* (1951), 73, 1371)

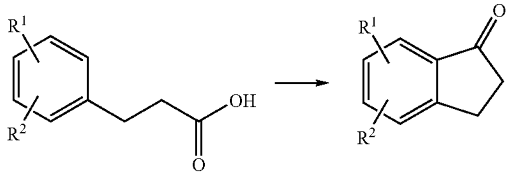

S1a S1b

Starting ketones of formula (S1b) may also be prepared from the oxidation of the corresponding alcohols of formula (S1c) or alkanes of formula (S1d) using various known oxidizing agents (For example, see Mandal, et al., *Tetrahedron Lett*, (1996), 37(21), 3769–3772; Ishihara, et al., *J. Org. Chem.* (1997), 62(17), 5664–5665).

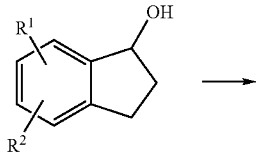

S1b

S1c

-continued

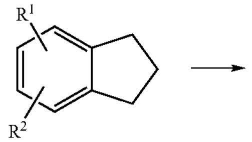

S1b

S1d

Starting pyridyl heteroaryl ketones may be prepared by condensation of diones of formula (S1e) or enaminones of formula (S1g) with propandiketals of formula (S1f) or propenaldehydes of formula (S1h), respectively (Examples see: Huang et al., *Synth. Commun.* (1998), 28(7), 1197–1200; Reimann et al., *Pharmazie* (1995), 50(9), 589–592).

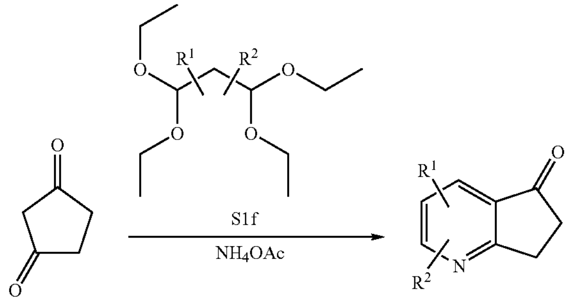

S1e S1h

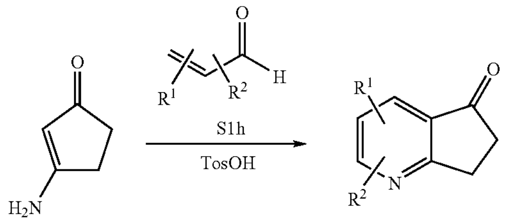

S1g S1h

Starting thienyl heteroaryl ketones may be prepared by Friedel-Crafts acylation of heteroarylpropanoic acids using aluminum chloride, polyphosphoric acid or trifouoroacetic acid etc. to provide the cyclized ketones. (For example see Cantrell et al., *Tetrahedron Lett* (1967), 4477; Muraro et al., C R Hebd Seances Acad Sci (1971), 273, 1362; Macdowell, et al., *J. Org. Chem.* (1967), 32,1226; Binder, et al., *Monatsh Chem (*1998), 129(8), 887–896).

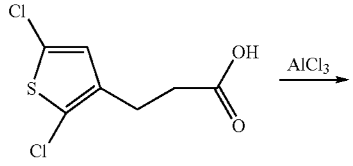

S1i

-continued

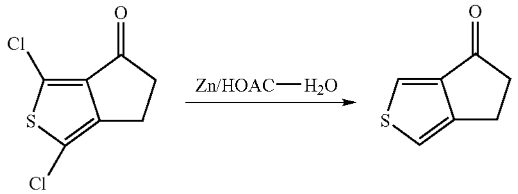

S1j S1k

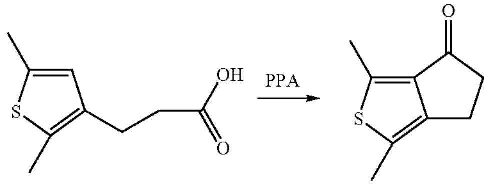

S1l S1m

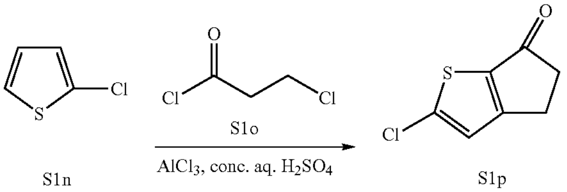

S1n S1p

Starting furanyl heteroaryl ketones of the Formula (S1) may also be prepared according to procedures described Kraus et al., *Synlett* (1997), 11, 1259–1260; Hoye, et al., *J. Org. Chem.* (1990), 55 (15), 4518; and Lee, et al., *Bull Korean Chem. Soc.* (1998), 19 (10), 1080–1083.

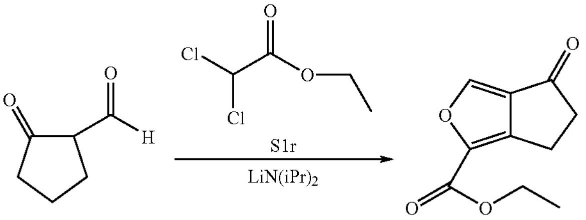

S1q S1s

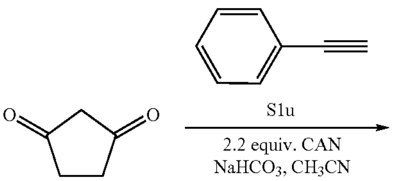

S1t

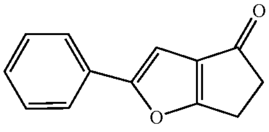

S1v

-continued

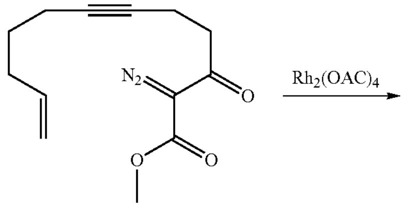

S1w

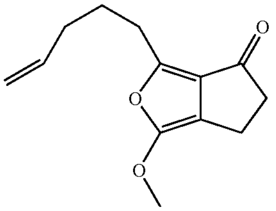

S1x

Starting pyrrolylketones may be prepared via intramolecular cyaloaddition of azomethide ylides with tethered alkynes as shown below (Nayyar, et al., *J. Org. Chem.* (1997), 62(4), 982–991). Alternatively, the starting pyrrole ketones may be prepared from diketones by reacting with α-bromoketones or alpha-bromopyruvates and then by carrying out Paal-Knorr cyclization with suitably substituted amines (For example, see Stojanovic et al., *J. Serb. Chem. Soc.* (1997), 62(9), 749–7530. )

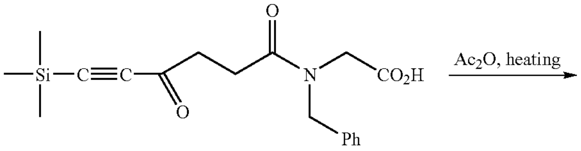

S1y

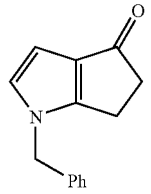

S1z

S1t

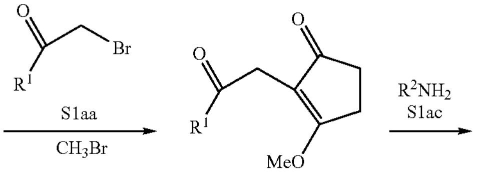

S1ab

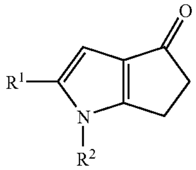

S1ad

Thiazolyl heteroaryl ketones may be prepared via the condensation of bromoketones with thioacetamides as described in Maillard, et al., *Eur. J. Med. Chem. Ther* (1984), 19 (5), 451.

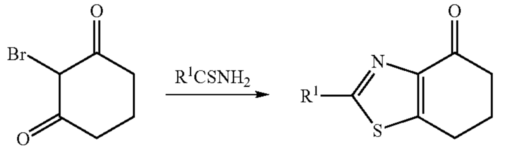

S1

Oxazole ketones and furanyl ketones may be prepared via Rhodium catalyzed cycloadditions of alpha-diazo-diketones with nitriles or acetylenes. Similarly, lodonium ylides may undergo $Rh_2(OAc)_4$ catalyzed thermal [3+2]-cycloaddition with acetylenes and nitrites to form the corresponding furans and oxazoles, respectively. (For example see Lee, et al., Heterocycles (1998), 48(5), 875–883; and Gogonas, et. al, *Tetrahedron Lett.* (2000), 41(48), 9299–9303).

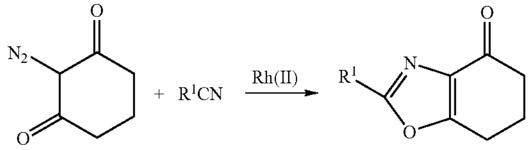

S1

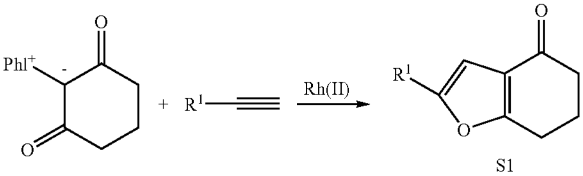

S1

Starting isoxazole ketones may be prepared by cycloaddition of N-oxides with cyclic diketones or enones in a one-step reaction as show below (For example see Akhrem et al., *Khim. Geterotsikl. Soedin.* (1974), 7, 901–4; Akhrem, et al., *Synthesis* (1978), 1, 43).

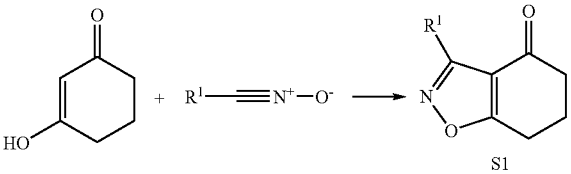

S1

(MeO, $MeO_2C$, Cl, $NH_2$, 1-pyrrolidinyl, mopholino)

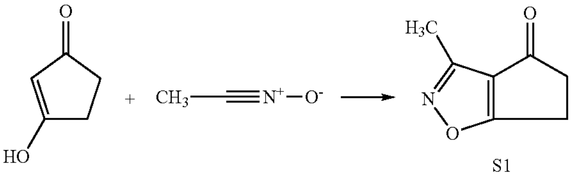

S1

One skilled in the art will recognize that for the preparation of the compounds of the instant invention, the starting materials, i.e., compounds of Formula (S1), supra are known compounds or are compounds which may be prepared according to known methods, for example, as outlined above. Starting compounds of Formula (S1) wherein n is selected from 2 to 4, are similarly known compounds, or may similarly be prepared according to known methods or by modification of the above noted examplary procedures.

Method A

Compounds of Formula (I) may be prepared according to the process outlined in Method A.

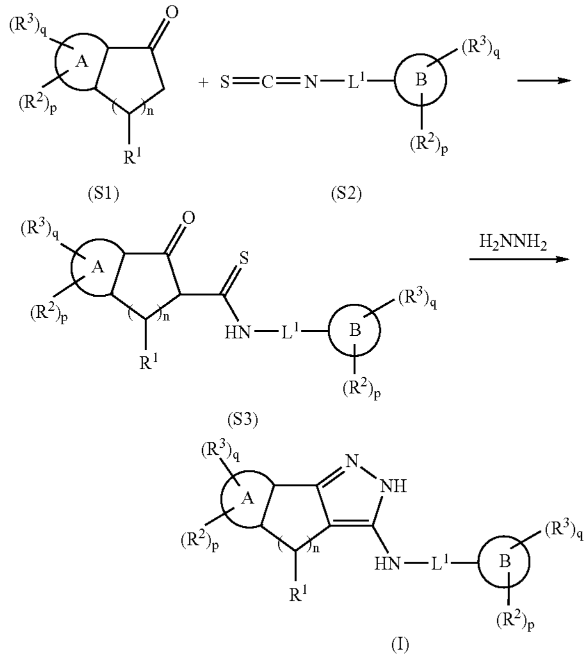

(S1) (S2) (S3) (I)

Accordingly, a compound of Formula (S1), a known compound or compound prepared by known methods, is reacted with a suitably substituted compound of Formula (S2), a known compound or compound prepared by known methods, at a temperature in the range of about −78 to about 100° C., in an aprotic organic solvent such as THF, dioxane, DMF, and the like, in the presence of a base such as lithium bis(trimethylsilyl)amide, sodium bis(trimethylsilyl)amide, lithium diisopropylamide, and the like, to yield the corresponding compound of Formula (S3).

The compound of Formula (S3) is reacted with hydrazine, preferably in the presence of about one equivalent of an acid such as acetic acid, hydrochloric acid, and the like, at an elevated temperature, preferably at about reflux temperature, to yield the corresponding compound of Formula (I).

Examples of β-ketothioamide cyclization (S3 to I) with hydrazine forms anilinopyrrazoles similar to those described in the second step of Method A above, have been reported in literature (For example, see M. Suesse and S. John, *J. Prakt. Chem.*; (1986), 328(4), 635–9). Additionally, some ketothioamides are reported in the literatures, for example Wesolowska et al., *Pol. J. Chem.* (2001), 75(3), 387–400; Hansen, et al., *J. Mol. Struct.* (1996), 378(1), 45–59; Augustin, et al., *J. Prakt. Chem.* (1979), 321(2), 205–14; Schoen et al., *Rocz. Chem.* (1971), 45(1), 73–60.

Method B

Compounds of Formula (I) may alternatively be prepared according to the process outlined in Method B.

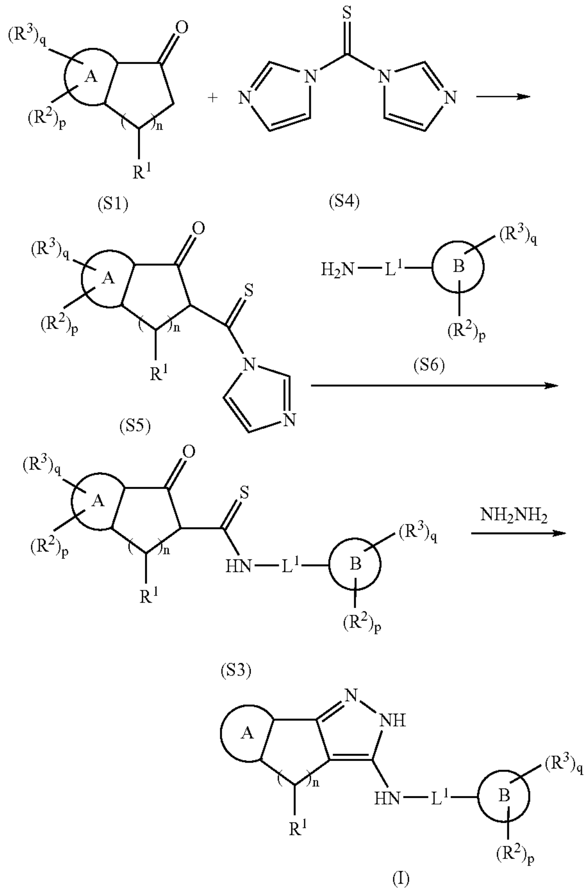

(S1) (S4) (S6) (S5) (S3) (I)

Accordingly, a compound of Formula (S1), a known compound or compound prepared by known methods, is reacted with a compound of Formula (S4) (1,1'-thiocarbonyldiimidazole), at a reduced temperature in the range of about −78° C. to about 0° C., in an aprotic organic solvent such as THF, dioxane, DMF, and the like, in the presence of a strong base such as sodium hydride, lithium bis(trimethylsilyl) amide, sodium bis(trimethylsilyl)amide, lithium diisopropylamide, and the like, to yield the corresponding compound of Formula (S5).

The compound of Formula (S5) is reacted with a suitably substituted compound of Formula (S6), a known compound or compound prepared by known methods, in an aprotic organic solvent such as THF, dioxane, methylene chloride, chloroform, DMF, and the like, to yield the corresponding compound of Formula (S3).

The compound of Formula (S3) is reacted with hydrazine, preferably in the presence of about one equivalent of an acid such as acetic acid, hydrochloric acid, and the like, at an elevated temperature, preferably at about reflux temperature, to yield the corresponding compound of Formula (I).

The present invention is further directed to a process for the preparation of a compound of Formula (I), as decribed in more detail in method B above. In one embodiment of the present invention the invention relates to a process for the preparation of a compound of Formula (S5), using Method B above. In another embodiment the invention relates to a process for the preparation of a compound of Formula (S3), using the process outlined in Method B above.

Method C

Compounds of Formula (I) may alternatively be prepared according to the process outlined in Method C.

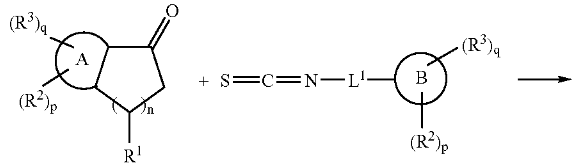

(S1) (S2)

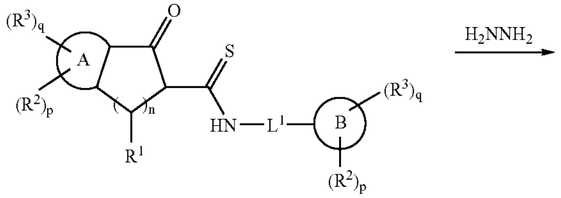

(S3)

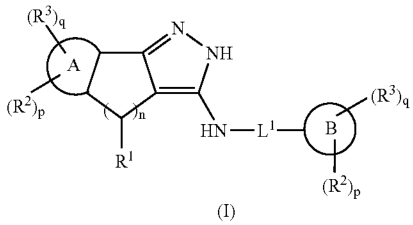

(I)

More particularly, the compound of Formula (S1), a known compound or compound prepared by known methods, is reacted with a suitably substituted compound of Formula (S2), a known compound or compound prepared by known methods, at a temperature in the range of about 0 to about 120° C., in an aprotic organic solvent such as THF, DMF, and the like, in the presence of sodium hydride, to yield the corresponding compound of Formula (S3).

The compound of Formula (S3) is reacted with hydrazine, preferably in the presence of about one equivalent of an acid such as acetic acid, hydrochloric acid, and the like, at an elevated temperature, preferably at about reflux temperature, to yield the corresponding compound of Formula (I).

Method D

Compounds of Formula (I) may alternatively be prepared according to the process outlined in Method D.

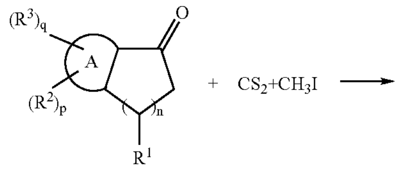

(S1)

-continued

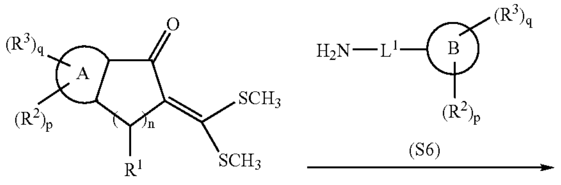

(S6)

(S7)

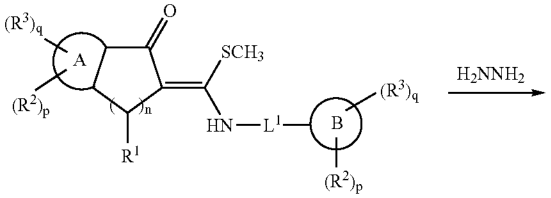

(S8)

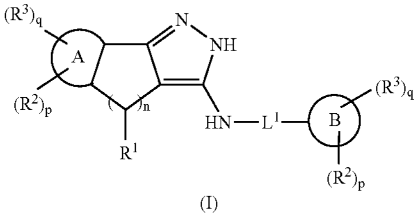

(I)

Accordingly, a compound of Formula (S1), a known compound or compound prepared by known methods, is reacted with carbon disulfide and methyl iodide, in the presence of a base such as sodium hydride, lithium bis (trimethylsilyl) amide, sodium bis(trimethylsilyl)amide, lithium diisopropylamide, and the like, in an aprotic organic solvent such THF, DMF, and the like, at an elevated temperature in the range of about 25° to about 100° C., to yield the corresponding compound of Formula (S7). Some compounds of Formula (S7) are known, for example as disclosed in Villemin et al., *Synthesis* (1991), (4), 301–3; Augustin, et al., *J. Prakt. Chem.* (1979), 321(2), 215–25; and in WIPO publication WO 95/07893.

The compound of Formula (S7) is reacted with a suitably substituted compound of Formula (S6), a known compound or compound prepared by known methods, in an aprotic organic solvent such as THF, DMF, and the like, at an elevated temperature in the range of about 25° to about 150° C., in the presence of a catalytic amount of an acid such as acetic acid, sulfuric acid, p-toluene sulfonic acid, and the like, to yield the corresponding compound of Formula (S8).

The compound of Formula (S8) is reacted with hydrazine, preferably in the presence of about one equivalent of an acid such as acetic acid, hydrochloric acid, and the like, at an elevated temperature, preferably at about reflux temperature, to yield the corresponding compound of Formula (I).

Method E

Compounds of Formula (I) may alternatively be prepared according to the process outlined in Method E.

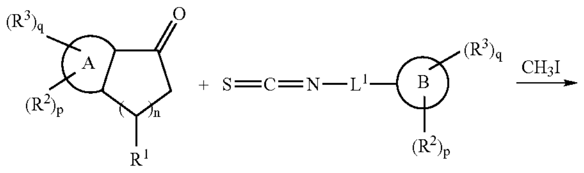

(S1) (S2)

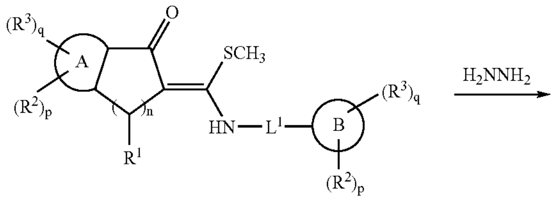

(S8)

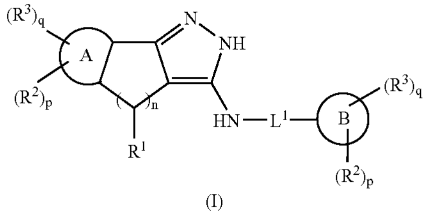

(I)

Accordingly, a compound of Formula (S1), a known compound or compound prepared by known methods, is reacted with a suitably substituted compound of Formula (S2), a known compound or compound prepared by known methods, in the presence of methyl iodide and a base such as DBU, NaH, lithium bis(trimethylsilyl) amide, sodium bis(trimethylsilyl)amide, lithium diisopropylamide, and the like, in an aprotic organic solvent such as acetonitrile, THF, DMF, and the like, at an elevated temperature in the range of about 0 to about 100° C., to yield the corresponding compound of Formula (S8).

The compound of Formula (S8) is reacted with hydrazine, preferably in the presence of about one equivalent of an acid such as acetic acid, hydrochloric acid, and the like, at an elevated temperature, preferably at about reflux temperature, to yield the corresponding compound of Formula (I).

Method F

Compounds of Formula (II), of the structure (IIa), may be prepared according to the process outlined in Method F.

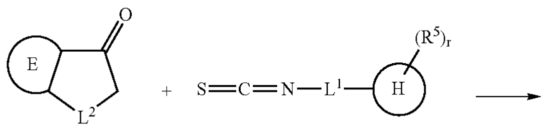

(T1) (T2)

-continued

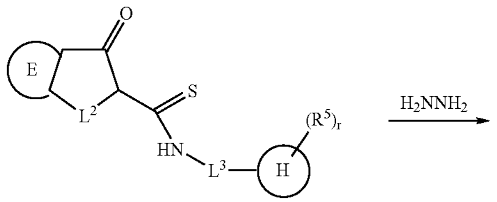

(T3)

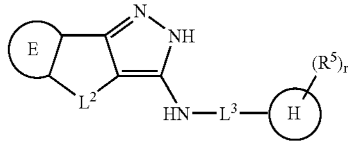

(IIa)

Accordingly, a compound of Formula (T1), a known compound or compound prepared by known methods, is reacted with a suitably substituted compound of Formula (T2), a known compound or compound prepared by known methods, at a temperature in the range of about −78 to about 100° C., in an aprotic organic solvent such as THF, dioxane, DMF, and the like, in the presence of a base such as lithium bis(trimethylsilyl)amide, sodium bis(trimethylsilyl)amide, lithium diisopropylamide, and the like, to yield the corresponding compound of Formula (T3).

Compoud of Formula (T1) where L2 containing oxygen, sulfur or nitrogen atom can also be prepared by known methods (For example, see A. R. Deshpande, et al., Synthetic Communications, (1990), 20(6), 809–816; W -S. Li, et al., Tetrahedron Letters, (2002), 43, 1923–1925; C. Brian, et al., Tetrahedron, (1987), 43(1), 69–76; H. Winfvoid, et al., Chemie, (1970), 10(9), 343: C. Mukerjee, et al., Synletters, (2002), (2), 325–327; T. Sugasawa, et al., J. Org. Chem., (1979), 44(4), 578–586: S; and Torii, et al., J. Org. Chem., (1978), 43(14), 2882–2885. )

The compound of Formula (T3) is reacted with hydrazine, preferably in the presence of about one equivalent of an acid such as acetic acid, hydrochloric acid, and the like, at an elevated temperature, preferably at about reflux temperature, to yield the corresponding compound of Formula (IIa).

Examples of β-ketothioamide cyclization (T3 to IIa) with hydrazine forms anilinopyrrazoles similar to those described in the second step of Method F above, have been reported in literature (For example, see M. Suesse and S. John, *J. Prakt. Chem.*; (1986), 328(4), 635–9). Additionally, some ketothioamides are reported in the literatures, for example Wesolowska et al., *Pol. J. Chem.* (2001), 75(3), 387–400; Hansen, et al., *J. Mol. Struct.* (1996), 378(1), 45–59; Augustin, et al., *J. Prakt. Chem.* (1979), 321(2), 205–14; Schoen et al., *Rocz. Chem.* (1971), 45(1), 73–60.

Method G

Compounds of Formula (II), of the structure (IIa), may alternatively be prepared according to the process outlined in Method G.

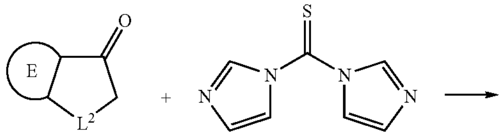

(T1) (T4)

-continued

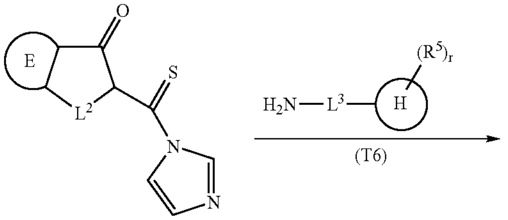

(T5)

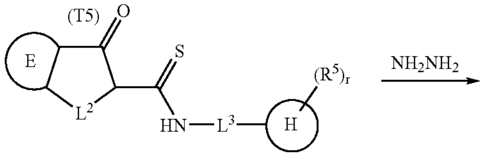

(T3)

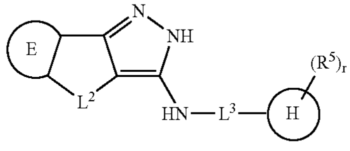

(IIa)

Accordingly, a compound of Formula (T1), a known compound or compound prepared by known methods, is reacted with a compound of Formula (T4) (1,1'-thiocarbonyldiimidazole), at a reduced temperature in the range of about −78° C. to about 0° C., in an aprotic organic solvent such as THF, dioxane, DMF, and the like, in the presence of a strong base such as sodium hydride, lithium bis(trimethylsilyl) amide, sodium bis(trimethylsilyl)amide, lithium diisopropylamide, and the like, to yield the corresponding compound of Formula (T5).

The compound of Formula (T5) is reacted with a suitably substituted compound of Formula (T6), a known compound or compound prepared by known methods, in an aprotic organic solvent such as THF, dioxane, methylene chloride, chloroform, DMF, and the like, to yield the corresponding compound of Formula (T3).

The compound of Formula (T3) is reacted with hydrazine, preferably in the presence of about one equivalent of an acid such as acetic acid, hydrochloric acid, and the like, at an elevated temperature, preferably at about reflux temperature, to yield the corresponding compound of Formula (IIa).

The present invention is further directed to a process for the preparation of a compound of Formula (IIa), as decribed in more detail in method G above. In one embodiment of the present invention the invention relates to a process for the preparation of a compound of Formula (T5), using Method G above. In another embodiment the invention relates to a process for the preparation of a compound of Formula (T3), using the process outlined in Method G above.

Method H

Compounds of Formula (II), of the structure (IIa), may alternatively be prepared according to the process outlined in Method H.

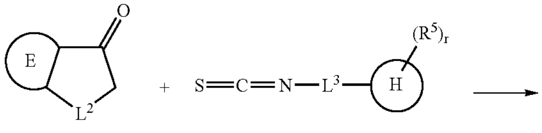

(T1) (T2)

-continued

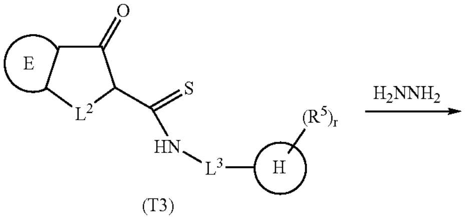

(T3)

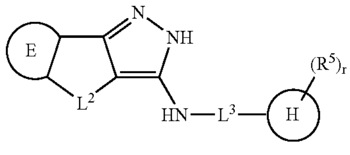

(IIa)

More particularly, the compound of Formula (T1), a known compound or compound prepared by known methods, is reacted with a suitably substituted compound of Formula (T2), a known compound or compound prepared by known methods, at a temperature in the range of about 0 to about 120° C., in an aprotic organic solvent such as THF, DMF, and the like, in the presence of sodium hydride, to yield the corresponding compound of Formula (T3).

The compound of Formula (T3) is reacted with hydrazine, preferably in the presence of about one equivalent of an acid such as acetic acid, hydrochloric acid, and the like, at an elevated temperature, preferably at about reflux temperature, to yield the corresponding compound of Formula (IIa).

Method I

Compounds of Formula (II), of the structure (IIa), may alternatively be prepared according to the process outlined in Method I.

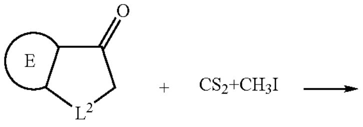

(T1)

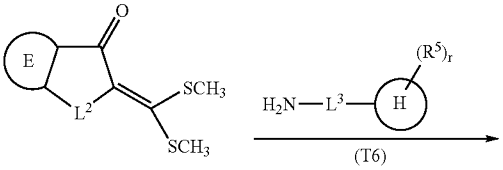

(T7)

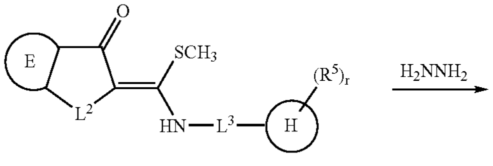

(T8)

-continued

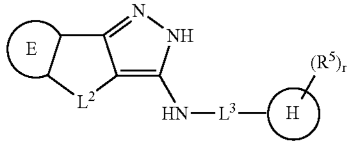

(IIa)

Accordingly, a compound of Formula (T1), a known compound or compound prepared by known methods, is reacted with carbon disulfide and methyl iodide, in the presence of a base such as sodium hydride, lithium bis (trimethylsilyl) amide, sodium bis(trimethylsilyl)amide, lithium diisopropylamide, and the like, in an aprotic organic solvent such THF, DMF, and the like, at an elevated temperature in the range of about 25° to about 100° C., to yield the corresponding compound of Formula (T7).

The compound of Formula (T7) is reacted with a suitably substituted compound of Formula (T6), a known compound or compound prepared by known methods, in an aprotic organic solvent such as THF, DMF, and the like, at an elevated temperature in the range of about 25° to about 150° C., in the presence of a catalytic amount of an acid such as acetic acid, sulfuric acid, p-toluene sulfonic acid, and the like, to yield the corresponding compound of Formula (T8).

The compound of Formula (T8) is reacted with hydrazine, preferably in the presence of about one equivalent of an acid such as acetic acid, hydrochloric acid, and the like, at an elevated temperature, preferably at about reflux temperature, to yield the corresponding compound of Formula (IIa).

Method J

Compounds of Formula (II), of the structure (IIa), may alternatively be prepared according to the process outlined in Method J.

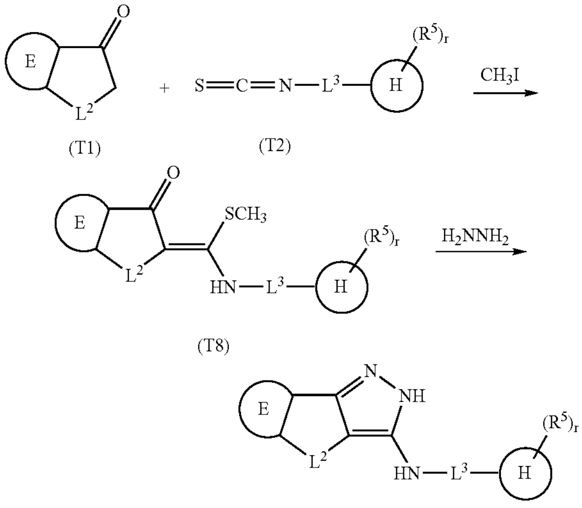

(T1) (T2) (T8) (IIa)

Accordingly, a compound of Formula (T1), a known compound or compound prepared by known methods, is reacted with a suitably substituted compound of Formula (T2), a known compound or compound prepared by known methods, in the presence of methyl iodide and a base such as DBU, NaH, lithium bis(trimethylsilyl) amide, sodium bis(trimethylsilyl)amide, lithium diisopropylamide, and the like, in an aprotic organic solvent such as acetonitrile, THF, DMF, and the like, at an elevated temperature in the range of about 0 to about 100° C., to yield the corresponding compound of Formula (T8).

The compound of Formula (T8) is reacted with hydrazine, preferably in the presence of about one equivalent of an acid such as acetic acid, hydrochloric acid, and the like, at an elevated temperature, preferably at about reflux temperature, to yield the corresponding compound of Formula (IIa).

The present invention includes compounds of Formula (II) wherein one of $R^6$ or $R^7$ is present and other than hydrogen (i.e., compounds of formula (IIb), (IIc), (IId), (IId), (IIe), (IIf), (IIg), (IIh), (IIj), (IIk), (IIm) (IIn), (IIo), (IIp), (IIq), (IIr) and (IIs) as defined in more detail below). Said compounds are potentially prodrugs of compounds of Formulae (I) and (II). The present invention further includes process for the preparation of said compounds of formula (IIb), (IIc), (IId), (IId), (IIe), (IIf), (IIg), (IIh), (IIj), (IIk), (IIm) (IIn), (IIo), (IIp), (IIq), (IIr) and (IIs).

As prodrugs, compounds of Formula (II) wherein one of $R^6$ or $R^7$ is present and other than hydrogen are believed to be absorbed in vivo and then metabolized or hydrolyzed to the corresponding compounds of Formulae (I) or (II). The compounds of formula (II) wherein one of $R^6$ or $R^7$ is present and other than hydrogen may further have intrinsic biological activity similar to the parent compounds of Formula (I) and/or (II).

Method L

Compounds of formula (IIb) and (IIc) wherein one of $R^6$ or $R^7$ is selected from the group consisting of paragraph (c) of Formula (II) may be prepared according to the process outlined in Method L.

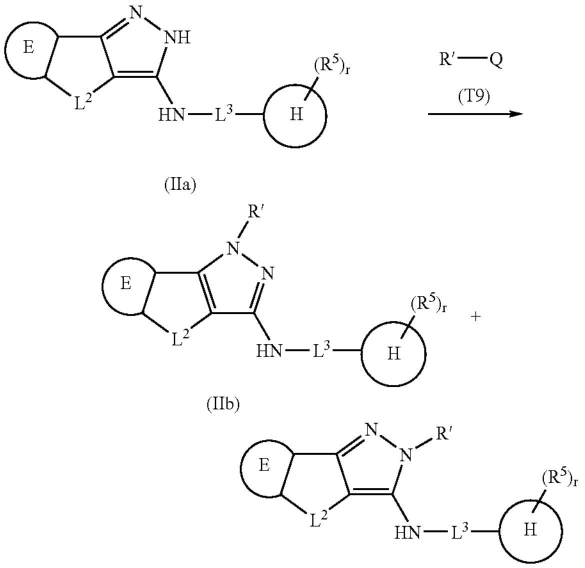

(IIa) (IIb) (IIc)

Accordingly, a suitably substituted compound of Formula (IIa) is reacted with a suitably substituted alkylating agent, a compound of formula (T9), a known compound, for example methyl iodide, dimethyl sulfate, chloromethylpivalate, ethylene oxide, and the like, or compound prepared by known methods, for example as halide, mesylate, tosylate, epoxide and triflate, and the like, at a temperature in a range of −70° to 100° C., in an aprotic solvent such as THF, DMF, and the like; in the presence of a base, such as potassium carbonate, cesium carbonate, pyridine, triethylamine, diisopropylethylamine, and the like, to yield a mixture of the corresponding regioisomers, compounds of formula (IIb) and (IIc). The ratio of the two regioisomers is dependent on the base and solvent used. Preferably, the two regioisomers are separated by silica gel column chromatography or reverse phase column chromatography to yield compounds of formula (IIb) and (IIc).

Method M

Compounds of formula (IId) and (IIe) wherein one of $R^6$ or $R^7$ is selected from the group consisting of consisting of paragraphs (d), (e), (f), (g), (h) and (hh) of Formula (II) may be prepared according to the process outlined in Method M.

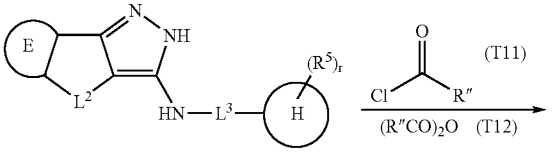

(IIa)

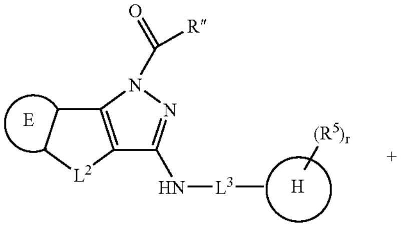

(IId)

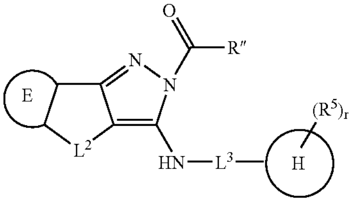

(IIe)

Accordingly, a suitably substituted compound of Formula (IIa) is reacted with a suitable acylating agent, a compound of formula (T11) or (T12), a known compound or compound prepared by known methods, for example, acetyl chloride, isobutyryl chloride, succinic anhydride, methoxylacetylchloride, benzyloxylacetylchloride, benzoyl chloride, and the like, at a temperature in a range of about between about −70° and about 100° C., in an aprotic solvent, such as THF, DMF, pyridine and the like, in the presence of base, such as pyridine, triethylamine, diisopropylethylamine, and the like, to yield a mixture of the corresponding regioisomers, compounds of formula (IId) and (IIe). The ratio of the two regioisomers is dependent on the base and solvent used. Preferably, the two regioisomers are separated by silica gel column chromatography or reverse phase column chromatography to yield compounds of formula (IId) and (IIe).

Method N

Compounds of formula (IId) and (IIe), wherein one of $R^6$ or $R^7$ is selected from the group consisting of paragraphs (d), (e), (f), (g), (h) and (hh) of Formula (II) may alternatively be prepared according to the process outlined in Method N.

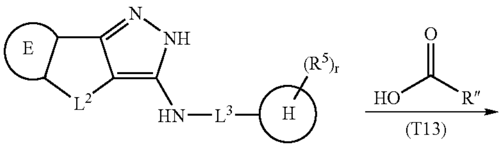

(IIa)

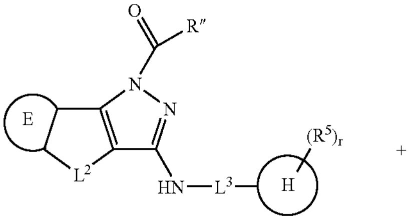

(IId)

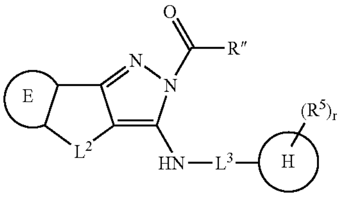

(IIe)

Accordingly, a suitably substituted compound of formula (IIa), is reacted with a suitably substituted carboxilc acid, a compound of formula (T13), a known compound or compound prepared by known methods, for example, 3-oxo-3-pyrrolidin-1-propionic acid, and the like, at a temperature in a range of between about −70° and about 100° C., in an aprotic solvent such as THF, DMF, and the like, in the presence of base, such as triethylamine, diisopropylethylamine, and the like, to yield a mixture of the corresponding regioisomers, compounds of formula (IId) and (IIe). The ratio of the two regioisomers is dependent on the base and solvent used. Preferably, the two regioisomers are separated by silica gel column chromatography or reverse phase column chromatography to yield compounds of formula (IId) and (IIe).

One skilled in the art will recognize that when the carboxylic acid of formula (T13) such as benzoic acid, propanoic acid, and the like, the reaction is completed in the presence of a suitable peptide coupling reagent, such as 1-(3-dimethylaminopropyl)-3-ethylcarbodiimide (EDC) and hydroxybenzotriazole hydrate (HOBT), and the like.

Method O

Compounds of formula (IIf) and (IIg), wherein one of $R^6$ or $R^7$ is selected from the group consisting of paragraphs (i), (j), and (k) of Formula (II) may may be prepared according to the process outlined in Method O.

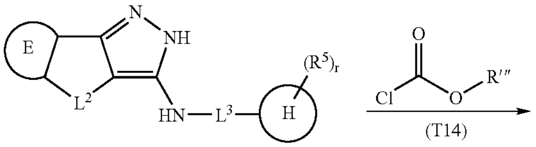

(T14)

(IIa)

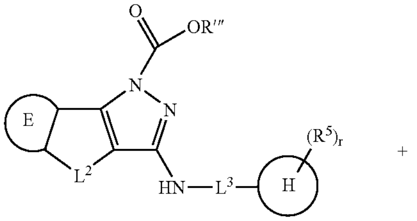

(IIf)

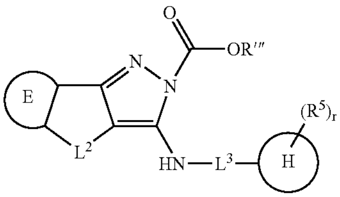

(IIg)

Accordingly, a suitably substituted compound of formula (IIa) is reacted with a suitably substituted chloroformate, a compound of formula (T14), a known compound or compound prepared by known methods, for example, ethyl chloroformate, 2-methoxyethyl chloroformate, isopropylchloroformate, tri(ethyleneglycol), bis(chloroformate), and the like, at the temperature in a range of between about −70° and bout 100° C., in an aprotic solvent such as THF, DMF, DCM, and the like, in the presence of base such as pyridine, triethylamine, diisopropylethylamine, and the like, to yield a mixture of the corresponding regioisomers, compounds of formula (IIf) and (IIg). The ratio of the two regioisomers is dependent on the base and solvent used. Preferably, the two regioisomers are separated by silica gel column chromatography or reverse phase column chromatography to yield compounds of formula (IIf) and (IIg).

Method P

Compounds of formula (IIh) and (IIj), wherein one of $R^6$ or $R^7$ is selected from the group consisting of paragraphs (I), (m), (n) and (o) of Formula (II) may be prepared according to the process outlined in Method P.

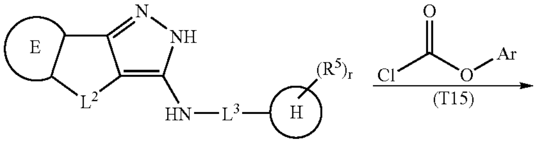

(T15)

(IIa)

-continued

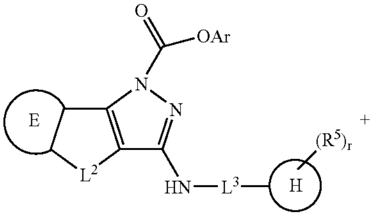

(T16)

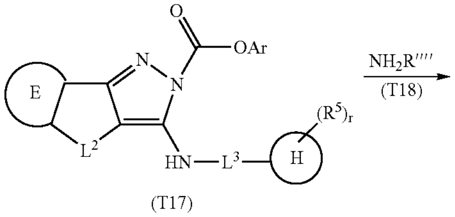

$NH_2R''''$ (T18)

(T17)

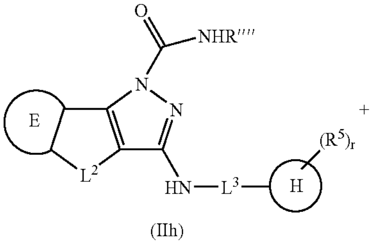

(IIh)

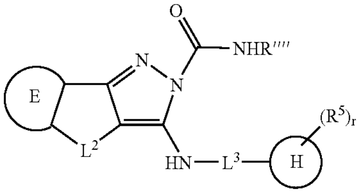

(IIj)

Accordingly, a suitably substituted compound of Formula (IIa) is reacted with a suitably substituted aryl chloroformate, a compound of formula (T15), a known compound or compound prepared by known methods, for example, phenyl chloroformate, 4-nitrophenyl chloroformate, and the like, at a temperature in a range of between about −70° and about 100° C., in an aprotic solvent, such as THF, DMF, DCM, and the like, in the presence of base such as pyridine, triethylamine, diisopropylethylamine, and the like, to yield a mixture of the corresponding regioisomers, compounds of formula (T16) and (T17). Compounds of formula (T16) and (T17) are separated by silica gel column chromatography or reverse column chromatography.

The compounds of formula (T16) and (T17), separately, are reacted with a suitably substituted amine, a compound of formula (T18), a known compound or compound prepared by known methods, for example, 1-methyl-1-ethyl-1,2-diamine, propylamine, 3-(morpholin-4-yl)-1-propylamine, and the like, in an aprotic solvent such as DMF, DMSO, THF, and the like, at the temperature in a range of between about −70° and about 100° C. to yield the corresponding compounds of formula (IIh) and (IIj).

Alternatively, the compounds of formula (T16) and (T17) as a mixture are reacted with a suitably substituted amine, a compound of formula (T18), to yield a mixture of compounds of formula (IIh) and (IIj). The compounds of formula (IIh) and (IIj) are then separated by known methods, for example by silica gel column chromatography or reverse phase column.

Both sequences give the desired compounds of formula (IIh) and (IIi). Preparation of a library of compounds is achieved more efficiently by reacting the compounds of formula (T16) and (T17) separately than by reacting a mixture of compounds of formula (T16) and (T17) followed by separation.

Method Q

Compounds of formula (IIk) and (IIm), wherein one of $R^6$ or $R^7$ is selected from the group consisting of paragraphs (l), (m), (n), (o), (p) and (q) of Formula (II) may be prepared according to the process outlined in Method Q.

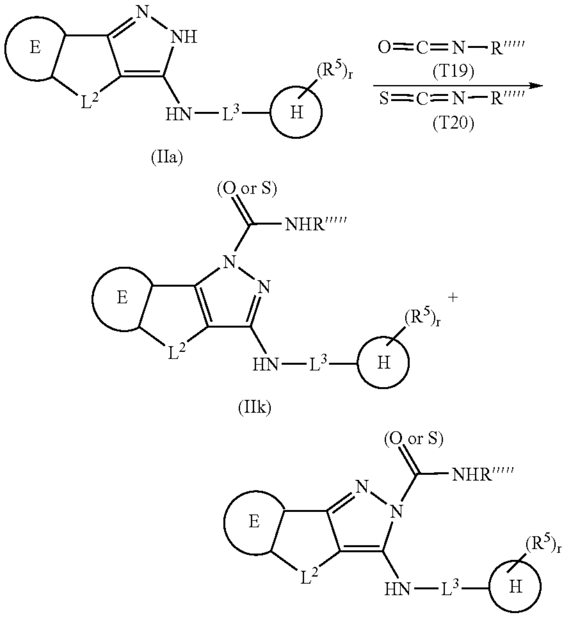

(IIa)
+
(IIk)
(IIm)

Accordingly, a suitably substituted compound of Formula (IIa) is reacted with a suitably substituted isocyanate, a compound of formula (T19) or a suitably substituted thioisocyanate, a compound of formula (T20), for example, phenylisocyanate, methylisocyanate, methylthioisocyanate, and the like, at a temperature in a range of between about −20° and about 100° C., in an aprotic solvent, such as THF, DMF, DCM, and the like, in the presence of base, such as pyridine, triethylamine, diisopropylethylamine, and the like, to yield a mixture of the corresponding regioisomers, compounds of formula (IIk) and (IIm). The ratio of the two regioisomers is dependent on the base and solvent used. Preferably, the two regioisomers are separated by silica gel column chromatography or reverse phase column chromatography to yield compounds of formula (IIk) and (IIm).

One skilled in the art will recognize that when the compound of formula (IIa) is reacted with an isocyanate, then the corresponding compounds of formula (IIk) and (IIm) will have $R^6$ or $R^7$ substituents of —C(O)NHR'''''. Similarly, when the compound of formula (IIa) is reacted with an thioisocyanate, then the corresponding compounds of formula (IIk) and (IIm) will have $R^6$/or $R^7$ substituent of —C(S)NHR'''''.

Method R

Compounds of formula (IIn) and (IIo), wherein one of $R^6$ or $R^7$ is selected from the group consisting of paragraphs (s), (t) and (u) of Formula (II) may be prepared according to the process outlined in Method R.

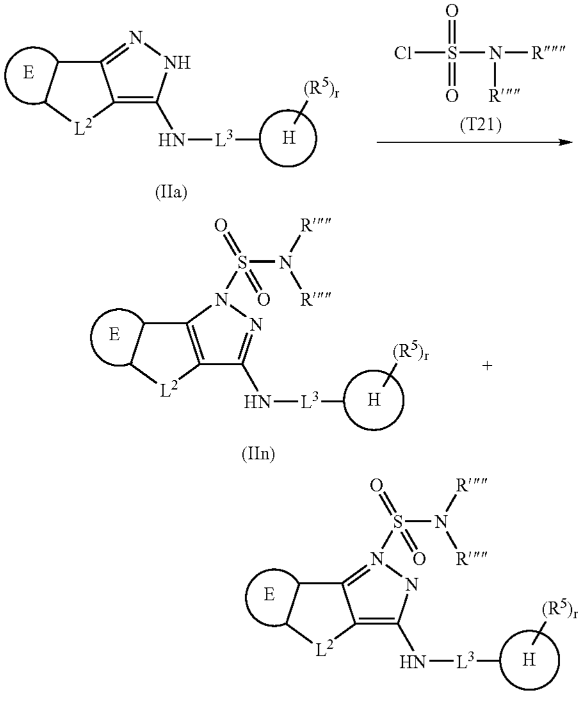

(IIa)
+
(IIn)
(IIo)

Accordingly, a suitably substituted compound of Formula (IIa) is reacted with a suitably substituted sulfamoyl chloride, a compound of formula (T21), a known compound, for example, dimethylsulfamoyl chloride, ethylsulfamoyl chloride, and the like, or a compound prepared by known methods, at a temperature in a range of between about −20° and about 100° C., in an aprotic solvent, such as THF, DMF, DCM, and the like, in the presence of base, such as pyridine, triethylamine, diisopropylethylamine, and the like, to yield a mixture of the corresponding regioisomers, compounds of formula (IIn) and (IIo). The ratio of the two regioisomers is dependent on the base and solvent used. Preferably, the two regioisomers are separated by silica gel column chromatography or reverse phase column chromatography to yield compounds of formula (IIn) and (IIo).

One skilled in the art will recognize that when the compound of formula (IIa) is reacted with an sulfamyl, then the corresponding compounds of formula (IIo) and (IIp) will have $R^6$ or $R^7$ substituents of $—SO_2NHR'''''$ and $—SO_2N(R''''')_2$.

Method S

Compounds of formula (IIp) and (IIq), wherein one of $R^6$ or $R^7$ is selected from the group consisting of paragraphs (v) and (w) of Formula (II) may be prepared according to the process outlined in Method S.

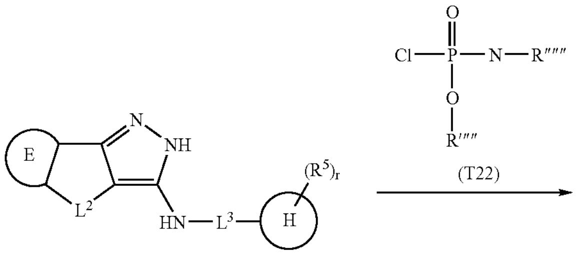

(IIa)

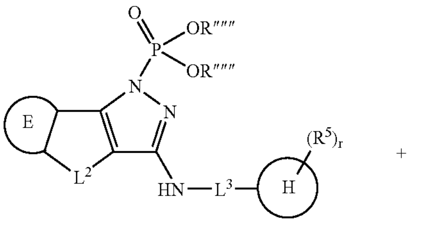

(IIp)

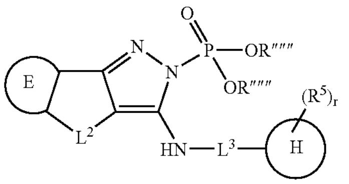

(IIq)

Accordingly, a suitably substituted compound of Formula (IIa) is reacted with a suitably alkyl chlorophosphate, a compound of formula (T22), a known compound, for example, dimethylchlorophosphate, diethylchlorophosphate, and the like, or a compound prepared by known methods, at a temperature in a range of between about −20° and about 100° C., in an aprotic solvent, such as THF, DMF, DCM, and the like, in the presence of base, such as pyridine, triethylamine, diisopropylethylamine, and the like, to yield a mixture of the corresponding regioisomers, compounds of formula (IIp) and (IIq). The ratio of the two regioisomers is dependent on the base and solvent used. Preferably, the two regioisomers are separated by silica gel column chromatography or reverse phase column chromatography to yield compounds of formula (IIp) and (IIq).

One skilled in the art will recognize that when the compound of formula (IIa) is reacted with a dialkyl chlorophosphate, then the corresponding compounds of formula (IIp) and (IIq) will have $R^6$ or $R^7$ substituents of —P(═O)$(O(C_1-C_3)alkyl)_2$ Method T Compounds of formula (IIr) and (IIs), wherein one of $R^6$ or $R^7$ is selected from the group consisting of paragraph (r) of Formula (II) may be prepared according to the process outlined in Method T.

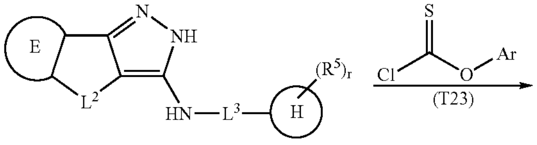

(IIa)

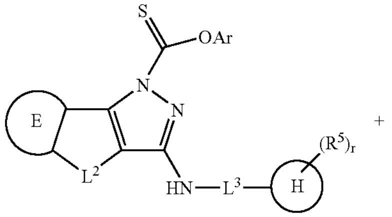

(T24)

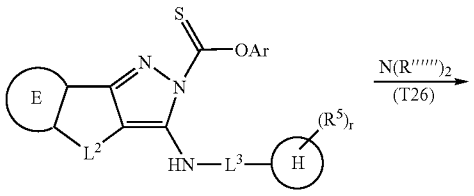

(T25)

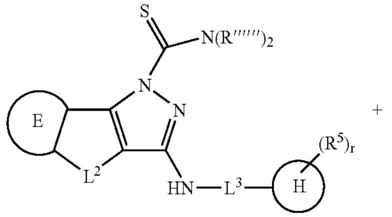

(IIr)

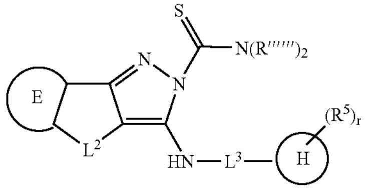

(IIs)

Accordingly, a suitably substituted compound of Formula (IIa) is reacted with a suitably substituted aryl thionochloroformate, a compound of formula (T23), a known compound or compound prepared by known methods, for example, phenylthionochloroformate, and the like, at a temperature in a range of between about −70° and about 100° C., in an aprotic solvent, such as THF, DMF, DCM, and the like, in the presence of base such as pyridine, triethylamine, diisopropylethylamine, and the like, to yield a mixture of the corresponding regioisomers, compounds of formula (T24) and (T25). Compounds of formula (T24) and (T25) are seprated by silica gel column chromatography or reverse phase column chromatography.

The compounds of formula (T24) and (T25), separately are reacted with a suitably substituted amine, a compound of formula (T26), a known compound or compound prepared by known methods, for example, piperidine, morpholine. Dimethylamine, pyrrolidine and the like, in an aprotic solvent such as DMF, DMSO, THF, and the like, at the temperature in a range of between about −70° and about 100° C. to yield the corresponding compounds of formula (IIr) and (IIs).

Alternatively, the compounds of formula (T24) and (T25) as a mixture are reacted with a suitably substituted amine, a compound of formula (T26), to yield a mixture of compounds of formula (IIr) and (IIs). The compounds of formula (IIr) and (IIs) are then separated by known methods, for example by silica gel column chromatography or reverse phase column.

Both sequences give the desired compounds of formula (IIr) and (IIs). Preparation of a library of compounds is achieved more efficiently by reacting the compounds of formula (T24) and (T25) separately than by reacting a mixture of compounds of formula (T24) and (T25) followed by separation.

N-Glucuronide Synthesis

To varying degrees the compounds of this invention may undergo the in vivo N-glucuronidation by various endogenous isozymes of the UDP-glucuronosyltransferase family (Chiu, S-H L; Huskey, S-E W; 1996 *ASPET N-glucuronidation of xenobiotics symposium: Species differences in N-glucuronidation*, Drug Metabolism and Disposition 1998, 26(9): 838–847).

One skilled in the art will understand that in vivo metabolites of compounds of Formulae (I) and (II) may be readily reverted to compounds of Formulae (1) and (II) by action of endogenous β-glucuronidase. The scientific literature details that tumor tissue generally contains elevated levels of endogenous β-glucuronidase. By action of endogenous β-glucuronidase, the in situ re-generation of compounds of Formulae (I) and (II) can be accomplished. In this way, the ability of the compounds of the present invention to be reversibly glucuronidated allows for the targeting of the present compounds to tumor tissue (Sperker, B; Backman, J T; Kroemer, H K, *The role of β-glucuronidase in drug disposition and drug targeting in humans*, Clin. Pharmacokinet., 1997, 33(1): 18–31).

Furthermore, reversible glucuronidation of the present compounds may also be recognized by one skilled in the art as a potential method for the detoxification of compounds of Formulae (I) and (II) (Caldwell, J; *The significance of phase II conjugation reactions in drug disposition and toxicity*, Life Sci, 1979, 24: 571–578), thus allowing the N-glucuronide metabolites formed to serve as a potential non-toxic reservoir for compounds of Formulae (I) and (II) which can then be readily unmasked to fully biologically active compounds of Formulae (I) and (II) in situ by tumor associated β-glucuronidase.

The N-glucuronide metabolites of compounds of Formulae (I) and (II) will have the structures shown below as GLU A, GLU B, and GLU C:

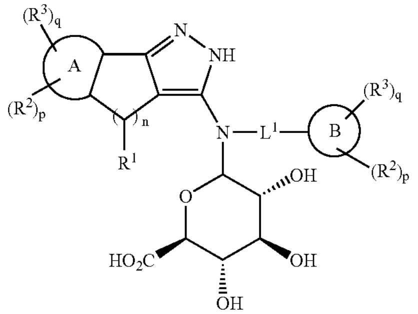

GLU A Derivative of Formula (I)

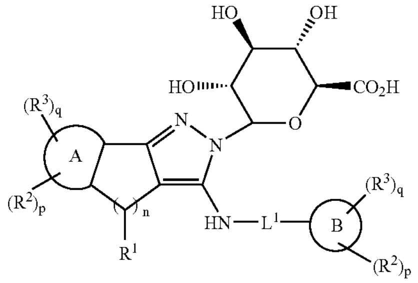

GLU B Derivative of Formula (I)

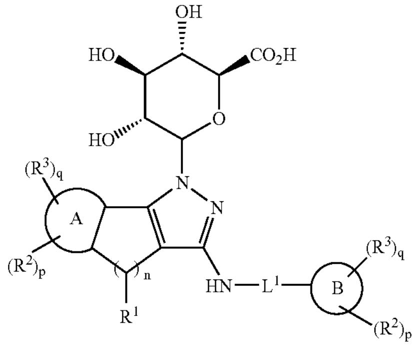

GLU C Derivative of Formula (I)

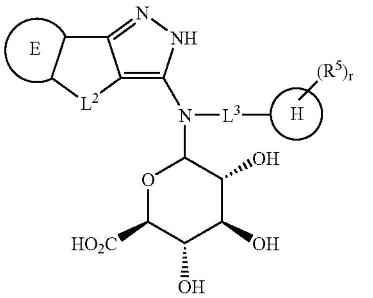

GLU A Derivative of Formula (II)

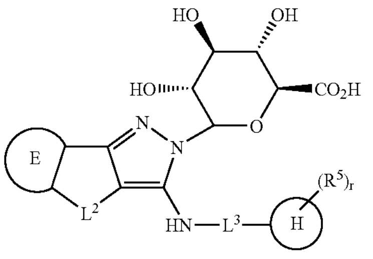

GLU B Derivative of Formula (II)

-continued

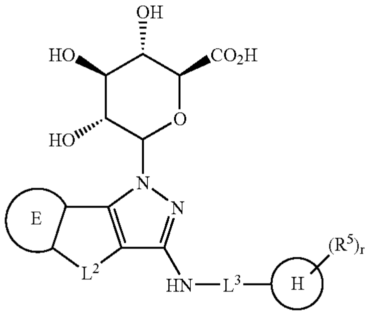

GLU C Derivative of Formula (II)

Usually, the glucuronidated compounds will have a β-configuration about the anomeric carbon atom, especially if the glucuronide is produced by well-established enzymatic methods known to persons skilled in the art (Luukkanen, L; Kilpelaeinen, I; Kangas, H; Ottoila, P; Elovaara, E; Taskinen, J, *Enzyme-Assisted Synthesis and Structural Characterization of Nitrocatechol Glucuronides*, Bioconjugate Chemistry (1999), 10(1), 150–154).

The N-glucuronides may also be prepared by direct synthesis by reacting compounds of Formulae (I) and (II) with suitably protected glucuronosyl halides by synthetic methodology know to persons skilled in the art (Upadhyaya, Pramod; Mclntee, Edward J.; Hecht, Stephen S., *Preparation of Pyridine-N-glucuronides of Tobacco-Specific Nitrosamines.*, Chemical Research in Toxicology (2001), 14(5), 555–561).

One skilled in the art will recognize that the GLU A, GLU B and GLU C derivatives of the compounds of Formulae (I) and (II) may be prepared by known methods, by adapting the procedures cited above.

Alternative Methods

One skilled in the art will further recognize that the $R^2$ and/or $R^3$ groups on the

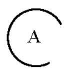

and/or

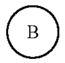

rings may alternatively be incorporated into the compound of Formula (I) by known methods, after formation of the core structure of Formula (I), a compound of Formula (Icore)

(Icore)

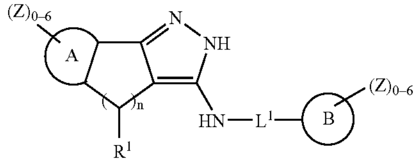

wherein each Z is bound directly to the

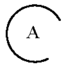 or 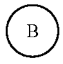

ring or to a portion of an $R^2$ or $R^3$ substituent (for example wherein the desired $R^2$ group is X-$A^1$-Y-$A^2$, the Z group may be bound to an X-$A^1$ group bound to an

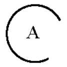 or 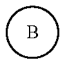.

For example, if one or more of the Z groups are hydroxy, the hydroxy group may be reacted according to known methods with an alkyl halide, to form the corresponding —O-alkyl substituent; with Cl—C(O)-alkyl or Cl—C(O)-aryl to form the corresponding —C(O)-alkyl or —C(O)-aryl substituent; with Cl—C(O)O— alkyl or Cl—C(O)O-aryl to form the corresponding —C(O)O-alkyl or —C(O)O-aryl substituent; or with C(O)N(alkyl) or C(O)C(aryl) to form the corresponding —OC(O)N(alkyl) or —OC(O)N(aryl) substituent.

If one or more of the Z groups is amino, the amino group may be reacted according to known methods with HC(O)-alkyl or HC(O)-aryl to form the corresponding —$NHCH_2$-alkyl or —$NHCH_2$-aryl substituent; with Cl—C(O)-alkyl or Cl—C(O)-aryl to form the corresponding —NHC(O)-alkyl or —NHC(O)aryl substituent; with C(O)N-alkyl or C(O)N-aryl to form the corresponding —NHC(O)NH-alkyl or —NHC(O)NH-aryl substituent; with Cl—C(O)O-alkyl or Cl—C(O)O-aryl to form the corresponding —NHC(O)O-alkyl or —NHC(O)O-aryl substituent; or with Cl—$SO_2$-alkyl or Cl—$SO_2$-aryl to form the corresponding —$NHSO_2$-alkyl or —$NHSO_2$-aryl substituent. One skilled in the art will further recognize that if the Z group is an alkyl amino or aryl amino group, similar chemistry may be preformed to yield corresponding substituents where the N group bound directly to the A or B ring remains substituted with the alkyl or aryl group.

If one or more of the Z groups is thio, the thio group may be reacted according to known methods with an alkyl halide to form the corresponding alkyl thio substituent. If one or more of the Z groups is alkylthio, the alkylthio group may be reacted according to known methods to form the corresponding alkyl sulfonyl substituent.

If one or more of the Z groups is carboxy, the carboxy group may be reacted according to known methods to form the corresponding —C(O)Cl group, which in turn may be further reacted to form the desired $R^2$ and/or $R^3$ substituents.

If one or more of the Z groups is —C(O)Cl, the —C(O)Cl group may be reacted according to known methods with an alkoxy to form the corresponding —C(O)O-alkyl substituent; with —NH(alkyl) or $N(alkyl)_2$ to form the corresponding —C(O)NH(alkyl) or $—C(O)N(alkyl)_2$ substituent.

If one or more of the Z groups is a halogen such as iodine or bromine, the halogen may be reacted according to known methods with $B(OH)_2$-alkyl, $B(OH)_2$-aryl or $B(OH)_2$-heteroaryl to displace the halogen with the corresponding -alkyl, -aryl or -heteroaryl group.

Alternatively, if one or more of the Z groups is a halogen such as iodine or bromine, the halogen may be reacted according to known methods with an alkylamine, a dialkylamine, an arylamine, a heteroarylamine or a heterocycloalkylamine to displace the halogen with the corresponding —NH— alkyl, $—N(alkyl)_2$, —N-aryl, —NH-heteroaryl or —NH-heterocycloalkyl group.

Alternatively, if one or more of the Z groups is a halogen such as iodine or bromine, the halogen may be reacted according to known methods with HO-alkyl, HO-aryl, HO-heteroaryl or HO-heterocycloalkyl to displace the halogen with the corresponding —O-alkyl, —O-aryl, —O-heteroaryl or —O-heterocycloalkyl group.

Alternatively, if one or more of the Z groups is a halogen such as iodine or bromine, the halogen may be reacted according to known methods with HS-alkyl, HS-aryl, HS-heteroaryl or HS-heterocycloalkyl to displace the halogen with the corresponding —S-alkyl, —S-aryl, —S-heteroaryl or —S-heterocycloalkyl group.

If one or more of the Z groups is $—O—SO_2$-aryl or $—OSO_2$-alkyl, the $—O—SO_2$aryl or $—OSO_2$-alkylgroup may be reacted according to known methods with an alkyl amine, a dialkylamine an aryl amine or a heteroarylamino to form the corresponding —NH(alkyl), $—N(alkyl)_2$, —NH (aryl) or —NH(heteroaryl) group.

Alternatively, If one or more of the Z groups is $—O—SO_2$-aryl or $—OSO_2$-alkyl, the $—O—SO_2$aryl or $—OSO_2$-alkylgroup may be reacted according to known methods to displace the $—O—SO_2$ group with a halogen such as Br or I, to form a reactive intermediate which can then be further reacted to form the desired substituent.

If one or more of the Z groups is —S-alkyl, —S-aryl, —S-heteroaryl or —S-heterocycloalkyl, the S may be oxidized according to known methods to form the corresponding $—SO_2$-alkyl, $—SO_2$-aryl, $—S O_2$-heteroaryl or $—SO_2$-heterocycloalkyl substituent.

If one or more of the Z groups contains a terminal unsaturated bond, the Z group may be reacted according to known methods to form the corresponding epoxide, which in turn may be reacted with a substituted amine such as an alkylamino, a dialkylamine, an arylamine, a heteroarylamine, a heterocycloalkylamine, or a cyclic amine (such as piperidine, morpholine, imidazole, and the like), to form the corresponding $—CH(OH)CH_2—NH$-alkyl, $—CH(OH)CH_2—N(alkyl)_2$, $—CH(OH)CH_2—NH$-aryl, $—CH(OH)CH_2—NH$-heteroaryl, $—CH(OH)CH_2—NH$-heterocycloalkyl or $—CH(OH)CH_2$-(cyclic amine bound through the N atom) substituent.

One skilled in the art will further recognize transformation or reactions similar to those described above may be employed in (or applied to) the preparation of compounds of formula (II). More particularly, the processes described above for the introduction of $R^2$ and/or $R^3$ groups on the

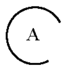

and/or

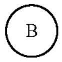

rings may be used to incorporate $R^5$, $R^9$ and/or $R^{10}$ substituents onto the

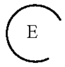 and 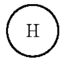

and rings on the compounds of formula (II).

One skilled in the art will recognize that compounds of Formula (I) wherein $R^1$ is oxo (═O) may be converted according to known methods to form compounds of Formula (I) wherein $R^1$ is hydroxy (by reduction) or converted to intermediate compounds wherein $R^1$ is ═NHOH (by reacting with $NH_4OH$). The intermediate compounds wherein $R^1$ is ═NHOH may then be reduced according to known methods to the corresponding amine, which may then be further optionally functionalized to the corresponding substituted amine.

Compounds of Formula (I) wherein $R^1$ is hydroxy may be converted according to known methods to form intermediate compounds wherein $R^1$ is $—O—SO_2$-aryl or $—O—SO_2$-alkyl by reacting the intermediate compound with the corresponding $Cl—SO_2$-aryl or $Cl—SO_2$-alkyl reagent. The $—O—SO_2$-aryl or $—O—SO_2$-alkyl $R^1$ group may then be further optionally reacted according to known methods to form an amine (by reacting with $NaN_3$ followed by reduction).

Alternatively, compounds of Formula (I) wherein $R^1$ is hydroxy may be converted according to known methods to form compounds of Formula (I) wherein $R^1$ is —O-alkyl by reacting with the corresponding alkyl halide.

Compounds of Formula (I) wherein $R^1$ is amine or alkyl amine may be reacted according to known methods to form compounds of Formula (I) wherein $R^1$ is $—NH—CH_2$-alkyl or $—NH—(CH_2\text{-alkyl})_2$ by reacting with HC(O)-alkyl.

One skilled in the art will further recognize that transformation or reactions similar to those described above may be employed in (or applied to) the preparation of compounds of formula (II). More particularly, the processes described above for the introduction and optional conversion of $R^1$ groups in the compounds of formula (I) may be similarly applied to the preparation of compounds of formula (II), wherein such transformations are appropriate in the preparation of desired $L^2$ groups.

One skilled in the art will further recognize that the above examples for the inclusion of desired substituent groups into the compounds of Formula (I) and/or compounds of formula (II) are not intended to be all inclusive, but rather are intended to provide examples of known chemistry for the incorporation of representative substituents. Additional substituents groups not specifically described herein may be incorporated into the compounds of Formula (I) and/or compounds of formula (II) by known methods.

Representative compounds of the present invention synthesized by the aforementioned methods are presented below. Examples of the synthesis of specific compounds are presented thereafter.
| Cpd | Structure |
|---|---|
| 1 | 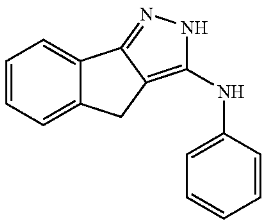 |
| 2 | 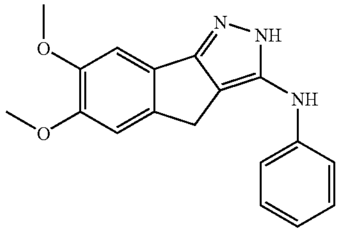 |
| 3 | 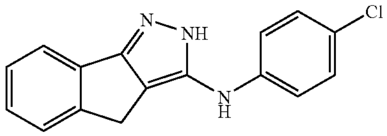 |
| 4 | 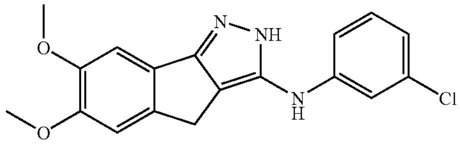 |
| 5 | 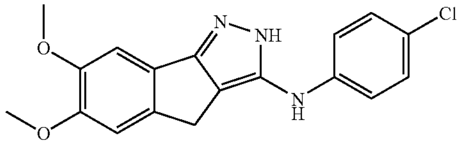 |
| 6 | 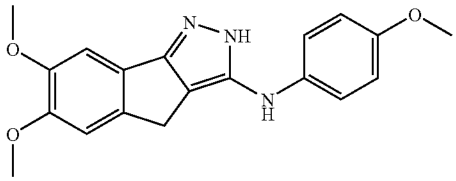 |
| 7 | 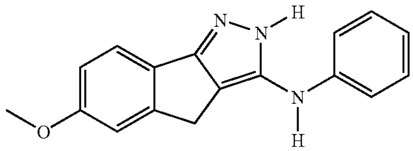 |

-continued
| Cpd | Structure |
|---|---|
| 8 | 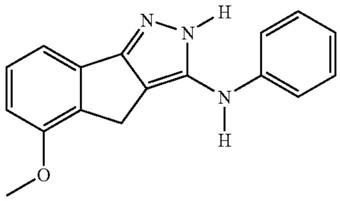 |
| 9 | 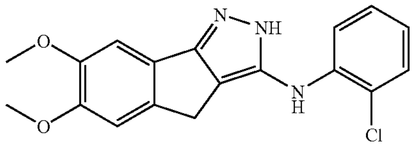 |
| 10 | 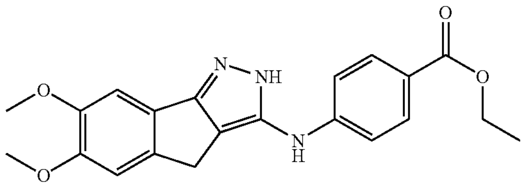 |
| 11 | 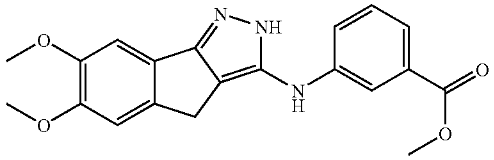 |
| 12 | 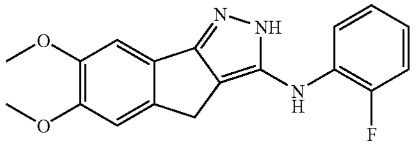 |
| 13 | 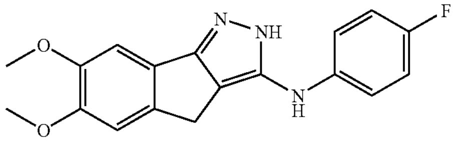 |
| 14 | 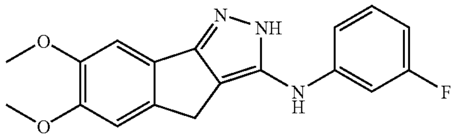 |
| 15 | 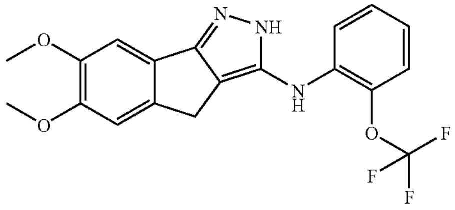 |

-continued
| Cpd | Structure |
|---|---|
| 16 | 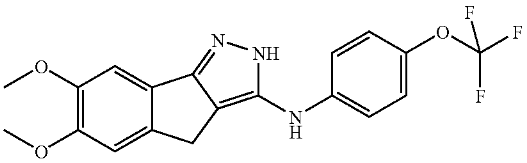 |
| 17 | 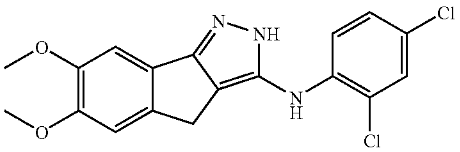 |
| 18 | 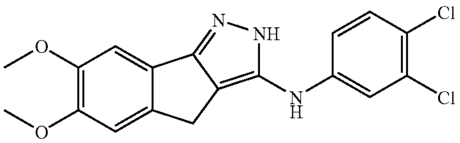 |
| 19 | 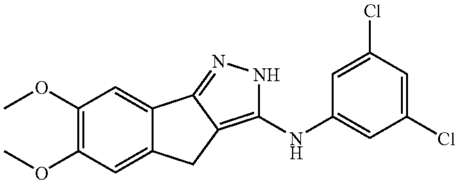 |
| 20 | 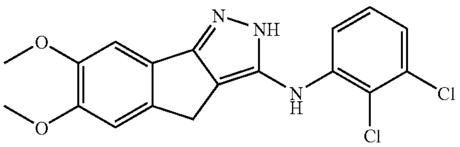 |
| 21 | 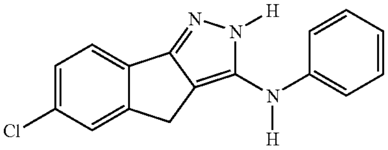 |
| 22 | 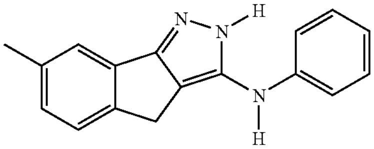 |
| 23 | 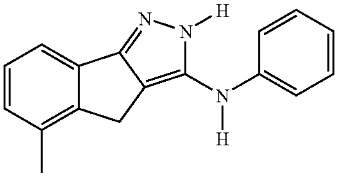 |
| 24 | 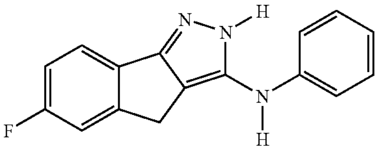 |

-continued
| Cpd | Structure |
|---|---|
| 25 | 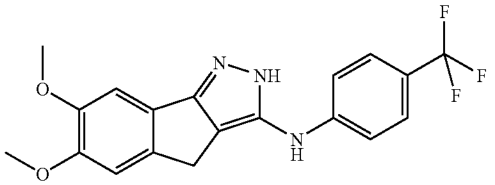 |
| 26 | 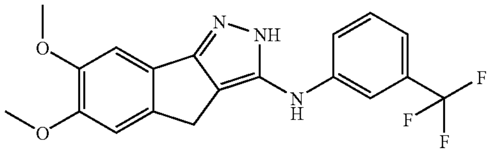 |
| 27 | 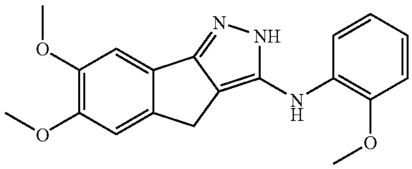 |
| 28 | 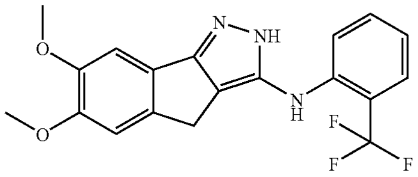 |
| 29 | 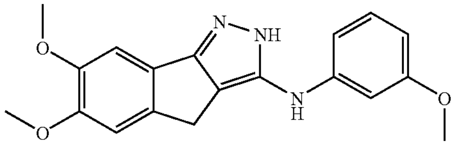 |
| 30 | 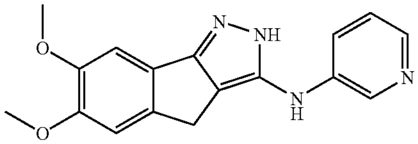 |
| 31 | 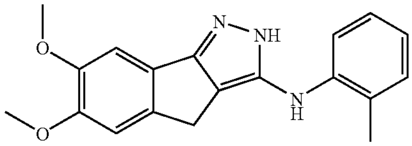 |
| 32 | 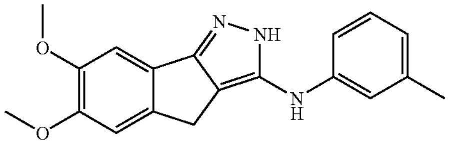 |
| 33 | 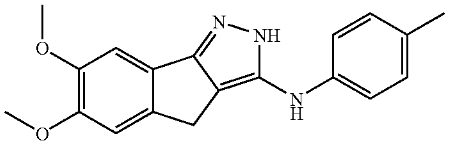 |

-continued
| Cpd | Structure |
|---|---|
| 34 | 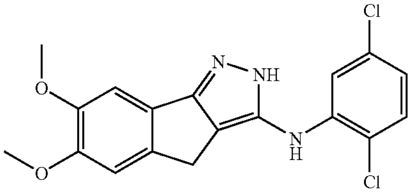 |
| 35 | 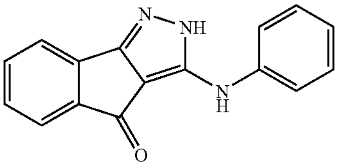 |
| 36 | 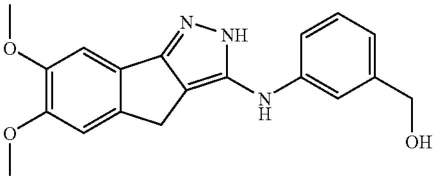 |
| 37 | 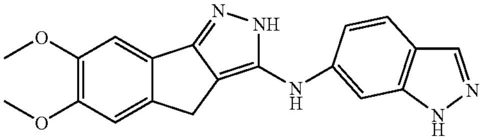 |
| 38 | 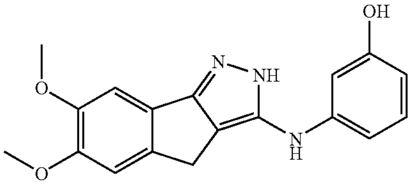 |
| 39 | 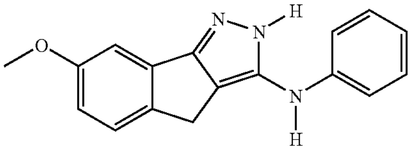 |
| 40 | 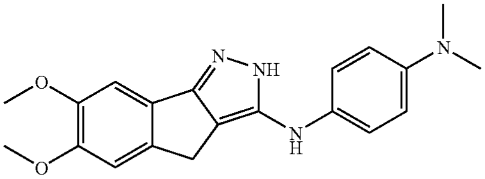 |
| 41 | 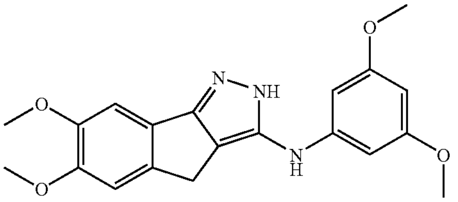 |

-continued
| Cpd | Structure |
|---|---|
| 42 | 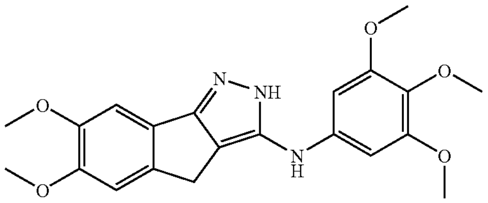 |
| 43 | 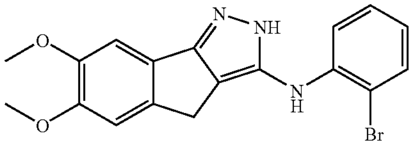 |
| 44 | 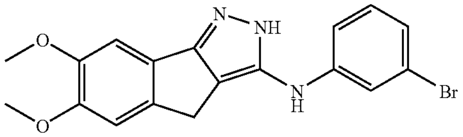 |
| 45 | 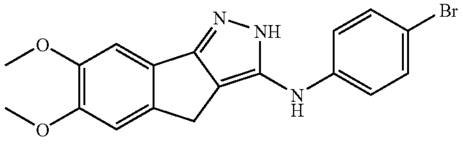 |
| 46 | 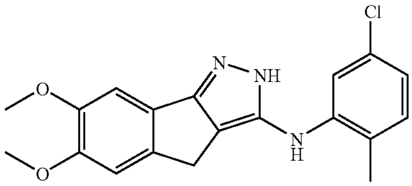 |
| 47 | 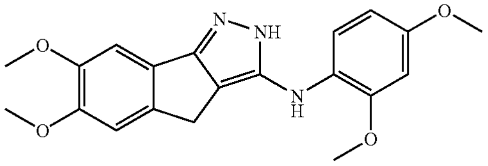 |
| 48 | 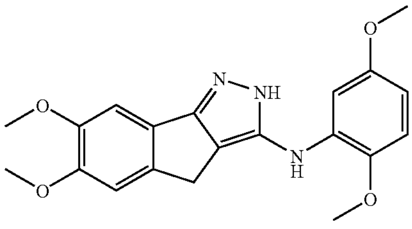 |
| 49 | 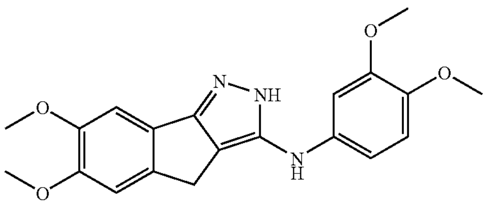 |

-continued
| Cpd | Structure |
|---|---|
| 50 | 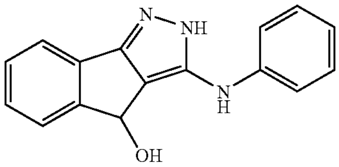 |
| 51 | 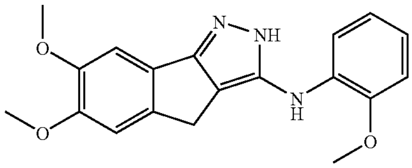 |
| 52 | 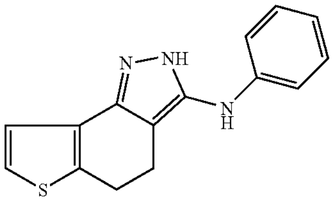 |
| 53 | 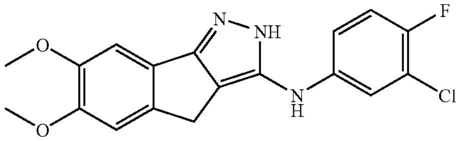 |
| 54 | 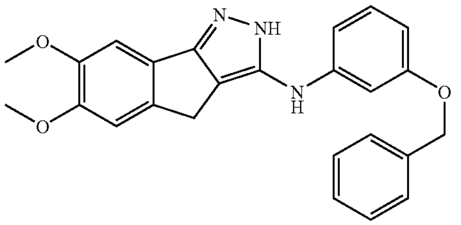 |
| 55 | 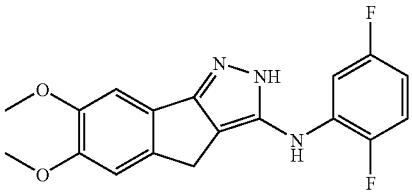 |
| 56 | 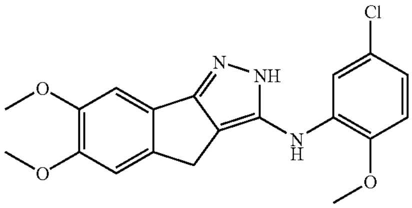 |
| 57 | 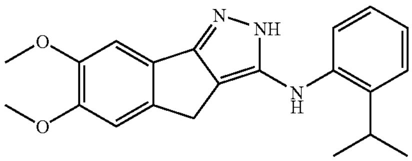 |

-continued
| Cpd | Structure |
|---|---|
| 58 | 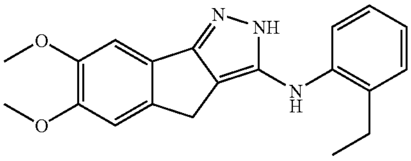 |
| 59 | 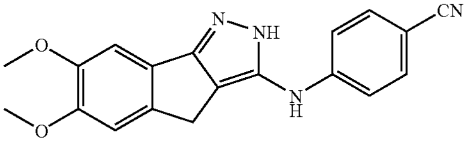 |
| 61 | 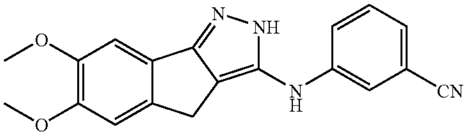 |
| 62 | 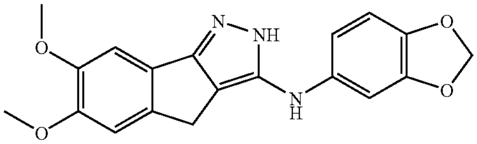 |
| 63 | 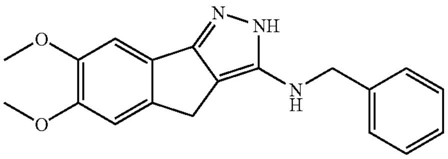 |
| 64 | 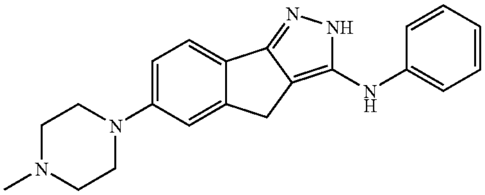 |
| 65 | 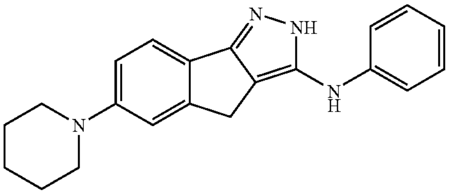 |
| 66 | 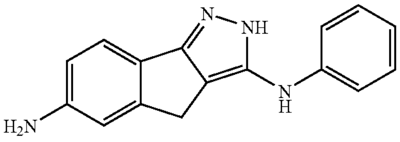 |
| 67 | 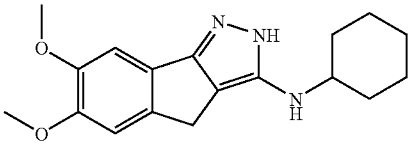 |

-continued
| Cpd | Structure |
|---|---|
| 69 | 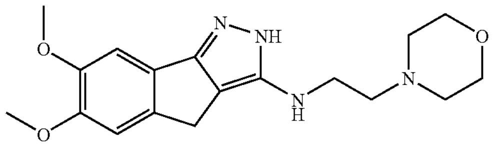 |
| 70 | 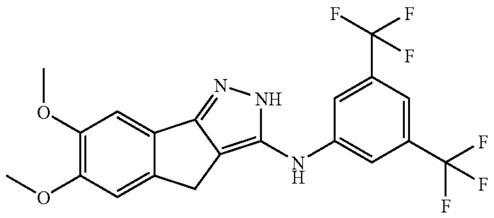 |
| 71 | 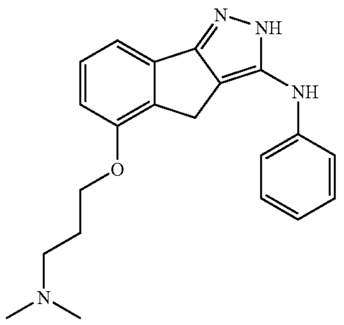 |
| 72 | 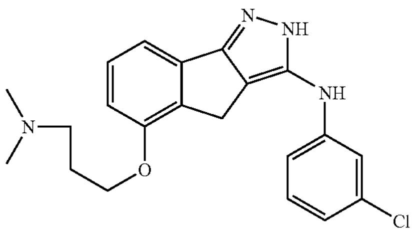 |
| 73 | 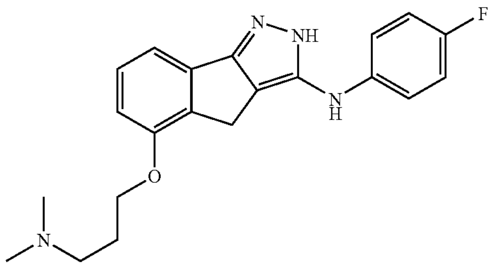 |
| 74 | 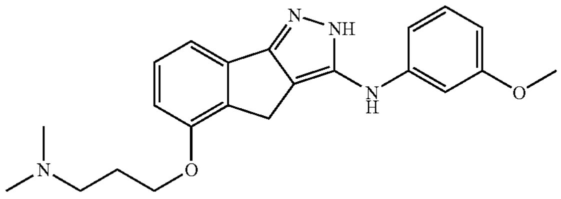 |

-continued
| Cpd | Structure |
|---|---|
| 75 | 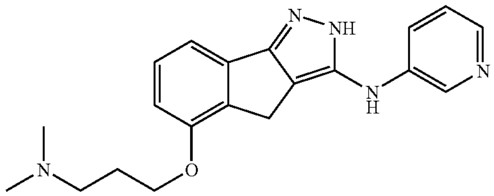 |
| 76 | 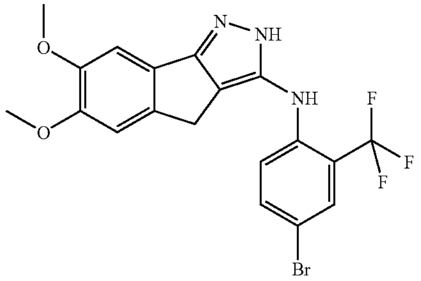 |
| 77 | 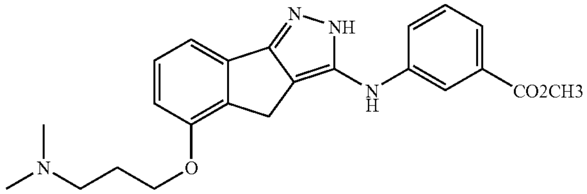 |
| 78 | 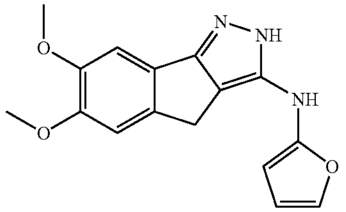 |
| 79 | 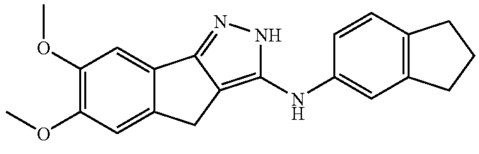 |
| 81 | 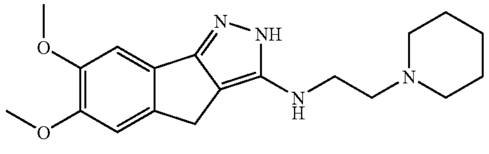 |
| 82 | 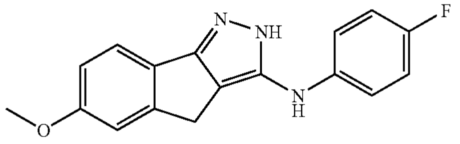 |
| 83 | 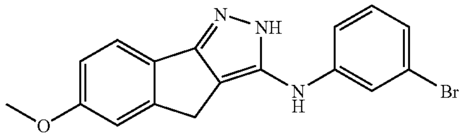 |

-continued
| Cpd | Structure |
| --- | --- |
| 84 | 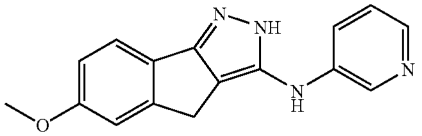 |
| 85 | 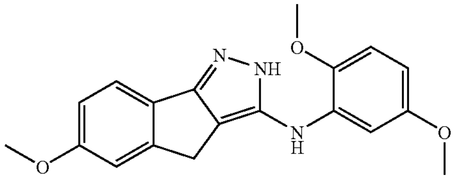 |
| 86 | 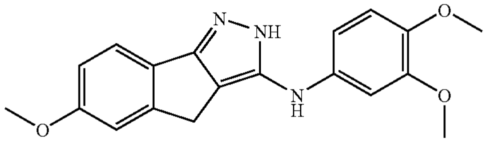 |
| 87 | 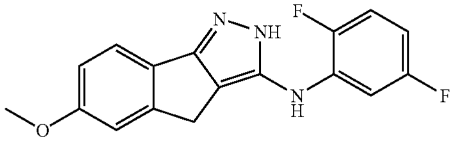 |
| 88 | 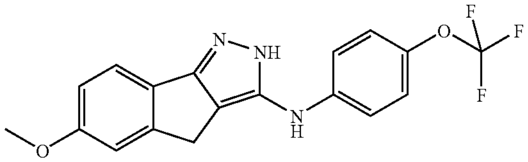 |
| 89 | 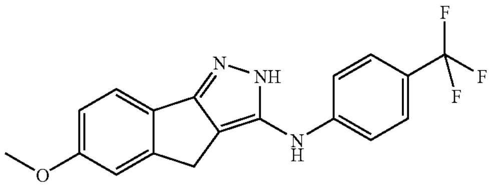 |
| 90 | 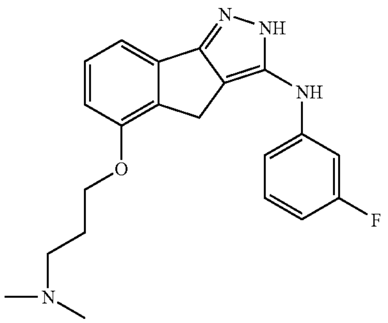 |

-continued
| Cpd | Structure |
|---|---|
| 91 | 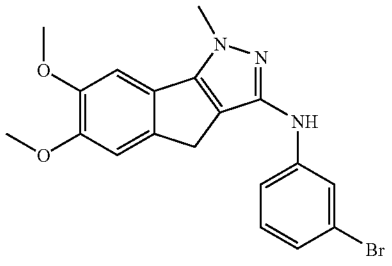 |
| 92 | 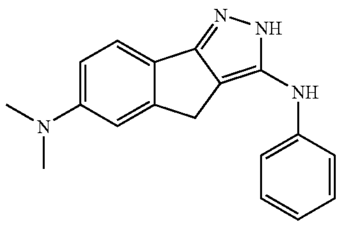 |
| 93 | 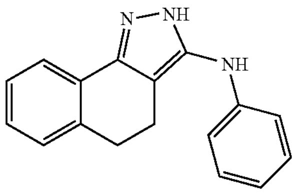 |
| 94 | 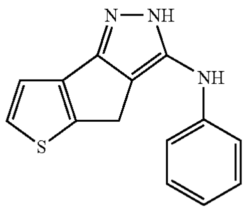 |
| 95 | 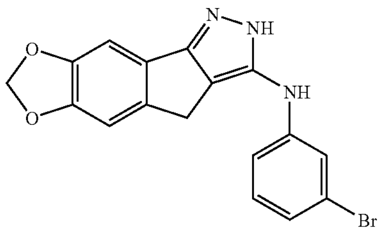 |
| 96 | 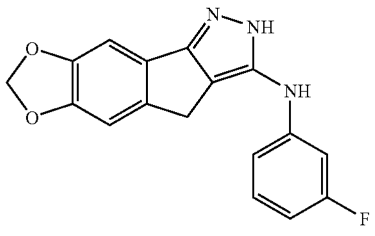 |

-continued
| Cpd | Structure |
|---|---|
| 97 | 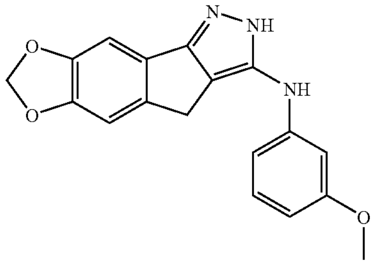 |
| 98 | 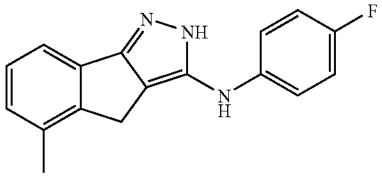 |
| 99 | 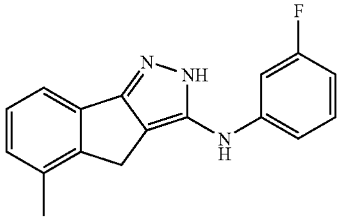 |
| 100 | 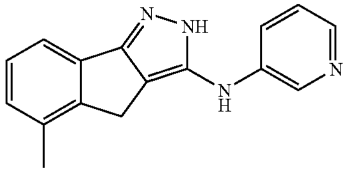 |
| 101 | 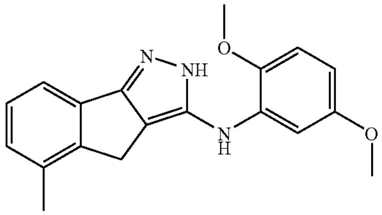 |
| 102 | 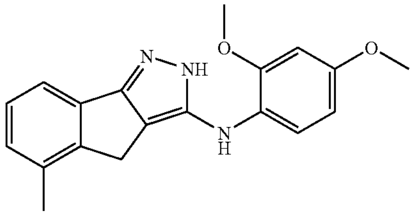 |
| 103 | 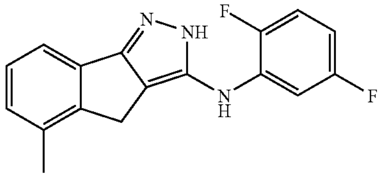 |

-continued
| Cpd | Structure |
|---|---|
| 104 | 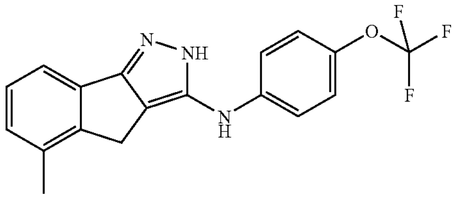 |
| 105 | 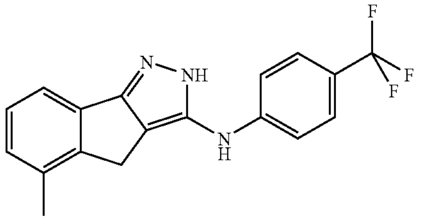 |
| 106 | 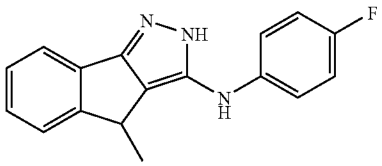 |
| 107 | 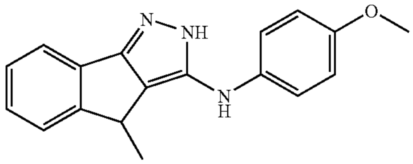 |
| 108 | 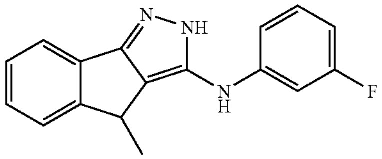 |
| 109 | 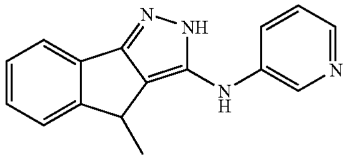 |
| 110 | 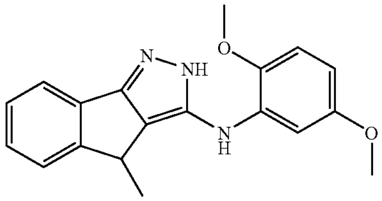 |
| 111 | 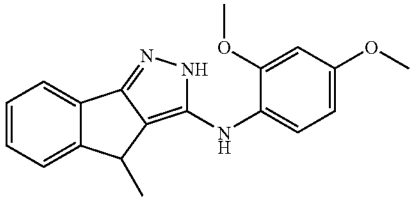 |

-continued
| Cpd | Structure |
|---|---|
| 112 | 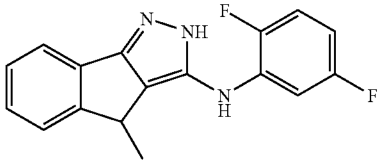 |
| 113 | 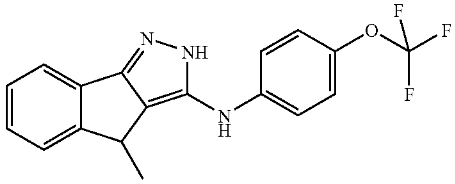 |
| 114 | 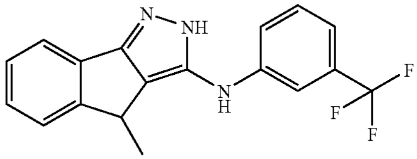 |
| 115 | 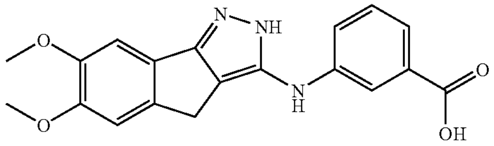 |
| 116 | 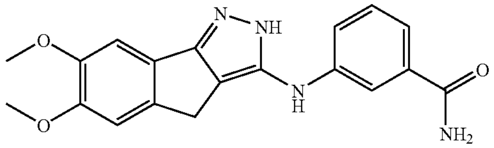 |
| 117 | 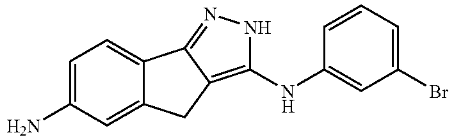 |
| 118 | 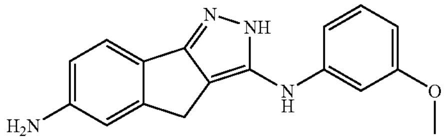 |
| 119 | 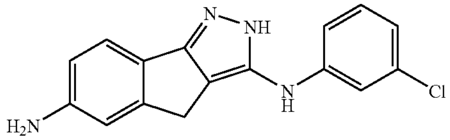 |
| 120 | 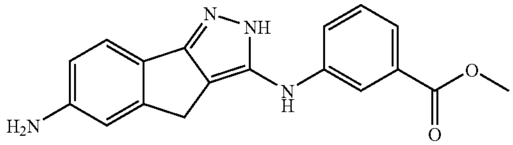 |

-continued
| Cpd | Structure |
|---|---|
| 121 | 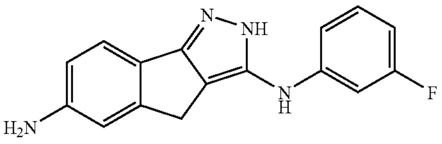 |
| 122 | 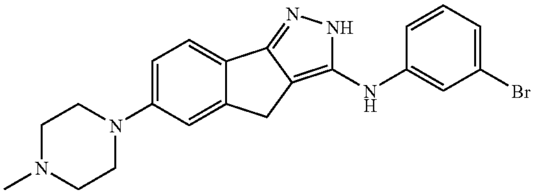 |
| 123 | 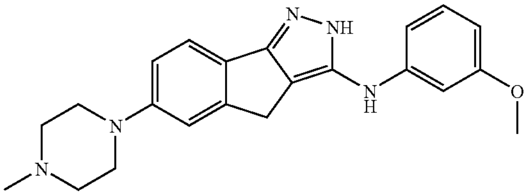 |
| 124 | 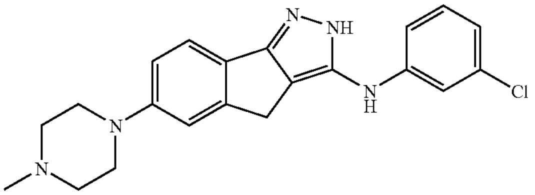 |
| 125 | 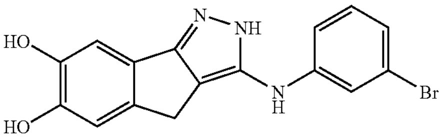 |
| 126 | 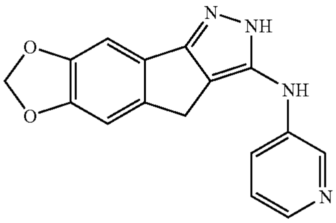 |
| 127 | 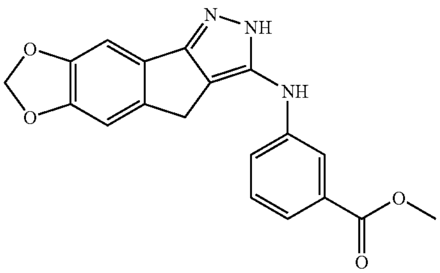 |

-continued
| Cpd | Structure |
|---|---|
| 128 | 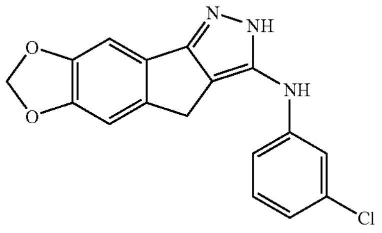 |
| 129 | 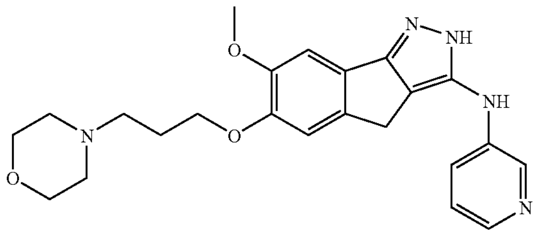 |
| 130 | 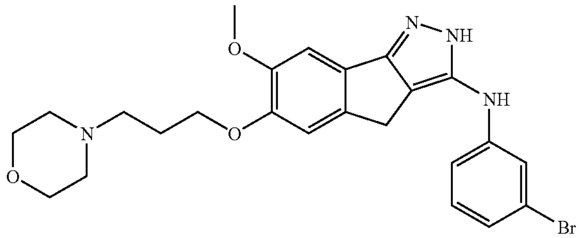 |
| 131 | 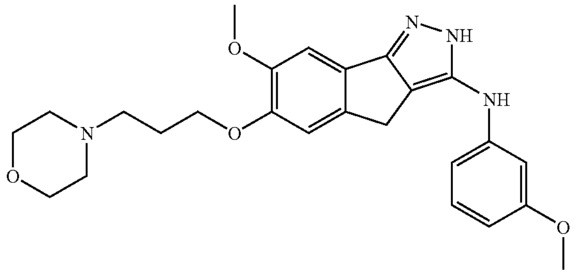 |
| 132 | 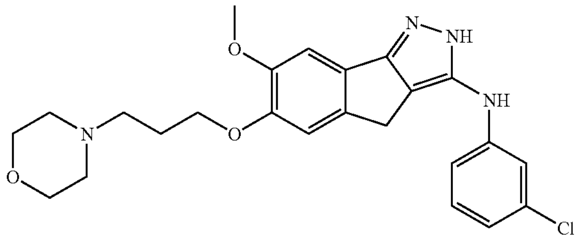 |
| 133 | 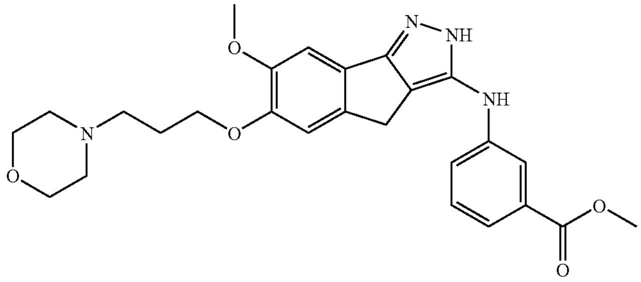 |

-continued
| Cpd | Structure |
|---|---|
| 134 | 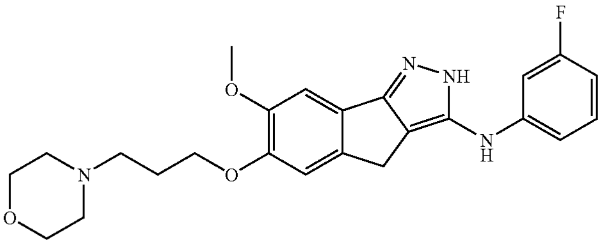 |
| 135 | 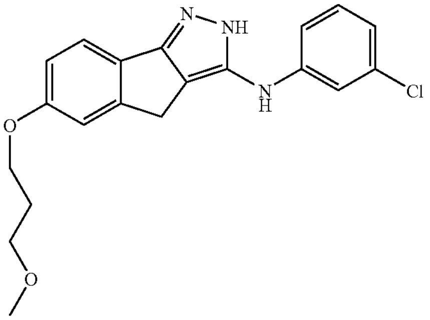 |
| 136 | 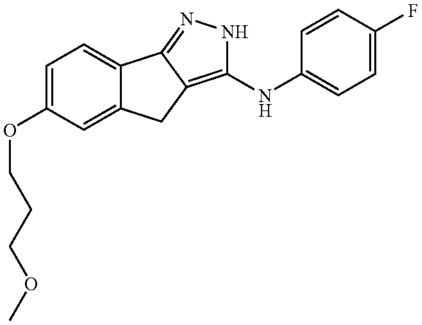 |
| 137 | 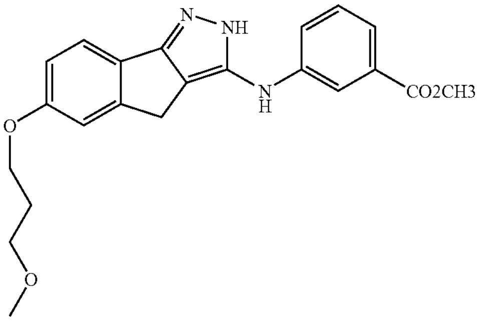 |
| 138 | 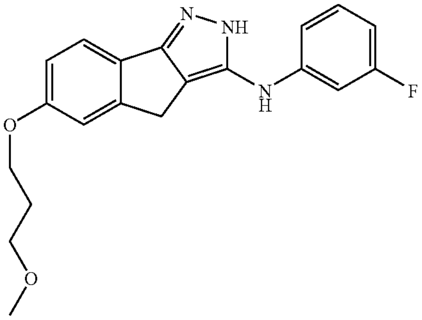 |

-continued
| Cpd | Structure |
| --- | --- |
| 139 | 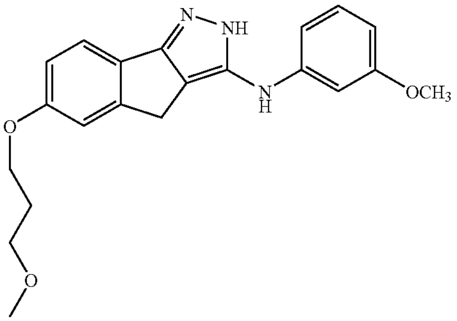 |
| 140 | 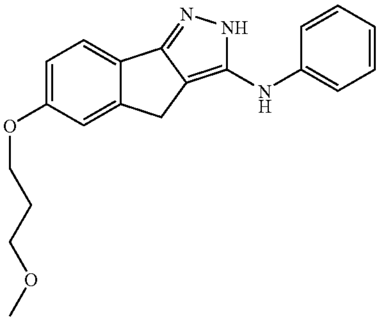 |
| 141 | 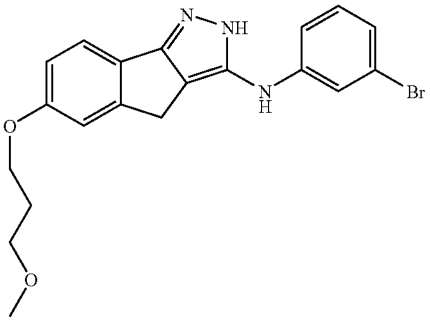 |
| 142 | 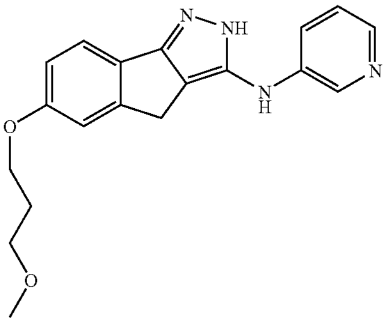 |

-continued
| Cpd | Structure |
| --- | --- |
| 143 | 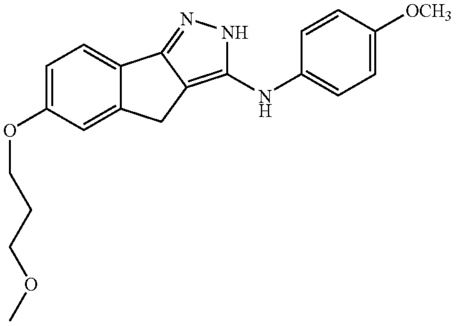 |
| 144 | 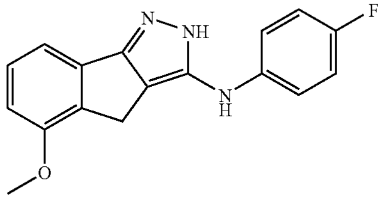 |
| 145 | 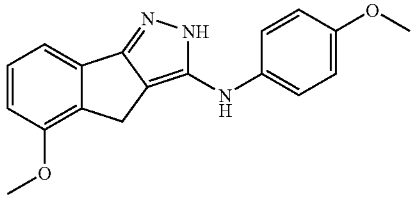 |
| 146 | 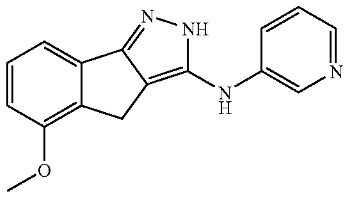 |
| 147 | 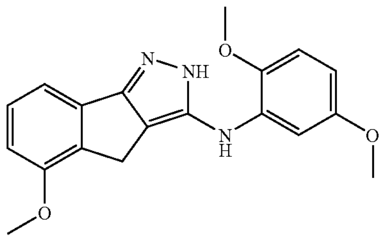 |
| 148 | 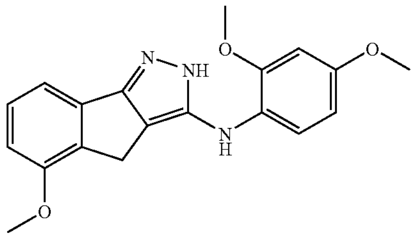 |

-continued
| Cpd | Structure |
|---|---|
| 149 | 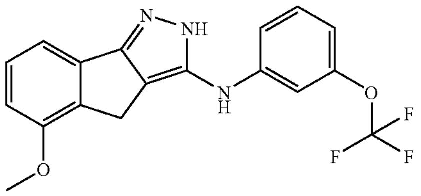 |
| 150 | 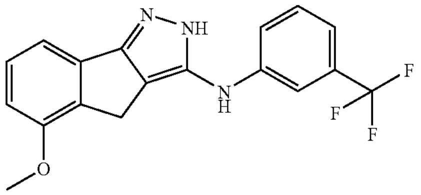 |
| 151 | 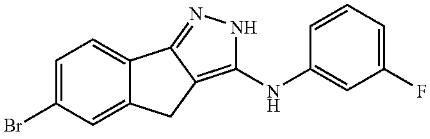 |
| 152 | 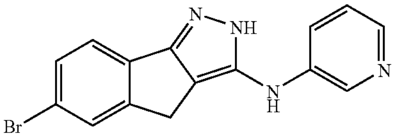 |
| 153 | 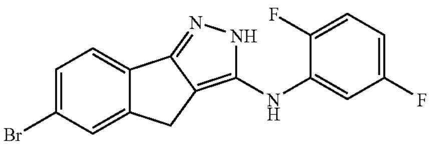 |
| 154 | 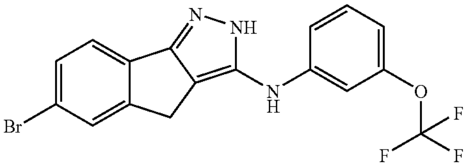 |
| 155 | 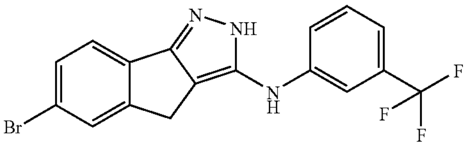 |
| 156 | 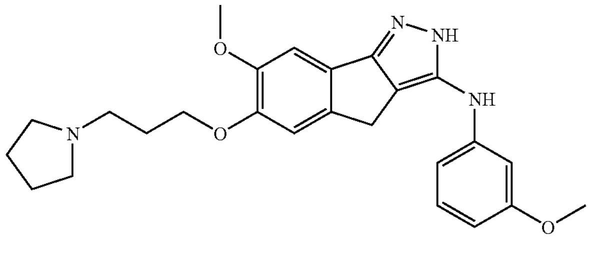 |

-continued
| Cpd | Structure |
| --- | --- |
| 157 | 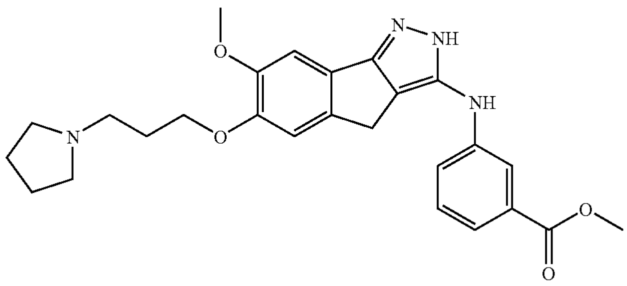 |
| 158 | 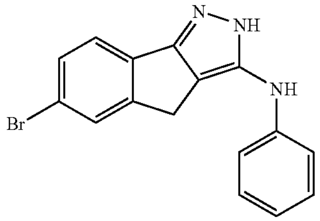 |
| 159 | 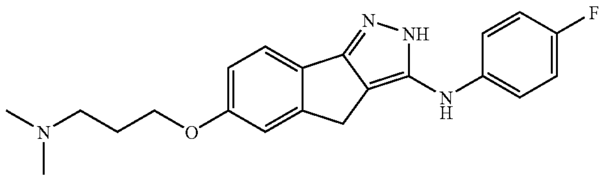 |
| 160 | 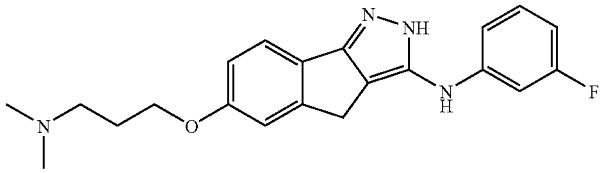 |
| 161 | 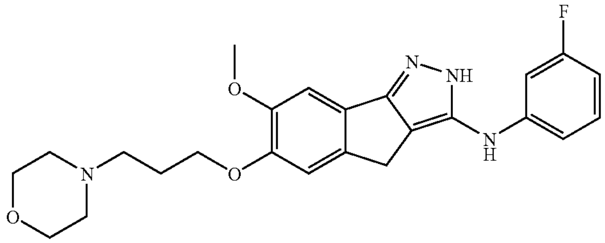 |
| 162 | 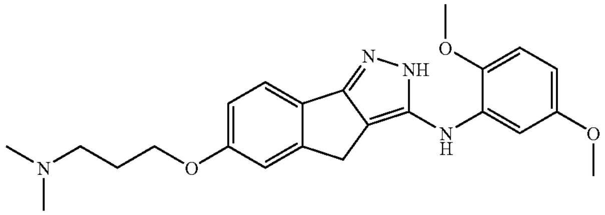 |
| 163 | 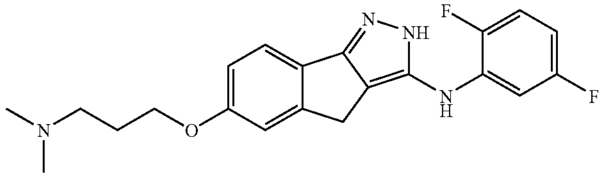 |

-continued
| Cpd | Structure |
|---|---|
| 165 | 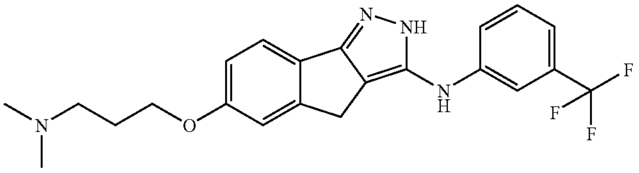 |
| 166 | 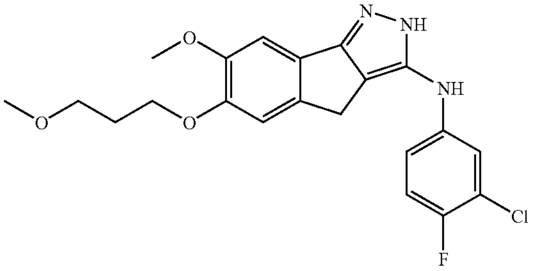 |
| 167 | 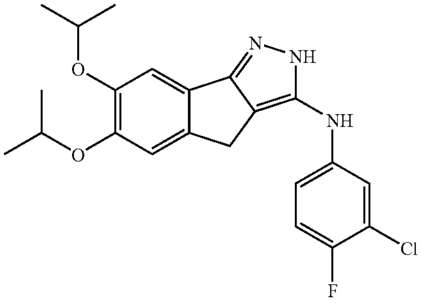 |
| 168 | 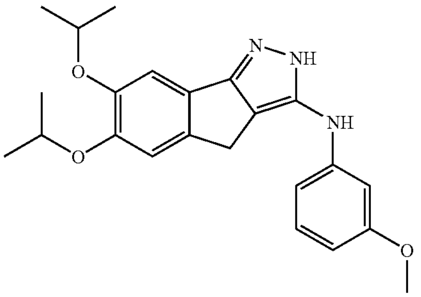 |
| 169 | 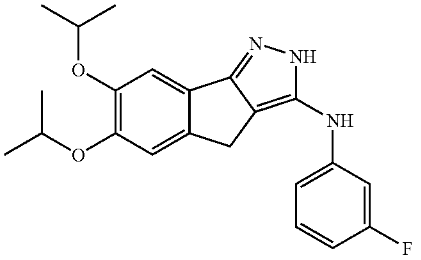 |
| 170 | 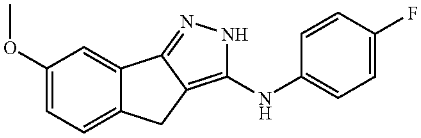 |

-continued
| Cpd | Structure |
| --- | --- |
| 171 | 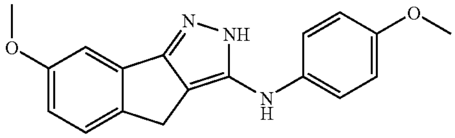 |
| 172 | 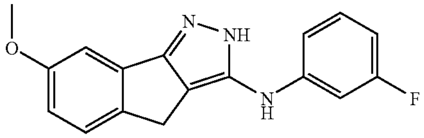 |
| 173 | 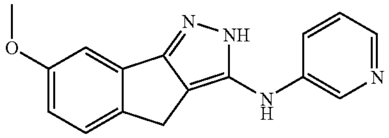 |
| 174 | 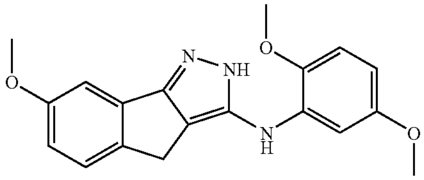 |
| 175 | 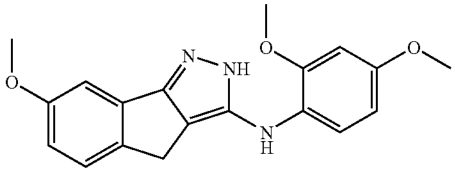 |
| 176 | 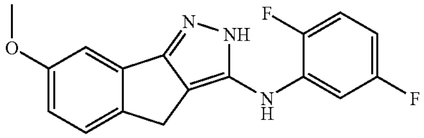 |
| 177 | 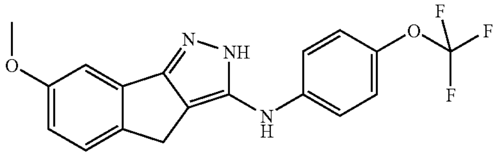 |
| 178 | 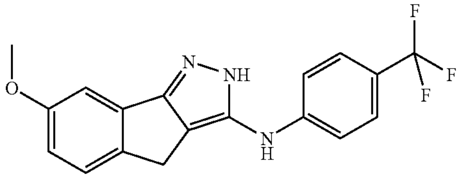 |

-continued
| Cpd | Structure |
| --- | --- |
| 179 | 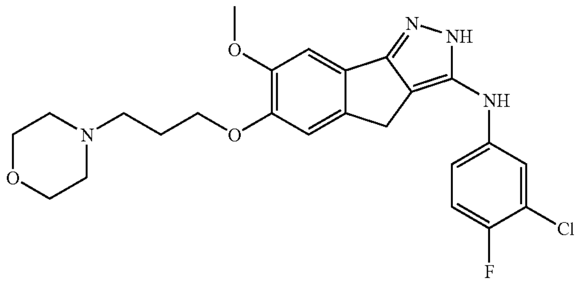 |
| 180 | 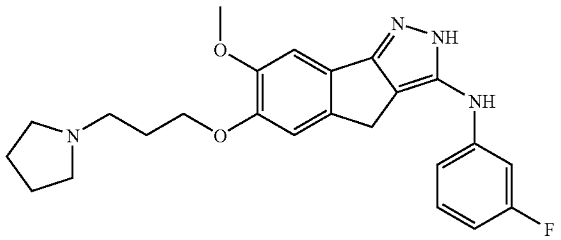 |
| 181 | 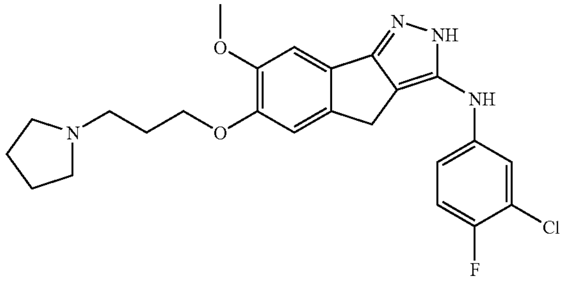 |
| 182 | 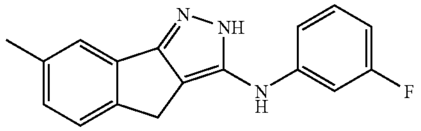 |
| 183 | 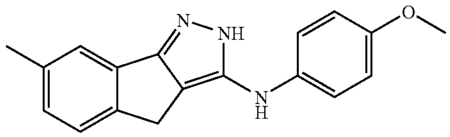 |
| 184 | 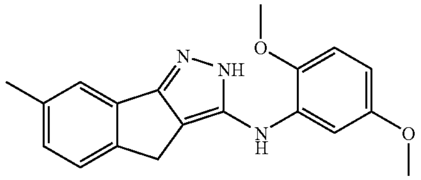 |
| 185 | 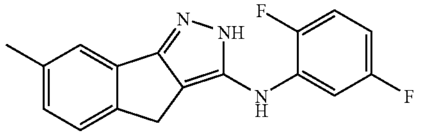 |

-continued
| Cpd | Structure |
| --- | --- |
| 186 | 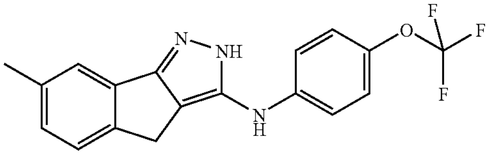 |
| 187 | 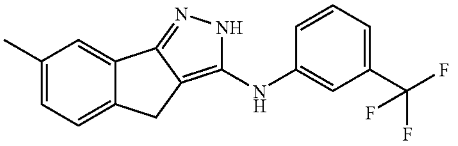 |
| 188 | 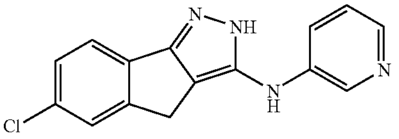 |
| 189 | 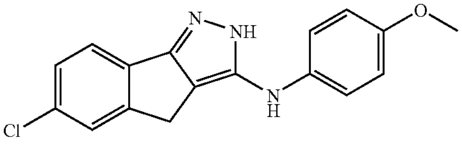 |
| 190 | 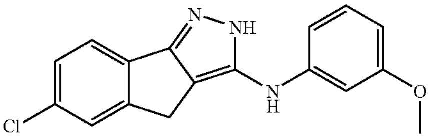 |
| 191 | 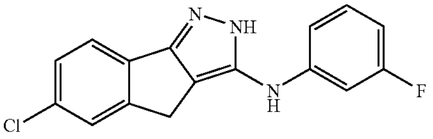 |
| 192 | 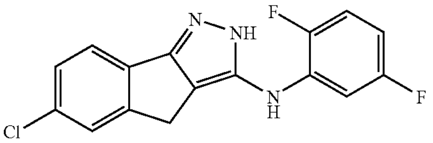 |
| 193 | 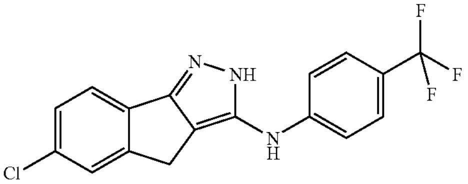 |
| 194 | 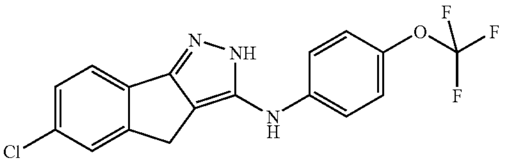 |

-continued
| Cpd | Structure |
|---|---|
| 195 | 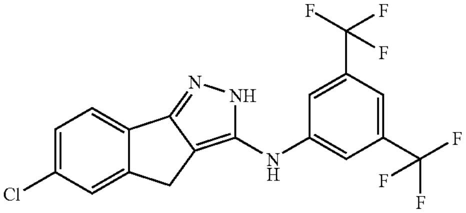 |
| 196 | 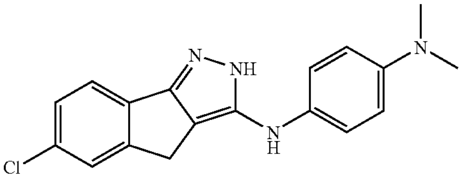 |
| 197 | 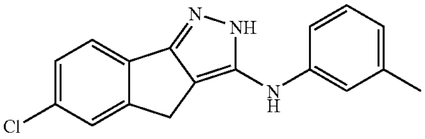 |
| 198 | 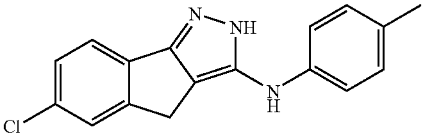 |
| 199 | 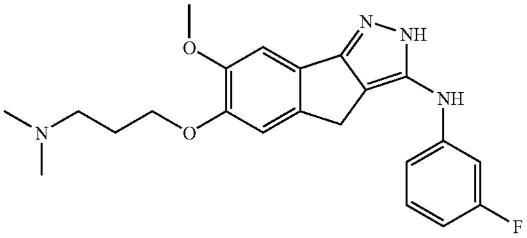 |
| 200 | 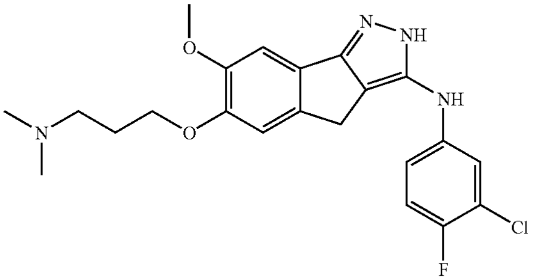 |
| 201 | 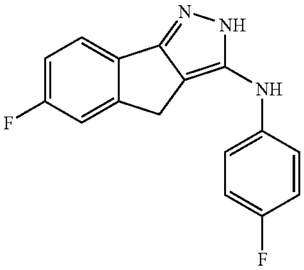 |

-continued
| Cpd | Structure |
| --- | --- |
| 202 | 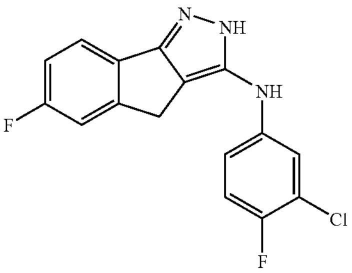 |
| 203 | 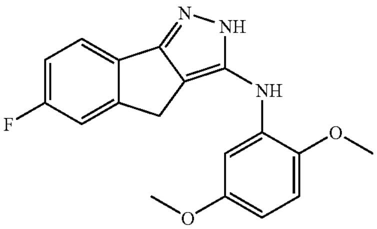 |
| 204 | 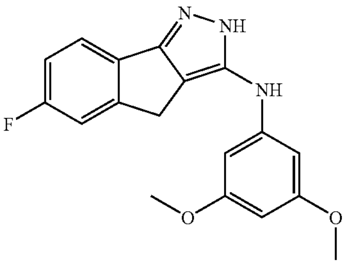 |
| 205 | 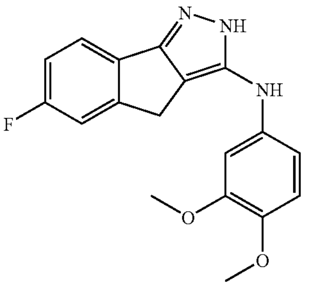 |
| 206 | 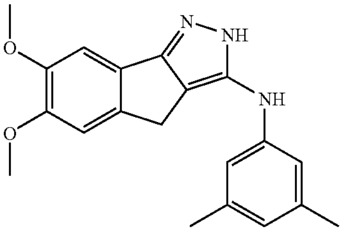 |
| 207 | 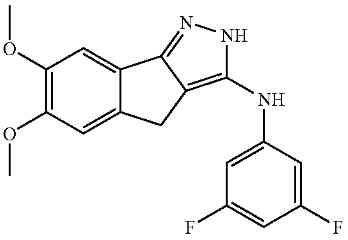 |

-continued
| Cpd | Structure |
|---|---|
| 208 | 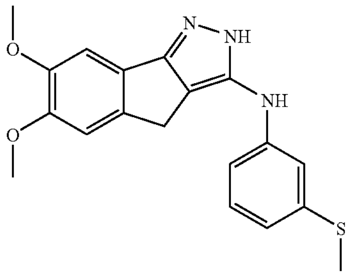 |
| 209 | 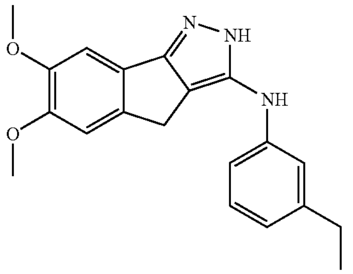 |
| 210 | 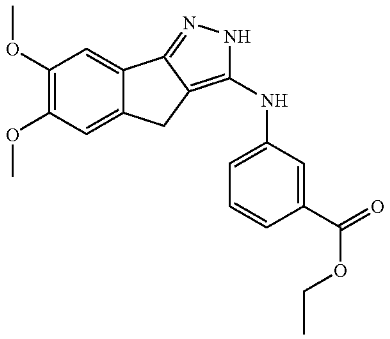 |
| 211 | 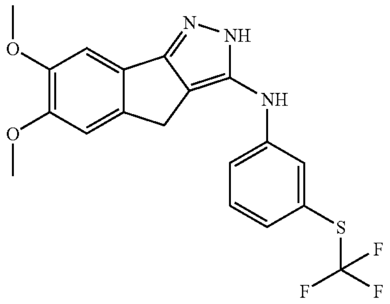 |
| 212 | 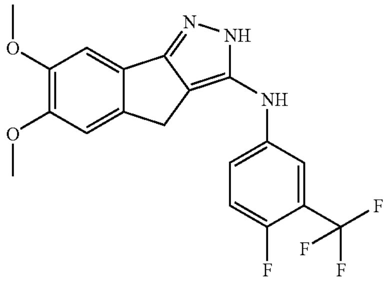 |

-continued
| Cpd | Structure |
|---|---|
| 213 | 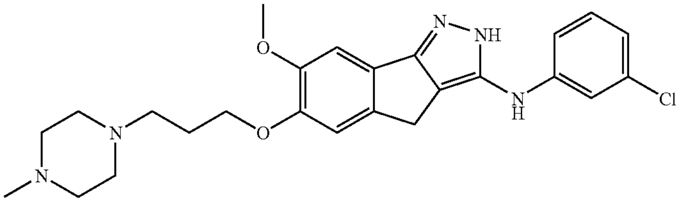 |
| 214 | 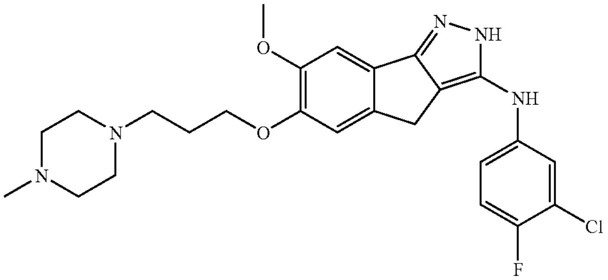 |
| 215 | 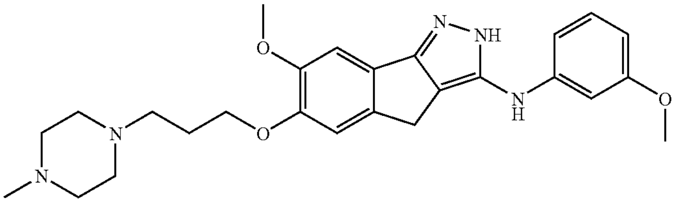 |
| 216 | 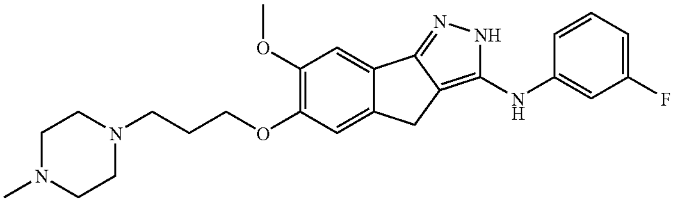 |
| 217 | 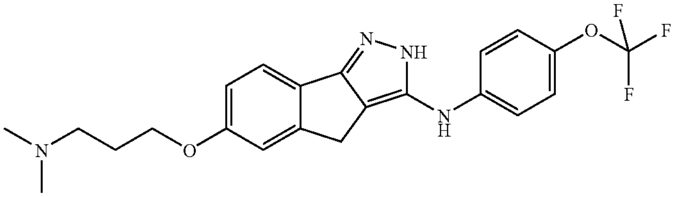 |
| 218 | 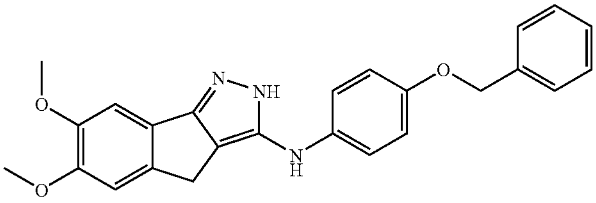 |
| 219 | 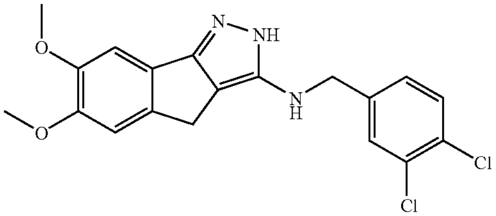 |

-continued
| Cpd | Structure |
|---|---|
| 220 | 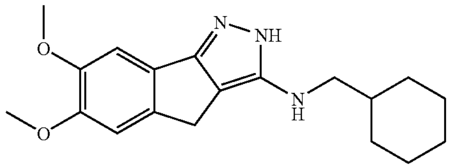 |
| 221 | 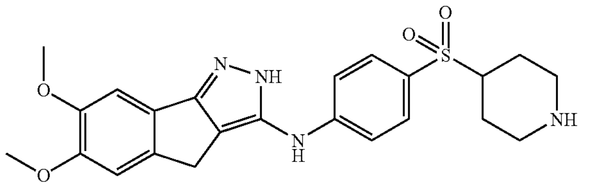 |
| 222 | 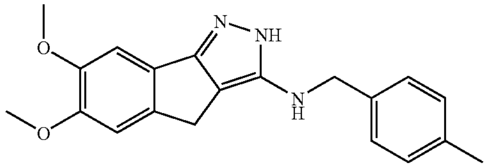 |
| 223 | 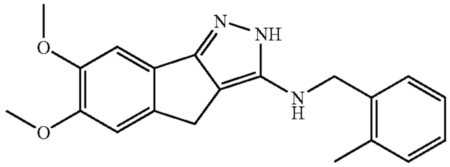 |
| 224 | 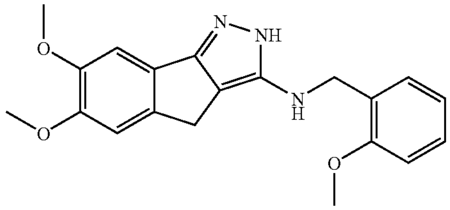 |
| 225 | 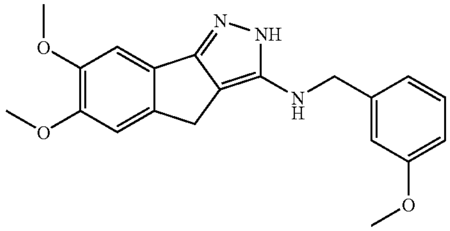 |
| 226 | 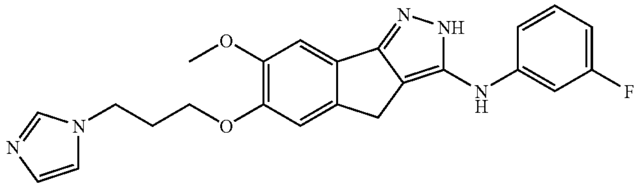 |

-continued
| Cpd | Structure |
|---|---|
| 227 | 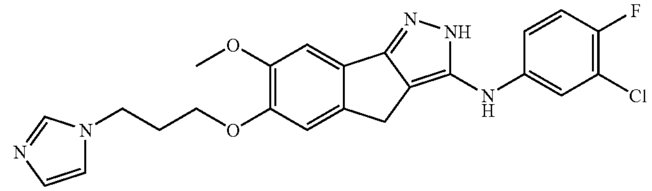 |
| 230 | 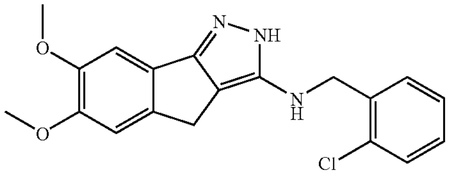 |
| 231 | 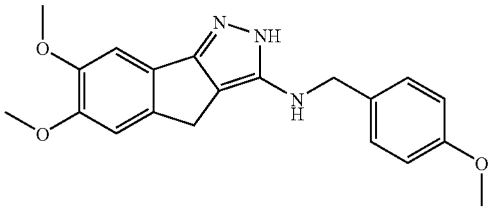 |
| 232 | 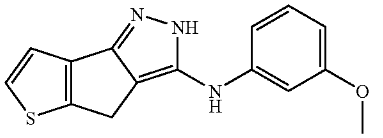 |
| 233 | 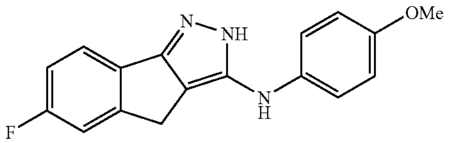 |
| 234 | 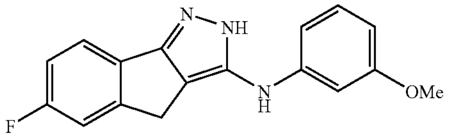 |
| 235 | 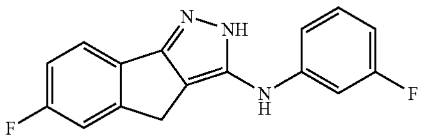 |
| 236 | 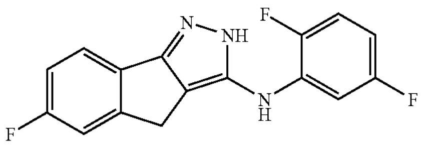 |
| 237 | 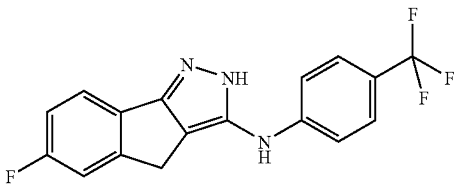 |

-continued
| Cpd | Structure |
|---|---|
| 238 | 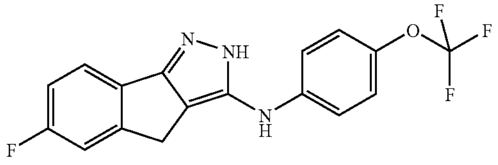 |
| 239 | 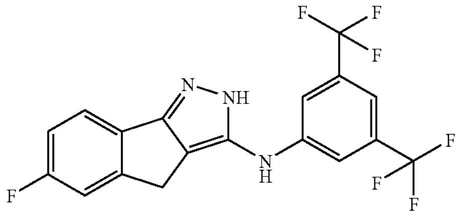 |
| 240 | 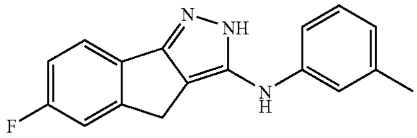 |
| 242 | 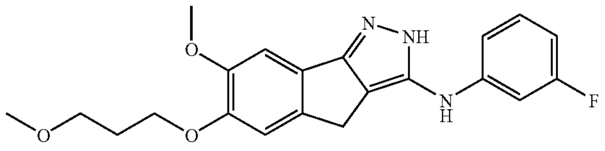 |
| 244 | 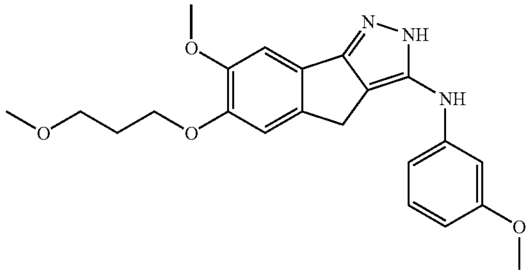 |
| 245 | 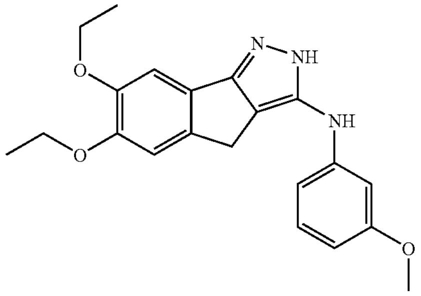 |

-continued
| Cpd | Structure |
|---|---|
| 246 | 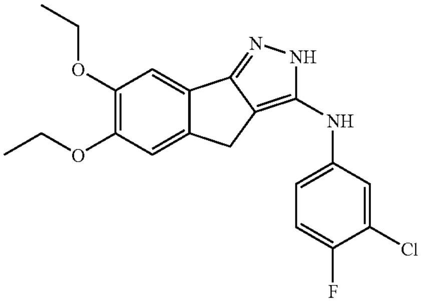 |
| 247 | 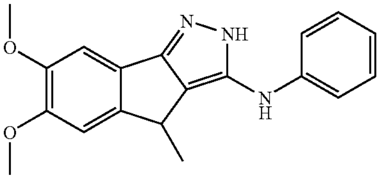 |
| 248 | 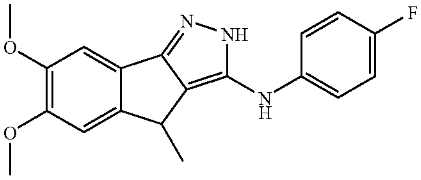 |
| 249 | 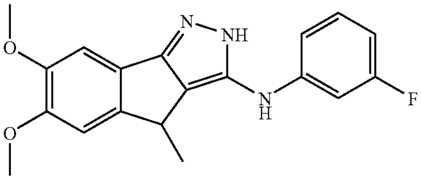 |
| 250 | 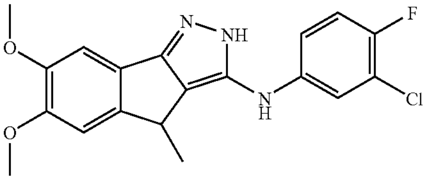 |
| 251 | 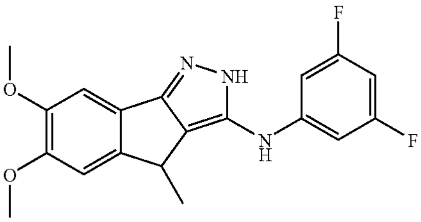 |
| 252 | 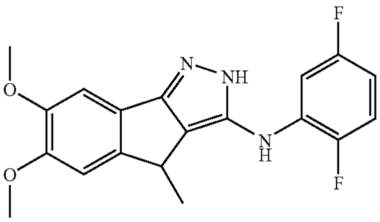 |

-continued
| Cpd | Structure |
|---|---|
| 253 | 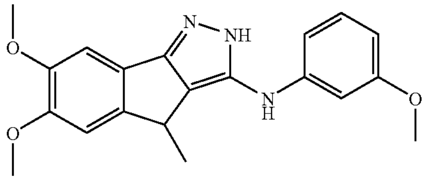 |
| 254 | 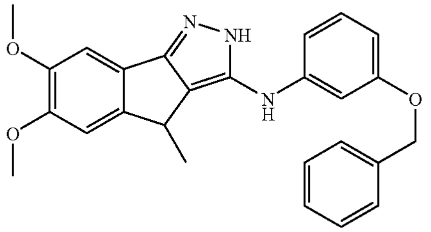 |
| 255 | 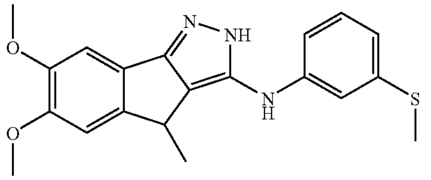 |
| 256 | 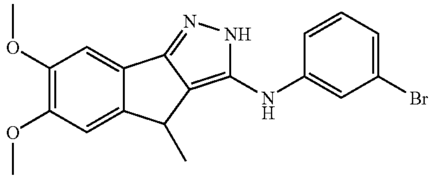 |
| 257 | 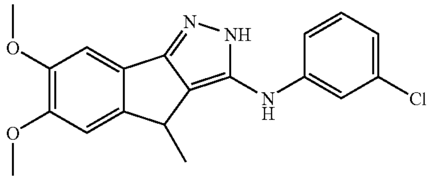 |
| 258 | 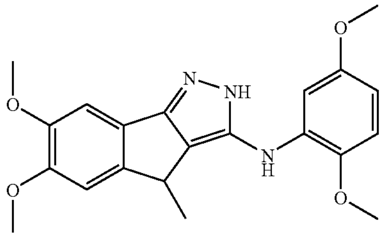 |
| 259 | 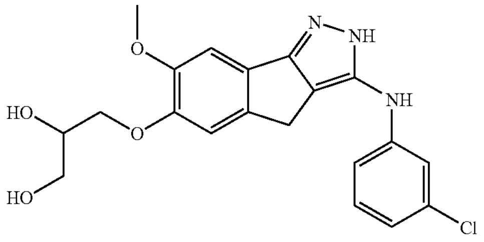 |

-continued
| Cpd | Structure |
| --- | --- |
| 260 | 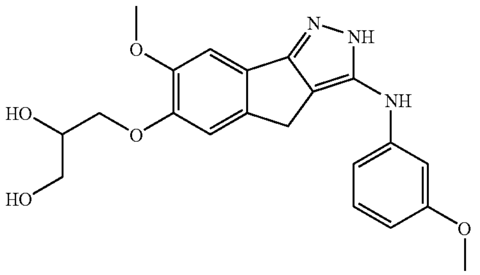 |
| 261 | 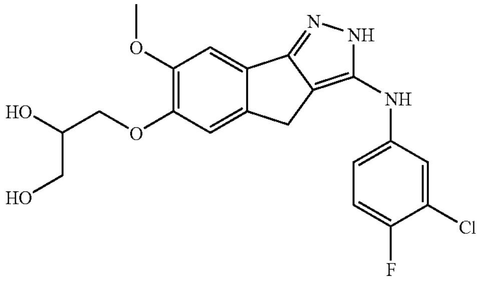 |
| 262 | 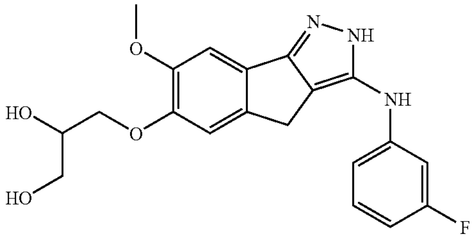 |
| 263 | 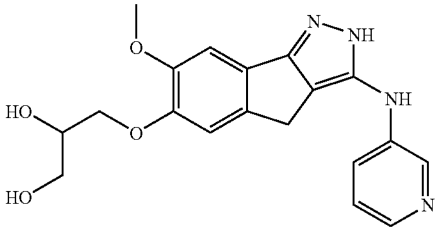 |
| 264 | 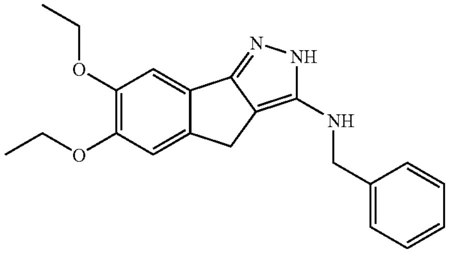 |
| 265 | 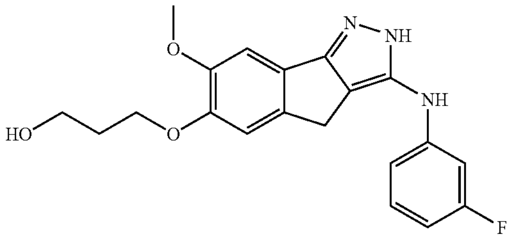 |

-continued
| Cpd | Structure |
|---|---|
| 266 | 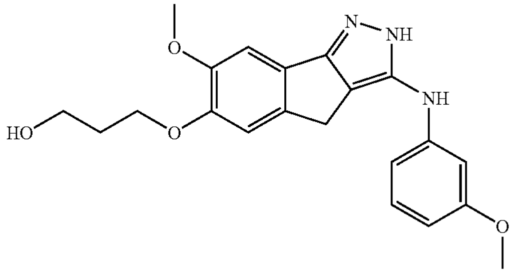 |
| 267 | 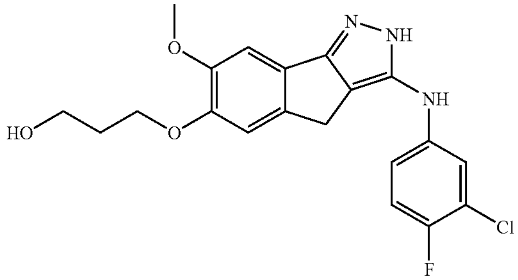 |
| 268 | 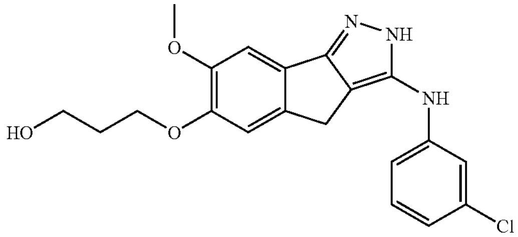 |
| 269 | 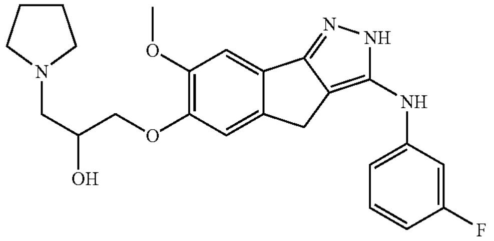 |
| 270 | 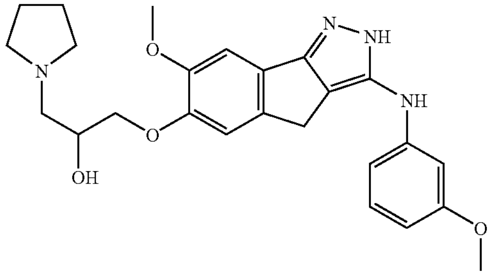 |

-continued
| Cpd | Structure |
|---|---|
| 271 | 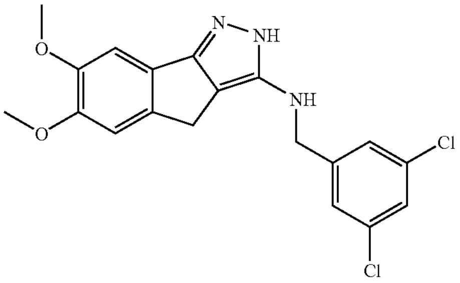 |
| 272 | 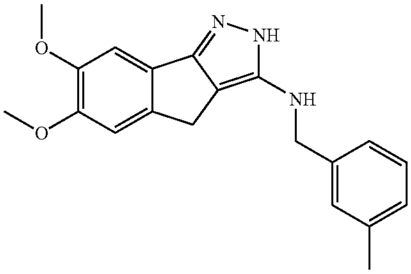 |
| 273 | 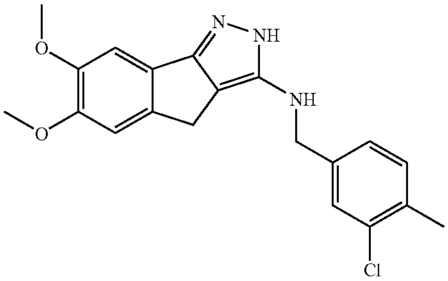 |
| 274 | 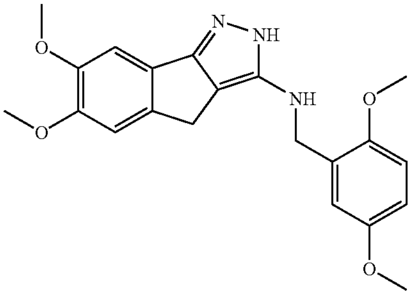 |
| 275 | 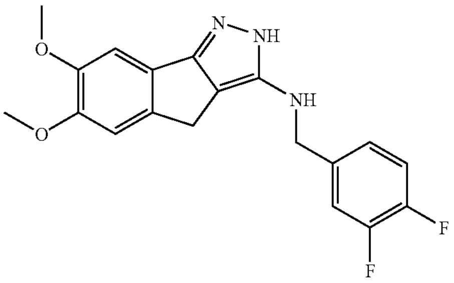 |

-continued
| Cpd | Structure |
|---|---|
| 276 | 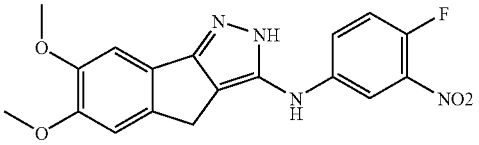 |
| 277 | 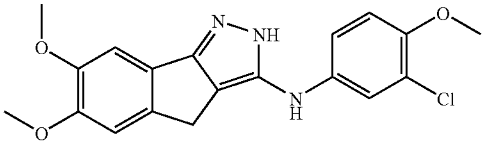 |
| 278 | 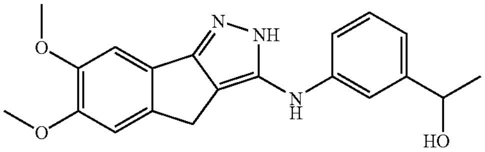 |
| 279 | 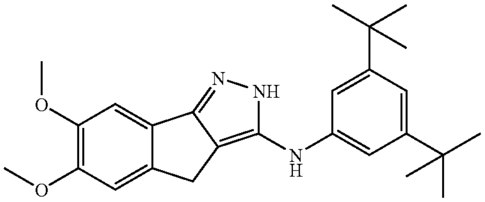 |
| 280 | 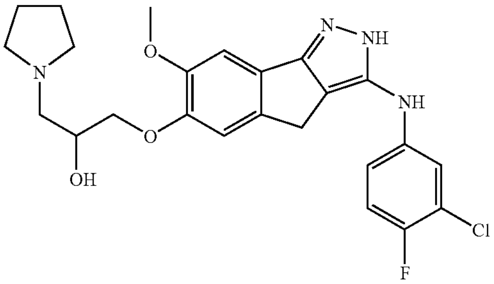 |
| 281 | 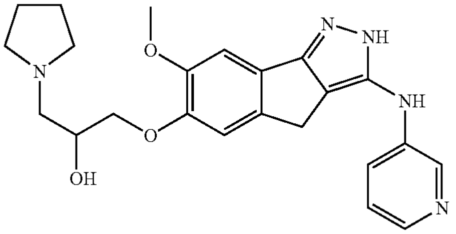 |
| 282 | 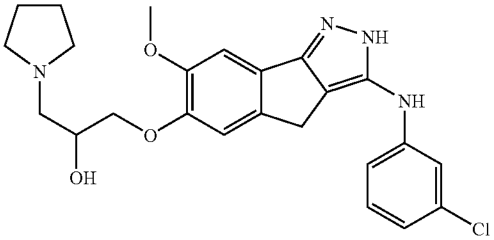 |

-continued
| Cpd | Structure |
|---|---|
| 283 | 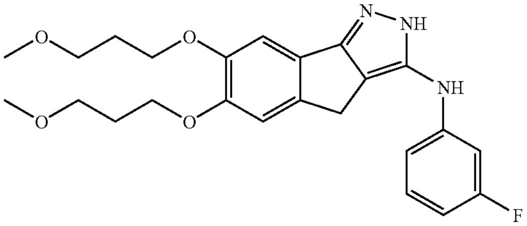 |
| 284 | 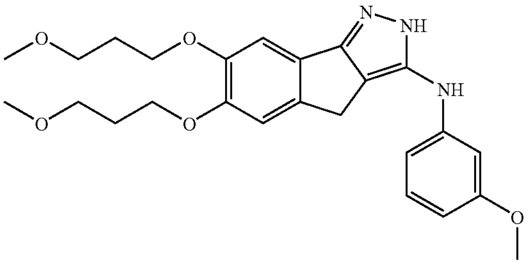 |
| 285 | 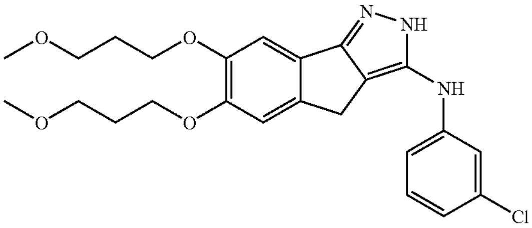 |
| 286 | 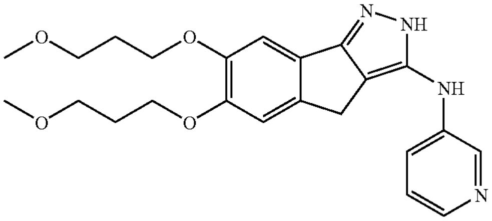 |
| 287 | 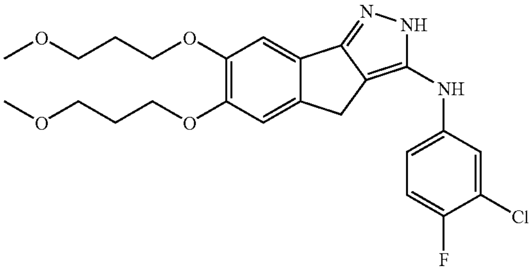 |
| 288 | 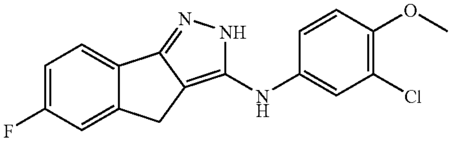 |
| 289 | 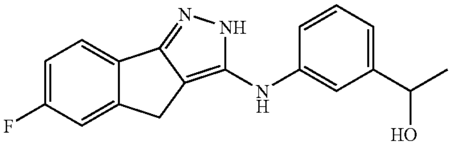 |

-continued
| Cpd | Structure |
|---|---|
| 290 | 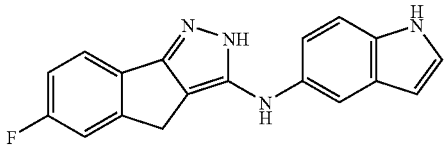 |
| 291 | 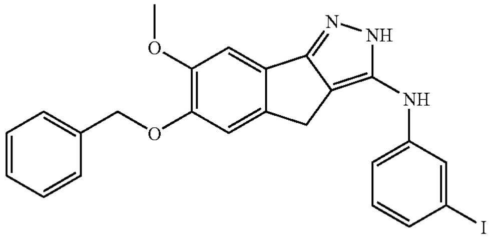 |
| 292 | 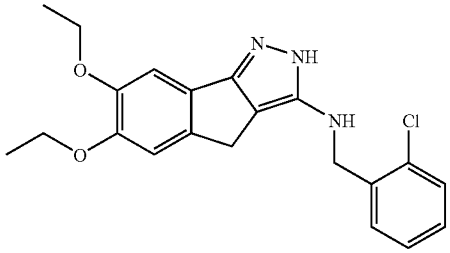 |
| 293 | 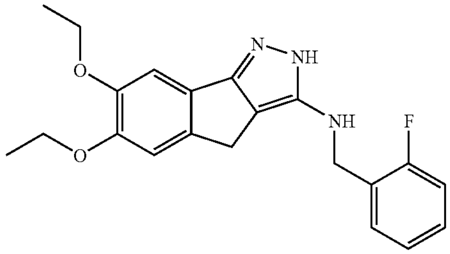 |
| 294 | 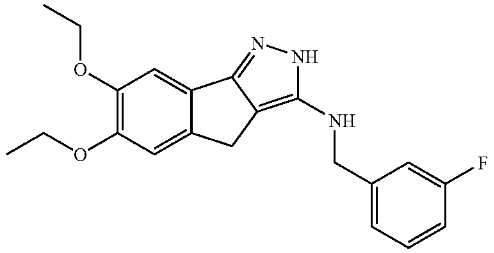 |
| 295 | 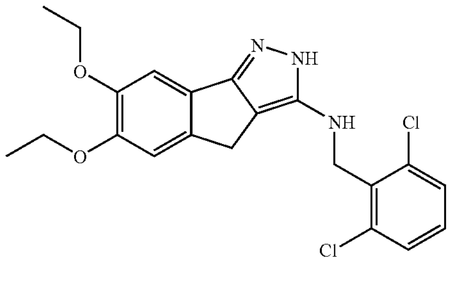 |

-continued
| Cpd | Structure |
|---|---|
| 296 | 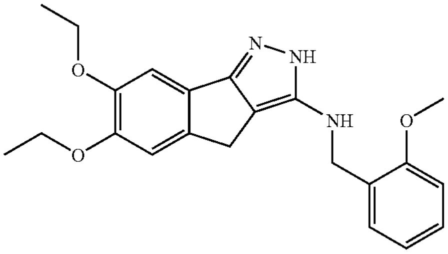 |
| 297 | 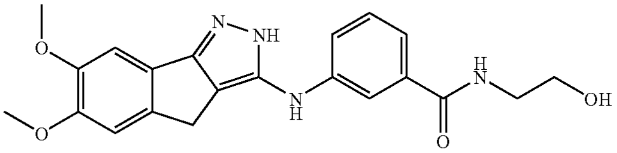 |
| 298 | 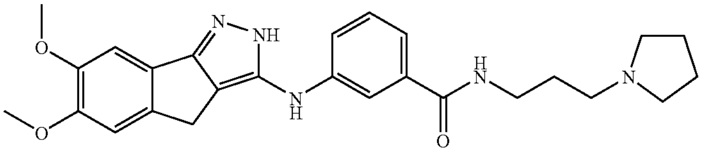 |
| 299 | 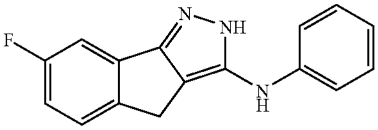 |
| 300 | 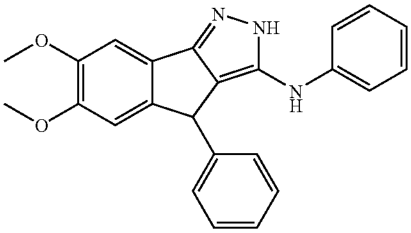 |
| 301 | 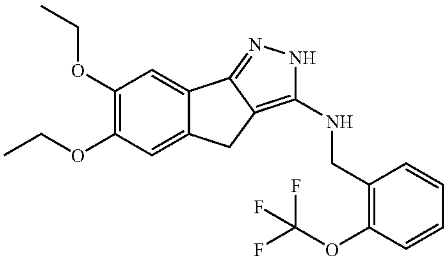 |
| 302 | 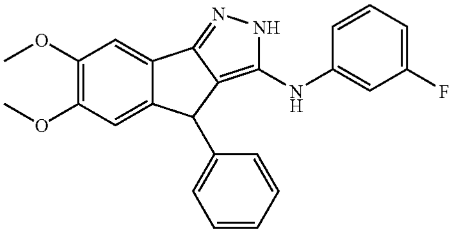 |

-continued
| Cpd | Structure |
|---|---|
| 303 | 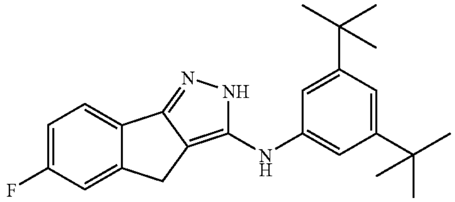 |
| 304 | 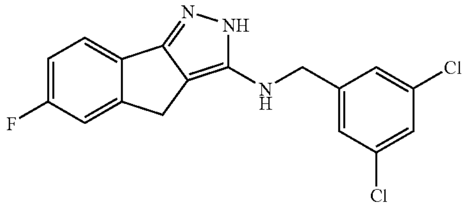 |
| 305 | 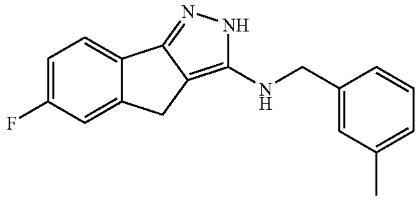 |
| 306 | 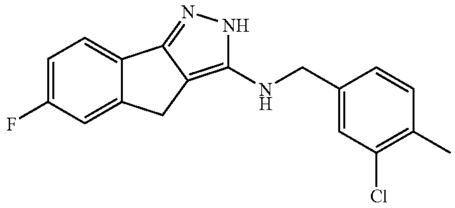 |
| 307 | 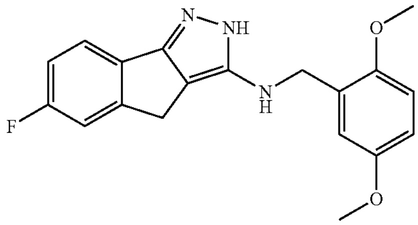 |
| 308 | 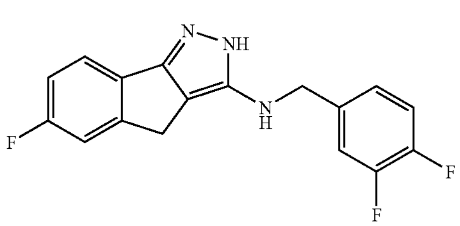 |
| 309 | 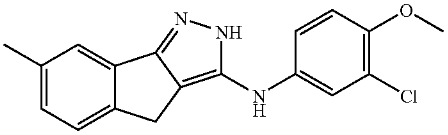 |

-continued
| Cpd | Structure |
|---|---|
| 310 | 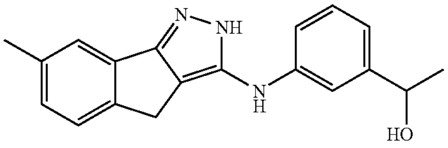 |
| 311 | 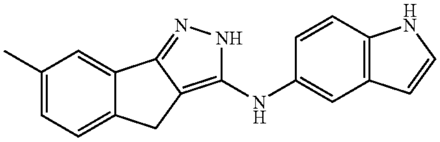 |
| 312 | 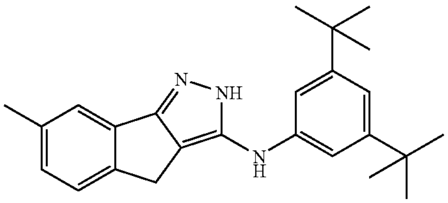 |
| 313 | 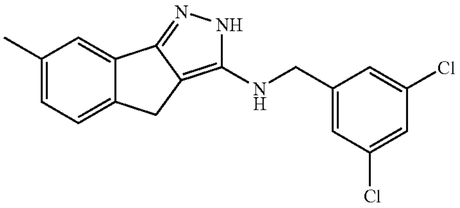 |
| 314 | 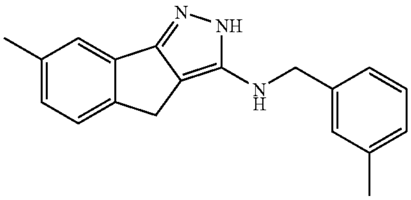 |
| 315 | 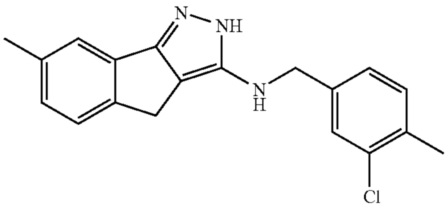 |
| 316 | 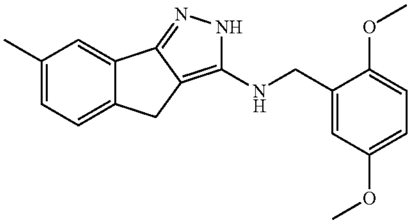 |

-continued
| Cpd | Structure |
|---|---|
| 317 | 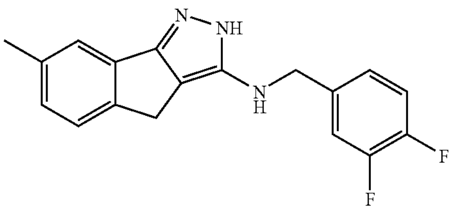 |
| 318 | 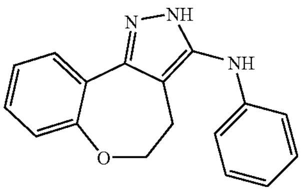 |
| 319 | 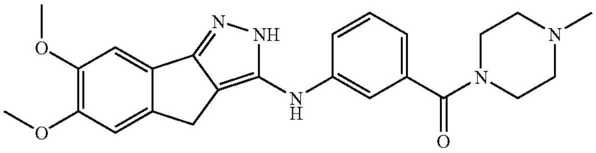 |
| 320 | 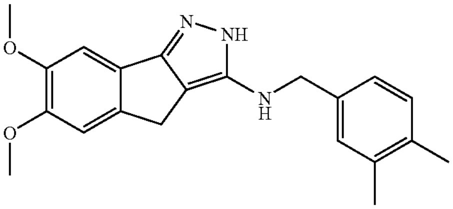 |
| 321 | 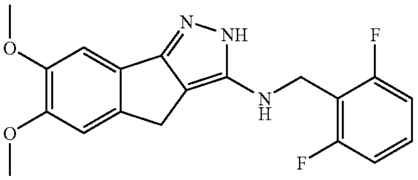 |
| 322 | 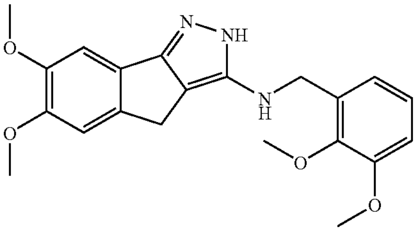 |
| 323 | 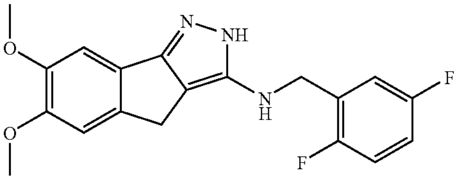 |

-continued
| Cpd | Structure |
|---|---|
| 324 | 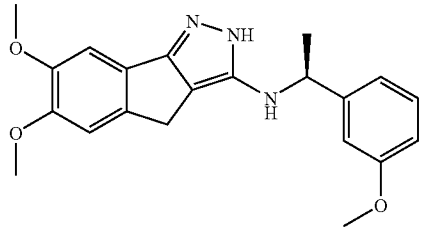 |
| 325 | 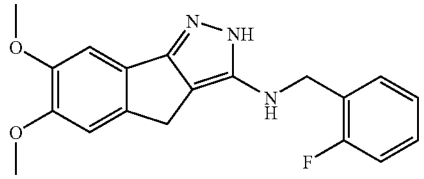 |
| 326 | 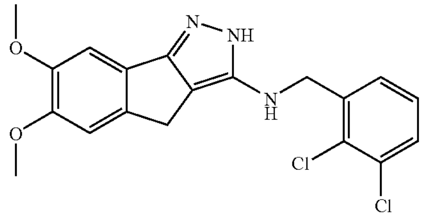 |
| 327 | 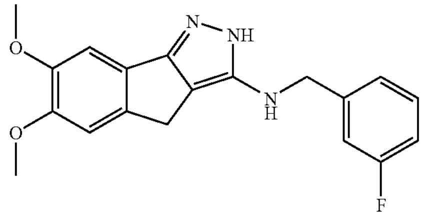 |
| 328 | 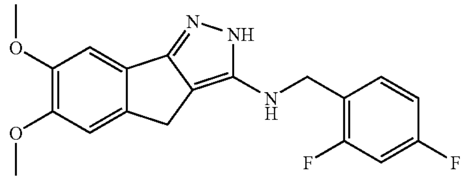 |
| 329 | 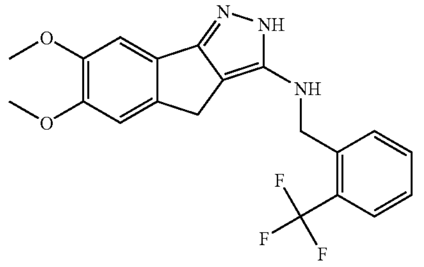 |
| 330 | 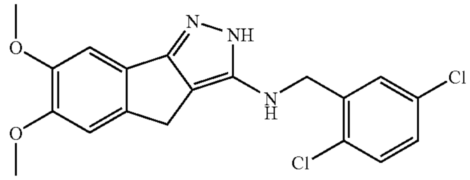 |

-continued
| Cpd | Structure |
|---|---|
| 331 | 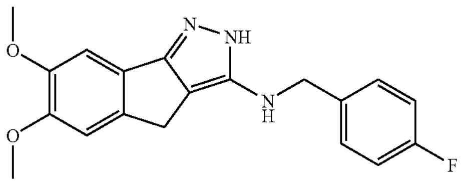 |
| 332 | 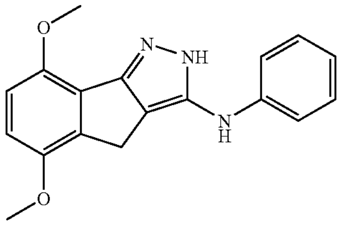 |
| 333 | 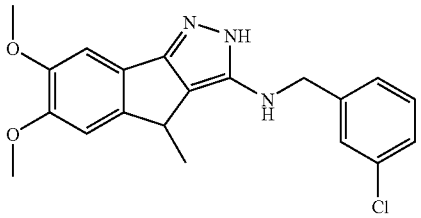 |
| 334 | 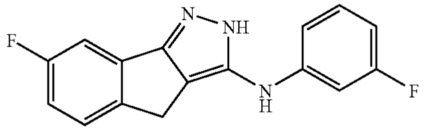 |
| 335 | 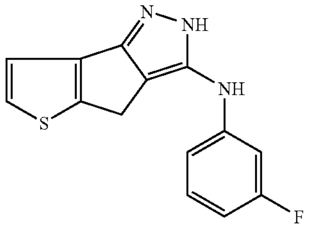 |
| 337 | 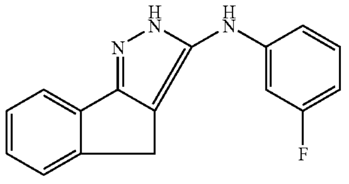 |
| 338 | 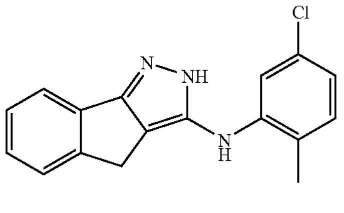 |

-continued
| Cpd | Structure |
|---|---|
| 339 | 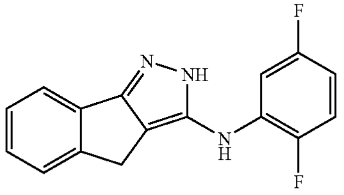 |
| 340 | 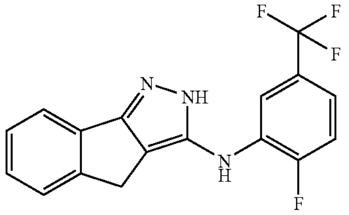 |
| 341 | 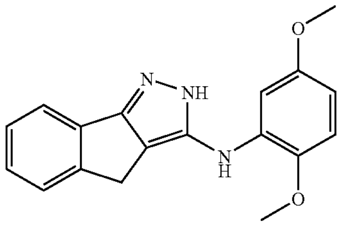 |
| 342 | 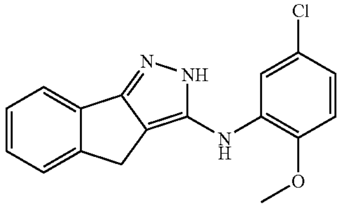 |
| 343 | 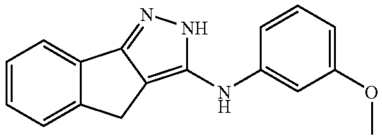 |
| 344 | 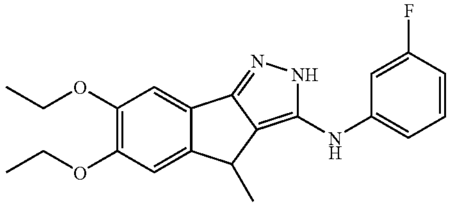 |
| 345 | 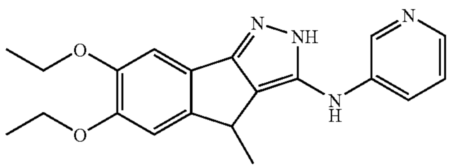 |

-continued
| Cpd | Structure |
|---|---|
| 346 | 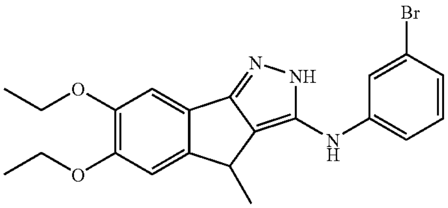 |
| 347 | 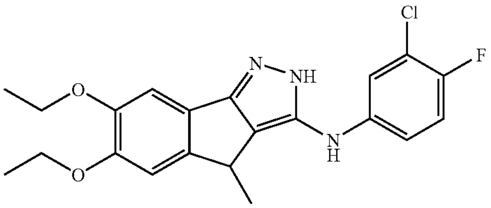 |
| 348 | 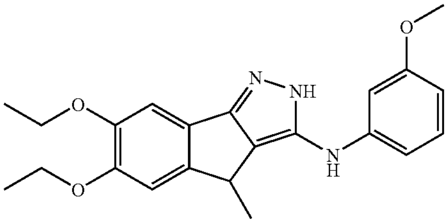 |
| 349 | 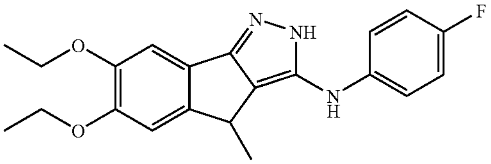 |
| 350 | 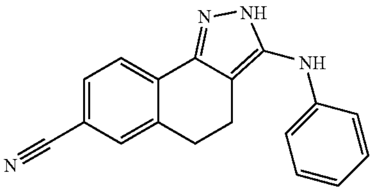 |
| 351 | 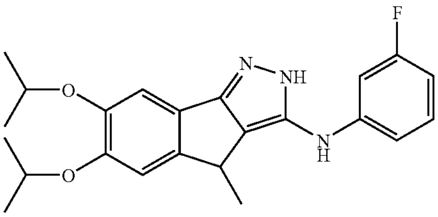 |
| 352 | 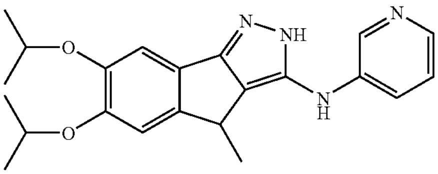 |

-continued
| Cpd | Structure |
|---|---|
| 353 | 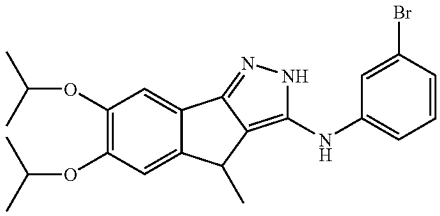 |
| 354 | 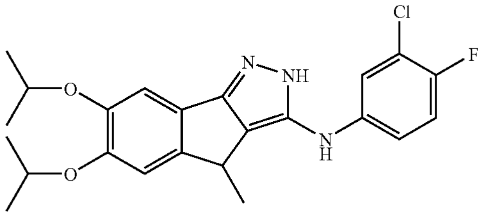 |
| 355 | 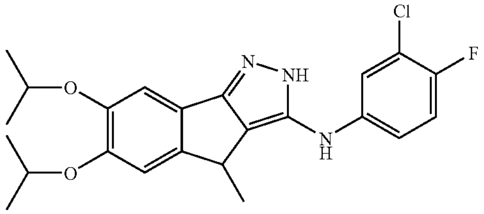 |
| 356 | 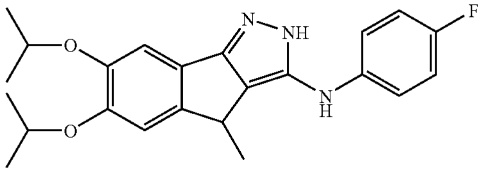 |
| 357 | 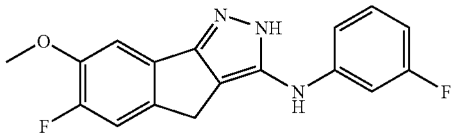 |
| 358 | 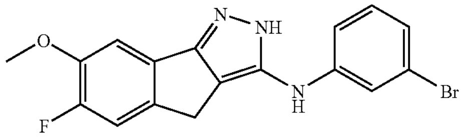 |
| 359 | 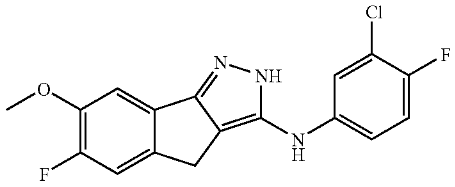 |
| 360 | 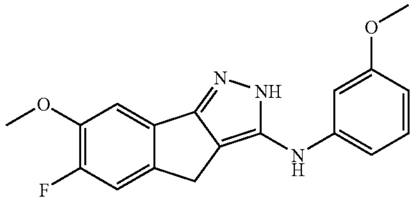 |

-continued
| Cpd | Structure |
|---|---|
| 361 | 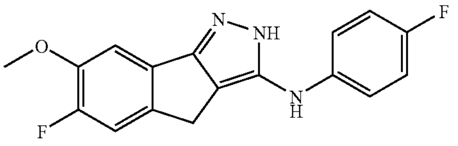 |
| 362 | 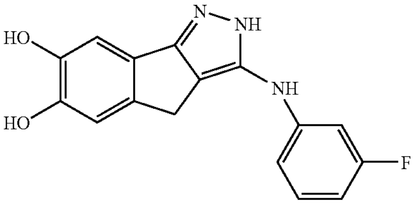 |
| 363 | 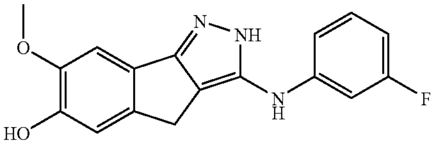 |
| 364 | 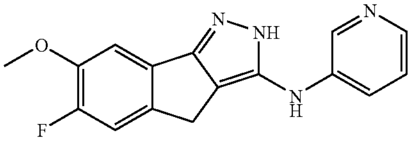 |
| 365 | 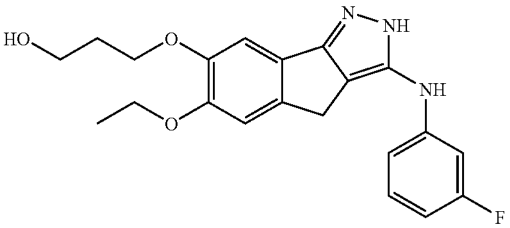 |
| 366 | 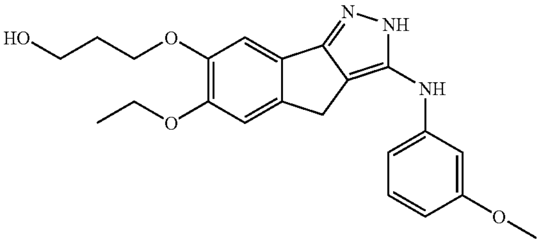 |
| 367 | 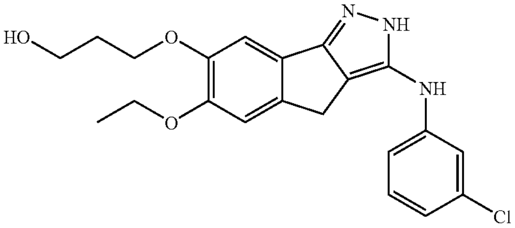 |

-continued
| Cpd | Structure |
|---|---|
| 368 | 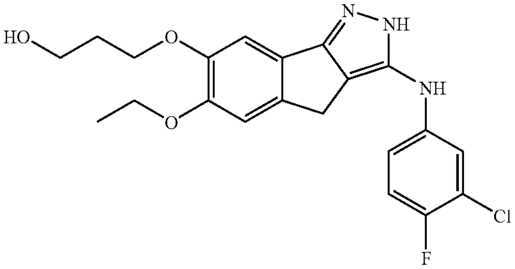 |
| 369 | 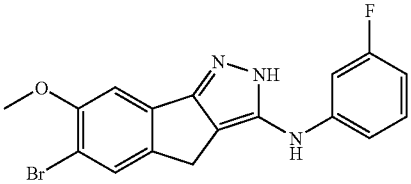 |
| 370 | 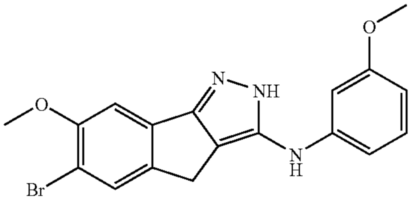 |
| 371 | 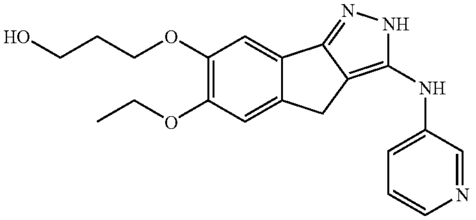 |
| 372 | 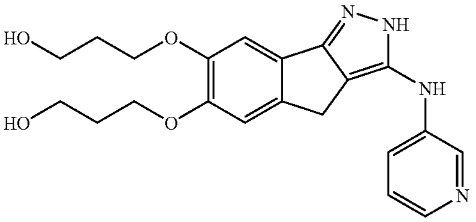 |
| 373 | 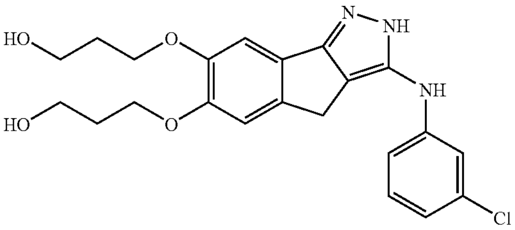 |

-continued
| Cpd | Structure |
|---|---|
| 374 | 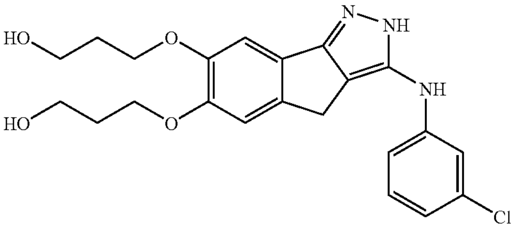 |
| 375 | 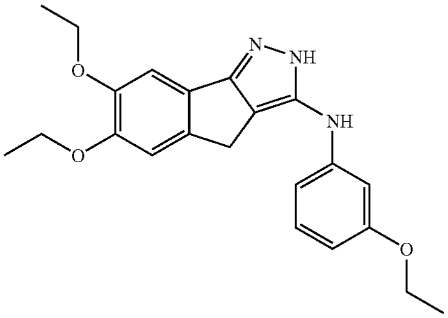 |
| 376 | 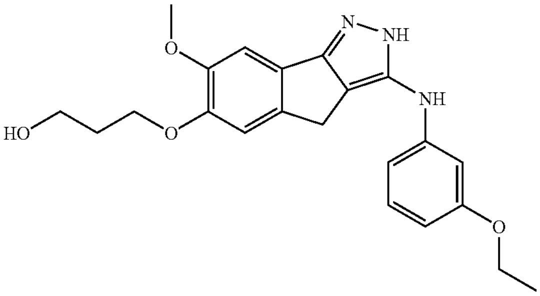 |
| 377 | 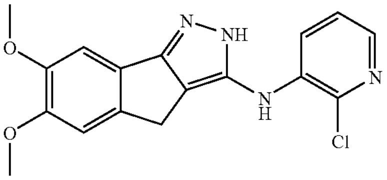 |
| 378 | 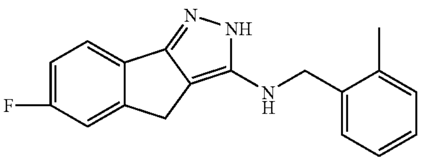 |
| 379 | 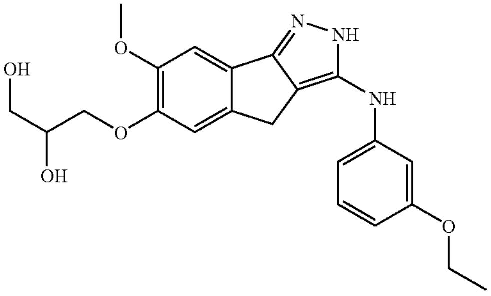 |

-continued
| Cpd | Structure |
|---|---|
| 380 | 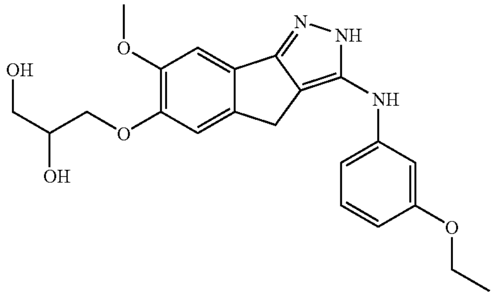 |
| 381 | 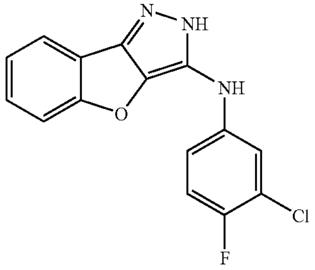 |
| 382 | 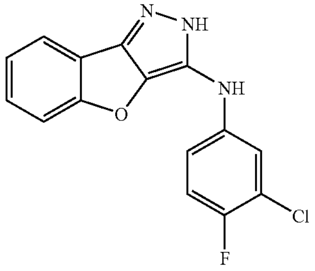 |
| 383 | 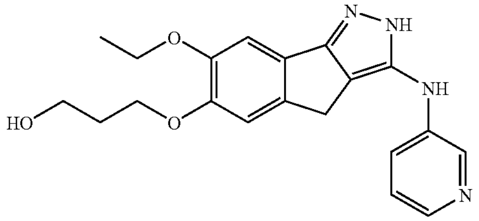 |
| 384 | 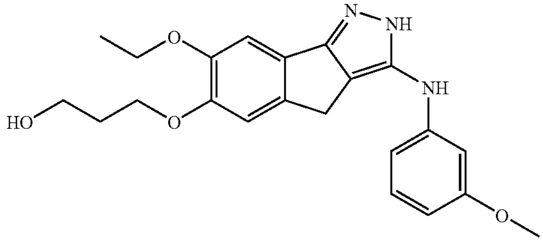 |
| 385 | 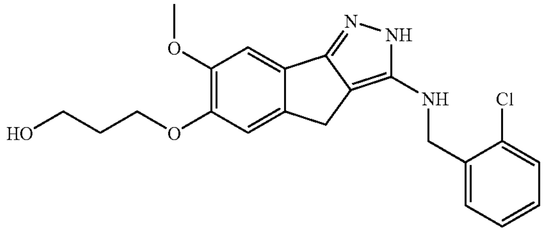 |

-continued
| Cpd | Structure |
|---|---|
| 386 | 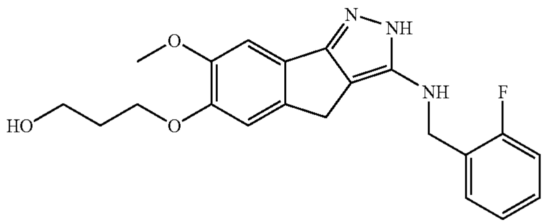 |
| 387 | 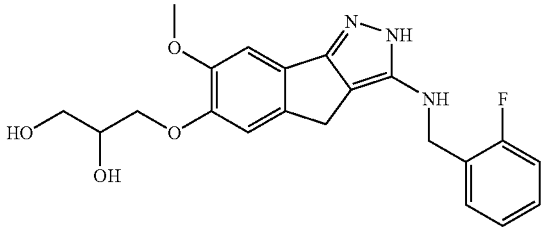 |
| 388 | 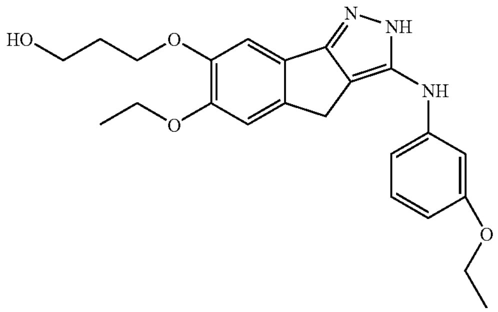 |
| 389 | 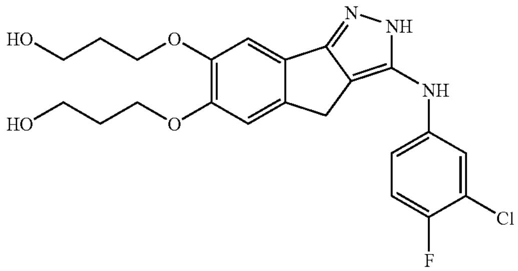 |
| 390 | 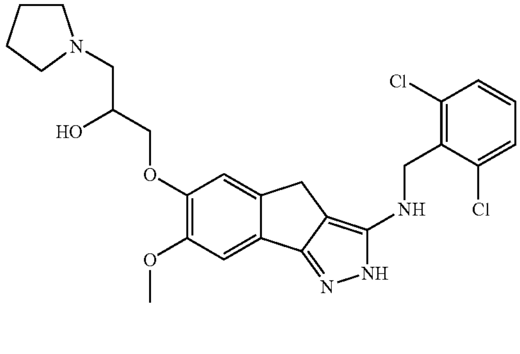 |

-continued
| Cpd | Structure |
|---|---|
| 391 | 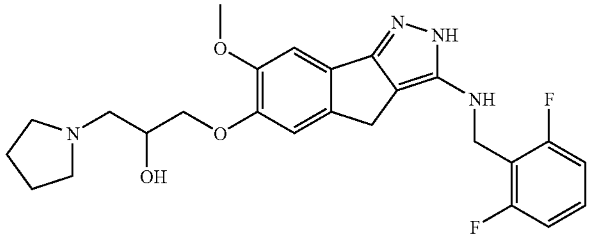 |
| 392 | 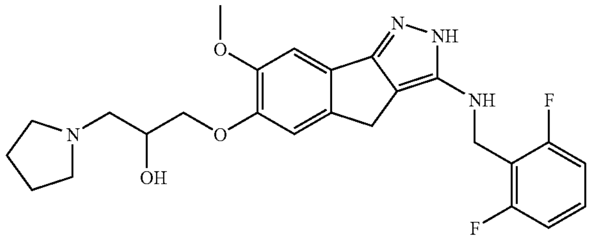 |
| 393 | 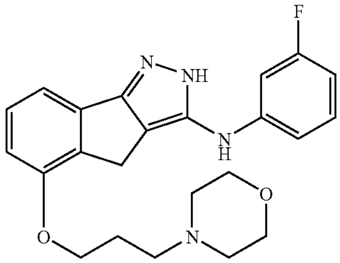 |
| 394 | 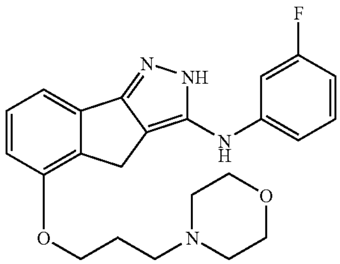 |
| 395 | 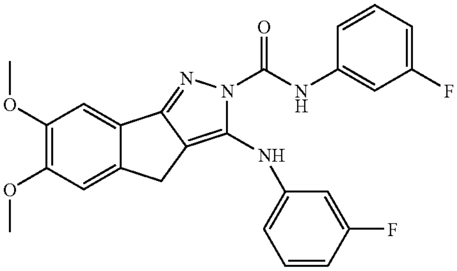 |

-continued
| Cpd | Structure |
|---|---|
| 396 | 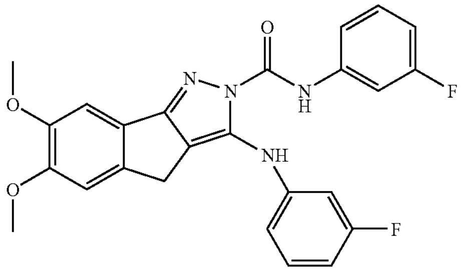 |
| 397 | 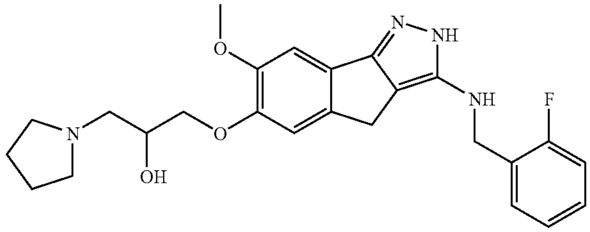 |
| 398 | 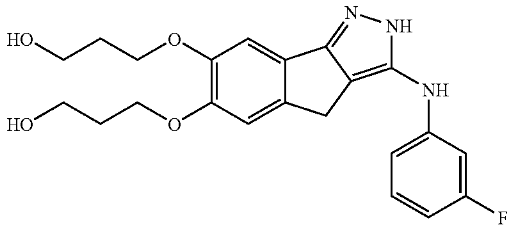 |
| 400 | 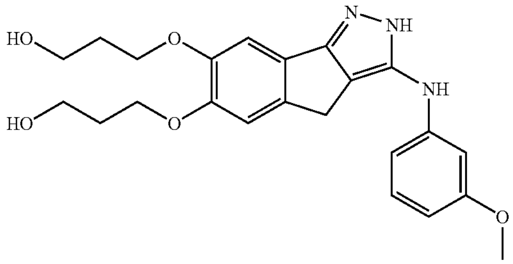 |
| 401 | 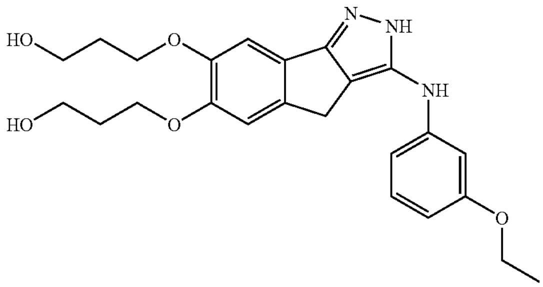 |
| 402 | 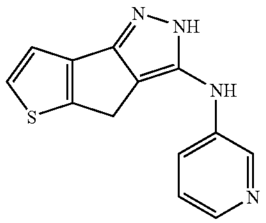 |

-continued
| Cpd | Structure |
|---|---|
| 403 | 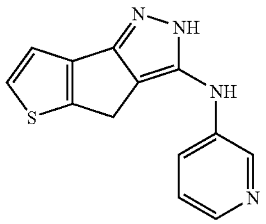 |
| 404 | 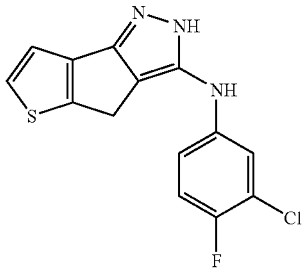 |
| 405 | 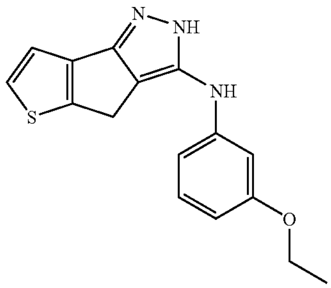 |
| 406 | 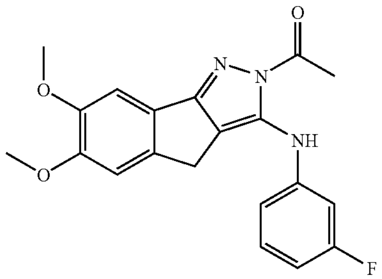 |
| 407 | 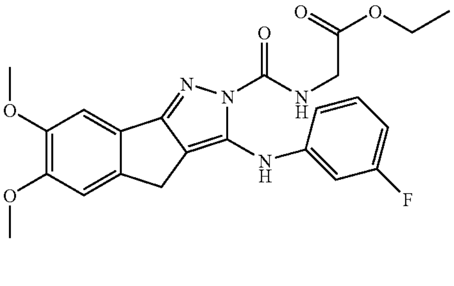 |

-continued
| Cpd | Structure |
|---|---|
| 408 | 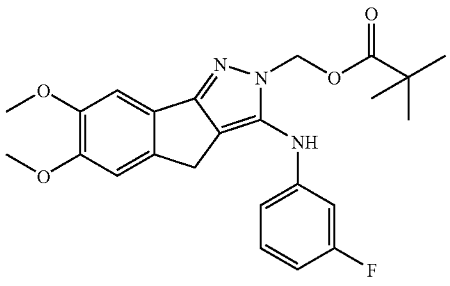 |
| 409 | 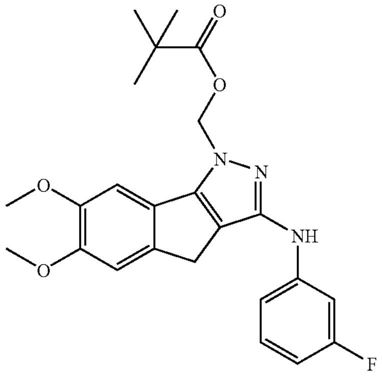 |
| 410 | 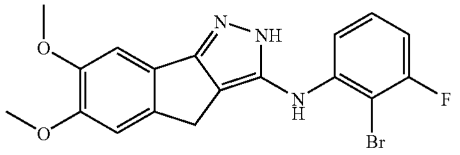 |
| 411 | 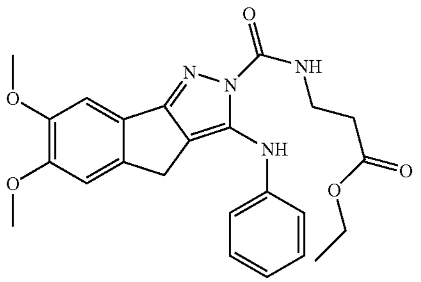 |
| 412 | 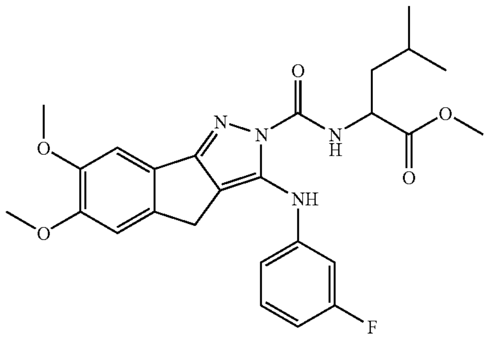 |

-continued
| Cpd | Structure |
|---|---|
| 413 | 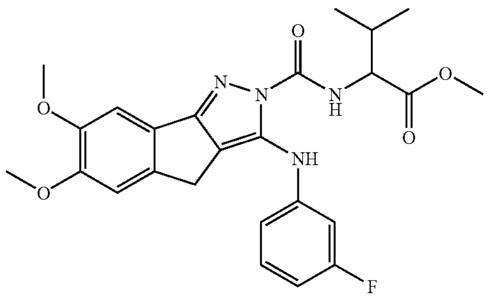 |
| 414 | 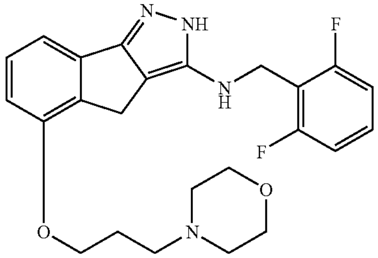 |
| 415 | 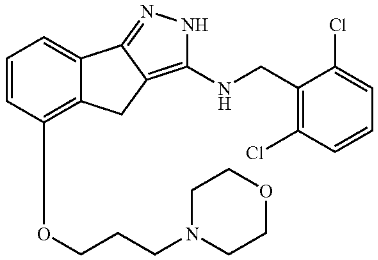 |
| 416 | 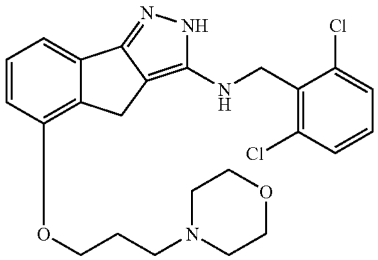 |
| 417 | 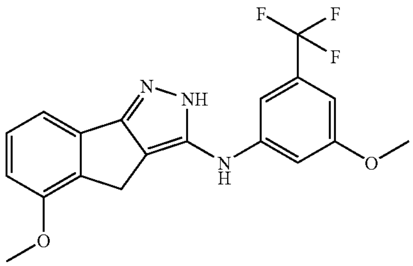 |
| 418 | 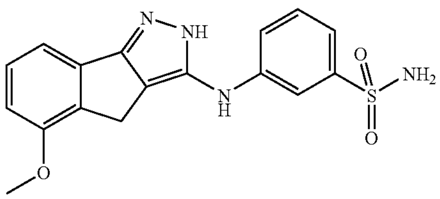 |

-continued
| Cpd | Structure |
|---|---|
| 419 | 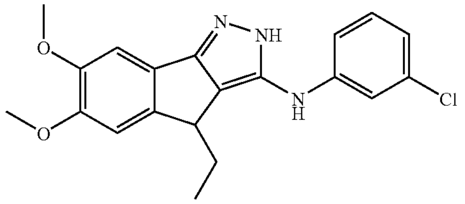 |
| 420 | 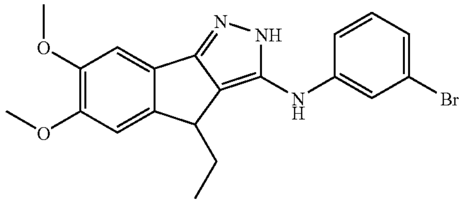 |
| 421 | 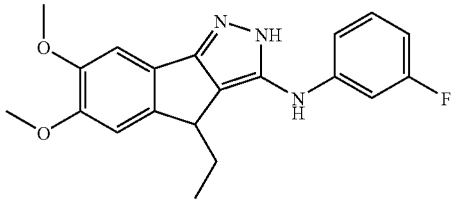 |
| 422 | 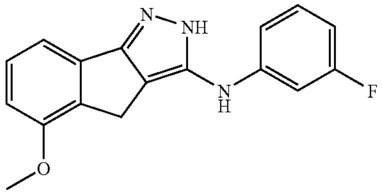 |
| 423 | 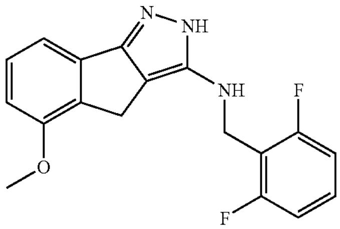 |
| 424 | 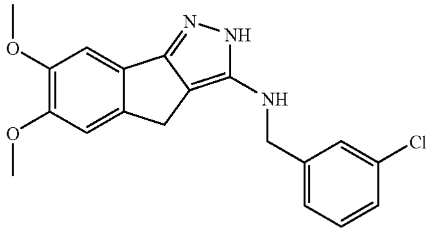 |
| 425 | 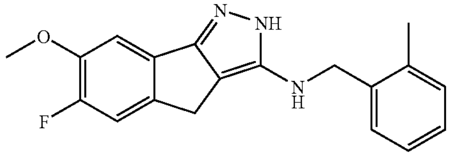 |

-continued
| Cpd | Structure |
|---|---|
| 426 | 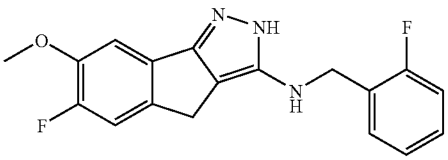 |
| 427 | 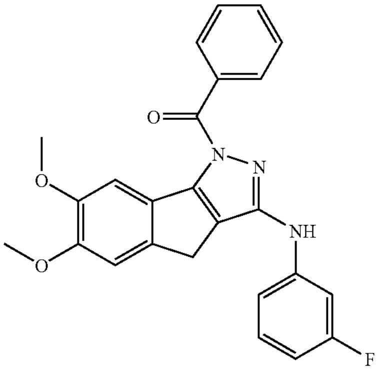 |
| 428 | 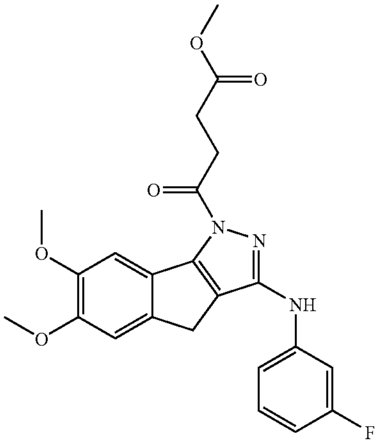 |
| 429 | 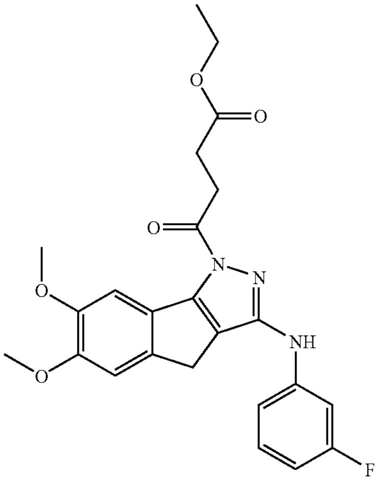 |

-continued
| Cpd | Structure |
|---|---|
| 430 | 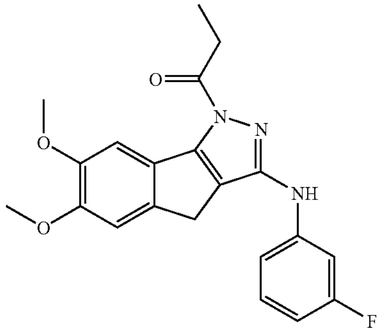 |
| 431 | 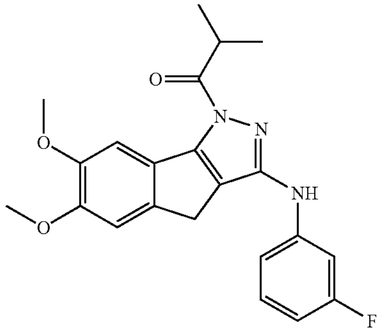 |
| 432 | 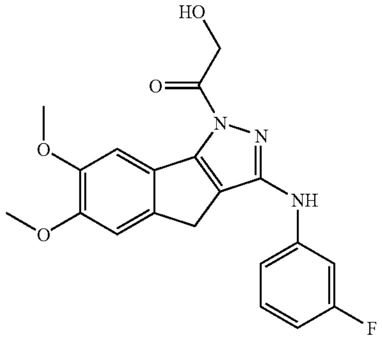 |
| 433 | 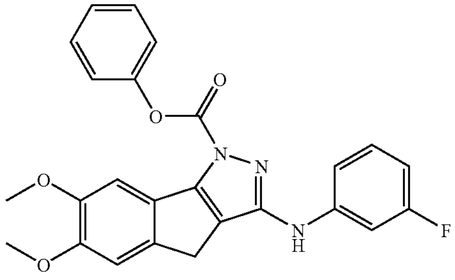 |
| 434 | 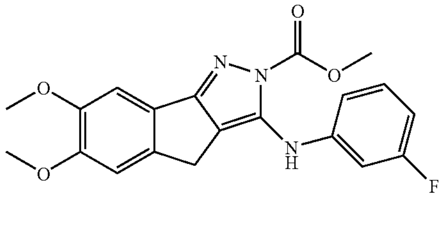 |

-continued
| Cpd | Structure |
|---|---|
| 435 | 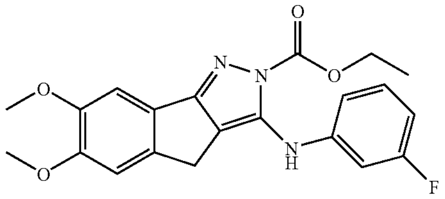 |
| 436 | 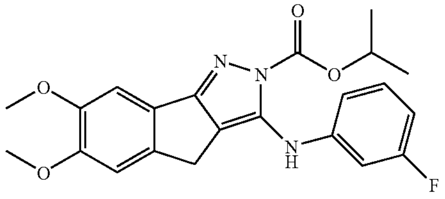 |
| 437 | 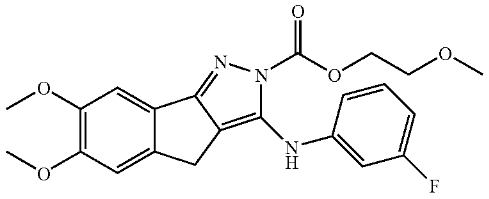 |
| 438 | 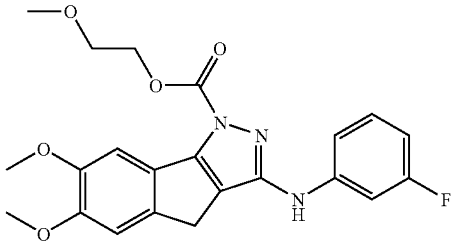 |
| 439 | 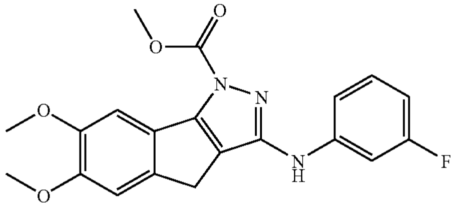 |
| 440 | 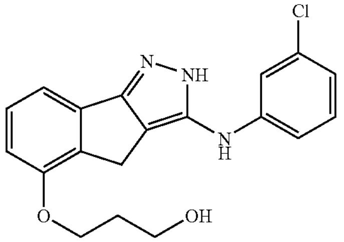 |

-continued
| Cpd | Structure |
|---|---|
| 441 | 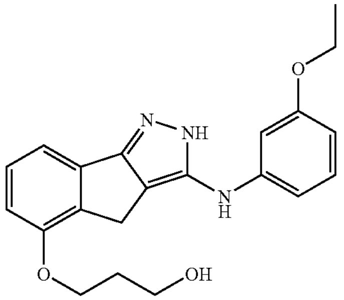 |
| 442 | 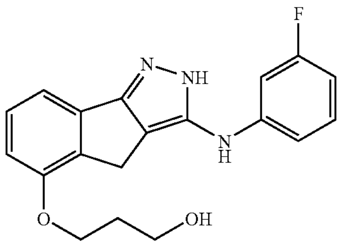 |
| 443 | 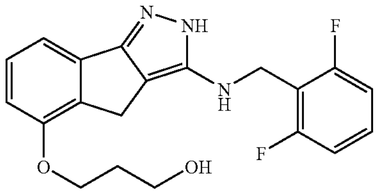 |
| 444 | 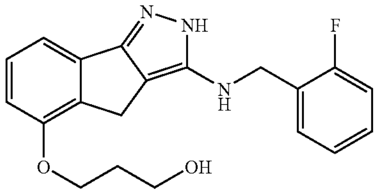 |
| 445 | 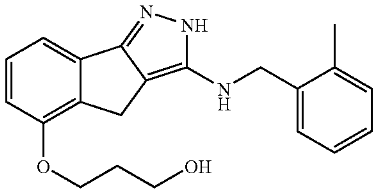 |
| 446 | 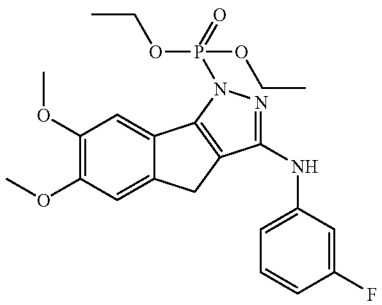 |

-continued
| Cpd | Structure |
|---|---|
| 447 | 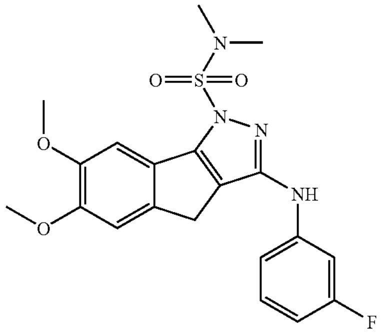 |
| 448 | 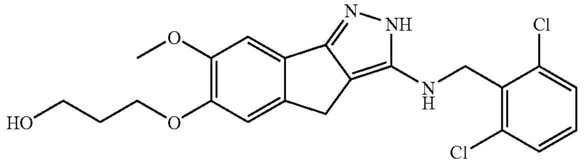 |
| 449 | 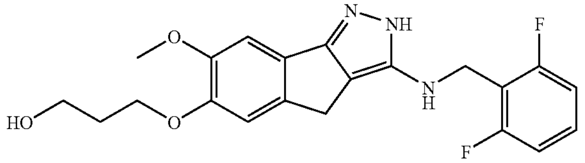 |
| 450 | 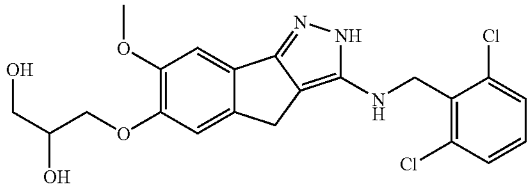 |
| 451 | 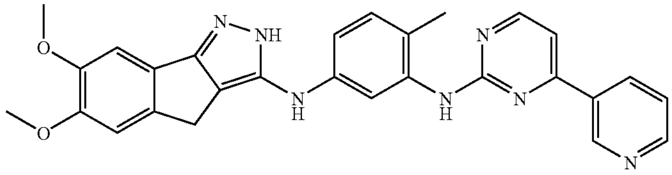 |
| 452 | 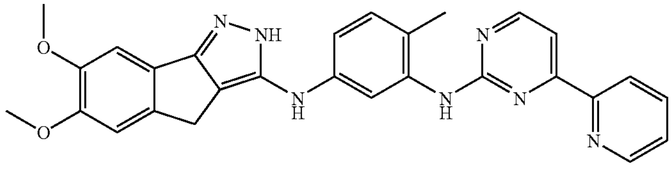 |
| 453 | 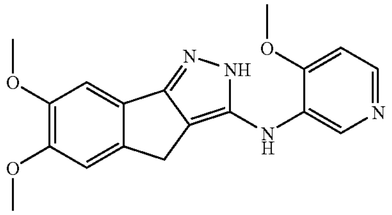 |

-continued
| Cpd | Structure |
|---|---|
| 454 | 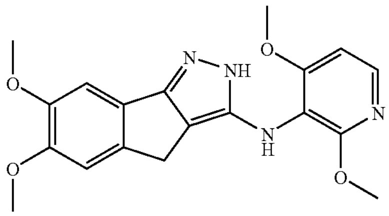 |
| 455 | 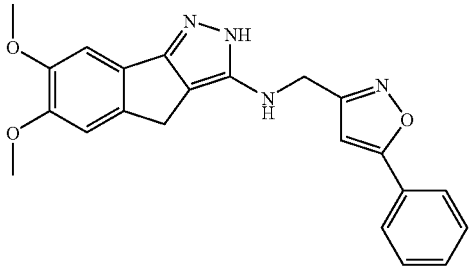 |
| 457 | 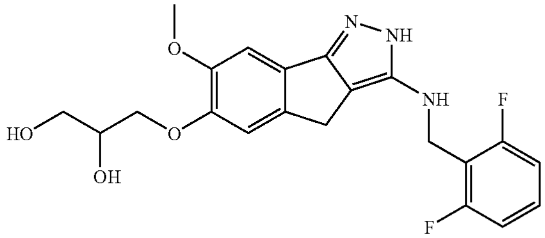 |
| 458 | 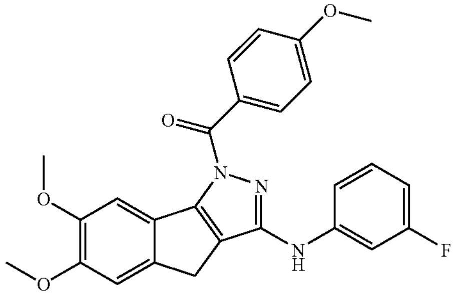 |
| 459 | 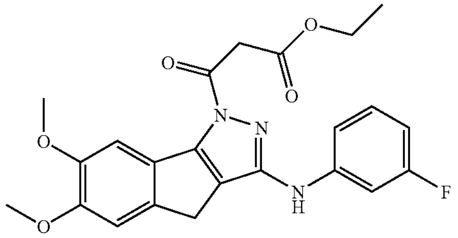 |
| 460 | 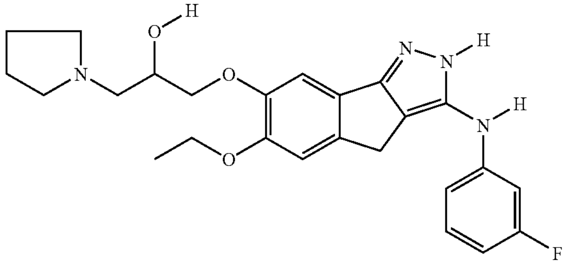 |

-continued
| Cpd | Structure |
|---|---|
| 461 | 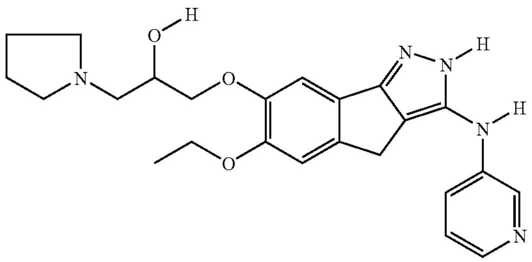 |
| 462 | 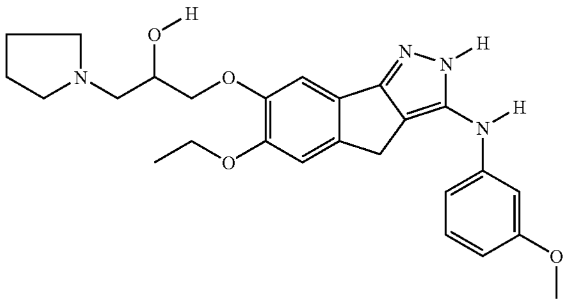 |
| 463 | 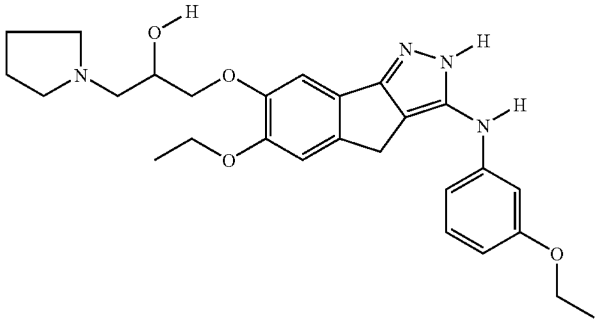 |
| 464 | 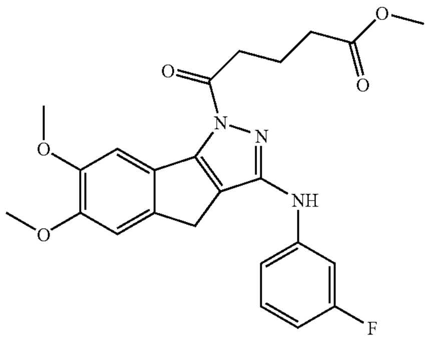 |
| 465 | 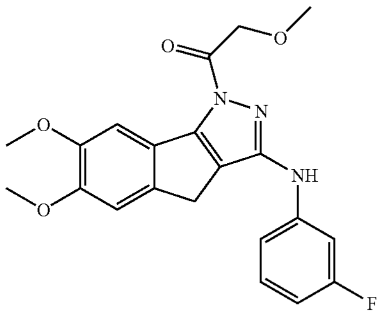 |

-continued
| Cpd | Structure |
|---|---|
| 466 | 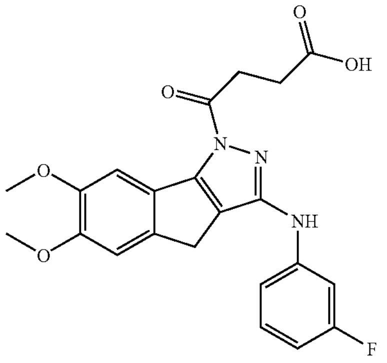 |
| 467 | 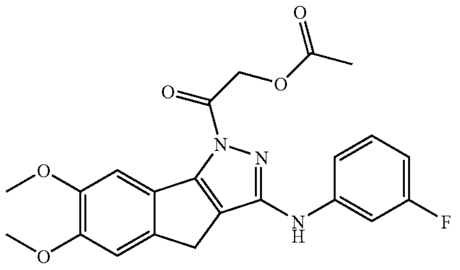 |
| 468 | 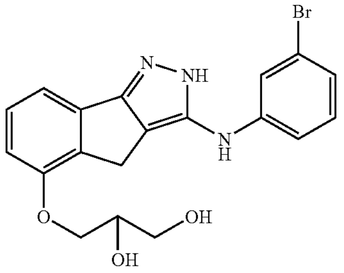 |
| 469 | 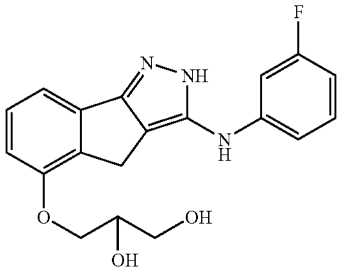 |

-continued
| Cpd | Structure |
|---|---|
| 470 | 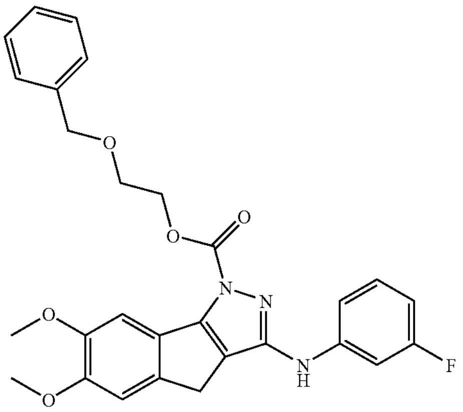 |
| 471 | 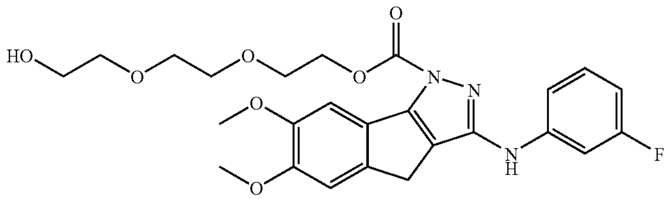 |
| 472 | 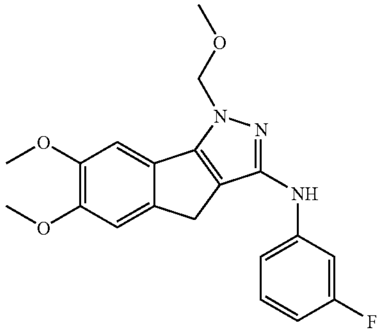 |
| 473 | 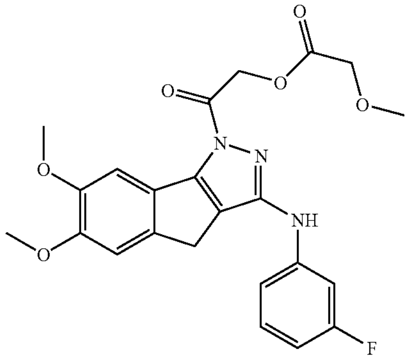 |

-continued
| Cpd | Structure |
|---|---|
| 474 | 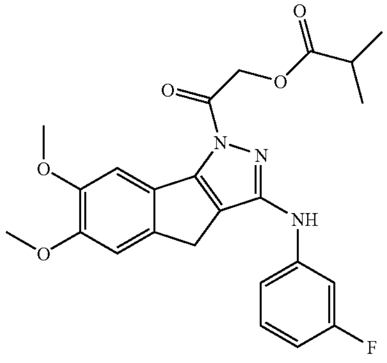 |
| 475 | 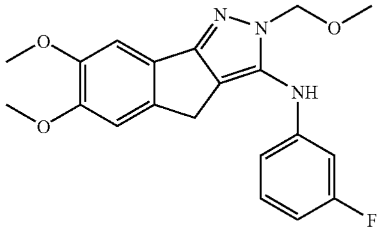 |
| 476 | 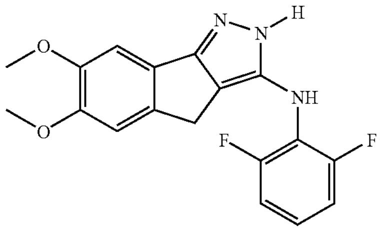 |
| 477 | 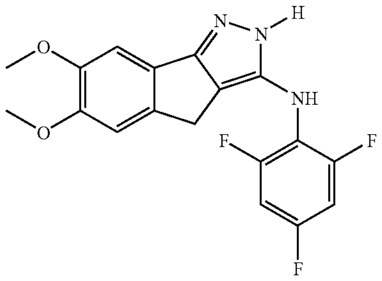 |
| 478 | 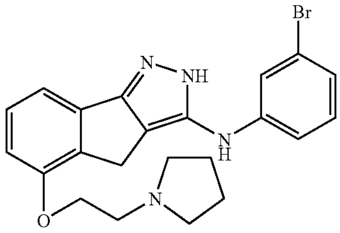 |

-continued
| Cpd | Structure |
|---|---|
| 479 | 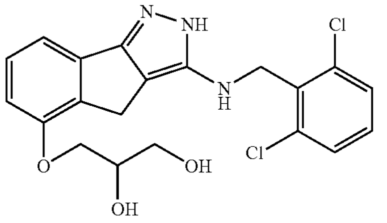 |
| 480 | 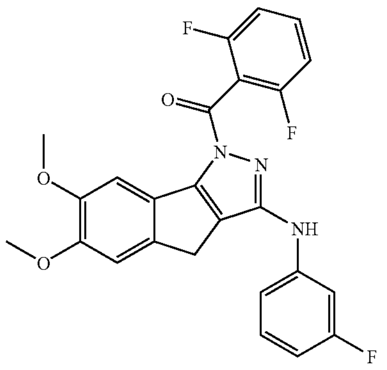 |
| 481 | 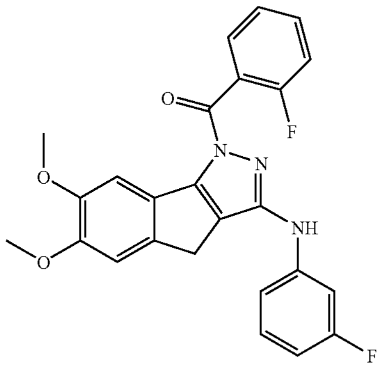 |
| 482 | 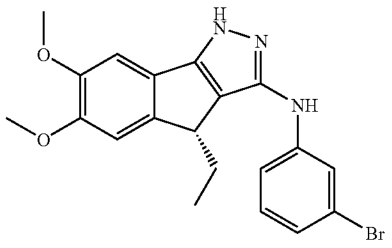 |
| 483 | 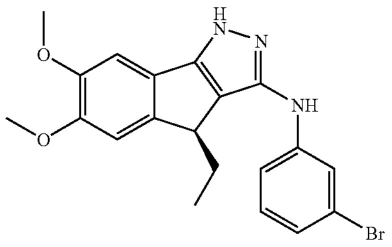 |

-continued
| Cpd | Structure |
|---|---|
| 484 | 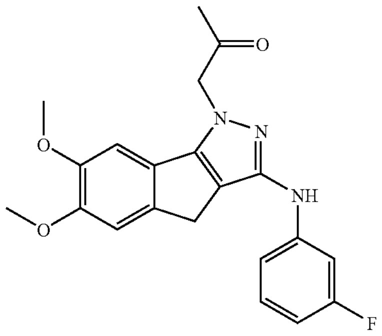 |
| 485 | 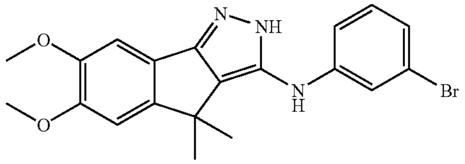 |
| 486 | 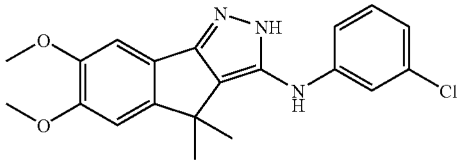 |
| 487 | 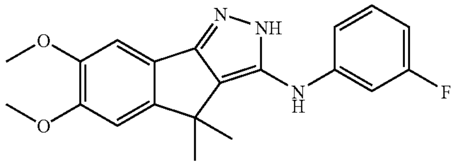 |
| 488 | 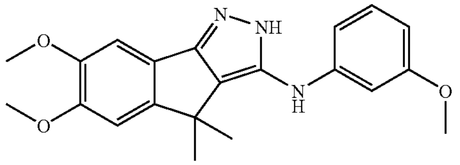 |
| 489 | 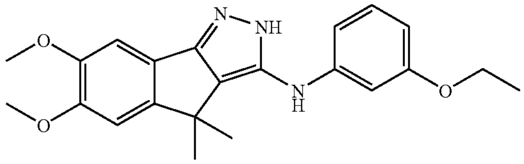 |

-continued
| Cpd | Structure |
|---|---|
| 490 | 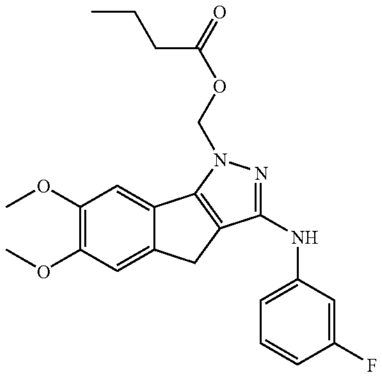 |
| 491 | 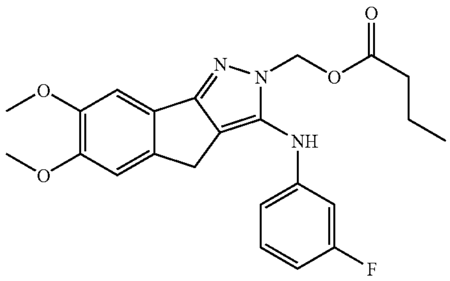 |
| 492 | 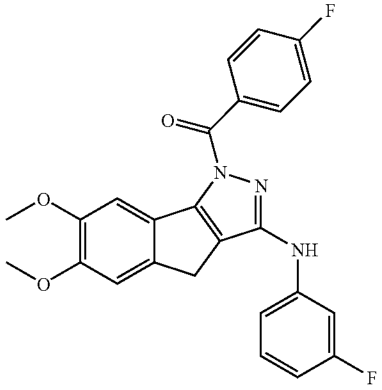 |
| 494 | 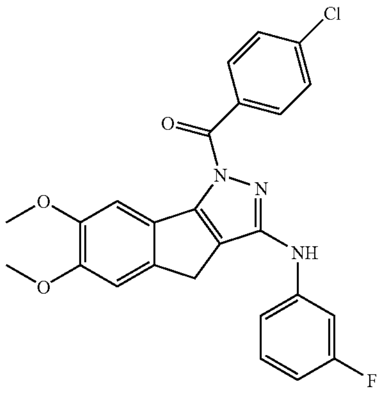 |

-continued
| Cpd | Structure |
|---|---|
| 496 | 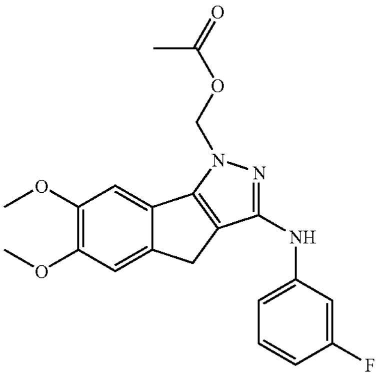 |
| 497 | 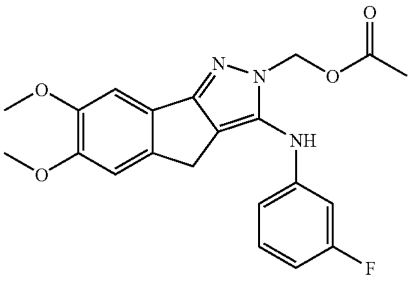 |
| 498 | 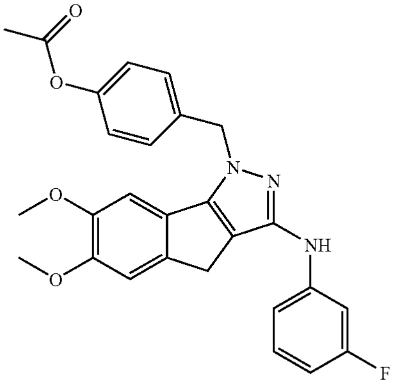 |
| 499 | 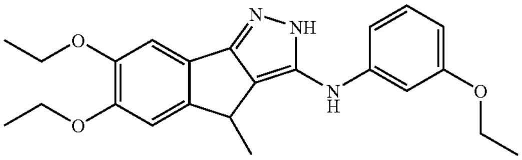 |
| 500 | 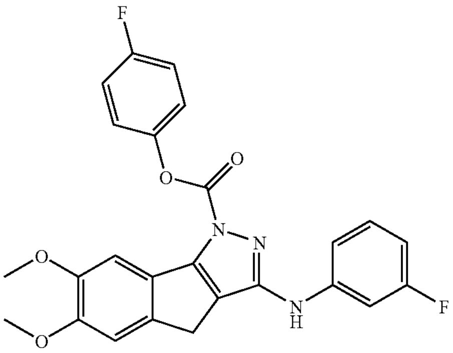 |

-continued
| Cpd | Structure |
|---|---|
| 501 | 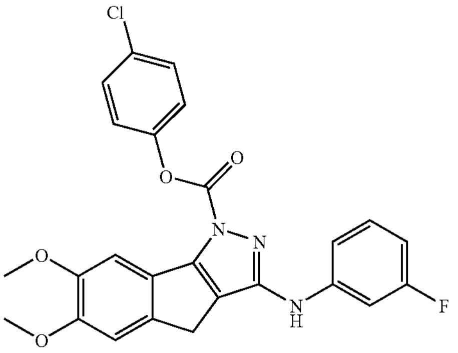 |
| 502 | 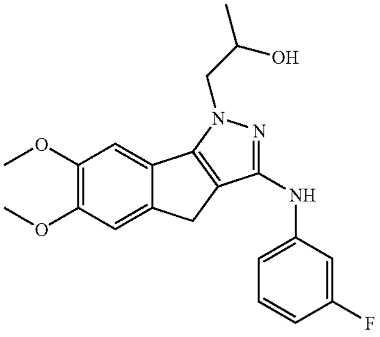 |
| 503 | 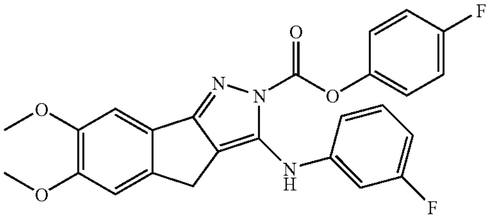 |
| 504 | 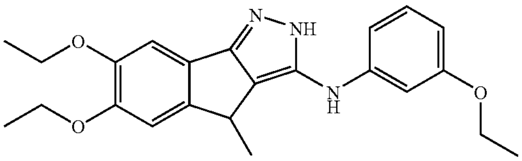 |
| 505 | 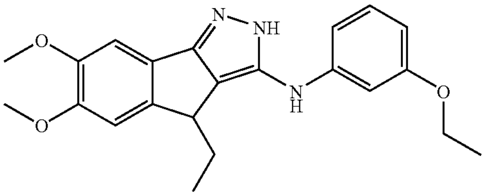 |

-continued
| Cpd | Structure |
|---|---|
| 506 | 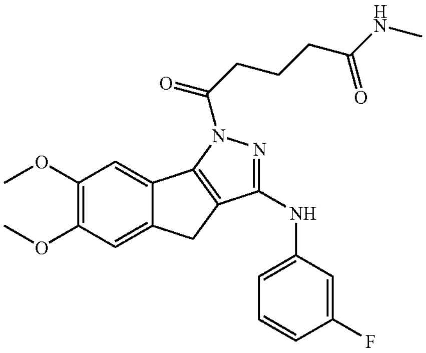 |
| 509 | 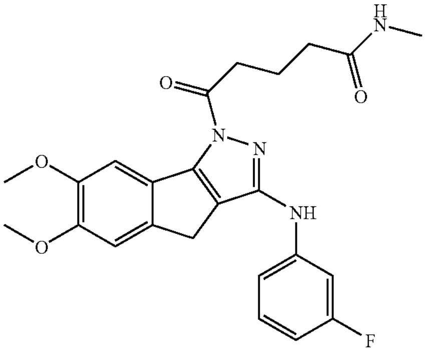 |
| 510 | 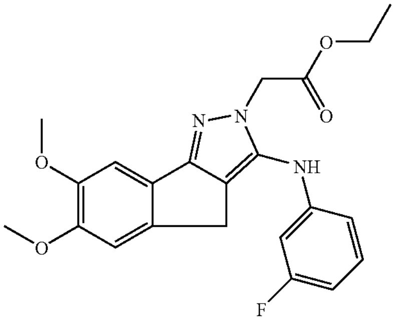 |
| 511 | 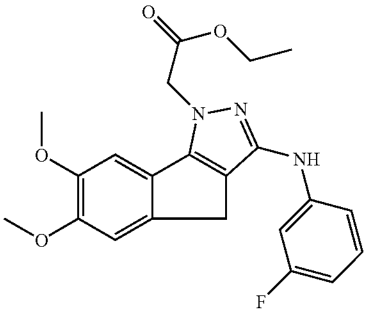 |
| 512 | 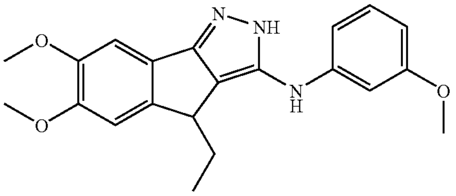 |

-continued
| Cpd | Structure |
|---|---|
| 513 | 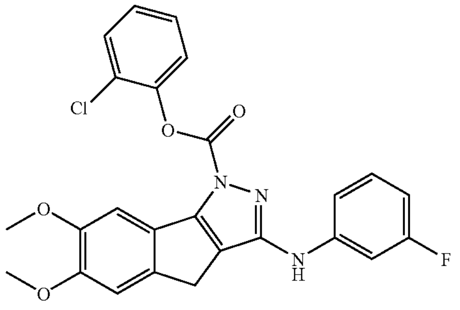 |
| 514 | 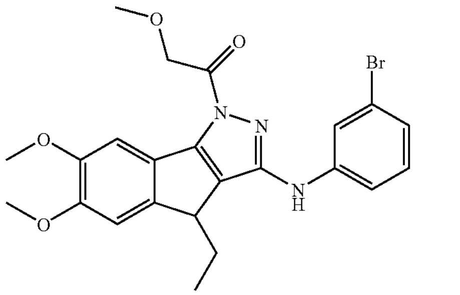 |
| 515 | 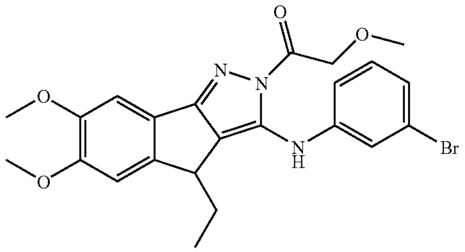 |
| 516 | 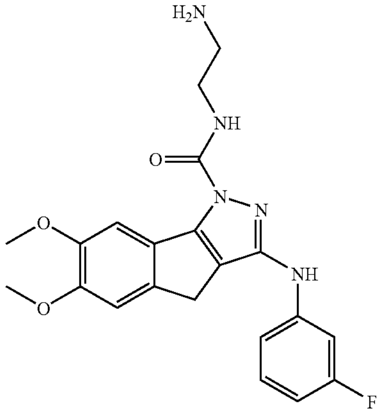 |

-continued
| Cpd | Structure |
|---|---|
| 517 | 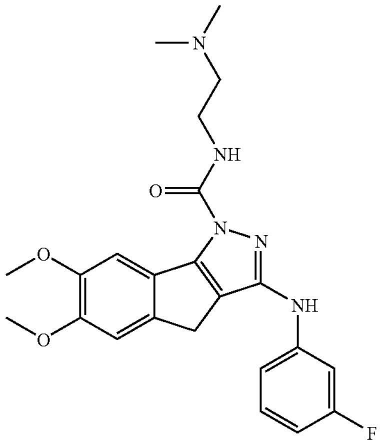 |
| 518 | 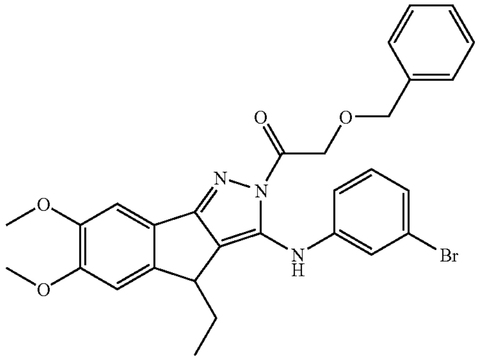 |
| 519 | 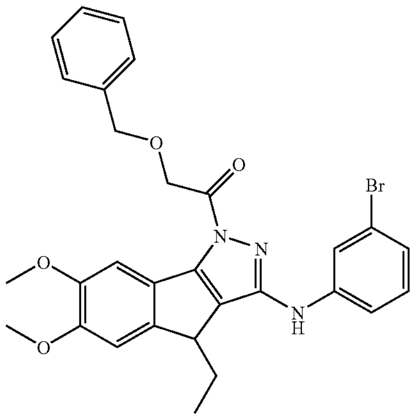 |
| 520 | 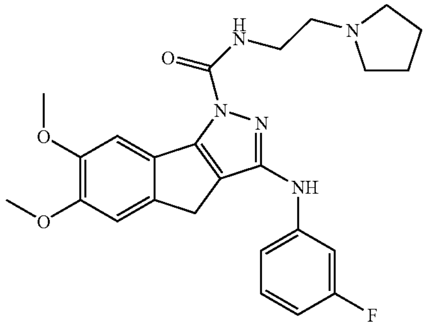 |

-continued
| Cpd | Structure |
|---|---|
| 521 | 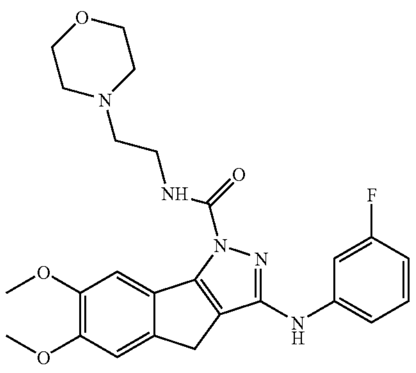 |
| 522 | 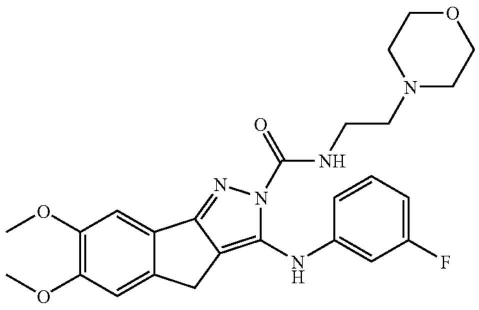 |
| 523 | 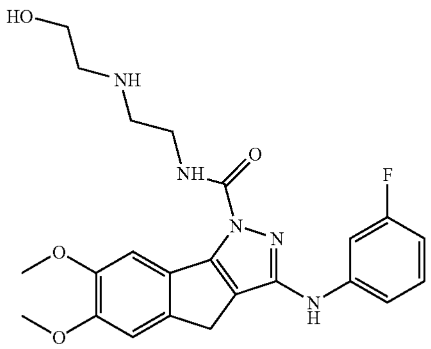 |
| 524 | 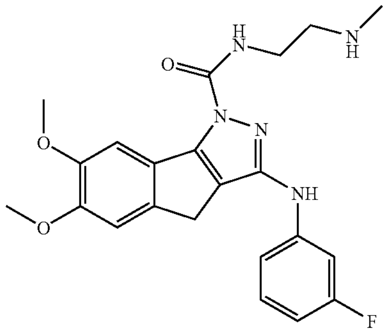 |

-continued
| Cpd | Structure |
|---|---|
| 525 | 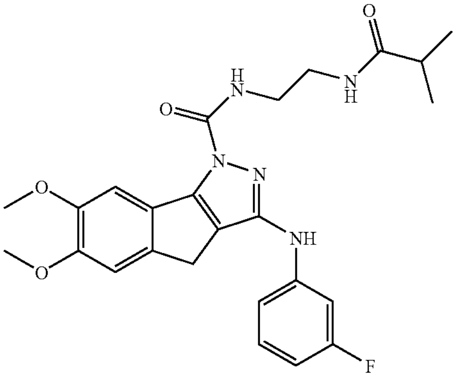 |
| 526 | 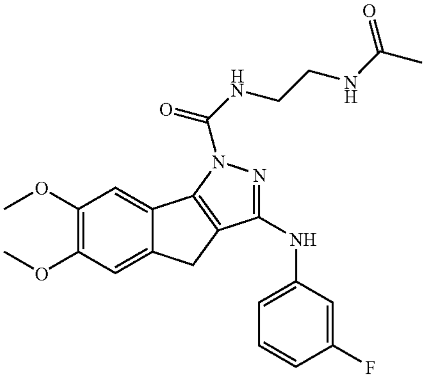 |
| 527 | 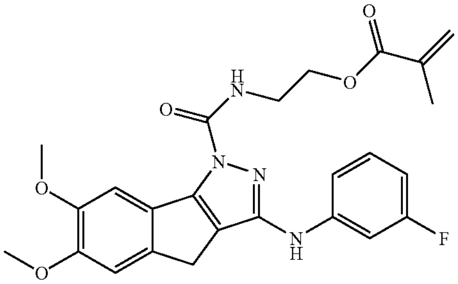 |
| 528 | 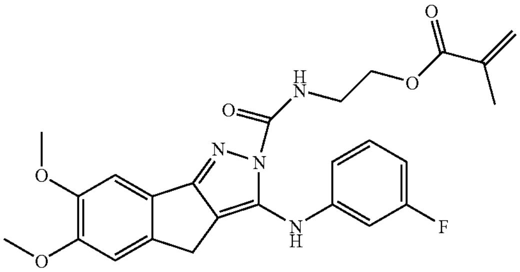 |

-continued
| Cpd | Structure |
|---|---|
| 529 | 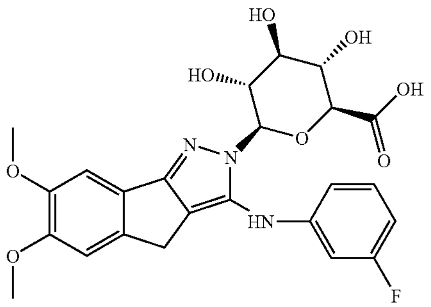 |
| 530 | 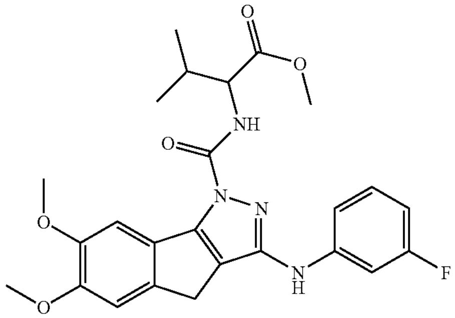 |
| 531 | 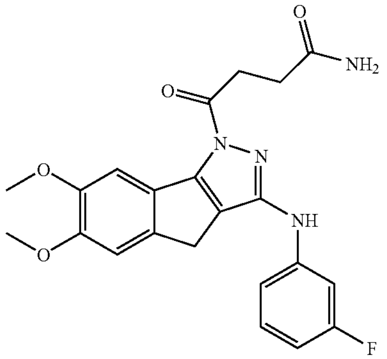 |
| 532 | 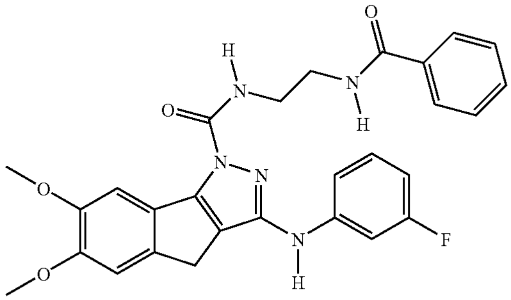 |
| 534 | 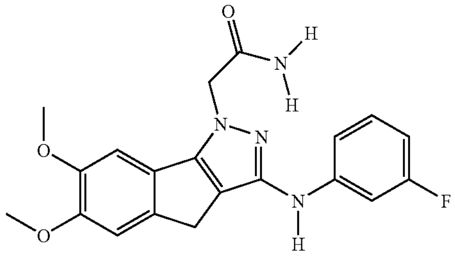 |

-continued
| Cpd | Structure |
|---|---|
| 535 | 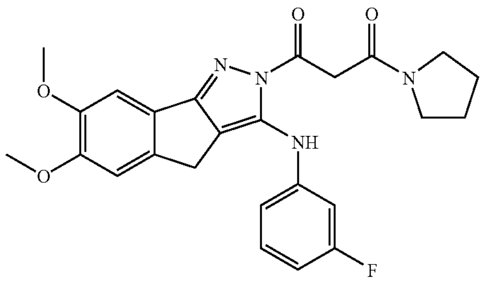 |
| 536 | 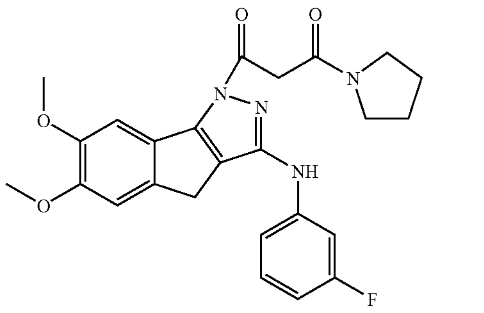 |
| 537 | 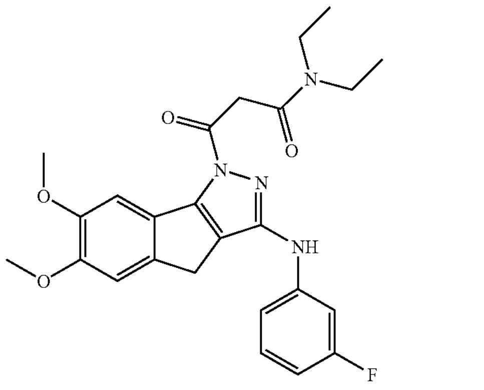 |
| 538 | 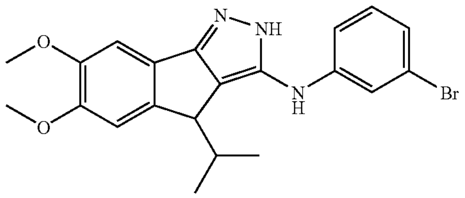 |
| 540 | 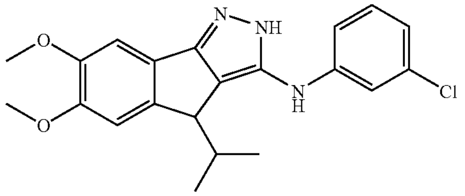 |

-continued
| Cpd | Structure |
|---|---|
| 541 | 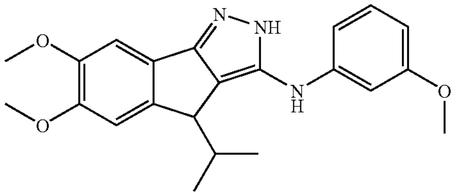 |
| 542 | 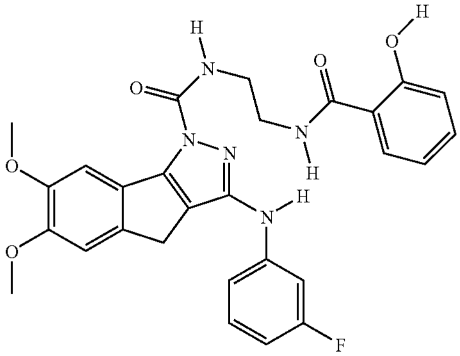 |
| 544 | 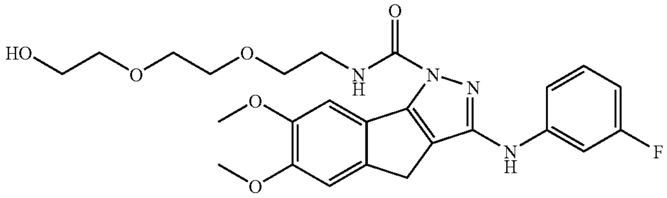 |
| 546 | 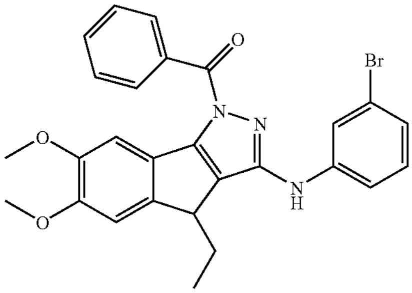 |
| 547 | 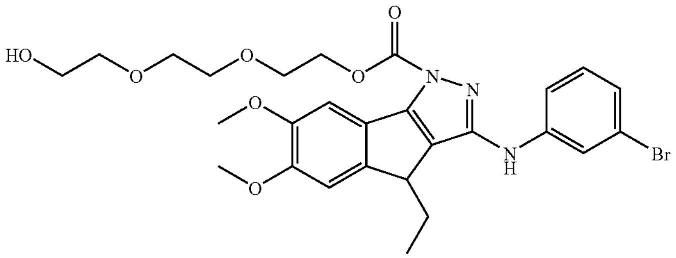 |
| 548 | 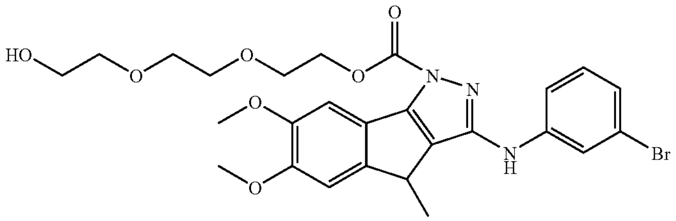 |

-continued
| Cpd | Structure |
|---|---|
| 549 | 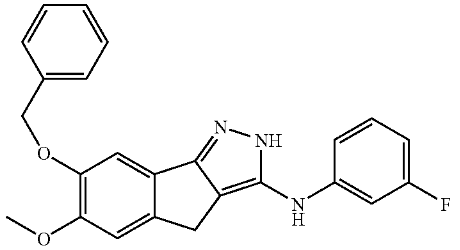 |
| 553 | 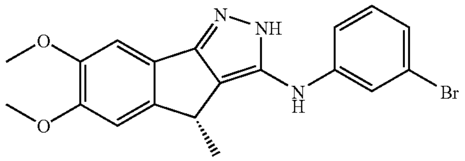 |
| 554 | 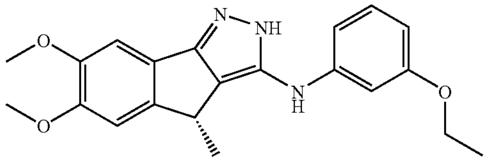 |
| 555 | 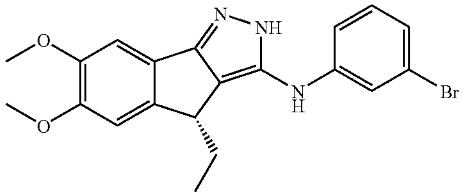 |
| 556 | 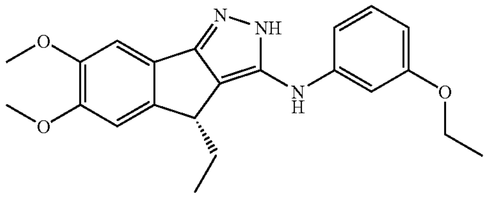 |
| 557 | 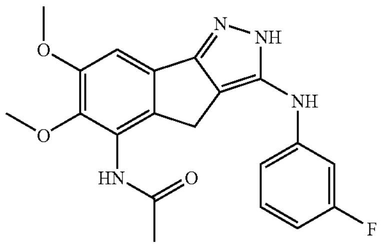 |
| 558 | 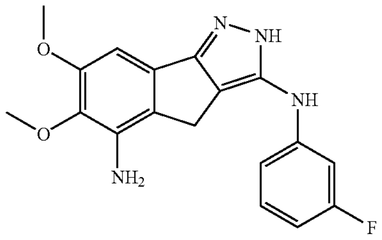 |

-continued
| Cpd | Structure |
|---|---|
| 559 | 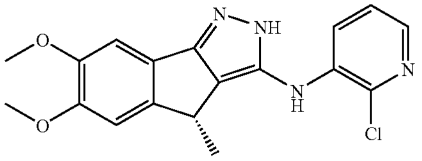 |
| 560 | 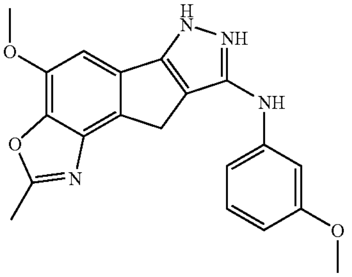 |
| 562 | 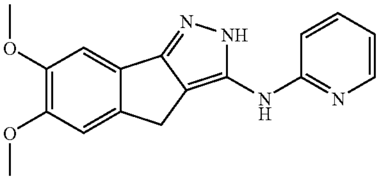 |
| 563 | 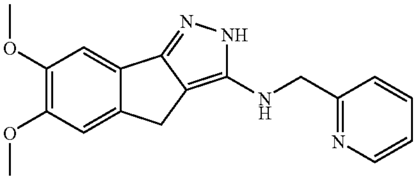 |
| 564 | 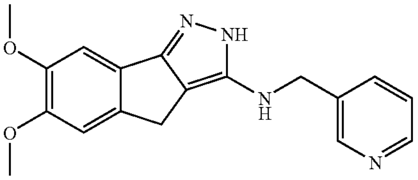 |
| 565 | 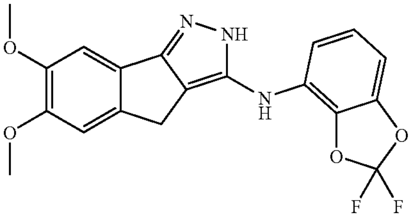 |
| 566 | 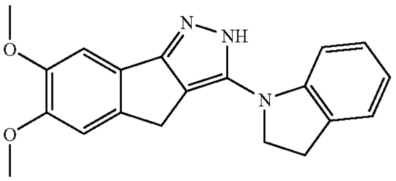 |

-continued
| Cpd | Structure |
|---|---|
| 567 | 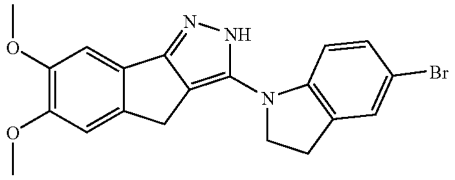 |
| 568 | 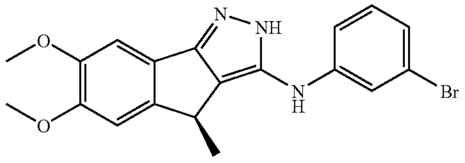 |
| 569 | 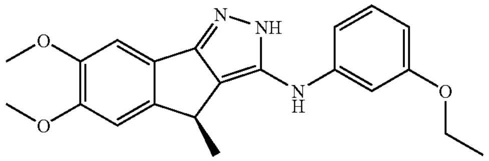 |
| 570 | 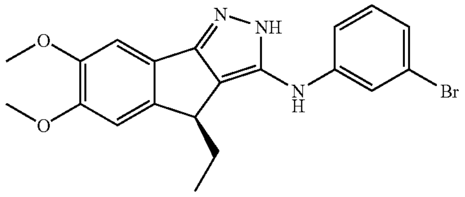 |
| 571 | 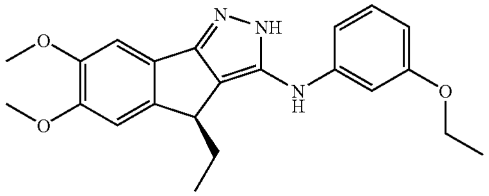 |
| 572 | 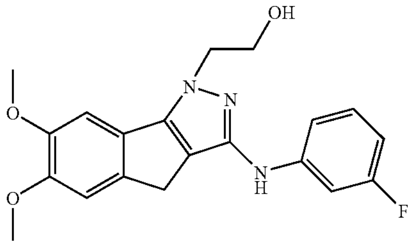 |
| 573 | 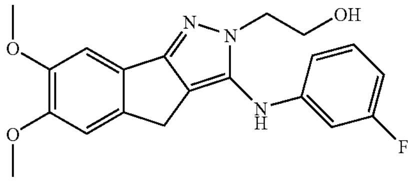 |

-continued
| Cpd | Structure |
|---|---|
| 574 | 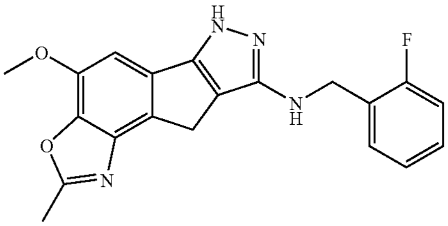 |
| 575 | 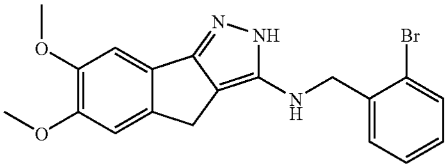 |
| 576 | 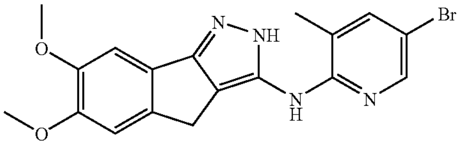 |
| 577 | 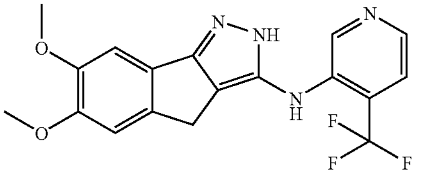 |
| 578 | 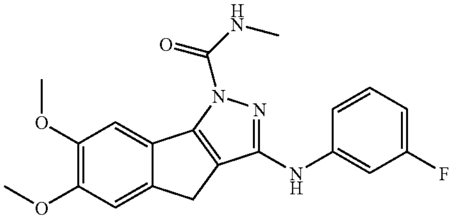 |
| 579 | 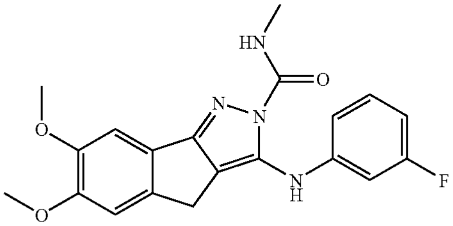 |
| 580 | 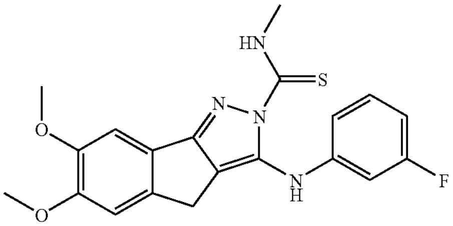 |

-continued
| Cpd | Structure |
|---|---|
| 581 | 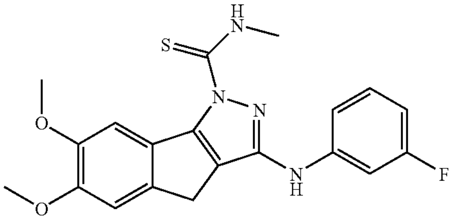 |
| 582 | 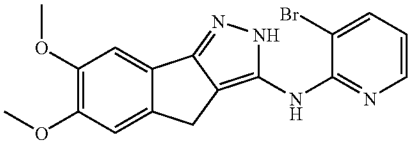 |
| 583 | 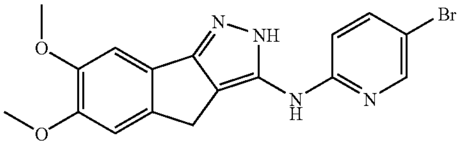 |
| 584 | 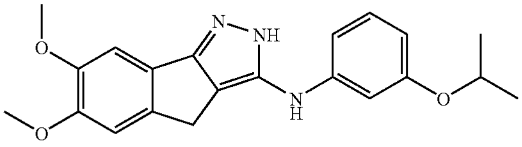 |
| 585 | 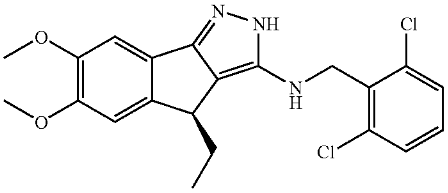 |
| 586 | 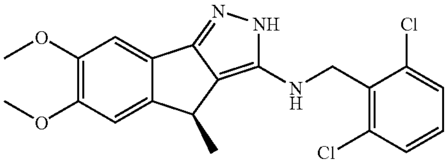 |
| 587 | 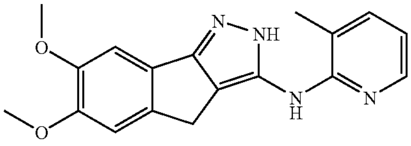 |
| 588 | 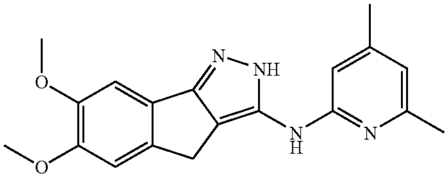 |

-continued
| Cpd | Structure |
|---|---|
| 591 | 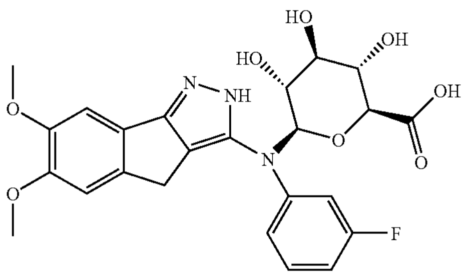 |
| 594 | 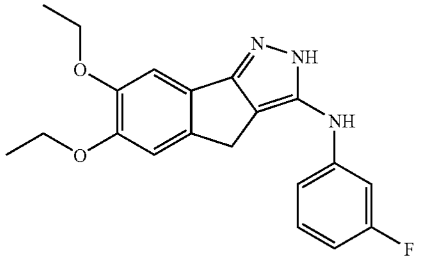 |
| 595 | 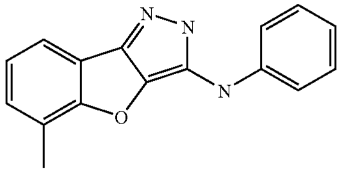 |
| 598 | 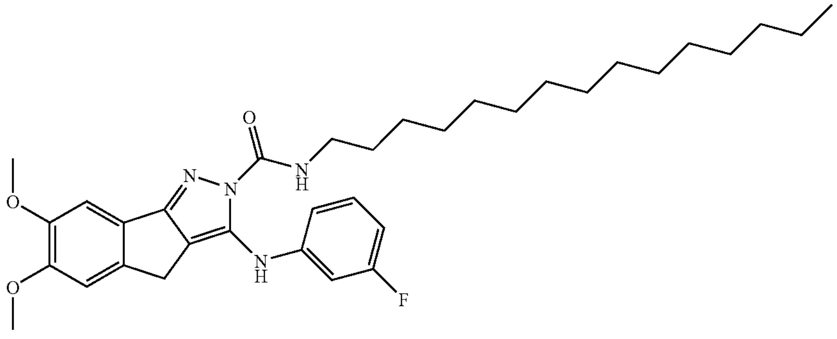 |
| 602 | 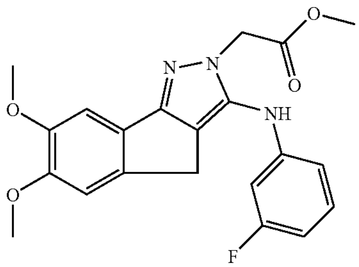 |

-continued
| Cpd | Structure |
|---|---|
| 604 | 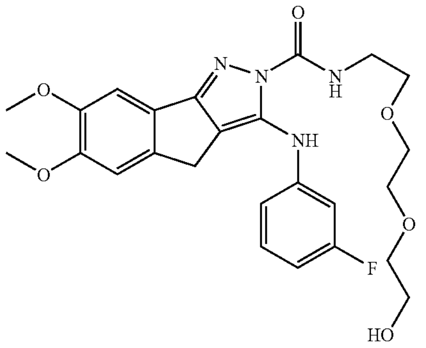 |
| 605 | 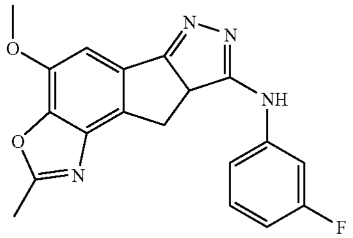 |
| 606 | 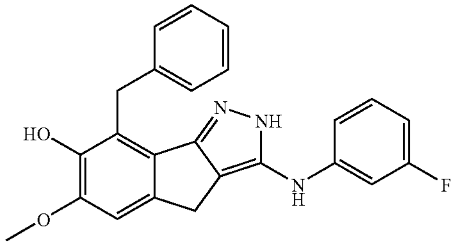 |
| 607 | 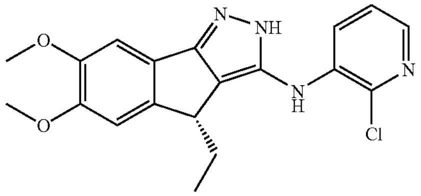 |
| 608 | 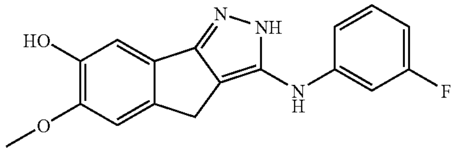 |
| 609 | 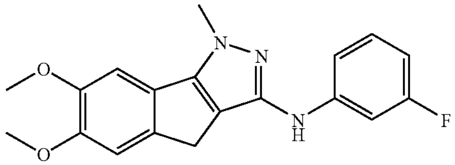 |
| 610 | 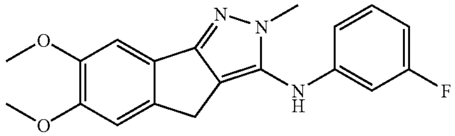 |

-continued

| Cpd | Structure |
|---|---|
| 611 | 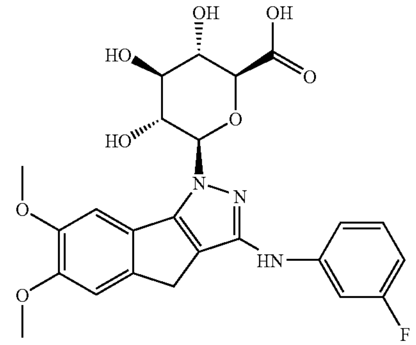 |

The following examples are given for the purpose of illustrating various synthetic methods for compounds of the invention and are not meant to limit the present invention in any fashion.

EXAMPLE 1

1-Oxo-indan-2-carbothioic acid phenylamide, Intermediate A (Method A)

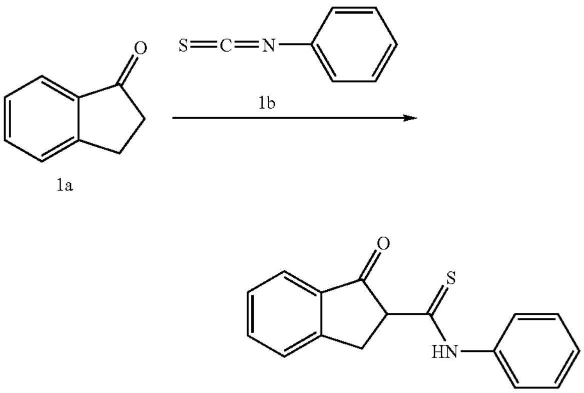

Intermediate A

NaH (60% dispersion in mineral oil, 0.25 g, 6 mmol) and indan-1-one, Compound 1a, (0.50 g, 3.79 mmole) in THF (5 mL) were mixed under argon. The mixture was stirred at ambient temperature for 5 min. Then, phenylisothiocyanate, Compound 1b, (0.46 mL, 3.79 mmole) was added to the mixture. After an additional 5 min, the reaction was completed as shown by TLC analysis and the reaction mixture was poured into $NH_4Cl$ solution and then filtered subsequently. 1-Oxo-indan-2-carbothioic acid phenylamide (Intermediate A), was crystallized from $CH_3CN$ as a yellow solid. MS m/z 268 $(M+H)^+$; $^1H$ NMR (DMSO-$d_6$):3.5 (dd, 0.3H), 3.8 (d, 0.15H), 3.9 (s, 1.55H), 4.3 (dd, 0.3H), 7.3 (t, 1H), 7.4–7.8 (m, 7.4H), 7.9 (d, 0.6H), 10.6 (s, 0.7H), 12.1 (s, 0.3H), 14.1 (s, 0.7H).

EXAMPLE 2

2,4-Dihydro-indeno[1,2-c]pyrazol-3-yl)-phenyl-amine, Compound 1 (Method A)

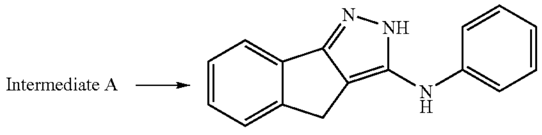

Compound 1

(Intermediate A) 1-Oxo-indan-2-carbothioic acid phenylamide (0.35 g, 1.31 mmole), ethanol (2 mL) and hydrazine (0.043 mL 1.38 mmole) were mixed in a flask under argon. The reaction mixture was heated on a steam bath for 1 hour, then cooled and the solvent evaporated to a brown oil. The oil was further dissolved in $CH_2Cl_2$, and was washed with 1N HCl, 3N NaOH and brine. The resulting organics (0.31 g) were dried ($Na_2SO_4$), filtered, and the solvent was removed in vacuo. The product was isolated by silica gel chromatography with 2% methanol:methylene chloride. The title compound (Compound 1) was subsequently crystallized from methylcyclohexane:toluene as a white solid. m.p. 148–149° C.; MS m/z 248 $(M+H)^+$; $^1H$ NMR (DMSO-$d_6$): 3.5 (s, 2H), 6.75 (t, 1H), 7.0–7.3 (m, 5H), 7.35 (t, 1H), 7.5 (dd, 2H), 8.4 (s, 1H), 12.3 (s, 1H).

EXAMPLE 3

(3,5-Dichloro-phenyl)-(6,7-dimethoxy-2,4-dihydro-indeno[1,2-c]pyrazol-3-yl)-amine, Compound 19 (Method A)

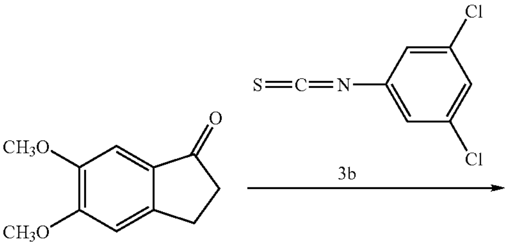

3a

-continued

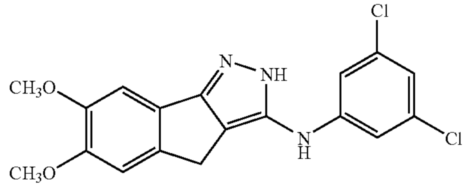

Compound 19

A mixture of 5,6-dimethoxyindan-1-one, Compound 3a, (4 g, 0.021 mole), 3,5-dichlorophenyl isothiocyanate, Compound 3b, (4.45 g, 0.022 mole) and THF (30 mL) was added to lithium hexamethyldisilane (26.9 mL, 0.269 mole) dropwise at room temperature with stirring. Hydrazine (1.04 mL, 0.032 mole) and acetic acid (1.65 mL) were added to the reaction mixture, which was then stirred at room temperature for 12 hrs. The reaction continued at 75° C. overnight. The resulting organics were first diluted with ethyl acetate (100 mL), then washed with water and brine solution, dried ($Na_2SO_4$), and solvent was removed in vacuo. The chemical residues were recrystallized from ethanol. The first and second crops of solid were combined and dissolved in hot $CH_3CN$, to which an equal volume of HCl-ether solution was added to precipitate the title compound (Compound 19), which was collected and dried under vacuum at 60° C. mp>270° C.; MS m/z 376 and 378 $(M+H)^+$; $^1$HNMR (DMSO-$d_6$): 3.44(s, 2H), 3.83(s, 3H), 3.82(s, 3H),6.93(s, 1H),7.19 (s, 1H), 7.21(s, 1H), 7.35(s, 2H).

EXAMPLE 4

(3-Fluoro-phenyl)-(6,7-dimethoxy-2,4-dihydro-indeno[1,2-c]pyrazol-3-yl)-amine, Compound 14 (Method A)

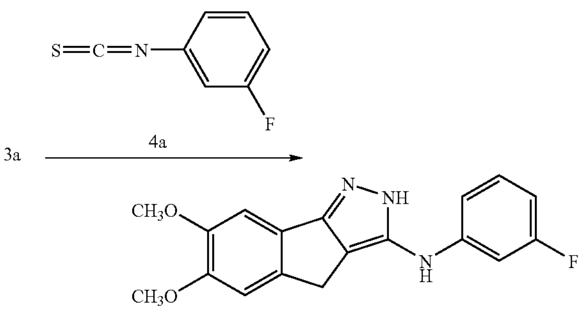

Compound 14

A mixture of 5,6 dimethoxyindan-1-one, Compound 3a, (3.0 g, 0.0154 mole), 3-fluoro-phenyl isothiocyanate, Compound 4a, (2.4 g, 0.0157 mole) and THF (3.0 mL) was added to lithium hexamethyldisilane (15.4 mL, 0.0154 mole) dropwise at room temperature with stirring. The reaction mixture was stirred for 12 hrs. Hydrazine (0.75 mL, 0.0154 mole) and acetic acid (0.96 mL) were added to the reaction mixture, which was then heated at the reflux temperature for 24 hrs. The resulting mixture was first added to water (30 mL) and then extracted with $CH_2Cl_2$. The organic layers were combined and washed with aqueous $NaHCO_3$ solution, then washed with water and brine solution, dried ($Na_2SO_4$), and solvent was removed in vacuo. The residue was dissolved in hot $CH_3CN$. To the mixture was then added one equivalent of an HCl-ether solution to yield a precipitate of the title compound. The precipitate was dissolved in $CH_3CN$ and decolorized with charcoal and re-crystallized to give Compound 14 as an off white solid. MS m/z 326 $(M+H)^+$; $^1$HNMR (DMSO-$d_6$): 3.44(s, 2H), 3.80(s, 3H), 3.81(s, 3H), 6.58(t, 1H),6.85 (d, 1H), 7.1(d, 1H), 7.21(s, 1H), 7.23(s, 1H), 7.3(m, 1H), 9.2(br s, 1H).

EXAMPLE 5

2-(Imidazole-1-carbothioyl)-5,6-dimethoxy-indan-1-one, Intermediate B (Method B)

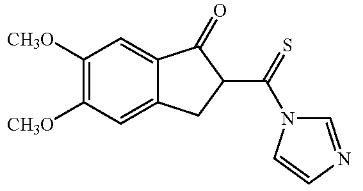

Lithium bis(trimethylsilyl)amide in THF (11 mL, 11 mmol) and THF (20 mL) were mixed with stirring in a dry flask under a nitrogen atmosphere. 5,6 dimethoxyindan-1-one (1.92 g, 10 mmol) in 15 mL THF was added to the flask. The reaction mixture was then cooled in a dry-ice-acetone bath. The reaction solution was stirred at −78° C. and thiodiimidazole (2.18 g, 11 mmol) in 15 mL of THF was added. The reaction mixture was stirred at −78° C. for 5 hrs, then quenched with 40 mL of saturated $NH_4Cl$ solution, and warmed to room temperature. The aqueous solution of the mixture was extracted with ethyl acetate twice to yield the title compound in the organic solution. The mixture was washed with water and saturated NaCl solution, dried ($Na_2SO_4$), and solvent was removed in vacuo. 2-(Imidazole-1-carbothioyl)-5,6-dimethoxy-indan-1-one was obtained as a yellow solid. HPLC analysis showed the product was pure. MS m/z 303 $(M+H)^+$; $^1$HNMR (DMSO-$d_6$): 3.60(s, 2H), 3.70(s, 3H), 3.85(s, 3H), 6.90(s, 1H), 7.1(s, 1H), 7.51(s, 1H), 7.60(s, 1H), 9.1(s, 1H).

EXAMPLE 6

[3-(6,7-Dimethoxy-2,4-dihydro-indeno[1,2-c]pyrazol-3-ylamino)-phenyl]-methanol, Compound 36 (Method B)

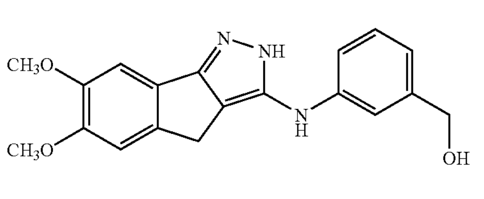

2-(Imidazole-1-carbothioyl)-5,6-dimethoxy-indan-1-one, Intermediate B, (1.0 g, 3.3 mmol) was mixed with 3-aminobenzyl alcohol (0.40 g, 3.3 mmol), and 30 mL THF in a flask. 5,6-Dimethoxy-1-oxo-indan-2-carbothioic acid (3-hydroxymethyl-phenyl)-amide was obtained after stirring the reaction mixture for 4 hours at room temperature. HPLC/MS m/z 358 $(M+H)^+$. The intermediate was not isolated, the mixture was mixed with hydrazine (0.13 mL, 4 mmol), and acetic acid (2–3 drops). The reaction was heated at 78° C. for 12 hours. The reaction solution was then diluted with ethyl acetate, washed with water, and dried over $Na_2SO_4$. The solvent was removed and the title compound was purified by HPLC with a C-18 reversed phase column and $CH_3CN$—$H_2O$-TFA as gradient solvents. The title compound, [3-(6, 7-Dimethoxy-2,4-dihydro-indeno[1,2-c]pyrazol-3-ylamino)-phenyl]-methanol, Compound 36, was obtained as a solid TFA salt. MS m/z 338 $(M+H)^+$; HPLC:100% (uv 214 mu);

$^1$HNMR (DMSO-$d_6$): 3.40(s, 2H), 4.54(s, 2H), 6.81 (d, 1H), 7.02 (d, 1H), 7.14(s, 1H), 7.22(d, 2H).

EXAMPLE 7

N3-Phenyl-2,4-dihydro-indeno[1,2-c]pyrazole-3,6-diamine, Compound 66 (Method C)

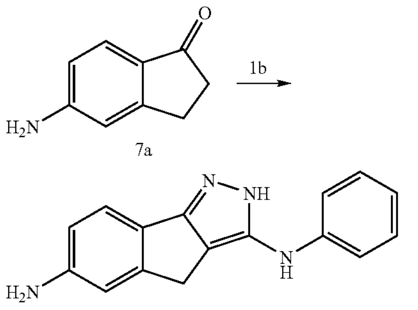

7a

Compound 66

NaH (60% dispersion in mineral oil (0.25 g, 6 mmol)) and dry THF (25 mL) were mixed in a flask under an Argon atmosphere. 5-aminoindan-1-one, Compound 7a, (0.22 g, 15 mmol) and phenylisothiocyanate, Compound 1b, (0.18 mL, 15 mmol) were then added to the reaction with stirring. After the reaction mixture was stirred at room temperature for one hour, hydrazine (0.45 mL, 75 mmol) followed by acetic acid (0.070 mL, 2.25 mmol) was added. The reaction was continued at 70° C. with stirring overnight. The reation was diluted with saturated aq. $NaHCO_3$, extracted with ethyl acetate, washed with brine, dried over sodium sulfate and the solvent was removed in vacuo. The crude material was purified by HPLC to yield the title compound (Compound 66) as a TFA salt. MS m/z 263 $(M+H)^+$; $^1$HNMR (DMSO-$d_6$):3.50(s, 2H), 6.80(m, 1H), 6.98(m, 1H), 7.14(m, 3H), 7.24(m, 2H), 7.32(t, 1H), 7.49(d, 1H), 7.56(d, 1H), 8.80(bs, 1H); HPLC:100% (uv 214).

EXAMPLE 8

2-(Bis-methylsulfanyl-methylene)-5,6-dimethoxy-indan-1-one, Intermediate D (Method D)

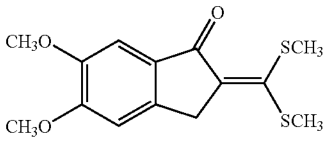

NaH (60% dispersion in mineral oil; 3.37 g, 44.3 mmol), carbon disulfide (3.37 g, 44.3 mmol) and THF (50 mL) were added to a dry flask under Nitrogen. The reaction flask was cooled with an ice-water bath and then 5,6-dimethoxy-indan-1-one, Compound 3a, (7.1 g, 37 mmol) in THF (50 mL) was added. The reaction mixture was stirred for 1 h. Then, methyliodide (5.2 mL, 44.3 mmol) was added. The resulting reaction solution was allowed to stir at room temperature overnight, then an aqueous $NH_4Cl$ solution (150 mL) was added followed by ethyl acetate (150 mL). The aqueous layer was separated and extracted with ethyl acetate twice. The organic solution was washed with water and a saturated NaCl solution was added. The solution was dried over $Na_2SO_4$, filtered and concentrated. The resulting solid was triturated with ethanol to yield 2-(Bis-methylsulfanyl-methylene)-5,6-dimethoxy-indan-1-one, Intermediate D, as a yellow solid. MS m/z 297 $(M+H)^+$; $^1$HNMR($CDCl_3$): 2.50(s, 3H),2.58(s, 3H), 3.80(s, 2H), 3.90(s, 3H), 4.0(s, 3H), 7.20(s, 1H), 7.22(s, 1H).

EXAMPLE 9

(6,7-Dimethoxy-2,4-dihydro-indeno[1,2-c]pyrazol-3-yl)-(4-methoxy-phenyl)-amine, Compound 6 (Method D)

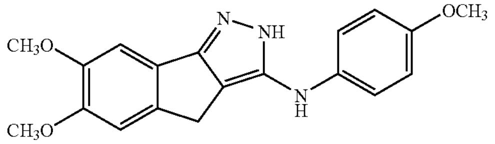

50 mg (0.17 mmol) of intermediate D (prepared as described in Example 8 above), 25 mg of 4-methoxyaniline (0.2 mmol) and 1 mL of acetic acid was placed in a reaction flask. The mixture was heated at 70° C. overnight. The mixture was then poured into water and extracted with ethyl acetate. The organic solution was washed, dried, and concentrated to give a dark brown residue. The residue was suspended in ethanol and mixed with 0.050 mL of hydrazine. The reaction mixture was then heated at 70° C. overnight, the mixture was diluted with ethyl acetate and then washed with water, dried and concentrated. The crude product was purified on a silica gel column using a mixture of methylene chloride and methanol as eluents. The pure fractions were collected and concentrated to yield the title compound (Compound 6), (6,7-Dimethoxy-2,4-dihydro-indeno[1,2-c]pyrazol-3-yl )-(4-methoxy-phenyl)-amine, as a brown solid. MS m/z 338 $(M+H)^+$; HPLC: 99% pure (uv); $^1$HNMR ($CDCl_3$): 3.29(s, 2H), 3.73(s, 3H), 3.80(s, 3H), 3.89(s, 3H), 6.80(d, 2H), 6.95(m, 3H), 7.3(s, 1H).

EXAMPLE 10

3-Phenylamino-2H-indeno[1,2-c]pyrazol-4-one, Compound 35 (Method E)

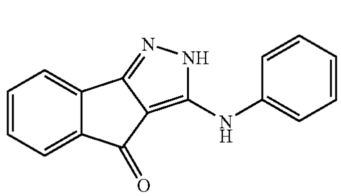

1,3-indione (5 g, 0.0342 mol) and phenyl isothiocyanate, Compound 1b, (4.1 mL, 0.0342 mol) were added into acetonitrile (50 mL) and cooled to 0° C. DBU (10.2 mL, 0.0684 mol) was then added dropwise and the reaction mixture was stirred at room temperature for two hours. The reaction mixture was cooled to 0° C., then methyl iodide (3.2 mL, 0.051 mol) was added slowly. The reaction mixture was stirred at room temperature for four hours, and then quenched with 50/50 acetic acid/water solution (300 mL). The precipitate was filtered and washed with water.

The precipiate (0.50 g, 0.0017 mol), hydrazine (0.08 mL, 0.0026 mol), and acetic acid (0.5 mL, 0.006 mol) were added together into acetonitrile (10 mL) and then stirred at 75° C. for four hours. The reaction mixture was quenched with saturated aq. $NaHCO_3$ solution, extracted with ethyl acetate, washed with brine, and dried over sodium sulfate. The solvent was removed in vacuo. The resulting crude material was triturated with dichloromethane and methanol to yield the title compound (Compound 35) 3-Phenylamino-2H-indeno[1,2-c]pyrazol-4-one. MS m/z 262 $(M+H)^+$; $^1$HNMR (DMSO-$d_6$): 6.92(m, 1H), 7.11(m, 2H), 7.27(m, 3H), 7.48(m, 3H) 9.60(s, 1H), 12.3(s, 1H).

EXAMPLE 11

3-Phenylamino-2,4-dihydro-indeno[1,2-c]pyrazol-4-ol, Compound 50 (Method E)

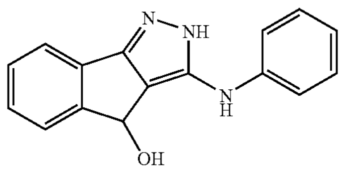

Compound 35, prepared as in Example 10, (0.15 g, 0.00057 mol) was suspended in a mixture of 50/50 DCM/MeOH (50 mL), to which sodium boronhydride (800 mg) was added. The reaction mixture was stirred for 2 hours. The reaction mixture was then quenched with saturated aq. $NaHCO_3$ solution, extracted with ethyl acetate, washed with brine, and dried over sodium sulfate. The solvent was removed in vacuo. The crude material was triturated with dichloromethane and methanol to yield the title compound, 3-Phenylamino-2,4-dihydro-indeno[1,2-c]pyrazol-4-ol. MS m/z 264 $(M+H)^+$;

$^1$HNMR (DMSO-$d_6$): 5.28(m, 2H), 6.70(m, 1H), 7.19(m, 6H), 7.34(m, 1H), 7.48(m, 1H) 8.32(s, 1H), 12.15(s, 1H).

EXAMPLE 12

5-Hydroxy-6-methoxy-indan-1-one, Intermediate H

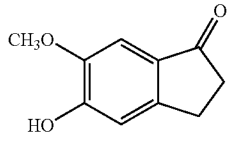

A mixture of 5,6 dimethoxyindan-1-one (25.0 g, 0.13 mole), lithium chloride (20.0 g, 0.47 mole) and DMF (200.0 mL) was stirred at 160° C. for 60 hrs. Water (400.0 mL) was added and the mixture washed with ethyl acetate. The aqueous layer was acidified with 2N HCl and extracted with ethyl acetate (2×300.0 mL). The organic layer was washed with brine and the solvent removed in vacuo. The crude material was purified on a silica gel column using DCM/MeOH(97/3) as the eluent. The solvent was removed in vacuo to yield 5-hydroxy-6-methoxy-indan-1-one (Intermediate H) as a light yellow solid. MS m/z 179 $(M+H)^+$: 179 m/z. The title compound (Intermediate H) is a known compound and may also be prepared by demethylation of 5,6 dimethyoxyindan-1-one using KCN/DMSO at 100° C. (J. M. Saa et al., *J. Org. Chem.* 1992, 57, 589).

EXAMPLE 13

5-(2,2-Dimethyl-1,3-dioxolan-4-ylmethoxy)-6-methoxy-indan-1-one, Intermediate I

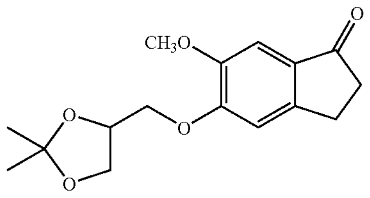

A mixture of 5-Hydroxy-6-indan-1-one, Intermediate H, (0.50 g, 0.0028 mol), 4-chloromethyl-2,2-dimethyl-1,3-dioxolane (0.766 mL, 0.0056 mol), potassium carbonate (1.54 g, 0.011 mol) and DMF (20.0 mL) was stirred at 95° C. for 3 days. Water (150.0 mL) was added and the mixture was extracted with ethyl acetate (2×150 mL). The organic layer was washed with sat. $NaHCO_3$, brine and dried over $Na_2SO_4$. The solvent was then removed in vacuo to yield 5-(2,2-dimethyl-[1,3]dioxolan-4-ylmethoxy)-6-methoxy-indan-1-one (Intermediate I) as light brown solid. MS m/z 293 $(M+H)^+$.

EXAMPLE 14

3-[3-[(3-Chloro-phenylamino)-7-methoxy-2,4-dihydro-indeno[1,2-c]pyrazol-6-yloxy]-propane-1,2-diol, Compound 259 (Method A)

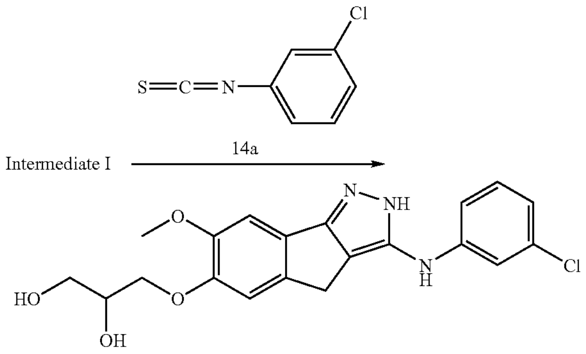

Compound 259

A mixture of 5-(2,2-dimethyl-[1,3]dioxolan-4-ylmethoxy)-6-methoxy-indan-1-one (Intermediate I) (0.30 g, 0.001 mole), 3-chloro-phenyl isothiocyanate (Compound 14a) (0.14 mL, 0.0011 mole) and THF (1.5 mL) was added to lithium hexamethyldisilane (1.2 mL, 0.0012 mole) dropwise at room temperature with stirring. The reaction mixture was stirred for 4 hrs. Hydrazine (0.070 mL, 0.0022 mole) and acetic acid (0.132 mL, 0.0022 mole) were added to the reaction mixture, which was then heated at the reflux temperature for 18 hrs. The resulting mixture was first added to water (10 mL) and then extracted with $CH_2Cl_2$. The organic layers were combined and washed with aqueous $NaHCO_3$ solution, then washed with water and brine solution, dried ($Na_2SO_4$), and the solvent was removed in vacuo. The crude material was purified on the reverse phase HPLC and converted to the desired product upon standing in the 0.1% TFA solution. Lyophilization yielded the title compound, 3-[3-[(3-Chloro-phenylamino)-7-methoxy-2,4-dihydro-indeno[1,2-c]pyrazol-6-yloxy]-propane-1,2-diol as a white powder. MS m/z 402 $(M+H)^+$; $^{1}$HNMR (DMSO-$d_6$): 3.41(s, 2H), 3.46(d, 2H), 3.78(s, 4H), 3.88(m, 1H), 4.00(m, 1H), 6.75(d, 1H), 7.15(m, 4H), 7.40(s, 1H), 8.80(br s, 1H).

EXAMPLE 15

5-(3-Bromo-propoxy)-6-methoxy-indan-1-one, Intermediate J

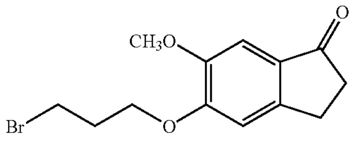

A mixture of 5-Hydroxy-6-methoxy-indan-1-one (Intermediate H) (5.0 g, 0.028 mole), 1,3-dibromopropane (5.7 mL, 0.056 mole) and sodium hydride (1.2 g, 0.028 mole) were stirred in 50 mL of DMF at room temperature overnight under Argon. The reaction mixture was quenched with water (150 mL), extracted with ethyl acetate, then washed with 1N HCl and brine. The extract was dried over sodium sulfate and the solvent removed in vacuo to yield the title compound, 5-(3-Bromo-propoxy)-6-methoxy-indan-1-one. MS m/z 297 $(M+H)^+$.

EXAMPLE 16

6-Methoxy-5-(3-pyrrolidin-1-yl-propoxy)-indan-1-one, Intermediate K

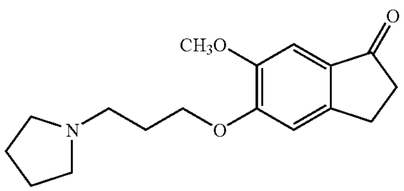

A mixture of 5-(3-bromo-propoxy)-6-methoxy-indan-1-one (Intermediate J) (2.0 g, 0.0066 mole) and pyrrolidine (1.7 mL, 0.02 mole) was stirred in 50 mL of DME (1,2-Dimethoxyethane) at room temperature overnight under Argon. The reaction was quenched with water (150 mL) and made acidic with 1N HCl (50 mL). The water solution was washed with ethyl acetate, made basic with 3N NaOH (25 mL) and extracted with ethyl acetate. After washing with brine and drying over sodium sulfate, the solvent was removed in vacuo to yield the title compound. MS m/z 290 $(M+H)^+$.

EXAMPLE 17

(3-Fluoro-phenyl)-[7-methoxy-6-(3-pyrrolidin-1-yl-propoxy)-2,4-dihydro-indeno[1,2-c]pyrazol-3-yl]-amine, Compound 180 (Method A)

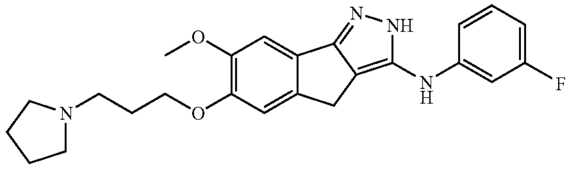

A mixture of 6-methoxy-5-(3-pyrrolidin-1-yl-propoxy)-indan-1-one (Intermediate K, 0.45 g, 0.00155 mole), 3-fluoro-phenyl isothiocyanate (Compound 4a) (0.19 mL, 0.0017 mole) and THF (1.5 mL) was added to lithium hexamethyldisilane (1.8 mL, 0.0018 mole) dropwise at room temperature with stirring. The reaction mixture was stirred for 4 hrs. Hydrazine (0.095 mL, 0.003 mole) and acetic acid (0.180 mL, 0.003 mole) were added to the reaction mixture. The reaction mixture was then heated at the reflux temperature for 18 hrs. The resulting mixture was first added to water (10 mL) and then extracted with $CH_2Cl_2$. The organic layers were combined and washed with aqueous $NaHCO_3$ solution, then washed with water and brine solution, dried ($Na_2SO_4$), and solvent was removed in vacuo. The crude material was purified on the reverse phase HPLC. Lyophilization yielded the title compound, (3-Fluoro-phenyl)-[7-methoxy-6-(3-pyrrolidin-1-yl-propoxy)-2,4-dihydro-indeno[1,2-c]pyrazol-3-yl]-amine as a white powder. MS m/z 423 $(M+H)^+$; $^{1}$HNMR (DMSO-$d_6$): 1.88(m, 2H), 2.00(m, 2H), 2.15(m, 2H), 3.02(m, 2H), 3.29(dd, 2H), 3.37(s, 2H), 3.61(m, 2H), 3.74(s, 3H), 4.04(t, 2H), 6.52(t, 1H), 6.93(d, 1H), 7.18(m, 4H), 8.8(br s, 1H), 9.7(br s, 1H).

EXAMPLE 18

6-Methoxy-5-[3-(tetrahydro-pyran-2-yloxy)-propoxy]-indan-1-one, Intermediate L

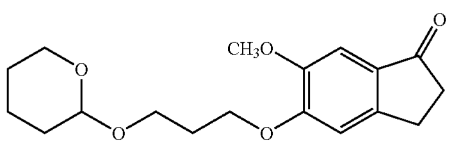

A mixture of 5-Hydroxy-6-methoxy-indan-1-one (Intermediate H, 2.98 g, 0.017 mole), 2-(3-chloro-propoxy)-tetrahydro-pyran (Compound 18a) (6.0 g, 0.034 mole), and potassium carbonate (10.0 g, 0.0725 mole) were stirred in 50 mL of DMF at 80° C. overnight under Argon. The reaction mixture was then diluted with 200 mL of ethyl acetate and washed 3 times with water. After drying over sodium sulfate, the solvent was removed in vacuo. The crude material solidified on standing to yield the title compound, 6-Methoxy-5-[3-(tetrahydro-pyran-2-yloxy)-propoxy]-indan-1-one. MS m/z 309 $(M+H)^+$.

EXAMPLE 19

3-[7-Mehoxy-3-(3-methoxy-phenylamino)-2,4-dihydro-indeno[1,2-c]pyrazol-6-yloxy]-propan-1-ol, Compound 266 (Method A)

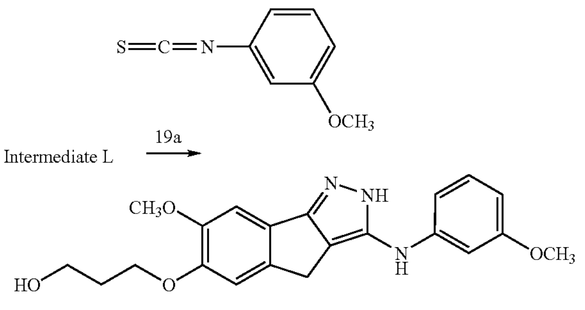

Compound 266

A mixture of 6-methoxy-5-[3-(tetrahydro-pyran-2-yloxy)-propoxy]-indan-1-one (Intermediate L) (0.16 g, 0.0005 mole), 3-methoxy-phenyl isothiocyanate (Compound 19a) (0.08 mL, 0.0006 mole) and THF (1.5 mL) was added to lithium hexamethyldisilane (0.7 mL, 0.0007 mole) dropwise at room temperature with stirring. The reaction mixture was stirred for 4 hrs. Hydrazine (0.035 mL, 0.0011 mole) and acetic acid (0.66 mL, 0.0011 mole) were added to the reaction mixture, which was then heated at the reflux temperature for 18 hrs. To the resulting mixture was first added water (10 mL) and then the reaction mixture was extracted with $CH_2Cl_2$. The organic layers were combined and washed with aqueous $NaHCO_3$ solution, then washed with water and brine solution, dried ($Na_2SO_4$), and solvent was removed in vacuo. The crude material was purified on the reverse phase HPLC and converted to the desired product upon standing in the 1% TFA in $CH_3CN$: water solution. Lyophilization yielded the title compound, 3-[7-Methoxy-3-(3-methoxy-phenylamino)-2,4-dihydro-indeno [1,2-c]pyrazol-6-yloxy]-propan-1-ol as a white powder. MS m/z 382 $(M+H)^+$; $^1$HNMR (DMSO-$d_6$): 1.88(m, 2H), 3.40 (s, 2H), 3.57(t, 2H), 3.72(s, 3H), 3.78(s, 3H), 4.05(t, 2H), 6.38(d, 1H), 6.68(d, 1H), 6.77(s, 1H), 7.10(m, 2H), 7.25(s, 1H), 8.75(br s, 1H).

EXAMPLE 20

6-Methoxy-5-oxiranylmethoxy-indan-1-one, Intermediate M

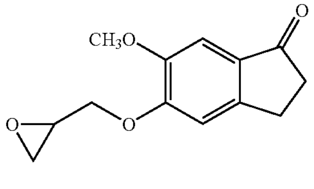

A mixture of 5-Hydroxy-6-methoxy-indan-1-one (Intermediate H, 5.0 g, 0.028 mole), 2-chloromethyl-oxirane (4.4 mL, 0.056 mole), and potassium carbonate (11.6 g, 0.084 mole) was stirred in 50 mL of DMF at 70° C. overnight under Argon. The reaction was then diluted with 200 mL of ethyl acetate and washed 3 times with water. The ethyl acetate solution was dried over sodium sulfate and the solvent removed in vacuo to yield the title compound (Intermediate M). MS m/z 236 $(M+H)^+$.

EXAMPLE 21

5-(2-Hydroxy-3-pyrrolidin-1-yl-propoxy)-6-methoxy-indan-1-one, Intermediate N

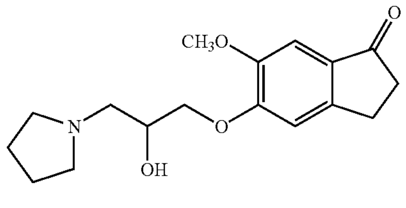

A mixture of 6-methoxy-5-oxiranylmethoxy-indan-1-one (Intermediate M, 2.5 g, 0.0106 mole) and pyrrolidine (0.9 mL, 0.011 mole) was stirred in 50 mL of DME at 50° C. for 5 hrs under Argon. Then, 150 mL of ethyl acetate was added and the solution washed with water (2×). Following extraction with 2N HCl, the aqueous acidic layer was made basic with 3N NaOH and extracted with ethyl acetate. The ethyl acetate extracts were washed with brine, dried over sodium sulfate and the solvent removed in vacuo. The resulting residue was triturated with diethyl ether to yield the title compound. MS m/z 306 $(M+H)^+$.

EXAMPLE 22

1-[7-Methoxy-3-(3-methoxy-phenylamino)-2,4-dihydro-indeno[1,2-c]pyrazol-6-yloxy]-3-pyrrolidin-1-yl-propan-2-ol, Compound 270 (Method A)

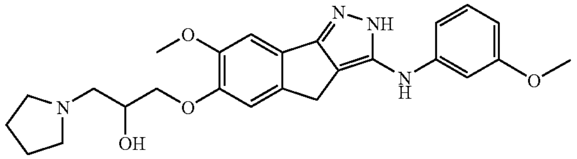

To a mixture of 5-(2-hydroxy-3-pyrrolidin-1-yl-propoxy)-6-methoxy-indan-1-one (Intermediate N) (0.16 g, 0.0005 mole), 3-methoxy-phenyl isothiocyanate (Compound 19a) (0.08 mL, 0.0006 mole) and THF (1.5 mL) was added to lithium hexamethyldisilane (0.7 mL, 0.0007 mole) dropwise at room temperature with stirring. The reaction mixture was stirred for 4 hrs. Hydrazine (0.035 mL, 0.0011 mole) and acetic acid (0.66 mL, 0.0011 mole) were added to the reaction mixture. The reaction mixture was then heated at the reflux temperature for 18 hrs. To the resulting mixture was first added water (10 mL) and then the reaction mixture was extracted with $CH_2Cl_2$. The organic layers were combined and washed with aqueous $NaHCO_3$ solution, then washed with water and brine solution, dried ($Na_2SO_4$), and solvent was removed in vacuo. The crude material was purified by reverse phase HPLC. Lyophilization yielded the title compound, 1-[7-Methoxy-3-(3-methoxy-phenylamino)-2,4-dihydro-indeno[1,2-c]pyrazol-6-yloxy]-3-pyrrolidin-1-yl-propan-2-ol as a white powder. MS m/z 451 $(M+H)^+$; $^1$HNMR (DMSO-$d_6$): 1.89(m, 2H), 2.02(m, 2H), 3.12(m, 2H), 3.34(m, 2H), 3.45(s, 2H), 3.62(s, 2H), 3.70(s, 3H), 3.85(s, 3H), 4.00(m, 2H), 4.20(m, 2H), 6.37(d, 1H), 6.71(d, 1H), 6.78(s, 1H), 7.10(t, 1H), 7.25(s, 1H), 7.3(s, 1H), 8.68(br s, 1H), 9.60(br s, 1H).

EXAMPLE 23

5,6-Dihydroxy-indan-1-one, Intermediate O

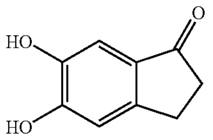

A solution of 5,6-dimethoxyindan-1-one (Compound 3a) (19 g, 0.094 mole) in 200 mL of methylene chloride was cooled at −78° C. with a dry-ice/iPrOH bath. To this solution was then added 200 mL (0.2 mole) of a 1M solution of $BBr_3$ in $CH_2Cl_2$ dropwise. The resulting solution was stirred at −78° C. for 1 hr and then at 0° C. for 1 hr. The solution was then cooled back to −78° C. with a dry-ice/iPrOH bath and quenched with 50 mL of MeOH. The solution was evaporated on a rotary evaporator to dryness, the solid was re-dissolved in MeOH and concentrated again for two more times. The red solid, the title compound, was used in subsequent reactions without further purification. MS m/z 165 $(M+H)^+$.

EXAMPLE 24

5,6-Diethoxy-indan-1-one, Intermediate P

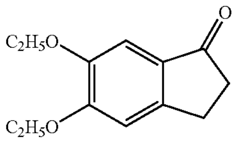

A mixture of 5,6-dihydroxy-indan-1-one (Intermediate O) (24 g, 0.146 mole), potassium carbonate (60 g, 0.43 mole) and diethyl bromide (56 mL, 0.75 mole) in DMF (200 mL) was stirred at 60° C. for 14 hrs. Water (150 mL) was added to the reaction and the reaction mixture was then extracted with ethyl acetate (2×150 mL). The ethyl acetate extracts were washed with saturated $NaHCO_3$, brine and dried over $Na_2SO_4$. The solvent was then removed in vacuo to yield the title compound as a brown solid. MS m/z 221 $(M+H)^+$.

EXAMPLE 26

4-[3-(3-Fluoro-phenylamino)-6,7-dimethoxy-4H-indeno[1,2-c]pyrazol-1-yl]-4-oxo-butyric acid methyl ester, Compound 428 (Method M)

Compound 14

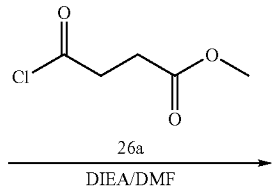

-continued

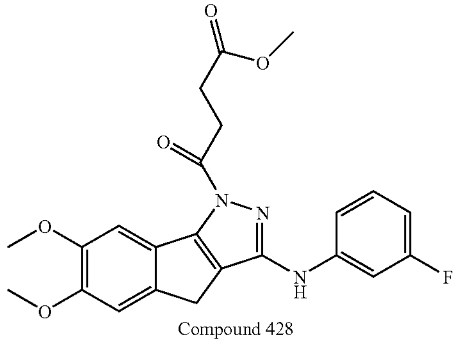

Compound 428

To a mixture of (6,7-Dimethoxy-1,4-dihydro-indeno[1,2-c]pyrazol-3-yl)-(3-fluoro-phenyl)-amine (Compound 14) (0.50 g, 1.5 mmol), 3-Chlorocarbonyl-propionic acid methyl ester (Compound 26a) (0.277 g, 1.8 mmole) and DMF (1.5 mL) was added Diisopropylethylamine (DIEA) (0.52 mL, 3.0 mmole) at room temperature with stirring. The reaction was stirred at room temperature over night. The reaction was quenched with water and extracted with EtOAc. The solvent was removed via rotovap and the crude material was prepped on the reverse phase HPLC. Lyophilization gave the title compound as a white powder. MS m/z439.9 $(M+H)^+$;

$^1$HNMR (DMSO-$d_6$): 2.78(t, 2H), 3.32(t, 2H), 3.45(s, 2H), 3.62(s, 3H), 3.79(s, 6H), 6.64(m, 1H), 7.15(s, 1H), 7.30(m, 2H), 7.62(d, 1H), 7.70(s, 1H), 9.45(s, 1H).

EXAMPLE 27

1-[3-(3-Fluoro-phenylamino)-6,7-dimethoxy-4H-indeno[1,2-c]pyrazol-1-yl]-2-hydroxy-ethanone, Compound 432 (Method M)

Compound 14

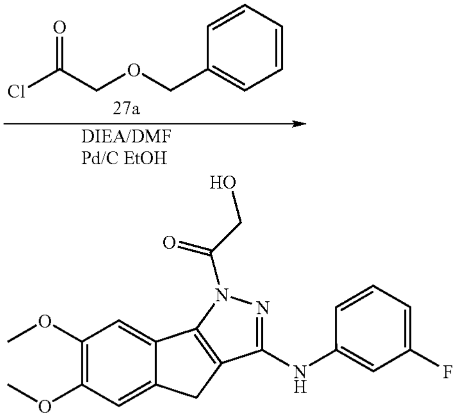

Compound 432

To a mixture of (6,7-Dimethoxy-1,4-dihydro-indeno[1,2-c]pyrazol-3-yl)-(3-fluoro-phenyl)-amine (Compound 14) (3.6 g, 10.0 mmol), Benzyloxy-acetyl chloride (Compound 27a) (2.2 g, 12.0 mmole) and DMF (50 mL) was added Diisopropylethylamine (5.2 mL, 30 mmole) at room temperature with stirring. The reaction was stirred at room temperature over night. The reaction was quenched with water and extracted with EtOAc. Dried over sodium sulfate and removed solvent in vacuo. The crude material was then taken up into ethanol and 0.5 g of Pd/C was added. The reaction was shaken on the hydrogenator over night. The reaction was filtered through Celite and removed solvent in vacuo. Triturated in a small amount of EtOAc. 3.2 g of ~90% pure material was produced. 300 mg of the crude material was prepped on the Gilson and lyophilization gave Compound 432 as a white powder. MS m/z 384 $(M+H)^+$;

$^1$HNMR (DMSO-$d_6$): 3.55(s, 2H), 3.82(s, 6H), 4.87(s, 2H), 5.40(br s, 1H), 6.65(m, 1H), 7.24(m, 3H), 7.58(d, 1H), 7.92(s, 1H), 9.50(s, 1H).

EXAMPLE 28

1-[3-(3-Fluoro-phenylamino)-6,7-dimethoxy-4H-indeno[1,2-c]pyrazol-1-yl]-3-pyrrolidin-1-yl-propane-1,3-dione, Compound 536 (Method N)

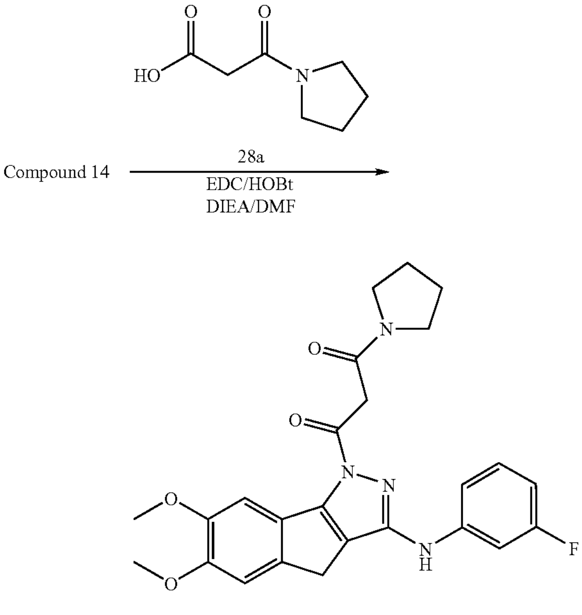

Compound 536

A mixture of (6,7-Dimethoxy-1,4-dihydro-indeno[1,2-c]pyrazol-3-yl)-(3-fluoro-phenyl)-amine (Compound 14) (0.36, 1.0 mmol), 3-Oxo-3-pyrrolidin-1-yl-propionic acid (Compound 28a) (0.157 g, 1.0 mmole), 1-(3-Dimethylaminopropyl)-3-ethylcarbodiimide (EDC) (0.24 g, 1.25 mmol), hydroxybenzo-triazole hydrate (HOBT) (0.17 g, 1.25 mmol) and DIEA (0.220 mL, 1.25 mmol) was stirred in 10 mL DMF over night at room temperature. The reaction was quenched with saturated $NaHCO_3$ and extracted with EtOAc. The solvent was removed in vacuo and the crude material was prepped on the Gilson. Lyophilization produced a white powder. MS m/z 465.1 $(M+H)^+$;

$^1$HNMR (DMSO-$d_6$): 1.82(m, 2H), 1.98(m, 2H), 3.34(s, 2H), 3.59(m, 4H), 3.79(s, 3H), 3.80(s, 3H), 4.09(s, 2H), 6.67(t, 1H), 7.27(m 3H), 7.65(d, 1H), 8.89(s, 1H), 9.50(s, 1H).

EXAMPLE 29

1-[3-(3-Fluoro-phenylamino)-6,7-dimethoxy-4H-indeno[1,2-c]pyrazol-2-yl]-3-pyrrolidin-1-yl-propane-1,3-dione, Compound 535 (Method N)

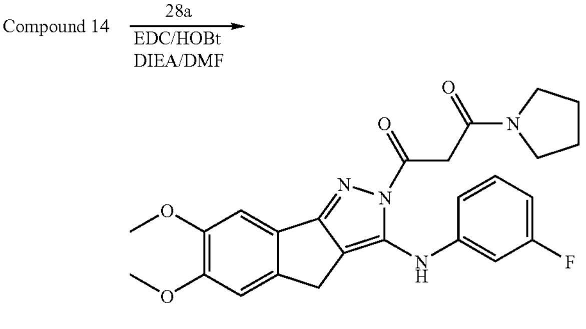

Compound 535

A mixture of (6,7-Dimethoxy-1,4-dihydro-indeno[1,2-c]pyrazol-3-yl)-(3-fluoro-phenyl)-amine (Compound 14) (0.36, 1.0 mmol), 3-Oxo-3-pyrrolidin-1-yl-propionic acid (Compound 28a) (0.157 g, 1.0 mmole), EDC (0.24 g, 1.25 mmol), HOBt (0.17 g, 1.25 mmol), and DIEA (0.220 mL, 1.25 mmol) was stirred in 10 mL DMF over night at room temperature. The reaction was quenched with saturated $NaHCO_3$ and extracted with EtOAc. The solvent was removed in vacuo and the crude material was prepped on the Gilson. Lyophilization produced Compound 535 as a white powder. MS m/z 465.1 $(M+H)^+$;

$^1$HNMR (DMSO-$d_6$): 1.82(m, 2H), 1.98(m, 2H), 3.34(s, 2H), 3.59(m, 4H), 3.79(s, 3H), 3.80(s, 3H), 4.09(s, 2H), 6.67(t, 1H), 7.27(m 3H), 7.65(d, 1H), 8.89(s, 1H), 9.50(s, 1H).

EXAMPLE 30

5-Hydroxy-6-methoxy-4-nitro-indan-1-one, Intermediate Q

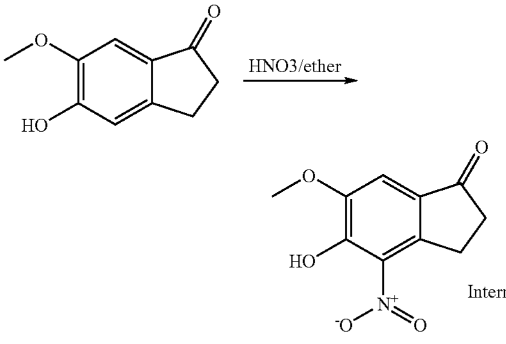

Intermediate Q

The intermediate H was a known compound and was prepared according to the literature procedure described in Jose M. saa, etal J. Org Chem., 57(2), 589, 1992. 5-Hydroxy-6-methoxy-indan-1-one (Intermediate H) (3.0 g. 0.017 mol) was taken into 100 mL diethyl ether and 7.5 mL of nitric acid was added dropwise. The reaction stirred at room temperature for two hours. The reaction was complete by HPLC. The precipitate was filtered off and washed with ether. 3.2 g of a yellow solid (Intermediate Q) was produced. MS m/z 224 $(M+H)^+$;

$^1$HNMR (DMSO-$d_6$): 2.64(m, 2H), 3.15(m, 2H), 3.92(s, 3H), 7.32(s, 1H), 11.75(s, 1H).

EXAMPLE 31

4-Amino-5-hydroxy-6-methoxy-indan-1-one, Intermediate R

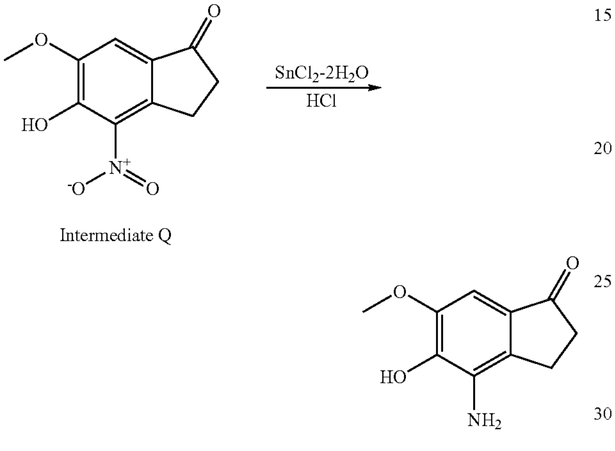

Intermediate Q

Intermediate R

The intermediate Q was a known compound and was prepared according to the literature procedure described in Jose M. saa, etal J. Org Chem., 57(2), 589, 1992. 5-Hydroxy-6-methoxy-4-nitro-indan-1-one (Intermediate Q) (2.0 g, 9.0 mmol) was added to the tinchloride dihydrate (10.0 g, 44 mmol) in 30 mL conc. HCl over an ice bath. The reaction stirred at room temperature overnight. The reaction was complete by HPLC. The reaction was quenched with water and made neutral with solid NaOH pellets. The solid precipitate that formed was filtered off through Celite. The aqueous layer was extracted with EtOAc, washed with brine, and dried over sodium sulfate. The solvent was removed via rotovap to produce 1.5 g of Intermediate R as a yellow solid. MS m/z 194 $(M+H)^+$;

$^1$HNMR (DMSO-$d_6$): 2.42(m, 2H), 2.76(m, 2H), 3.71(s, 3H), 6.50(s, 1H).

EXAMPLE 32

4-Methoxy-2-methyl-7,8-dihydro-indeno[4,5d]oxazol-6-one, Intermediate S

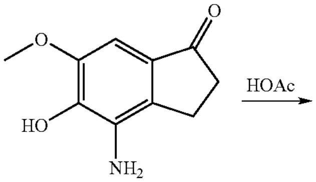

-continued

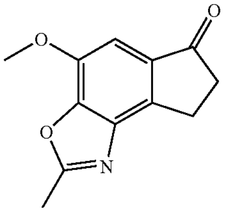

The intermediate R was a known compound and was prepared according to the literature procedure described in Jose M. saa, etal J. Org Chem., 57(2), 589, 1992. 4-Amino-5-hydroxy-6-methoxy-indan-1-one (Intermediate R) (1.5 g, 7.8 mmol) was taken into 40 mL of glacial acetic acid and gently refluxed overnight. Reaction not complete by HPLC so the reaction was continued for one more day. Quenched with water, made basic with 3N NaOH and extracted with EtOAc. Washed with brine, dried over $Na_2SO_4$ and removed solvent in vacuo. 1.2 g of a dark solid (Intermediate Q) was produced; MS m/z 218 $(M+H)^+$.

EXAMPLE 33

(3-Fluoro-phenyl)-(4-methoxy-2-methyl-7,9-dihydro-3-oxa-1,6,7-triaza-cyclopenta[b]-as-indacen-8-yl)-amine, Compound 605 (Method A)

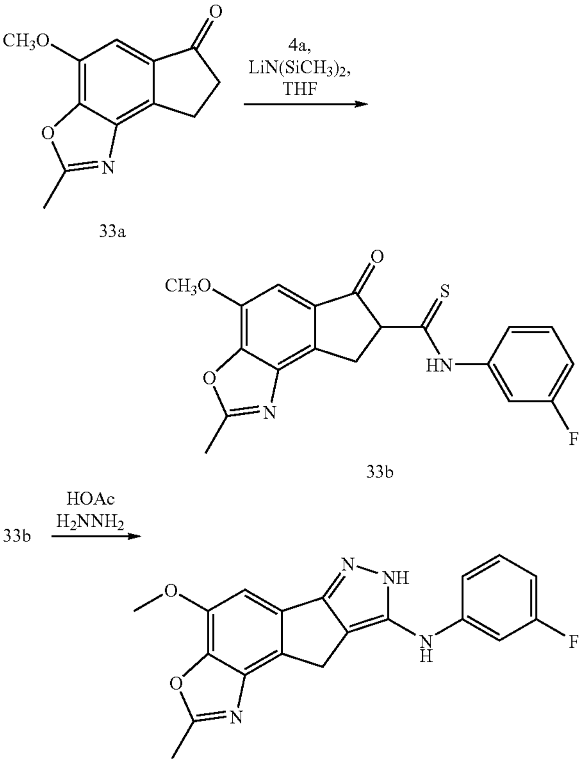

Compound 605

A mixture of 4-Methoxy-2-methyl-7,8-dihydro-indeno[4,5-d]oxazol-6-one (Compound 33a) (0.22 g, 0.001 mole), 3-fluoro-phenyl isothiocyanate (Compound 4a) (0.14 mL, 0.0011 mole) and THF (1.5 mL) was added to lithium hexamethyldisilane (1.2 mL, 0.0012 mole) dropwise at room temperature with stirring. The reaction mixture was stirred for 4 hrs to provide an intermediate product (Compound 33b) which was not isolated. Hydrazine (0.070 mL, 0.0022 mole) and acetic acid (0.132 mL, 0.0022 mole) were added to the reaction mixture, which was then heated at the reflux temperature for 18 hrs. The resulting mixture was first added to water (10 mL) and then extracted with EtOAc. The organic layers were combined and washed with aqueous $NaHCO_3$ solution, then washed with water and brine solution, dried ($Na_2SO_4$), and solvent was removed in vacuo. The crude material was prepped on the reverse phase HPLC. Lyophilization produced Compound 605 as a white powder. MS m/z 351.1 $(M+H)^+$;

$^1$HNMR (DMSO-$d_6$): 2.62(s, 3H), 3.60(s, 2H), 4.05(s, 3H), 6.54(t, 1H), 6.98(d, 1H), 7.22(m, 3H), 8.87(br, 1H).

EXAMPLE 34

5,6-Dimethoxy-4-nitro-indan-1-one, Intermediate T

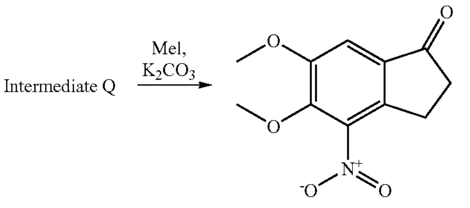

Intermediate T

5-Hydroxy-6-methoxy-4-nitro-indan-1-one (Intermediate Q) (4.4 g, 0.02 mol) and potassium carbonate (2.7 g, 0.02 mol) were taken up into DMF. Methyl iodide (5.0 mL, 0.08 mol) was added and the reaction stirred at room temperature overnight. Only 15% conversion by HPLC so the reaction was continued for 4 more days at 50° C. Quenched the reaction with water and extracted with EtOAc. Washed with brine, dried over $Na_2SO_4$ and removed solvent in vacuo. 3.4 g of crude material (Intermediate T) was produced. MS m/z 238 $(M+H)^+$.

EXAMPLE 35

4-Amino-5,6-dimethoxy-indan-1-one, Intermediate U

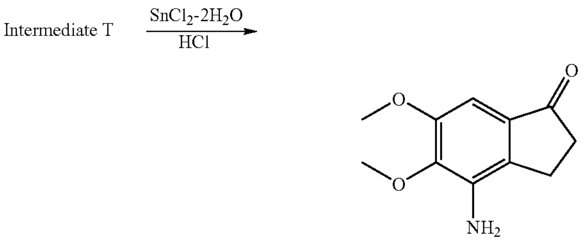

Intermediate U 5,6-Dimethoxy-4-nitro-indan-1-one (Intermediate T) (2.0 g, 8.4 mmol) was added to the tinchloride dihydrate(10.0 g, 44 mmol) in 30 mL conc. HCl over an ice bath. The reaction stirred at room temperature overnight. The reaction was complete by HPLC. The reaction was quenched with water and made neutral with solid NaOH pellets. The solid precipitate that formed was filtered off through Celite. The aqueous layer was extracted with EtOAc, washed with brine, and dried over sodium sulfate. The solvent was removed via rotovap to produce 1.2 g of yellow solid (Intermediate U). MS m/z 208 $(M+H)^+$;

$^1$HNMR ($CDCl_3$): 2.69(m, 2H), 2.80(m, 2H), 3.84(s, 3H), 3.87(s, 3H), 4.02(s, 2H), 6.72(s, 1H).

EXAMPLE 36

N-(5,6-Dimethoxy-1-oxo-indan-4-yl)-acetamide, Intermediate V

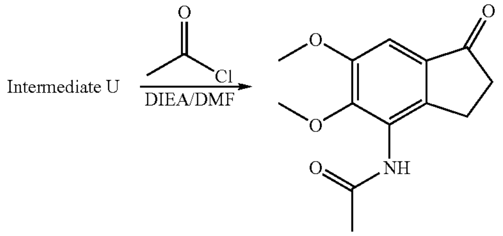

Intermediate V

4-Amino-5,6-dimethoxy-indan-1-one (Intermediate U) (0.214 g, 1.0 mmol) was taken up into 5 mL of DMF and acetyl chloride (0.071 mL, 1.0 mmol) and DIEA (0.18 mL, 1.0 mmol) were added. The reaction stirred overnight at room temperature. The reaction was quenched with sat. sodium bicarbonate and extracted with EtOAc. The organic layer was washed with brine, dried over Na2SO4 and removed in vacuo. 0.25 g of the crude material was produced (Intermediate V); MS m/z 250.1 $(M+H)^+$.

EXAMPLE 37

N-[3-(3-Fluoro-phenylamino)-6,7-dimethoxy-2,4-dihydro-indeno[1,2-c]pyrazol-5-yl]-acetamide, Compound 557 (Method A)

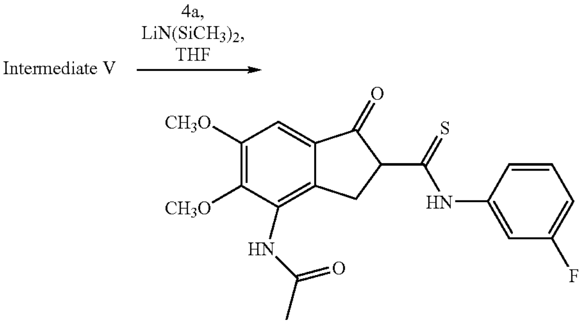

37a

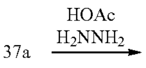

-continued

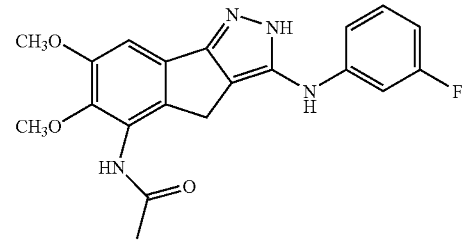

Compound 557

A mixture of N-(5,6-Dimethoxy-1-oxo-indan-4-yl)-acetamide (Intermediate V) (0.25 g, 0.001 mole), 3-fluoro-phenyl isothiocyanate (Compound 4a) (0.14 mL, 0.0011 mole) and THF (1.5 mL) was added to lithium hexamethyldisilane (1.2 mL, 0.0012 mole) dropwise at room temperature with stirring. The reaction mixture was stirred for 4 hrs to provide an intermediate product (Compound 37a) which was not isolated. Hydrazine (0.070 mL, 0.0022 mole) and acetic acid (0.132 mL, 0.0022 mole) were added to the reaction mixture then it was heated at the reflux temperature for 18 hrs. The resulting mixture was first added water (10 mL) and then extracted with EtOAc. The organic layers were combined and washed with aqueous $NaHCO_3$ solution, then washed with water and brine solution, dried ($Na_2SO_4$), and solvent was removed in vacuo. The crude material was prepped on the reverse phase HPLC. Lyophilization gave a white powder (Compound 557). MS m/z 383.1 $(M+H)^+$;

$^1$HNMR (DMSO-$d_6$): 2.07(s, 1H), 3.32(s, 1H), 3.40(s, 1H), 3.72(s, 3H), 3.89(s, 3H), 6.51(t, 1H), 6.92(t, 1H), 7.18(m, 3H), 8.87(br, 1H), 9.62(s, 1H).

EXAMPLE 38

3-(3-Fluoro-phenylamino)-6,7-dimethoxy-4H-indeno[1,2-c]pyrazole-1-carboxylic acid isopropyl ester, Compound 436 (Method O)

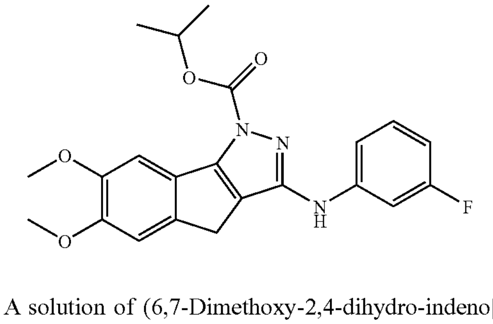

A solution of (6,7-Dimethoxy-2,4-dihydro-indeno[1,2-c]pyrazol-3-yl)-(3-fluoro-phenyl)-amine HCl (Compound 14) (0.50 g, 0.0014 mole), THF (10 mL), and Diisopropyl amine (0.512 mL, 0.00295 mole) was stirred until the solid completely dissolved. Isopropyl chloroformate (1.5 mL, 0.0015 mole) was added slowly at room temperature. The reaction mixture was stirred at room temperature overnight. The solvent was removed in vacuo from the resulting organics. Attempt to separate resulting isomers with reverse-phase chromatography was not successful. Placed isomer containing fractions in refrigerator. Much of major isomer crystallized. Filtered white crystals of title compound from solution (Compound 436). MS m/z 412 $(M+H)^+$;

$^1$HNMR (DMSO-$d_6$): 1.4 (d, 6H), 3.55 (s, 2H), 3.85 (s, 6H), 5.25 (sept, 1H), 6.65 (t, 1H), 7.25 (m, 3H), 7.65 (d, 1H), 7.8 (s, 1H), 9.4 (s, 1H).

EXAMPLE 39

3-(3-Fluoro-phenylamino)-6,7-dimethoxy-4H-indeno[1,2-c]pyrazole-1-carboxylic acid 2-methoxyethyl ester, Compound 438 (Method O)

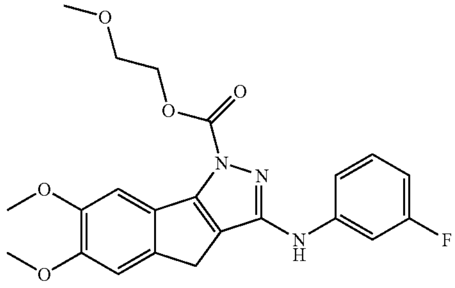

A solution of (6,7-Dimethoxy-2,4-dihydro-indeno[1,2-c]pyrazol-3-yl)-(3-fluoro-phenyl)-amine HCl (Compound 14) (0.50 g, 0.0014 mole), THF (10 mL), and Diisopropyl amine (0.512 mL, 0.00295 mole) was stirred until the solid completely dissolved. 2-Methoxyethyl chloroformate (0.178 mL, 0.00154 mole) was added dropwise at room temperature. After 2 hours of stirring, reaction was complete. Solvent was removed in vacuo and organic oil placed on reverse phase chromatography system for separation of the isomers. Separation was successful. Fractions were collected and lyophilized to yield a pale yellow solid (Compound 438). NMR showed the major isomer to be the title compound. MS m/z 428 $(M+H)^+$;

$^1$H NMR (DMSO-$d_6$): 3.35 (s, 3H), 3.6 (s, 2H), 3.75 (t, 2H), 3.85 (d, 6H), 4.6 (t, 2H), 6.7 (m, 1H), 7.3 (m, 3H), 7.7 (d, 1H), 7.8 (s, 1H), 9.4 (s, 1H).

EXAMPLE 40

3-(3-Fluoro-phenyl-amino)-6,7-dimethoxy-4H-indeno[1,2-c]pyrazole-2-carboxylic acid 2-methoxyethyl ester, Compound 437 (Method O)

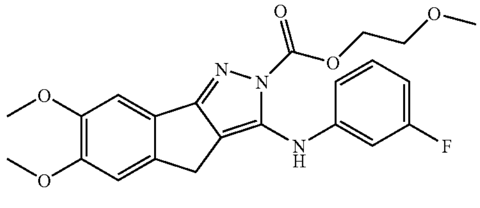

A solution of (6,7-Dimethoxy-2,4-dihydro-indeno[1,2-c]pyrazol-3-yl)-(3-fluoro-phenyl)-amine HCl (Compound 14) (0.50 g, 0.0014 mole), THF (10 mL), and Diisopropyl amine (0.512 mL, 0.00295 mole) was stirred until the solid completely dissolved. 2-Methoxyethyl chloroformate (0.178 mL, 0.00154 mole) was added dropwise at room temperature. After 2 hours of stirring, reaction was complete. Solvent was removed in vacuo and organic oil placed on reverse phase chromatography system for separation of the isomers. Separation was successful. Fractions were collected and lyophilized to yield a pale yellow solid (Compound 437). NMR showed the minor isomer to be the title compound. MS m/z 428 $(M+H)^+$;

$^1H$ NMR (DMSO-$d_6$): 3.35 (s, 3H), 3.4 (s, 2H), 3.7 (t, 2H), 3.8 (s, 3H), 3.9(s, 3H), 4.5 (t, 2H), 6.85 (t, 1H), 7.0 (m, 2H), 7.2 (s, 1H), 7.35 (m, 2H), 8.9 (s, 1H).

EXAMPLE 41

3-(3-Fluoro-phenyl-amino)-6,7-dimethoxy-4H-indeno[1,2-c]pyrazole-1-carboxylic acid 2-[2-(2-hydroxy-ethoxy)-ethoxy]-ethyl ester, Compound 471 (Method O)

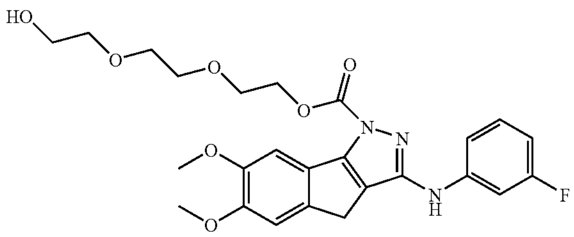

Two flasks were set up containing 50 mL of THF in each. Added (6,7-Dimethoxy-2,4-dihydro-indeno[1,2-c]pyrazol-3-yl)-(3-fluoro-phenyl)-amine HCl (Compound 14) (0.50 g, 0.0014 mole) and diisopropyl amine (0.512 mL, 0.00295 mole) to the first flask which was stirred under argon until the solid completely dissolved. Tri(ethyleneglycol) bis(chloroformate) (1.134 mL, 0.0055 mole) was added to the second flask and placed in dry ice/isopropyl alcohol bath under argon. The first flask was then added all at once to the second flask. Reaction was complete within 10 minutes. The reaction was allowed to come to room temperature. Solvent was removed in vacuo. The resulting brown oil was taken up in ethyl acetate and dichloromethane and washed with sodium bicarbonate. The resulting organics were dried (sodium sulfate), filtered, and the solvent was removed in vacuo. The major isomer (Compound 471) was separated from the minor by reverse phase chromatography. By $^1H$ NMR, the free chloroformate had hydrolyzed to the alcohol in the DMSO used to load the reverse phase column. Fractions of each isomer were collected and lyophilized. MS m/z 502 $(M+H)^+$;

$^1H$ NMR (DMSO-$d_6$): 3.3–3.7 (m, 12H), 3.85 (d, 6H), 4.6 (m, 2H), 6.7 (m, 1H), 7.3 (m, 3H), 7.7 (d, 1H), 7.8 (s, 1H), 9.4 (s, 1H).

EXAMPLE 42

(6,7-dimethoxy-1-methyl-1,4-dihydro-indeno[1,2-c]pyrazole-3-yl)-(3-fluoro-phenyl-amine, Compound 609 (Method L)

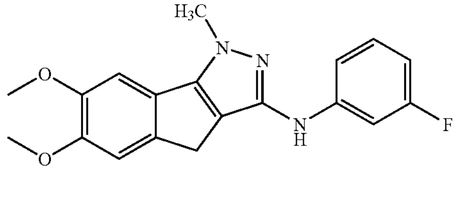

Iodomethane (0.141 g, 0.001 mole) was added to a mixture of (3-Fluoro-phenyl)-6,7-dimethoxy-2,4-dihydro-indeno[1,2-c]1-N-methyl-pyrazol-3-yl)-amine (Compound 14) (321 mg, 0.001 mole), diisopropylethylamine (0.129 g, 0.001 mole), and DCM (5 mL). The reaction mixture was stirred at room temperature with stirring for 18 hrs. The resulting mixture was first added to water (5 mL) and then extracted with $CH_2Cl_2$. the organic layers were combined and washed with aqueous $NaHCO_3$ solution, then wash with water, dried over $(Na_2SO_4)$, and solvent was removed in vacuum. The mixture contained two isomers based on hplc/ms analysis. The mixture was separated by HPLC with C-18 reversed phase column and $CH_3CN$—$H_2O$-TFA as gradient solvent. The title compound (Compound 609; major isomer) was obtained as a solid TFA salt.

HPLC: 100% (uv 214 mμ); MS m/z 340 $(M+H)^+$;

$^1$HNMR ($CDCl_3$-$d_1$): 3.33 (s, 2H), 3.84 (s, 3H), 3.90 (s, 3H), 3.95 (s, 3H), 6.48 (t, 1H), 6.66 (d, 1H), 6.57 (d, 1H), 7.0 (s, 1H), 7.1 (t, 2H).

EXAMPLE 43

(6,7-dimethoxy-2-methyl-1,4-dihydro-indeno[1,2-c]pyrazole-3-yl)-(3-fluoro-phenyl)-amine, Compound 610 (Method L)

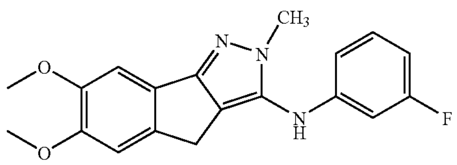

Iodomethane (0.141 g, 0.001 mole) was added to a mixture of (3-Fluoro-phenyl)-6,7-dimethoxy-2,4-dihydro-indeno [1,2-c] 1-N-methyl-pyrazol-3-yl)-amine (Compound 14) (321 mg, 0.001 mole), diisopropylethylamine (0.129 g, 0.001 mole), and DCM (5 mL). The reaction mixture was stirred at room temperature with stirring for 18 hrs. The resulting mixture was first added to water (5 mL) and then extracted with $CH_2Cl_2$. the organic layers were combined and washed with aqueous $NaHCO_3$ solution, then wash with water, dried over $(Na_2SO_4)$, and solvent was removed in vacuum. The mixture contained two isomers based on hplc/ms analysis. The mixture was separated by HPLC with C-18 reversed phase column and $CH_3CN$—$H_2O$-TFA as gradient solvent. The title compound (Compound 610; minor isomer) was obtained as a solid TFA salt. MS m/z 340 $(M+H)^+$;

$^1$HNMR ($CDCl_3$-$d_1$): 3.33 (s, 2H), 3.74 (s, 3H), 3.84 (s, 3H), 3.88 (s, 3H),6.37 (d, 1H), 6.46 (d, 1H), 6.53 (t, 1H), 7.0 (s, 1H), 7.1 (t, 1H), 7.2 (s, 1H).

EXAMPLE 44

3-(3-Fluoro-phenylamino)-6,7-dimethoxy-4H-indeno[1,2-c]pyrazole-2-carboxylic acid (3-fluoro-phenyl)-amide, Compound 395 (Method Q)

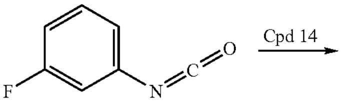

44a

-continued

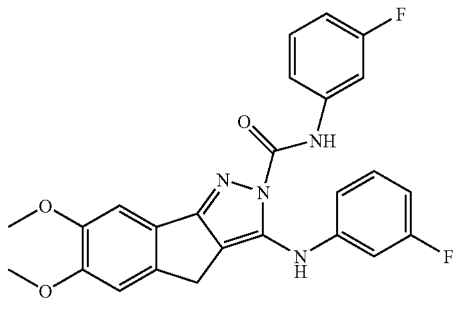

Compound 395

To a mixture of (3-Fluoro-phenyl)-6,7-dimethoxy-2,4-dihydro-indeno[1,2-c]1-N-methyl-pyrazol-3-yl)-amine (Compound 14) (321 mg, 0.001 mole), diisopropylethylamine (0.129 g, 0.001 mole), and DCM (5 mL) was added 3-fluorophenylisocyanate (Compound 44a) (0.137 g 0.001 mole). The reaction mixture was stirred at room temperature with stirring for 18 hrs. The resulting mixture was first added to water (5 mL) and then extracted with $CH_2Cl_2$. the organic layers were combined and washed with aqueous $NaHCO_3$ solution, then wash with water, dried over ($Na_2SO_4$), and solvent was removed in vacuum. The title compound was purified by HPLC with C-18 reversed phase column and $CH_3CN$—$H_2O$-TFA as gradient solvent. The title compound was obtained as a solid TFA salt. MS m/z 463 $(M+H)^+$;

$^1$HNMR ($CDCl_3$-$d_1$): 3.33 (s, 2H), 3.74 (s, 3H), 3.84 (s, 3H), 3.88 (s, 3H),6.377 (m, 1H), 7.21 (s 1H), 7.33 (m, 3H),7.4 (m, 2H), 7.6 (d, 1H), 7.85 (s, 1H), 7.9 (m, 1H), 9.31 (s, 1H), 9.54 (s, 1H).

EXAMPLE 46

(2-Chloro-pyrid-3-yl)-(6,7-dimethoxy-2,4-dihydro-indeno[1,2-c]pyrazol-3-yl)-amine, Compound 377 (Method B)

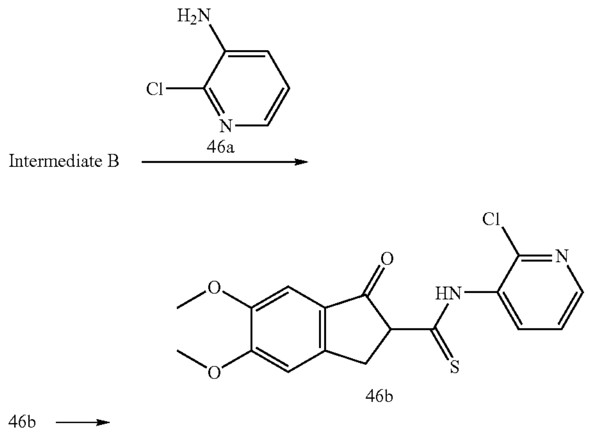

-continued

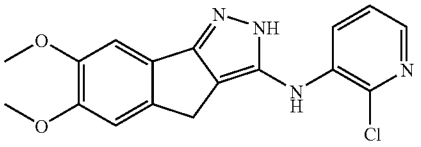

Compound 377

To a solution of 2-(Imidazole-1-carbothioyl)-5,6-dimethoxy-indan-1-one (Intermediate B) (0.302 g, 0.001 mole) (prepared as in example 5), was mixed with 3-amino-2-chloropyridine (Compound 46a) (0.128 g, 0.001 mole) and 10 mL THF in a flask. 5,6-Dimethoxy-1-oxo-indan-2-carbothioic acid (4-chloro-N-methyl-phenyl)-amide (Compound 46b) was obtained after stirring the reaction mixture for 4 hrs at room temperature as shown by HPLC/MS, HPLC/MS m/z 362 $(M+H)^+$.

The intermediate (Compound 46b) was not isolated and the mixture was subsequently treated with hydrazine (0.04 mL, 1.3 mmol), and acetic acid (2 drops). The reaction was heated at 75° C. for 18 hrs. The reaction solution was then diluted with $CH_2Cl_2$, and washed with aqueous $NaHCO_3$ solution, then wash with water, dried over ($Na_2SO_4$), and solvent was removed in vacuum. The title compound was purified by HPLC with C-18 reversed phase column and $CH_3CN$—$H_2O$-TFA as gradient solvent. The title compound (Compound 529) was obtained as a solid TFA salt. MS m/z 343 $(M+H)^+$;

$^1$HNMR ($CDCl_3$-$d_1$): 3.33 (s, 2H), 3.84 (s, 3H), 3.88 (s, 3H), 6.77 (t, 1H), 6.86 (d 1H), 7.6 (d, 1H), 7.9 (d, 1H), 8.23 (s, 1H).

EXAMPLE 47

5,6-Dimethoxy-3-ethyl-indan-1-one, Intermediate W

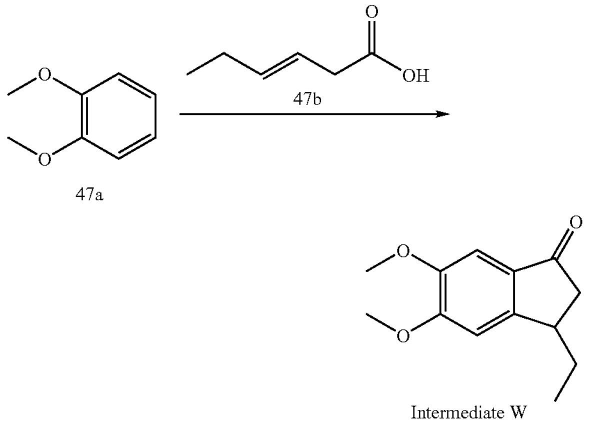

A mixture of 1,2-dimethoxy-benzene (Compound 47a) (21.9 mL, 0.170 mole) and pent-3-enoic acid (Compound 47b) (25.5 g, 0.255 mole) was stirred under argon in an ice bath. Polyphosphoric acid (230 g, 1.05 mole) was added slowly. After addition was complete, the ice bath was removed and the reaction heated for 16 hours at 60° C. The reaction was added to ice water and extracted with dichloromethane. The organic extracts were washed with 3N NaOH, water, brine and dried over $Na_2SO_4$. The solvent was then removed in vacuo to yield a red oil containing the crude title compound. The crude material was purified on a silica gel column using dichloromethane as eluent. The pure fractions were combined and concentrated to yield the racemic mixture of the title compound as an off-white solid. MS m/z 221 $(M+H)^+$;

HPLC: 99% pure (UV);

$^1$HNMR: 0.9 (t, 3H), 1.4 (m, 1H), 2.0 (m, 1H), 2.2 (d of d, 1H), 2.7 (d of d, 1H), 3.2 (m, 1H), 3.8 (s, 1H), 3.9 (s, 1H), 7.0 (s, 1H), 7.2 (s, 1H).

EXAMPLE 48

*R-5,6-Dimethoxy-3-ethyl-indan-1-one, Intermediate W(*R); *S-5,6-Dimethoxy-3-ethyl-indan-1-one, Intermediate W(*S)

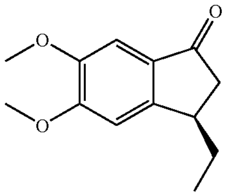

Intermediate W(*S)

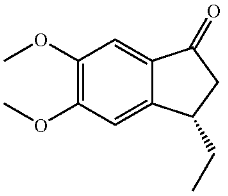

Intermediate W(*R)

The racemic mixture, prepared in Example 47, was for chiral separation. The separation was done on a ChiralpackAD column (500 g, 5 cm ID and 41 cm length) using hexane/ethanol:88/12 isocratically as the eluent. The pure enantiomers were collected and solvent removed in vacuo to yield off white crystals of the title compounds. MS m/z 221 $(M+H)^+$;

HPLC: 99% pure (UV);

$^1$HNMR: 0.9 (t, 3H), 1.4 (m, 1H), 2.0 (m, 1H), 2.2 (d of d, 1H), 2.7 (d of d, 1H), 3.2 (m, 1H), 3.8 (s, 1H), 3.9 (s, 1H), 7.0 (s, 1H), 7.2 (s, 1H).

*R and *S configurations are as drawn. The absolute configurations are not determined.

*R isomer has rotation: α(MeOH)=−20.55

*S isomer has rotation: α(MeOH)=+18.60

EXAMPLE 49

5,6-Dimethoxy-3-methyl-indan-1-one, Intermediate X

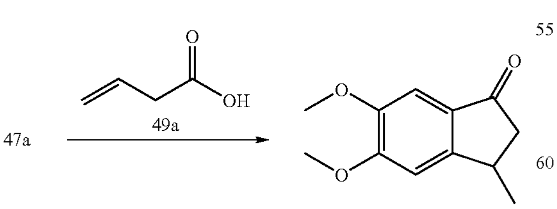

Intermediate X

A mixture of 1,2-dimethoxy-benzene (Compound 47a) (19.1 mL, 0.150 mole) and but-3-enoic acid (Compound 49a) (19.2 mL, 0.225 mole) was stirred under argon in an ice bath. Polyphosphoric acid (230 g, 1.05 mole) was added slowly. After addition was complete, the ice bath was removed and the reaction heated for 16 hours at 60° C. The reaction was added to ice water and extracted with ether. The organic extracts were washed with 3N NaOH, water, brine and dried over $Na_2SO_4$. The solvent was then removed in vacuo to yield a yellow solid containing a racemic mixture of the title compounds. The crude material was purified on a silica gel column using 1:2 EtOAc:hexane as the eluents. The pure fractions were combined and concentrated to yield the racemic mixture of the title compound (Intermediate X) as an off-white solid.

MS m/z 207 $(M+H)^+$;

$^1$HNMR: 1.3 (d, 3H), 2.1 (d of d, 1H), 2.8 (d of d, 1H), 3.3 (m, 1H), 3.8 (s, 3H), 3.9 (s, 3H), 7.0 (s, 1H), 7.2 (s, 1H).

EXAMPLE 50

(3R)-(5,6-dimethoxy-3-methyl)-indan-1-one, Intermediate X(*R); (3S)-(5,6-dimethoxy-3-methyl)-indan-1-one, Intermediate X(*S)

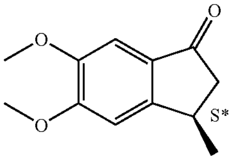

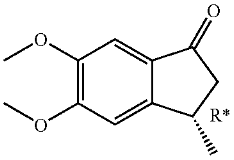

The racemic mixture (Intermediate X), prepared in Example 49, was for chiral separation. The separation was done on a Chiralpack AD column (500 g, 5 cm ID and 41 cm length) using hexane/ethanol:88/12 isocratically as the eluent. The pure enantiomers were collected and solvent removed in vacuo to yield off white crystals of the title compound. MS m/z 207 $(M+H)^+$; HPLC: 97% pure (UV);

$^1$HNMR: 1.3 (d, 3H), 2.1 (d of d, 1H), 2.8 (d of d, 1H), 3.3 (m, 1H), 3.8 (s, 3H), 3.9 (s, 3H), 7.0 (s, 1H), 7.2 (s, 1H).

*R and *S configurations are as drawn. The absolute configurations are not determined.

*R isomer has rotation: α(MeOH)=−5.85

*S isomer has rotation: α(MeOH)=+6.00

EXAMPLE 51

(4R)-N-(3-bromo-phenyl)-(6,7-dimethoxy-4-methyl-2,4-dihydro-indeno[1,2-c]pyrazol-3-yl)-amine Compound 553 (Method A)

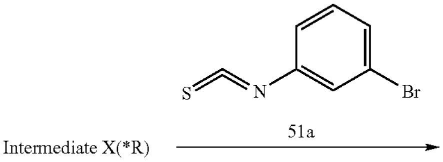

-continued

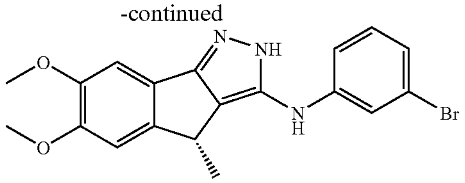

Compound 553

*R-5,6-Dimethoxy-3-methyl-indan-1-one (Intermediate X(*R)) (0.250 g, 0.0012 mole) was added to a flask under argon and stirred in THF until dissolved. Lithium hexamethyldisilane (1.22 mL, 0.00122 mole) was added dropwise. The solution stirred for 30 minutes until it turned deep red. 3-Br-isothiocyanate (Compound 51a) (0.261 g, 0.00122 mole) was added and the reaction became deeper red. Acetic acid (0.076 mL, 0.00132 mole) and hydrazine hydrate (0.059 mL, 0.00122 mole) were added. The reaction was refluxed at 80° C. for 18 hours. Upon completion, 1 mL of water was added to the reaction. The solution was poured over a drying column and extracted from the column using dichloromethane. The solvent was blown off with nitrogen gas and the crude material dissolved in DMSO for purification on reverse phase HPLC. The pure fractions were collected and lyophilized to yield the title compound (Compound 553) as a pale yellow solid. MS m/z 401 $(M+H)^+$;

HPLC: 100% pure (UV)

$^1$HNMR: 1.2(d, 3H), 3.7(q, 1H), 3.8(d, 6H), 7.0(m, 1H), 7.1(s, 1H), 7.2(d, 2H), 7.25(s, 1H), 7.55(s, 1H), 8.8(s, 1H).

*R isomer has rotation: α(MeOH)=+62.85

The absolute configuration has not been determined.

EXAMPLE 52

*S-(3-Bromo-phenyl)-(6,7-dimethoxy-4-methyl-2,4-dihydro-indeno[1,2-c]pyrazol-3-yl)-amine, Compound 568 (Method A)

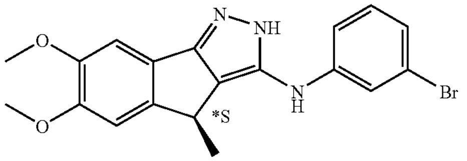

*S-5,6-Dimethoxy-3-methyl-indan-1-one (Intermediate X(*S)) (0.250 g, 0.0012 mole) was added to a flask under argon and stirred in THF until dissolved. Lithium hexamethyldisilane (1.22 mL, 0.00122 mole) was added dropwise. The solution stirred for 30 minutes until it turned deep red. 3-Br-isothiocyanate (Compound 51a) (0.261 g, 0.00122 mole) was added and the reaction became deeper red. Acetic acid (0.076 mL, 0.00132 mole) and hydrazine hydrate (0.059 mL, 0.00122 mole) were added. The reaction was refluxed at 80° C. for 18 hours. Upon completion, 1 mL of water was added to the reaction. The solution was poured over a drying column and extracted from the column using dichloromethane. The solvent was blown off with nitrogen gas and the crude material dissolved in DMSO for purification on reverse phase HPLC. The pure fractions were collected and lyophilized to yield the title compound (Compound 568) as a pale yellow solid. MS m/z 401 $(M+H)^+$;

HPLC: 100% pure (UV)

$^1$HNMR: 1.2(d, 3H), 3.7(q, 1H), 3.8(d, 6H), 7.0(m, 1H), 7.1(s, 1H), 7.2(d, 2H), 7.25(s, 1H), 7.55(s, 1H), 8.8(s, 1H).

*S isomer has rotation: α(MeOH)=−62.60

The absolute configuration has not been determined.

EXAMPLE 53

*R-(3-Bromo-phenyl)-(6,7-dimethoxy-4-ethyl-2,4-dihydro-indeno[1,2-c]pyrazol-3-yl)-amine Compound 555 (Method A)

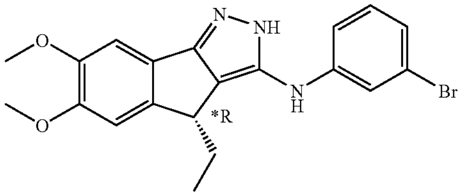

*R-5,6-Dimethoxy-3-ethyl-indan-1-one (Intermediate W(*R)) (0.250 g, 0.0011 mole) was added to a flask under argon and stirred in THF until dissolved. Lithium hexamethyldisilane (1.2 mL, 0.0012 mole) was added dropwise. The solution stirred for 30 minutes until it turned deep red. 3-Br-isothiocyanate (Compound 51a) (0.257 g, 0.0012 mole) was added and the reaction became deeper red. Acetic acid (0.069 mL, 0.00121 mole) and hydrazine hydrate (0.058 mL, 0.0012 mole) were added. The reaction was refluxed at 80° C. for 18 hours. Upon completion, 1 mL of water was added to the reaction. The solution was poured over a drying column and extracted from the column using dichloromethane. The solvent was blown off with nitrogen gas and the crude material dissolved in DMSO for purification on reverse phase HPLC. The pure fractions were collected and lyophilized to yield the title compound (Compound 555) as a pale yellow solid. MS m/z 415 $(M+H)^+$;

HPLC: 100% pure (UV);

$^1$HNMR: 0.5(t, 3H), 1.7(m, 1H), 1.8(m, 1H), 3.7(t, 1H), 3.8(d, 6H), 6.95(d, 1H), 7.1(d, 1H), 7.2(m, 3H), 7.3(s, 1H), 8.7(s, 1H).

*R isomer has rotation: α(MeOH)=+74.64

The absolute configuration has not been determined.

EXAMPLE 54

*S-(3-Bromo-phenyl)-(6,7-dimethoxy-4-ethyl-2,4-dihydro-indeno[1,2-c]pyrazol-3-yl)-amine, Compound 570 (Method A)

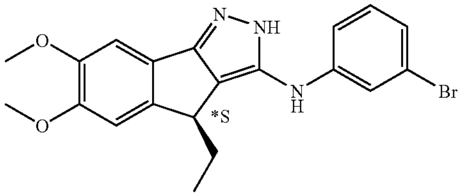

*S-5,6-Dimethoxy-3-ethyl-indan-1-one (Intermediate W(*S)) (0.250 g, 0.0011 mole) was added to a flask under argon and stirred in THF until dissolved. Lithium hexamethyldisilane (1.2 mL, 0.0012 mole) was added dropwise. The solution stirred for 30 minutes until it turned deep red. 3-Br-isothiocyanate (Compound 51a) (0.257 g, 0.0012 mole) was added and the reaction became deeper red. Acetic acid (0.069 mL, 0.00121 mole) and hydrazine hydrate (0.058 mL, 0.0012 mole) were added. The reaction was refluxed at 80° C. for 18 hours. Upon completion, 1 mL of water was added to the reaction. The solution was poured over a drying column and extracted from the column using dichloromethane. The solvent was blown off with nitrogen gas and the crude material dissolved in DMSO for purification on reverse phase HPLC. The pure fractions were collected and lyophilized to yield the title compound (Compound 570) as a pale yellow solid. MS m/z 415 $(M+H)^+$;

HPLC: 100% pure (UV);

$^1$HNMR: 0.5(t, 3H), 1.8(m, 2H), 3.7(t, 1H), 3.8(d, 6H), 6.95(d, 1H), 7.1(d, 1H), 7.2(m, 3H), 7.3(s, 1H), 8.7(s, 1H).

*S isomer has rotation: α(MeOH)=−53.85

The absolute configuration has not been determined.

EXAMPLE 55

3-(3-Fluoro-phenylamino)-6,7-dimethoxy-4H-indeno[1,2-c]pyrazole-1-carboxylic acid phenyl ester (Method O), Compound 433

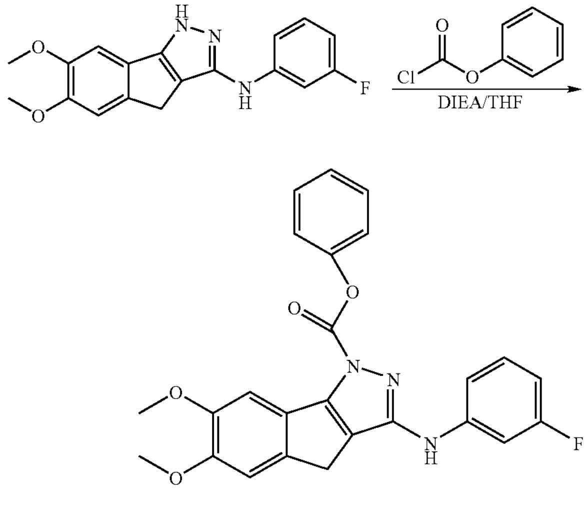

To a mixture of (6,7-Dimethoxy-1,4-dihydro-indeno[1,2-c]pyrazol-3-yl)-(3-fluoro-phenyl)-amine (Compound 14) (1.5 g g, 4.2 mmol), Phenyl chloroformate (Compound 55a) (0.76 mL, 6.3 mmole) and THF (10 mL) was added Diisopropylethylamine (DIPEA) (1.4 mL, 8.4 mmole) at room temperature with stirring. The reaction was stirred at room temperature over night. The reaction was quenched with saturated sodium bicarbonate and extracted with ethyl acetate. The solvent was dried over sodium sulfate and removed via rotovap to give a crude material (Compound 433). MS m/z 446.1 $(M+H)^+$.

EXAMPLE 56

3-(3-Fluoro-phenylamino)-6,7-dimethoxy-4H-indeno[1,2-c]pyrazole-1-carboxylic acid (2-methylamino-ethyl)-amide, Compound 524 (Method P)

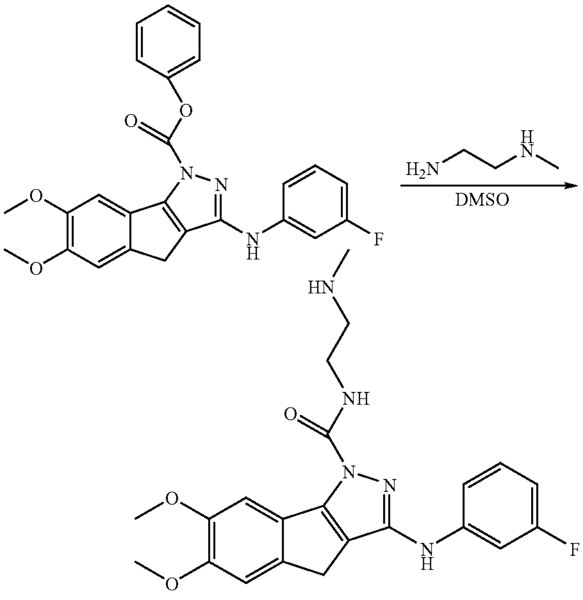

3-(3-Fluoro-phenylamino)-6,7-dimethoxy-4H-indeno[1,2-c]pyrazole-1-carboxylic acid phenyl ester (Compound 433) (0.50 g, 1.12 mmol) and N-1-Methyl-ethane-1,2-diamine (Compound 56a) (0.12 mL, 1.3 mmol) were taken up into 5 mL of DMSO. The reaction was stirred at room temperature over night. The reaction was quenched with sat. sodium bicarbonate and extracted with ethyl acetate.

The solvent was dried over sodium sulfate and removed via rotovap. The crude material was prepared on the Gilson HPLC and lyophilization produced the title compound as a TFA salt. MS m/z 426.3 $(M+H)^+$;

$^1$HNMR (DMSO-$d_6$): 2.60 (s, 3H), 3.12 (m, 2H), 3.24 (s, 2H), 3.58 (q, 2H), 3.78 (s, 3H), 3.81 (s, 3H), 6.55 (t, 1H), 7.21 (m, 2H), 7.32 (d, 1H), 7.49 (d, 1H), 7.90 (s, 1H), 8.15 (t, 1H), 8.60 (s, 1H), 9.22 (s, 1H).

EXAMPLE 57

(3-Fluoro-phenyl)-(2H-8-oxa-2,3-diaza-cyclopenta[a]inden-1-yl)-amine, Compound 380 (Method A)

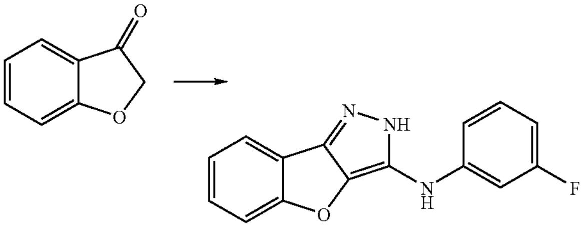

To a mixture of benzofuran-3-one (Compound 57a) (0.150 g, 0.00112 mol), 3-fluoro-phenyl isothiocyanate (Compound 4a) (0.259 g, 0.00134 mmol) and THF (2.00 mL) was added lithium hexamethyldisilane (1.34 mL, 0.00134 mol) dropwise at room temperature with stirring.

The reaction mixture was stirred for 12 h. Hydrazine (0.084 mL, 0.00268 mol) and acetic acid (0.154 mL, 0.00268 mol) was added to the reaction mixture, which was then heated at reflux temperature for 48 h. The reaction solution was then diluted with ethyl acetate, washed with water and dried over $MgSO_4$. The solvent was removed in vacuo and the title compound was purified by HPLC with a C-18 reversed phase column and $CH_3CN—H_2O$-TFA as gradient solvents. The title compound was obtained as a TFA salt. MS m/z 268 $(M+H)^+$;

$^1$HNMR (DMSO-$d_6$): 6.55(dt, 1H), 6.95(d, 1H), 7.05(d, 1H), 7.20(dd, 1H), 7.40(m, 2H), 7.65(d, 1H), 7.75(d, 1H), 9.00(br s, 1H).

EXAMPLE 58

2,2-Dimethyl-propionic acid 3-(3-fluoro-phenylamino)-6,7-dimethoxy-4H-indeno[1,2-c]pyrazol-1-ylm ethyl ester Compound 409 (Method L)

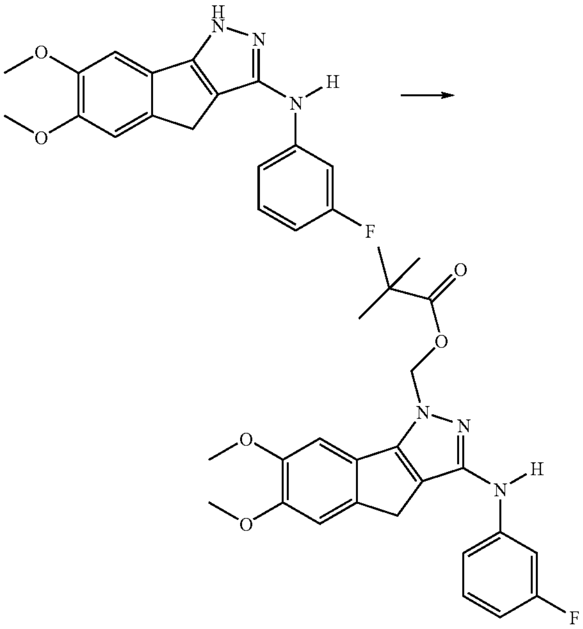

A mixture of (3-fluoro-phenyl)-6,7-dimethoxy-2,4-dihydro-indeno[1,2-c]pyrazol-3-yl)-amine (Compound 14) (1.25 g, 0.00385 mol) diisopropylethylamine (1.00 mL, 0.00578 mol), chloromethylpivalate (0.833 mL, 0.00578 mol) and potassium iodide (0.960 g, 0.00578 mol) in THF (19 mL) was heated to 75° C. for 12 h. The mixture was diluted with ethyl acetate and washed with brine and dried over $MgSO_4$. The title compound which came out first was separated by HPLC with C-18 reversed phase column and $CH_3CN—H_2O$-TFA as gradient solvents. However, this isomer was contaminated with the starting material (3-fluro-phenyl)-6,7-dimethoxy-2,4-dihydro-indeno[1,2-c]pyrazol-3-yl)-amine (Compound 14). The title compound was further purified by silica gel column chromatography (pre-washed with 1% $Et_3N$ in Hexanes) using 2:1 Hexanes:ethyl acetate as the eluent. MS m/z 440.1 $(M+H)^+$;

$^1$HNMR (DMSO-$d_6$): 1.20(s, 9H), 3.40(s, 2H), 3.90(s, 3H), 3.96(s, 3H), 6.20(s, 2H), 6.57(m, 1H), 6.82(d, 1H), 6.95(m, 1H), 7.03(s, 1H), 7.15(m, 1H), 7.27(s, 1H).

EXAMPLE 59

2,2-Dimethyl-propionic acid 3-(3-fluoro-phenylamino)-6,7-dimethoxy-4H-indeno[1,2-c]pyrazol-2-ylm ethyl ester Compound 408 (Method L)

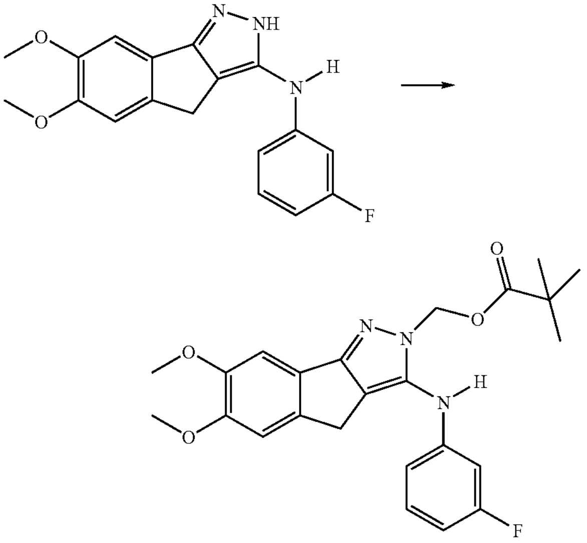

A mixture of (3-fluoro-phenyl)-6,7-dimethoxy-2,4-dihydro-indeno[1,2-c]pyrazol-3-yl)-amine (Compound 14) (1.25 g, 0.00385 mol) diisopropylethylamine (1.00 mL, 0.00578 mol), chloromethylpivalate (0.833 mL, 0.00578 mol) and potassium iodide (0.960 g, 0.00578 mol) in THF (19 mL) was heated to 75° C. for 12 h. The mixture was diluted with ethyl acetate and washed with brine and dried over $MgSO_4$. The title compound which came out second was separated by HPLC with C-1 8 reversed phase column and $CH_3CN—H_2O$-TFA as gradient solvents. However, this isomer was contaminated with the starting material (3-fluro-phenyl)-6,7-dimethoxy-2,4-dihydro-indeno[1,2-c]pyrazol-3-yl)-amine (Compound 14). The title compound was further purified by silica gel column chromatography (pre-washed with 1% $Et_3N$ in Hexanes) using 2:1 Hexanes ethyl acetate as the eluent. MS m/z 440.1 $(M+H)^+$;

$^1$HNMR (DMSO-$d_6$): 1.22(s, 9H), 3.40(s, 2H), 3.90(s, 3H), 3.93(s, 3H), 5.94(s, 2H), 6.62(m, 2H), 6.72(d, 1H), 6.97(s, 1H), 7.21(m, 1H), 7.33(s, 1H), 7.56(bs, 1H).

EXAMPLE 60

5,6-Bis[3-tetrahydro-pyran-2-yloxy)-propoxy]-indan-1-one, Intermediate Y

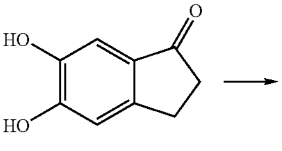

-continued

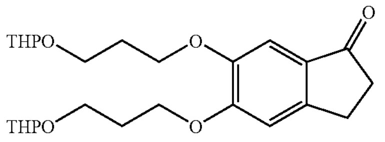

A mixture of 5,6-dihydroxy-indan-1-one (Intermediate O) (2.00 g, 0.0122 mole), potassium carbonate (4.22 g, 0.0305 mol), 2-(3-chloro-propoxy)-tetrahydro-pyran (Compound 18a) (4.36 g, 0.0244 mol) and potassium iodide (4.00 g, 0.0244 mol) in DMF (20 mL) was stirred at 60° C. for 36 h. The reaction mixture was then diluted with ethyl acetate, washed with water and dried over $MgSO_4$. The solvent was removed in vacuo and the title compound was purified by silica gel column chromatography using 3:1 Hexanes:ethyl acetate as the eluent. MS m/z 449 $(M+H)^+$;

$^1$HNMR ($CDCl_3$): 1.60(m, 12H), 2.13(m, 4H), 2.70(t, 2H), 3.12(t, 3H), 3.52(m, 4H), 3.90(m, 2H), 4.20(m, 4H), 4.60(s, 2H), 6.90(s, 1H), 7.18(s, 1H).

EXAMPLE 61

3-[3-(3-Fluoro-phenylamino)-6-(3-hydroxy-propoxy)-2,4-dihydro-indeno[1,2-c]pyrazol-7-yloxy]-propan-1-ol, Compound 398 (Method A)

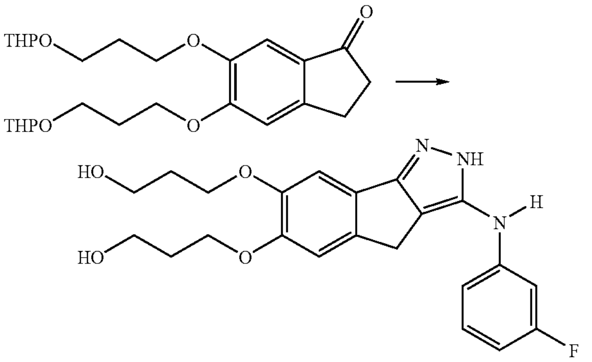

To a mixture of 5,6-bis[3-tetrahydro-pyran-2-yloxy)-propoxy]-indan-1 one (Intermediate Y) (0.100 g, 0.00022 mol) 3-fluorophenyl isothiocyanate (Compound 4a) (0.031 mL, 0.00026 mol) and THF (4 mL) was added lithium hexamethyldisilane (0.260 mL, 0.00026 mol) dropwise at room temperature with stirring. The reaction mixture was stirred for 12 h. Hydrazine (0.008 mL, 0.00026 mol) and acetic acid (0.015 mL, 0.00026 mol) was added to the reaction mixture, which was then heated at reflux temperature for 24 h. The reaction solution was then diluted with ethyl acetate, washed with water and dried over $MgSO_4$. The solvent was removed in vacuo and the title compound was purified by HPLC with a C-18 reversed phase column and $CH_3CN$—$H_2O$-TFA as gradient solvents. The title compound was obtained as a solid TFA salt. MS m/z 414.3 $(M+H)^+$;

$^1$HNMR (MeOH-$d_4$): 2.05(m, 4H), 3.50(s, 2H), 3.83(m, 4H), 4.20(t, 4H), 6.76(m, 1H), 6.95(m, 2H), 7.26(s, 1H), 7.28(s, 1H), 7.36(m, 1H).

EXAMPLE 62

5-Ethoxy-6-[3-(tetrahydro-pyran-2-yloxy)-propoxy-indan-1-one, Intermediate Z

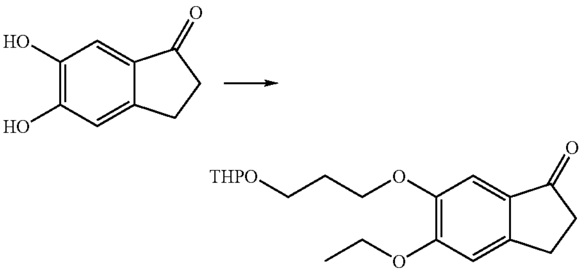

A mixture of 5,6-dihydroxy-indan-1-one (Intermediate O) (2.00 g, 0.0122 mole), potassium carbonate (4.22 g, 0.0305 mol) and ethyl bromide (0.911 mL, 0.0122 mol) in DMF (20 mL) was stirred at room temperature for 12 h. The reaction mixture was then diluted with ethyl acetate, washed with water and dried over $MgSO_4$. The solvent was removed in vacuo. The resulting 5-ethoxy-6-hydroxy-indan-1-one (Compound 62a) was purified by silica gel column chromatography using 3:1 Hexanes:ethyl acetate as the eluent.

The mixture of 5-ethoxy-6-hydroxy-indan-1-one (Compound 62a) (0.520 g, 0.00271 mol), 2-(3-chloro-propoxy)-tetrahydro-pyran (Compound 18a) (0.938 g, 0.00542 mol), potassium carbonate (0.936 g, 0.00678 mol) and potassium iodide (0.900 g, 0.00542 mol) in DMF (5.5 mL) was stirred at 60° C. for 12 h.

The reaction mixture was then diluted with ethyl acetate, washed with water and dried over $MgSO_4$. The solvent was removed in vacuo and the title compound was purified by silica gel column chromatography using 3:1 Hexanes:ethyl acetate as the eluent. MS m/z 334.2 $(M+H)^+$;

$^1$HNMR ($CDCl_3$): 1.60(m, 9H), 2.18(m, 2H), 2.65(t, 2H), 3.06(t, 2H), 3.38(m, 2H), 3.85(m, 2H), 4.18(m, 4H), 4.62(t, 1H), 6.84(s, 1H), 7.22(s, 1H).

EXAMPLE 63

3-[6-Ethoxy-3-(3-fluoro-phenylamino)-2,4-dihydro-indeno]1,2-c]pyrazol-7-yloxy]-propan-1-ol, Compound 365 (Method A)

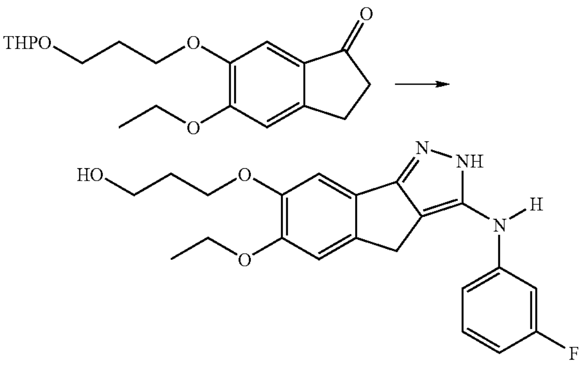

To a mixture of 5-Ethoxy-6-[3-(tetrahydro-pyran-2-yloxy)-propoxy]-indan-1-one (Intermediate Z) (0.100 g, 0.0003 mol), 3-fluorophenyl isothiocyanate (Compound 4a) (0.043 mL, 0.00036 mol) and THF (3 mL) was added lithium hexamethyldisilane (0.360 mL, 0.00036 mol) dropwise at room temperature with stirring. The reaction mixture was stirred for 5 h. Hydrazine (0.011 mL, 0.00036 mol) and acetic acid (0.021 mL, 0.00036 mol) was added to the reaction mixture, which was then heated at reflux temperature for 12 h. The reaction solution was then diluted with ethyl acetate, washed with water and dried over $MgSO_4$. The solvent was removed in vacuo and the crude material was purified on the reverse phase HPLC and converted to the desired product upon standing in the 0.1% TFA solution. Lyophilization yielded the title compound as a white powder. MS m/z 384.4 $(M+H)^+$;

$^1$HNMR ($CDCl_3$): 1.47(t, 3H), 2.12(m, 2H), 3.43(s, 2H), 3.90(t, 2H), 4.08(q, 2H), 4.22(t, 2H), 4.85(bs, 1H), 6.89(m, 2H), 6.97(s, 1H), 7.18(s, 1H), 7.32(m, 2H), 9.42(bs, 1H).

EXAMPLE 64

6-Ethoxy-5-f3-(tetrahydro-pyran-2-yloxy)-propoxy]-indan-1-one, Intermediate AA

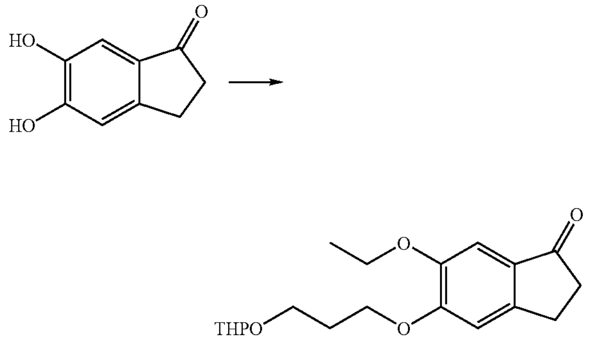

A mixture of 5,6-dihydroxy-indan-1-one (Intermediate O) (1.80 g, 0.01098 mole), potassium carbonate (3.80 g, 0.02744 mol), 2-(3-chloro-propoxy)-tetrahydro-pyran (Compound 18a) (1.37 g, 0.00769 mol) and potassium iodide (1.28 g, 0.00769 mol) in DMF (20 mL) was stirred at 60° C. for 4 hours. To this mixture was then added ethyl bromide (1.64 mL, 0.02196 mol) and continued to heat for further 4 h. The reaction mixture was then diluted with ethyl acetate, washed with water and dried over $MgSO_4$. The solvent was removed in vacuo and the title compound was purified by silica gel column chromatography using 3:1 Hexanes:ethyl acetate as the eluent. MS m/z 334.2 $(M+H)^+$;

$^1$HNMR ($CDCl_3$): 1.65(m, 9H), 2.20(m, 2H), 2.68(t, 2H), 3.15(t, 2H), 3.55(m, 2H), 4.10(m, 6H), 4.60(m, 1H), 6.92(s, 1H), 7.16(s, 1H).

EXAMPLE 65

3-[7-Ethoxy-3-(3-fluoro-phenylamino)-2,4-dihydro-indeno[1,2-c]pyrazol-6-yloxy]-propan-1-ol, Compound 382 (Method A)

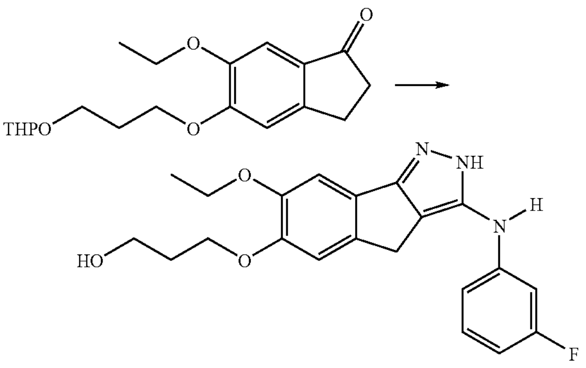

To a mixture of 6-Ethoxy-5-[3-(tetrahydro-pyran-2-yloxy)-propoxy]-indan-1-one (Intermediate AA) (0.100 g, 0.0003 mol), 3-fluorophenyl isothiocyanate (Compound 4a) (0.043 mL, 0.00036 mol) and THF (3 mL) was added lithium hexamethyldisilane (0.360 mL, 0.00036 mol) dropwise at room temperature with stirring. The reaction mixture was stirred for 48 h. Hydrazine (0.011 mL, 0.00036 mol) and acetic acid (0.021 mL, 0.00036 mol) was added to the reaction mixture, which was then heated at reflux temperature for 12 h. The reaction solution was then diluted with ethyl acetate, washed with water and dried over $MgSO_4$. The solvent was removed in vacuo and the crude material was purified on the reverse phase HPLC and converted to the desired product upon standing in the 0.1% TFA solution. Lyophilization yielded the title compound as a white powder. MS m/z 384.2 $(M+H)^+$;

$^1$HNMR (DMSO-$d_6$): 1.28(t, 3H), 2.90(m, 2H), 3.42(s, 2H), 3.60(t, 2H), 4.12(m, 4H), 6.54(m, 1H), 6.88(d, 1H), 7.20(m, 4H), 8.80(bs, 1H).

EXAMPLE 66

3-thiophene-2-yl-acrylic acid, Intermediate AB

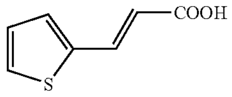

A mixture of thiophene-2-carbaldehyde (Compound 66a) (1.20 g, 0.0107 mol), malonic acid (1.11 g, 0.0107 mol) and ammonium acetate (0.825 g, 0.0107 mol) in DMF (8.5 mL) was heated to 100° C. for 3 h. The system was diluted with ethyl acetate and washed with water and dried over $MgSO_4$. The solvent was removed in vacuo and the title compound was purified by silica gel column chromatography using 3:1 Hexanes:ethyl acetate as the eluent.

$^1$HNMR (CDCl3): 6.25(d, 1H), 7.08(m, 1H), 7.30(d, 1H), 7.42(d, 1H), 7.88(d, 1H).

EXAMPLE 67

3-thiophene-2-yl-propionic acid, Intermediate AC

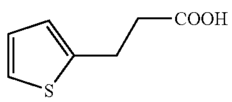

A mixture of 3-thiophene-2-yl-acrylic acid (Intermediate AB) (2.00 g, 0.01299 mol), 10% Pd on C (2.00 g) in methanol (200 mL) was stirred under the atmosphere of $H_2$ (50 PSI) for 18 h. The resulting system was purged with $N_2$ and then filtered through a pad of celite. Organics were dried over $MgSO_4$ and the solvent was removed in vacuo to provide 3-thiophene-2-yl-propionic acid.

$^1$HNMR (CDCl3): 2.76(t, 2H), 3.20(t, 2H), 6.82(d, 1H), 6.95(m, 1H), 7.15(d, 1H)

EXAMPLE 68

5,6-dihydro-cyclopenta[b]thiophen-4-one, Intermediate AD

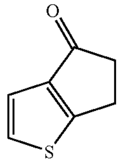

To a solution of 3-thiophene-2-yl-propionic acid (Intermediate AC) (1.75 g, 0.01122 mol) in dichloromethane (50 mL) was added $SOCl_2$ (1.67 mL, 0.02244 mol) and stirred at room temperature for 6 h. This solution was added dropwise to a suspension of $AlCl_3$ (2.98 g, 0.02244 mol) in dichloromethane (50 mL) over 45 minutes. The resulting mixture was stirred at room temperature for 12 h. The system was quenched by dropwise addition of water (10 mL) and extracted with dichloromethane. The organics were dried with $MgSO_4$ and the solvent was removed in vacuo. The title compound was purified by silica gel column chromatography using 4:1 Hexanes:ethyl acetate as the eluent. MS m/z 139.1 $(M+H)^+$;

$^1$HNMR ($CDCl_3$): 3.01(t, 2H), 3.18(t, 2H), 7.15(d, 1H), 7.32(d, 1H).

EXAMPLE 69

(5,7-Dihydro-1-thia-4,5-diaza-cyclopenta[a]pentalen-6-yl)-(3-ethoxy-phenyl)-amine, Compound 405 (Method A)

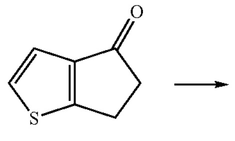

-continued

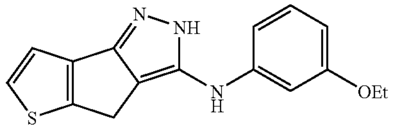

To a mixture of 5,6-dihydro-cyclopenta[b]thiophen-4-one (Intermediate AD) (0.065 g, 0.00047 mol) 3-ethoxy-phenyl isothiocyanate (Compound 69a) (0.108 g, 0.00056 mol) and THF (2.5 mL) was added lithium hexamethyldisilane (0.560 mL, 0.00056 mol) dropwise at room temperature with stirring. The reaction mixture was stirred for 3 h. Hydazine (0.036 mL, 0.00112 mol) and acetic acid (0.0032 mL, 0.00056 mol) was added to the reaction mixture, which was then heated to 50° C. for 8 h. The reaction solution was then diluted with ethyl acetate, washed with water and dried over $MgSO_4$. The solvent was removed in vacuo and the title compound was purified by HPLC with a C-18 reversed phase column and $CH_3CN—H_2O$-TFA as gradient solvents. The title compound was obtained as a solid TFA salt. MS m/z 298.2 $(M+H)^+$;

$^1$HNMR (DMSO-$d_6$): 1.25(t, 1H), 3.52(s, 2H), 3.88(q, 2H), 5.80(bs, 1H), 6.28(m, 1H), 6.65(m, 2H), 7.05(t, 1H), 7.18(d, 1H), 7.58(d, 1H), 8.60(bs, 1H).

EXAMPLE 70

3–6-Ethoxy-3-(3-ethoxy-phenylamino)-2,4-dihydro-indeno{1,2-c}pyrazol-7-yloxyl-propan-1-ol, Compound 388 (Method A)

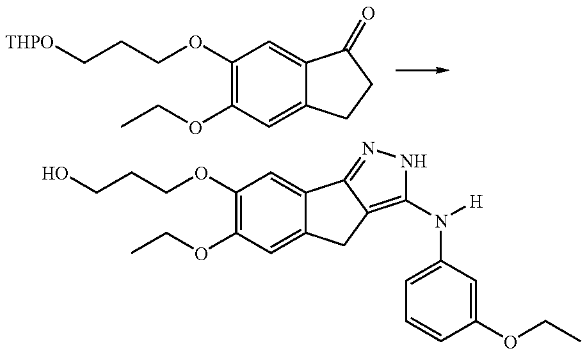

To a mixture of 5-Ethoxy-6-[3-(tetrahydro-pyran-2-yloxy)-propoxy]-indan-1-one (Intermediate Z) (0.100 g, 0.0003 mol), 3-ethoxyphenyl isothiocyanate (Compound 69a) (0.043 mL, 0.00036 mol) and THF (3 mL) was added lithium hexamethyldisilane (0.360 mL, 0.00036 mol) dropwise at room temperature with stirring. The reaction mixture was stirred for 5 h. Hydrazine (0.011 mL, 0.00036 mol) and acetic acid (0.021 mL, 0.00036 mol) was added to the reaction mixture, which was then heated at reflux temperature for 12 h. The reaction solution was then diluted with ethyl acetate, washed with water and dried over $MgSO_4$. The solvent was removed in vacuo and the crude material was purified on the reverse phase HPLC and converted to the desired product upon standing in the 0.1% TFA solution. Lyophilization yielded the title compound as a white powder. MS m/z 410.2 $(M+H)^+$;

$^{1}$HNMR (DMSO-$d_6$): 8.65(bs, 1H), 7.14(m, 3H), 6.79(s, 1H), 6.71(d, 1H), 6.37(d, 1H), 4.03(m, 6H), 3.60(t, 2H), 3.40(s, 1H), 1.88(m, 2H), 1.30(m, 6H).

Biological Activity

Biological Activities of the Compounds of the Invention

Compounds within the scope of this invention were subjected to various biological tests. Results of these tests showed that compounds within the scope of this invention inhibited PDGF-R kinase activity. Compounds within the scope of this invention also exhibited inhibitory activity against c-Abl kinase. In addition, compounds within the scope of this invention inhibited cell (including normal tissue cells, tumor cells and leukemia cells) proliferation in the presence or absence of PDGF stimulation. Other studies demonstrated that compounds within the scope of this invention inhibited angiogenesis and compounds were shown to have anti-tumor activity. Further, compounds within the scope of this invention sensitized tumor cells for radiation treatment. Pro-drugs of compounds within the scope of the invention were demonstrated to convert back to parent compounds in vivo.

The following representative assays were performed in determining the biological activities of compounds within the scope of the invention. They are given to illustrate the invention in a non-limiting fashion.

1. Inhibition of PDGF-Receptor Kinase Activity

PDGF-R kinase activity was assayed by its ability to phosphorylate one of its target proteins, PLCγ, in a cell-free system, in particular, a PLC1 peptide comprising the tyrosine residue where the phosphorylation occurs was used for the assay.

Materials

The following reagents were prepared for the assay:

10× Kinase Buffer (500 mM Tris-HCl pH=8, 100 mM $MgCl_2$, 1 mM $Na_3VO_4$); 10 mM DTT (final concentration at 1 mM in assay); 10 mM ATP (final concentration at 5 μM in assay); $^{33}$P-γ-ATP (Cat. No.: NEG/602H. 2000-3000 Ci/mmol) purchased from NEN; Purified, soluble, recombinant PDGF-receptor beta enzyme comprising the tyrosine kinase domain (from amino acid 545 to 1106 of GenBank Access NO: AAA36427 ) at 0.4 mg/mL; Enzyme Dilution Buffer (50 mM Tris-HCl pH=8.0, 0.1% BSA); Wash/Stop Buffer (PBS +100 mM EDTA); NEN Streptavidin Flashplates (Cat. No.: SMP-103) which binds to the biotinylated PLC1 peptide but not the PDGF-R enzyme; PLC1 peptide (Biotin-KHKKLAEGSAYEEV-Amide) at 1 mM in 50 mM Tris-HCL with pH of 8.0.

Procedure

Reagents were first mixed according the following regimen:

| | ONE PLATE (μl) | PER WELL (μl) |
|---|---|---|
| 10X Kinase Buffer | 1100 | 10 |
| 10 mM DTT | 1100 | 10 |
| 10 mM cold ATP | 5.5 | 0.05 |
| 1 mM PLC1 Peptide | 2.75 | 0.025 |
| $^{33}$P-γ-ATP (10 μCi/μl) | 8.8 | 0.08 |
| $H_2O$ | 5475 | 49.77 |

The above reaction mixture was dispensed into each well of a Flashplate at 70 μl/well. To test the effect of a compound on PDGF-R kinase activity, the test compound either in a fixed concentration or in serially diluted concentrations in 100% DMSO was added to appropriate wells at 1 μl/well.

Enzyme PDGF-R was diluted in Enzyme dilution buffer as following:

| | |
|---|---|
| Enzyme Dilution Buffer | 3289 μl |
| PDGF-R enzyme | 100 μl |

The kinase reaction was initiated by adding 30 μl of diluted PDGF-R enzyme solution to each well on the Flashplate containing hot ATP and PLC1, except wells of column 12 rows E through H, which were used to calculate the plate background. The Flashplate was swirled to mix and was incubated at 30° C. for 60 minutes. Then, the reaction mixture was discarded and the Flashplate was washed 3 times each with 200 μl Wash/Stop Buffer. Subsequently, each well on the Flashplate was filled with 200 μl of Wash/Stop buffer. The amount of $^{33}$P retained in each well was measured using a Packard TopCount after the plate was sealed with a transparent plate sealer.

When a test compound inhibited the PDGF-R kinase activity, the well containing such a compound contained less $^{33}$P as compared to the well without the compound. The percentage of inhibition of the test compound on PDGF-R kinase activity is defined as the amount of $^{33}$P retained in the well containing the compound divided by the amount of $^{33}$P in the well without the compound. Tested under the described assay conditions, more than 600 compounds within the scope of the invention at a final concentration of 10 μM have demonstrated inhibitory effect on PDGF-R kinase activity.

In order to test the potency of inhibition of present compounds, an $IC_{50}$ for an individual compound was measured using the above procedure. As used herein, the $IC_{50}$ for PDGF-R kinase activity refers to the concentration of an inhibitor at which the activity of the PDGF-R kinase is reduced by one-half as compared with reactions containing no inhibitor.

Inhibition of PDGF-R kinase activity preferably refers to an $IC_{50}$ of less than or equal to about 75 μM using the assay described above. Preferably, the compound can inhibit PDGF-R kinase activity with an $IC_{50}$ of less than or equal to about 10 μM, more preferably less than or equal to about 1 μM, most preferably less than or equal to about 0.1 μM. Lower $IC_{50}$ values are preferred because the $IC_{50}$ provides an indication as to the effectiveness of the compound. Other factors known in art, such as compound half-life, biodistribution, and toxicity should also be considered for therapeutic uses. Such factors may enable a compound with a higher $IC_{50}$ to have greater in vivo efficacy than a compound having a lower $IC_{50}$.

Representative compounds of the present invention were tested for PDGF-R kinase activity with % inhibition and/or $IC_{50}$ results as listed in Table A.

TABLE A

IC50 and percent of inhibition of compounds on PDGF-R kinase activity

| CPD | NAME | Percent Inhibition @ 10 uM | IC50 (μM) |
|---|---|---|---|
| 1 | (2,4-Dihydro-indeno[1,2-c]pyrazol-3-yl)-phenyl-amine | 91 | 0.317 |
| 2 | (6,7-Dimethoxy-2,4-dihydro-indeno[1,2-c]pyrazol-3-yl)-phenyl-amine | 91 | 0.006 |
| 3 | (4-Chloro-phenyl)-(2,4-dihydro-indeno[1,2-c]pyrazol-3-yl)-amine | 90 | 0.157 |
| 4 | (3-Chloro-phenyl)-(6,7-dimethoxy-2,4-dihydro-indeno[1,2-c]pyrazol-3-yl)-amine | 90 | 0.003 |
| 5 | (4-Chloro-phenyl)-(6,7-dimethoxy-2,4-dihydro-indeno[1,2-c]pyrazol-3-yl)-amine | 91 | 0.659 |
| 6 | (6,7-Dimethoxy-2,4-dihydro-indeno[1,2-c]pyrazol-3-yl)-(4-methoxy-phenyl)-amine | 75 | 0.131 |
| 7 | (6-Methoxy-2,4-dihydro-indeno[1,2-c]pyrazol-3-yl)-phenyl-amine | 92 | 0.217 |
| 8 | (5-Methoxy-2,4-dihydro-indeno[1,2-c]pyrazol-3-yl-phenyl-amine | 98 | 0.054 |
| 9 | (2-Chloro-phenyl)-(6,7-dimethoxy-2,4-dihydro-indeno[1,2-c]pyrazol-3-yl)-amine | 89 | 0.11 |
| 10 | 4-(6,7-Dimethoxy-2,4-dihydro-indeno[1,2-c]pyrazol-3-ylamino)-benzoic acid ethyl ester | 68 | 2.07 |
| 11 | 3-(6,7-Dimethoxy-2,4-dihydro-indeno[1,2-c]pyrazol-3-ylamino)-benzoic acid methyl ester | 97 | 0.0157 |
| 12 | (6,7-Dimethoxy-2,4-dihydro-indeno[1,2-c]pyrazol-3-yl)-(2-fluoro-phenyl)-amine | 76 | 0.056 |
| 13 | (6,7-Dimethoxy-2,4-dihydro-indeno[1,2-c]pyrazol-3-yl)-(4-fluoro-phenyl)-amine | 91 | 0.0065 |
| 14 | (6,7-Dimethoxy-2,4-dihydro-indeno[1,2-c]pyrazol-3-yl)-(3-fluoro-phenyl)-amine | 108 | 0.0017 |
| 15 | (6,7-Dimethoxy-2,4-dihydro-indeno[1,2-c]pyrazol-3-yl)-(2-trifluoromethoxy-phenyl)-amine | 79 | 1.92 |
| 16 | (6,7-Dimethoxy-2,4-dihydro-indeno[1,2-c]pyrazol-3-yl)-(4-trifluoromethoxy-phenyl)-amine | 79 | 4 |
| 17 | (2,4-Dichloro-phenyl)-(6,7-dimethoxy-2,4-dihydro-indeno[1,2-c]pyrazol-3-yl)-amine | 79 | 3.54 |
| 18 | (3,4-Dichloro-phenyl)-(6,7-dimethoxy-2,4-dihydro-indeno[1,2-c]pyrazol-3-yl)-amine | 65 | 0.23 |
| 19 | (3,5-Dichloro-phenyl)-(6,7-dimethoxy-2,4-dihydro-indeno[1,2-c]pyrazol-3-yl)-amine | 91 | 0.174 |
| 20 | (2,3-Dichloro-phenyl)-(6,7-dimethoxy-2,4-dihydro-indeno[1,2-c]pyrazol-3-yl)-amine | 77 | 1.095 |
| 21 | (6-Chloro-2,4-dihydro-indeno[1,2-c]pyrazol-3-yl)-phenyl-amine | 103 | 0.121 |
| 22 | (7-Methyl-2,4-dihydro-indeno[1,2-c]pyrazol-3-yl)-phenyl-amine | 96 | 0.045 |
| 23 | (5-Methyl-2,4-dihydro-indeno[1,2-c]pyrazol-3-yl)-phenyl-amine | 87 | 1.94 |
| 24 | (6-Fluoro-2,4-dihydro-indeno[1,2-c]pyrazol-3-yl)-phenyl-amine | 71 | 0.084 |
| 25 | (6,7-Dimethoxy-2,4-dihydro-indeno[1,2-c]pyrazol-3-yl)-(4-trifluoromethyl-phenyl)-amine | 62 | 4.766 |
| 26 | (6,7-Dimethoxy-2,4-dihydro-indeno[1,2-c]pyrazol-3-yl)-(3-trifluoromethyl-phenyl)-amine | 92 | 0.037 |
| 27 | (6,7-Dimethoxy-2,4-dihydro-indeno[1,2-c]pyrazol-3-yl)-(2-methoxy-phenyl)-amine | 71 | 0.655 |
| 28 | (6,7-Dimethoxy-2,4-dihydro-indeno[1,2-c]pyrazol-3-yl)-(2-trifluoromethyl-phenyl)-amine | 96 | 19.14 |
| 29 | (6,7-Dimethoxy-2,4-dihydro-indeno[1,2-c]pyrazol-3-yl)-(3-methoxy-phenyl)-amine | 99 | 0.01 |
| 30 | (6,7-Dimethoxy-2,4-dihydro-indeno[1,2-c]pyrazol-3-yl)-pyridin-3-yl-amine | 107 | 0.016 |
| 31 | (6,7-Dimethoxy-2,4-dihydro-indeno[1,2-c]pyrazol-3-yl)-o-tolyl-amine | 59 | 0.115 |
| 32 | (6,7-Dimethoxy-2,4-dihydro-indeno[1,2-c]pyrazol-3-yl)-m-tolyl-amine | 79 | 0.012 |
| 33 | (6,7-Dimethoxy-2,4-dihydro-indeno[1,2-c]pyrazol-3-yl)-p-tolyl-amine | 59 | 1.415 |
| 34 | (2,5-Dichloro-phenyl)-(6,7-dimethoxy-2,4-dihydro-indeno[1,2-c]pyrazol-3-yl)-amine | 57 | 6.987 |
| 35 | 3-Phenylamino-2H-indeno[1,2-c]pyrazol-4-one | 88 | 2.063 |
| 36 | [3-(6,7-Dimethoxy-2,4-dihydro-indeno[1,2-c]pyrazol-3-ylamino)-phenyl]-methanol | 85 | 0.033 |

TABLE A-continued

IC50 and percent of inhibition of compounds on PDGF-R kinase activity

| CPD | NAME | Percent Inhibition @ 10 uM | IC50 (μM) |
|---|---|---|---|
| 37 | (6,7-Dimethoxy-2,4-dihydro-indeno[1,2-c]pyrazol-3-yl)-(1H-indazol-6-yl)-amine | 80 | 1.978 |
| 38 | 3-(6,7-Dimethoxy-2,4-dihydro-indeno[1,2-c]pyrazol-3-ylamino)-phenol | 74 | 0.031 |
| 39 | (7-Methoxy-2,4-dihydro-indeno[1,2-c]pyrazol-3-yl)-phenyl-amine | 92 | 0.018 |
| 40 | N-(6,7-Dimethoxy-2,4-dihydro-indeno[1,2-c]pyrazol-3-yl)-N',N''-dimethyl-benzene-1,2-diamine | 63 | 5.95 |
| 41 | (6,7-Dimethoxy-2,4-dihydro-indeno[1,2-c]pyrazol-3-yl)-(3,5-dimethoxy-phenyl)-amine | 83 | 0.0336 |
| 42 | (6,7-Dimethoxy-2,4-dihydro-indeno[1,2-c]pyrazol-3-yl)-(3,4,5-trimethoxy-phenyl)-amine | 85 | 0.692 |
| 43 | (2-Bromo-phenyl)-(6,7-dimethoxy-2,4-dihydro-indeno[1,2-c]pyrazol-3-yl)-amine | 60 | 0.195 |
| 44 | (3-Bromo-phenyl)-(6,7-dimethoxy-2,4-dihydro-indeno[1,2-c]pyrazol-3-yl)-amine | 94 | 0.00054 |
| 45 | (4-Bromo-phenyl)-(6,7-dimethoxy-2,4-dihydro-indeno[1,2-c]pyrazol-3-yl)-amine | 86 | 2.164 |
| 46 | (5-Chloro-2-methyl-phenyl)-(6,7-dimethoxy-2,4-dihydro-indeno[1,2-c]pyrazol-3-yl)-amine | 51 | 14.15 |
| 47 | (6,7-Dimethoxy-2,4-dihydro-indeno[1,2-c]pyrazol-3-yl)-(2,4-dimethoxy-phenyl)-amine | 47 | NT |
| 48 | (6,7-Dimethoxy-2,4-dihydro-indeno[1,2-c]pyrazol-3-yl)-(2,5-dimethoxy-phenyl)-amine | 39 | NT |
| 49 | (6,7-Dimethoxy-2,4-dihydro-indeno[1,2-c]pyrazol-3-yl)-(3,4-dimethoxy-phenyl)-amine | 72 | 3.066 |
| 50 | 3-Phenylamino-2,4-dihydro-indeno[1,2-c]pyrazol-4-ol | 38 | 11.37 |
| 51 | (6,7-Dimethoxy-2,4-dihydro-indeno[1,2-c]pyrazol-3-yl)-[4-(4-methyl-piperazin-1-yl)-phenyl]-amine | 30 | 26.75 |
| 52 | (4,5-Dihydro-2H-6-thia-1,2-diaza-as-indacen-3-yl)-phenyl-amine | 71 | 2.4 |
| 53 | (3-Chloro-4-fluoro-phenyl)-(6,7-dimethoxy-2,4-dihydro-indeno[1,2-c]pyrazol-3-yl)-amine | 94 | 0.05859 |
| 54 | (3-Benzyloxy-phenyl)-(6,7-dimethoxy-2,4-dihydro-indeno[1,2-c]pyrazol-3-yl)-amine | 76 | 0.0348 |
| 55 | (2,5-Difluoro-phenyl)-(6,7-dimethoxy-2,4-dihydro-indeno[1,2-c]pyrazol-3-yl)-amine | 76 | 0.636 |
| 56 | (5-Chloro-2-methoxy-phenyl)-(6,7-dimethoxy-2,4-dihydro-indeno[1,2-c]pyrazol-3-yl)-amine | 36 | 8.402 |
| 57 | (6,7-Dimethoxy-2,4-dihydro-indeno[1,2-c]pyrazol-3-yl)-(2-isopropyl-phenyl)-amine | 71 | 2.151 |
| 58 | (6,7-Dimethoxy-2,4-dihydro-indeno[1,2-c]pyrazol-3-yl)-(2-ethyl-phenyl)-amine | 40 | 8.524 |
| 59 | 4-(6,7-Dimethoxy-2,4-dihydro-indeno[1,2-c]pyrazol-3-ylamino)-benzonitrile | 71 | 1.818 |
| 61 | 3-(6,7-Dimethoxy-2,4-dihydro-indeno[1,2-c]pyrazol-3-ylamino)-benzonitrile | 71 | 0.137 |
| 62 | Benzo[1,3]dioxol-5-yl-(6,7-dimethoxy-2,4-dihydro-indeno[1,2-c]pyrazol-3-yl)-amine | 85 | 0.313 |
| 63 | Benzyl-(6,7-dimethoxy-2,4-dihydro-indeno[1,2-c]pyrazol-3-yl)-amine | 94 | 0.1909 |
| 64 | [6-(4-Methyl-piperazin-1-yl)-2,4-dihydro-indeno[1,2-c]pyrazol-3-yl]-phenyl-amine | 118 | 0.449 |
| 65 | Phenyl-(6-piperidin-1-yl-2,4-dihydro-indeno[1,2-c]pyrazol-3-yl)-amine | 76 | 1.535 |
| 66 | N3-Phenyl-2,4-dihydro-indeno[1,2-c]pyrazole-3,6-diamine | 108 | 0.092 |
| 67 | Cyclohexyl-(6,7-dimethoxy-2,4-dihydro-indeno[1,2-c]pyrazol-3-yl)-amine | 77 | 0.617 |
| 69 | (6,7-Dimethoxy-2,4-dihydro-indeno[1,2-c]pyrazol-3-yl)-(2-morpholin-4-yl-ethyl)-amine | 18 | |
| 70 | (3,5-Bis-trifluoromethyl-phenyl)-(6,7-dimethoxy-2,4-dihydro-indeno[1,2-c]pyrazol-3-yl)-amine | 41.5 | 16.85 |
| 71 | [5-(3-Dimethylamino-propoxy)-2,4-dihydro-indeno[1,2-c]pyrazol-3-yl]-phenyl-amine | 110 | 0.185 |
| 72 | (3-Chloro-phenyl)-[5-(3-dimethylamino-propoxy)-2,4-dihydro-indeno[1,2-c]pyrazol-3-yl]-amine | 96 | 0.283 |
| 73 | [5-(3-Dimethylamino-propoxy)-2,4-dihydro-indeno[1,2-c]pyrazol-3-yl]-(4-fluoro-phenyl)-amine | ~30 | >>50 |
| 74 | [5-(3-Dimethylamino-propoxy)-2,4-dihydro-indeno[1,2-c]pyrazol-3-yl]-(3-methoxy-phenyl)-amine | 102 | 0.424 |

TABLE A-continued

IC50 and percent of inhibition of compounds on PDGF-R kinase activity

| CPD | NAME | Percent Inhibition @ 10 uM | IC50 (μM) |
|---|---|---|---|
| 75 | [5-(3-Dimethylamino-propoxy)-2,4-dihydro-indeno[1,2-c]pyrazol-3-yl]-pyridin-3-yl-amine | 115 | 0.575 |
| 76 | (4-Bromo-2-trifluoromethyl-phenyl)-(6,7-dimethoxy-2,4-dihydro-indeno[1,2-c]pyrazol-3-yl)-amine | 16 | >>50 |
| 77 | 3-[5-(3-Dimethylamino-propoxy)-2,4-dihydro-indeno[1,2-c]pyrazol-3-ylamino]-benzoic acid methyl ester | 108 | 0.217 |
| 78 | (6,7-Dimethoxy-2,4-dihydro-indeno[1,2-c]pyrazol-3-yl)-furan-2-yl-amine | 85 | 1.291 |
| 79 | (6,7-Dimethoxy-2,4-dihydro-indeno[1,2-c]pyrazol-3-yl)-indan-5-yl-amine | 56 | 3.705 |
| 81 | (6,7-Dimethoxy-2,4-dihydro-indeno[1,2-c]pyrazol-3-yl)-(2-piperidin-1-yl-ethyl)-amine | 29 | 85.95 |
| 82 | (4-Fluoro-phenyl)-(6-methoxy-2,4-dihydro-indeno[1,2-c]pyrazol-3-yl)-amine | 79 | 0.273 |
| 83 | (3-Bromo-phenyl)-(6-methoxy-2,4-dihydro-indeno[1,2-c]pyrazol-3-yl)-amine | 93 | 0.0719 |
| 84 | (6-Methoxy-2,4-dihydro-indeno[1,2-c]pyrazol-3-yl)-pyridin-3-yl-amine | 86 | 0.71 |
| 85 | (2,5-Dimethoxy-phenyl)-(6-methoxy-2,4-dihydro-indeno[1,2-c]pyrazol-3-yl)-amine | 61 | 5.823 |
| 86 | (3,4-Dimethoxy-phenyl)-(6-methoxy-2,4-dihydro-indeno[1,2-c]pyrazol-3-yl)-amine | 57 | 2.532 |
| 87 | (2,5-Difluoro-phenyl)-(6-methoxy-2,4-dihydro-indeno[1,2-c]pyrazol-3-yl)-amine | 91 | 0.069 |
| 88 | (6-Methoxy-2,4-dihydro-indeno[1,2-c]pyrazol-3-yl)-(4-trifluoromethoxy-phenyl)-amine | 42 | 20.8 |
| 89 | (6-Methoxy-2,4-dihydro-indeno[1,2-c]pyrazol-3-yl)-(4-trifluoromethyl-phenyl)-amine | 88 | 0.886 |
| 90 | [5-(3-Dimethylamino-propoxy)-2,4-dihydro-indeno[1,2-c]pyrazol-3-yl]-(3-fluoro-phenyl)-amine | 97 | 0.0087 |
| 91 | (3-Bromo-phenyl)-(6,7-dimethoxy-1-methyl-1,4-dihydro-indeno[1,2-c]pyrazol-3-yl)-amine | 76 | 2.969 |
| 92 | N6,N6-Dimethyl-N3-phenyl-2,4-dihydro-indeno[1,2-c]pyrazole-3,6-diamine | 75 | 0.383 |
| 93 | (4,5-Dihydro-2H-benzo[g]indazol-3-yl)-phenyl-amine | 88 | 1.027 |
| 94 | (5,7-Dihydro-1-thia-4,5-diaza-cyclopenta[a]pentalen-6-yl)-phenyl-amine | 95 | 0.415 |
| 95 | (3-Bromo-phenyl)-(2,9-dihydro-5,7-dioxa-2,3-diaza-cyclopenta[a]-s-indacen-1-yl)-amine | 91.0 | 0.063 |
| 96 | (2,9-Dihydro-5,7-dioxa-2,3-diaza-cyclopenta[a]-s-indacen-1-yl)-(3-fluoro-phenyl)-amine | 93.0 | 0.076 |
| 97 | (2,9-Dihydro-5,7-dioxa-2,3-diaza-cyclopenta[a]-s-indacen-1-yl)-(3-methoxy-phenyl)-amine | 91.0 | 0.054 |
| 98 | (4-Fluoro-phenyl)-(5-methyl-2,4-dihydro-indeno[1,2-c]pyrazol-3-yl)-amine | 26 | 30.69 |
| 99 | (3-Fluoro-phenyl)-(5-methyl-2,4-dihydro-indeno[1,2-c]pyrazol-3-yl)-amine | 87.5 | 1.468 |
| 100 | (5-Methyl-2,4-dihydro-indeno[1,2-c]pyrazol-3-yl)-pyridin-3-yl-amine | 81 | 1.723 |
| 101 | (2,5-Dimethoxy-phenyl)-(5-methyl-2,4-dihydro-indeno[1,2-c]pyrazol-3-yl)-amine | 52 | 1.092 |
| 102 | (2,4-Dimethoxy-phenyl)-(5-methyl-2,4-dihydro-indeno[1,2-c]pyrazol-3-yl)-amine | 50 | 3.404 |
| 103 | (2,5-Difluoro-phenyl)-(5-methyl-2,4-dihydro-indeno[1,2-c]pyrazol-3-yl)-amine | 43 | 4.099 |
| 104 | (5-Methyl-2,4-dihydro-indeno[1,2-c]pyrazol-3-yl)-(4-trifluoromethoxy-phenyl)-amine | 36 | 0.666 |
| 105 | (5-Methyl-2,4-dihydro-indeno[1,2-c]pyrazol-3-yl)-(4-trifluoromethyl-phenyl)-amine | 69 | 1.884 |
| 106 | (4-Fluoro-phenyl)-(4-methyl-2,4-dihydro-indeno[1,2-c]pyrazol-3-yl)-amine | 38 | 1.048 |
| 107 | (4-Methoxy-phenyl)-(4-methyl-2,4-dihydro-indeno[1,2-c]pyrazol-3-yl)-amine | 56 | 1.275 |
| 108 | (3-Fluoro-phenyl)-(4-methyl-2,4-dihydro-indeno[1,2-c]pyrazol-3-yl)-amine | 82 | 0.3 |
| 109 | (4-Methyl-2,4-dihydro-indeno[1,2-c]pyrazol-3-yl)-pyridin-3-yl-amine | 83 | 0.537 |
| 110 | (2,5-Dimethoxy-phenyl)-(4-methyl-2,4-dihydro-indeno[1,2-c]pyrazol-3-yl)-amine | 80 | 0.189 |
| 111 | (2,4-Dimethoxy-phenyl)-(4-methyl-2,4-dihydro-indeno[1,2-c]pyrazol-3-yl)-amine | 95 | 0.11 |

TABLE A-continued

IC50 and percent of inhibition of compounds on PDGF-R kinase activity

| CPD | NAME | Percent Inhibition @ 10 uM | IC50 (μM) |
|---|---|---|---|
| 112 | (2,5-Difluoro-phenyl)-(4-methyl-2,4-dihydro-indeno[1,2-c]pyrazol-3-yl)-amine | 72 | 0.083 |
| 113 | (4-Methyl-2,4-dihydro-indeno[1,2-c]pyrazol-3-yl)-(4-trifluoromethoxy-phenyl)-amine | 60 | 2.45 |
| 114 | (4-Methyl-2,4-dihydro-indeno[1,2-c]pyrazol-3-yl)-(3-trifluoromethyl-phenyl)-amine | 80 | 1.37 |
| 115 | 3-(6,7-Dimethoxy-2,4-dihydro-indeno[1,2-c]pyrazol-3-ylamino)-benzoic acid | 82 | 3.056 |
| 116 | 3-(6,7-Dimethoxy-2,4-dihydro-indeno[1,2-c]pyrazol-3-ylamino)-benzamide | 96 | 0.0053 |
| 117 | N3-(3-Bromo-phenyl)-2,4-dihydro-indeno[1,2-c]pyrazole-3,6-diamine | 98 | 0.13 |
| 118 | N3-(3-Methoxy-phenyl)-2,4-dihydro-indeno[1,2-c]pyrazole-3,6-diamine | 74 | 0.0213 |
| 119 | N3-(3-Chloro-phenyl)-2,4-dihydro-indeno[1,2-c]pyrazole-3,6-diamine | 90 | 0.0198 |
| 120 | 3-(6-Amino-2,4-dihydro-indeno[1,2-c]pyrazol-3-ylamino)-benzoic acid methyl ester | 87 | 0.308 |
| 121 | N3-(3-Fluoro-phenyl)-2,4-dihydro-indeno[1,2-c]pyrazole-3,6-diamine | 92 | 0.143 |
| 122 | (3-Bromo-phenyl)-[6-(4-methyl-piperazin-1-yl)-2,4-dihydro-indeno[1,2-c]pyrazol-3-yl]-amine | 70 | 0.0162 |
| 123 | (3-Methoxy-phenyl)-[6-(4-methyl-piperazin-1-yl)-2,4-dihydro-indeno[1,2-c]pyrazol-3-yl]-amine | 87 | 0.228 |
| 124 | (3-Chloro-phenyl)-[6-(4-methyl-piperazin-1-yl)-2,4-dihydro-indeno[1,2-c]pyrazol-3-yl]-amine | 94 | 0.0163 |
| 125 | 3-(3-Bromo-phenylamino)-2,4-dihydro-indeno[1,2-c]pyrazole-6,7-diol | 71 | 3.44 |
| 126 | (2,9-Dihydro-5,7-dioxa-2,3-diaza-cyclopenta[a]-s-indacen-1-yl)-pyridin-3-yl-amine | 65 | 0.1758 |
| 127 | 3-(2,9-Dihydro-5,7-dioxa-2,3-diaza-cyclopenta[a]-s-indacen-1-ylamino)-benzoic acid methyl ester | 89 | 0.421 |
| 128 | (3-Chloro-phenyl)-(2,9-dihydro-5,7-dioxa-2,3-diaza-cyclopenta[a]-s-indacen-1-yl)-amine | 88 | 0.05958 |
| 129 | [7-Methoxy-6-(3-morpholin-4-yl-propoxy)-2,4-dihydro-indeno[1,2-c]pyrazol-3-yl]-pyridin-3-yl-amine | 53.5 | 0.0367 |
| 130 | (3-Bromo-phenyl)-[7-methoxy-6-(3-morpholin-4-yl-propoxy)-2,4-dihydro-indeno[1,2-c]pyrazol-3-yl]-amine | 94.5 | 0.002148 |
| 131 | [7-Methoxy-6-(3-morpholin-4-yl-propoxy)-2,4-dihydro-indeno[1,2-c]pyrazol-3-yl]-(3-methoxy-phenyl)-amine | 97 | 0.01297 |
| 132 | (3-Chloro-phenyl)-[7-methoxy-6-(3-morpholin-4-yl-propoxy)-2,4-dihydro-indeno[1,2-c]pyrazol-3-yl]-amine | 79 | 0.00537 |
| 133 | 3-[7-Methoxy-6-(3-morpholin-4-yl-propoxy)-2,4-dihydro-indeno[1,2-c]pyrazol-3-ylamino]-benzoic acid methyl ester | 53 | 0.03789 |
| 134 | (3-Fluoro-phenyl)-[7-methoxy-6-(3-morpholin-4-yl-propoxy)-2,4-dihydro-indeno[1,2-c]pyrazol-3-yl]-amine | 96 | 0.01006 |
| 135 | (3-Chloro-phenyl)-[6-(3-methoxy-propoxy)-2,4-dihydro-indeno[1,2-c]pyrazol-3-yl]-amine | 87 | 0.202 |
| 136 | (4-Fluoro-phenyl)-[6-(3-methoxy-propoxy)-2,4-dihydro-indeno[1,2-c]pyrazol-3-yl]-amine | 64.5 | 1.331 |
| 137 | 3-[6-(3-Methoxy-propoxy)-2,4-dihydro-indeno[1,2-c]pyrazol-3-ylamino]-benzoic acid methyl ester | 71 | 2.11 |
| 138 | (3-Fluoro-phenyl)-[6-(3-methoxy-propoxy)-2,4-dihydro-indeno[1,2-c]pyrazol-3-yl]-amine | 79.5 | 0.3011 |
| 139 | (3-Methoxy-phenyl)-[6-(3-methoxy-propoxy)-2,4-dihydro-indeno[1,2-c]pyrazol-3-yl]-amine | 80 | 0.09822 |
| 140 | [6-(3-Methoxy-propoxy)-2,4-dihydro-indeno[1,2-c]pyrazol-3-yl]-phenyl-amine | 56.5 | 0.01366 |
| 141 | (3-Bromo-phenyl)-[6-(3-methoxy-propoxy)-2,4-dihydro-indeno[1,2-c]pyrazol-3-yl]-amine | 83.5 | 0.3192 |
| 142 | [6-(3-Methoxy-propoxy)-2,4-dihydro-indeno[1,2-c]pyrazol-3-yl]-pyridin-3-yl-amine | 82.5 | 0.4534 |
| 143 | (4-Methoxy-phenyl)-[6-(3-methoxy-propoxy)-2,4-dihydro-indeno[1,2-c]pyrazol-3-yl]-amine | 67 | 8.124 |
| 144 | (4-Fluoro-phenyl)-(5-methoxy-2,4-dihydro-indeno[1,2-c]pyrazol-3-yl)-amine | 96.5 | 0.8359 |

TABLE A-continued

IC50 and percent of inhibition of compounds on PDGF-R kinase activity

| CPD | NAME | Percent Inhibition @ 10 uM | IC50 (μM) |
|---|---|---|---|
| 145 | (5-Methoxy-2,4-dihydro-indeno[1,2-c]pyrazol-3-yl)-(4-methoxy-phenyl)-amine | 48.5 | 13.93 |
| 146 | (5-Methoxy-2,4-dihydro-indeno[1,2-c]pyrazol-3-yl)-pyridin-3-yl-amine | 78.5 | 0.1603 |
| 147 | (2,5-Dimethoxy-phenyl)-(5-methoxy-2,4-dihydro-indeno[1,2-c]pyrazol-3-yl)-amine | 32 | 2.984 |
| 148 | (2,4-Dimethoxy-phenyl)-(5-methoxy-2,4-dihydro-indeno[1,2-c]pyrazol-3-yl)-amine | 57 | 8.601 |
| 149 | (5-Methoxy-2,4-dihydro-indeno[1,2-c]pyrazol-3-yl)-(3-trifluoromethoxy-phenyl)-amine | 27.5 | 8.37 |
| 150 | (5-Methoxy-2,4-dihydro-indeno[1,2-c]pyrazol-3-yl)-(3-trifluoromethyl-phenyl)-amine | 85 | 0.8226 |
| 151 | (6-Bromo-2,4-dihydro-indeno[1,2-c]pyrazol-3-yl)-(3-fluoro-phenyl)-amine | 79 | 0.09184 |
| 152 | (6-Bromo-2,4-dihydro-indeno[1,2-c]pyrazol-3-yl)-pyridin-3-yl-amine | 80 | 0.1739 |
| 153 | (6-Bromo-2,4-dihydro-indeno[1,2-c]pyrazol-3-yl)-(2,5-difluoro-phenyl)-amine | 79 | 1.033 |
| 154 | (6-Bromo-2,4-dihydro-indeno[1,2-c]pyrazol-3-yl)-(3-trifluoromethoxy-phenyl)-amine | 29 | 41.62 |
| 155 | (6-Bromo-2,4-dihydro-indeno[1,2-c]pyrazol-3-yl)-(3-trifluoromethyl-phenyl)-amine | 53 | 8.11 |
| 156 | (3-Methoxy-phenyl)-[7-methoxy-6-(3-pyrrolidin-1-yl-propoxy)-2,4-dihydro-indeno[1,2-c]pyrazol-3-yl]-amine | 87.5 | 0.001 |
| 157 | 3-[7-Methoxy-6-(3-pyrrolidin-1-yl-propoxy)-2,4-dihydro-indeno[1,2-c]pyrazol-3-ylamino]-benzoic acid methyl ester | 85 | 0.007 |
| 158 | (6-Bromo-2,4-dihydro-indeno[1,2-c]pyrazol-3-yl)-phenyl-amine | 87.5 | 0.1859 |
| 159 | [6-(3-Dimethylamino-propoxy)-2,4-dihydro-indeno[1,2-c]pyrazol-3-yl]-(4-fluoro-phenyl)-amine | 92.5 | 0.09887 |
| 160 | [6-(3-Dimethylamino-propoxy)-2,4-dihydro-indeno[1,2-c]pyrazol-3-yl]-(3-fluoro-phenyl)-amine | 94.5 | 0.05855 |
| 161 | [6-(3-Dimethylamino-propoxy)-2,4-dihydro-indeno[1,2-c]pyrazol-3-yl]-pyridin-3-yl-amine | 84 | 0.3825 |
| 162 | (2,5-Dimethoxy-phenyl)-[6-(3-dimethylamino-propoxy)-2,4-dihydro-indeno[1,2-c]pyrazol-3-yl]-amine | 21.5 | 54.87 |
| 163 | (2,5-Difluoro-phenyl)-[6-(3-dimethylamino-propoxy)-2,4-dihydro-indeno[1,2-c]pyrazol-3-yl]-amine | 32 | 22.65 |
| 165 | [6-(3-Dimethylamino-propoxy)-2,4-dihydro-indeno[1,2-c]pyrazol-3-yl]-(3-trifluoromethyl-phenyl)-amine | 92.5 | 0.1009 |
| 166 | (3-Chloro-4-fluoro-phenyl)-[7-methoxy-6-(3-methoxy-propoxy)-2,4-dihydro-indeno[1,2-c]pyrazol-3-yl]-amine | 88 | 0.085 |
| 167 | (3-Chloro-4-fluoro-phenyl)-(6,7-diisopropoxy-2,4-dihydro-indeno[1,2-c]pyrazol-3-yl)-amine | 92 | 0.5111 |
| 168 | (6,7-Diisopropoxy-2,4-dihydro-indeno[1,2-c]pyrazol-3-yl)-(3-methoxy-phenyl)-amine | 91 | 0.0688 |
| 169 | (6,7-Diisopropoxy-2,4-dihydro-indeno[1,2-c]pyrazol-3-yl)-(3-fluoro-phenyl)-amine | 89 | 0.036 |
| 170 | (4-Fluoro-phenyl)-(7-methoxy-2,4-dihydro-indeno[1,2-c]pyrazol-3-yl)-amine | 95.5 | 0.02676 |
| 171 | (7-Methoxy-2,4-dihydro-indeno[1,2-c]pyrazol-3-yl)-(4-methoxy-phenyl)-amine | 92.5 | 0.1232 |
| 172 | (3-Fluoro-phenyl)-(7-methoxy-2,4-dihydro-indeno[1,2-c]pyrazol-3-yl)-amine | 55 | 0.0133 |
| 173 | (7-Methoxy-2,4-dihydro-indeno[1,2-c]pyrazol-3-yl)-pyridin-3-yl-amine | 87 | 0.2146 |
| 174 | (2,5-Dimethoxy-phenyl)-(7-methoxy-2,4-dihydro-indeno[1,2-c]pyrazol-3-yl)-amine | 83 | 0.3459 |
| 175 | (2,4-Dimethoxy-phenyl)-(7-methoxy-2,4-dihydro-indeno[1,2-c]pyrazol-3-yl)-amine | 71 | 3.929 |
| 176 | (2,5-Difluoro-phenyl)-(7-methoxy-2,4-dihydro-indeno[1,2-c]pyrazol-3-yl)-amine | 46.5 | 0.3183 |
| 177 | (7-Methoxy-2,4-dihydro-indeno[1,2-c]pyrazol-3-yl)-(4-trifluoromethoxy-phenyl)-amine | 65.5 | 0.5226 |
| 178 | (7-Methoxy-2,4-dihydro-indeno[1,2-c]pyrazol-3-yl)-(4-trifluoromethyl-phenyl)-amine | 98.5 | 0.1324 |

TABLE A-continued

IC50 and percent of inhibition of compounds on PDGF-R kinase activity

| CPD | NAME | Percent Inhibition @ 10 uM | IC50 (μM) |
|---|---|---|---|
| 179 | (3-Chloro-4-fluoro-phenyl)-[7-methoxy-6-(3-morpholin-4-yl-propoxy)-2,4-dihydro-indeno[1,2-c]pyrazol-3-yl]-amine | 92 | 0.07124 |
| 180 | (3-Fluoro-phenyl)-[7-methoxy-6-(3-pyrrolidin-1-yl-propoxy)-2,4-dihydro-indeno[1,2-c]pyrazol-3-yl]-amine | 98.5 | 0.0133 |
| 181 | (3-Chloro-4-fluoro-phenyl)-[7-methoxy-6-(3-pyrrolidin-1-yl-propoxy)-2,4-dihydro-indeno[1,2-c]pyrazol-3-yl]-amine | 74.5 | 0.01536 |
| 182 | (3-Fluoro-phenyl)-(7-methyl-2,4-dihydro-indeno[1,2-c]pyrazol-3-yl)-amine | 107 | 0.005 |
| 183 | (4-Methoxy-phenyl)-(7-methyl-2,4-dihydro-indeno[1,2-c]pyrazol-3-yl)-amine | 53 | 0.5455 |
| 184 | (2,5-Dimethoxy-phenyl)-(7-methyl-2,4-dihydro-indeno[1,2-c]pyrazol-3-yl)-amine | 94 | 1.1 |
| 185 | (2,5-Difluoro-phenyl)-(7-methyl-2,4-dihydro-indeno[1,2-c]pyrazol-3-yl)-amine | 84 | 0.05 |
| 186 | (7-Methyl-2,4-dihydro-indeno[1,2-c]pyrazol-3-yl)-(4-trifluoromethoxy-phenyl)-amine | 78 | 0.4141 |
| 187 | (7-Methyl-2,4-dihydro-indeno[1,2-c]pyrazol-3-yl)-(3-trifluoromethyl-phenyl)-amine | 35 | |
| 188 | (6-Chloro-2,4-dihydro-indeno[1,2-c]pyrazol-3-yl)-pyridin-3-yl-amine | 74 | 0.0437 |
| 189 | (6-Chloro-2,4-dihydro-indeno[1,2-c]pyrazol-3-yl)-(4-methoxy-phenyl)-amine | 92 | 0.1989 |
| 190 | (6-Chloro-2,4-dihydro-indeno[1,2-c]pyrazol-3-yl)-(3-methoxy-phenyl)-amine | 80 | 0.04 |
| 191 | (6-Chloro-2,4-dihydro-indeno[1,2-c]pyrazol-3-yl)-(3-fluoro-phenyl)-amine | 88 | 0.0686 |
| 192 | (6-Chloro-2,4-dihydro-indeno[1,2-c]pyrazol-3-yl)-(2,5-difluoro-phenyl)-amine | 67 | 0.103 |
| 193 | (6-Chloro-2,4-dihydro-indeno[1,2-c]pyrazol-3-yl)-(4-trifluoromethyl-phenyl)-amine | 49 | |
| 194 | (6-Chloro-2,4-dihydro-indeno[1,2-c]pyrazol-3-yl)-(4-trifluoromethoxy-phenyl)-amine | 87 | 2.608 |
| 195 | (3,5-Bis-trifluoromethyl-phenyl)-(6-chloro-2,4-dihydro-indeno[1,2-c]pyrazol-3-yl)-amine | 76 | 2.28 |
| 196 | N-(6-Chloro-2,4-dihydro-indeno[1,2-c]pyrazol-3-yl)-N',N'-dimethyl-benzene-1,4-diamine | 70 | 1.293 |
| 197 | (6-Chloro-2,4-dihydro-indeno[1,2-c]pyrazol-3-yl)-m-tolyl-amine | 8 | |
| 198 | (6-Chloro-2,4-dihydro-indeno[1,2-c]pyrazol-3-yl)-p-tolyl-amine | 72 | 0.1384 |
| 199 | [6-(3-Dimethylamino-propoxy)-7-methoxy-2,4-dihydro-indeno[1,2-c]pyrazol-3-yl]-(3-fluoro-phenyl)-amine | 83 | 0.0059 |
| 200 | (3-Chloro-4-fluoro-phenyl)-[6-(3-dimethylamino-propoxy)-7-methoxy-2,4-dihydro-indeno[1,2-c]pyrazol-3-yl]-amine | 87 | 0.002 |
| 201 | (6-Fluoro-2,4-dihydro-indeno[1,2-c]pyrazol-3-yl)-(4-fluoro-phenyl)-amine | 96 | 0.009 |
| 202 | (3-Chloro-4-fluoro-phenyl)-(6-fluoro-2,4-dihydro-indeno[1,2-c]pyrazol-3-yl)-amine | 77 | 0.01238 |
| 203 | (2,5-Dimethoxy-phenyl)-(6-fluoro-2,4-dihydro-indeno[1,2-c]pyrazol-3-yl)-amine | 86 | 0.01595 |
| 204 | (3,5-Dimethoxy-phenyl)-(6-fluoro-2,4-dihydro-indeno[1,2-c]pyrazol-3-yl)-amine | 90 | 0.038 |
| 205 | (3,4-Dimethoxy-phenyl)-(6-fluoro-2,4-dihydro-indeno[1,2-c]pyrazol-3-yl)-amine | 86 | 0.047 |
| 206 | (6,7-Dimethoxy-2,4-dihydro-indeno[1,2-c]pyrazol-3-yl)-(3,5-dimethyl-phenyl)-amine | 63 | 0.6401 |
| 207 | (3,5-Difluoro-phenyl)-(6,7-dimethoxy-2,4-dihydro-indeno[1,2-c]pyrazol-3-yl)-amine | 89 | 0.01 |
| 208 | (6,7-Dimethoxy-2,4-dihydro-indeno[1,2-c]pyrazol-3-yl)-(3-methylsulfanyl-phenyl)-amine | 82 | 0.003 |
| 209 | (6,7-Dimethoxy-2,4-dihydro-indeno[1,2-c]pyrazol-3-yl)-(3-ethyl-phenyl)-amine | 99 | 0.03281 |
| 210 | 3-(6,7-Dimethoxy-2,4-dihydro-indeno[1,2-c]pyrazol-3-ylamino)-benzoic acid ethyl ester | 90 | 0.06723 |
| 211 | (6,7-Dimethoxy-2,4-dihydro-indeno[1,2-c]pyrazol-3-yl)-(3-trifluoromethylsulfanyl-phenyl)-amine | 87 | 0.05 |

TABLE A-continued

IC50 and percent of inhibition of compounds on PDGF-R kinase activity

| CPD | NAME | Percent Inhibition @ 10 uM | IC50 (μM) |
|---|---|---|---|
| 212 | (6,7-Dimethoxy-2,4-dihydro-indeno[1,2-c]pyrazol-3-yl)-(4-fluoro-3-trifluoromethyl-phenyl)-amine | 84 | 0.775 |
| 213 | (3-Chloro-phenyl)-{7-methoxy-6-[3-(4-methyl-piperazin-1-yl)-propoxy]-2,4-dihydro-indeno[1,2-c]pyrazol-3-yl}-amine | 82 | 0.0027 |
| 214 | (3-Chloro-4-fluoro-phenyl)-{7-methoxy-6-[3-(4-methyl-piperazin-1-yl)-propoxy]-2,4-dihydro-indeno[1,2-c]pyrazol-3-yl}-amine | 46 | |
| 215 | {7-Methoxy-6-[3-(4-methyl-piperazin-1-yl)-propoxy]-2,4-dihydro-indeno[1,2-c]pyrazol-3-yl}-(3-methoxy-phenyl)-amine | 99 | 0.0057 |
| 216 | (3-Fluoro-phenyl)-{7-methoxy-6-[3-(4-methyl-piperazin-1-yl)-propoxy]-2,4-dihydro-indeno[1,2-c]pyrazol-3-yl}-amine | 100 | 0.0058 |
| 217 | [6-(3-Dimethylamino-propoxy)-2,4-dihydro-indeno[1,2-c]pyrazol-3-yl]-(4-trifluoromethoxy-phenyl)-amine | 51 | 3.479 |
| 218 | (4-Benzyloxy-phenyl)-(6,7-dimethoxy-2,4-dihydro-indeno[1,2-c]pyrazol-3-yl)-amine | 81 | 2.01 |
| 219 | (3,4-Dichloro-benzyl)-(6,7-dimethoxy-2,4-dihydro-indeno[1,2-c]pyrazol-3-yl)-amine | 39 | |
| 220 | Cyclohexylmethyl-(6,7-dimethoxy-2,4-dihydro-indeno[1,2-c]pyrazol-3-yl)-amine | 73 | 3.29 |
| 221 | (6,7-Dimethoxy-2,4-dihydro-indeno[1,2-c]pyrazol-3-yl)-[4-(piperidine-4-sulfonyl)-phenyl]-amine | 71 | 1.598 |
| 222 | (6,7-Dimethoxy-2,4-dihydro-indeno[1,2-c]pyrazol-3-yl)-(4-methyl-benzyl)-amine | 70 | 0.806 |
| 223 | (6,7-Dimethoxy-2,4-dihydro-indeno[1,2-c]pyrazol-3-yl)-(2-methyl-benzyl)-amine | 97 | 0.04593 |
| 224 | (6,7-Dimethoxy-2,4-dihydro-indeno[1,2-c]pyrazol-3-yl)-(2-methoxy-benzyl)-amine | 24 | |
| 225 | (6,7-Dimethoxy-2,4-dihydro-indeno[1,2-c]pyrazol-3-yl)-(3-methoxy-benzyl)-amine | 90 | 0.07443 |
| 226 | (3-Fluoro-phenyl)-[6-(3-imidazol-1-yl-propoxy)-7-methoxy-2,4-dihydro-indeno[1,2-c]pyrazol-3-yl]-amine | 102 | 0.003 |
| 227 | (3-Chloro-4-fluoro-phenyl)-[6-(3-imidazol-1-yl-propoxy)-7-methoxy-2,4-dihydro-indeno[1,2-c]pyrazol-3-yl]-amine | 83.5 | 0.03487 |
| 230 | (2-Chloro-benzyl)-(6,7-dimethoxy-2,4-dihydro-indeno[1,2-c]pyrazol-3-yl)-amine | 90 | 0.0019 |
| 231 | (6,7-Dimethoxy-2,4-dihydro-indeno[1,2-c]pyrazol-3-yl)-(4-methoxy-benzyl)-amine | 37 | |
| 232 | (5,7-Dihydro-1-thia-4,5-diaza-cyclopenta[a]pentalen-6-yl)-(3-methoxy-phenyl)-amine | 102 | 0.0396 |
| 233 | (6-Fluoro-2,4-dihydro-indeno[1,2-c]pyrazol-3-yl)-(4-methoxy-phenyl)-amine | 50 | 0.02759 |
| 234 | (6-Fluoro-2,4-dihydro-indeno[1,2-c]pyrazol-3-yl)-(3-methoxy-phenyl)-amine | 101 | 0.3581 |
| 235 | (6-Fluoro-2,4-dihydro-indeno[1,2-c]pyrazol-3-yl)-(3-fluoro-phenyl)-amine | 86 | 0.2114 |
| 236 | (2,5-Difluoro-phenyl)-(6-fluoro-2,4-dihydro-indeno[1,2-c]pyrazol-3-yl)-amine | 82 | 0.005 |
| 237 | (6-Fluoro-2,4-dihydro-indeno[1,2-c]pyrazol-3-yl)-(4-trifluoromethyl-phenyl)-amine | 88 | 0.05 |
| 238 | (6-Fluoro-2,4-dihydro-indeno[1,2-c]pyrazol-3-yl)-(4-trifluoromethoxy-phenyl)-amine | 87 | 0.4187 |
| 239 | (3,5-Bis-trifluoromethyl-phenyl)-(6-fluoro-2,4-dihydro-indeno[1,2-c]pyrazol-3-yl)-amine | 91 | 0.138 |
| 240 | (6-Fluoro-2,4-dihydro-indeno[1,2-c]pyrazol-3-yl)-m-tolyl-amine | 92 | 0.002 |
| 242 | (3-Fluoro-phenyl)-[7-methoxy-6-(3-methoxy-propoxy)-2,4-dihydro-indeno[1,2-c]pyrazol-3-yl]-amine | 104 | 0.013 |
| 244 | [7-Methoxy-6-(3-methoxy-propoxy)-2,4-dihydro-indeno[1,2-c]pyrazol-3-yl]-(3-methoxy-phenyl)-amine | 101 | 0.0002 |
| 245 | (6,7-Diethoxy-2,4-dihydro-indeno[1,2-c]pyrazol-3-yl)-(3-methoxy-phenyl)-amine | 87 | 0.001 |
| 246 | (3-Chloro-4-fluoro-phenyl)-(6,7-dioethoxy-2,4-dihydro-indeno[1,2-c]pyrazol-3-yl)-amine | 77 | 0.0121 |
| 247 | (6,7-Dimethoxy-4-methyl-2,4-dihydro-indeno[1,2-c]pyrazol-3-yl)-phenyl-amine | 96 | 0.07 |

TABLE A-continued

IC50 and percent of inhibition of compounds on PDGF-R kinase activity

| CPD | NAME | Percent Inhibition @ 10 uM | IC50 (μM) |
|---|---|---|---|
| 248 | (6,7-Dimethoxy-4-methyl-2,4-dihydro-indeno[1,2-c]pyrazol-3-yl)-(4-fluoro-phenyl)-amine | 68 | 0.4099 |
| 249 | (6,7-Dimethoxy-4-methyl-2,4-dihydro-indeno[1,2-c]pyrazol-3-yl)-(3-fluoro-phenyl)-amine | 96 | 0.006 |
| 250 | (3-Chloro-4-fluoro-phenyl)-(6,7-dimethoxy-4-methyl-2,4-dihydro-indeno[1,2-c]pyrazol-3-yl)-amine | 88 | 0.2234 |
| 251 | (3,5-Difluoro-phenyl)-(6,7-dimethoxy-4-methyl-2,4-dihydro-indeno[1,2-c]pyrazol-3-yl)-amine | 84 | 0.3222 |
| 252 | (2,5-Difluoro-phenyl)-(6,7-dimethoxy-4-methyl-2,4-dihydro-indeno[1,2-c]pyrazol-3-yl)-amine | 16 | |
| 253 | (6,7-Dimethoxy-4-methyl-2,4-dihydro-indeno[1,2-c]pyrazol-3-yl)-(3-methoxy-phenyl)-amine | 94 | 0.0165 |
| 254 | (3-Benzyloxy-phenyl)-(6,7-dimethoxy-4-methyl-2,4-dihydro-indeno[1,2-c]pyrazol-3-yl)-amine | 89 | 0.1808 |
| 255 | (6,7-Dimethoxy-4-methyl-2,4-dihydro-indeno[1,2-c]pyrazol-3-yl)-(3-methylsulfanyl-phenyl)-amine | 90 | 0.1615 |
| 256 | (3-Bromo-phenyl )-(6,7-dimethoxy-4-methyl-2,4-dihydro-indeno[1,2-c]pyrazol-3-yl)-amine | 89 | 0.008 |
| 257 | (3-Chloro-phenyl )-(6,7-dimethoxy-4-methyl-2,4-dihydro-indeno[1,2-c]pyrazol-3-yl)-amine | 35 | |
| 258 | (6,7-Dimethoxy-4-methyl-2,4-dihydro-indeno[1,2-c]pyrazol-3-yl)-(2,5-dimethoxy-phenyl)-amine | 39 | |
| 259 | 3-[3-(3-Chloro-phenylamino)-7-methoxy-2,4-dihydro-indeno[1,2-c]pyrazol-6-yloxy]-propane-1,2-diol | 93 | 0.002045 |
| 260 | 3-[7-Methoxy-3-(3-methoxy-phenylamino)-2,4-dihydro-indeno[1,2-c]pyrazol-6-yloxy]-propane-1,2-diol | 91 | 0.0015 |
| 261 | 3-[3-(3-Chloro-4-fluoro-phenylamino)-7-methoxy-2,4-dihydro-indeno[1,2-c]pyrazol-6-yloxy]-propane-1,2-diol | 71 | 0.01 |
| 262 | 3-[3-(3-Fluoro-phenylamino)-7-methoxy-2,4-dihydro-indeno[1,2-c]pyrazol-6-yloxy]-propane-1,2-diol | 90 | 0.001 |
| 263 | 3-[7-Methoxy-3-(pyridn-3-ylamino)-2,4-dihydro-indeno[1,2-c]pyrazol-6-yloxy]-propane-1,2-diol | 103 | 0.046 |
| 264 | Benzyl-(6,7-diethoxy-2,4-dihydro-indeno[1,2-c]pyrazol-3-yl)-amine | 86 | 0.08519 |
| 265 | 3-[3-(3-Fluoro-phenylamino)-7-methoxy-2,4-dihydro-indeno[1,2-c]pyrazol-6-yloxy]-propan-1-ol | 63 | 0.005535 |
| 266 | 3-[7-Methoxy-3-(3-methoxy-phenylamino)-2,4-dihydro-indeno[1,2-c]pyrazol-6-yloxy]-propan-1-ol | 110 | 0.001534 |
| 267 | 3-[3-(3-Choloro-4-fluoro-phenylamino)-7-methoxy-2,4-dihydro-indeno[1,2-c]pyrazol-6-yloxy]-propan-1-ol | 93.5 | 0.01059 |
| 268 | 3-[3-(3-Chloro-phenylamino)-7-methoxy-2,4-dihydro-indeno[1,2-c]pyrazol-6-yloxy]-propan-1-ol | 84 | 0.001134 |
| 269 | 1-[3-(3-Fluoro-phenylamino)-7-methoxy-2,4-dihydro-indeno[1,2-c]pyrazol-6-yloxy]-3-pyrrolidin-1-yl-propan-2-ol | 94 | 0.0005914 |
| 270 | 1-[7-Methoxy-3-(3-methoxy-phenylamino)-2,4-dihydro-indeno[1,2-c]pyrazol-6-yloxy]-3-pyrrolidin-1-yl-propan-2-ol | 107 | 0.0004287 |
| 271 | (3,5-Dichloro-benzyl)-(6,7-dimethoxy-2,4-dihydro-indeno[1,2-c]pyrazol-3-yl)-amine | 54.5 | 6.987 |
| 272 | (6,7-Dimethoxy-2,4-dihydro-indeno[1,2-c]pyrazol-3-yl)-(3-methyl-benzyl)-amine | 61 | 0.3888 |
| 273 | (3-Chloro-4-methyl-benzyl)-(6,7-dimethoxy-2,4-dihydro-indeno[1,2-c]pyrazol-3-yl)-amine | 77 | 1.584 |
| 274 | (2,5-Dimethoxy-benzyl)-(6,7-dimethoxy-2,4-dihydro-indeno[1,2-c]pyrazol-3-yl)-amine | 57.5 | 2.61 |
| 275 | (3,4-Difluoro-benzyl)-(6,7-dimethoxy-2,4-dihydro-indeno[1,2-c]pyrazol-3-yl)-amine | 80.5 | 0.5006 |
| 276 | (6,7-Dimethoxy-2,4-dihydro-indeno[1,2-c]pyrazol-3-yl)-(4-fluoro-3-nitro-phenyl)-amine | 11 | 0.2874 |
| 277 | (3-Chloro-4-methoxy-phenyl)-(6,7-dimethoxy-2,4-dihydro-indeno[1,2-c]pyrazol-3-yl)-amine | 88 | 1.361 |
| 278 | 1-[3-(6,7-Dimethoxy-2,4-dihydro-indeno[1,2-c]pyrazol-3-ylamino)-phenyl]-ethanol | 97 | 0.02949 |
| 279 | (3,5-Di-tert-butyl-phenyl)-(6,7-dimethoxy-2,4-dihydro-indeno[1,2-c]pyrazol-3-yl)-amine | 19.5 | 203.1 |
| 280 | 1-[3-(3-Chloro-4-fluoro-phenylamino)-7-methoxy-2,4-dihydro-indeno[1,2-c]pyrazol-6-yloxy]-3-pyrrolidin-1-yl-propan-2-ol | 102 | 0.00172 |

TABLE A-continued

IC50 and percent of inhibition of compounds on PDGF-R kinase activity

| CPD | NAME | Percent Inhibition @ 10 uM | IC50 (μM) |
|---|---|---|---|
| 281 | 1-[7-Methoxy-3-(pyridin-3-ylamino)-2,4-dihydro-indeno[1,2-c]pyrazol-6-yloxy]-3-pyrrolidin-1-yl-propan-2-ol | 67 | 0.002599 |
| 282 | 1-[3-(3-Chloro-phenylamino)-7-methoxy-2,4-dihydro-indeno[1,2-c]pyrazol-6-yloxy]-3-pyrrolidin-1-yl-propan-2-ol | 99 | 0.000089 |
| 283 | [6,7-Bis-(3-methoxy-propoxy)-2,4-dihydro indeno[1,2-c]pyrazol-3-yl]-(3-fluoro-phenyl)-amine | 86.5 | 0.004356 |
| 284 | [6,7-Bis-(3-methoxy-propoxy)-2,4-dihydro indeno[1,2-c]pyrazol-3-yl]-(3-methoxy-phenyl)-amine | 84.6 | 0.00509 |
| 285 | [6,7-Bis-(3-methoxy-propoxy)-2,4-dihydro indeno[1,2-c]pyrazol-3-yl]-(3-chloro-phenyl)-amine | 18.5 | 0.002779 |
| 286 | [6,7-Bis-(3-methoxy-propoxy)-2,4-dihydro-indeno[1,2-c]pyrazol-3-yl]-pyridin-3-yl-amine | 95.5 | 0.01624 |
| 287 | [6,7-Bis-(3-methoxy-propoxy)-2,4-dihydro-indeno[1,2-c]pyrazol-3-yl]-(3-Chloro-4-fluoro-phenyl)-amine | 92.5 | 0.02616 |
| 288 | (3-Chloro-4-methoxy-phenyl)-(6-fluoro-2,4-dihydro-indeno[1,2-c]pyrazol-3-yl)-amine | 88.5 | 0.2194 |
| 289 | 1-[3-(6-Fluoro-2,4-dihydro-indeno[1,2-c]pyrazol-3-ylamino)-phenyl]-ethanol | 93.5 | 0.01853 |
| 290 | (6-Fluoro-2,4-dihydro-indeno[1,2-c]pyrazol-3-yl)-(1H-indol-5-yl)-amine | 87.5 | 0.06142 |
| 291 | (6-Benzyloxy-7-methoxy-2,4-dihydro-indeno[1,2-c]pyrazol-3-yl)-(3-fluoro-phenyl)-amine | 95 | 0.2052 |
| 292 | (2-Chloro-benzyl )-(6,7-diethoxy-2,4-dihydro-indeno[1,2-c]pyrazol-3-yl)-amine | 86.5 | 0.01822 |
| 293 | (6,7-Diethoxy-2,4-dihydro-indeno[1,2-c]pyrazol-3-yl)-(2-fluoro-benzyl)-amine | 96.5 | 0.06916 |
| 294 | (6,7-Diethoxy-2,4-dihydro-indeno[1,2-c]pyrazol-3-yl)-(3-fluoro-benzyl)-amine | 81 | 0.2637 |
| 295 | (2,6-Dichloro-benzyl)-(6,7-diethoxy-2,4-dihydro-indeno[1,2-c]pyrazol-3-yl)-amine | 81.5 | 0.001645 |
| 296 | (6,7-Diethoxy-2,4-dihydro-indeno[1,2-c]pyrazol-3-yl)-(2-methoxy-benzyl)-amine | 72.5 | 1.821 |
| 297 | 3-(6,7-Dimethoxy-2,4-dihydro-indeno[1,2-c]pyrazol-3-ylamino)-N-(2-hydroxy-ethyl)-benzamide | 90.5 | 0.2749 |
| 298 | 3-(6,7-Dimethoxy-2,4-dihydro-indeno[1,2-c]pyrazol-3-ylamino)-N-(3-pyrrolidin-1-yl-propyl)-benzamide | 92 | 0.4082 |
| 299 | (7-Fluoro-2,4-dihydro-indeno[1,2-c]pyrazol-3-yl)-phenyl-amine | 80 | 0.01928 |
| 300 | (6,7-Dimethoxy-4-phenyl-2,4-dihydro-indeno[1,2-c]pyrazol-3-yl)-phenyl-amine | 40 | |
| 301 | (6,7-Diethoxy-2,4-dihydro-indeno[1,2-c]pyrazol-3-yl)-(2-trifluoromethoxy-benzyl)-amine | 72 | |
| 302 | (6,7-Dimethoxy-4-phenyl-2,4-dihydro-indeno[1,2-c]pyrazol-3-yl)-(3-fluoro-phenyl)-amine | 47 | |
| 303 | (3,5-Di-tert-butyl-phenyl)-(6-fluoro-2,4-dihydro-indeno[1,2-c]pyrazol-3-yl)-amine | 50 | 9.338 |
| 304 | (3,5-Dichloro-benzyl)-(6-fluoro-2,4-dihydro-indeno[1,2-c]pyrazol-3-yl)-amine | 38 | 3.456 |
| 305 | (6-Fluoro-2,4-dihydro-indeno[1,2-c]pyrazol-3-yl)-(3-methyl-benzyl)-amine | 87 | 0.4577 |
| 306 | (3-Chloro-4-methyl-benzyl)-(6-fluoro-2,4-dihydro indeno[1,2-c]pyrazol-3-yl)-amine | 47.5 | 8.589 |
| 307 | (2,5-Dimethoxy-benzyl)-(6-fluoro-2,4-dihydro-indeno[1,2-c]pyrazol-3-yl)-amine | 59 | 3.401 |
| 308 | (3,4-Difluoro-benzyl)-(6-fluoro-2,4-dihydro-indeno[1,2-c]pyrazol-3-yl)-amine | 14 | 0.5108 |
| 309 | (3-Chloro-4-methoxy-phenyl)-(7-methyl-2,4-dihydro-indeno[1,2-c]pyrazol-3-yl)-amine | 92.5 | 0.03022 |
| 310 | 1-[3-(7-Methyl-2,4-dihydro-indeno[1,2-c]pyrazol-3-ylamino)-phenyl]-ethanol | 95.5 | 0.0202 |
| 311 | (1H-Indol-5-yl)-(7-methyl-2,4-dihydro-indeno[1,2-c]pyrazol-3-yl)-amine | 68.5 | 0.07478 |
| 312 | (3,5-Di-tert-butyl-phenyl)-(7-methyl-2,4-dihydro-indeno[1,2-c]pyrazol-3-yl)-amine | 56.5 | 5.672 |
| 313 | (3,5-Dichloro-benzyl)-(7-methyl-2,4-dihydro-indeno[1,2-c]pyrazol-3-yl)-amine | 62.5 | 3.503 |
| 314 | (3-Methyl-benzyl)-(7-methyl-2,4-dihydro-indeno[1,2-c]pyrazol-3-yl)-amine | 76 | 0.8944 |

TABLE A-continued

IC50 and percent of inhibition of compounds on PDGF-R kinase activity

| CPD | NAME | Percent Inhibition @ 10 uM | IC50 (μM) |
|---|---|---|---|
| 315 | (3-Chloro-4-methyl-benzyl)-(7-methyl-2,4-dihydro-indeno[1,2-c]pyrazol-3-yl)-amine | 17.5 | 1.924 |
| 316 | (2,5-Dimethoxy-benzyl)-(7-methyl-2,4-dihydro-indeno[1,2-c]pyrazol-3-yl)-amine | 66 | 4.906 |
| 317 | (3,4-Difluoro-benzyl)-(7-methyl-2,4-dihydro-indeno[1,2-c]pyrazol-3-yl)-amine | 79 | 1.247 |
| 318 | (4,5-Dihydro-2H-6-oxa-1,2-diaza-benzo[e]azulen-3-yl)-phenyl-amine | 23 | 34.38 |
| 319 | [3-(6,7-Dimethoxy-2,4-dihydro-indeno[1,2-c]pyrazol-3-ylamino)-phenyl]-(4-methyl-piperazin-1-yl)-methanone | 80.5 | 2.201 |
| 320 | (6,7-Dimethoxy-2,4-dihydro-indeno[1,2-c]pyrazol-3-yl)-(3,4-dimethyl-benzyl)-amine | 70.5 | 1.958 |
| 321 | (2,6-Difluoro-benzyl)-(6,7-dimethoxy-2,4-dihydro-indeno[1,2-c]pyrazol-3-yl)-amine | 77 | 0.007454 |
| 322 | (2,3-Dimethoxy-benzyl )-(6,7-dimethoxy-2,4-dihydro-indeno[1,2-c]pyrazol-3-yl)-amine | 22 | 0.05466 |
| 323 | (2,5-Difluoro-benzyl)-(6,7-dimethoxy-2,4-dihydro-indeno[1,2-c]pyrazol-3-yl)-amine | 60.5 | 8.711 |
| 324 | (6,7-Dimethoxy-2,4-dihydro-indeno[1,2-c]pyrazol-3-yl)-[1-(3-methoxy-phenyl)-ethyl]-amine | 74.5 | 1.325 |
| 325 | (6,7-Dimethoxy-2,4-dihydro-indeno[1,2-c]pyrazol-3-yl)-(2-fluoro-benzyl)-amine | 61 | 0.09669 |
| 326 | (2,3-Dichloro-benzyl)-(6,7-dimethoxy-2,4-dihydro-indeno[1,2-c]pyrazol-3-yl)-amine | 82 | 0.2671 |
| 327 | (6,7-Dimethoxy-2,4-dihydro-indeno[1,2-c]pyrazol-3-yl)-(3-fluoro-benzyl)-amine | 52 | 10.62 |
| 328 | (2,4-Difluoro-benzyl)-(6,7-dimethoxy-2,4-dihydro-indeno[1,2-c]pyrazol-3-yl)-amine | 78.5 | 0.6971 |
| 329 | (6,7-Dimethoxy-2,4-dihydro-indeno[1,2-c]pyrazol-3-yl)-(2-trifluoromethyl-benzyl)-amine | 58 | 0.0762 |
| 330 | (2,5-Dichloro-benzyl)-(6,7-dimethoxy-2,4-dihydro-indeno[1,2-c]pyrazol-3-yl)-amine | 100 | 0.0162 |
| 331 | (6,7-Dimethoxy-2,4-dihydro-indeno[1,2-c]pyrazol-3-yl)-(4-fluoro-benzyl)-amine | 93 | 0.1886 |
| 332 | (5,8-Dimethoxy-2,4-dihydro-indeno[1,2-c]pyrazol-3-yl)-phenyl-amine | 90 | 0.3716 |
| 333 | (3-Chloro-benzyl)-(6,7-dimethoxy-4-methyl-2,4-dihydro-indeno[1,2-c]pyrazol-3-yl)-amine | 73.5 | 2.55 |
| 334 | (7-Fluoro-2,4-dihydro-indeno[1,2-c]pyrazol-3-yl)-(3-fluoro-phenyl)-amine | 99.5 | 0.008693 |
| 335 | (5,7-Dihydro-1-thia-4,5-diaza-cyclopenta[a]pentalen-6-yl)-(3-fluoro-phenyl)-amine | 100 | 0.1292 |
| 337 | (2,4-Dihydro-indeno[1,2-c]pyrazol-3-yl)-(3-fluoro-phenyl)-amine | 100 | 0.008804 |
| 338 | (5-Chloro-2-methyl-phenyl)-(2,4-dihydro-indeno[1,2-c]pyrazol-3-yl)-amine | 78.5 | 0.4512 |
| 339 | (2,5-Difluoro-phenyl)-(2,4-dihydro-indeno[1,2-c]pyrazol-3-yl)-amine | 100 | 0.1174 |
| 340 | (2,4-Dihydro-indeno[1,2-c]pyrazol-3-yl)-(2-fluoro-5-trifluoromethyl-phenyl)-amine | 92.5 | 0.1046 |
| 341 | (2,4-Dihydro-indeno[1,2-c]pyrazol-3-yl)-(2,5-dimethoxy-phenyl)-amine | 92.5 | 0.04118 |
| 342 | (5-Chloro-2-methoxy-phenyl)-(2,4-dihydro-indeno[1,2-c]pyrazol-3-yl)-amine | 56.5 | 0.02668 |
| 343 | (2,4-Dihydro-indeno[1,2-c]pyrazol-3-yl)-(3-methoxy-phenyl-amine | 99.5 | 0.008075 |
| 344 | (6,7-Diethoxy-4-methyl-2,4-dihydro-indeno[1,2-c]pyrazol-3-yl)-(3-fluoro-phenyl)-amine | 100 | 0.06465 |
| 345 | (6,7-Diethoxy-4-methyl-2,4-dihydro-indeno[1,2-c]pyrazol-3-yl)-pyridin-3-yl-amine | 88 | 0.0893 |
| 346 | (3-Bromo-phenyl)-(6,7-diethoxy-4-methyl-2,4-dihydro-indeno[1,2-c]pyrazol-3-yl)-amine | 98 | 0.07392 |
| 347 | (3-Chloro-4-fluoro-phenyl)-(6,7-diethoxy-4-methyl-2,4-dihydro-indeno]1,2-c]pyrazol-3-yl)-amine | 90.5 | 0.5453 |
| 348 | (6,7-Diethoxy-4-methyl-2,4-dihydro-indeno[1,2-c]pyrazol-3-yl)-(3-methoxy-phenyl)-amine | 97.5 | 0.02529 |
| 349 | (6,7-Diethoxy-4-methyl-2,4-dihydro-indeno[1,2-c]pyrazol-3-yl)-(4-fluoro-phenyl)-amine | 78 | 0.08089 |
| 350 | 3-Phenylamino-4,5-dihydro-2H-benzo[g]indazole-7-carbonitrile | 91 | 0.6512 |

TABLE A-continued

IC50 and percent of inhibition of compounds on PDGF-R kinase activity

| CPD | NAME | Percent Inhibition @ 10 uM | IC50 (μM) |
|---|---|---|---|
| 351 | (6,7-Diisopropoxy-4-methyl-2,4-dihydro-indeno[1,2-c]pyrazol-3-yl)-(3-fluoro-phenyl)-amine | 93 | 0.3998 |
| 352 | (6,7-Diisopropoxy-4-methyl-2,4-dihydro-indeno[1,2-c]pyrazol-3-yl)-pyridin-3-yl-amine | 86.5 | 0.7554 |
| 353 | (3-Bromo-phenyl)-(6,7-diisopropoxy-4-methyl-2,4-dihydro-indeno[1,2-c]pyrazol-3-yl)-amine | 88 | 0.3594 |
| 354 | (3-Chloro-4-fluoro-phenyl)-(6,7-diisopropoxy-4-methyl-2,4-dihydro-indeno[1,2-c]pyrazol-3-yl)-amine | 62 | 2.45 |
| 355 | (6,7-Diisopropoxy-4-methyl-2,4-dihydro-indeno[1,2-c]pyrazol-3-yl)-(3-methoxy-phenyl)-amine | 85 | 1.026 |
| 356 | (6,7-Diisopropoxy-4-methyl-2,4-dihydro-indeno[1,2-c]pyrazol-3-yl)-(4-fluoro-phenyl)-amine | 70 | 1.953 |
| 357 | (6-Fluoro-7-methoxy-2,4-dihydro-indeno[1,2-c]pyrazol-3-yl)-(3-fluoro-phenyl)-amine | 98.5 | 0.009417 |
| 358 | (3-Bromo-phenyl)-(6-fluoro-7-methoxy-2,4-dihydro-indeno[1,2-c]pyrazol-3-yl)-amine | 92 | 0.00877 |
| 359 | (3-Chloro-4-fluoro-phenyl)-(6-fluoro-7-methoxy-2,4-dihydro-indeno[1,2-c]pyrazol-3-yl)-amine | 98.5 | 0.04151 |
| 360 | (6-Fluoro-7-methoxy-2,4-dihydro-indeno[1,2-c]pyrazol-3-yl)-(3-methoxy-phenyl)-amine | 98 | 0.007501 |
| 361 | (6-Fluoro-7-methoxy-2,4-dihydro-indeno[1,2-c]pyrazol-3-yl)-(4-fluoro-phenyl)-amine | 100 | 0.01156 |
| 362 | 3-(3-Fluoro-phenylamino)-2,4-dihydro-indeno[1,2-c]pyrazole-6,7-diol | 80.5 | 0.7844 |
| 363 | 3-(3-Fluoro-phenylamino)-7-methoxy-2,4-dihydro-indeno[1,2-c]pyrazol-6-ol | 76.5 | 0.005466 |
| 364 | (6-Fluoro-7-methoxy-2,4-dihydro-indeno[1,2-c]pyrazol-3-yl)-pyridin-3-yl-amine | 100 | 0.01506 |
| 365 | 3-[6-Ethoxy-3-(3-fluoro-phenylamino)-2,4-dihydro-indeno[1,2-c]pyrazol-7-yloxy]-propan-1-ol | 99.5 | 0.01131 |
| 366 | 3-[6-Ethoxy-3-(3-methoxy-phenylamino)-2,4-dihydro-indeno[1,2-c]pyrazol-7-yloxy]-propan-1-ol | 100 | 0.01209 |
| 367 | 3-[3-(3-Chloro-phenylamino)-6-ethoxy-2,4-dihydro-indeno[1,2-c]pyrazol-7-yloxy]-propan-1-ol | 97 | 0.00814 |
| 368 | 3-[3-(3-Chloro-4-fluoro-phenylamino)-6-ethoxy-2,4-dihydro-indeno[1,2-c]pyrazol-7-yloxy]-propan-1-ol | 89.5 | 0.06293 |
| 369 | (6-Bromo-7-methoxy-2,4-dihydro-indeno[1,2-c]pyrazol-3-yl)-(3-fluoro-phenyl)-amine | 100 | 0.0187 |
| 370 | (6-Bromo-7-methoxy-2,4-dihydro-indeno[1,2-c]pyrazol-3-yl)-(3-methoxy-phenyl)-amine | 94 | 0.01218 |
| 371 | 3-[6-Ethoxy-3-(pyridin-3-ylamino)-2,4-dihydro-indeno[1,2-c]pyrazol-7-yloxy]-propan-1-ol | 100 | 0.0476 |
| 372 | 3-[7-(3-Hydroxy-propoxy)-3-(pyridin-3-ylamino)-2,4-dihydro-indeno[1,2-c]pyrazol-6-yloxy]-propan-1-ol | 100 | 0.01553 |
| 373 | 3-[3-(3-Chloro-phenylamino)-7-(3-hydroxy-propoxy)-2,4-dihydro-indeno[1,2-c]pyrazol-6-yloxy]-propan-1-ol | 100 | 0.003772 |
| 374 | (6,7-Dimethoxy-2,4-dihydro-indeno[1,2-c]pyrazol-3-yl)-(3-ethoxy-phenyl)-amine | 100 | 0.01412 |
| 375 | (6,7-Diethoxy-2,4-dihydro-indeno[1,2-c]pyrazol-3-yl)-(3-ethoxy-phenyl)-amine | 96.5 | 0.1028 |
| 376 | 3-[3-(3-Ethoxy-phenylamino)-7-methoxy-2,4-dihydro-indeno[1,2-c]pyrazol-6-yloxy]-propan-1-ol | 100 | 0.009096 |
| 377 | (2-Chloro-pyridin-3-yl)-(6,7-dimethoxy-2,4-dihydro-indeno[1,2-c]pyrazol-3-yl)-amine | 99 | 0.008572 |
| 378 | (6-Fluoro-2,4-dihydro-indeno[1,2-c]pyrazol-3-yl)-(2-methyl-benzyl)-amine | 94.5 | 0.467 |
| 379 | 3-[3-(3-Ethoxy-phenylamino)-7-methoxy-2,4-dihydro-indeno[1,2-c]pyrazol-6-yloxy]-propane-1,2-diol | 100 | 0.008119 |
| 380 | (3-Fluoro-phenyl)-(2H-8-oxa-2,3-diaza-cyclopenta[a]inden-1-yl)-amine | 99.5 | 0.01533 |
| 381 | (3-Chloro-4-fluoro-phenyl)-(2H-8-oxa-2,3-diaza-cyclopenta[a]inden-1-yl)-amine | 100 | 0.05492 |
| 382 | 3-[7-Ethoxy-3-(3-fluoro-phenylamino)-2,4-dihydro-indeno[1,2-c]pyrazol-6-yloxy]-propan-1-ol | 100 | 0.01185 |
| 383 | 3-[7-Ethoxy-3-(pyridin-3-ylamino)-2,4-dihydro-indeno[1,2-c]pyrazol-6-yloxy]-propan-1-ol | 93 | 0.02533 |
| 384 | 3-[7-Ethoxy-3-(3-methoxy-phenylamino)-2,4-dihydro-indeno[1,2-c]pyrazol-6-yloxy]-propan-1-ol | 100 | 0.005607 |
| 385 | 3-[3-(2-Chloro-benzylamino)-7-methoxy-2,4-dihydro-indeno[1,2-c]pyrazol-6-yloxy]-propan-1-ol | 98.5 | 0.004072 |

TABLE A-continued

IC50 and percent of inhibition of compounds on PDGF-R kinase activity

| CPD | NAME | Percent Inhibition @ 10 uM | IC50 (μM) |
|---|---|---|---|
| 386 | 3-[3-(2-Fluoro-benzylamino)-7-methoxy-2,4-dihydro-indeno[1,2-c]pyrazol-6-yloxy]-propan-1-ol | 95.5 | 0.01101 |
| 387 | 3-[3-(2-Fluoro-benzylamino)-7-methoxy-2,4-dihydro-indeno[1,2-c]pyrazol-6-yloxy]-propane-1,2-diol | 100 | 0.01162 |
| 388 | 3-[6-Ethoxy-3-(3-ethoxy-phenylamino)-2,4-dihydro-indeno[1,2-c]pyrazol-7-yloxy]-propan-1-ol | 96 | 0.03667 |
| 389 | 3-[3-(3-Chloro-4-fluoro-phenylamino)-7-(3-hydroxy-propoxy)-2,4-dihydro-indeno[1,2-c]pyrazol-6-yloxy]-propan-1-ol | 98 | 0.01511 |
| 390 | 1-[3-(2,6-Dichloro-benzylamino)-7-methoxy-2,4-dihydro-indeno[1,2-c]pyrazol-6-yloxy]-3-pyrrolidin-1-yl-propan-2-ol | 99 | 0.002029 |
| 391 | 1-[3-(2,6-Difluoro-benzylamino)-7-methoxy-2,4-dihydro-indeno[1,2-c]pyrazol-6-yloxy]-3-pyrrolidin-1-yl-propan-2-ol | 99 | 0.006796 |
| 392 | (3-Chloro-phenyl)-[5-(3-morpholin-4-yl-propoxy)-2,4-dihydro-indeno[1,2-c]pyrazol-3-yl]-amine | 80 | 0.1528 |
| 393 | (3-Fluoro-phenyl)-[5-(3-morpholin-4-yl-propoxy)-2,4-dihydro-indeno[1,2-c]pyrazol-3-yl]-amine | 94.5 | 0.1737 |
| 394 | (3-Ethoxy-phenyl)-[5-(3-morpholin-4-yl-propoxy)-2,4-dihydro-indeno[1,2-c]pyrazol-3-yl]-amine | 91 | 0.3289 |
| 395 | 3-(3-Fluoro-phenylamino)-6,7-dimethoxy-4H-indeno[1,2-c]pyrazole-2-carboxylic acid (3-fluoro-phenyl)-amide | 88 | 0.6861 |
| 396 | 1-[3-(2-Chloro-benzylamino)-7-methoxy-2,4-dihydro-indeno[1,2-c]pyrazol-6-yloxy]-3-pyrrolidin-1-yl-propan-2-ol | 99.5 | 0.005129 |
| 397 | 1-[3-(2-Fluoro-benzylamino)-7-methoxy-2,4-dihydro-indeno[1,2-c]pyrazol-6-yloxy]-3-pyrrolidin-1-yl-propan-2-ol | 92 | 0.007701 |
| 398 | 3-[3-(3-Fluoro-phenylamino)-7-(3-hydroxy-propoxy)-2,4-dihydro-indeno[1,2-c]pyrazol-6-yloxy]-propan-1-ol | 96 | 0.00682 |
| 400 | 3-[7-(3-Hydroxy-propoxy)-3-(3-methoxy-phenylamino)-2,4-dihydro-indeno[1,2-c]pyrazol-6-yloxy]-propan-1-ol | 98.5 | 0.002918 |
| 401 | 3-[3-(3-Ethoxy-phenylamino)-7-(3-hydroxy-propoxy)-2,4-dihydro-indeno[1,2-c]pyrazol-6-yloxy]-propan-1-ol | 98.5 | 0.02203 |
| 402 | (5,7-Dihydro-1-thia-4,5-diaza-cyclopenta[a]pentalen-6-yl)-pyridin-3-yl-amine | 90 | 0.1957 |
| 403 | (3-Chloro-phenyl)-(5,7-dihydro-1-thia-4,5-diaza-cyclopenta[a]pentalen-6-yl)-amine | 96 | 0.08588 |
| 404 | (3-Chloro-4-fluoro-phenyl)-(5,7-dihydro-1-thia-4,5-diaza-cyclopenta[a]pentalen-6-yl)-amine | 74.5 | 1.115 |
| 405 | (5,7-Dihydro-1-thia-4,5-diaza-cyclopenta[a]pentalen-6-yl)-(3-ethoxy-phenyl)-amine | 94.5 | 0.06354 |
| 406 | 1-[3-(3-Fluoro-phenylamino)-6,7-dimethoxy-4H-indeno[1,2-c]pyrazol-2-yl]-ethanone | 96 | 0.07502 |
| 407 | {[3-(3-Fluoro-phenylamino)-6,7-dimethoxy-4H-indeno[1,2-c]pyrazole-2-carbonyl]-amino}-acetic acid ethyl ester | 39 | 9.883 |
| 408 | 2,2-Dimethyl-propionic acid 3-(3-fluoro-phenylamino)-6,7-dimethoxy-4H-indeno[1,2-c]pyrazol-2-ylmethyl ester | 83 | 0.6866 |
| 409 | 2,2-Dimethyl-propionic acid 3-(3-fluoro-phenylamino)-6,7-dimethoxy-4H-indeno[1,2-c]pyrazol-1-ylmethyl ester | 85.5 | 0.1076 |
| 410 | (2-Bromo-3-fluoro-phenyl)-(6,7-dimethoxy-2,4-dihydro-indeno[1,2-c]pyrazol-3-yl)-amine | 83.5 | 1.076 |
| 411 | 3-[(6,7-Dimethoxy-3-phenlylamino-4H-indeno[1,2-c]pyrazole-2-carbonyl)-amino]-propionic acid ethyl ester | 14.5 | 0.08233 |
| 412 | 2-{[3-(3-Fluoro-phenylamino)-6,7-dimethoxy-4H-indeno[1,2-c]pyrazole-2-carbonyl]-amino}-4-methyl-pentanoic acid methyl ester | 44 | 12.72 |
| 413 | 2-{[3-(3-Fluoro-phenylamino)-6,7-dimethoxy-4H-indeno[1,2-c]pyrazole-2-carbonyl]-amino}-3-methyl-butyric acid methyl ester | 71 | 1.14 |
| 414 | (2,6-Difluoro-benzyl)-[5-(3-morpholin-4-yl-propoxy)-2,4-dihydro-indeno[1,2-c]pyrazol-3-yl]-amine | 80.5 | 0.5639 |

TABLE A-continued

IC50 and percent of inhibition of compounds on PDGF-R kinase activity

| CPD | NAME | Percent Inhibition @ 10 uM | IC50 (μM) |
|---|---|---|---|
| 415 | (2,6-Dichloro-benzyl)-[5-(3-morpholin-4-yl-propoxy)-2,4-dihydro-indeno[1,2-c]pyrazol-3-yl]-amine | 98 | 0.02581 |
| 416 | (2-Fluoro-benzyl)-[5-(3-morpholin-4-yl-propoxy)-2,4-dihydro-indeno[1,2-c]pyrazol-3-yl]-amine | 72.5 | 1.185 |
| 417 | (5-Methoxy-2,4-dihydro-indeno[1,2-c]pyrazol-3-yl)-(3-methoxy-5-trifluoromethyl-phenyl)-amine | 27.5 | 12.2 |
| 418 | 3-(5-Methoxy-2,4-dihydro-indeno[1,2-c]pyrazol-3-ylamino)-benzenesulfonamide | 82.5 | 0.8916 |
| 419 | (3-Chloro-phenyl)-(4-ethyl-6,7-dimethoxy-2,4-dihydro-indeno[1,2-c]pyrazol-3-yl)-amine | 100 | 0.06214 |
| 420 | (3-Bromo-phenyl)-(4-ethyl-6,7-dimethoxy-2,4-dihydro-indeno[1,2-c]pyrazol-3-yl)-amine | 100 | 0.05236 |
| 421 | (4-Ethyl-6,7-dimethoxy-2,4-dihydro-indeno[1,2-c]pyrazol-3-yl)-(3-fluoro-phenyl )-amine | 100 | 0.08219 |
| 422 | (3-Fluoro-phenyl)-(5-methoxy-2,4-dihydro-indeno[1,2-c]pyrazol-3-yl)-amine | 83 | 0.02966 |
| 423 | (2,6-Difluoro-benzyl)-(5-methoxy-2,4-dihydro-indeno[1,2-c]pyrazol-3-yl)-amine | 90 | 0.1815 |
| 424 | (3-Chloro-benzyl)-(6,7-dimethoxy-2,4-dihydro-indeno[1,2-c]pyrazol-3-yl )-amine | 100 | 0.07912 |
| 425 | (6-Fluoro-7-methoxy-2,4-dihydro-indeno[1,2-c]pyrazol-3-yl)-(2-methyl-benzyl)-amine | 96 | 0.002296 |
| 426 | (2-Fluoro-benzyl)-(6-fluoro-7-methoxy-2,4-dihydro-indeno[1,2-c]pyrazol-3-yl)-amine | 97 | 0.2415 |
| 427 | [3-(3-Fluoro-phenylamino)-6,7-dimethoxy-4H-indeno[1,2-c]pyrazol-1-yl]-phenyl-methanone | 80 | 1.15 |
| 428 | 4-[3-(3-Fluoro-phenylamino)-6,7-dimethoxy-4H-indeno[1,2-c]pyrazol-1-yl]-4-oxo-butyric acid methyl ester | 85.5 | 0.432 |
| 429 | 4-[3-(3-Fluoro-phenylamino)-6,7-dimethoxy-4H-indeno[1,2-c]pyrazol-1-yl]-4-oxo-butyric acid ethyl ester | 72 | 0.6706 |
| 430 | 1-[3-(3-Fluoro-phenylamino)-6,7-dimethoxy-4H-indeno[1,2-c]pyrazol-1-yl]-propan-1-one | 61.5 | 0.571 |
| 431 | 1-[3-(3-Fluoro-phenylamino)-6,7-dimethoxy-4H-indeno[1,2-c]pyrazol-1-yl]-2-methyl-propan-1-one | 84.5 | 0.4437 |
| 432 | 1-[3-(3-Fluoro-phenylamino)-6,7-dimethoxy-4H-indeno[1,2-c]pyrazol-1-yl]-2-hydroxy-ethanone | 95.5 | 0.03804 |
| 433 | 3-(3-Fluoro-phenylamino)-6,7-dimethoxy-4H-indeno[1,2-c]pyrazole-1-carboxylic acid phenyl ester | 71 | 0.5849 |
| 434 | 3-(3-Fluoro-phenylamino)-6,7-dimethoxy-4H-indeno[1,2-c]pyrazole-2-carboxylic acid methyl ester | 86 | 0.503 |
| 435 | 3-(3-Fluoro-phenylamino)-6,7-dimethoxy-4H-indeno[1,2-c]pyrazole-2-carboxylic acid ethyl ester | 67 | 1.588 |
| 436 | 3-(3-Fluoro-phenylamino)-6,7-dimethoxy-4H-indeno[1,2-c]pyrazole-2-carboxylic acid isopropyl ester | 9.5 | 0.9619 |
| 437 | 3-(3-Fluoro-phenylamino)-6,7-dimethoxy-4H-indeno[1,2-c]pyrazole-2-carboxylic acid 2-methoxy-ethyl ester | 83.5 | 0.2914 |
| 438 | 3-(3-Fluoro-phenylamino)-6,7-dimethoxy-4H-indeno[1,2-c]pyrazole-1-carboxylic acid 2-methoxy-ethyl ester | 77.5 | 0.9923 |
| 439 | 3-(3-Fluoro-phenylamino)-6,7-dimethoxy-4H-indeno[1,2-c]pyrazole-1-carboxylic acid methyl ester | 69.5 | 0.6202 |
| 440 | 3-[3-(3-Chloro-phenylamino)-2,4-dihydro-indeno[1,2-c]pyrazol-5-yloxy]-propan-1-ol | 89.5 | 0.04574 |
| 441 | 3-[3-(3-Ethoxy-phenylamino)-2,4-dihydro-indeno[1,2-c]pyrazol-5-yloxy]-propan-1-ol | 96 | 0.2058 |
| 442 | 3-[3-(3-Fluoro-phenylamino)-2,4-dihydro-indeno[1,2-c]pyrazol-5-yloxy]-propan-1-ol | 94.5 | 0.2048 |
| 443 | 3-[3-(2,6-Difluoro-benzylamino)-2,4-dihydro-indeno[1,2-c]pyrazol-5-yloxy]-propan-1-ol | 89.5 | 0.09795 |
| 444 | 3-[3-(2-Fluoro-benzylamino)-2,4-dihydro-indeno[1,2-c]pyrazol-5-yloxy]-propan-1-ol | 79.5 | 0.5185 |
| 445 | 3-[3-(2-Methyl-benzylamino)-2,4-dihydro-indeno[1,2-c]pyrazol-5-yloxy]-propan-1-ol | 95 | 0.02526 |
| 446 | [3-(3-Fluoro-phenylamino)-6,7-dimethoxy-4H-indeno[1,2-c]pyrazol-1-yl]-phosphonic acid diethyl ester | 93.5 | 0.2656 |
| 447 | 3-(3-Fluoro-phenylamino)-6,7-dimethoxy-4H-indeno[1,2-c]pyrazole-1-sulfonic acid dimethylamide | 7 | |

TABLE A-continued

IC50 and percent of inhibition of compounds on PDGF-R kinase activity

| CPD | NAME | Percent Inhibition @ 10 uM | IC50 (μM) |
|---|---|---|---|
| 448 | 3-[3-(2,6-Dichloro-benzylamino)-7-methoxy-2,4-dihydro-indeno[1,2-c]pyrazol-6-yloxy]-propan-1-ol | 100 | 0.001767 |
| 449 | 3-[3-(2,6-Difluoro-benzylamino)-7-methoxy-2,4-dihydro-indeno[1,2-c]pyrazol-6-yloxy]-propan-1-ol | 98.5 | 0.004098 |
| 450 | 3-[3-(2,6-Dichloro-benzylamino)-7-methoxy-2,4-dihydro-indeno[1,2-c]pyrazol-6-yloxy]-propane-1,2-diol | 100 | 0.0009382 |
| 451 | 3-[3-(2-Chloro-benzylamino)-7-methoxy-2,4-dihydro-indeno[1,2-c]pyrazol-6-yloxy]-propane-1,2-diol | 99.5 | 0.002004 |
| 452 | N1-(6,7-Dimethoxy-2,4-dihydro-indeno[1,2-c]pyrazol-3-yl)-4-methyl-N3-(4-pyridin-3-yl-pyrimidin-2-yl)-benzene-1,3-diamine | 72 | 1.096 |
| 453 | (6,7-Dimethoxy-2,4-dihydro-indeno[1,2-c]pyrazol-3-yl)-(4-methoxy-pyridin-3-yl)-amine | 88 | 0.8294 |
| 454 | (6,7-Dimethoxy-2,4-dihydro-indeno[1,2-c]pyrazol-3-yl)-(2,4-dimethoxy-pyridin-3-yl)-amine | 99 | 0.2579 |
| 455 | (6,7-Dimethoxy-2,4-dihydro-indeno[1,2-c]pyrazol-3-yl)-(5-phenyl-isoxazol-3-ylmethyl)-amine | 95 | 0.1532 |
| 457 | 3-[3-(2,6-Difluoro-benzylamino)-7-methoxy-2,4-dihydro-indeno[1,2-c]pyrazol-6-yloxy]-propane-1,2-diol | 100 | 0.003414 |
| 458 | [3-(3-Fluoro-phenylamino)-6,7-dimethoxy-4H-indeno[1,2-c]pyrazol-1-yl]-(4-methoxy-phenyl)-methanone | 70.5 | 6.998 |
| 459 | 3-[3-(3-Fluoro-phenylamino)-6,7-dimethoxy-4H-indeno[1,2-c]pyrazol-1-yl]-3-oxo-propionic acid ethyl ester | 100 | 0.03654 |
| 460 | 1-[6-Ethoxy-3-(3-fluoro-phenylamino)-2,4-dihydro-indeno[1,2-c]pyrazol-7-yloxy]-3-pyrrolidin-1-yl-propan-2-ol | 97.5 | 0.00427 |
| 461 | 1-[6-Ethoxy-3-(pyridin-3-ylamino)-2,4-dihydro-indeno[1,2-c]pyrazol-7-yloxy]-3-pyrrolidin-1-yl-propan-2-ol | 97.5 | 0.007552 |
| 462 | 1-[6-Ethoxy-3-(3-methoxy-phenylamino)-2,4-dihydro-indeno[1,2-c]pyrazol-7-yloxy]-3-pyrrolidin-1-yl-propan-2-ol | 99 | 0.00215 |
| 463 | 1-[6-Ethoxy-3-(3-ethoxy-phenylamino)-2,4-dihydro-indeno[1,2-c]pyrazol-7-yloxy]-3-pyrrolidin-1-yl-propan-2-ol | 98.5 | 0.01095 |
| 464 | 5-[3-(3-Fluoro-phenylamino)-6,7-dimethoxy-4H-indeno[1,2-c]pyrazol-1-yl]-5-oxo-pentanoic acid methyl ester | 92 | 0.2446 |
| 465 | 1-[3-(3-Fluoro-phenylamino)-6,7-dimethoxy-4H-indeno[1,2-c]pyrazol-1-yl]-2-methoxy-ethanone | 96 | 0.006728 |
| 466 | 4-[3-(3-Fluoro-phenylamino)-6,7-dimethoxy-4H-indeno[1,2-c]pyrazol-1-yl]-4-oxo-butyric acid | 96 | 0.03113 |
| 467 | Acetic acid 2-[3-(3-fluoro-phenylamino)-6,7-dimethoxy-4H-indeno[1,2-c]pyrazol-1-yl]-2-oxo-ethyl ester | 96.5 | 0.01763 |
| 468 | 3-[3-(3-Bromo-phenylamino)-2,4-dihydro-indeno[1,2-c]pyrazol-5-yloxy]-propane-1,2-diol | 95.5 | 0.04784 |
| 469 | 3-[3-(3-Fluoro-phenylamino)-2,4-dihydro-indeno[1,2-c]pyrazol-5-yloxy]-propane-1,2-diol | 96 | 0.1598 |
| 470 | 3-(3-Fluoro-phenylamino)-6,7-dimethoxy-4H-indeno[1,2-c]pyrazole-1-carboxylic acid 2-benzyloxy-ethyl ester | 96 | 0.197 |
| 471 | 3-(3-Fluoro-phenylamino)-6,7-dimethoxy-4H-indeno[1,2-c]pyrazole-1-carboxylic acid 2-[2-(2-hydroxy-ethoxy)-ethoxy]-ethyl ester | 90.5 | 0.1347 |
| 472 | (6,7-Dimethoxy-1-methoxymethyl-1,4-dihydro-indeno[1,2-c]pyrazol-3-yl)-(3-fluoro-phenyl)-amine | 35 | |
| 473 | Methoxy-acetic acid 2-[3-(3-fluoro-phenylamino)-6,7-dimethoxy-4H-indeno[1,2-c]pyrazol-1-yl]-2-oxo-ethyl ester | 98.5 | 0.008962 |
| 474 | Isobutyric acid 2-[3-(3-fluoro-phenylamino)-6,7-dimethoxy-4H-indeno[1,2-c]pyrazol-1-yl]-2-oxo-ethyl ester | 91.5 | 0.06342 |
| 475 | (6,7-Dimethoxy-2-methoxymethyl-2,4-dihydro-indeno[1,2-c]pyrazol-3-yl)-(3-fluoro-phenyl)-amine | 65.5 | 5.035 |
| 476 | (2,6-Difluoro-phenyl)-(6,7-dimethoxy-2,4-dihydro-indeno[1,2-c]pyrazol-3-yl)-amine | 88.5 | 0.2495 |

TABLE A-continued

IC50 and percent of inhibition of compounds on PDGF-R kinase activity

| CPD | NAME | Percent Inhibition @ 10 uM | IC50 (μM) |
|---|---|---|---|
| 477 | (6,7-Dimethoxy-2,4-dihydro-indeno[1,2-c]pyrazol-3-yl)-(2,4,6-trifluoro-phenyl)-amine | 95 | 0.2293 |
| 478 | (3-Bromo-phenyl)-[5-(2-pyrrolidin-1-yl-ethoxy)-2,4-dihydro-indeno[1,2-c]pyrazol-3-yl]-amine | 93.5 | 0.1617 |
| 479 | 3-[3-(2,6-Dichloro-benzylamino)-2,4-dihydro-indeno[1,2-c]pyrazol-5-yloxy]-propane-1,2-diol | 94.5 | 0.6238 |
| 480 | (2,6-Difluoro-phenyl)-[3-(3-fluoro-Phenylamino)-6,7-dimethoxy-4H-indeno[1,2-c]pyrazol-1-yl]-methanone | 8 | |
| 481 | (2-Fluoro-phenyl)-[3-(3-fluoro-phenylamino)-6,7-dimethoxy-4H-indeno[1,2-c]pyrazol-1-yl]-methanone | 59 | 3.764 |
| 482 | (3-Bromo-phenyl)-(4-ethyl-6,7-dimethoxy-1,4-dihydro-indeno[1,2-c]pyrazol-3-yl)-amine | 100 | 0.03863 |
| 483 | (3-Bromo-phenyl)-(4-ethyl-6,7-dimethoxy-1,4-dihydro-indeno[1,2-c]pyrazol-3-yl)-amine | 78.5 | 4.97 |
| 484 | 1-[3-(3-Fluoro-phenylamino)-6,7-dimethoxy-4H-indeno[1,2-c]pyrazol-1-yl]-propan-2-one | 87 | 0.218 |
| 485 | (3-Bromo-phenyl)-(6,7-dimethoxy-4,4-dimethyl-2,4-dihydro-indeno[1,2-c]pyrazol-3-yl)-amine | 32 | 59.03 |
| 486 | (3-Chloro-phenyl)-(6,7-dimethoxy-4,4-dimethyl-2,4-dihydro-indeno[1,2-c]pyrazol-3-yl)-amine | 34.5 | 15.76 |
| 487 | (6,7-Dimethoxy-4,4-dimethyl-2,4-dihydro-indeno[1,2-c]pyrazol-3-yl)-(3-fluoro-phenyl)-amine | 43 | 37.47 |
| 488 | (6,7-Dimethoxy-4,4-dimethyl-2,4-dihydro-indeno[1,2-c]pyrazol-3-yl)-(3-methoxy-phenyl)-amine | 33.5 | 39.29 |
| 489 | (6,7-Dimethoxy-4,4-dimethyl-2,4-dihydro-indeno[1,2-c]pyrazol-3-yl)-(3-ethoxy-phenyl)-amine | 25.5 | |
| 490 | Butyric acid 3-(3-fluoro-phenylamino)-6,7-dimethoxy-4H-indeno[1,2-c]pyrazol-1-ylmethyl ester | 96 | 0.0285 |
| 491 | Butyric acid 3-(3-fluoro-phenylamino)-6,7-dimethoxy-4H-indeno[1,2-c]pyrazol-2-ylmethyl ester | 92 | 0.3142 |
| 492 | (4-Fluoro-phenyl)-[3-(3-fluoro-phenylamino)-6,7-dimethoxy-4H-indenol[1,2-c]pyrazol-1-yl]-methanone | 78 | 0.4716 |
| 494 | (4-Chloro-phenyl)-[3-(3-fluoro-phenylamino)-6,7-dimethoxy-4H-indeno[1,2-c]pyrazol-1-yl]-methanone | 83 | 1.541 |
| 496 | Acetic acid 3-(3-fluoro-phenylamino)-6,7-dimethoxy-4H-indeno[1,2-c]pyrazol-1-ylmethyl ester | 88.5 | 0.0136 |
| 497 | Acetic acid 3-(3-fluoro-phenylamino)-6,7-dimethoxy-4H-indeno[1,2-c]pyrazol-2-ylmethyl ester | 97 | 0.07774 |
| 498 | Acetic acid 4-[3-(3-fluoro-phenylamino)-6,7-dimethoxy-4H-indeno[1,2-c]pyrazol-1-ylmethyl]-phenyl ester | 51.5 | 8.326 |
| 499 | Acetic acid 4-[3-(3-fluoro-phenylamino)-6,7-dimethoxy-4H-indeno[1,2-c]pyrazol-2-ylmethyl]-phenyl ester | 87 | 1.743 |
| 500 | 3-(3-Fluoro-phenylamino)-6,7-dimethoxy-4H-indeno[1,2-c]pyrazole-1-carboxylic acid 4-fluoro-phenyl ester | 80.5 | 0.4923 |
| 501 | 3-(3-Fluoro-phenylamino)-6,7-dimethoxy-4H-indeno[1,2-c]pyrazole-1-carboxylic acid 4-chloro-phenyl ester | 90 | 0.09598 |
| 502 | 1-[3-(3-Fluoro-phenylamino)-6,7-dimethoxy-4H-indeno[1,2-c]pyrazol-1-yl]-propan-2-ol | 60.5 | 54.02 |
| 503 | 3-(3-Fluoro-phenylamino)-6,7-dimethoxy-4H-indeno[1,2-c]pyrazole-2-carboxylic acid 4-fluoro-phenyl ester | 103 | 0.04509 |
| 504 | (6,7-Diethoxy-4-methyl-2,4-dihydro-indeno[1,2-c]pyrazol-3-yl)-(3-ethoxy-p henyl)-amine | 101 | 0.1419 |
| 505 | (3-Ethoxy-phenyl)-(4-ethyl-6,7-dimethoxy-2,4-dihydro-indeno[1,2-c]pyrazol-3-yl)-amine | 97 | 0.134 |
| 506 | 5-[3-(3-Fluoro-phenylamino)-6,7-dimethoxy-4H-indeno[1,2-c]pyrazol-1-yl]-5-oxo-pentanoic acid methylamide | 97 | 0.0294 |
| 509 | [3-(3-Fluoro-phenylamino)-6,7-dimethoxy-4H-indeno[1,2-c]pyrazol-1-yl]-acetic acid methyl ester | 30.5 | |
| 510 | [3-(3-Fluoro-phenylamino)-6,7-dimethoxy-4H-indeno[1,2-c]pyrazol-2-yl]-acetic acid ethyl ester | 57 | 26.62 |
| 511 | [3-(3-Fluoro-phenylamino)-6,7-dimethoxy-4H-indeno[1,2-c]pyrazol-1-yl]-acetic acid ethyl ester | 51 | 12.52 |
| 512 | (4-Ethyl-6,7-dimethoxy-2,4-dihydro-indeno[1,2-c]pyrazol-3-yl)-(3-methoxy-phenyl)-amine | 92 | 0.1834 |

TABLE A-continued

IC50 and percent of inhibition of compounds on PDGF-R kinase activity

| CPD | NAME | Percent Inhibition @ 10 uM | IC50 (μM) |
|---|---|---|---|
| 513 | 3-(3-Fluoro-phenylamino)-6,7-dimethoxy-4H-indeno[1,2-c]pyrazole-1-carboxylic acid 2-chloro-phenyl ester | 86 | 0.7726 |
| 514 | 1-[3-(3-Bromo-phenylamino)-4-ethyl-6,7-dimethoxy-4H-indeno[1,2-c]pyrazol-1-yl]-2-methoxy-ethanone | 85 | 0.24 |
| 515 | 1-[3-(3-Bromo-phenylamino)-4-ethyl-6,7-dimethoxy-4H-indeno[1,2-c]pyrazol-2-yl]-2-methoxy-ethanone | 90 | 0.1357 |
| 516 | 3-(3-Fluoro-phenylamino)-6,7-dimethoxy-4H-indeno[1,2-c]pyrazole-1-carboxylic acid (2-amino-ethyl)-amide | 68.5 | 10.04 |
| 517 | 3-(3-Fluoro-phenylamino)-6,7-dimethoxy-4H-indeno[1,2-c]pyrazole-1-carboxylic acid (2-dimethylamino-ethyl)-amide | 75.5 | 1.793 |
| 518 | 2-Benzyloxy-1-[3-(3-bromo-phenylamino)-4-ethyl-6,7-dimethoxy-4H-indeno[1,2-c]pyrazol-2-yl]-ethanone | 92.5 | 0.1838 |
| 519 | 2-Benzyloxy-1-[3-(3-bromo-phenylamino)-4-ethyl-6,7-dimethoxy-4H-indeno[1,2-c]pyrazol-1-yl]-ethanone | 97.5 | 0.139 |
| 520 | 3-(3-Fluoro-phenylamino)-6,7-dimethoxy-4H-indeno[1,2-c]pyrazole-1-carboxylic acid (2-pyrrolidin-1-yl-ethyl)-amide | 100 | 0.06525 |
| 521 | 3-(3-Fluoro-phenylamino)-6,7-dimethoxy-4H-indeno[1,2-c]pyrazole-1-carboxylic acid (2-morpholin-4-yl-ethyl)-amide | 97 | 0.05587 |
| 522 | 3-(3-Fluoro-phenylamino)-6,7-dimethoxy-4H-indeno[1,2-c]pyrazole-2-carboxylic acid (2-morpholin-4-yl-ethyl)-amide | 94 | 0.7909 |
| 523 | 3-(3-Fluoro-phenylamino)-6,7-dimethoxy-4H-indeno[1,2-c]pyrazole-1-carboxylic acid [2-(2-hydroxy-ethylamino)-ethyl]-amide | 98.5 | 0.1927 |
| 524 | 3-(3-Fluoro-phenylamino)-6,7-dimethoxy-4H-indeno[1,2-c]pyrazole-1-carboxylic acid (2-methylamino-ethyl)-amide | 78 | 2.482 |
| 525 | 3-(3-Fluoro-phenylamino)-6,7-dimethoxy-4H-indeno[1,2-c]pyrazole-1-carboxylic acid (2-isobutyrylamino-ethyl)-amide | 33 | 43.16 |
| 526 | 3-(3-Fluoro-phenylamino)-6,7-dimethoxy-4H-indeno[1,2-c]pyrazole-1-carboxylic acid (2-acetylamino-ethyl)-amide | 73 | 8.091 |
| 527 | 2-Methyl-acrylic acid 2-{[3-(3-fluoro-phenylamino)-6,7-dimethoxy-4H-indeno[1,2-c]pyrazole-1-carbonyl]-amino}-ethyl ester | 46.5 | 17.47 |
| 528 | 2-Methyl-acrylic acid 2-{[3-(3-fluoro-phenylamino)-6,7-dimethoxy-4H-indeno[1,2-c]pyrazole-2-carbonyl]-amino}-ethyl ester | 93.5 | 0.196 |
| 529 | 6-[3-(3-Fluoro-phenylamino)-6,7-dimethoxy-4H-indeno[1,2-c]pyrazol-2-yl]-3,4,5-trihydroxy-tetrahydro-pyran-2-carboxylic acid | 44 | 10.64 |
| 530 | 2-{[3-(3-Fluoro-phenylamino)-6,7-dimethoxy-4H-indeno[1,2-c]pyrazole-1-carbonyl]-amino}-3-methyl-butyric acid methyl ester | 71.5 | 4.151 |
| 531 | 4-[3-(3-Fluoro-phenylamino)-6,7-dimethoxy-4H-indeno[1,2-c]pyrazol-1-yl]-4-oxo-butyramide | 90 | 0.02404 |
| 532 | 3-(3-Fluoro-phenylamino)-6,7-dimethoxy-4H-indeno[1,2-c]pyrazole-1-carboxylic acid (2-benzoylamino-ethyl)-amide | 42 | |
| 534 | 2-[3-(3-Fluoro-phenylamino)-6,7-dimethoxy-4H-indeno[1,2-c]pyrazol-1-yl]-acetamide | 94 | 0.9332 |
| 535 | 1-[3-(3-Fluoro-phenylamino)-6,7-dimethoxy-4H-indeno[1,2-c]pyrazol-2-yl]-3-pyrrolidin-1-yl-propane-1,3-dione | 105 | 0.03224 |
| 536 | 1-[3-(3-Fluoro-phenylamino)-6,7-dimethoxy-4H-indeno[1,2-c]pyrazol-1-yl]-3-pyrrolidin-1-yl-propane-1,3-dione | 88 | 0.4362 |
| 537 | N,N-Diethyl-3-[3-(3-fluoro-phenylamino)-6,7-dimethoxy-4H-indeno[1,2-c]pyrazol-1-yl]-3-oxo-propionamide | 104 | 0.3303 |
| 538 | (3-Bromo-phenyl)-(4-isopropyl-6,7-dimethoxy-2,4-dihydro-indeno[1,2-c]pyrazol-3-yl)-amine | 65 | |
| 540 | (3-Chloro-phenyl)-(4-isopropyl-6,7-dimethoxy-2,4-dihydro-indeno[1,2-c]pyrazol-3-yl)-amine | 47 | 14.68 |

TABLE A-continued

IC50 and percent of inhibition of compounds on PDGF-R kinase activity

| CPD | NAME | Percent Inhibition @ 10 uM | IC50 (μM) |
|---|---|---|---|
| 541 | (4-Isopropyl-6,7-dimethoxy-2,4-dihydro-indeno[1,2-c]pyrazol-3-yl)-(3-methoxy-phenyl)-amine | 50 | 44.22 |
| 542 | 3-(3-Fluoro-phenylamino)-6,7-dimethoxy-4H-indeno[1,2-c]pyrazole-1-carboxylic acid [2-(2-hydroxy-benzoylamino)-ethyl]-amide | 21 | |
| 544 | 3-(3-Fluoro-phenylamino)-6,7-dimethoxy-4H-indeno[1,2-c]pyrazole-1-carboxylic acid {2-[2-(2-hydroxy-ethoxy)-ethoxy]-ethyl}-amide | 60 | |
| 546 | [3-(3-Bromo-phenylamino)-4-ethyl-6,7-dimethoxy-4H-indeno[1,2-c]pyrazol-1-yl]-phenyl-methanone | 72.5 | |
| 547 | 3-(3-Bromo-phenylamino)-4-ethyl-6,7-dimethoxy-4H-indeno[1,2-c]pyrazole-1-carboxylic acid 2-[2-(2-hydroxy-ethoxy)-ethoxy]-ethyl ester | 68.5 | |
| 548 | 3-(3-Bromo-phenylamino)-6,7-dimethoxy-4-methyl-4H-indeno[1,2-c]pyrazole-1-carboxylic acid 2-[2-(2-hydroxy-ethoxy)-ethoxy]-ethyl ester | 82.5 | 0.2144 |
| 549 | (7-Benzyloxy-6-methoxy-2,4-dihydro-indeno[1,2-c]pyrazol-3-yl)-(3-fluoro-phenyl)-amine | 106 | 0.09114 |
| 553 | (3-Bromo-phenyl)-(6,7-dimethoxy-4-methyl-2,4-dihydro-indeno[1,2-c]pyrazol-3-yl)-amine | 99.5 | 0.006501 |
| 554 | (6,7-Dimethoxy-4-methyl-2,4-dihydro-indeno[1,2-c]pyrazol-3-yl)-(3-ethoxy-phenyl)-amine | 102 | 0.0208 |
| 555 | (3-Bromo-phenyl)-(4-ethyl-6,7-dimethoxy-2,4-dihydro-indeno[1,2-c]pyrazol-3-yl)-amine | 97.5 | 0.02094 |
| 556 | (3-Ethoxy-phenyl)-(4-ethyl-6,7-dimethoxy-2,4-dihydro-indeno[1,2-c]pyrazol-3-yl)-amine | 98 | 0.0104 |
| 557 | N-[3-(3-Fluoro-phenylamino)-6,7-dimethoxy-2,4-dihydro-indeno[1,2-c]pyrazol-5-yl]-acetamide | 101.5 | 0.03248 |
| 558 | N3-(3-Fluoro-phenyl)-6,7-dimethoxy-2,4-dihydro-indeno[1,2-c]pyrazole-3,5-diamine | 102 | 0.01214 |
| 559 | (2-Chloro-pyridin-3-yl)-(6,7-dimethoxy-4-methyl-2,4-dihydro-indeno[1,2-c]pyrazol-3-yl)-amine | 102 | 0.03706 |
| 560 | (4-Methoxy-2-methyl-6,9-dihydro-3-oxa-1,6,7-triaza-cyclopenta[b]-as-indacen-8-yl)-(3-methoxy-phenyl)-amine | 102 | 0.02471 |
| 562 | (6,7-Dimethoxy-2,4-dihydro-indeno[1,2-c]pyrazol-3-yl)-pyridin-2-yl-amine | 93.5 | 0.08399 |
| 563 | (6,7-Dimethoxy-2,4-dihydro-indeno[1,2-c]pyrazol-3-yl)-pyridin-2-ylmethyl-amine | 89 | 1.449 |
| 564 | (6,7-Dimethoxy-2,4-dihydro-indeno[1,2-c]pyrazol-3-yl)-pyridin-3-ylmethyl-amine | 99.5 | 0.8864 |
| 565 | (2,2-Difluoro-benzo[1,3]dioxol-4-yl)-(6,7-dimethoxy-2,4-dihydro-indeno[1,2-c]pyrazol-3-yl)-amine | 41.5 | |
| 566 | 3-(2,3-Dihydro-indol-1-yl)-6,7-dimethoxy-2,4-dihydro-indeno[1,2-c]pyrazole | 54 | |
| 567 | 3-(5-Bromo-2,3-dihydro-indol-1-yl)-6,7-dimethoxy-2,4-dihydro-indeno[1,2-c]pyrazole | 39.5 | |
| 568 | (3-Bromo-phenyl)-(6,7-dimethoxy-4-methyl-2,4-dihydro-indeno[1,2-c]pyrazol-3-yl)-amine | 78 | 0.7904 |
| 569 | (6,7-Dimethoxy-4-methyl-2,4-dihydro-indeno[1,2-c]pyrazol-3-yl)-(3-ethoxy-phenyl)-amine | 64 | 5.098 |
| 570 | (3-Bromo-phenyl)-(4-ethyl-6,7-dimethoxy-2,4-dihydro-indeno[1,2-c]pyrazol-3-yl)-amine | 77.5 | 2.048 |
| 571 | (3-Ethoxy-phenyl)-(4-ethyl-6,7-dimethoxy-2,4-dihydro-indeno[1,2-c]pyrazol-3-yl)-amine | 66 | 3.886 |
| 572 | 2-[3-(3-Fluoro-phenylamino)-6,7-dimethoxy-4H-indeno[1,2-c]pyrazol-1-yl]-ethanol | 67 | 7.332 |
| 573 | 2-[3-(3-Fluoro-phenylamino)-6,7-dimethoxy-4H-indeno[1,2-c]pyrazol-2-yl]-ethanol | 52 | |
| 574 | (2-Fluoro-benzyl)-(4-methoxy-2-methyl-6,9-dihydro-3-oxa-1,6,7-triaza-cyclopenta[b]-as-indacen-8-yl)-amine | 99 | 0.163 |
| 575 | (2-Bromo-benzyl)-(6,7-dimethoxy-2,4-dihydro-indeno[1,2-c]pyrazol-3-yl)-amine | 99.5 | 0.002129 |
| 576 | (5-Bromo-3-methyl-pyridin-2-yl)-(6,7-dimethoxy-2,4-dihydro-indeno[1,2-c]pyrazol-3-yl)-amine | 18 | 33.33 |
| 577 | (6,7-Dimethoxy-2,4-dihydro-indeno[1,2-c]pyrazol-3-yl)-(4-trifluoromethyl-pyridin-3-yl)-amine | 19 | 361.5 |
| 578 | 3-(3-Fluoro-phenylamino)-6,7-dimethoxy-4H-indeno[1,2-c]pyrazole-1-carboxylic acid methylamide | 80 | 4.023 |

TABLE A-continued

IC50 and percent of inhibition of compounds on PDGF-R kinase activity

| CPD | NAME | Percent Inhibition @ 10 uM | IC50 (μM) |
|---|---|---|---|
| 579 | 3-(3-Fluoro-phenylamino)-6,7-dimethoxy-4H-indeno[1,2-c]pyrazole-2-carboxylic acid methylamide | 28 | |
| 580 | 3-(3-Fluoro-phenylamino)-6,7-dimethoxy-4H-indeno[1,2-c]pyrazole-2-carbothioic acid methylamide | 93 | 0.1255 |
| 581 | 3-(3-Fluoro-phenylamino)-6,7-dimethoxy-4H-indeno[1,2-c]pyrazole-1-carbothioic acid methylamide | 90.5 | 1.139 |
| 582 | (3-Bromo-pyridin-2-yl)-(6,7-dimethoxy-2,4-dihydro-indeno[1,2-c]pyrazol-3-yl)-amine | 82.5 | 1.247 |
| 583 | (5-Bromo-pyridin-2-yl)-(6,7-dimethoxy-2,4-dihydro-indeno[1,2-c]pyrazol-3-yl)-amine | 82 | 1.101 |
| 584 | (6,7-Dimethoxy-2,4-dihydro-indeno[1,2-c]pyrazol-3-yl)-(3-isopropoxy-phenyl)-amine | 109 | 0.01113 |
| 585 | (2,6-Dichloro-benzyl)-(4-ethyl-6,7-dimethoxy-2,4-dihydro-indeno[1,2-c]pyrazol-3-yl)-amine | 101.5 | 0.4287 |
| 586 | (2,6-Dichloro-benzyl)-(6,7-dimethoxy-4-methyl-2,4-dihydro-indeno[1,2-c]pyrazol-3-yl)-amine | 100.5 | 0.02776 |
| 587 | (6,7-Dimethoxy-2,4-dihydro-indeno[1,2-c]pyrazol-3-yl)-(3-methyl-pyridin-2-yl)-amine | 86 | 1.704 |
| 588 | (6,7-Dimethoxy-2,4-dihydro-indeno[1,2-c]pyrazol-3-yl)-(4,6-dimethyl-pyridin-2-yl)-amine | 103 | 0.5564 |
| 591 | 6-[(6,7-Dimethoxy-2,4-dihydro-indeno[1,2-c]pyrazol-3-yl)-(3-fluoro-phenyl)-amino]-3,4,5-trihydroxy-tetrahydro-pyran-2-carboxylic acid | 96 | 0.6623 |
| 594 | (6,7-Diethoxy-2,4-dihydro-indeno[1,2-c]pyrazol-3-yl)-(3-fluoro-phenyl)-amine | 64 | 0.0156 |
| 595 | (7-Methoxy-2H-8-oxa-2,3-diaza-cyclopenta[a]inden-1-yl)-phenyl-amine | 71 | 0.02488 |
| 598 | 3-(3-Fluoro-phenylamino)-6,7-dimethoxy-4H-indeno[1,2-c]pyrazole-2-carboxylic acid pentadecylamide | 0 | 98.43 |
| 601 | 3-(6,7-Dimethoxy-2,4-dihydro-indeno[1,2-c]pyrazol-3-ylamino)-N-{2-[2-(2-{2-[5-(2-oxo-hexahydro-thieno[3,4-d]imidazol-6-yl)-pentanoylamino]-ethoxy}-ethoxy)-ethoxy]-ethyl}-benzamide | 89 | 2.29 |
| 602 | [3-(3-Fluoro-phenylamino)-6,7-dimethoxy-4H-indeno[1,2-c]pyrazol-2-yl]-acetic acid methyl ester | 40 | |
| 604 | 3-(3-Fluoro-phenylamino)-6,7-dimethoxy-4H-indeno[1,2-c]pyrazole-2-carboxylic acid {2-[2-(2-hydroxy-ethoxy)-ethoxy]-ethyl}-amide | 79.5 | 2.127 |
| 605 | (3-Fluoro-phenyl)-(4-methoxy-2-methyl-8a,9-dihydro-3-oxa-1,6,7-triaza-cyclopenta[b]-as-indacen-8-yl)-amine | 97.5 | 0.0051 |
| 606 | 8-Benzyl-3-(3-fluoro-phenylamino)-6-methoxy-2,4-dihydro-indeno[1,2-c]pyrazol-7-ol | 53.5 | |
| 607 | (2-Chloro-pyridin-3-yl)-(4-ethyl-6,7-dimethoxy-2,4-dihydro-indeno[1,2-c]pyrazol-3-yl)-amine | 78 | 0.5475 |
| 608 | 3-(3-Fluoro-phenylamino)-6-methoxy-2,4-dihydro-indeno[1,2-c]pyrazol-7-ol | 106 | 0.02596 |
| 609 | (6,7-Dimethoxy-1-methyl-1,4-dihydro-indeno[1,2-c]pyrazol-3-yl)-(3-fluoro-phenyl)-amine | 84 | 4.683 |
| 610 | (6,7-Dimethoxy-2-methyl-2,4-dihydro-indeno[1,2-c]pyrazol-3-yl)-(3-fluoro-phenyl)-amine | 51.5 | 9.377 |
| 611 | 6-[3-(3-fluoro-phenylamino)-6,7-dimethoxy-4H-indeno[1,2-c]pyrazol-1-yl]-3,4,5-trihydroxy-tetrahydro-pyran-2-carboxylic acid | | |

2. Inhibition of c-Abl Kinase Activity

Previous studies have shown that a selective PDGF-R kinase inhibitor STI-571 (supra) was also a selective inhibitor for c-Abl kinase activity and therefore was a selective inhibitor for the Bcr-Abl oncogene product (for a review on therapeutic interventions on Bcr-Abl see Kindler et al., 2002, *Expert Opin Ther Targets;* 6(1): 85–101). Variants of Bcr-Abl have been associated with distinct types of human leukemias, such as chronic myelogenous leukemia (CML); acute lymphocytic leukemia (ALL); chronic neutrophilic leukemia (CNL); acute undifferentiated leukemia (AUL); and acute myelogenous leukemia (AML) (Anjali et al., 2002, *Leukemia Research,* 26(8): 713–720). The inhibitory activity of compounds within the scope of the invention on c-Abl kinase activity was tested according to the following procedure.

Materials 1. 10× Kinase Buffer [500 mM Tris-HCl pH=8, 100 mM $MgCl_2$, 1 mM $Na_3VO_4$]
2. 10 mM DTT [final concentration 1 mM]
3. 10 mM ATP [final concentration 5 μM] (Gibco, Cat No:18330-019, Carlsbad, Calif.)
4. $^{33}$P-γ-ATP [NEG-602H; 2000–3000 Ci/mmol], 2 μCuries per well at 10 μCi/μl (0.2 μl/well)
5. Abl enzyme (New England Biolabs, Cat No. P6050L, Beverly, Mass.) at 100 Units/μl use 10 Units/well (0.1 μl/well)
6. Enzyme Dilution Buffer [50 mM Tris-HCl pH=8.0, 0.1% BSA]
7. Wash/Stop Buffer [PBS+100 mM EDTA]
8. NEN Streptavidin Flashplates (New England Nuclear, Cat No. SMP-103, Boston, Mass.).
9. Abl Peptide Substrate (Biotin-EAIYAAPFAKKK-amide) at 1 mM in 50 mM Tris-HCL pH=8.0. (Use at 1.0 μM).

Procedure

Reagents were first mixed according to the following regimen:

| | ONE PLATE (ul) | PER WELL (μl) |
|---|---|---|
| 10X Kinase Buffer | 1100 | 10 |
| 10 mM DTT | 1100 | 10 |
| 10 mM cold ATP | 5.5 | 0.05 |
| 1 mM Abl Peptide | 11 | 0.1 |
| $^{33}$P-γ-ATP at 10 μCi/μl | 22 | 0.2 |
| $H_2O$ | 5462 | 49.65 |

The above reaction mixture was dispensed into each well of a Flashplate at 70 μl/well. To test the effect of a compound on Abl kinase activity, the test compound either in a fixed concentration or in serially diluted concentrations in 100% DMSO was added to appropriate wells at 1 μl/well.

Enzyme Abl was diluted in enzyme dilution buffer as following:

| | |
|---|---|
| Enzyme Dilution Buffer | 3289 μl |
| Abl enzyme (100 Units/μl) | 11 μl |

The kinase reaction was started by adding 30 μl of diluted Abl enzyme solution to each well on the Flashplate containing hot ATP (2 μCi/well) and Abl peptide substrate (at 1 μM final conc.), except wells of column 12 rows E and F, which were used to calculate the plate background. The Flashplate was swirled to mix and was incubated at 30° C. for 60 minutes. Then, the reaction mixture was discarded and the Flashplate was washed 3 times each with 200 μL Wash/Stop Buffer. Subsequently, each well on the Flashplate was filled with 200 μl of Wash/Stop buffer. The amount of $^{33}$P retained in each well was measured using a Packard TopCount after the plate was sealed with a transparent plate sealer.

When a test compound inhibited c-Abl kinase activity, the well containing such the test compound contained less $^{33}$P as compared to the well without the compound. Tested under the described assay conditions, compounds within the scope of the invention demonstrated inhibitory effect on c-Abl kinase.

In order to test the potency of inhibition of present compounds, an $IC_{50}$ for an individual compound was measured using the above procedure. As used herein, the $IC_{50}$ for c-Abl kinase activity refers to the concentration of an inhibitor at which the activity of c-Abl kinase is reduced by one-half as compared with reactions containing no inhibitor. The $IC_{50}$ for c-Abl kinase activity of individual representative compounds of the present invention are listed in Table B.

TABLE B

IC50 of compounds for the c-Abl kinase activity

| Compound Number | IC50 (uM) |
|---|---|
| 2 | 0.011 |
| 8 | 0.694 |
| 11 | 0.118 |
| 12 | 0.020 |
| 13 | 0.173 |
| 14 | 0.038 |
| 22 | 0.019 |
| 26 | 0.134 |
| 29 | 0.005 |
| 30 | 0.491 |
| 32 | 0.002 |
| 36 | 0.064 |
| 38 | 0.002 |
| 39 | 0.013 |
| 41 | 0.078 |
| 44 | 0.007 |
| 54 | 0.971 |
| 63 | 0.419 |
| 90 | 10.290 |
| 97 | 0.227 |
| 116 | 0.386 |
| 118 | 0.427 |
| 119 | 0.524 |
| 122 | 1.260 |
| 124 | 1.850 |
| 128 | 0.313 |
| 129 | 10.780 |
| 129 | 2.360 |
| 130 | 0.236 |
| 132 | 0.665 |
| 133 | 0.498 |
| 134 | 1.160 |
| 140 | 1.410 |
| 156 | 0.089 |
| 157 | 0.371 |
| 160 | 1.020 |
| 170 | 0.075 |
| 172 | 0.084 |
| 179 | 0.870 |
| 180 | 0.082 |
| 181 | 0.056 |
| 182 | 0.093 |
| 185 | 0.666 |
| 188 | 1.400 |
| 190 | 0.069 |
| 199 | 0.027 |
| 200 | 0.020 |
| 201 | 0.217 |
| 202 | 2.650 |
| 203 | 0.160 |
| 204 | 0.165 |
| 205 | 0.328 |
| 207 | 0.062 |
| 208 | 0.009 |
| 209 | 0.007 |
| 218 | 0.439 |
| 226 | 0.245 |
| 227 | 0.641 |
| 247 | 0.033 |
| 249 | 0.035 |
| 253 | 0.03795 |
| 256 | 0.055 |
| 260 | 0.013 |
| 261 | 0.064 |
| 262 | 0.027 |
| 263 | 0.512 |

TABLE B-continued

IC50 of compounds for the c-Abl kinase activity

| Compound Number | IC50 (uM) |
|---|---|
| 265 | 0.085 |
| 266 | 0.015 |
| 267 | 0.326 |
| 268 | 0.020 |
| 269 | 0.101 |
| 270 | 0.036 |
| 280 | 0.363 |
| 281 | 1.580 |
| 282 | 0.043 |
| 283 | 0.340 |
| 284 | 0.069 |
| 286 | 2.950 |
| 287 | 3.450 |
| 289 | 2.400 |
| 292 | 0.001 |
| 299 | 0.198 |
| 309 | 0.822 |
| 310 | 1.471 |
| 330 | 0.091 |
| 334 | 3.300 |
| 337 | 2.742 |
| 339 | 2.180 |
| 341 | 0.350 |
| 348 | 0.011 |
| 358 | 0.338 |
| 359 | 0.143 |
| 360 | 0.077 |
| 361 | 0.043 |
| 363 | 0.001 |
| 369 | 0.047 |
| 370 | 0.006 |
| 371 | 0.905 |
| 373 | 0.010 |
| 374 | 0.051 |
| 376 | 0.060 |
| 379 | 0.014 |
| 380 | 0.327 |
| 381 | 1.496 |
| 382 | 0.019 |
| 383 | 0.183 |
| 384 | 0.004 |
| 385 | 0.012 |
| 386 | 0.020 |
| 388 | 0.046 |
| 389 | 0.017 |
| 390 | 0.000 |
| 391 | 0.014 |
| 396 | 0.002 |
| 398 | 0.010 |
| 400 | 0.005 |
| 401 | 0.014 |
| 415 | 0.219 |
| 419 | 0.292 |
| 420 | 0.335 |
| 422 | 3.078 |
| 432 | 0.096 |
| 448 | 0.003 |
| 449 | 0.023 |
| 457 | 0.004 |
| 459 | 0.070 |
| 460 | 0.004 |
| 461 | 0.337 |
| 462 | 0.000 |
| 463 | 0.008 |
| 465 | 0.051 |
| 466 | 0.191 |
| 467 | 0.244 |
| 468 | 0.603 |
| 469 | 0.027 |
| 490 | 0.038 |
| 595 | 0.460 |

3. Anti-Cell Proliferation Assays

In addition to the above cell-free assays, the biological activities of the compounds of the invention were also measured in cell-based assays. One such assay is to measure the effect of the compound on cell proliferation in the presence or absence of PDGF stimulation in various cell types.

3a. Anti-cell Proliferation in Normal Cells in the Presence of PDGF Stimulation

The effect of compounds of the invention on cell proliferation in normal human primary cells, in particular, cryopreserved human coronary artery smooth muscle cells (HCASMC), in the presence of PDGF stimulation was tested based on incorporation of $^{14}C$-thymidine into DNA of cells.

Materials

The following materials were purchased from their respective sources: Recombinant human PDGF beta homodimer, rhPDGF-BB (herein after referred as "PDGF-BB") purchased from R&D System (Minneapolis, Minn., Cat. No 220-BB); Cryopreserved human coronary artery smooth muscle cells (HCASMC), tissue culture medium for HCASMC, and smooth muscle growth supplement (SMGS) purchased from Cascade Biologics (Portland, Oreg., HCASMC Cat. No: C-017-5C; Medium 231 Cat. No: M-231-500; and SMGS Cat. No: S-007-25); 96-well CytoStar tissue culture treated scintillating microplates purchased from Amersham (Piscataway, N.J., Cat. No: RPNQ0160); Methyl $^{14}C$-thymidine at 56 mCi/mmol (250 µCi/2.5 mL) purchased from NEN (Cat. No.: NEC568); DMSO from Sigma (St. Louis, Mo., Cat. No: D-5879); Sterile reagent reservoirs from Costar (VWR International, Inc., West Chester, Pa., Cat. No: 4870); Dulbecco's PBS from Gibco (Cat. No: 14190-136); Backing tape white plate cover for bottom of CytoStar plate from Packard (Cat. No: 6005199)

Procedure

HCASMC were seeded at approx. 4000 cells/well in a volume of 100 µl of complete Medium 231 with SMGS. Cells were grown for 48 hrs until they reach 80% confluence. They were then quiesced in SMGS-free Medium 231 for 24 hrs. Cell media were replenished with SMGS-free Medium 231 containing PDGF-BB at 50 ng/mL in a total volume of 100 µl/well; and 1 µl of test compounds in serially diluted concentrations in 100% DMSO was added to each well. For the maximum growth control wells, only 1 µl of 100% DMSO was added; for minimum growth (blank) wells, 1 µl of 10 mM cycloheximide was added to each well. After 24 hours incubation, 20 µl of $^{14}C$-thymidine mix was added to each well and the $^{14}C$-thymidine mix was made according the following regimen:

| Reagent: | One Plate (µl) | One well (µl) |
|---|---|---|
| $^{14}C$-thymidine | 220 | 2 |
| SMGS-free Medium 231 | 1980 | 18 |
| Total Mix | 2200 | 20 |

Cells were incubated for an additional 24 hrs in media containing test compounds, PDGF-BB and $^{14}C$-thymidine. Then, the reaction mixture was discarded and the plate was washed 3 times each with 200 µl PBS. Subsequently, each well on the plate was filled with 200 µl of PBS. The top of the plate was sealed with transparent plate sealer and white plate backing sealers were applied to the bottom of plates. The retained $^{14}C$ inside each well was measured using a Packard TopCount.

The amount of $^{14}C$ retained in a well correlates to the proliferation of cells inside the well. When a test compound inhibited PDGF-BB induced HCASMC proliferation, the well containing such a compound retained less $^{14}C$ as compared to the maximum growth control wells without the compound. In order to test the potency of inhibition of the present compound, $IC_{50}$ of an individual compound on the inhibition of PDGF-BB induced HCASMC proliferation was measured using the above procedure. As used herein, said $IC_{50}$ refers to the concentration of the test compound at which the amount of PDGF-BB induced HCASMC proliferation is reduced by one-half as compared to the maximum growth control wells without the compound. Table C shows examples of the $IC_{50}$ for representative compounds of the invention.

3b. Anti-cell Proliferation in Normal Cells in the Absence of PDGF Stimulation

The effect of compounds of the invention on cell proliferation in normal human primary cell, in particular, human umbilical vein endothelial cells (HUVEC), in the absence of PDGF stimulation was tested based on incorporation of BrdU into DNA of cells.

Materials:

The following materials were purchased from their respective sources: HUVEC cells from Cascade Biologics, Cat No: C-015-10C; Medium 200 from Cascade Biologics, Cat No: M-200-500; Low serum growth supplements (LSGS) from Cascade Biologics, Cat No: S-003-10; F12-K medium from Gibco/BRL, Cat No: 21127-022; BrdU kit from Roche, Cat No: 1 647 229; and Trypsin/EDTA solution from Cascade Biologics, Cat No: R-001-100.

Procedure

For propigation, HUVEC cells were grown in M-200 medium supplemented with LSGS. For studies, cells were detached with Trypsin/EDTA solution and washed three times with 10 mL of F12K (LS, low serum) medium and then centrifuged at 400×G for 5 minutes. F-12K (LS) medium is F-12K medium containing 0.2% heat-treated fetal bovine serum.

Cell concentration was adjusted to about $5 \times 10^4$ cells/mL in F-12K (LS) medium, and 200 µl (approx. $1 \times 10^4$ cells) were added to each well of a 96-well plate. Cells were then incubated for 16 to 20 hours at 37° C. under 95% air/5% $CO_2$ to allow the cells to attach and become quiescent.

Cell proliferation was stimulated by adding 50 µL of a 1:10 dilution of LSGS in F12K (LS). Maximum-stimulated control wells were prepared by adding 50 µl of a 1:10 dilution of LSGS. Zero control wells contained 50 SL of F-12K (LS) medium only. Test compounds in 100% DMSO were added at a volume of 2.5 µl to achieve the desired final drug concentration. Replicates of eight wells per condition were tested. Cells were incubated at 37° C. overnight. On the next day 25 µL of BrdU (1:100 dilution of stock in F-12K (LS) medium) was added to each well.

Cells were incubated for an additional 20–24 hours. The medium was removed and the cells were fixed by adding 200 µL of FixDent solution (included in the BrdU kit) to each well and then incubated at room temperature for an additional 30 minutes. FixDent was removed by flicking and blotting the plates, and 100 µL of anti-BrdU-POD (included in the BrdU kit) diluted at a 1:100 dilution in antibody dilution solution (included in the BrdU kit) was added to each well. The diluted anti-BrdU-POD solution was prepared shortly before use. The plates were incubated at room temperature for 90 minutes.

The unbound antibody was removed by washing three times with Wash Solution (200 uL per wash). Wash Solution was prepared by making a 1:10 dilution of Wash Buffer Stock (included in the BrdU kit) with distilled water. Substrate solution (included in the BrdU kit) (100 uL) was added to each well and incubated for an additional 30–40 minutes. Plates were then read at 405 nm on a 96-well plate reader.

In order to test the potency of inhibition of the present compound, $IC_{50}$ of an individual compound on the inhibition of PDGF-BB independent HUVEC proliferation was measured using the above procedure. As used herein, said $IC_{50}$ refers to the concentration of the test compound at which the amount of HUVEC proliferation is reduced by one-half as compared to the maximum growth control wells without the compound. Table C shows examples of the $IC_{50}$ for representative compounds of the invention.

3c. Anti-cell Proliferation in Tumor Cells

The effect of compounds of the invention on cell proliferation in various tumor cells was tested based on incorporation of $^{14}C$-thymidine into DNA of cells.

Materials

Similar to those described above in 3a, except that different cells, cell growth medium, and growth supplements were used. Human tumor cell lines derived from various human tissue origins (LoVo from colon, H460 from lung, T47D from breast, PC3 from prostate, A375 from melanoma, AsPC1 from pancreas) were obtained from the American Type Culture Collection (ATCC) and cultured under specified conditions required for each cell type, as provided by ATCC. Complete medium was obtained from Cellgro: Iscove's medium with 10% Fetal Bovine Serium (FBS) (Mediatech, Inc., Herndon, Va. 20171, Cat. No. 10-016-CV).

Procedure

Tumor cells were seeded at approx. 3000–8000 cells per well in a volume of 100 µl of complete medium. Cells were grown for 24 hours in complete medium, and 1 µl of test compound was serially diluted in 100% DMSO and added to each well. For maximum growth control wells, only 1 µl of 100% DMSO was added. After 24 hours incubation, 20 µl of $^{14}C$-thymidine master mix was added to each well and the $^{14}C$-thymidine master mix was pepared according to the following regimen:

| Reagent: | One Plate (µl) | One well (µl) |
|---|---|---|
| $^{14}C$-thymidine | 220 | 2 |
| Complete medium | 1980 | 18 |
| Total Mix | 2200 | 20 |

Cells were incubated for an additional 24 hours at 37° C. in medium containing test compound and $^{14}C$-thymidine. Then, the reaction mixture was discarded and the plate was washed 2 times each with 200 µl PBS. Subsequently, each well on the plate was filled with 200 µl of PBS. The top of the plate was sealed with transparent plate sealer and white plate backing sealers were applied to the bottom of plates. The retained $^{14}C$ inside each well was measured using a Packard TopCount.

In order to test the potency of inhibition of the present compound, $IC_{50}$ of an individual compound on the inhibition of tumor cell line proliferation was measured using the above procedure. As used herein, said $IC_{50}$ refers to the concentration of the test compound at which the amount of tumor cell proliferation is reduced by one-half as compared to the maximum growth control wells without the compound. Table C shows examples of the $IC_{50}$ for representative compounds of the invention.

TABLE C $IC_{50}$ of representative compounds on cell proliferation

| Cpd No. | HCASMC (PDGF-BB) (μM) | HUVEC (LSGS) (μM) | H460 (μM) | LoVo (μM) | PC3 (μM) | T47D (μM) | A375 (μM) | AsPC1 (μM) |
|---|---|---|---|---|---|---|---|---|
| 4 | 0.268 | 1.730 | 0.030 | 0.012 | 0.048 | 0.030 | 1.580 | 0.427 |
| 11 | 0.014 | 0.002 | 0.033 | 0.002 | 0.014 | 0.007 | 0.005 | 0.03 |
| 12 | 0.106 | 0.031 | 0.003 | 0.011 | 0.013 | 0.031 | 0.011 | 0.077 |
| 14 | 0.003 | 4.870 | 0.010 | 0.011 | 0.02 | 0.032 | 0.007 | 0.592 |
| 22 | 0.278 | 2.150 | 9.270 | 13.450 | 49.500 | 0.381 | 11.550 | >10 |
| 30 | 0.002 | >1.0 | 0.290 | 0.423 | 0.175 | 8.200 | 0.507 | >10 |
| 39 | 0.009 | 0.015 | 9.950 | 10.530 | >10 | >10 | >50 | >10 |
| 63 | 0.014 | 2.460 | 3.67 | 2.4 | 6.12 | 2.6 | 2.84 | 10.3 |
| 91 | | | | 0.071 | | | 0.004 | |
| 97 | 0.019 | 1.910 | 0.424 | 0.225 | 1.68 | 0.622 | 0.362 | 5.67 |
| 122 | 0.125 | 0.223 | 14.300 | 3.840 | 6.340 | 10.500 | 14.400 | >10 |
| 157 | 0.008 | 0.218 | 3.590 | 2.140 | 3.130 | 1.900 | 1.230 | >10 |
| 330 | | 0.049 | 1.200 | 3.700 | 0.303 | 0.355 | 2.176 | 1.550 |
| 388 | | | 0.006 | 0.018 | 0.004 | 0.003 | 0.002 | 0.155 |
| 432 | | | | 0.035 | 0.012 | 0.006 | 0.002 | 0.040 |
| 420 | | | 4.100 | 3.800 | 0.276 | 0.822 | 0.214 | 4.300 |

3d. Anti-cell Proliferation in Leukemia Cells

The effect of compounds of the invention on cell proliferation in leukemia cells, in particular, the human chronic myelogenous leukemia (CML) K562 cell line, was tested using flow cytometry and trypan blue exclusion cell counting assays. The CML K562 cell line has been found to express the oncogene bcr/abl, the genetic hallmark of human CML (Wu et al., 1995, *Leukemia,* 9(5):58–862).

Material and Procedure

The human chronic myelogenous leukemia (CML) K562 cell line was obtained from American Type Culture Collection (ATCC) and cultured under specified conditions, as provided by ATCC. A Becton Dickinson FACSCalibur instrument was used for flow cytometry analyses. A CycleTEST PLUS DNA Reagent Kit (Cat. No. 340242, Becton Dickinson) was used in the study for cell staining. The standard operating procedure and a protocol for CycleTEST PLUS DNA Reagent Kit from Becton Dickinson have been followed to carry out the study. Briefly, flow cytometric analysis of the differentially stained CML K562 cell line was used to estimate the DNA content and cell cycle phase distribution of cells treated with various concentrations of the compound for 24 hours. CML K562 cells treated with compound No.14 were first stained with propidium iodide followed by fluorescence analysis to quantitate the cell cycle profile. Data analysis was carried out using the ModFit LT cell cycle data analysis program (Verity Software House, Topsham, Me. 04086, www.vsh.com). Cell viability test was performed using a Trypan Blue exclusion assay (Trypan Blue from Sigma, Cat No. T 0776) following procedures known to those skilled in the art.

Flow cytometry spectra demonstrated that after 24 hours of treatment the compound caused accumulation of cells in the G2/ M phase of the cycle and growth arrest of human CML K562 cells in a concentration-dependent fashion (Table D).

TABLE D

Percent of cells at various growth phases after compound treatment

| Compound Conc. (nM) | G0–G1 (%) | S phase (%) | G2/M (%) |
|---|---|---|---|
| 0 | 37 | 45 | 18 |
| 1 | 35 | 53 | 11 |

TABLE D-continued

Percent of cells at various growth phases after compound treatment

| Compound Conc. (nM) | G0–G1 (%) | S phase (%) | G2/M (%) |
|---|---|---|---|
| 10 | 31 | 41 | 28 |
| 100 | 2 | 0 | 98 |
| 1000 | 3 | 4 | 93 |
| 10000 | 5 | 5 | 90 |

Cell viability studies using the trypan blue exclusion assay demonstrated that treating the K562 cells with compound No. 14 for 24 hours caused a concentration-dependent decrease of cell proliferation in K562 cells. The IC50 for compound No. 14 on K562 (i.e., the concentration of the compound at which the amount of K562 cell proliferation is reduced by one—half as compared to the maximum growth control without the compound) was about 10 nM as measured from the trypan blue exclusion assay.

Using similar protocols in flowcytometry and trypan blue exclusion cell counting assays, it was found that compound No. 14 also blocked growth of other cell types such as H460 and LoVo in the G2/M cell cycle phase.

Any compound within the scope of the invention could be tested for their ability to inhibit cell proliferation using various protocols described herein.

4. Anti-Angiogenesis Assay.

Angiogenesis inhibitory activity of a compound of this invention can be measured in vivo using the matrigel mouse model (MM Assay) of angiogenesis (Passaniti et al., *Laboratory Investigation,* 67: 519–528, 1992). The matrigel mouse assay is a well-established method to quantify angiogenesis (see e g. Capogrossi et al., *Methods in Molecular Medicine, Vascular Disease: Molecular Biology and Gene Therapy Protocols*, Edited by: A. H. Baker, Humana Press Inc., Totowa, N.J., 1999). The model has been characterized extensively for its relevance as a mimic of the process of angiogenesis and has been used extensively to evaluate in vivo both potential angiogenic and anti-angiogenic activity of numerous compounds/agents. Compounds with demonstrated anti-angiogenic activity in other angiogenesis models (eg. RAR assay) have been shown to be potent inhibitors of angiogenesis in the MM assay and produce tumor growth reduction in human tumor xenograft models. All procedures involving animals were conducted in an animal facility fully accredited by the American Association for Assessment and Accreditation of Laboratory Animal Care (AAALAC) and in accordance with The Guide for the Care and Use of Laboratory Animals (NIH). Protocols were approved by the RWJ-PRI Internal Animal Care and Use Committee (IACUC).

Procedure

Normal male mice (C57BL/6J) were injected subcutaneously (ventrally below rib cage at abdominal midline) with 1.0 mL of chilled matrigel supplemented with a single purified pro-angiogenic growth factor (100–500 ng/mL of either rhPDGF-BB (supra), recombinant human basic fibroblast growth factor, rhFGF-basic (R&D System Cat. No 233-FB) or recombinant human vascular endothelial growth factor, rhVEGF (PanVera Cat. No R2951) and heparin (35 U/mL). Compounds are formulated as 0.1% suspensions (1 mg/mL final concentration) in 0.5% methylcellulose. Vehicle or test compounds (8–10 mice per treatment group) were administered orally by gavage beginning two hours after matrigel injections. Dosing continued for three consecutive days (ie. qd dosing on day 1, bid dosing on day 2, and bid dosing on day 3). Approximately 18 hours after the last dose of vehicle or drug, mice were euthanized and the matrigel plugs were surgically removed intact (overlying skin removed and plug cut out retaining some of the peritoneal lining for support). The plug was placed in prelabeled tubes containing 1.0 mL distilled water, minced and extracted for hemoglobin (Hb) overnight in a 37° C. water bath with light shaking. The tubes were centrifuged the next day at 3000 rpm for 20 minutes. Supernatants were removed and the hemoglobin concentration in the plug extract was measured spectrophotometrically using the Drabkin's assay method (Drabkin's reagent kit 525-A; SIGMA) and read on a Beckman DU 7400 Spectrophotometer. Hemoglobin content of the plug was used as an indirect index of the angiogenic response and a reduction of plug hemoglobin content was indicative of in vivo anti-angiogenic activity. The ability of compounds to inhibit PDGF-BB-stimulated angiogenesis in vivo was compared directly to vehicle-treated control mice. Group differences were analyzed statistically using the Mann-Whitney Test, with a p-value of 0.05 or less considered statistically significant.

Any compound within the scope of the invention can be tested using the in vivo MM assay protocol described herein. Results for representative compounds of the invention from the in vivo MM assay supplemented with PDGF are shown in Table E.

TABLE E

Representative Compounds Inhibit Angiogenesis in in vivo MM Assay supplemented with PDGF-BB.

| Compound No. | % Inhibition @ 30 mg/kg po |
|---|---|
| 14 | 40 |
| 12 | 45 |
| 26 | 42 |

5. Anti-tumor Assay

The anti-tumor activity of experimental compounds was evaluated in vivo using the human tumor nude mouse xenograft model. All procedures involving animals were conducted in an animal facility fully accredited by the American Association for Assessment and Accreditation of Laboratory Animal Care (AAALAC) and in accordance with The Guide for the Care and Use of Laboratory Animals (NIH). Protocols were approved by the RWJ-PRI Internal Animal Care and Use Committee (IACUC).

Human tumor cell lines (LoVo, MDA-MB-231, H460 etc.) were obtained from American Type Culture Collection and cultured under specified conditions required for each cell type. Female athymic nude mice (Charles River nu/nu) were injected subcutaneously in the inguinal region of the thigh with 1–2×$10^6$ tumor cells in 0.1 mL volume on day zero. For growth delay studies, mice were dosed orally with vehicle (control group) or experimental drugs beginning three days after tumor cell inoculation. Compounds were prepared in 0.5% methylcellulose and treatments were administered bid for 30–35 consecutive days. Tumor growth was measured twice a week using calipers for the duration of the treatment. Tumor areas ($mm^2$) were calculated as a product of length×width. Body weights were obtained twice a week and loss of body weight was used as a measure of gross toxicity. At study termination, mice were euthanized and solid tumors were surgically excised intact and weighed. Final tumor weight served as the primary efficacy endpoint. Differences between treated and control mice were analyzed statistically by ANOVA and Dunnett's t-test.

Any compound within the scope of the invention can be tested in vivo using the human tumor nude mouse xenograft model described herein. A representative compound, compound No.14, inhibited tumor growth by 72% with 50 mg/kg of the drug from the in vivo human tumor nude mouse xenograft model study.

6. Treatment in Combination with Irradiation

Radiotherapy is a major therapeutic modality in treating many types of cancers including human prostate and ovarian cancers. The anti-proliferative activity of compounds within the scope of the invention was tested in combination with irradiation treatment. A clonogenicity assay was performed on two different human cancer cell lines, DU145 (prostate cancer) and MDAH2774 (ovarian cancer) after the combined treatment of irradiation and a representative compound of the invention, compound No. 14.

Materials:

Cells DU145 (prostate cancer) and MDAH2774 (ovarian cancer) were obtained from ATCC; growth media MEM medium (Mediatech, Herndon, Va.) was supplemented with 8% FBS, 5 U/ml penicillin and 50 μg/ml Streptomycin (Hyclone, Logan, Utah), 2 mM L-glutamine (Hyclone, Logan, Utah), 25 mM HEPES (Hyclone, Logan, Utah); McCoy's 5A medium (Mediatech, Herndon, Va.) was supplemented with 8% FBS, 50 U/ml penicillin and 50 μg/ml-Strep (Hyclone, Logan, Utah) and Glutamine 2 mM L-glutamine (Hyclone, Logan, Utah), $^{137}$CS γ-source was a Gammacell 1000 Elite irradiator (MDS Nordion, Kanata, Ontario, Canada); DMSO; 1× PBS; Methanol; 0.25% Crystal Violet, and 60 mm tissue culture dishes.

Procedure:

DU145 or MDAH2774 cells at desired cell number were plated in early log phase on 60 mm dishes in MEM medium supplemented with 8% FBS, Penicillin, Streptomycin, L-glutamine, or McCoys medium supplemented with 8% FBS, Penicillin, Streptomycin and Glutamine, respectively. Cells were plated in triplicate. Compound No. 14 at various concentrations was added to the cells 14 h after the plating. The final concentrations of the compound in the cell media ranged from 1 to 100 nM. After 24 h incubation with the test compound plates were split in two groups of equal size. The plates in the first group were irradiated with 7.3 Gy (plates containing DU145 cells) or 5.4 Gy (plates containing MDAH2774 cells) using a $^{137}Cs$ γ-source (dose rate 3.32 Gy/min). The second group of plates were treated identically but not irradiated. Cells were incubated for an additional 24 hours in medium containing test compound. Then, the cells were replenished with fresh compound-free identical medium and allowed to grow for an additional 11 days. Cells were then fixed with methanol, stained with 0.25% crystal violet, and the clones containing more than 50 cells were counted.

The results from these studies showed that starting at the 30 nM concentration, compound No. 14 showed marked inhibitory activities against colony formation in both DU145 and MDAH2774 cells in the presence or absence of radiation, but clearly the inhibitory effect was greater with radiation (Table F). The activity appeared to be concentration-dependent with more dramatic effects achieved at 100 nM compound with radiation in either cell line. The results are consistent with the observation that compound No. 14 caused G2/ M growth arrest in proliferating cancer cells, because cells under G2/ M growth arrest are expected to be more vulnerable and sensitive to additional insult, such as radiation.

Any compound within the scope of the invention could be tested for their ability to sensitize cells for radiation treatment using the protocols described herein.

TABLE F

Clonogenicity assays on the combined treatment of irradiation and compound No. 14.

| Compound Conc. (nM) | No. of DU145 Clones (average of three plates) W/o Radiation (200 cells initially plated) | No. of DU145 Clones (average of three plates) w/Radiation (1200 cells initially plated) | No. of MDAH2774 Clones (average of three plates) w/o Radiation (200 cells initially plated) | No. of MDAH2774 Clones (average of three plates) w/Radiation (1000 cells initially plated |
|---|---|---|---|---|
| 0 | 133 | 134 | 101 | 121 |
| 1 | 118 | 117 | 98 | 121 |
| 3 | 108 | 100 | 96 | 125 |
| 10 | 111 | 126 | 110 | 121 |
| 30 | 100 | 57 | 35 | 8 |
| 100 | 22 | 5 | 8 | 3 |

This study indicated that cancer cells that were pre-treated with low concentrations of compound of the invention showed a greater reduction of colony formation in combination with radiation, compared to either compound or irradiation alone. These preliminary studies support the principal of using compound of the invention in combination with radiation therapy in cancers where radiotherapy is a standard therapeutic modality.

7. Conversion of Pro-drugs to Parent Compounds

It has been demonstrated that the chemical modification of an active agent can significantly change the chemical-physical properties such as solubility, stability, absorption, transport and bio-availability in terms of a particular bio-space (see *Bioreversible Carrier in Drug Design*, by Edward B. Roche, Pergamon Press, 1987). Prodrugs are molecules that can be reversibly hydrolyzed back to the active agent by enzymes such as esterases. Pro-drugs of compounds within the scope of the invention were evaluated in in vitro and in vivo assay systems for their possible in vivo conversion to parent compounds.

Various pro-drugs of a representative compound of the invention, compound No. 14, were incubated in freshly prepared rat plasma for 2 hours. The PDGF-R kinase inhibitory activities of these pro-drugs were assayed prior to and after the plasma incubation. The PDGF-R kinase inhibition assay was performed as described supra. It was shown that 2 h incubation in plasma increased the PDGF-R kinase inhibitory activity of the pro-drugs significantly. This suggests that a significant amount of pro-drug had been converted to the parent drug in rat plasma. Indeed, a significant amount of parent compound had been detected by HPLC analyses following the 2 h incubation with rat plasma (Table G).

Furthermore, pro-drugs have been administered orally to rats (10 mg/kg) in pharmacokinetics studies, and the conversion of pro-drugs to the parent compound was montitored by HPLC/MS/MS analyses. Parent compound or the glucuronide conjugates of the parent compound was detected in the rat plasma from the pharmacokinetics studies (Table G).

TABLE G conversion of representative pro-drugs to parent compound No. 14 measured by HPLC.

| Compound No. | Incubation in rat plasma (2 h) % of Parent | Fast PK (0.5 h) (conc. μM) Prodrug | Fast PK (0.5 h) (conc. μM) Parent | Fast PK (0.5 h) (conc. μM) Glucuronide conjugates |
|---|---|---|---|---|
| 578 | 0% | 7.8 | 0 | 0.007 |
| 432 | 22% | 0.08 | 0.05 | 0.9 |
| 465 | 6% | 0.223 | 0 | 6.664 |
| 433 | 47% | 0.06 | 0.1 | 3.9 |
| 471 | 56% | 0 | 1.856 | 34.79 |
| 436 | 1.5% | 0.038 | 0 | 3.347 |

The conversion of pro-drugs to any parent compound within the scope of the invention could be tested using the protocols described herein.

Methods of use of the Compounds of the Invention

Compounds of the invention can be used in methods of treatment/prevention for cell proliferation disorders or a disorder related to PDGF-R. They can also be used in methods of identifying new PDGF-R inhibitors, for example via rational design.

1. Methods of Identifying Novel PDGF-R Kinase Inhibitors Based on Rational Design.

In one aspect of this invention, compounds of the invention can be used to identify novel PDGF-R kinase inhibitors based on rational design.

As used herein, “rational design” refers to the process of designing a PDGF-R kinase inhibitor based on the three-dimensional structure of an inhibitor of PDGF-R kinase, preferably the method involving the three-dimensional structure of an inhibitor of PDGF-R kinase complexed with a PDGF-R protein, preferably a human PDGF-R protein, and more preferably a kinase catalytic domain of human PDGF-R protein. As used herein, “PDGF-R kinase catalytic domain” refers to a polypeptide consisting of a minimal amino acid sequence required for PDGF-R kinase activity, wherein the minimal amino acid sequence required for PDGF-R kinase activity can be readily determined by those skilled in the art. The catalytic domain can be that of a PDGF-R from human or an animal. For example, the “PDGF-R kinase catalytic domain” can comprise amino acid 545 to 1106 of GenBank Access NO: AAA36427.

Structure based rational design has been used successfully for identifying novel small molecule inhibitors for a variety of enzymes, such as proteases and protein tyrosine phosphatases. A method for identifying novel PDGF-R kinase inhibitors based on rational design comprises the steps of: (a) determining a three-dimensional structure of the compound of Fomula I or II in the absence or presence of a polypeptide comprising the PDGF-R kinase catalytic domain; (b) analyzing the three-dimensional structure for the compound alone or for the intermolecular interaction between said compound and PDGF-R; (c) selecting a compound that mimics the structure for the compound alone or incorporates the predictive interaction; (d) synthesizing said designed compound; and (e) determining the ability of the molecule to bind and inhibit PDGF-R kinase activity. These steps can be repeated to obtain the optimal compounds by fine tuning the interaction features.

The three-dimensional structure can be obtained by, for example, X-ray crystallography, nuclear magnetic resonance, or homology modeling, all of which are well-known methods.

A particular method of the invention comprises analyzing the three-dimensional structure for the intermolecular interaction between said compound and PDGF-R, preferably the active kinase domain of PDGF-R. The present invention encompasses the use of information of the three-dimensional structure of the compound of Fomula (I) or (II) complexed with PDGF-R in molecular modeling software systems to assist in analyzing intermolecular interactions. The likely binding site on PDGF-R as well as the key residues on the compound of Formula (I) or (II), which are critical for the intermolecular interaction, will be identified and analyzed.

Another particular method of the invention comprises designing a compound that incorporates the predictive interaction identified above. Such computer-assisted modeling and drug design may utilize information such as chemical conformational analysis, electrostatic potential of the molecules, protein folding, etc. Therefore, depending on the intermolecular interaction between the compound of Formula (I) or (II) and PDGF-R, novel PDGF-R kinase inhibitors will be designed to allow the specific binding of the designed compound to PDGF-R. The compound of Formula (I) or (II) may serve as a template for the initial design.

Another particular method of the invention comprises synthesizing the designed compounds that incorporate the predictive interaction identified above. Such a class of compounds can be synthesized using a variety of methods known in the art. For example, the synthesis methods described herein or the modification of these methods may prove to be useful to synthesize the designed compounds.

Yet another particular method of the invention comprises assaying the new compounds for their ability to bind and inhibit PDGF-R activity. The ability of a compound to inhibit PDGF-R kinase activity can be measured using any of the biological assays described supra, including the cell-free PDGF-R kinase assay; the PDGF-BB stimulated HCASMC cell proliferation and the human tumor cell proliferation assay; the in vivo anti-angiogenesis MM assay; and the human tumor mouse xenograft assay.

Because compounds within the scope of the invention also exhibited inhibitory activity for the c-Abl kinase, novel c-Abl kinase inhibitors can be identified by rational design using procedure similar to that described herein.

Such a method comprises the steps of:

(a) determining a three-dimensional structure of the compound of Fomula I or II in the absence or presence of a polypeptide comprising the c-Abl kinase catalytic domain;

(b) analyzing the three-dimensional structure for the compound alone or for the intermolecular interaction between said compound and c-Abl;

(c) selecting a compound that mimics the structure for the compound alone or incorporates the predictive interaction;

(d) synthesizing said designed compound; and (e) determining the ability of the molecule to bind and inhibit c-Abl kinase activity.

2. Methods of Treatment/Prevention

In another aspect of this invention, compounds of the invention can be used to inhibit or reduce PDGF-R kinase or c-Abl kinase activity in a cell or a subject, or to treat disorders related to PDGF-R or cell proliferation in a subject.

In one embodiment to this aspect, the present invention provides a method for reducing or inhibiting the kinase activity of PDGF-R or c-Abl in a cell comprising the step of contacting the cell with a compound of Formula (l) or (II). The present invention also provides a method of inhibiting the kinase activity of PDGF-R or c-Abl in a subject comprising the step of administering a compound of Formula (I) or (II) to the subject. The present invention further provides a method of inhibiting cell proliferation in a cell comprising the step of contacting the cell with a compound of Formula (I) or (II).

The kinase activity of PDGF-R or c-Abl in a cell or a subject can be determined by procedures well known in the art, such as the PDGF-R kinase assay or the c-Abl kinase assay described supra.

The term "subject" as used herein, refers to an animal, preferably a mammal, most preferably a human, who has been the object of treatment, observation or experiment.

In other embodiments to this aspect, the present invention provides both prophylactic and therapeutic methods for treating a subject at risk of (or susceptible to) developing a cell proliferative disorder or a disorder related to PDGF-R.

In one example, the invention provides methods for preventing in a subject a cell proliferative disorder or a disorder related to PDGF-R, by administering to the subject prophylactically effective amount of a pharmaceutical composition comprising the compound of Formula (I) or (II) and a pharmaceutically acceptable carrier. Administration of said prophylactic agent can occur prior to the manifestation of symptoms characteristic of the cell proliferative disorder or disorder related to PDGF-R, such that a disease or disorder is prevented or, alternatively, delayed in its progression.

In another example, the invention pertains to methods of treating in a subject a cell proliferative disorder or a disorder related to PDGF-R by administering to the subject therapeutically effective amount of a pharmaceutical composition comprising the compound of Formula (I) or (II) and a pharmaceutically acceptable carrier. Administration of said therapeutic agent can occur concurrently with the manifestation of symptoms characteristic of the disorder, such that said therapeutic agent serves as a therapy to compensate for the cell proliferative disorder or disorders related to PDGF-R.

The term "prophylactically effective amount" refers to an amount of an active compound or pharmaceutical agent that inhibits or delays in a subject the onset of a disorder as being sought by a researcher, veterinarian, medical doctor or other clinician.

The term "therapeutically effective amount" as used herein, refers to an amount of active compound or pharmaceutical agent that elicits the biological or medicinal response in a subject that is being sought by a researcher, veterinarian, medical doctor or other clinician, which includes alleviation of the symptoms of the disease or disorder being treated.

Methods are known in the art for determining therapeutically and prophylactically effective doses for the instant pharmaceutical composition.

As used herein, the term "composition" is intended to encompass a product comprising the specified ingredients in the specified amounts, as well as any product which results, directly or indirectly, from combinations of the specified ingredients in the specified amounts.

As used herein, the terms "disorders related to PDGF-R", or "disorders related to PDGF receptor", or "disorders related to PDGF receptor tyrosine kinase" shall include diseases associated with or implicating PDGF-R activity, for example, the overactivity of PDGF-R, and conditions that accompany with these diseases. The term "overactivity of PDGF-R" refers to either 1) PDGF-R expression in cells which normally do not express PDGF-R; 2) PDGF expression by cells which normally do not express PDGF; 3) increased PDGF-R expression leading to unwanted cell proliferation; 4) increased PDGF expression leading to unwanted cell proliferation; or 5) mutations leading to constitutive activation of PDGF-R. Examples of "disorders related to PDGF-R" include disorders resulting from over stimulation of PDGF-R due to abnormally high amount of PDGF or mutations in PDGF, or disorders resulting from abnormally high amount of PDGF-R activity due to abnormally high amount of PDGF-R or mutations in PDGF-R. It is known that overactivity of PDGF has been implicated in the pathogenesis of a number of serious diseases, including cancers (glioma, lung, breast, colorectal, prostate, gastric and esophageal, leukemias and lymphomas), and other cell proliferative disorders, such as atherosclerosis, transplantation-induced vasculopathies, neointima formation, lung fibrosis, restenosis, pulmonary fibrosis, glomerulonephritis, glomerulosclerosis, congenital multicystic renal dysplasia, kidney fibrosis, and rheumatoid arthritis (Ostman A, Heldin C H., *Adv. Cancer Res,* 80:1–38, 2001, and references therein).

The term "cell proliferative disorders" refers to unwanted cell proliferation of one or more subset of cells in a multicellular organism resulting in harm (i.e., discomfort or decreased life expectancy) to the multicellular organisms. Cell proliferative disorders can occur in different types of animals and humans. For example, as used herein "cell proliferative disorders" include neoplastic and other cell proliferative disorders. As used herein, a "neoplastic disorder" refers to a tumor resulting from uncontrolled cellular overgrowth. Examples of neoplastic disorders include but are not limited to cancers such as, glioma cancers, lung cancers, breast cancers, colorectal cancers, prostate cancers, gastric cancers, esophageal cancers, colon cancers, pancreatic cancers, ovarian cancers, myelodysplasia, multiple myeloma, leukemias and lymphomas. Examples of leukemias include, but are not limited to chronic myelogenous leukemia (CML); acute lymphocytic leukemia (ALL); chronic neutrophilic leukemia (CNL); acute undifferentiated leukemia (AUL); and acute myelogenous leukemia (AML). Examples of other cell proliferative disorders, include but are not limited to, atherosclerosis, transplantation-induced vasculopathies, neointima formation, lung fibrosis, macular degeneration, restenosis, pulmonary fibrosis, glomerulonephritis, glomerulosclerosis, congenital multicystic renal dysplasia, kidney fibrosis, diabetic retinopathy and rheumatoid arthritis.

In a further embodiment to this aspect, the invention encompasses a combination therapy for treating or inhibiting the onset of a cell proliferative disorder or a disorder related to PDGF-R in a subject. The combination therapy comprises administering to the subject a therapeutically or prophylactically effective amount of the compound of Formulae (I) or (II), and one or more other anti-cell proliferation therapy including chemotherapy, radiation therapy, gene therapy and immunotherapy.

In an embodiment of the present invention, the compound of the present invention may be administered in combination with chemotherapy. As used herein, chemotherapy refers to a therapy involving a chemotherapeutic agent. A variety of chemotherapeutic agents may be used in the combined treatment methods disclosed herein. Chemotherapeutic agents contemplated as exemplary including, but not limited to, adriamycin, dactinomycin, mitomycin, carminomycin, daunomycin, doxorubicin, tamoxifen, taxol, taxotere, vincristine, vinblastine, vinorelbine, etoposide (VP-16), 5-fluorouracil (5FU), cytosine arabinoside, cyclophohphamide, thiotepa, methotrexate, camptothecin, herceptin, actinomycin-D, mitomycin C, cisplatin (CDDP), aminopterin, combretastatin(s) and derivatives and prodrugs thereof.

In another embodiment of the present invention, the compound of the present invention may be administered in combination with radiation therapy. As used herein, "radiation therapy" refers to a therapy that comprises exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

In another embodiment of the present invention, the compound of the present invention may be administered in combination with a gene therapy. As used herein, "gene therapy" refers to a therapy targeting on particular genes involved in tumor development. Possible gene therapy strategies include the restoration of defective cancer-inhibitory genes, cell transduction or transfection with antisense DNA corresponding to genes coding for growth factors and their receptors, or with the so-called 'suicide genes'.

In other embodiments of this invention, the compound of the present invention may be administered in combination with an immunotherapy. As used herein, "immunotherapy" refers to a therapy targeting particular protein involved in tumor development via antibodies specific to such protein. For example, monoclonal antibodies against vascular endothelial growth factor have been used in treating cancers.

Where a second pharmaceutical is used in addition to the compound of the invention, the two pharmaceuticals may be administered together in a single composition, separately, sequentially, at approximately the same time, or on separate dosing schedules.

As will be understood by those of ordinary skill in the art, the appropriate doses of chemotherapeutic agents will be generally similar to or less than those already employed in clinical therapies wherein the chemotherapeutics are administered alone or in combination with other chemotherapeutics. By way of example only, agents such as cisplatin, and other DNA alkylating agents are used widely to treat cancer. The efficacious doses of cisplatin used in clinical applications is of 20 $mg/m^2$ for 5 days every three weeks for a total of three courses. Cisplatin is not absorbed orally and must therefore be delivered via injection intravenously, subcutaneously, intratumorally or intraperitoneally. Further useful agents include compounds that interfere with DNA replication, mitosis and chromosomal segregation. Such chemotherapeutic compounds including adriamycin, also known as doxorubicin, etoposide, verapamil, podophyllotoxin, and the like, are widely used in a clinical setting for the treatment of neoplasms. These compounds are administered through bolus injections intravenously at doses ranging from 25–75 $mg/m^2$ at 21 day intervals for adriamycin, to 35–50 $mg/m^2$ for etoposide intravenously or double the intravenous dose orally. Agents that disrupt the synthesis and fidelity of polynucleotide precursors such as 5-fluorouracil (5-FU) are preferentially used to target neoplastic cells. Although quite toxic, 5-FU is commonly used via intravenous administration with doses ranging from 3 to 15 mg/kg/day.

The compound of the invention can be administered to a subject systemically, for example, intravenously, orally, subcutaneously, intramuscular, intradermal, or parenterally. The compound of the invention can also be administered to a subject locally. Non-limiting examples of local delivery systems include the use of intraluminal medical devices that include intravascular drug delivery catheters, wires, pharmacological stents and endoluminal paving. The compound of the invention can further be administered to a subject in combination with a targeting agent to achieve high local concentration of the compound at the target site. In addition, the compound may be formulated for fast-release or slow-release with the objective of maintaining the drugs or agents in contact with target tissues for a period ranging from hours to weeks.

The present invention also provides a pharmaceutical composition comprising the compound of Formula (I) or (II), or an optical isomer, enantiomer, diastereomer, racemate or pharmaceutically acceptable salt thereof, in association with a pharmaceutically acceptable carrier. The pharmaceutical composition may contain between about 0.1 mg and 1000 mg, preferably about 100 to 500 mg, of the compound, and may be constituted into any form suitable for the mode of administration selected. The phrases "pharmaceutically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

The pharmaceutical composition of the present invention also includes a pharmaceutical composition for slow release of the compound of the invention. The composition includes a slow release carrier (typically, a polymeric carrier) and a compound of the invention. Slow release biodegradable carriers are well known in the art. These are materials that may form particles that capture therein an active compound (s) and slowly degrade/dissolve under a suitable environment (e.g., aqueous, acidic, basic, etc) and thereby degrade/dissolve in body fluids and release the active compound(s) therein. The particles are preferably nanoparticles (i.e., in the range of about 1 to 500 nm in diameter, preferably about 50–200 nm in diameter, and most preferably about 100 nm in diameter).

The present invention also provides methods to prepare the pharmaceutical compositions of this invention. Compound of Formulae (I) or (II) or an optical isomer, enantiomer, ester, diastereomer, racemate or racemic mixture thereof, and salt thereof, as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. In preparation for slow release, a slow release carrier, typically a polymeric carrier, and a compound of the invention are first dissolved or dispersed in an organic solvent. The obtained organic solution is then added into an aqueous solution to obtain an oil-in-water-type emulsion. Preferably, the aqueous solution includes surface-active agent(s). Subsequently, the organic solvent is evaporated from the oil-in-water-type emulsion to obtain a colloidal suspension of particles containing the slow release carrier and the compound of the invention.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, from about 0.01 mg to 200 mg/kg of body weight per day. Preferably, the range is from about 0.03 to about 100 mg/kg of body weight per day, most preferably, from about 0.05 to about 10 mg/kg of body weight per day. The compounds may be administered on a regimen of 1 to 5 times per day. The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the lafter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, acetyl alcohol and cellulose acetate.

The liquid forms in which the compound of Formulae (I) or (II) may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Advantageously, compounds of Formulae (I) or (II) may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The daily dosage of the products may be varied over a wide range from 1 to 5000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 200 mg/kg of body weight per day. Particularly, the range is from about 0.03 to about 15 mg/kg of body weight per day, and more particularly, from about 0.05 to about 10 mg/kg of body weight per day. The compounds may be administered on a regimen up to four or more times per day, preferably of 1 to 2 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The compound of the present invention can also be administered in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof. They may either contain cholesterol or may be cholesterol-free.

The compound of the present invention can also be administered locally. Any delivery device, such as intravascular drug delivery catheters, wires, pharmacological stents and endoluminal paving, may be utilized. It is preferred that the delivery device comprises a stent that includes a coating or sheath which elutes or releases the compounds. The delivery system for such a device may comprise a local infusion catheter that delivers the compound at a rate controlled by the administor.

The present invention provides a drug delivery device comprising an intraluminal medical device, preferably a stent, and a therapeutic dosage of a compound of the invention.

The term "stent" refers to any device capable of being delivered by a catheter. A stent is routinely used to prevent vascular closure due to physical anomalies such as unwanted inward growth of vascular tissue due to surgical trauma. It often has a tubular, expanding lattice-type structure appropriate to be left inside the lumen of a duct to relieve an obstruction. The stent has a lumen wall-contacting surface and a lumen-exposed surface. The lumen-wall contacting surface is the outside surface of the tube and the lumen-exposed surface is the inner surface of the tube. The stent can be polymeric, metallic or polymeric and metallic, and it can optionally be biodegradable.

Commonly, stents are inserted into the lumen in a non-expanded form and are then expanded autonomously, or with the aid of a second device in situ. A typical method of expansion occurs through the use of a catheter-mounted angioplastry balloon which is inflated within the stenosed vessel or body passageway in order to shear and disrupt the obstructions associated with the wall components of the vessel and to obtain an enlarged lumen. Self-expanding stents as described in US 2002/0016625 A1 (Falotico et al., in pending) may also be utilized. The combination of a stent with drugs, agents or compounds which prevent inflammation and proliferation, may provide the most efficacious treatment for post-angioplastry restenosis.

Compounds of the invention can be incorporated into or affixed to the stent in a number of ways and in utilizing any number of biocompatible materials. In one exemplary embodiment, the compound is directly incorporated into a polymeric matrix, such as the polymer polypyrrole, and subsequently coated onto the outer surface of the stent. Essentially, the compound elutes from the matrix by diffusion through the polymer molecules. Stents and methods for coating drugs on stents are discussed in detail in WIPO publication WO9632907. In another exemplary embodiment, the stent is first coated with as a base layer comprising a solution of the compound, ethylene-co-vinylacetate, and polybutylmethacrylate. Then, the stent is further coated with an outer layer comprising only polybutylmethacrylate. The outlayer acts as a diffusion barrier to prevent the compound from eluting too quickly and entering the surrounding tissues. The thickness of the outer layer or topcoat determines the rate at which the compound elutes from the matrix. Stents and methods for coating are discussed in detail in U.S. Publication No. 2002/0016625 and references disclosed therein.

The solution of the compound of the invention and the biocompatible materials/polymers may be incorporated into or onto a stent in a number of ways. For example, the solution may be sprayed onto the stent or the stent may be dipped into the solution. In a preferred embodiment, the solution is sprayed onto the stent and then allowed to dry. In another exemplary embodiment, the solution may be electrically charged to one polarity and the stent electrically changed to the opposite polarity. In this manner, the solution and stent will be attracted to one another. In using this type of spraying process, waste may be reduced and more control over the thickness of the coat may be achieved. Compound is preferably only affixed to the outer surface of the stent which makes contact with one tissue. However, for some compounds, the entire stent may be coated. The combination of the dose of compound applied to the stent and the polymer coating that controls the release of the drug is important in the effectiveness of the drug. The compound preferably remains on the stent for at least three days up to approximately six months and more, preferably between seven and thirty days.

Any number of non-erodible biocompatible polymers may be utilized in conjunction with the compound of the invention. It is important to note that different polymers may be utilized for different stents. For example, the above-described ethylene-co-vinylacetate and polybutylmethacrylate matrix works well with stainless steel stents. Other polymers may be utilized more effectively with stents formed from other materials, including materials that exhibit superelastic properties such as alloys of nickel and titanium.

The present invention further provides a method for the treatment of disorders related to PDGF-R, particularly restenosis, intimal hyperplasia or inflammation, in blood vessel walls, which comprises the controlled delivery, by release from an intraluminal medical device, such as a stent, of a compound of the invention in therapeutic effective amounts.

Methods for introducing a stent into a lumen of a body are well known and the compound-coated stents of this invention are preferably introduced using a catheter. As will be appreciated by those of ordinary skill in the art, methods will vary slightly based on the location of stent implantation. For coronary stent implantation, the balloon catheter bearing the stent is inserted into the coronary artery and the stent is positioned at the desired site. The balloon is inflated, expanding the stent. As the stent expands, the stent contacts the lumen wall. Once the stent is positioned, the balloon is deflated and removed. The stent remains in place with the lumen-contacting surface bearing the compound directly contacting the lumen wall surface. Stent implantation may be accompanied by anticoagulation therapy as needed.

Optimum conditions for delivery of the compounds for use in the stent of the invention may vary with the different local delivery systems used, as well as the properties and concentrations of the compounds used. Conditions that may be optimized include, for example, the concentrations of the compounds, the delivery volume, the delivery rate, the depth of penetration of the vessel wall, the proximal inflation pressure, the amount and size of perforations and the fit of the drug delivery catheter balloon. Conditions may be optimized for inhibition of smooth muscle cell proliferation at the site of injury such that significant arterial blockage due to restenosis does not occur, as measured, for example, by the proliferative ability of the smooth muscle cells, or by changes in the vascular resistance or lumen diameter. Optimum conditions can be determined based on data from animal model studies using routine computational methods.

Another alternative method for administering compounds of this invention may be by conjugating the compound to a targeting agent which directs the conjugate to its intended site of action, i.e., to vascular endothelial cells, or to tumor cells. Both antibody and non-antibody targeting agents may be used. Because of the specific interaction between the targeting agent and its corresponding binding partner, a compound of this invention can be administered with high local concentrations at or near a target site and thus treats the disorder at the target site more effectively.

The antibody targeting agents include antibodies or antigen-binding fragments thereof, that bind to a targetable or accessible component of a tumor cell, tumor vasculature, or tumor stroma. The "targetable or accessible component" of a tumor cell, tumor vasculature or tumor stroma, is preferably a surface-expressed, surface-accessible or surface-localized component. The antibody targeting agents also include antibodies or antigen-binding fragments thereof, that bind to an intracellular component that is released from a necrotic tumor cell. Preferably such antibodies are monoclonal antibodies, or antigen-binding fragments thereof, that bind to insoluble intracellular antigen(s) present in cells that may be induced to be permeable, or in cell ghosts of substantially all neoplastic and normal cells, but are not present or accessible on the exterior of normal living cells of a mammal.

As used herein, the term "antibody" is intended to refer broadly to any immunologic binding agent such as IgG, IgM, IgA, IgE, F(ab')2, a univalent fragment such as Fab', Fab, Dab, as well as engineered antibodies such as recombinant antibodies, humanized antibodies, bispecific antibodies, and the like. The antibody can be either the polyclonal or the monoclonal, although the monoclonal is preferred. There is a very broad array of antibodies known in the art that have immunological specificity for the cell surface of virtually any solid tumor type (see a Summary Table on monoclonal antibodies for solid tumors in U.S. Pat. No.

5,855,866 to Thorpe et al). Methods are known to those skilled in the art to produce and isolate antibodies against tumor (see i.e., U.S. Pat. No. 5,855,866 to Thorpe et al., and U.S. Pat. No. 6,342,219 to Thorpe et al.).

The non-antibody targeting agents includes growth factors, such as PDGF, VEGF and FGF; peptides containing the tripeptide R-G-D, that bind specifically to the tumor vasculature; and other targeting components such as annexins and related ligands. In addition, a variety of other organic molecules can also be used as targeting agents for tumors, examples are hyaluronan oligosaccharides which specifically recognize Hyaluronan-binding protein, a cell surface protein expressed during tumor cell and endothelial cell migration and during capillary-like tubule formation (U.S. Pat. No. 5,902,795, Toole et al.), and polyanionic compounds, particularly polysulphated or polysulphonated compounds such as N- and O-sulfated polyanionic polysaccharides, polystyrene sulfonate and other polyanionic compounds described in U.S. Pat. No. 5,762,918 (Thorpe), which selectively bind to vascular endothelial cells.

Techniques for conjugating therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985). Similar techniques can also be applied to attach compounds of the invention to non-antibody targeting agents. Those skilled in the art will know, or be able to determine, methods of forming conjugates with non-antibody targeting agents, such as small molecules, oligopeptides, polysaccharides, or other polyanionic compounds.

Although any linking moiety that is reasonably stable in blood, can be used to link the compound of the invention to the targeting agent, biologically-releasable bonds and/or selectively cleavable spacers or linkers is preferred. "Biologically-releasable bonds" and "selectively cleavable spacers or linkers" still have reasonable stability in the circulation, but are releasable, cleavable or hydrolyzable only or preferentially under certain conditions, i.e., within a certain environment, or in contact with a particular agent. Such bonds include, for example, disulfide and trisulfide bonds and acid-labile bonds, as described in U.S. Pat. Nos. 5,474,765 and 5,762,918 and enzyme-sensitive bonds, including peptide bonds, esters, amides, phosphodiesters and glycosides as described in U.S. Pat. Nos. 5,474,765 and 5,762,918. Such selective-release design features facilitate sustained release of the compounds from the conjugates at the intended target site.

The present invention provides a pharmaceutical composition that comprises an effective amount of the compound of the invention conjugated to a targeting agent and a pharmaceutically acceptable carrier described supra.

The present invention further provides a method of treating of a disorder related to PDGF-R, particularly a tumor, which comprises administering to the subject a therapeutic effective amount of compound of Formulae (I) or (II) conjugated to a targeting agent. When proteins such as antibodies or growth factors, or polysaccharides are used as targeting agents, they are preferably administered in the form of injectable compositions. The injectable antibody solution will be administered into a vein, artery or into the spinal fluid over the course of from 2 minutes to about 45 minutes, preferably from 10 to 20 minutes. In certain cases, intradermal and intracavitary administration are advantageous for tumors restricted to areas close to particular regions of the skin and/or to particular body cavities. In addition, intrathecal administrations may be used for tumors located in the brain.

Therapeutically effective doses of the compound of the invention conjugated to a targeting agent depend on the individual, the disease type, the disease state, the method of administration and other clinical variables. The effective dosages are readily determinable using data from an animal model. Experimental animals bearing solid tumors are frequently used to optimize appropriate therapeutic doses prior to translating to a clinical environment. Such models are known to be very reliable in predicting effective anti-cancer strategies. For example, mice bearing solid tumors, are widely used in pre-clinical testing to determine working ranges of therapeutic agents that give beneficial anti-tumor effects with minimal toxicity.

One skilled in the art will recognize that the compounds of Formulae (I) or (II) may have one or more asymmetric carbon atoms in their structure. It is intended that the present invention includes within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

Some of the compounds of the present invention may have trans and cis isomers. In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their component enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography. The scope of the present invention is intended to cover all such isomers or stereoisomers per se, as well as mixtures of cis and trans isomers, mixtures of diastereomers and racemic mixtures of enantiomers (optical isomers) as well.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I):

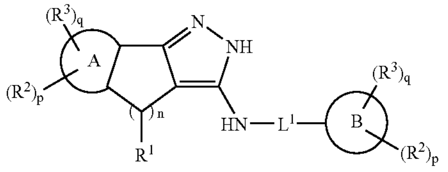

(I)

wherein, n is an integer from 1 to 4;

$R^1$ is selected from the group consisting of hydrogen, lower alkyl, —OH, alkoxy, —oxo, —$NH_2$, —NH (alkyl) and —$N(alkyl)_2$;

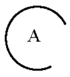

is aryl;

p is an integer from 0 to 2;

$R^2$ is selected from the group consisting of

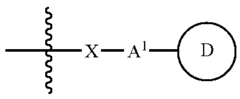

, and —X-$A^1$-Y-$A^2$;

wherein,

X and Y are each independently absent or selected from the group consisting of —O—, —NH—, —N(alkyl)-, —S—, —SO—, —$SO_2$—, OC(═O), —C(═O)O—, —NHC(═O)—, —N(alkyl)C(═O)—, —C(═O)NH—, —C(═O)N(alkyl)-, —OC(═O)O—, —NHC(═O)O—, —OC(═O)NH—, —N(alkyl)C(═O)O—, —OC(═O)N(alkyl)-, —NHC(═O)NH—, —NHC(═O)N(alkyl)-, —N(alkyl)C(═O)NH—, —N(alkyl)C(═O)N(alkyl)-, —$NHSO_2$—, —$SO_2$NH—, —N(alkyl)$SO_2$— and —$SO_2$N(alkyl)-;

$A^1$ is absent or selected from alkyl or alkenyl; $A^2$ is selected from alkyl, alkenyl, or H; wherein, when $A^1$ or $A^2$ is alkyl or alkenyl, the alkyl or alkenyl group may be optionally substituted with one or more groups independently selected from halogen, cyano, hydroxy, alkoxy, thio, halogenated alkoxy, —OC(═O)alkyl, —OC(═O)Oalkyl, amino, alkylamino, —NHC(═O)alkyl, —N(alkyl)C(═O)alkyl, dialkylamino, —NHC(═O)$NH_2$, —NHC(═O)NHalkyl, —N(alkyl)C(═O)NHalkyl, —N(alkyl)C(═O)$NH_2$, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)$N(alkyl)_2$, —N(alkyl)C(═O)$N(alkyl)_2$ or —OC(═O)$N(alkyl)_2$;

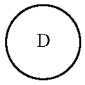

is selected from the group consisting of an aryl, a cycloalkyl, a partially unsaturated carbocycle, a heteroaryl, a heterocycloalkyl, a nine to ten membered benzo-fused cycloalkyl, and a nine to ten membered benzo-fused heterocycloalkyl; wherein, the aryl, cycloalkyl, partially unsaturated carbocycle, heteroaryl, heterocycloalkyl, benzo-fused cycloalkyl, or benzo-fused heterocycloalkyl,is optionally substituted with one or more substituents independently selected from halogen, hydroxy, amino, thio, nitro, cyano, alkyl, halogenated alkyl, alkoxy, halogenated alkoxy, alkylamino, —NHC(═O)alkyl, —N(alkyl)C(═O)alkyl, or dialkylamino, —NHC(═O)$NH_2$, —NHC(═O)NHalkyl, —N(alkyl)C(═O)NHalkyl, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)$N(alkyl)_2$, —N(alkyl)C(═O)$N(alkyl)_2$ or —OC(═O)$N(alkyl)_2$;

q is an integer from 0 to 4;

$R^3$ is selected from the group consisting of halogen, hydroxy, amino, thio, nitro, cyano, alkyl, halogenated alkyl, alkoxy, halogenated alkyloxy, alkylamino, —NHC(═O)alkyl, —N(alkyl)C(═O)alkyl, or dialkylamino, —NHC(═O)$NH_2$, —NHC(═O)NHalkyl, —N(alkyl)C(═O)NHalkyl, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)$N(alkyl)_2$, —N(alkyl)C(═O)$N(alkyl)_2$ and —OC(═O)$N(alkyl)_2$;

provided that the sum of p and q is an integer from 0 to 4;

$L^1$ is absent;

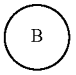

is aryl;

or an optical isomer, enantiomer, diastereomer, racemate, or pharmaceutically acceptable salt thereof.

2. A compound as in claim 1 of the formula (Ia)

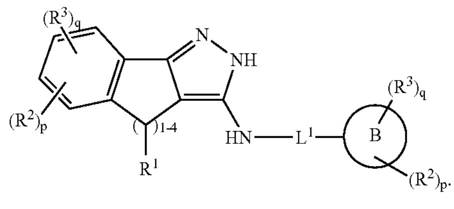

(Ia)

3. A compound as in claim 1 wherein n is an integer from 1 to 2;

$R^1$ is hydrogen;

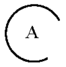

is phenyl;

p is an integer from 0 to 2;

$R^2$ is selected from the group consisting of di(lower alkyl)amino-alkoxy, lower alkyl-alkoxy, hydroxy substituted alkoxy and

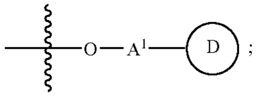

wherein $A^1$ is selected from the group consisting of lower alkyl; wherein the lower alkyl is optionally substituted with one to two substituents independently selected from hydroxy, amino, alkylamino or dialkylamino; and wherein

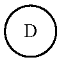

is selected from the group consisting of a five or six membered heteroaryl and a five or six membered heterocycloalkyl; wherein the heteroaryl or heterocycloalkyl is optionally substituted with one to two substituents independently selected from halogen, lower alkyl, lower alkoxy, amino, lower alkylamino or di(lower alkyl)amino;

q is an integer from 0 to 2;

$R^3$ is selected from the group consisting of lower alkyl and lower alkoxy, and halogen;

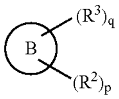

is phenyl wherein the phenyl is optionally substituted with one to two substituents independently selected from halogen, lower alkyl, lower alkoxy or benzyloxy;

or an optical isomer, enantiomer, diastereomer, racemate or pharmaceutically acceptable salt thereof.

4. A compound as in claim 1 wherein n is an integer from 1 to 2;

$R^1$ is hydrogen;

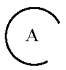

is phenyl;

p is an integer from 0 to 2;

$R^2$ is selected from the group consisting of 3-dimethylamino-propoxy, 3-methoxy-propoxy, 2,3-dihydroxy-n-propoxy, 3-hydroxy-propoxy, 2-hydroxy-3-pyrrolidin-1-yl-propoxy and 3-(4-methyl-piperazin-1-yl-propoxy;

q is an integer from 0 to 2;

$R^3$ is selected from the group consisting of methyl, methoxy, and ethoxy;

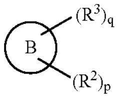

is phenyl wherein the phenyl is optionally substituted with one to two substituents independently selected from fluoro, chloro, methyl, methoxy or benzyloxy;

or an optical isomer, enantiomer, diastereomer, racemate or pharmaceutically acceptable salt thereof.

5. A compound as in claim 1 wherein

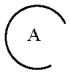

is phenyl;

p is an integer from 0 to 2;

$R^2$ is selected from the group consisting of heterocycloalkyl, benzyloxy, di(lower alkyl)amino-lower alkoxy, lower alkoxy-lower alkoxy, heteroaryl-lower alkoxy, heterocycloalkyl-lower alkoxy and lower alkoxy; wherein the heterocycloalkyl, whether alone or as part of a substituent group is optionally substituted with a substituent selected from lower alkyl or hydroxy; wherein the lower alkoxy, whether alone or as part of a subtituent group is optionally substituted with one to two hydroxy;

q is an integer from 0 to 2;

$R^3$ is selected from the group consisting of hydroxy, lower alkoxy, lower alkyl, halogen, amino, (lower alkyl) amino and di(lower alkyl)amino;

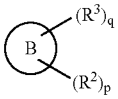

is phenyl; wherein the phenyl is optionally substituted with one to three substituents independently selected from hydroxy, carboxy, halogen, lower alkyl, hydroxy substituted lower alkyl, lower alkoxy, lower alkoxycarbonyl, trifluoromethyl, trifluoromethoxy, lower alkylamino, di(lower alkyl)amino, cyano, nitro, aminocarbonyl, lower alkylaminocarbonyl, di(lower alkyl) aminocarbonyl, (hydroxy substituted lower alkyl)-aminocarbonyl, (heteroaryl-lower alkyl)-aminocarbonyl, lower alkyl-thio, trifluoromethylthio, aralkyloxy, heterocycloalkyl, lower alkyl substituted heterocycloalkyl or heterocycloalkyl-sulfonyl;

or an optical isomer, enantiomer, diastereomer, racemate or pharmaceutically acceptable salt thereof.

6. A compound as in claim 5, wherein

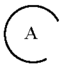

is phenyl;

$R^1$ is selected from the group consisting of hydrogen, hydroxy, oxo and methyl;

p is an integer from 0 to 2;

$R^2$ is selected from the group consisting of piperidinyl, 4-methyl-piperizin-1-yl, 3-(4-methyl-piperazin-1-yl)-propoxy, 3-dimethylamino-propoxy, 3-methoxy-propoxy, 3-morpholin-1-yl-propoxy, 3-pyrrolidin-1-yl-propoxy, 3-imidazol-1-yl-propoxy, 2,3-dihydroxy-propoxy, 3-hydroxy-propoxy, 2-hydroxy-3-pyrrolidin-1-yl-propoxy, and benzyloxy;

q is an integer from 0 to 2;

$R^3$ is selected from the group consisting of hydroxy, methoxy, ethoxy, isopropoxy, methyl, bromo, fluoro, chloro, amino and dimethylamino;

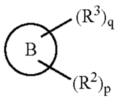

is selected from the group consisting of phenyl, 4-chlorophenyl, 3-chlorophenyl, 2-chlorophenyl, 2-fluorophenyl, 3-fluorophenyl, 4-fluorophenyl, 2-bromophenyl, 3-bromophenyl, 4-bromophenyl, 2-methylphenyl, 3-methylphenyl, 4-methylphenyl, 2-ethylphenyl, 3-ethylphenyl, 2-isopropylphenyl, 2-methoxyphenyl, 3-methoxyphenyl, 4-methoxyphenyl, 3-methoxycarbonylphenyl, 3-ethoxycarbonylphenyl, 4-ethoxycarbonylphenyl, 3-hydroxyphenyl, 3-cyanophenyl, 4-cyanophenyl, 3-carboxyphenyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 3-hydroxymethyl-phenyl, 3-(1-hydroxyethyl)phenyl, 3-methylthiophenyl, 3-trifluoromethylthiophenyl, 3-benzyloxy-phenyl, 4-benzyloxyphenyl, 4-methylaminophenyl, 4-dimethylaminophenyl, 3-aminocarbonylphenyl, 2,5-difluorophenyl, 3,4-difluorophenyl, 3,5-difluorophenyl, 2,4-dichiorophenyl, 2,5-dichiorophenyl, 2,6-dichiorophenyl, 3,4-dichiorophenyl, 3,5-dichiorophenyl, 3,5-dimethyiphenyl, 2,4-dimethoxyphenyl, 2,5-dimethoxyphenyl, 3,4-dimethoxyphenyl, 3,5-dimethoxyphenyl, 3,5-di(trifluoromethyl)-phenyl, 3,5-di(tert-butyl)-phenyl, 3-chloro-4-fluoro-phenyl, 3-chloro-4-methoxy-phenyl, 4-chloro-3-methyl-phenyl, 5-chloro-2-methyl-phenyl, 5-chloro-2-methoxy-phenyl, 4-bromo-2-trifluoromethyl-phenyl, 4-fluoro-3-trifluoromethyl-phenyl, 4-fluoro-3-nitro-phenyl, 3,4,5-trimethoxyphenyl, 4-(4-methyl -piperidin-1-yl)-phenyl, 4-(piperidine-4-sulfonyl)-phenyl, 3-(2-hydroxy-ethylaminocarbonyl)-phenyl, and 3-(3-pyrrolidn-1-yl-propylaminocarbonyl)-phenyl;

or an optical isomer, enantiomer, diastereomer, racemate or pharmaceutically acceptable salt thereof.

7. A compound of Formula (II):

(II)

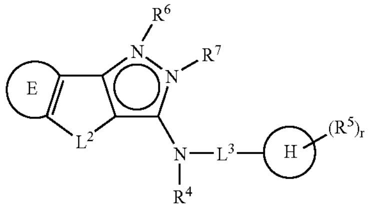

wherein:

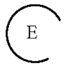

is Formulae A-1:

(Formula A-1)

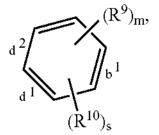

wherein Formula A-1 is attached on the $b^1$ side of Formula A-1 to the $L^2$ ring of formula (II);

$R^9$ is independently selected from the group consisting of: alkoxy, alkyl, alkylamino, amino, cyano, dialkylamino, halogen, halogenated alkyl, halogenated alkyloxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, nitro, —OC(═O)N(alkyl)$_2$, —OC(═O)NHalkyl, —$SO_2$alkyl, thio and thioalkyl;

$L^2$ is a linking group selected from the group consisting of: —$(CH_2)_{1-4}$—, —CH($R^{100}$)—, —C(═$R^{100}$)—, and —C$(R^{100})_2$—; wherein $R^{100}$ is selected from: alkyl, hydroxy, aryl, alkoxy, oxo, —$NH_2$, —NH(alkyl) —N(alkyl)$_2$, ═N(OH) or —$NH_2OH$; provided that when $L^2$ is —$CH_2CH_2$—, neither $R^6$ nor $R^7$ is —$CH_2$—(C═O)NHalkyl, —$CH_2$—(C═O)N(alkyl)$_2$ or $CH_2C$(═O)Oalkyl;

$R^{10}$ is independently selected from the group consisting of

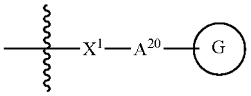

and —$X^1$-$A^{20}$-$Y^1$-$A^{21}$;

wherein $X^1$ and $Y^1$ are each independently absent or selected from the group consisting of: —(alkyl)C(═O)N(alkyl)-, —C(═O)N(alkyl)-, —C(═O)NH—, —C(═O)O—, —N(alkyl)-, —N(alkyl)C(═O)—, —N(alkyl)C(═O)NH—, —N(alkyl)C(═O)O—, —N(alkyl)$SO_2$—, —NH—, —NHC(═O)—, —NHC (=O)N(alkyl)-, —NHC(=O)NH, —NHC(=O)O—, —$NHSO_2$—, —O—, —OC(=O), —OC(=O)N(alkyl)-, —OC(=O)NH—, —OC(=O)O—, —S—, —SO—, —$SO_2$—, —$SO_2$N(alkyl)-, and —$SO_2$NH—;

$A^{20}$ is absent or selected from alkyl or alkenyl; and $A^{21}$ is selected from alkyl, alkenyl, or H;

wherein when $A^{20}$ or $A^{21}$ is alkyl or alkenyl, the alkyl or alkenyl may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy, —N(alkyl)C(=O)alkyl, —N(alkyl)C(=O)N(alkyl)$_2$, —N(alkyl)C(=O)$NH_2$, —N(alkyl)C(=O)NHalkyl, —N(alkyl)C(=O)Oalkyl, —N(alkyl)$SO_2$alkyl, —NHC(=O)alkyl, —NHC(=O)N(alkyl)$_2$, —NHC(=O)$NH_2$, —NHC(=O)NHalkyl, —NHC(=O)Oalkyl, —$NHSO_2$alkyl, —OC(=O)alkyl, —OC(=O)N(alkyl)$_2$, —OC(=O)NHalkyl, —OC(=O)Oalkyl, —$SO_2$alkyl, thio or thioalkyl;

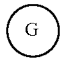

is selected from the group consisting of aryl, cycloalkyl, partially unsaturated carbocycle, heteroaryl, heterocycloalkyl, nine to ten membered benzo-fused cycloalkyl, and nine to ten membered benzo-fused heterocycloalkyl; wherein, the aryl, cycloalkyl, partially unsaturated carbocycle, heteroaryl, heterocycloalkyl, benzo-fused cycloalkyl, or benzo-fused heterocycloalkyl, are optionally substituted with one or more substituents independently selected from halogen, hydroxy, amino, thio, nitro, cyano, alkyl, halogenated alkyl, alkoxy, halogenated alkoxy, alkylamino, —NHC(=O)alkyl, —N(alkyl)C(=O)alkyl, or dialkylamino, —NHC(=O)$NH_2$, —NHC(=O)NHalkyl, —N(alkyl)C(=O)NHalkyl, —OC(=O)NHalkyl, —NHC(=O)Oalkyl, —N(alkyl)C(=O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(=O)N(alkyl)$_2$, —N(alkyl)C(=O)N(alkyl)$_2$ or —OC(=O)N(alkyl)$_2$;

s is an integer from 0 to 2;

m is an integer from 0 to 4; provided that the sum of m and s is an integer from 0 to 4;

$R^6$ and $R^7$ are independently selected from the group consisting of:

(a) H;

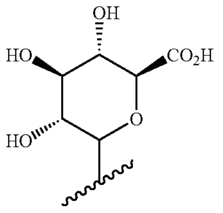

(b) provided that $R^4$ is not

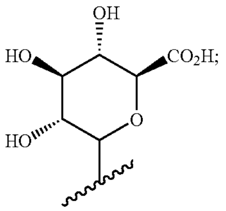

(c) —$CH_2$— substituted with one group selected from: —H, -methyl, —Oalkyl, —$CH_2$OH, —CH($CH_3$)OH, —O(C=O)alkyl, —(C=O)OH, —C(=O)Oalkyl, —C(=O)Oaryl, —C(=O)Oheteroaryl, —(C=O)$NH_2$, —(C=O)NHalkyl, —(C=O)N(alkyl)$_2$, —C(=O)alkyl, -phenyl-$OCH_3$ or -phenyl-OC(=O)alkyl;

(d) —C(=O)($CH_2CH_2$O—)$_{1-10}$ terminating with H, methyl, ethyl, or benzyl;

(e) —C(=O)$CH_2$O($CH_2CH_2$O—)$_{1-10}$ terminating with H, methyl, ethyl, or benzyl;

(f) —C(=O)alkyl, or —C(=O)($C_{3-6}$)cycloalkyl, wherein said —C(=O)alkyl, and —C(=O)($C_{3-6}$)cycloalkyl may be optionally substituted with one or more groups independently selected from: —OH, —Oalkyl, —Oalkylaryl, —$NH_2$, —NHalkyl, —N(alkyl)$_2$, heterocycloalkyl, —NHC(=O)alkyl, —$NHSO_2$alkyl, or —OC(=O)alkyl;

(g) —C(=O)($CH_2$)$_{1-3}$aryl, —C(=O)aryl, —C(=O)($CH_2$)$_{1-3}$heteroaryl, or —C(=O)heteroaryl, wherein said —C(=O)($CH_2$)$_{1-3}$aryl, —C(=O)aryl, —C(=O)($CH_2$)$_{1-3}$heteroaryl, and —C(=O)heteroaryl may be optionally substituted with one or more groups independently selected from: —OH, —Oalkyl, —$NH_2$, —NHalkyl, —N(alkyl)$_2$, heterocycloalkyl, —NHC(=O)alkyl, —$NHSO_2$alkyl, halogen, nitrile, or —OC(=O)alkyl;

(h) —C(=O)($CH_2$)$_{1-6}$C(=O)— terminating with methyl, ethyl, —OH, —Oalkyl, —$NH_2$, —NHalkyl, —N(alkyl)$_2$, or heterocycloalkyl;

(hh) —C(=O)alkylOC(=O)alkyl- terminating with —OH, —Oalkyl, —$NH_2$, —NHalkyl, —N(alkyl)$_2$, or heterocycloalkyl;

(i) —C(=O)O($CH_2CH_2$O—)$_{1-10}$ terminating with H, methyl, ethyl, or benzyl;

(j) —C(=O)Oalkyl, or —C(=O)O($C_{3-6}$)cycloalkyl, wherein said —C(=O)Oalkyl, and —C(=O)O($C_{3-6}$)cycloalkyl may be optionally substituted with one or more groups independently selected from: —OH, —Oalkyl, —$NH_2$, —NHalkyl, —N(alkyl)$_2$, heterocycloalkyl, —NHC(=O)alkyl, —$NHSO_2$alkyl, —OC(=O)alkyl, —C(O)OH, —C(=O)Oalkyl, —C(=O)$NH_2$, —C(=O)NHalkyl, or —C(=O)N(alkyl)$_2$;

(k) —C(=O)O($CH_2$)$_{1-3}$aryl, —C(=O)Oaryl, —C(=O)O($CH_2$)$_{1-3}$heteroaryl, or —C(=O)Oheteroaryl, wherein said —C(=O)O($CH_2$)$_{1-3}$aryl, —C(=O)Oaryl, —C(=O)O($CH_2$)$_{1-3}$heteroaryl, or —C(=O)Oheteroaryl may be optionally substituted with one or more groups independently selected from: —OH, —Oalkyl, —$NH_2$, —NHalkyl, —N(alkyl)$_2$, heterocycloalkyl, —NHC(=O)alkyl, —$NHSO_2$alkyl, halogen, nitrile, or —OC(=O)alkyl;

(l) —C(=O)NH($CH_2CH_2$O—)$_{1-10}$ terminating with —H, methyl, ethyl, benzyl, —$CH_2CH_2NH_2$, —$CH_2CH_2$NHalkyl, —$CH_2CH_2$N(alkyl)$_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl or —C(═O)alkyl;

(m) —C(═O)$NH_2$, —C(═O)NH($C_{1-20}$)alkyl, —C(═O)NH($C_{3-6}$)cycloalkyl, or —C(═O)N(alkyl)$_2$, wherein said —C(═O)NH($C_{1-20}$)alkyl, —C(═O)NH($C_{3-6}$)cycloalkyl, and —C(═O)N(alkyl)$_2$ may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, —OC(═O)alkyl, —OC(═O)alkenyl, —NHC(═O)aryl, —C(═O)OH, —C(═O)O-alkyl, —C(═O)$NH_2$, —C(═O)NHalkyl, or —C(═O)N(alkyl)$_2$; and, wherein the aryl portion of said —NHC(═O)aryl may be optionally substituted with one or more groups independently selected from: alkyl, —OH, —O-alkyl, —$NH_2$, —NHalkyl, —N(alkyl)$_2$, halogen or nitrile;

(n) —C(═O)NH($CH_2$)$_{1-3}$aryl, —C(═O)NHaryl, —C(═O)NH($CH_2$)$_{1-3}$heteroaryl, or —C(═O)NHheteroaryl, wherein said —C(═O)NH($CH_2$)$_{1-3}$aryl, —C(═O)NHaryl, —C(═O)NH($CH_2$)$_{1-3}$heteroaryl, and —C(═O)NHheteroaryl may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or —OC(═O)alkyl;

(o) —C(═O)$NHCH_2CH_2NH$($CH_2CH_2NH$—)$_{0-3}$ terminating with H, methyl, ethyl, —$CH_2CH_2$NHalkyl, —$CH_2CH_2$N(alkyl)$_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl, —$CH_2CH_2OH$, —$CH_2CH_2OCH_3$, —$CH_2CH_2OCH_2CH_3$, —$CH_2CH_2$OC(═O)alkyl, or —C(═O)aryl; wherein the aryl portion of said —C(═O)aryl may be optionally substituted with one or more groups independently selected from: alkyl, —OH, —O-alkyl, —$NH_2$, —NHalkyl, —N(alkyl)$_2$, halogen or nitrile;

(p) —C(═S)$NH_2$;

(q) —C(═S)NHalkyl;

(r) —C(═S)N(alkyl)$_2$;

(s) —$SO_2NH_2$;

(t) —$SO_2$NHalkyl;

(u) —$SO_2$N(alkyl)$_2$;

(v) —P(═O)($OCH_3$)$_2$; and (w) —P(═O)($OCH_2CH_3$)$_2$;

provided that when $R^6$ is present, $R^7$ is absent; and provided that when $R^7$ is present, $R^6$ is absent;

$R^4$ is selected from the group consisting of: H and

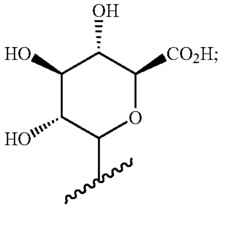

provided that if one of $R^6$ and $R^7$ is

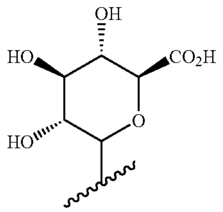

then $R^4$ is H; and $L^3$ is absent; and

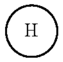

is aryl;

r is an integer from 0 to 4; and $R^5$ is independently selected from the group consisting of: alkyl, alkyl amino, alkyloxy, amino, —C(═O)$NH_2$, —C(═O)Oalkyl, —C(═O)OH, —$CH_2OH$, cyano, dialkylamino, halogen, halogenated alkyl, halogenated alkyloxy, halogenated $SO_2$-alkyl, halogenated thioalkyl, hydroxy, hydroxy alkyl, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, nitro, —OC(═O)N(alkyl)$_2$, —OC(═O)NHalkyl, —$SO_2$alkyl, —$SO_2NH_2$, thio, thioalkyl,

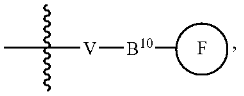

and —V—$B^{10}$—W—$B^{20}$; wherein,

V and W are each independently absent or selected from the group consisting of: —C(═O), —C(═O)N(alkyl)-, —C(═O)NH—, —C(═O)O—, —N(alkyl)-, —N(alkyl)C(═O)—, —N(alkyl)C(═O)N(alkyl)-, —N(alkyl)C(═O)NH—, —N(alkyl)C(═O)O—, —N(alkyl)$SO_2$—, —NH—, —NHC(═O)—, —NHC(═O)N(alkyl)-, —NHC(═O)NH—, —NHC(═O)O—, —$NHSO_2$—, —O—, —OC(═O), —OC(═O)N(alkyl)-, —OC(═O)NH—, —OC(═O)O—, —S—, —SO—, —$SO_2$—, —$SO_2$N(alkyl)- and —$SO_2$NH—;

$B^{10}$ is absent or selected from alkyl or alkenyl;

$B^{20}$ is absent or selected from alkyl, alkenyl, or H;

wherein, when $B^{10}$ or $B^{20}$ is alkyl or alkenyl, the alkyl or alkenyl group may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy —N(alkyl)C(═O)alkyl, —N(alkyl)C(═O)N(alkyl)$_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, —OC(═O)

alkyl, —OC(═O)N(alkyl)$_2$, —OC(═O)NHalkyl, —OC(═O)Oalkyl, —SO$_2$alkyl, thio or thioalkyl; and

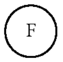

is selected from the group consisting of: aryl, a cycloalkyl, a partially unsaturated carbocycle, a heteroaryl, a heterocycloalkyl, a nine to ten membered benzo-fused cycloalkyl, and a nine to ten membered benzo-fused heterocycloalkyl, wherein, the aryl, cycloalkyl, partially unsaturated carbocycle, heteroaryl, heterocycloalkyl, benzo-fused cycloalkyl, or benzo-fused heterocycloalkyl,is optionally substituted with one or more substituents independently selected from: alkoxy, alkylamino, amino, cyano, dialkylamino, halogen, halogenated alkoxy, halogenated alkyl, halogenated —SO$_2$alkyl, halogenated thioalkyl, heteroaryl, hydroxy, hydroxy alkyl, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)SO$_2$alkyl, —NHC(═O)alkyl, —NHC(═O)N(alkyl)$_2$, —NHC(═O)NH$_2$, —NHC(═O)NHalkyl, —NHC(═O)Oalkyl, —NHSO$_2$alkyl, nitro, —OC(═O)N(alkyl)$_2$, —OC(═O)NHalkyl, —SO$_2$alkyl, thio or thioalkyl; or an optical isomer, enantiomer, diastereomer, racemate, or pharmaceutically acceptable salt thereof.

8. A compound as in claim 7 wherein:

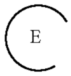

is:

(Formula A-1)

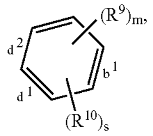

wherein Formula A-1 is attached on the b[1] side of Formula A-1 to the L$^2$ ring of formula (II); and wherein m is an integer from 0 to 4.

9. A compound as in claim 7 wherein: L$^2$ is a linking group selected from the group consisting of: —(CH$_2$)—, —(CH$_2$)$_{3-4}$—, —CH(R$^{100}$)—, —C(═R$^{100}$)—, and —C(R$^{100}$)$_2$—.

10. A compound as in claim 7 wherein: R$^9$ and R$^{10}$ are independently selected from the group consisting of: 1-piperidinyl, 2-(pyrrolidin-1-yl)-ethoxy, 2,3-dihydroxy-propoxy, 2-hydroxy-3-pyrrolidin-1-yl-propoxy, 3-(4-methyl-piperazin-1-yl)-propoxy, 3-(N,N-dimethyl-amino)-propoxy, 3-hydroxy-propoxy, 3-imidazol-1-yl-propoxy, 3-methoxy-propoxy, 3-morpholin-4-yl-propoxy, 3-pyrrolid in-1-yl-2-hydroxy-propoxy, 3-pyrrolidin-1-yl-propoxy, 4-methyl-piperazin-1-yl, amino, benzyl, benzyloxy, bromo, chloro, cyano, ethoxy, fluoro, H, hydroxy, isopropoxy, methoxy, methyl, N-(1-oxo-ethyl)-amino, and N,N-dimethyl-amino.

11. A compound as in claim 7 wherein: R$^6$ and R$^7$ are independently selected from the group consisting of:

(a) H;

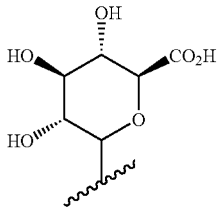

(b) provided that R$^4$ is not

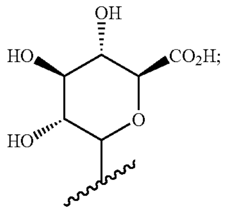

(c) —CH$_2$— substituted with one group selected from: —H, -methyl, —Oalkyl, —CH$_2$OH, —CH(CH$_3$)OH, —O(C═O)alkyl, —C(═O)Oalkyl, —(C═O)NH$_2$, —C(═O)alkyl or -phenyl-OC(═O)alkyl;

(f) —C(═O)alkyl optionally substituted with one or more groups independently selected from: —OH, —Oalkyl, —Oalkyl-phenyl or —OC(═O)alkyl;

(g) —C(═O)phenyl optionally substituted with one or more groups independently selected from: —Oalkyl, chloro or fluoro;

(h) —C(═O)(CH$_2$)$_{1-6}$C(═O)— terminating with —OH, —Oalkyl, —NH$_2$, —NHalkyl, —N(alkyl)$_2$, or pyrrolidinyl;

(hh) —C(═O)alkylOC(═O)alkyl- terminating with —Oalkyl;

(i) —C(═O)O(CH$_2$CH$_2$O—)$_{1-10}$ terminating with H or benzyl;

(j) —C(═O)Oalkyl optionally substituted with one or more —Oalkyl groups;

(k) —C(═O)Ophenyl optionally substituted with one or more chloro or fluoro groups;

(l) —C(═O)NH(CH$_2$CH$_2$O—)$_{1-10}$ terminating with —H;

(m) —C(═O)NH(C$_{1-20}$)alkyl optionally substituted with one or more groups independently selected from: —NH$_2$, —NHalkyl, —N(alkyl)$_2$, pyrrolidinyl, morpholinyl, —NHC(═O)alkyl, —OC(═O)alkenyl, —NHC(═O)phenyl or —C(═O)Oalkyl; and, wherein the phenyl portion of said —NHC(═O)phenyl may be optionally substituted with one or more groups independently selected from: alkyl, —OH, —Oalkyl, —NH$_2$, —NHalkyl, —N(alkyl)$_2$, halogen and nitrile;

(n) —C(═O)NHphenyl optionally substituted with one or more fluoro groups;

(o) —C(═O)NHCH$_2$CH$_2$NH(CH$_2$CH$_2$NH—)$_{0-3}$ terminating with —CH$_2$CH$_2$OH and —C(═O)phenyl; wherein the phenyl portion of said —C(═O)phenyl may be optionally substituted with one or more —OH groups;

(p) —C(═S)NH$_2$;

(u) —SO$_2$N(alkyl)$_2$; and (w) —P(═O)(OCH$_2$CH$_3$)$_2$;

provided that when $R^6$ is present, $R^7$ is absent; and provided that when $R^7$ is present, $R^6$ is absent.

12. A compound as in claim 7 wherein: $R^6$ and $R^7$ are independently selected from the group consisting of: H,

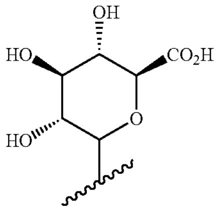

provided that $R^4$ is not

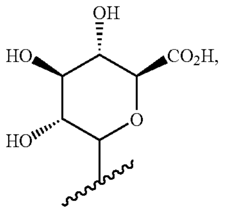

1-methoxy-1-oxo-ethyl, 1-methyl-ethoxy-carbonyl, 1-oxo-butoxy-methyl, 1-oxo-ethoxy-methyl, 1-oxo-ethyl, 1-oxo-propyl, 2-(1-oxo-ethoxy)-1-oxo-ethyl, 2-(2-methoxy-1-oxo-ethoxy)-1-oxo-ethyl, 2-(2-methyl-1-oxo-propoxy)-1-oxo-ethyl, 2-amino-2-oxo-ethyl, 2,2-dimethyl-1-oxo-propoxy-methyl, 2-ethoxy2-oxo-ethyl, 2-methoxy-2-oxo-ethyl, 2,6-difluoro-benzoyl, 2-[2-(2-hydroxy-ethoxy)-ethoxy]-ethoxy-carbonyl, 2-benzyloxy-1-oxo-ethyl, 2-benzyloxy-ethoxy-carbonyl, 2-chloro-phenoxy-carbonyl, 2-fluoro-benzoyl, 2-hydroxy-1-oxo-ethyl, 2-hydroxy-ethyl, 2-hydroxy-propyl, 2-methoxy-1-oxo-ethyl, 2-methoxy-ethoxy-carbonyl, 2-methyl-1-oxo-propyl, 2-oxo-propyl, 3-(N,N-diethyl amino)-1,3-dioxo-propyl, 3-1H-pyrrolid in-1-yl-1,3-dioxo-propyl, 3-ethoxy-1,3-dioxo-propyl, 3-1H-pyrrolidin-1-yl-1,3-dioxo-propyl, 4-(1-oxo-ethoxy)-benzyl, 4-amino-1,4-dioxo-n-butyl, 4-ethoxy-1,4-dioxo-n-butyl, 4-hydroxy-1,4-dioxo-n-butyl, 4-methoxy-1,4-dioxo-n-butyl, 4-chloro-benzoyl, 4-chloro-phenoxy-carbonyl, 4-fluoro-benzoyl, 4-fluoro-phenoxy-carbonyl, 4-methoxy-benzoyl, 5-(N-methyl-amino)-1,5-dioxo-pentyl, 5-methoxy-1,5-dioxo-pentyl, benzoyl, diethoxy-phosphinyl, ethoxy-carbonyl, methoxy-carbonyl, methoxy-methyl, methyl, N-(2-ethoxy-2-oxo-ethyl)-amino-carbonyl, N-(2-1H-pyrrolidin-1-yl-ethyl)-amino-carbonyl, N-(2-amino-ethyl)-amino-carbonyl, N-(2-morpholin-4-yl-ethyl)-amino-carbonyl, N-(3-ethoxy-3-oxo-propyl )-amino-carbonyl, N-(3-fluoro-phenyl )-amino-carbonyl, N-(pentadecyl)-amino-carbonyl, N,N-dimethyl-amino-sulfonyl, N-[2-(2-methenyl-1-oxo-propoxy)-ethyl]-amino-carbonyl, N-[2-(3-methyl-1-methoxy-1-oxo)-n-butyl]-amino-carbonyl, N-[2-(4-methyl-1-methoxy-1-oxo)-pentyl]-amino-carbonyl, N-[2-(N,N-dimethyl-amino)-ethyl]-amino-carbonyl, N-[2-(N-benzoyl-amino)-ethyl]-amino-carbonyl, N-[2-(N-methyl-amino)-ethyl]-amino-carbonyl, N-[2-[2-(2-hydroxy-ethoxy)-ethoxy]-ethyl]-amino-carbonyl, N-[2-[N-(1-oxo-ethyl)-amino]-ethyl]-amino-carbonyl, N-[2-[N-(2-hydroxy-benzoyl)-amino]-ethyl]-amino-carbonyl, N-[2-[N-(2-hydroxy-ethyl)-amino]-ethyl]-amino-carbonyl, N-[2-[N-(2-methyl-1-oxo-propyl)-amino]-ethyl]-amino-carbonyl, N-methyl-amino-carbonyl, N-methyl-amino-thiocarbonyl, and phenoxy-carbonyl, provided that when $R^6$ is present, $R^7$ is absent; and provided that when $R^7$ is present, $R^6$ is absent.

13. A compound as in claim 8 wherein:

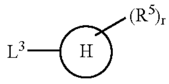

is selected from the group consisting of: 2,3-dichloro-phenyl; 2,4,6-trifluoro-phenyl; 2,4-dichloro-phenyl; 2,4-dimethoxy-phenyl; 2,4-dimethoxy-phenyl; 2,5-dichloro-phenyl; 2,5-difluoro-phenyl; 2,5-dimethoxy-phenyl; 2,6-difluoro-phenyl; 2-bromo-3-fluoro-phenyl; 2-bromo-phenyl; 2-chloro-phenyl; 2-ethyl-phenyl; 2-isopropyl-phenyl; 2-methoxy-phenyl; 2-methyl-phenyl; 2-trifluoromethoxy-phenyl; 2-trifluoromethyl-4-bromo-phenyl; 2-trifluoromethyl-phenyl; 3-(1-hydroxy-ethyl)-phenyl; 3-(2-hydroxy-ethyl-amino-carbonyl)-phenyl; 3-(4-methyl-piperazinyl-carbonyl)-phenyl; 3-(amino-carbonyl)-phenyl; 3-(amino-sulfonyl)-phenyl; 3-(ethoxy-carbonyl)-phenyl; 3-(methoxy-carbonyl)-phenyl; 3-(trifluoromethyl-thio)-phenyl; 3,4,5-trimethoxy-phenyl; 3,4-dichloro-phenyl; 3,4-dimethoxy-phenyl; 3,4-methylenedioxy-phenyl; 3,5-di(tert-butyl)-phenyl; 3,5-di (trifluoromethyl)-phenyl; 3,5-dichloro-phenyl; 3,5-difluoro-phenyl; 3,5-dimethoxy-phenyl; 3,5-dimethyl-phenyl; 3-[N-(3-pyrrolid in-1-yl-propyl)-amino-carbonyl]-phenyl; 3-benzyloxy-phenyl; 3-bromo-phenyl; 3-carboxy-phenyl; 3-chloro-4-fluoro-phenyl; 3-chloro-4-methoxy-phenyl; 3-chloro-phenyl; 3-cyano-phenyl; 3-methoxy-phenyl; 3-ethoxy-phenyl; 3-ethyl-phenyl; 3-fluoro-phenyl; 3-hydroxymethyl-phenyl; 3-hydroxy-phenyl; 3-isopropoxy-phenyl; 3-methoxy-5-trifluoromethyl-phenyl; 3-methyl-phenyl; 3-methylthio-phenyl; 3-trifluoromethoxy-phenyl; 3-trifluoromethyl-phenyl; 4-(4-methyl-piperazin-1-yl)-phenyl; 4-(ethoxy-carbonyl)-phenyl; 4-(N,N-dimethyl-amino)-phenyl; 4-(piperidin-4-yl-sulfonyl)-phenyl; 4-benzyloxy-phenyl; 4-bromo-phenyl; 4-chloro-phenyl; 4-cyano-phenyl; 4-dimethylamino-phenyl; 4-fluoro-3-chloro-phenyl; 4-fluoro-3-nitro-phenyl; 4-fluoro-3-trifluoromethyl-phenyl; 4-fluoro-phenyl; 4-methyl-3-[N-[4-(3-pyridyl)-pyrimidin-2-yl]amino]-phenyl; 4-methyl-phenyl; 4-trifluoromethoxy-phenyl;

4-trifluoromethyl-phenyl; 5-bromo-2,3-dihydro-1H-indol-1-yl; 5-chloro-2-methoxy-phenyl; 5-chloro-2-methyl-phenyl; 5-trifluoromethyl-2-fluoro-phenyl; and phenyl.

14. A compound of Formula (II-AA):

(II-AA)

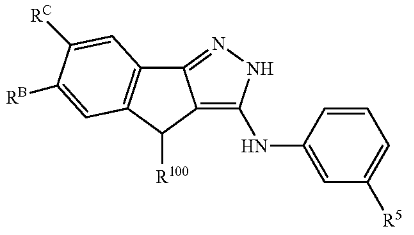

wherein:

$R^{100}$ is selected from the group consisting of: H and alkyl;

$R^B$ and $R^C$ are independently selected from the group consisting of: alkoxy; and $R^5$ is selected from the group consisting of: alkoxy and halogen;

or an optical isomer, enantiomer, diastereomer, racemate, or pharmaceutically acceptable salt thereof.

15. A compound as in claim 14, wherein $R_{100}$ is selected from the group consisting of: H, methyl, and ethyl; $R^B$ and $R^C$ are independently selected from the group consisting of: methoxy and ethoxy; and $R^5$ is selected from the group consisting of: methoxy, ethoxy, isopropoxy, chloro, bromo, and fluoro.

16. A compound of Formula (II-BB):

(II-BB)

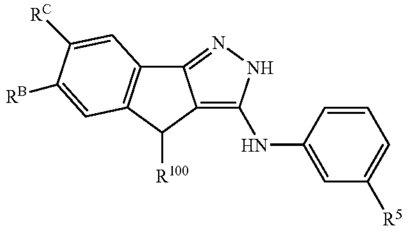

wherein $R^C$ is $—O(CH_2)_3OH$;

$R^{100}$ is selected from the group consisting of: H and alkyl;

$R^B$ is selected from the group consisting of: alkoxy; and $R^5$ is selected from the group consisting of: alkoxy and halogen;

or an optical isomer, enantiomer, diastereomer, racemate, or pharmaceutically acceptable salt thereof.

17. A compound as in claim 16, wherein $R^{100}$ is selected from the group consisting of: H, methyl, and ethyl; $R^B$ is selected from the group consisting of: methoxy and ethoxy; and $R^5$ is selected from the group consisting of: methoxy, ethoxy, isopropoxy, chloro, bromo, and fluoro.

18. A compound of Formula (II-FF)

(II-FF)

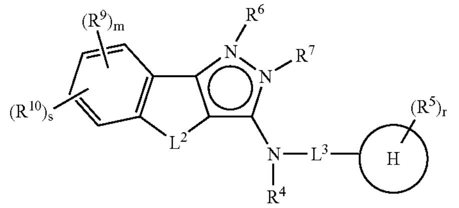

wherein $R^9$ is independently selected from the group consisting of: alkoxy, alkyl, alkylamino, amino, cyano, dialkylamino, halogen, halogenated alkyl, halogenated alkyloxy, halogenated $—SO_2$alkyl, halogenated thioalkyl, hydroxy, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)SO$_2$alkyl, —NHC(═O)alkyl, —NHC(═O)N(alkyl)$_2$, —NHC(═O)NH$_2$, —NHC(═O)NHalkyl, —NHC(═O)Oalkyl, —NHSO$_2$alkyl, nitro, —OC(═O)N(alkyl)$_2$, —OC(═O)NHalkyl, —SO$_2$alkyl, thio and thioalkyl;

$L^2$ is a linking group selected from the group consisting of: $—(CH_2)_{1-4}—$, $—CH(R^{100})—$, $—C(═R^{100})—$, $—C(R^{100})_2—$; wherein $R^{100}$ is selected from: alkyl, hydroxy, aryl, alkoxy, oxo, $—NH_2$, —NH(alkyl) —N(alkyl)$_2$, =N(OH) or $—NH_2OH$; provided that when $L^2$ is $—CH_2CH_2—$, neither $R^6$ nor $R^7$ is $—CH_2—$(C═O)NHalkyl, $—CH_2—$(C═O)N(alkyl)$_2$ or $—CH_2C$(═O)Oalkyl;

$R^{10}$ is independently selected from the group consisting of

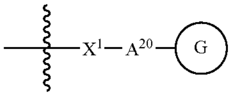

and $—X^1A^{20}Y^1A^{21}$;

wherein $X^1$ and $Y^1$ are each independently absent or selected from the group consisting of: -(alkyl)C(═O)N(alkyl)-, —C(═O)N(alkyl)-, —C(═O)NH—, —C(═O)O—, —N(alkyl)-, —N(alkyl)C(═O)—, —N(alkyl)C(═O)NH—, —N(alkyl)C(═O)O—, —N(alkyl)SO$_2$—, —NH—, —NHC(═O)—, —NHC(═O)N(alkyl)-, —NHC(═O)NH, —NHC(═O)O—, —NHSO$_2$—, —O—, —OC(═O), —OC(═O)N(alkyl)-, —OC(═O)NH—, —OC(═O)O—, —S—, —SO—, —SO$_2$—, —SO$_2$N(alkyl)-, and —SO$_2$NH—;

$A^{20}$ is absent or selected from alkyl or alkenyl; and $A^{21}$ is selected from alkyl, alkenyl, or H;

wherein when $A^{20}$ or $A^{21}$ is alkyl or alkenyl, the alkyl or alkenyl may be optionally substituted with one or more groups independently selected from: alkoxy, alkylamino, amino, cyano, dialkylamino, halogen, halogenated alkoxy, halogenated —SO$_2$alkyl, halogenated thioalkyl, hydroxy, —N(alkyl)C(═O)alkyl, —N(alkyl)C(═O)N(alkyl)$_2$, —N(alkyl)C(═O)NH$_2$, —N(alkyl)C(═O)NHalkyl, —N(alkyl)C(═O)Oalkyl, —N(alkyl)SO$_2$alkyl, —NHC(═O)alkyl, —NHC(═O)N(alkyl)$_2$, —NHC(═O)NH$_2$, —NHC(═O)NHalkyl, —NHC(═O)Oalkyl, —NHSO$_2$alkyl, —OC(═O)alkyl, —OC(═O)N(alkyl)$_2$, —OC(═O)NHalkyl, —OC(═O)Oalkyl, —SO$_2$alkyl, thio or thioalkyl;

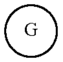

is selected from the group consisting of aryl, cycloalkyl, partially unsaturated carbocycle, heteroaryl, heterocycloalkyl, nine to ten membered benzo-fused cycloalkyl, and nine to ten membered benzo-fused heterocycloalkyl; wherein, the aryl, cycloalkyl, partially unsaturated carbocycle, heteroaryl, heterocycloalkyl, benzo-fused cycloalkyl, or benzo-fused heterocycloalkyl, are optionally substituted with one or more substituents independently selected from halogen, hydroxy, amino, thio, nitro, cyano, alkyl, halogenated alkyl, alkoxy, halogenated alkoxy, alkylamino, —NHC(═O)alkyl, —N(alkyl)C(═O)alkyl, or dialkylamino, —NHC(═O)$NH_2$, —NHC(═O)NHalkyl, —N(alkyl)C(═O)NHalkyl, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)N(alkyl)$_2$, —N(alkyl)C(═O)N(alkyl)$_2$ or —OC(═O)N(alkyl)$_2$;

s is an integer from 0 to 2;

m is an integer from 0 to 4; provided that the sum of m and s is an integer from 0 to 4;

$R^6$ and $R^7$ are independently selected from the group consisting of:

(a) H;

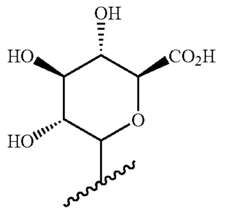

(b) provided that $R^4$ is not

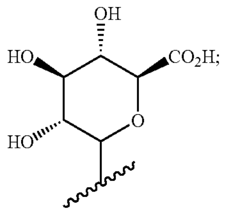

(c) —$CH_2$— substituted with one group selected from: —H, -methyl, —Oalkyl, —$CH_2$OH, —CH($CH_3$)OH, —O(C═O)alkyl, —(C═O)OH, —C(═O)Oalkyl, —C(═O)Oaryl, —C(═O)Oheteroaryl, —(C═O)$NH_2$, —(C═O)NHalkyl, —(C═O)N(alkyl)$_2$, —C(═O)alkyl, -phenyl-$OCH_3$ or -phenyl-OC(═O)alkyl;

(d) —C(═O)($CH_2CH_2O$—)$_{1-10}$ terminating with H, methyl, ethyl, or benzyl;

(e) —C(═O)$CH_2O$($CH_2CH_2O$—)$_{1-10}$ terminating with H, methyl, ethyl, or benzyl;

(f) —C(═O)alkyl, or —C(═O)($C_{3-6}$)cycloalkyl, wherein said —C(═O)alkyl, and —C(═O)($C_{3-6}$)cycloalkyl may be optionally substituted with one or more groups independently selected from: —OH, —Oalkyl, —Oalkylaryl, —$NH_2$, —NHalkyl, —N(alkyl)$_2$, heterocycloalkyl, —NHC(═O)alkyl, —$NHSO_2$alkyl, or —OC(═O)alkyl;

(g) —C(═O)($CH_2$)$_{1-3}$aryl, —C(═O)aryl, —C(═O)($CH_2$)$_{1-3}$heteroaryl, or —C(═O)heteroaryl, wherein said —C(═O)($CH_2$)$_{1-3}$aryl, —C(═O)aryl, —C(═O)($CH_2$)$_{1-3}$heteroaryl, and —C(═O)heteroaryl may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or —OC(═O)alkyl;

(h) —C(═O)($CH_2$)$_{1-6}$C(═O)— terminating with methyl, ethyl, —OH, —Oalkyl, —$NH_2$, —NHalkyl, —N(alkyl)$_2$, or heterocycloalkyl;

(hh) —C(═O)alkylOC(═O)alkyl- terminating with —OH, —Oalkyl, —$NH_2$, —NHalkyl, —N(alkyl)$_2$, or heterocycloalkyl;

(i) —C(═O)O($CH_2CH_2O$—)$_{1-10}$ terminating with H, methyl, ethyl, or benzyl;

(j) —C(═O)Oalkyl, or —C(═O)O($C_{3-6}$)cycloalkyl, wherein said —C(═O)Oalkyl, and —C(═O)O($C_{3-6}$)cycloalkyl may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, —OC(═O)alkyl, —C(O)OH, —C(═O)Oalkyl, —C(═O)$NH_2$, —C(═O)NHalkyl, or —C(═O)N(alkyl)$_2$;

(k) —C(═O)O($CH_2$)$_{1-3}$aryl, —C(═O)Oaryl, —C(═O)O($CH_2$)$_{1-3}$heteroaryl, or —C(═O)Oheteroaryl, wherein said —C(═O)O($CH_2$)$_{1-3}$aryl, —C(═O)Oaryl, —C(═O)O($CH_2$)$_{1-3}$heteroaryl, or —C(═O)Oheteroaryl may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or —OC(═O)alkyl;

(l) —C(═O)NH($CH_2CH_2O$—)$_{1-10}$ terminating with —H, methyl, ethyl, benzyl, —$CH_2CH_2NH_2$, —$CH_2CH_2$NHalkyl, —$CH_2CH_2$N(alkyl)$_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl or —C(═O)alkyl;

(m) —C(═O)$NH_2$, —C(═O)NH($C_{1-20}$)alkyl, —C(═O)NH($C_{3-6}$)cycloalkyl, or —C(═O)N(alkyl)$_2$, wherein said —C(═O)NH($C_{1-20}$)alkyl, —C(═O)NH($C_{3-6}$)cycloalkyl, and —C(═O)N(alkyl)$_2$ may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, —OC(═O)alkyl, —OC(═O)alkenyl, —NHC(═O)aryl, —C(═O)OH, —C(═O)Oalkyl, —C(═O)$NH_2$, —C(═O)NHalkyl, or —C(═O)N(alkyl)$_2$; and, wherein the aryl portion of said —NHC(═O)aryl may be optionally substituted with one or more groups independently selected from: alkyl, —OH, —Oalkyl, —$NH_2$, —NHalkyl, —N(alkyl)$_2$, halogen or nitrile;

(n) —C(═O)NH($CH_2$)$_{1-3}$aryl, —C(═O)NHaryl, —C(═O)NH($CH_2$)$_{1-3}$heteroaryl, or —C(═O)NHheteroaryl, wherein said —C(═O)NH($CH_2$)$_{1-3}$aryl, —C(═O)NHaryl, —C(═O)NH($CH_2$)$_{1-3}$heteroaryl, and —C(═O)NHheteroaryl may be optionally substituted with one or more groups independently selected from: —OH, —Oalkyl, —$NH_2$, —NHalkyl, —$N(alkyl)_2$, heterocycloalkyl, —NHC(=O)alkyl, —$NHSO_2$alkyl, halogen, nitrile, or —OC(=O)alkyl;

(o) —C(=O)$NHCH_2CH_2NH(CH_2CH_2NH—)_{0-3}$ terminating with H, methyl, ethyl, —$CH_2CH_2$NHalkyl, —$CH_2CH_2N(alkyl)_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl, —$CH_2CH_2OH$, —$CH_2CH_2OCH_3$, —$CH_2CH_2OCH_2CH_3$, —$CH_2CH_2$OC(=O)alkyl, or —C(=O)aryl; wherein the aryl portion of said —C(=O)aryl may be optionally substituted with one or more groups independently selected from: alkyl, —OH, —Oalkyl, —$NH_2$, —NHalkyl, —$N(alkyl)_2$, halogen or nitrile;

(p) —C(=S)$NH_2$;

(q) —C(=S)NHalkyl;

(r) —C(=S)$N(alkyl)_2$;

(s) —$SO_2NH_2$;

(t) —$SO_2$NHalkyl;

(u) —$SO_2N(alkyl)_2$;

(v) —P(=O)$(OCH_3)_2$; and (w) —P(=O)$(OCH_2CH_3)_2$;

provided that when $R^6$ is present, $R^7$ is absent; and provided that when $R^7$ is present, $R^6$ is absent;

$R^4$ is selected from the group consisting of: H and

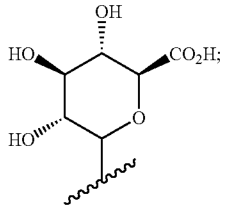

provided that if one of $R^6$ and $R^7$ is

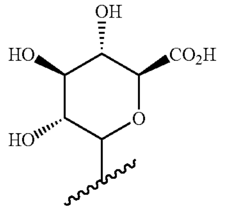

then $R^4$ is H; and $L^3$ is absent;

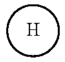

is aryl;

r is an integer from 0 to 4; and $R^5$ is independently selected from the group consisting of: alkyl, alkyl amino, alkyloxy, amino, —C(=O)$NH_2$, —C(=O)Oalkyl, —C(=O)OH, —$CH_2OH$, cyano, dialkylamino, halogen, halogenated alkyl, halogenated alkyloxy, halogenated $SO_2$-alkyl, halogenated thioalkyl, hydroxy, hydroxy alkyl, —N(alkyl)C(=O)alkyl, —N(alkyl)C(=O)$N(alkyl)_2$, —N(alkyl)C(=O)NHalkyl, —N(alkyl)C(=O)Oalkyl, —N(alkyl)$SO_2$alkyl, —NHC(=O)alkyl, —NHC(=O)$N(alkyl)_2$, —NHC(=O)$NH_2$, —NHC(=O)NHalkyl, —NHC(=O)Oalkyl, —$NHSO_2$alkyl, nitro, —OC(=O)$N(alkyl)_2$, —OC(=O)NHalkyl, —$SO_2$alkyl, —$SO_2NH_2$, thio, thioalkyl,

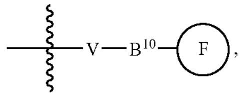

and —V—$B^{10}$—W—$B^{20}$; wherein,

V and W are each independently absent or selected from the group consisting of: —C(=O), —C(=O)N(alkyl)-, —C(=O)NH—, —C(=O)O—, —N(alkyl)-, —N(alkyl)C(=O)—, —N(alkyl)C(=O)N(alkyl)-, —N(alkyl)C(=O)NH—, —N(alkyl)C(=O)O—, —N(alkyl)$SO_2$—, —NH—, —NHC(=O)—, —NHC(=O)N(alkyl)-, —NHC(=O)NH—, —NHC(=O)O—, —$NHSO_2$—, —O—, —OC(=O), —OC(=O)N(alkyl)-, —OC(=O)NH—, —OC(=O)O—, —S—, —SO—, —$SO_2$—, —$SO_2$N(alkyl)- and —$SO_2NH$—;

$B^{10}$ is absent or selected from alkyl or alkenyl;

$B^{20}$ is absent or selected from alkyl, alkenyl, or H;

wherein, when $B^{10}$ or $B^{20}$ is alkyl or alkenyl, the alkyl or alkenyl group may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy —N(alkyl)C(=O)alkyl, —N(alkyl)C(=O)$N(alkyl)_2$, —N(alkyl)C(=O)$NH_2$, —N(alkyl)C(=O)NHalkyl, —N(alkyl)C(=O)Oalkyl, —N(alkyl)$SO_2$alkyl, —NHC(=O)alkyl, —NHC(=O)$N(alkyl)_2$, —NHC(=O)$NH_2$, —NHC(=O)NHalkyl, —NHC(=O)Oalkyl, —$NHSO_2$alkyl, —OC(=O)alkyl, —OC(=O)$N(alkyl)_2$, —OC(=O)NHalkyl, —OC(=O)Oalkyl, —$SO_2$alkyl, thio or thioalkyl; and

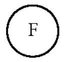

is selected from the group consisting of: an aryl, a cycloalkyl, a partially unsaturated carbocycle, a heteroaryl, a heterocycloalkyl, a nine to ten membered benzo-fused cycloalkyl, and a nine to ten membered benzo-fused heterocycloalkyl, wherein, the aryl, cycloalkyl, partially unsaturated carbocycle, heteroaryl, heterocycloalkyl, benzo-fused cycloalkyl, or benzo-fused heterocycloalkyl, is optionally substituted with one or more substituents independently selected from: alkoxy, alkylamino, amino, cyano, dialkylamino, halogen, halogenated alkoxy, halogenated alkyl, halogenated —$SO_2$alkyl, halogenated thioalkyl, heteroaryl, hydroxy, hydroxy alkyl, —N(alkyl)C(=O)alkyl, —N(alkyl)C(=O)$N(alkyl)_2$, —N(alkyl)C(=O)NHalkyl, —N(alkyl)C(=O)Oalkyl, —N(alkyl)$SO_2$alkyl, —NHC(=O)alkyl, —NHC(=O)$N(alkyl)_2$, —NHC(=O)$NH_2$, —NHC(=O)NHalkyl, —NHC(=O)Oalkyl, —$NHSO_2$alkyl, nitro, —OC(=O)$N(alkyl)_2$, —OC(=O)NHalkyl, —$SO_2$alkyl, thio or thioalkyl;

or an optical isomer, enantiomer, diastereomer, racemate, or pharmaceutically acceptable salt thereof.

19. A compound of Formula (II-GG):

(II-GG)

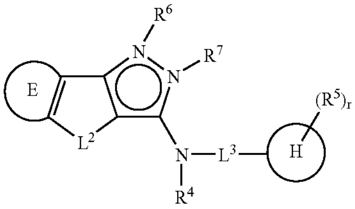

wherein:

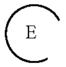

is Formulae A-1:

(Formula A-1)

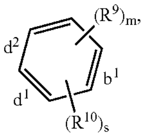

wherein Formula A-1is attached on the $b^1$ side of Formula A-1to the $L^2$ ring of Formula (II-GG);

$R^9$ is independently selected from the group consisting of: alkoxy, alkyl, alkylamino, amino, cyano, dialkylamino, halogen, halogenated alkyl, halogenated alkyloxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, nitro, —OC(═O)N(alkyl)$_2$, —OC(═O)NHalkyl, —$SO_2$alkyl, thio and thioalkyl;

$L^2$ is a linking group selected from the group consisting of: —$(CH_2)_{1-4}$—, —CH($R^{100}$)—, —C(═$R^{100}$)—, —C($R^{100}$)2—; wherein $R^{100}$ is selected from: alkyl, hydroxy, aryl, alkoxy, oxo, —$NH_2$, —NH(alkyl) —N(alkyl)$_2$, ═N(OH) or —$NH_2$OH;

$R^{10}$ is independently selected from the group consisting of

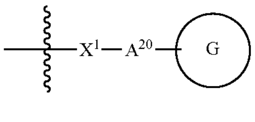

and —$X^1$-$A^{20}$-$Y^1$-$A^{21}$;

wherein $X^1$ and $Y^1$ are each independently absent or selected from the group consisting of: -(alkyl)C(═O)N(alkyl)-, —C(═O)N(alkyl)-, —C(═O)NH—, —C(═O)O—, —N(alkyl)-, —N(alkyl)C(═O)—, —N(alkyl)C(═O)NH—, —N(alkyl)C(═O)O—, —N(alkyl)$SO_2$—, —NH—, —NHC(═O)—, —NHC(═O)N(alkyl)-, —NHC(═O)NH, —NHC(═O)O—, —$NHSO_2$—, —O—, —OC(═O), —OC(═O)N(alkyl)-, —OC(═O)NH—, —OC(═O)O—, —S—, —SO—, —$SO_2$—, —$SO_2$N(alkyl)-, and —$SO_2$NH—;

$A^{20}$ is absent or selected from alkyl or alkenyl; and $A^{21}$ is selected from alkyl, alkenyl, or H;

wherein when $A^{20}$ or $A^{21}$ is alkyl or alkenyl, the alkyl or alkenyl may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy, —N(alkyl)C(═O)alkyl, —N(alkyl)C(═O)N(alkyl)$_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N(alkyl)$_2$, —NHC(═O)$NH_2$, —NHC(═O)NHalkyl, —NHC(═O)Oalkyl, —$NHSO_2$alkyl, —OC(═O)alkyl, —OC(═O)N(alkyl)$_2$, —OC(═O)NHalkyl, —OC(═O)Oalkyl, —$SO_2$alkyl, thio or thioalkyl;

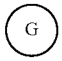

is selected from the group consisting of aryl, cycloalkyl, partially unsaturated carbocycle, heteroaryl, heterocycloalkyl, nine to ten membered benzo-fused cycloalkyl, and nine to ten membered benzo-fused heterocycloalkyl; wherein, the aryl, cycloalkyl, partially unsaturated carbocycle, heteroaryl, heterocycloalkyl, benzo-fused cycloalkyl, or benzo-fused heterocycloalkyl, are optionally substituted with one or more substituents independently selected from halogen, hydroxy, amino, thio, nitro, cyano, alkyl, halogenated alkyl, alkoxy, halogenated alkoxy, alkylamino, —NHC(═O)alkyl, —N(alkyl)C(═O)alkyl, or dialkylamino, —NHC(═O)$NH_2$, —NHC(═O)NHalkyl, —N(alkyl)C(═O)NHalkyl, —OC(═O)NHalkyl, —NHC(═O)Oalkyl, —N(alkyl)C(═O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(═O)N(alkyl)$_2$, —N(alkyl)C(═O)N(alkyl)$_2$ or —OC(═O)N(alkyl)$_2$;

s is an integer from 0 to 2;

m is an integer from 0 to 4; provided that the sum of m and s is an integer from 0 to 4;

$R^6$ and $R^7$ are independently selected from the group consisting of:

(a) H;

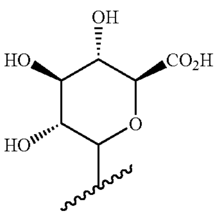

(b) provided that $R^4$ is not

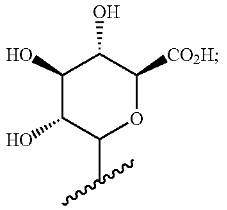

(c) alkyl (d) —C(═O)alkylOH; and (e) —C(═O)$CH_2$Oalkoxy;

provided that when $R^6$ is present, $R^7$ is absent; and provided that when $R^7$ is present, $R^6$ is absent;

$R^4$ is selected from the group consisting of: H and

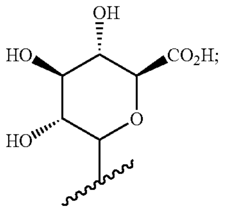

provided that if one of $R^6$ and $R^7$ is

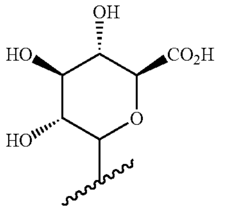

then $R^4$ is H;

$L^3$ is absent;

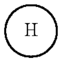

is aryl;

r is an integer from 0 to 4; and $R^5$ is independently selected from the group consisting of: alkyl, alkyl amino, alkyloxy, amino, —C(═O)$NH_2$, —C(═O)Oalkyl, —C(═O)OH, —$CH_2$OH, cyano, dialkylamino, halogen, halogenated alkyl, halogenated alkyloxy, halogenated $SO_2$-alkyl, halogenated thioalkyl, hydroxy, hydroxy alkyl, —N(alkyl)C(═O)alkyl, —N(alkyl)C(═O)N$(alkyl)_2$, —N(alkyl)C(═O)NHalkyl, —N(alkyl)C(═O)Oalkyl, —N(alkyl)$SO_2$alkyl, —NHC(═O)alkyl, —NHC(═O)N$(alkyl)_2$, —NHC(═O)$NH_2$, —NHC(═O)NHalkyl, —NHC(═O)Oalkyl, —$NHSO_2$alkyl, nitro, —OC(═O)N$(alkyl)_2$, —OC(═O)NHalkyl, —$SO_2$alkyl, —$SO_2NH_2$, thio, thioalkyl,

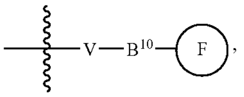

and —V—$B^{10}$—W—$B^{20}$; wherein,

V and W are each independently absent or selected from the group consisting of: —C(═O), —C(═O)N(alkyl)-, —C(═O)NH—, —C(═O)O—, —N(alkyl)-, —N(alkyl)C(═O)—, —N(alkyl)C(═O)N(alkyl)-, —N(alkyl)C(═O)NH—, —N(alkyl)C(═O)O—, —N(alkyl)$SO_2$—, —NH—, —NHC(═O)—, —NHC(═O)N(alkyl)-, —NHC(═O)NH—, —NHC(═O)O—, —$NHSO_2$—, —O—, —OC(═O), —OC(═O)N(alkyl)-, —OC(═O)NH—, —OC(═O)O—, —S—, —SO—, —$SO_2$—, —$SO_2$N(alkyl)- and —$SO_2$NH—;

$B^{10}$ is absent or selected from alkyl or alkenyl;

$B^{20}$ is absent or selected from alkyl, alkenyl, or H;

wherein, when $B^{10}$ or $B^{20}$ is alkyl or alkenyl, the alkyl or alkenyl group may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy —N(alkyl)C(═O)alkyl, —N(alkyl)C(═O)N$(alkyl)_2$, —N(alkyl)C(═O)$NH_2$, —N(alkyl)C(═O)NHalkyl, —N(alkyl)C(═O)Oalkyl, —N(alkyl)$SO_2$alkyl, —NHC(═O)alkyl, —NHC(═O)N$(alkyl)_2$, —NHC(═O)$NH_2$, —NHC(═O)NHalkyl, —NHC(═O)Oalkyl, —$NHSO_2$alkyl, —OC(═O)alkyl, —OC(═O)N$(alkyl)_2$, —OC(═O)NHalkyl, —OC(═O)Oalkyl, —$SO_2$alkyl, thio or thioalkyl; and

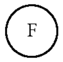

is selected from the group consisting of: an aryl, a cycloalkyl, a partially unsaturated carbocycle, a heteroaryl, a heterocycloalkyl, a nine to ten membered benzo-fused cycloalkyl, and a nine to ten membered benzo-fused heterocycloalkyl, wherein, the aryl, cycloalkyl, partially unsaturated carbocycle, heteroaryl, heterocycloalkyl, benzo-fused cycloalkyl, or benzo-fused heterocycloalkyl, is optionally substituted with one or more substituents independently selected from: alkoxy, alkylamino, amino, cyano, dialkylamino, halogen, halogenated alkoxy, halogenated alkyl, halogenated —$SO_2$alkyl, halogenated thioalkyl, heteroaryl, hydroxy, hydroxy alkyl, —N(alkyl)C(═O)alkyl, —N(alkyl)C(═O)N$(alkyl)_2$, —N(alkyl)C(═O)NHalkyl, —N(alkyl)C(═O)Oalkyl, —N(alkyl)$SO_2$alkyl, —NHC(═O)alkyl, —NHC(═O)N$(alkyl)_2$, —NHC(═O)$NH_2$, —NHC(═O)NHalkyl, —NHC(═O)Oalkyl, —$NHSO_2$alkyl, nitro, —OC(═O)N$(alkyl)_2$, —OC(═O)NHalkyl, —$SO_2$alkyl, thio or thioalkyl;

or an optical isomer, enantiomer, diastereomer, racemate, or pharmaceutically acceptable salt thereof.

20. A compound as in claim 19, wherein $R^7$ is absent, and $R^6$ is selected from the group consisting of:

(a) H;

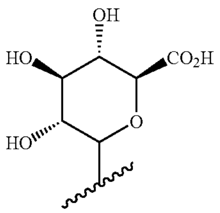

(b) provided that $R^4$ is not

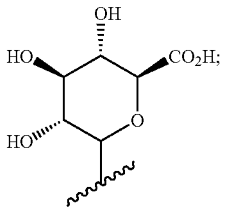

(c) methyl (d) —C(0)$CH_2OH$; and (e) —C(=O)$CH_2$Omethoxy.

21. A compound as in claim 20 wherein $R^6$ is methyl.

22. A compound as in claim 21 wherein $R^5$ is alkyloxy or halo; $R^9$ is alkoxy; and $R^{10}$ is —$X^1$-$A^{20}$-$Y^1$-$A^{21}$, wherein $X^1$ and $Y^1$ are —O— and $A^{20}$ is alkyl and $A^{21}$ is H.

23. A compound of Formula (II-HH):

(II-HH)

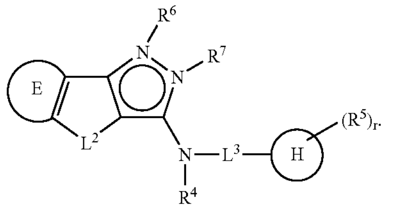

wherein:

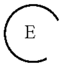

is Formula A-1:

(Formula A-1)

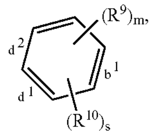

wherein Formula A-1is attached on the $b^1$ side of Formula A-1 to the $L^2$ ring of formula (II-HH);

$R^9$ is independently selected from the group consisting of: alkoxy, alkyl, alkylamino, amino, cyano, dialkylamino, halogen, halogenated alkyl, halogenated alkyloxy, halogenated —$SO_2$alkyl, halogenated thioalkyl, hydroxy, —N(alkyl)C(=O)alkyl, —N(alkyl)C(=O)N(alkyl)$_2$, —N(alkyl)C(=O)NHalkyl, —N(alkyl)C(=O)Oalkyl, —N(alkyl)$SO_2$alkyl, —NHC(=O)alkyl, —NHC(=O)N(alkyl)$_2$, —NHC(=O)$NH_2$, —NHC(=O)NHalkyl, —NHC(=O)Oalkyl, —$NHSO_2$alkyl, nitro, —OC(=O)N(alkyl)$_2$, —OC(=O)NHalkyl, —$SO_2$alkyl, thio and thioalkyl;

$L^2$ is a linking group selected from the group consisting of: —($CH_2$)—, —CH($CH_3$)—, and —CH($CH_2CH_3$)—;

$R^{10}$ is independently selected from the group consisting of

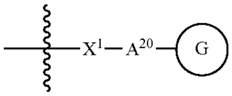

and —$X^1$-$A^{20}$-$Y^1$-$A^{21}$;

wherein $X^1$ and $Y^1$ are each independently absent or selected from the group consisting of: -(alkyl)C(=O)N(alkyl)-, —C(=O)N(alkyl)-, —C(=O)NH—, —C(=O)O—, —N(alkyl)-, —N(alkyl)C(=O)—, —N(alkyl)C(=O)NH—, —N(alkyl)C(=O)O—, —N(alkyl)$SO_2$—, —NH—, —NHC(=O)—, —NHC(=O)N(alkyl)-, —NHC(=O)NH, —NHC(=O)O—, —$NHSO_2$—, —O—, —OC(=O), —OC(=O)N(alkyl)-, —OC(=O)NH—, —OC(=O)O—, —S—, —SO—, —$SO_2$—, —$SO_2$N(alkyl)-, and —$SO_2$NH—;

$A^{20}$ is absent or selected from alkyl or alkenyl; and $A^{21}$ is selected from alkyl, alkenyl, or H;

wherein when $A^{20}$ or $A^{21}$ is alkyl or alkenyl, the alkyl or alkenyl may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy, —N(alkyl)C(=O)alkyl, —N(alkyl)C(=O)N(alkyl)$_2$, —N(alkyl)C(=O)$NH_2$, —N(alkyl)C(=O)NHalkyl, —N(alkyl)C(=O)Oalkyl, —N(alkyl)$SO_2$alkyl, —NHC(=O)alkyl, —NHC(=O)N(alkyl)$_2$, —NHC(=O)$NH_2$, —NHC(=O)NHalkyl, —NHC(=O)Oalkyl, —$NHSO_2$alkyl, —OC(=O)alkyl, —OC(=O)N(alkyl)$_2$, —OC(=O)NHalkyl, —OC(=O)Oalkyl, —$SO_2$alkyl, thio or thioalkyl;

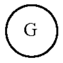

is selected from the group consisting of aryl, cycloalkyl, partially unsaturated carbocycle, heteroaryl, heterocycloalkyl, nine to ten membered benzo-fused cycloalkyl, and nine to ten membered benzo-fused heterocycloalkyl; wherein, the aryl, cycloalkyl, partially unsaturated carbocycle, heteroaryl, heterocycloalkyl, benzo-fused cycloalkyl, or benzo-fused heterocycloalkyl, are optionally substituted with one or more substituents independently selected from halogen, hydroxy, amino, thio, nitro, cyano, alkyl, halogenated alkyl, alkoxy, halogenated alkoxy, alkylamino, —NHC(=O)alkyl, —N(alkyl)C(=O)alkyl, or dialkylamino, —NHC(=O)$NH_2$, —NHC(=O)NHalkyl, —N(alkyl)C(=O)NHalkyl, —OC(=O)NHalkyl, —NHC(=O)Oalkyl, —N(alkyl)C(=O)Oalkyl, —$NHSO_2$alkyl, —N(alkyl)$SO_2$alkyl, thioalkyl, halogenated thioalkyl, —$SO_2$alkyl, halogenated —$SO_2$alkyl, —NHC(=O)N(alkyl)$_2$, —N(alkyl)C(=O)N(alkyl)$_2$ or —OC(=O)N(alkyl)$_2$;

s is an integer from 0 to 2;

m is an integer from 0 to 4; provided that the sum of m and s is an integer from 0 to 4;

$R^6$ and $R^7$ are independently selected from the group consisting of:

(a) H;

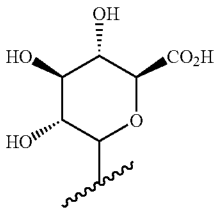

(b) provided that $R^4$ is not

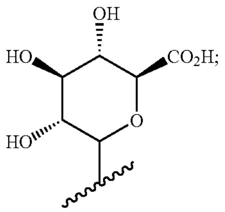

(c) —$CH_2$— substituted with one group selected from: —H, -methyl, —Oalkyl, —$CH_2$OH, —CHCH$_3$)OH, —O(C=O)alkyl, —(C=O)OH, —C(=O)Oalkyl, —C(=O)Oaryl, —C(=O)Oheteroaryl, —(C=O)NH$_2$, —(C=O)NHalkyl, —(C=O)N(alkyl)$_2$, —C(=O)alkyl, -phenyl-OCH$_3$ or -phenyl-OC(=O)alkyl;

(d) —C(=O)(CH$_2$CH$_2$O—)$_{1-10}$ terminating with H, methyl, ethyl, or benzyl;

(e) —C(=O)CH$_2$O(CH$_2$CH$_2$O—)$_{1-10}$ terminating with H, methyl, ethyl, or benzyl;

(f) —C(=O)alkyl, or —C(=O)(C$_{3-6}$)cycloalkyl, wherein said —C(=O)alkyl, and —C(=O)(C$_{3-6}$)cycloalkyl may be optionally substituted with one or more groups independently selected from: —OH, —Oalkyl, —Oalkylaryl, —NH$_2$, —NHalkyl, —N(alkyl)$_2$, heterocycloalkyl, —NHC(=O)alkyl, —NHSO$_2$alkyl, or —OC(=O)alkyl;

(g) —C(=O)(CH$_2$)$_{1-3}$aryl, —C(=O)aryl, —C(=O)(CH$_2$)$_{1-3}$heteroaryl, or —C(=O)heteroaryl, wherein said —C(=O)(CH$_2$)$_{1-3}$aryl, —C(=O)aryl, —C(=O)(CH$_2$)$_{1-3}$heteroaryl, and —C(=O)heteroaryl may be optionally substituted with one or more groups independently selected from: —OH, —Oalkyl, —NH$_2$, —NHalkyl, —N(alkyl)$_2$, heterocycloalkyl, —NHC(=O)alkyl, —NHSO$_2$alkyl, halogen, nitrile, or —OC(=O)alkyl;

(h) —C(=O)(CH$_2$)$_{1-6}$C(=O)— terminating with methyl, ethyl, —OH, —Oalkyl, —NH$_2$, —NHalkyl, —N(alkyl)$_2$, or heterocycloalkyl;

(hh) —C(=O)alkylOC(=O)alkyl- terminating with —OH, —Oalkyl, —NH$_2$, —NHalkyl, —N(alkyl)$_2$, or heterocycloalkyl;

(i) —C(=O)O(CH$_2$CH$_2$O—)$_{1-10}$ terminating with H, methyl, ethyl, or benzyl;

(j) —C(=O)Oalkyl, or —C(=O)O(C$_{3-6}$)cycloalkyl, wherein said —C(=O)Oalkyl, and —C(=O)O(C$_{3-6}$)cycloalkyl may be optionally substituted with one or more groups independently selected from: —OH, —Oalkyl, —NH$_2$, —NHalkyl, —N(alkyl)$_2$, heterocycloalkyl, —NHC(=O)alkyl, —NHSO$_2$alkyl, —OC(=O)alkyl, —C(O)OH, —C(=O)Oalkyl, —C(=O)NH$_2$, —C(=O)NHalkyl, or —C(=O)N(alkyl)$_2$;

(k) —C(=O)O(CH$_2$)$_{1-3}$aryl, —C(=O)Oaryl, —C(=O)O(CH$_2$)$_{1-3}$heteroaryl, or —C(=O)Oheteroaryl, wherein said —C(=O)O(CH$_2$)$_{1-3}$aryl, —C(=O)Oaryl, —C(=O)O(CH$_2$)$_{1-3}$heteroaryl, or —C(=O)Oheteroaryl may be optionally substituted with one or more groups independently selected from: —OH, —Oalkyl, —NH$_2$, —NHalkyl, —N(alkyl)$_2$, heterocycloalkyl, —NHC(=O)alkyl, —NHSO$_2$alkyl, halogen, nitrile, or —OC(=O)alkyl;

(l) —C(=O)NH(CH$_2$CH$_2$O—)$_{1-10}$ terminating with —H, methyl, ethyl, benzyl, —CH$_2$CH$_2$NH$_2$, —CH$_2$CH$_2$NHalkyl, —CH$_2$CH$_2$N(alkyl)$_2$, —CH$_2$CH$_2$-1-pyrrolidinyl, —CH$_2$CH$_2$-1-piperidinyl, —CH$_2$CH$_2$-4-morpholinyl, —CH$_2$CH$_2$-1-piperazinyl, —CH$_2$CH$^2$-1-(4-CH$_3$)-piperazinyl or —C(=O)alkyl;

(m) —C(=O)NH$_2$, —C(=O)NH(C$_{1-20}$)alkyl, —C(=O)NH(C$_{3-6}$)cycloalkyl, or —C(=O)N(alkyl)$_2$, wherein said —C(=O)NH(C$_{1-20}$)alkyl, —C(=O)NH(C$_{3-6}$)cycloalkyl, and —C(=O)N(alkyl)$_2$ may be optionally substituted with one or more groups independently selected from: —OH, —Oalkyl, —NH$_2$, —NHalkyl, —N(alkyl)$_2$, heterocycloalkyl, —NHC(=O)alkyl, —NHSO$_2$alkyl, —OC(=O)alkyl, —OC(=O)alkenyl, —NHC(=O)aryl, —C(=O)OH, —C(=O)Oalkyl, —C(=O)NH$_2$, —C(=O)NHalkyl, or —C(=O)N(alkyl)$_2$; and, wherein the aryl portion of said —NHC(=O)aryl may be optionally substituted with one or more groups independently selected from: alkyl, —OH, —Oalkyl, —NH$_2$, —NHalkyl, —N(alkyl)$_2$, halogen or nitrile;

(n) —C(=O)NH(CH$_2$)$_{1-3}$aryl, —C(=O)NHaryl, —C(=O)NH(CH$_2$)$_{1-3}$heteroaryl, or —C(=O)NHheteroaryl, wherein said —C(=O)NH(CH$_2$)$_{1-3}$aryl, —C(=O)NHaryl, —C(=O)NH(CH$_2$)$_{1-3}$heteroaryl, and —C(=O)NHheteroaryl may be optionally substituted with one or more groups independently selected from: —OH, —Oalkyl, —NH$_2$, —NHalkyl, —N(alkyl)$_2$, heterocycloalkyl, —NHC(=O)alkyl, —NHSO$_2$alkyl, halogen, nitrile, or —OC(=O)alkyl;

(o) —C(=O)NHCH$_2$CH$_2$NH(CH$_2$CH$_2$NH—)$_{0-3}$ terminating with H, methyl, ethyl, —CH$_2$CH$_2$NHalkyl, —CH$_2$CH$_2$N(alkyl)$_2$, —CH$_2$CH$_2$-1-pyrrolidinyl, —CH$_2$CH$_2$-1-piperidinyl, —CH$_2$CH$_2$-4-morpholinyl, —CH$_2$CH$_2$-1-piperazinyl, —CH$_2$CH$_2$-1-(4-CH$_3$)-piperazinyl, —CH$_2$CH$_2$OH, —CH$_2$CH$_2$OCH$_3$, —CH$_2$CH$_2$OCH$_2$CH$_3$, —CH$_2$CH$_2$OC(=O)alkyl, or —C(=O)aryl; wherein the aryl portion of said —C(=O)aryl may be optionally substituted with one or more groups independently selected from: alkyl, —OH, —Oalkyl, —NH$_2$, —NHalkyl, —N(alkyl)$_2$, halogen or nitrile;

(p) —C(=S)NH$_2$;

(q) —C(=S)NHalkyl;

(r) —C(=S)N(alkyl)$_2$;

(s) —SO$_2$NH$_2$;

(t) —SO$_2$NHalkyl;

(u) —SO$_2$N(alkyl)$_2$;

(v) —$P(=O)(OCH_3)_2$; and (w) —$P(=O)(OCH_2CH_3)_2$;

provided that when $R^6$ is present, $R^7$ is absent; and provided that when $R^7$ is present, $R^6$ is absent;

$R^4$ is selected from the group consisting of: H and

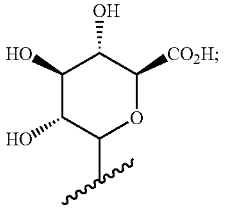

provided that if one of $R^6$ and $R^7$ is

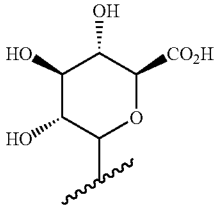

then $R^4$ is H;

$L^3$ is absent;

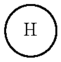

is aryl;

r is an integer from 0 to 4; and $R^5$ is independently selected from the group consisting of: alkyl, alkyl amino, alkyloxy, amino, —$C(=O)NH_2$, —C(=O)Oalkyl, —C(=O)OH, —$CH_2OH$, cyano, dialkylamino, halogen, halogenated alkyl, halogenated alkyloxy, halogenated $SO_2$-alkyl, halogenated thioalkyl, hydroxy, hydroxy alkyl, —N(alkyl)C(=O)alkyl, —N(alkyl)C(=O)N(alkyl)$_2$, —N(alkyl)C(=O)NHalkyl, —N(alkyl)C(=O)Oalkyl, —N(alkyl)$SO_2$alkyl, —NHC(=O)alkyl, —NHC(=O)N(alkyl)$_2$, —NHC(=O)$NH_2$, —NHC(=O)NHalkyl, —NHC(=O)Oalkyl, —$NHSO_2$alkyl, nitro, —OC(=O)N(alkyl)$_2$, —OC(=O)NHalkyl, —$SO_2$alkyl, —$SO_2NH_2$, thio, thioalkyl,

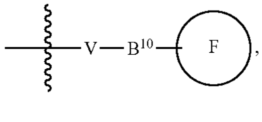, and —V—$B^{10}$—W—$B^{20}$; wherein,

V and W are each independently absent or selected from the group consisting of: —C(=O), —C(=O)N(alkyl)-, —C(=O)NH—, —C(=O)O—, —N(alkyl)-, —N(alkyl)C(=O)—, —N(alkyl)C(=O)N(alkyl)-, —N(alkyl)C(=O)NH—, —N(alkyl)C(=O)O—, —N(alkyl)$SO_2$—, —NH—, —NHC(=O)—, —NHC(=O)N(alkyl)-, —NHC(=O)NH—, —NHC(=O)O—, —$NHSO_2$—, —O—, —OC(=O), —OC(=O)N(alkyl)-, —OC(=O)NH—, —OC(=O)O—, —S—, —SO—, —$SO_2$—, —$SO_2$N(alkyl)- and —$SO_2NH$—;

$B^{10}$ is absent or selected from alkyl or alkenyl;

$B^{20}$ is absent or selected from alkyl, alkenyl, or H;

wherein, when $B^{10}$ or $B^{20}$ is alkyl or alkenyl, the alkyl or alkenyl group may be optionally substituted with one or more groups independently selected from: alkoxy, alkylamino, amino, cyano, dialkylamino, halogen, halogenated alkoxy, halogenated —$SO_2$alkyl, halogenated thioalkyl, hydroxy —N(alkyl)C(=O)alkyl, —N(alkyl)C(=O)N(alkyl)$_2$, —N(alkyl)C(=O)$NH_2$, —N(alkyl)C(=O)NHalkyl, —N(alkyl)C(=O)Oalkyl, —N(alkyl)$SO_2$alkyl, —NHC(=O)alkyl, —NHC(=O)N(alkyl)$_2$, —NHC(=O)$NH_2$, —NHC(=O)NHalkyl, —NHC(=O)Oalkyl, —$NHSO_2$alkyl, —OC(=O)alkyl, —OC(=O)N(alkyl)$_2$, —OC(=O)NHalkyl, —OC(=O)Oalkyl, —$SO_2$alkyl, thio or thioalkyl; and

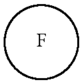

is selected from the group consisting of: an aryl, a cycloalkyl, a partially unsaturated carbocycle, a heteroaryl, a heterocycloalkyl, a nine to ten membered benzo-fused cycloalkyl, and a nine to ten membered benzo-fused heterocycloalkyl, wherein, the aryl, cycloalkyl, partially unsaturated carbocycle, heteroaryl, heterocycloalkyl, benzo-fused cycloalkyl, or benzo-fused heterocycloalkyl, is optionally substituted with one or more substituents independently selected from: alkoxy, alkylamino, amino, cyano, dialkylamino, halogen, halogenated alkoxy, halogenated alkyl, halogenated —$SO_2$alkyl, halogenated thioalkyl, heteroaryl, hydroxy, hydroxy alkyl, —N(alkyl)C(=O)alkyl, —N(alkyl)C(=O)N(alkyl)$_2$, —N(alkyl)C(=O)NHalkyl, —N(alkyl)C(=O)Oalkyl, —N(alkyl)$SO_2$alkyl, —NHC(=O)alkyl, —NHC(=O)N(alkyl)$_2$, —NHC(=O)$NH_2$, —NHC(=O)NHalkyl, —NHC(=O)Oalkyl, —$NHSO_2$alkyl, nitro, —OC(=O)N(alkyl)$_2$, —OC(=O)NHalkyl, —$SO_2$alkyl, thio or thioalkyl;

or an optical isomer, enantiomer, diastereomer, racemate, or pharmaceutically acceptable salt thereof.

24. A compound as in claim 23, wherein $L^2$ is a linking group selected from the group consisting of: —$(CH_2)$—, —$CHCH_3)$—, —$CH(CH_2CH_3)$—.

25. A compound of Formula (II-JJ):

(II-JJ)

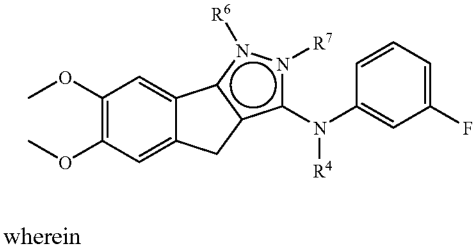

wherein $R^6$ and $R^7$ are independently selected from the group consisting of:

(a) H;

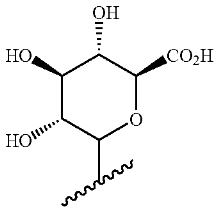

(b) provided that $R^4$ is not

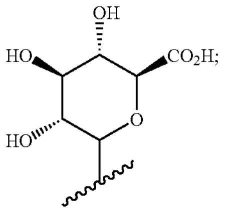

(c) —$CH_2$— substituted with one group selected from: —H, -methyl, —Oalkyl, —$CH_2OH$, —$CH(CH_3)OH$, —O(C═O)alkyl, —(C═O)OH, —C(═O)Oalkyl, —C(═O)Oaryl, —C(═O)Oheteroaryl, —(C═O)$NH_2$, —(C═O)NHalkyl, —(C═O)N(alkyl)$_2$, —C(═O)alkyl, -phenyl-$OCH_3$ or -phenyl-OC(═O)alkyl;

(d) —C(═O)($CH_2CH_2O$—)$_{1-10}$ terminating with H, methyl, ethyl, or benzyl;

(e) —C(═O)$CH_2$O($CH_2CH_2O$—)$_{1-10}$ terminating with H, methyl, ethyl, or benzyl;

(f) —C(═O)alkyl, or —C(═O)($C_{3-6}$)cycloalkyl, wherein said —C(═O)alkyl, and —C(═O)($C_{3-6}$)cycloalkyl may be optionally substituted with one or more groups independently selected from: —OH, —Oalkyl, —Oalkylaryl, —$NH_2$, —NHalkyl, —N(alkyl)$_2$, heterocycloalkyl, —NHC(═O)alkyl, —$NHSO_2$alkyl, or —OC(═O)alkyl;

(g) —C(═O)($CH_2$)$_{1-3}$aryl, —C(═O)aryl, —C(═O)($CH_2$)$_{1-3}$heteroaryl, or —C(═O)heteroaryl, wherein said —C(═O)($CH_2$)$_{1-3}$aryl, —C(═O)aryl, —C(═O)($CH_2$)$_{1-3}$heteroaryl, and —C(═O)heteroaryl may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or —OC(═O)alkyl;

(h) —C(═O)($CH_2$)$_{1-6}$C(═O)— terminating with methyl, ethyl, —OH, —Oalkyl, —$NH_2$, —NHalkyl, —N(alkyl)$_2$, or heterocycloalkyl;

(hh) —C(═O)alkylOC(═O)alkyl- terminating with —OH, —Oalkyl, —$NH_2$, —NHalkyl, —N(alkyl)$_2$, or heterocycloalkyl;

(i) —C(═O)O($CH_2CH_2O$—)$_{1-10}$ terminating with H, methyl, ethyl, or benzyl;

(j) —C(═O)Oalkyl, or —C(═O)O($C_{3-6}$)cycloalkyl, wherein said —C(═O)Oalkyl, and —C(═O)O($C_{3-6}$)cycloalkyl may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, —OC(═O)alkyl, —C(O)OH, —C(═O)Oalkyl, —C(═O)$NH_2$, —C(═O)NHalkyl, or —C(═O)N(alkyl)$_2$;

(k) —C(═O)O($CH_2$)$_{1-3}$aryl, —C(═O)Oaryl, —C(═O)O($CH_2$)$_{1-3}$heteroaryl, or —C(═O)Oheteroaryl, wherein said —C(═O)O($CH_2$)$_{1-3}$aryl, —C(═O)Oaryl, —C(═O)O($CH_2$)$_{1-3}$heteroaryl, or —C(═O)Oheteroaryl may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or —OC(═O)alkyl;

(l) —C(═O)NH($CH_2CH_2O$—)$_{1-10}$ terminating with —H, methyl, ethyl, benzyl, —$CH_2CH_2NH_2$, —$CH_2CH_2$NHalkyl, —$CH_2CH_2$N(alkyl)$_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl or —C(═O)alkyl;

(m) —C(═O)$NH_2$, —C(═O)NH($C_{1-20}$)alkyl, —C(═O)NH($C_{3-6}$)cycloalkyl, or —C(═O)N(alkyl)$_2$, wherein said —C(═O)NH($C_{1-20}$)alkyl, —C(═O)NH($C_{3-6}$)cycloalkyl, and —C(═O)N(alkyl)$_2$ may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, —OC(═O)alkyl, —OC(═O)alkenyl, —NHC(═O)aryl, —C(═O)OH, —C(═O)Oalkyl, —C(═O)$NH_2$, —C(═O)NHalkyl, or —C(═O)N(alkyl)$_2$;and, wherein the aryl portion of said NHC(═O)aryl may be optionally substituted with one or more groups independently selected from: alkyl, —OH, —Oalkyl, —$NH_2$, —NHalkyl, —N(alkyl)$_2$, halogen or nitrile;

(n) —C(═O)NH($CH_2$)$_{1-3}$aryl, —C(═O)NHaryl, —C(═O)NH($CH_2$)$_{1-3}$heteroaryl, or —C(═O)NHheteroaryl, wherein said —C(═O)NH($CH_2$)$_{1-3}$aryl, —C(═O)NHaryl, —C(═O)NH($CH_2$)$_{1-3}$heteroaryl, and —C(═O)NHheteroaryl may be optionally substituted with one or more groups independently selected from: —OH, —Oalkyl, —$NH_2$, —NHalkyl, —N(alkyl)$_2$, heterocycloalkyl, —NHC(═O)alkyl, —$NHSO_2$alkyl, halogen, nitrile, or —OC(═O)alkyl;

(o) —C(═O)$NHCH_2CH_2$NH($CH_2CH_2NH$—)$_{0-3}$ terminating with H, methyl, ethyl, —$CH_2CH_2$NHalkyl, —$CH_2CH_2$N(alkyl)$_2$, —$CH_2CH_2$-1-pyrrolidinyl, —$CH_2CH_2$-1-piperidinyl, —$CH_2CH_2$-4-morpholinyl, —$CH_2CH_2$-1-piperazinyl, —$CH_2CH_2$-1-(4-$CH_3$)-piperazinyl, —$CH_2CH_2OH$, —$CH_2CH_2OCH_3$, —$CH_2CH_2OCH_2CH_3$, —$CH_2CH_2$OC(═O)alkyl, or —C(═O)aryl; wherein the aryl portion of said —C(═O)aryl may be optionally substituted with one or more groups independently selected from: alkyl, —OH, —Oalkyl, —$NH_2$, —NHalkyl, —N(alkyl)$_2$, halogen or nitrile;

(p) —C(S)$NH_2$;

(q) —C(═S)NHalkyl;

(r) —C(═S)N(alkyl)$_2$;

(s) —$SO_2NH_2$;

(t) —$SO_2$NHalkyl;

(u) —$SO_2$N(alkyl)$_2$;

(v) —P(═O)($OCH_3$)$_2$; and (w) —P(═O)($OCH_2CH_3$)$_2$;

provided that when $R^6$ is present, $R^7$ is absent; and provided that when $R^7$ is present, $R^6$ is absent;

$R^4$ is selected from the group consisting of: H and
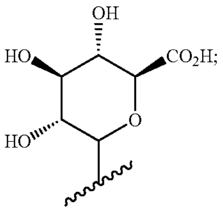
provided that if one of $R^6$ and $R^7$ is
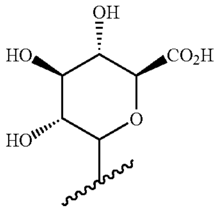
then $R^4$ is H;
or an optical isomer, enantiomer, diastereomer, racemate, or pharmaceutically acceptable salt thereof.
26. A compound selected from the group consisting of:
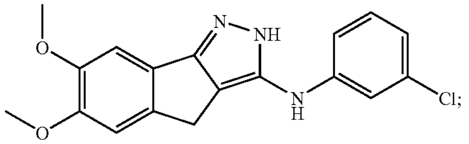
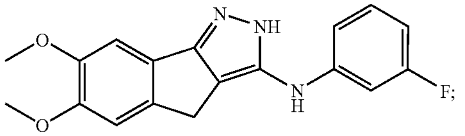
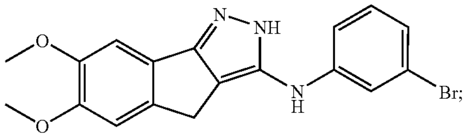
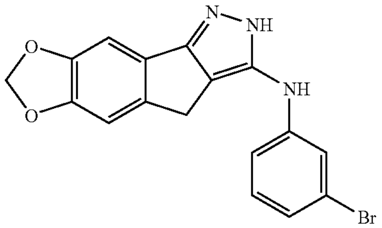
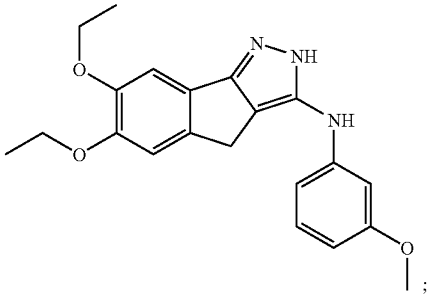
-continued
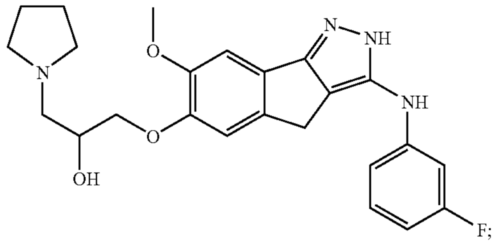
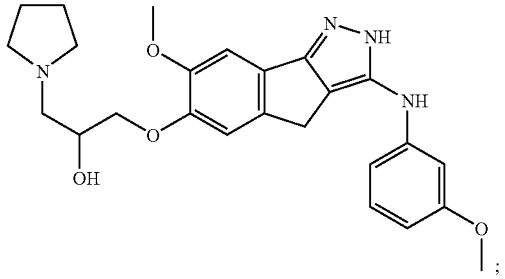
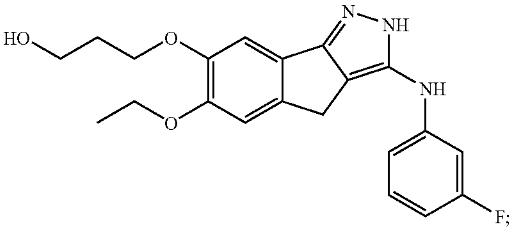
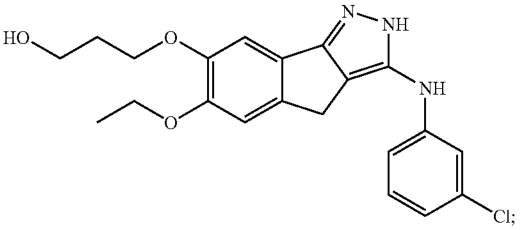
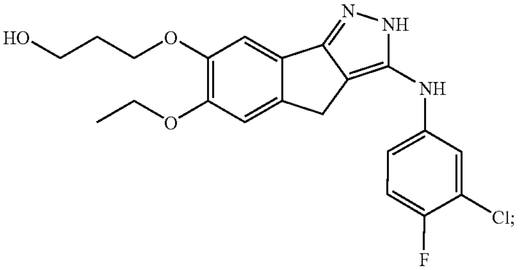
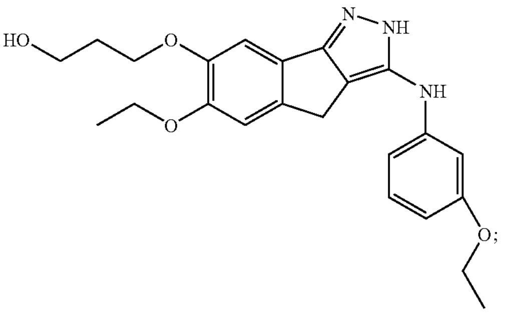

-continued
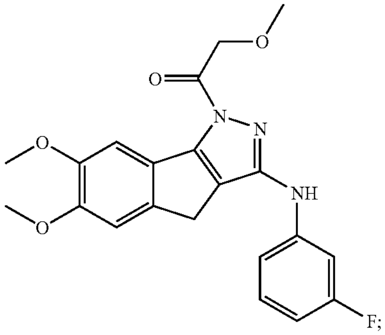
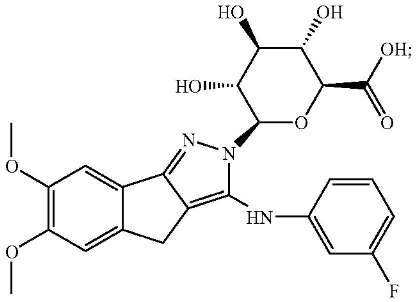
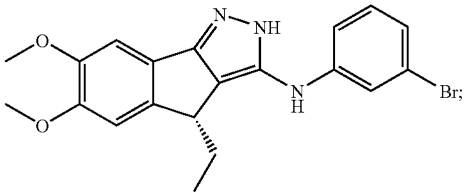
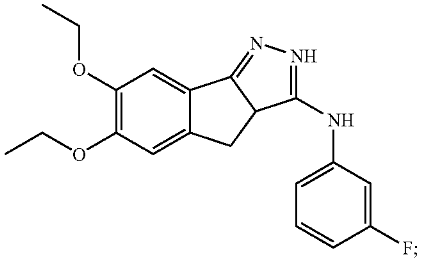
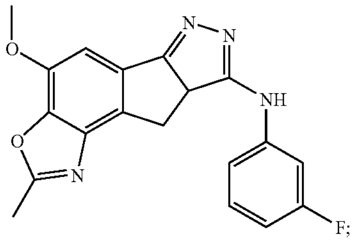
and
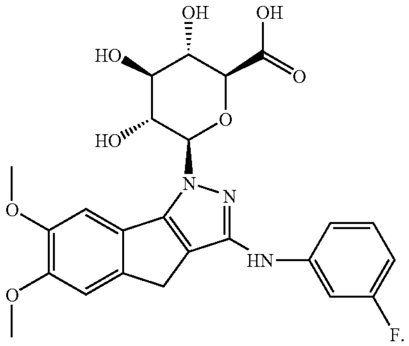
27. A compound selected from the group consisting of:
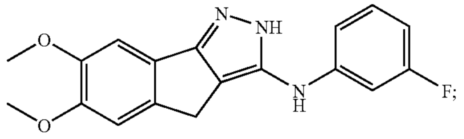
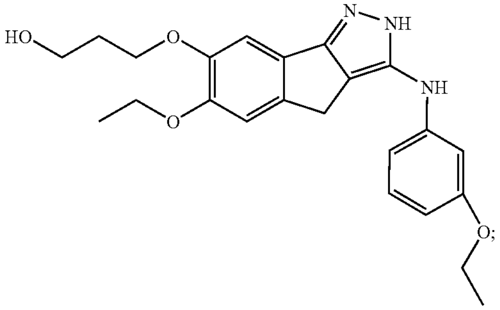
and
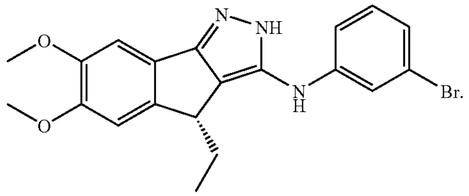
28. A compound of the following formula:
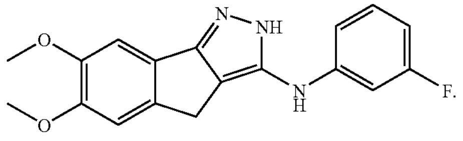
29. A compound of the following formula:
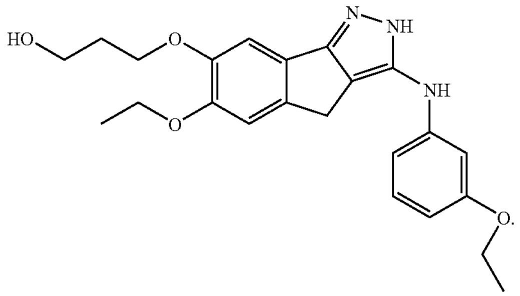
30. A compound of the following formula:
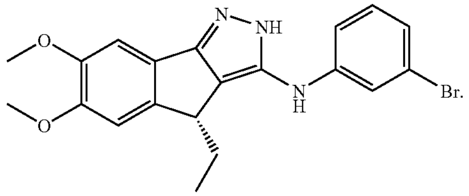

31. A pharmaceutical composition comprising a pharmaceutically acceptable carrier and a compound of claim 1.

32. A pharmaceutical composition comprising a pharmaceutically acceptable carrier and a compound of claim 7.

33. A pharmaceutical composition comprising a pharmaceutically acceptable carrier and a compound of claim 14.

34. A pharmaceutical composition comprising a pharmaceutically acceptable carrier and a compound of claim 16.

35. A pharmaceutical composition comprising a pharmaceutically acceptable carrier and a compound of claim 25.

36. A pharmaceutical composition comprising a pharmaceutically acceptable carrier and a compound of claim 26.

37. A pharmaceutical composition comprising a pharmaceutically acceptable carrier and a compound of claim 27.

* * * * *